United States Patent [19]
Bauer et al.

[11] Patent Number: 6,017,523
[45] Date of Patent: *Jan. 25, 2000

[54] THERAPEUTIC METHODS EMPLOYING MUTANT HUMAN INTERLEUKIN-3 (IL-3) POLYPEPTIDES

[75] Inventors: S. Christopher Bauer, New Haven; Sarah Ruth Braford-Goldberg, St. Louis; Maire Helena Caparon, Chesterfield; Alan Michael Easton, Maryland Heights; John Patrick McKearn, Pacific; Peter Olafs Olins, Glencoe, all of Mo.

[73] Assignee: G.D. Searle & Co., Chicago, Ill.

[*] Notice: This patent is subject to a terminal disclaimer.

[21] Appl. No.: 08/471,039

[22] Filed: Jun. 6, 1995

Related U.S. Application Data

[60] Division of application No. 08/411,796, filed as application No. PCT/US93/11198, Nov. 22, 1993, Pat. No. 5,677,149, which is a continuation-in-part of application No. 07/981,044, Nov. 24, 1992, abandoned.

[51] Int. Cl.$^7$ .......................... A61K 38/20; C12N 15/24; C07K 14/54
[52] U.S. Cl. .......................................... 424/85.2; 930/141
[58] Field of Search ........................ 530/351; 435/69.52; 424/85.2; 930/141

[56] References Cited

U.S. PATENT DOCUMENTS

| | | | |
|---|---|---|---|
| 4,877,729 | 10/1989 | Clark et al. | 435/68 |
| 4,959,455 | 9/1990 | Clark et al. | 530/351 |
| 5,032,395 | 7/1991 | Clark et al. | 424/85.1 |
| 5,166,322 | 11/1992 | Shaw et al. | 530/351 |
| 5,591,427 | 1/1997 | Vadas | 424/85.2 |
| 5,677,149 | 10/1997 | Bauer et al. | 435/69.52 |

FOREIGN PATENT DOCUMENTS

| | | | |
|---|---|---|---|
| 275598 | 7/1988 | European Pat. Off. | C12N 15/00 |
| 413383 | 2/1991 | European Pat. Off. | C12N 15/27 |
| 3/236400 | 10/1991 | Japan | C07K 13/00 |
| 4/63595 | 2/1992 | Japan | C12N 15/24 |
| 2210883 | 6/1989 | United Kingdom | C12N 15/00 |
| 88/00598 | 1/1988 | WIPO | C07K 13/00 |
| 88/04691 | 6/1988 | WIPO | C12N 15/00 |
| 88/05469 | 7/1988 | WIPO | C12P 21/00 |
| 88/06161 | 8/1988 | WIPO | C07K 13/00 |
| 90/01039 | 2/1990 | WIPO | C07K 13/00 |
| 90/10705 | 9/1990 | WIPO | C12P 21/02 |
| 90/12874 | 11/1990 | WIPO | C12N 15/27 |
| 91/00350 | 1/1991 | WIPO | C12N 15/27 |
| 91/02754 | 3/1991 | WIPO | C12N 15/62 |
| 93/07171-A1 | 4/1993 | WIPO | |

OTHER PUBLICATIONS

Yang et al, in Cell 47:3 (1986).
Dorsers et al, Gene 55:115 (1987).
Phillips et al, Gene, 84, 501 (1989).
Clark–Lewis et al, Science 231:134 (1986).
Clark–Lewis et al, Proc.Nat.Acad.Sci.USA 85:7897 (1988).
Lokker et al, J. Biol. Chem., 266 (16):10624 (1991).
Clark–Lewis et al, Immune Regulation by Characterized Polypeptides, Alan R. Liss, Inc. (1987) pp. 323–334.
Ihle et al, J. Immunol. 126:2184 (1981).
Fung et al, Nature, 307, 233 (1984).
Yokota et al, Proc.Nat.Acad.Sci. USA 81:1070 (1984).
Dorssers et al, J.Biol.Chem 266 (31):21310 (1991).
Koshansky et al, J.Clin.Invest, 90:1879 (1992).
Lopez et al, Proc.Natl.Acad.Sci. USA 89:11842–11846 (1992).
Lokker et al, The EMBO Jour. 10:2125–2131 (1991).

*Primary Examiner*—David L. Fitzgerald
*Attorney, Agent, or Firm*—Dennis A. Bennett

[57] ABSTRACT

The present invention relates to recombinant human interleukin-3 (hIL-3) variant or mutant proteins (muteins). These hIL-3 muteins contain one to three amino acid substitutions and may also have amino acid deletions at both the N- and C- termini. The invention also relates to pharmaceutical compositions containing the hIL-3 muteins and methods for using them. Additionally, the present invention relates to recombinant expression vectors comprising nucleotide sequences encoding the hIL-3 muteins, related microbial expression systems, and processes for making the hIL-3 muteins using the microbial expression systems. Included in the present invention are deletion mutants of hIL-3 in which from 1 to 14 amino acids have been deleted from the N-terminus, and from 1 to 15 amino acids (corresponding to residues 119 to 133) have been deleted from the C-terminus, and which also contain one to three amino acid substitutions in the polypeptide. These hIL-3 mutant polypeptides may have biological activities similar to or better than hIL-3 and, in some cases, may also have an improved side effect profile.

90 Claims, 16 Drawing Sheets

```
        1                       5                              10
ATG  GCT  CCA  ATG  ACT  CAG  ACT  ACT  TCT  CTT  AAG  ACT  TCT
Met  Ala  Pro  Met  Thr  Gln  Thr  Thr  Ser  Leu  Lys  Thr  Ser 15                       20                       25
TGG  GTT  AAC  TGC  TCT  AAC  ATG  ATC  GAT  GAA  ATT  ATA  ACA
Trp  Val  Asn  Cys  Ser  Asn  Met  Ile  Asp  Glu  Ile  Ile  Thr 30                  35
CAC  TTA  AAG  CAG  CCA  CCT  TTG  CCT  TTG  CTG  GAC  TTC  AAC
His  Leu  Lys  Gln  Pro  Pro  Leu  Pro  Leu  Leu  Asp  Phe  Asn 40                       45                       50
AAC  CTC  AAT  GGG  GAA  GAC  CAA  GAC  ATT  CTG  ATG  GAA  AAT
Asn  Leu  Asn  Gly  Glu  Asp  Gln  Asp  Ile  Leu  Met  Glu  Asn 55                       60
AAC  CTT  CGA  AGG  CCA  AAC  CTG  GAG  GCA  TTC  AAC  AGG  GCT
Asn  Leu  Arg  Arg  Pro  Asn  Leu  Glu  Ala  Phe  Asn  Arg  Ala 65                       70                       75
GTC  AAG  AGT  TTA  CAG  AAT  GCA  TCA  GCA  ATT  GAG  AGC  ATT
Val  Lys  Ser  Leu  Gln  Asn  Ala  Ser  Ala  Ile  Glu  Ser  Ile 80                       85                       90
CTT  AAA  AAT  CTC  CTG  CCA  TGT  CTG  CCC  CTG  GCC  ACG  GCC
Leu  Lys  Asn  Leu  Leu  Pro  Cys  Leu  Pro  Leu  Ala  Thr  Ala 95                       100
GCA  CCC  ACG  CGA  CAT  CCA  ATC  CAT  ATC  AAG  GAC  GGT  GAC
Ala  Pro  Thr  Arg  His  Pro  Ile  His  Ile  Lys  Asp  Gly  Asp 105                      110                      115
TGG  AAT  GAA  TTC  CGT  CGT  AAA  CTG  ACC  TTC  TAT  CTG  AAA
Trp  Asn  Glu  Phe  Arg  Arg  Lys  Leu  Thr  Phe  Tyr  Leu  Lys 120                      125
ACC  TTG  GAG  AAC  GCG  CAG  GCT  CAA  CAG  ACC  ACT  CTG  TCG
Thr  Leu  Glu  Asn  Ala  Gln  Ala  Gln  Gln  Thr  Thr  Leu  Ser

130
CTA  GCG  ATC  TTT  TAA  TAA        [SEQ ID NO:144]
Leu  Ala  Ile  Phe  END  END        [SEQ ID NO:128]
```

FIG-1

```
                 ClaI
aa20    ATCGATGAAATCATCACCCACCTGAAGCAGCCACCGCTGCTGGACTTCAACAAC
     1  ---------+---------+---------+---------+---------+---------+   60
        IleAspGluIleIleThrHisLeuLysGlnProProLeuLeuAspPheAsnAsn
                            E               x
                            c               h
                            o               o
                            R               I
                            V

CTCAATGGTGAAGACCAAGATATCCTGATGGAAAATAACCTTCGTCGTCCAAACCTCGAG
    61  ---------+---------+---------+---------+---------+---------+  120
        LeuAsnGlyGluAspGlnAspIleLeuMetGluAsnAsnLeuArgArgProAsnLeuGlu
                                              P     N
                                              s     s
                                              t     i
                                              I     I

GCATTCAACCGTGCTGTCAAGTCTCTGCAGAATGCAT [SEQ ID NO:145] aa70
   121  ---------+---------+---------+-------                157
        AlaPheAsnArgAlaValLysSerLeuGlnAsnAla  [SEQ ID NO:146]
```

ClaI to NsiI Replacement Fragment

Fig-2

```
                N                                                          H
                c                                                          p
                o                                                          a
                I                                                          I
      CCATGGCTCCAATGACTCAGACTACTTCTCTTAAGACTTCTTGGGTTAACTGCTCTAACA
   1  ---------+---------+---------+---------+---------+---------+  60
      GGTACCGAGGTTACTGAGTCTGATGAAGAGAATTCTGAAGAACCCAATTGACGAGATTGT

MetAlaProMetThrGlnThrThrSerLeuLysThrSerTrpValAsnCysSerAsnMet

C
                         l
                         a
                         I
      TGATCGATGAAATTATAACACACTTAAAGCAGCCACCTTTGCCTTTGCTGGACTTCAACA
  61  ---------+---------+---------+---------+---------+---------+ 120
      ACTAGCTACTTTAATATTGTGTGAATTTCGTCGGTGGAAACGGAAACGACCTGAAGTTGT

IleAspGluIleIleThrHisLeuLysGlnProProLeuProLeuLeuAspPheAsnAsn

ACCTCAATGGGGAAGACCAAGACATTCTGATGGAAAATAACCTTCGAAGGCCAAACCTGG
 121  ---------+---------+---------+---------+---------+---------+ 180
      TGGAGTTACCCCTTCTGGTTCTGTAAGACTACCTTTTATTGGAAGCTTCCGGTTTGGACC

LeuAsnGlyGluAspGlnAspIleLeuMetGluAsnAsnLeuArgArgProAsnLeuGlu

N
                                                    S
                                                    i
                                                    I
      AGGCATTCAACAGGGCTGTCAAGAGTTTACAGAATGCATCAGCAATTGAGAGCATTCTTA
 181  --------+---------+---------+---------+---------+---------+- 240
      TCCGTAAGTTGTCCCGACAGTTCTCAAATGTCTTACGTAGTCGTTAACTCTCGTAAGAAT

AlaPheAsnArgAlaValLysSerLeuGlnAsnAlaSerAlaIleGluSerIleLeuLys

AAAATCTCCTGCCATGTCTGCCCCTGGCCACGGCCGCACCCACGCGACATCCAATCCATA
 240  ---------+---------+---------+---------+---------+---------+ 300
      TTTTAGAGGACGGTACAGACGGGGACCGGTGCCGGCGTGGGTGCGCTGTAGGTTAGGTAT

AsnLeuLeuProCysLeuProLeuAlaThrAlaAlaProThrArgHisProIleHisIle
```

Fig- 3

```
                                        E
                                        c
                                        o
                                        R
                                        I
         TCAAGGACGGTGACTGGAATGAATTCCGTCGTAAACTGACCTTCTATCTGAAAACCTTGG
301      ---------+---------+---------+---------+---------+---------+ 360
         AGTTCCTGCCACTGACCTTACTTAAGGCAGCATTTGACTGGAAGATAGACTTTTGGAACC

LysAspGlyAspTrpAsnGluPheArgArgLysLeuThrPheTyrLeuLysThrLeuGlu
```

```
                                                                  H
                                                                  i
                                                                  n
                                              N                   d
                                              h                   I
                                              e                   I
                                              I                   I
         AGAACGCGCAGGCTCAACAGACCACTCTGTCGCTAGCGATCTTTTAATAAGCTT
361      ---------+---------+---------+---------+---------+---+ 414
         TCTTGCGCGTCCGAGTTGTCTGGTGAGACAGCGATCGCTAGAAAATTATTCGAA

AsnAlaGlnAlaGlnGlnThrThrLeuSerLeuAlaIlePheEndEnd
```

Fig - 4

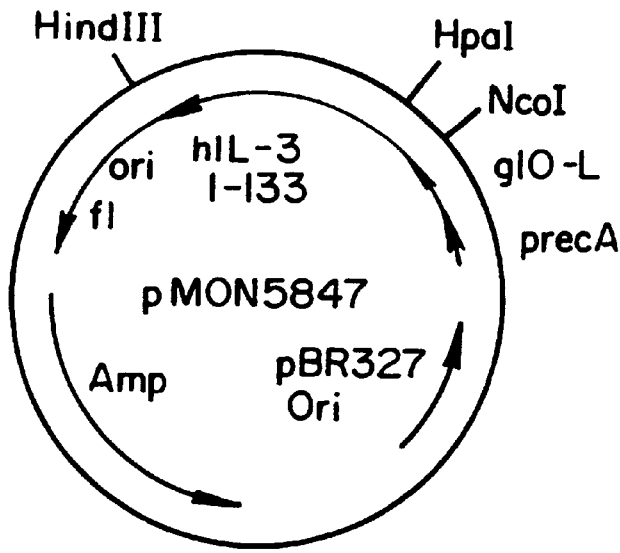
Cleave with NcoI and HpaI.
Klenow fill NcoI end to render it blunt.
Ligate the Blunt ends.
Transform E. coli JM101 to ampicillin resistance
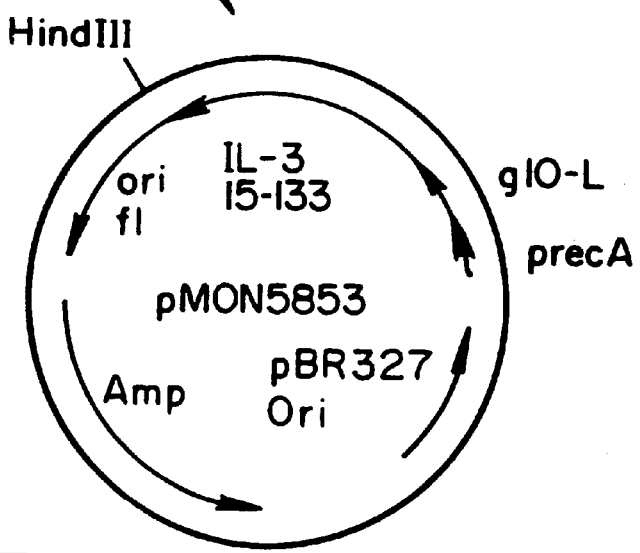
Fig-7

```
     ATGATGATTACTCTGCGCAAACTTCCTCTGCGGTTGCCGTCGCAGGGGGCGTAATGTCT
1    ------+---------+---------+---------+---------+---------+  60
     TACTACTAATGAGACGCGTTTGAAGGAGACGCCAACGGCAGCGTCCCCGCATTACAGA

MetMetIleThrLeuArgLysLeuProLeuAlaValAlaValAlaAlaGlyValMetSer    [SEQ ID NO: 149]

[SEQ ID NO: 150]
       N
       c
       o
       I                                                            [SEQ ID NO: 14]

GCTCAGGCCATGGCTAACTGC
61   ------+---------+---  81
     CGAGTCCGGTACCGATTGACG

AlaGlnAlaMetAlaAsnCys
``` lamB Signal Peptide

Fig - 9

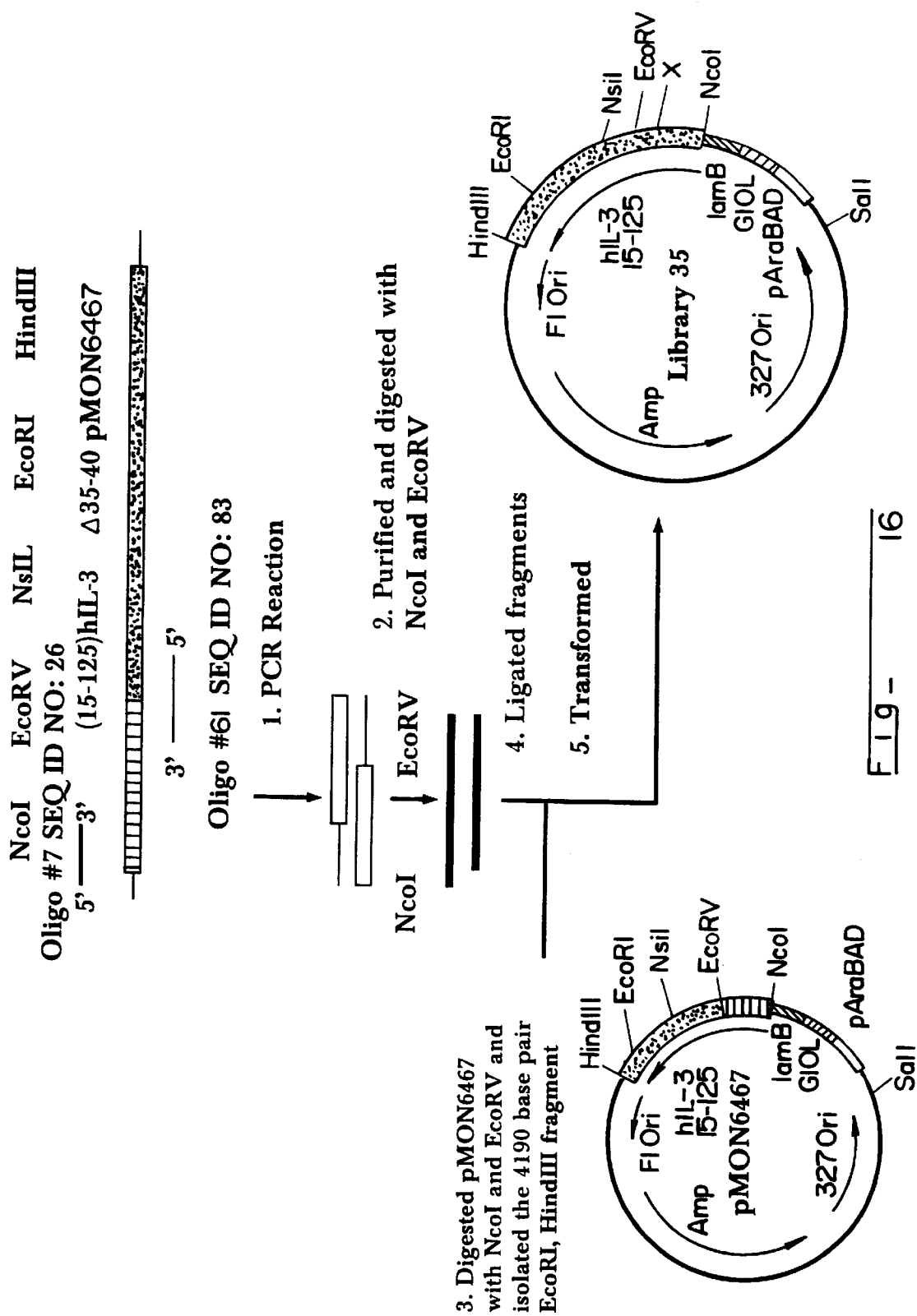
FIG—16

THERAPEUTIC METHODS EMPLOYING MUTANT HUMAN INTERLEUKIN-3 (IL-3) POLYPEPTIDES

This is a divisional of U.S. Ser. No. 08/411,796, filed Apr. 6, 1995, now U.S. Pat. No. 5,677,149, which was filed as international application PCT/US93/11198 on Nov. 22, 1993 and which entered the U.S. national stage under 35 U.S.C. § 371 on Apr. 06, 1995; and PCT/US93/11198 is a continuation-in-part of U.S. Ser. No. 07/981,044, filed Nov. 24, 1992 which is now abandoned.

FIELD OF THE INVENTION

The present invention relates to mutants or variants of human interleukin-3 (hIL-3) which contain one or more amino acid substitutions and which may have portions of the native hIL-3 molecule deleted. These hIL-3 single and multiple mutation polypeptides retain one or more activities of native hIL-3 and may also show improved hematopoietic cell-stimulating activity and/or an improved activity profile which may include reduction of undesirable biological activities associated with native hIL-3.

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, mega-karyocyte and pure and mixed erythroid colonies.

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 126:2184 (1981) as a factor which induced expression of a T cell associated enzyme, 20-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., NATURE 307:233 (1984) and Yokota, et al., PROC. NATL. ACAD. SCI. USA 81:1070 (1984)). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., GENE 55:115 (1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. No. 4,877,729 and U.S. Pat. No. 4,959,455 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231:134 (1986) performed a functional analysis of murine IL-3 analogues synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $Cys^{140}{\rightarrow}Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. NATL. ACAD. SCI. USA 85:7897 (1988)).

International Patent Application (PCT) WO 88/00598 discloses gibbon- and human-like IL-3. The hIL-3 contains a $Ser^8{\rightarrow}Pro^8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1{\rightarrow}Asp^1$, $Trp^{13}{\rightarrow}Arg^{13}$ (pGB/IL-302) and $Ala^1{\rightarrow}Asp^1$, $Met^3{\rightarrow}Thr^3$ (pGB/IL-304) and one triple mutant $Ala^1{\rightarrow}Asp^1$, $Leu^9{\rightarrow}Pro^9$, $Trp^{13}{\rightarrow}Arg^{13}$ (pGB/IL-303).

WO 88/05469 describes how deglycosylation mutants can be obtained and suggests mutants of $Arg^{54}Arg^{55}$ and $Arg^{108}Arg^{109}Lys^{110}$ might avoid proteolysis upon expression in Saccharomyces cerevisiae by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral.

The only actually performed mutations are Met$^2$→Ile$^2$ and Ile$^{131}$→Leu$^{131}$. It is not disclosed whether the contemplated neutralities were obtained for these two mutations.

WO 91/00350 discloses nonglycosylated hIL-3 analog proteins, for example, hIL-3 (Pro$^8$Asp$^{15}$Asp$^{70}$), Met$^3$ rhuI-3 (Pro$^8$Asp$^{15}$Asp$^{70}$); Thr$^4$ rhuL-3 (Pro$^8$Asp$^{15}$Asp$^{70}$)and Thr$^6$ rhuIL-3 (Pro$^8$Asp$^{15}$Asp$^{70}$). It is said that these protein compositions do not exhibit certain adverse side effects associated with native hIL-3 such as urticaria resulting from infiltration of mast cells and lymphocytes into the dermis. The disclosed analog hIL-3 proteins may have N termini at Met$^3$, Thr$^4$, or Thr$^6$.

WO 90/12874 discloses cysteine added variants (CAVs) of IL-3 which have at least one Cys residue substituted for a naturally occurring amino acid residue.

SUMMARY OF THE INVENTION

The present invention relates to recombinant human interleukin-3 (hIL-3) variant or mutant proteins (muteins). These hIL-3 muteins contain amino acid substitutions and may also have amino acid deletions at either/or both the N- and C-termini. Preferably, these mutant polypeptides of the present invention contain one to three amino acids which differ from the amino acids found at the corresponding positions in the native hIL-3 polypeptide. The invention also relates to pharmaceutical compositions containing the hIL-3 muteins, DNA coding for the muteins, and methods for using the muteins. Additionally, the present invention relates to recombinant expression vectors comprising nucleotide sequences encoding the hIL-3 muteins, related microbial expression systems, and processes for making the hIL-3 muteins using the microbial expression systems.

The present invention includes mutants of hIL-3 in which from 1 to 14 amino acids have been deleted from the N-terminus and/or from 1 to 15 amino acids have been deleted from the C-terminus, and in which from one to three amino acid substitutions have been made. Preferred muteins of the present invention are those in which amino acids 1 to 14 have been deleted from the N-terminus, or amino acids 126 to 133 have been deleted from the C-terminus, and which both also contain from one to three amino acid substitutions in the polypeptide sequence. These hIL-3 multiple mutation polypeptides may have biological activities similar to or better than hIL-3 and, in some cases, may also have an improved side effect profile, i.e., some muteins may have a better therapeutic index than native hIL-3. The present invention also provides muteins which may function as IL-3 antagonists or as discrete antigenic fragments for the production of antibodies useful in immunoassay and immunotherapy protocols. In addition to the use of the hIL-3 mutant polypeptides of the present invention in vivo, it is envisioned that in vitro uses would include the ability to stimulate bone marrow and blood cell activation and growth before infusion into patients.

Antagonists of hIL-3 would be particularly useful in blocking the growth of certain cancer cells like AML, CML and certain types of B lymphoid cancers. Other conditions where antagonists would be useful include those in which certain blood cells are produced at abnormally high numbers or are being activated by endogenous ligands. Antagonists would effectively compete for ligands, presumably naturally occurring hemopoietins including and not limited to IL-3, GM-CSF and IL-5, which might trigger or augment the growth of cancer cells by virtue of their ability to bind to the IL-3 receptor complex while intrinsic activation properties of the ligand are diminished. IL-3, GM-CSF and or IL-5 also play a role in certain asthmatic responses. An antagonist of the IL-3 receptor may have utility in this disease by blocking receptor-mediated activation and recruitment of inflammatory cells.

BRIEF DESCRIPTION OF THE DRAWINGS

FIG. 1 is the human IL-3 gene for *E. coli* expression (pMON5873), encoding the polypeptide sequence of natural (wild type) human IL-3 [SEQ ID NO:128], plus an initiator methionine, as expressed in *E. coli*, with the amino acids numbered from the N-terminus of the natural hIL-3.

FIG. 2: ClaI to NsiI Replacement Fragment. FIG. 2 shows the nucleotide sequence of the replacement fragment used between the ClaI and NsiI sites of the hIL-3 gene. The codon choice used in the fragment corresponds to that found in highly expressed *E. coli* genes (Gouy and Gautier, 1982). Three new unique restriction sites, EcoRV, XhoI and PstI were introduced for the purpose of inserting synthetic gene fragments. The portion of the coding sequence shown encodes hIL-3 amino acids 20–70.

FIGS. 3 and 4 show the nucleotide and amino acid sequence of the gene in pMON5873 with the sequence extending from NcoI through HindIII. The codon choices used to encode amino acids 1–14 and 107–133 correspond to that found in highly expressed *E. coli* genes.

FIG. 7 shows the construction of plasmid vector pMON5853 which encodes [Met-(15–133) hIL-3 (Arg$^{129}$)].

FIG. 9 shows the DNA sequence and resulting amino acid sequence of the lamB signal peptide.

FIG. 16 shows the construction of single amino acid substitutions at position 35 of hIL-3 using site-directed PCR mutagenesis methods. The mutagenesis results in 20 different single amino substitutions, which is referred to as a "library", at position 35 of hIL-3.

DETAILED DESCRIPTION OF THE INVENTION

Figure 5:
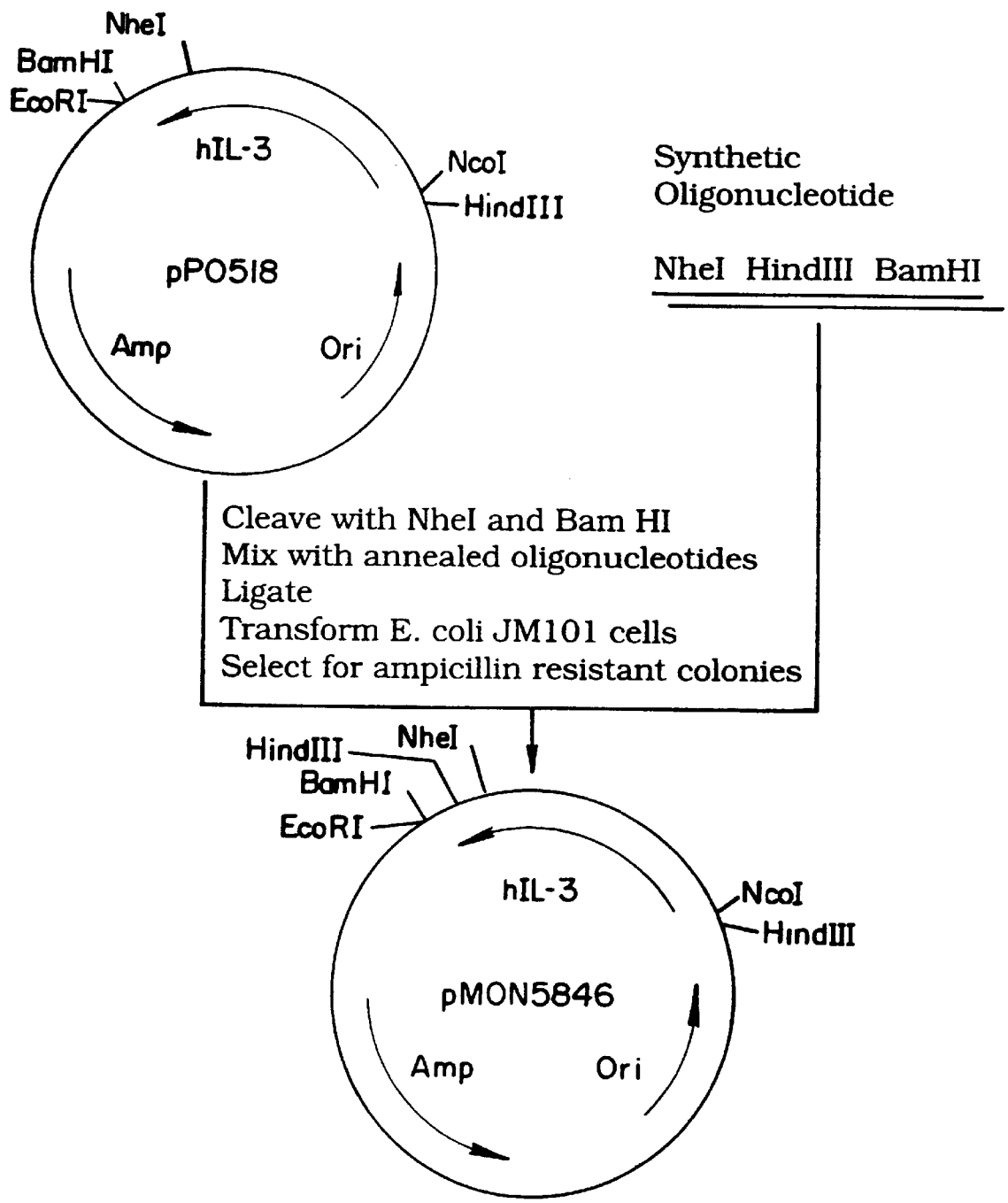
FIG. 5 shows the construction of the plasmid vector pMON5846 which encodes [Met-(1–133) hIL-3 (Arg$^{129}$)].
Figure 6:
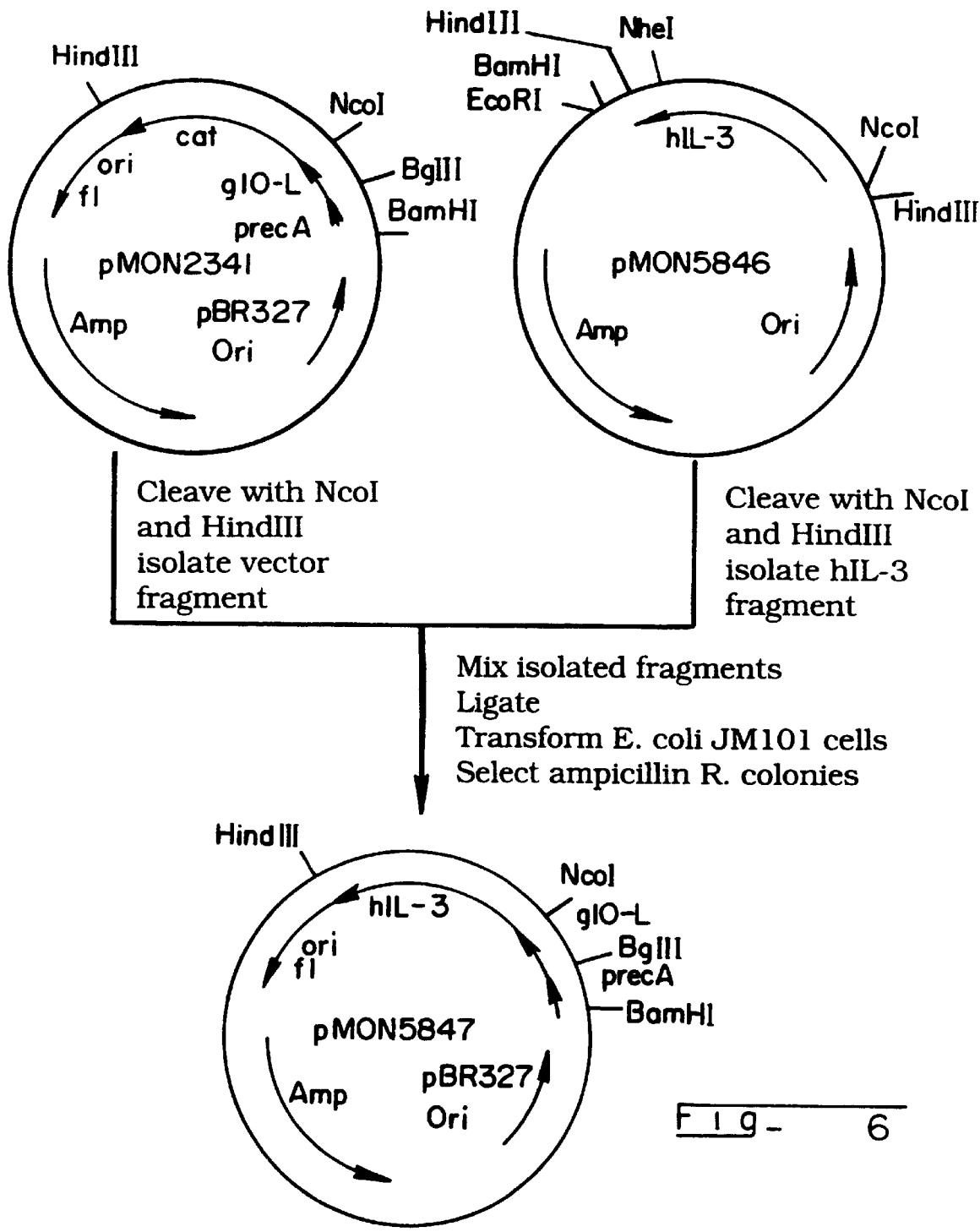
FIG. 6 shows the construction of the plasmid vector pMON5847 (ATCC 68912) which encodes [Met-(1–133) IL-3 (Arg$^{129}$)].

The present invention relates to muteins of human interleukin-3 (hIL-3) in which amino acid substitutions have been made at from one to three positions in the amino acid sequence of the polypeptide and to hIL-3 muteins which have substantially the same structure and substantially the same biological activity. Preferred muteins of the present invention are (15–125)hIL-3 deletion mutants which have deletions of amino acids 1 to 14 at the N-terminus and/or 126 to 133 at the C-terminus and which both also have from one to three amino acid substitutions in the polypeptide and muteins having substantially the same structure and substantially the same biological activity. As used herein human interleukin-3 corresponds to the amino acid sequence antagonists or as antigenic fragments for the production of antibodies useful in immunoassay and immunotherapy protocols.

The mutant hIL-3 polypeptides of the present invention may also have methionine, alanine, or methionine-alanine residues inserted at the N-terminus.

The present invention includes hIL-3 mutant polypeptides of the formula I:

```
Ala Pro Met Thr Gln Thr Thr Ser Leu Lys Thr Ser Trp Val Asn [SEQ ID NO:15]
 1           5                   10                   15

Cys Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Asn Xaa Xaa Xaa Xaa Xaa
             35                  40                  45

Xaa Xaa Xaa Xaa Xaa Xaa Xaa Xaa Xaa Xaa Xaa Xaa Xaa Xaa
             50                  55                  60

Xaa Xaa Xaa Xaa Xaa Xaa Xaa Xaa Xaa Xaa Xaa Xaa Xaa Xaa
             65                  70                  75

Xaa Xaa Xaa Xaa Xaa Xaa Xaa Xaa Xaa Xaa Xaa Xaa Xaa Xaa
             80                  85                  90

Xaa Xaa Xaa Xaa Xaa Xaa Xaa Xaa Xaa Xaa Xaa Xaa Xaa Xaa
             95                 100                 105

Xaa Phe Xaa Xaa Xaa Xaa Xaa Xaa Xaa Xaa Xaa Xaa Xaa Xaa
            110                 115                 120

Xaa Xaa Xaa Gln Gln Thr Thr Leu Ser Leu Ala Ile Phe
            125                 130
```

(1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

The present invention also includes the DNA sequences which code for the mutant polypeptides, DNA sequences which are substantially similar and perform substantially the same function, and DNA sequences which differ from the DNAs encoding the muteins of the invention only due to the degeneracy of the genetic code.

Included in the present invention are novel mutant human interleukin-3 polypeptides comprising a polypeptide having the amino acid sequence of native human interleukin-3 wherein amino acids 126 to 133 have been deleted from the C-terminus of the native human interleukin-3 polypeptide and amino acids 1 to 14 have been deleted from the N-terminus of the native human interleukin-3 polypeptide and, in addition, polypeptides of the present invention also have one to three amino acid substitutions in the polypeptide sequence. The muteins of the present invention can have from one to three amino acid substitutions in the hIL-3 polypeptide chain and, in addition, can have deletions of amino acids at the N-terminus and/or the C-terminus.

Also included in the present invention are the DNA sequences coding for the muteins of the present invention; the oligonucleotide intermediates used to construct the mutant DNAs; and the polypeptides coded for by these oligonucleotides. These polypeptides may be useful as wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp, Pro, Met, Lys, His, Thr, Val, Tyr, Glu, Asn, Ser, Ala, Gly, Ile, Leu, or Gln;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from one to three of the amino acids designated by Xaa are different from the corresponding amino acids of native (1–133) human interleukin-3 with the proviso that when Xaa at position 22 is Leu, and/or Xaa at position 34 is Gly or Glu, and/or Xaa at position 44 is Ala, and/or Xaa at position 46 is Lys or Ala, and/or Xaa at position 50 is Lys, and/or Xaa at position 59 is Pro or Arg, and/or Xaa at position 63 is Lys, and/or Xaa at position 75 is Gly or Arg, and/or Xaa at position 94 is Pro, and/or Xaa at position 98 is Arg, and/or Xaa at position 106 is Lys, and/or Xaa at position 110 is Ala or Glu, and/or Xaa at position 111 is Met, then there must be at least one additional substitution besides the ones indicated.

Included in the present invention are (1–133)hIL-3 mutant polypeptides of the Formula II:

```
Ala Pro Met Thr Gln Thr Thr Ser Leu Lys Thr Ser Trp Val Asn [SEQ ID NO:16]
 1           5                  10                      15

Cys Xaa Xaa Xaa Xaa Xaa Glu Xaa Xaa Xaa Xaa Leu Xaa Xaa Xaa
             20                  25                      30

Xaa Xaa Xaa Xaa Xaa Xaa Xaa Xaa Asn Leu Xaa Xaa Glu Xaa Xaa
             35                  40                      45

Xaa Xaa Leu Xaa Xaa Xaa Xaa Xaa Xaa Xaa Xaa Asn Leu Xaa Xaa
             50                  55                      60

Xaa Xaa Xaa Xaa Xaa Xaa Xaa Xaa Xaa Xaa Xaa Xaa Xaa Xaa Xaa
             65                  70                      75

Xaa Xaa Leu Xaa Xaa Xaa Xaa Xaa Cys Xaa Pro Xaa Xaa Xaa Xaa
             80                  85                      90

Xaa Xaa Xaa Arg Xaa Xaa Xaa Xaa Xaa Xaa Xaa Asp Xaa Xaa
             95                  100                     105

Xaa Phe Xaa Xaa Lys Leu Xaa Phe Xaa Xaa Xaa Xaa Leu Xaa Xaa
             110                 115                     120

Xaa Xaa Xaa Gln Gln Thr Thr Leu Ser Leu Ala Ile Phe
             125                 130
``` wherein
Xaa at position 17 is Ser, Gly, Asp, Met, or Gln;
Xaa at position 18 is Asn, His, Leu, Ile, Phe, Arg, or Gln;
Xaa at position 19 is Met, Phe, Ile, Arg, or Ala;
Xaa at position 20 is Ile or Pro;
Xaa at position 21 is Asp or Glu;
Xaa at position 23 is Ile, Val, Ala, Leu, or Gly;
Xaa at position 24 is Ile, Val, Phe, or Leu;
Xaa at position 25 is Thr, His, Gly, Gln, Arg, Pro, or Ala;
Xaa at position 26 is His, Phe, Gly, Arg, or Ala;
Xaa at position 28 is Lys, Leu, Gln, Gly, Pro, or Val;
Xaa at position 29 is Gln, Asn, Leu, Arg, or Val;
Xaa at position 30 is Pro, His, Thr, Gly, or Gln;
Xaa at position 31 is Pro, Asp, Gly, Ala, Arg, Leu, or Gln;
Xaa at position 32 is Leu, Arg, Gln, Asn, Gly, Ala, or Glu;
Xaa at position 33 is Pro, Leu, Gln, Ala, or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 36 is Asp or Leu;
Xaa at position 37 is Phe, Ser, Pro, Trp, or Ile;
Xaa at position 38 is Asn or Ala;
Xaa at position 41 is Asn, Cys, Arg, His, Met, or Pro;
Xaa at position 42 is Gly, Asp, Ser, Cys, Ala, Asn, Ile, Leu, Met, Tyr, Val or Arg;
Xaa at position 44 is Asp or Glu;
Xaa at position 45 is Gln, Val, Met, Leu, Thr, Lys, Ala, Asn, Glu, Ser, or Trp;
Xaa at position 46 is Asp, Phe, Ser, Thr, Cys, Ala, Asn, Gln, Glu, His, Ile, Lys, Tyr, Val or Gly;
Xaa at position 47 is Ile, Val, or His;
Xaa at position 49 is Met, Asn, or Asp;
Xaa at position 50 is Glu, Thr, Ala, Asn, Ser or Asp;
Xaa at position 51 is Asn, Arg, Met, Pro, Ser, Thr, or His;
Xaa at position 52 is Asn or Gly;
Xaa at position 53 is Leu, Met, or Phe;
Xaa at position 54 is Arg, Ala, or Ser;
Xaa at position 55 is Arg, Thr, Val, Leu, or Gly;
Xaa at position 56 is Pro, Gly, Cys, Ser, Gln, Ala, Arg, Asn, Glu, His, Leu, Thr, Val or Lys;
Xaa at position 59 is Glu, Tyr, His, Leu, or Arg;
Xaa at position 60 is Ala, Ser, Asn, or Thr;
Xaa at position 61 is Phe or Ser;
Xaa at position 62 is Asn, Val, Pro, Thr, or Ile;
Xaa at position 63 is Arg, Tyr, Lys, Ser, His, or Val;
Xaa at position 64 is Ala or Asn;

Xaa at position 65 is Val, Thr, Leu, or Ser;
Xaa at position 66 is Lys, Ile, Arg, Val, Asn, Glu, or Ser;
Xaa at position 67 is Ser, Phe, Val, Gly, Asn, Ile, or His;
Xaa at position 68 is Leu, Val, Ile, Phe, or His;
Xaa at position 69 is Gln, Ala, Pro, Thr, Glu, Arg, or Gly;
Xaa at position 70 is Asn or Pro;
Xaa at position 71 is Ala, Met, Pro, Arg, Glu, Thr, or Gln;
Xaa at position 72 is Ser, Glu, Met, Ala, His, Asn, Arg, or Asp;
Xaa at position 73 is Ala, Glu, Asp, Leu, Ser, Gly, Thr, Arg, or Pro;
Xaa at position 74 is Ile or Met;
Xaa at position 75 is Glu, Gly, Asp, Ser, or Gln;
Xaa at position 76 is Ser, Val, Ala, Asn, Glu, Pro, Gly, or Asp;
Xaa at position 77 is Ile, Ser, or Leu;
Xaa at position 79 is Lys, Thr, Asn, Met, Arg, Ile, Gly, or Asp;
Xaa at position 80 is Asn, Val, Gly, Thr, Leu, Glu, or Arg;
Xaa at position 81 is Leu, or Val;
Xaa at position 82 is Leu, Gln, Trp, Arg, Asp, Ala, Asn, Glu, His, Met, Phe, Ser, Thr, Tyr or wherein Xaa at position 17 is Ser, Gly, Asp, Met, or Gln;
Xaa at position 18 is Asn, His, or Ile;
Xaa at position 19 is Mot or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Asn, Met, Arg, Ile, Gly, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Arg, Gln, Leu, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp, Pro, Met, Lys, His, Thr, Pro, Asn, Ile, Leu or Tyr;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys, Thr, Val, Trp, Ser, Ala, His, Met, Phe, Tyr or Ile;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

and which can additionally have Met- preceding the amino acid in position 1; and wherein from 1 to 14 amino acids can be deleted from the N-terminus and/or from 1 to 15 amino acids can be deleted from the C-terminus; and wherein from one to three of the amino acids designated by Xaa are different from the corresponding amino acids of native (1–133) human interleukin-3 with the proviso that when Xaa at position 22 is Leu, and/or Xaa at position 34 is Gly or Glu, and/or Xaa at position 44 is Ala, and/or Xaa at position 46 is Lys or Ala, and/or Xaa at position 50 is Lys, and/or Xaa at position 59 is Pro or Arg, and/or Xaa at position 63 is Lys, and/or Xaa at position 75 is Gly or Arg, and/or Xaa at position 94 is Pro, and/or Xaa at position 98 is Arg, and/or Xaa at position 106 is Lys, and/or Xaa at position 110 is Ala or Glu, and/or Xaa at position 111 is Met, then there must be at least one additional substitution besides the ones indicated, and which can additionally have Met- preceding the amino acid in position 1; and wherein from 1 to 14 amino acids can be deleted from the N-terminus and/or from 1 to 15 amino acids can be deleted from the C-terminus; and wherein from one to three of the amino acids designated by Xaa are different from the corresponding amino acids of native (1–133)human interleukin-3 with the proviso that when Xaa at position 34 is Gly and/or Xaa at position 46 is Lys or Ala, and/or Xaa at position 63 is Lys, and/or Xaa at position 98 is Arg, then two or three of the amino acid designated by Xaa are different from the corresponding amino acids of the native (1–133) human interleukin-3.

Included in the present invention are (1–133)hIL-3 mutant polypeptides of the Formula IV:

```
Ala Pro Met Thr Gln Thr Thr Ser Leu-
  Lys Thr Ser Trp Val Asn
1             5                  10                     15

C

```
Asn Cys Xaa Xaa Xaa Xaa Xaa Xaa Xaa Xaa Xaa Xaa Xaa Xaa Xaa [SEQ ID NO:19]
1           5                   10                  15

Xaa Xaa Xaa Xaa Xaa Xaa Xaa Xaa Asn Xaa Xaa Xaa Xaa Xaa
                20                  25                  30

Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa
                50                  55                  60

Xaa Xaa Xaa Xaa Xaa Xaa Xaa Xaa Xaa Xaa Xaa Xaa Xaa Xaa
                65                  70                  75

Xaa Xaa Xaa Xaa Xaa Xaa Xaa Xaa Xaa Xaa Xaa Xaa Xaa Xaa
                80                  85                  90

Xaa Xaa Phe Xaa Xaa Xaa Xaa Xaa Xaa Xaa Xaa Xaa Xaa Xaa
                95                  100                 105

Xaa Xaa Xaa Xaa Gln Gln
                110
``` wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, Met, or;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp, Pro, Met, Lys, His, Thr, Val, Tyr, Glu, Asn, Ser, Ala, Gly, Ile, Leu or Gln;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys, Leu, Pro, Thr, Met, Asp, Val, Glu, Arg, Trp, Ser, Asn, His, Ala, Tyr, Phe, Gln, or Ile;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

and which can additionally have Met- or Met-Ala- preceding the amino acid in position 1; and wherein from one to three of the amino acids designated by Xaa are different from the corresponding native amino acids of (1–133) human interleukin-3; or a polypeptide having substantially the same structure and substantially the same biological activity.

Included in the present invention are (15–125)hIL-3 mutant polypeptides of the Formula VI:

```
Asn Cys Xaa Xaa Xaa Xaa Xaa Glu Xaa Xaa Xaa Xaa Leu Xaa Xaa  [SEQ ID NO:20]
 1           5                  10                  15

Xaa Xaa Xaa Xaa Xaa Xaa Xaa Xaa Xaa Asn Leu Xaa Xaa Glu Xaa
             20                  25                  30

Xaa Xaa Xaa Leu Xaa Xaa Xaa Xaa Xaa Xaa Xaa Asn Leu Xaa
             35                  40                  45

Xaa Xaa Xaa Xaa Xaa Xaa Xaa Xaa Xaa Xaa Xaa Xaa Xaa Xaa Xaa
             50                  55                  60

Xaa Xaa Xaa Leu Xaa Xaa Xaa Xaa Xaa Cys Xaa Pro Xaa Xaa Xaa
             65                  70                  75

Xaa Xaa Xaa Xaa Arg Xaa Xaa Xaa Xaa Xaa Xaa Xaa Asp Xaa
             80                  85                  90
```

```
Xaa Xaa Phe Xaa Xaa Lys Leu Xaa Phe Xaa Xaa Xaa Xaa Leu Xaa
            95              100                 105
Xaa Xaa Xaa Xaa Gln Gln
            110
``` wherein

Xaa at position 3 is Ser, Gly, Asp, Met, or Gln;
Xaa at position 4 is Asn, His, Leu, Ile, Phe, Arg, or Gln;
Xaa at position 5 is Met, Phe, Ile, Arg, or Ala;
Xaa at position 6 is Ile or Pro;
Xaa at position 7 is Asp, or Glu;
Xaa at position 9 is Ile, Val, Ala, Leu, or Gly;
Xaa at position 10 is Ile, Val, Phe, or Leu;
Xaa at position 11 is Thr, His, Gly, Gln, Arg, Pro, or Ala;
Xaa at position 12 is His, Phe, Gly, Arg, or Ala;
Xaa at position 14 is Lys, Leu, Gln, Gly, Pro, or Val;
Xaa at position 15 is Gln, Asn, Leu, Arg, or Val;
Xaa at position 16 is Pro, His, Thr, Gly, or Gln;
Xaa at position 17 is Pro, Asp, Gly, Ala, Arg, Leu, or Gln;
Xaa at position 18 is Leu, Arg, Gln, Asn, Gly, Ala, or Glu;
Xaa at position 19 is Pro, Leu, Gln, Ala, or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 22 is Asp or Leu;
Xaa at position 23 is Phe, Ser, Pro, Trp, or Ile;
Xaa at position 24 is Asn or Ala;
Xaa at position 27 is Asn, Cys, Arg, His, Met, or Pro;
Xaa at position 28 is Gly, Asp, Ser, Cys, Ala, Asn, Ile, Leu, Met, Tyr, or Arg;
Xaa at position 30 is Asp, or Glu;
Xaa at position 31 is Gln, Val, Met, Leu, Thr, Lys, Ala, Asn Glu, Ser or Trp;
Xaa at position 32 is Asp, Phe, Ser, Thr, Cys, Ala, Asn, Gln, Glu, His, Ile, Lys, Tyr, Val or Gly;
Xaa at position 33 is Ile, Val, or His;
Xaa at position 35 is Met, Asn, or Asp;
Xaa at position 36 is Glu, Thr, Ala, Asn, Ser or Asp;
Xaa at position 37 is Asn, Arg, Met, Pro, Ser, Thr, or His;
Xaa at position 38 is Asn or Gly;
Xaa at position 39 is Leu, Met, or Phe;
Xaa at position 40 is Arg, Ala or Ser;
Xaa at position 41 is Arg, Thr, Val, Leu, or Gly;
Xaa at position 42 is Pro, Gly, Cys, Ser, Gln, Ala, Arg, Asn, Glu, His, Leu, Thr, Val or Lys;
Xaa at position 45 is Glu, Tyr, His, Leu, or Arg;
Xaa at position 46 is Ala, Ser, Asn, or Thr;
Xaa at position 47 is Phe or Ser;
Xaa at position 48 is Asn, Val, Pro, Thr, or Ile;
Xaa at position 49 is Arg, Tyr, Lys, Ser, His, or Val;
Xaa at position 50 is Ala or Asn;
Xaa at position 51 is Val, Thr, Leu, or Ser;
Xaa at position 52 is Lys, Ile, Arg, Val, Asn, Glu, or Ser;
Xaa at position 53 is Ser, Phe, Val, Gly, Asn, Ile, or His;
Xaa at position 54 is Leu, Val, Ile, Phe, or His;
Xaa at position 55 is Gln, Ala, Pro, Thr, Glu, Arg, or Gly;
Xaa at position 56 is Asn or Pro;
Xaa at position 57 is Ala, Met, Pro, Arg, Glu, Thr, or Gln;
Xaa at position 58 is Ser, Glu, Met, Ala, His, Asn, Arg, or Asp;
Xaa at position 59 is Ala, Glu, Asp, Leu, Ser, Gly, Thr, Arg, or Pro;
Xaa at position 60 is Ile or Met;
Xaa at position 61 is Glu, Gly, Asp, Ser, or Gln;
Xaa at position 62 is Ser, Val, Ala, Asn, Glu, Pro, Gly, or Asp;
Xaa at position 63 is Ile, Ser, or Leu;
Xaa at position 65 is Lys, Thr, Gly, Asn, Met, Arg, Ile, or Asp;
Xaa at position 66 is Asn, Val, Gly, Thr, Leu, Glu, or Arg;
Xaa at position 67 is Leu, or Val;
Xaa at position 68 is Leu, Gln, Trp, Arg, Asp, Ala, Asn, Glu, His, Met, Phe, Ser, Thr, Tyr or Val;
Xaa at position 69 is Pro, Ala, Thr, Trp, or Met;
Xaa at position 71 is Leu or Val;
Xaa at position 73 is Leu or Ser;
Xaa at position 74 is Ala, Arg, or Trp;
Xaa at position 75 is Thr, Asp, Glu, His, Asn, or Ser;
Xaa at position 76 is Ala, Asp, or Met;
Xaa at position 77 is Ala, Pro, Ser, Thr, Phe, Leu, or Asp;
Xaa at position 78 is Pro or Ser;
Xaa at position 79 is Thr, Asp, Ser, Pro, Ala, Leu, or Arg;
Xaa at position 81 is His, Pro, Arg, Val, Leu, Gly, Asn, Ile, Phe, Ser or Thr;
Xaa at position 82 is Pro or Tyr;
Xaa at position 83 is Ile, Val, or Ala;
Xaa at position 84 is His, Ile, Asn, Leu, Asp, Ala, Thr, Arg, Gln, Glu, Lys, Met, Ser, Tyr, Val or Pro;
Xaa at position 85 is Ile, Leu, Val, or Phe;
Xaa at position 86 is Lys, Leu, His, Arg, Ile, Gln, Pro or Ser;
Xaa at position 87 is Asp, Pro, Met, Lys, His, Thr, Val, Asn, Ile, Leu or Tyr;
Xaa at position 88 is Gly, Glu, Lys, or Ser;
Xaa at position 90 is Trp, Val, Tyr, Met, or Leu;
Xaa at position 91 is Asn, Pro, Ala, Phe, Ser, Trp, Gln, Tyr, Leu, Lys, Ile, Asp, or His;
Xaa at position 92 is Glu, Ser, Ala, or Gly;
Xaa at position 94 is Arg, Ala, Gln, Ser or Lys;
Xaa at position 95 is Arg, Thr, Glu, Leu, Ser, or Gly;
Xaa at position 98 is Thr, Val, Gln, Glu, His, or Ser;
Xaa at position 100 is Tyr or Trp;
Xaa at position 101 is Leu or Ala;
Xaa at position 102 is Lys, Thr, Met, Val, Trp, Ser, Leu, Ala, Asn, Gln, His, Met, Phe, Tyr or Ile;
Xaa at position 103 is Thr, Ser, or Asn;
Xaa at position 105 is Glu, Ser, Pro, Leu, Thr, or Tyr;
Xaa at position 106 is Asn, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

and which can additionally have Met- or Met-Ala- preceding the amino acid in position 1; and wherein from one to three of the amino acids designated by Xaa are different from the corresponding amino acids of native (1–133) human interleukin-3; or a polypeptide having substantially the same structure and substantially the same biological activity.

Included in the present invention are (15–125)hIL-3 mutant polypeptides of the Formula VII:

```
Asn Cys Xaa Xaa Xaa Ile Xaa Glu Xaa Xaa Xaa Xaa Leu Lys Xaa  [SEQ ID NO:21]
 1           5               10                      15

Xaa Xaa Xaa Xaa Xaa Xaa Asp Xaa Xaa Asn Leu Asn Xaa Glu Xaa
            20                  25                      30

Xaa Xaa Ile Leu Met Xaa Xaa Asn Leu Xaa Xaa Xaa Asn Leu Glu
                35              40                      45

Xaa Phe Xaa Xaa Xaa Xaa Xaa Xaa Xaa Asn Xaa Xaa Xaa Xaa Ile
                50                  55                      60

Glu Xaa Xaa Leu Xaa Xaa Leu Xaa Xaa Cys Xaa Pro Xaa Xaa Thr
                65                  70                      75

Ala Xaa Pro Xaa Arg Xaa Xaa Xaa Xaa Xaa Xaa Gly Asp Xaa
                80                  85                      90

Xaa Xaa Phe Xaa Xaa Lys Leu Xaa Phe Xaa Xaa Xaa Xaa Leu Glu
                95                  100                     105

Xaa Xaa Xaa Xaa Gln Gln
                110
``` wherein

Xaa at position 3 is Ser, Gly, Asp, Met, or Gln;

Xaa at position 4 is Asn, His, or Ile;

Xaa at position 5 is Met or Ile;

Xaa at position 7 is Asp or Glu;

Xaa at position 9 is Ile, Ala, Leu, or Gly;

Xaa at position 10 is Ile, Val, or Leu;

Xaa at position 11 is Thr, His, Gln, or Ala;

Xaa at position 12 is His or Ala;

Xaa at position 15 is Gln, Asn, or Val;

Xaa at position 16 is Pro, Gly, or Gln;

Xaa at position 17 is Pro, Asp, Gly, or Gln;

Xaa at position 18 is Leu, Arg, Gln, Asn, Gly, Ala, or Glu;

Xaa at position 19 is Pro or Glu;

Xaa at position 20 is Leu, Val, Gly, Ser, Lys, Ala, Arg, Gln, Glu, Ile, Phe, Thr or Met;

Xaa at position 21 is Leu, Ala, Asn, Pro, Gln, or Val;

Xaa at position 23 is Phe, Ser, Pro, or Trp;

Xaa at position 24 is Asn or Ala;

Xaa at position 28 is Gly, Asp, Ser, Cys, Ala, Asn, Ile, Leu, Met Tyr or Arg;

Xaa at position 30 is Asp or Glu;

Xaa at position 31 is Gln, Val, Met, Leu, Thr, Ala, Asn, Glu, Ser or Lys;

Xaa at position 32 is Asp, Phe, Ser, Thr, Ala, Asn, Gln, Glu, His, Ile, Lys, Tyr, Val or Cys;

Xaa at position 36 is Glu, Ala, Asn, Ser or Asp;

Xaa at position 37 is Asn, Arg, Met, Pro, Ser, Thr, or His;

Xaa at position 40 is Arg or Ala;

Xaa at position 41 is Arg, Thr, Val, Leu, or Gly;

Xaa at position 42 is Pro, Gly, Ser, Gln, Ala, Arg, Asn, Glu, Leu, Thr, Val or Lys;

Xaa at position 46 is Ala or Ser;

Xaa at position 48 is Asn, Pro, Thr, or Ile;

Xaa at position 49 is Arg or Lys;

Xaa at position 50 is Ala or Asn;

Xaa at position 51 is Val or Thr;

Xaa at position 52 is Lys or Arg;

Xaa at position 53 is Ser, Phe, or His;

Xaa at position 54 is Leu, Ile, Phe, or His;

Xaa at position 55 is Gln, Ala, Pro, Thr, Glu, Arg, or Gly;

Xaa at position 57 is Ala, Pro, or Arg;

Xaa at position 58 is Ser, Glu, Arg, or Asp;

Xaa at position 59 is Ala or Leu;

Xaa at position 62 is Ser, Val, Ala, Asn, Glu, Pro, or Gly;

Xaa at position 63 is Ile or Leu;

Xaa at position 65 is Lys, Thr, Asn, Met, Arg, Ile, Gly, or Asp;

Xaa at position 66 is Asn, Gly, Glu, or Arg;

Xaa at position 68 is Leu, Gln, Trp, Arg, Asp, Ala, Asn, Glu, His, Ile, Met, Phe, Ser, Thr, Tyr or Val;

Xaa at position 69 is Pro or Thr;

Xaa at position 71 is Leu or Val;

Xaa at position 73 is Leu or Ser;

Xaa at position 74 is Ala or Trp;

Xaa at position 77 is Ala or Pro;

Xaa at position 79 is Thr, Asp, Ser, Pro, Ala, Leu, or Arg;

Xaa at position 81 is His, Pro, Arg, Val, Leu, Gly, Asn, Phe, Ser or Thr;

Xaa at position 82 is Pro or Tyr;

Xaa at position 83 is Ile or Val;

Xaa at position 84 is His, Ile, Asn, Leu, Ala, Thr, Arg, Gln, Lys, Met, Ser, Tyr, Val or Pro;

Xaa at position 85 is Ile, Leu, or Val;

Xaa at position 86 is Lys, Arg, Ile, Gln, Pro, or Ser;

Xaa at position 87 is Asp, Pro, Met, Lys, His, Thr, Asn, Ile, Leu or Tyr;

Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys, Thr, Val, Trp, Ser, Ala, His, Met, Phe, Tyr or Ile;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

which can additionally have Met- or Met-Ala- preceding the amino acid in position 1; and wherein from one to three of the amino acids designated by Xaa are different from the corresponding amino acids of native (15–125) human interleukin-3; or a polypeptide having substantially the same structure and substantially the same biological activity.

Included in the present invention are (15–125)hIL-3 mutant polypeptides of the Formula VIII:

```
Asn Cys Xaa Xaa Met Ile Asp Glu Xaa Ile Xaa Xaa Leu Lys Xaa    [SEQ ID NO:22]
 1           5                    10                  15

Xaa Pro Xaa Pro Xaa Xaa Asp Phe Xaa Asn Leu Asn Xaa Glu Asp
            20                  25                  30

Xaa Xaa Ile Leu Met Xaa Xaa Asn Leu Arg Xaa Xaa Asn Leu Glu
            35                  40                  45

Ala Phe Xaa Arg Xaa Xaa Lys Xaa Xaa Xaa Asn Ala Ser Ala Ile
            50                  55                  60

Glu Xaa Xaa Leu Xaa Xaa Leu Xaa Pro Cys Leu Pro Xaa Xaa Thr
            65                  70                  75

Ala Xaa Pro Xaa Arg Xaa Pro Ile Xaa Xaa Xaa Xaa Gly Asp Trp
            80                  85                  90

Xaa Glu Phe Xaa Xaa Lys Leu Xaa Phe Tyr Leu Xaa Xaa Leu Glu
            95                  100                 105

Xaa Xaa Xaa Xaa Gln Gln
            110
``` wherein
Xaa at position 3 is Ser, Gly, Asp, or Gln;
Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp, Pro, Met, Lys, His, Pro, Asn, Ile, Leu or Tyr;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys, Val, Trp, or Ile;
Xaa at position 103 is Thr, Ala, His, Phe, Tyr or Ser;
Xaa at position 106 is Asn, Pro, Leu, His, Val, or Gln;

Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
and which can additionally have Met- or Met-Ala- preceding the amino acid in position 1; and wherein from one to three of the amino acids designated by Xaa are different from the corresponding amino acids of native (1–133)human interleukin-3; or a polypeptide having substantially the same structure and substantially the same biological activity.

In Formulas V, VI, VII and VIII the Asn in position 1 corresponds to the Asn in position 15 of native hIL-3 and positions 1 to 111 correspond to positions 15 to 125 in the native hIL-3 sequence shown in FIG. 1.

Also included in the present invention are polypeptides of the following formula (IX):

[SEQ ID NO:129]

```
              1               5                  10
(Met)_m-Ala Pro Met Thr Gln Thr Thr Ser Leu Lys Thr
             15                  20
Ser Trp Val Asn Cys Ser Xaa Met Ile Asp Glu Ile Ile
 25                  30                  35
Xaa His Leu Lys Xaa Pro Pro Xaa Pro Leu Leu Asp Xaa
             40                  45                  50
Asn Asn Leu Asn Xaa Glu Asp Xaa Asp Ile Leu Met Glu
                 55                  60
Xaa Asn Leu Arg Xaa Pro Asn Leu Xaa Xaa Phe Xaa Arg
     65                  70                  75
Ala Val Lys Xaa Leu Xaa Asn Ala Ser Xaa Ile Glu Xaa
             80                  85
Ile Leu Xaa Asn Leu Xaa Pro Cys Leu Pro Xaa Ala Thr
 90                  95                  100
Ala Ala Pro Xaa Arg His Pro Ile Xaa Ile Lys Xaa Gly
         105                 110                 115
Asp Trp Xaa Glu Phe Arg Xaa Lys Leu Thr Phe Tyr Leu
                 120                 125
Xaa Thr Leu Glu Xaa Ala Gln Xaa Gln Gln Thr Thr Leu
     130
Ser Leu Ala Ile Phe
``` wherein m is 0 or 1; Xaa at position 18 is Asn or Ile; Xaa at position 25 is Thr or His; Xaa at position 29 is Gln, Arg, or Val; Xaa at position 32 is Leu, Ala, or Asn; Xaa at position 37 is Phe, Pro, or Ser; Xaa at position 42 is Glu, Ala, or Ser; Xaa at position 45 is Gln, Val, or Met; Xaa at position 51 is Asn or Arg; Xaa at position 55 is Arg, Leu, or Thr; Xaa at position 59 is Glu or Leu; Xaa at position 60 is Ala or Ser; Xaa at position 62 is Asn or Val; Xaa at position 67 is Ser, Asn, or His; Xaa at position 69 is Gln or Glu; Xaa at position 73 is Ala or Gly; Xaa at position 76 is Ser or Ala; Xaa at position 79 is Lys or Arg; Xaa at position 82 is Leu, Glu, or Val; Xaa at position 87 is Leu or Ser; Xaa at position 93 is Pro or Ser; Xaa at position 98 is His, Ile, or Thr; Xaa at position 101 is Asp or Ala; Xaa at position 105 is Asn or Glu; Xaa at position 109 is Arg or Glu; Xaa at position 116 is Lys or Val; Xaa at position 120 is Asn, Gln, or His; Xaa at position 123 is Ala or Glu; wherein from one to three of the amino acids designated by Xaa are different from the corresponding amino acids of native human interleukin-3; or a polypeptide having substantially the same structure and substantially the same biological activity.

Polypeptides of the present invention include those (15–125)hIL-3 muteins of the following formula (X):

[SEQ ID NO:130]

```
                  1                   5
(Met_m-Ala_n)_p-Asn Cys Ser Xaa Met Ile Asp Glu Ile
 10                  15                  20
Ile Xaa His Leu Lys Xaa Pro Pro Xaa Pro Leu Leu Asp
         25                  30                  35
Xaa Asn Asn Leu Asn Xaa Glu Asp Xaa Asp Ile Leu Met
                 40                  45
Glu Xaa Asn Leu Arg Xaa Pro Asn Leu Xaa Xaa Phe Xaa
     50                  55                  60
Arg Ala Val Lys Xaa Leu Xaa Asn Ala Ser Xaa Ile Glu
             65                  70
Xaa Ile Leu Xaa Asn Leu Xaa Pro Cys Leu Pro Xaa Ala
 75                  80                  85
Thr Ala Ala Pro Xaa Arg His Pro Ile Xaa Ile Lys Xaa
         90                  95                  100
Gly Asp Trp Xaa Glu Phe Arg Xaa Lys Leu Thr Phe Tyr
                 105                 110
Leu Xaa Thr Leu Glu Xaa Ala Gln Xaa Gln Gln
``` wherein m is 0 or 1; n is 0 or 1; p is 0 or 1; Xaa at position 4 is Asn or Ile; Xaa at position 11 is Thr or His; Xaa at position 15 is Gln, Arg, or Val; Xaa at position 18 is Leu, Ala, or Asn; Xaa at position 23 is Phe, Pro, or Ser; Xaa at position 28 is Glu, Ala, or Ser; Xaa at position 31 is Gln, Val, or Met; Xaa at position 37 is Asn or Arg; Xaa at position 41 is Arg, Leu, or Thr; Xaa at position 45 is Glu or Leu; Xaa at position 46 is Ala or Ser; Xaa at position 48 is Asn or Val; Xaa at position 53 is Ser, Asn, or His; Xaa at position 55 is Gln or Glu; Xaa at position 59 is Ala or Gly; Xaa at position 62 is Ser or Ala; Xaa at position 65 is Lys or Arg; Xaa at position 68 is Leu, Glu, or Val; Xaa at position 73 is Leu or Ser; Xaa at position 79 is Pro or Ser; Xaa at position 84 is His, Ile, or Thr; Xaa at position 87 is Asp or Ala; Xaa at position 91 is Asn or Glu; Xaa at position 95 is Arg or Glu; Xaa at position 102 is Lys or Val; Xaa at position 106 is Asn, Gln, or His; Xaa at position 109 is Ala or Glu;
wherein from one to three of the amino acids designated by Xaa are different from the corresponding amino acids of native (15–125)human interleukin-3; or a polypeptide having substantially the same structure and substantially the same biological activity.

The present invention includes polypeptides of Formula IX and Formula X above wherein from one to three of the amino acids designated by Xaa are different from the corresponding amino acids of native human interleukin-3 or native (15–125) human interleukin-3; or a polypeptide having substantially the same structure and substantially the same biological activity.

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence" refers to an amino acid or nucleic acid sequence which is identical to a wild-type or native form of a gene or protein.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. (1990); Ganser, A., et al. (1990); Falk, S., et al. (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Many or all of these biological activities of hIL-3 involve signal transduction and high affinity receptor binding. Mutant polypeptides of the present invention may exhibit useful properties such as having similar or greater biological activity when compared to native hIL-3 or by having improved half-life or decreased adverse side effects, or a combination of these properties. They may also be useful as antagonists. hIL-3 mutant polypeptides which have little or no activity when compared to native hIL-3 may still be useful as antagonists, as antigens for the production of antibodies for use in immunology or immunotherapy, as genetic probes or as intermediates used to construct other useful hIL-3 muteins. Since hIL-3 functions by binding to its receptor(s) and triggering second messages resulting in competent signal transduction, hIL-3 muteins of this invention may be useful in helping to determine which specific amino acid sequences are responsible for these activities.

The novel hIL-3 mutant polypeptides of the present invention will preferably have at least one biological property of human IL-3 or of an IL-3-like growth factor and may have more than one IL-3-like biological property, or an improved property, or a reduction in an undesirable biological property of human IL-3. Some mutant polypeptides of the present invention may also exhibit an improved side effect profile. For example, they may exhibit a decrease in leukotriene release or histamine release when compared to native hIL-3 or (15–125) hIL-3. Such hIL-3 or hIL-3-like biological properties may include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3-like biological property is the stimulation of granulocytic type colonies, megakaryocytic type colonies, monocyte/macrophage type colonies, and erythroid bursts. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Human IL-3 also has some biological activities which may in some cases be undesirable, for example the ability to stimulate leukotriene release and the ability to stimulate increased histamine synthesis in spleen and bone marrow cultures and in vivo.

Biological activity of hIL-3 and hIL-3 mutant proteins of the present invention is determined by DNA synthesis by human acute myelogenous leukemia cells (AML). The factor-dependent cell line AML 193 was adapted for use in testing biological activity.

One object of the present invention is to provide hIL-3 muteins and hIL-3 deletion muteins with one or more amino acid substitutions in the polypeptide sequence which have similar or improved biological activity in relation to native hIL-3 or native (15–125)hIL-3.

The present invention includes mutant polypeptides comprising minimally amino acid residues 15 to 118 of hIL-3 with or without additional amino acid extensions to the N-terminus and/or C-terminus which further contain from one to three or more amino acid substitutions in the amino acid sequence of the polypeptide. It has been found that the (15–125)hIL-3 mutant is more soluble than is hIL-3 when expressed in the cytoplasm of E. coli, and the protein is secreted to the periplasm in E. coli at higher levels compared to native hIL-3.

When expressed in the E. coli cytoplasm, the above-mentioned mutant hIL-3 polypeptides of the present invention may also be constructed with Met-Ala- at the N-terminus so that upon expression the Met is cleaved off leaving Ala at the N-terminus. These mutant hIL-3 polypeptides may also be expressed in E. coli by fusing a signal peptide to the N-terminus. This signal peptide is cleaved from the polypeptide as part of the secretion process. Secretion in E. coli can be used to obtain the correct amino acid at the N-terminus (e.g., $Asn^{15}$ in the (15–125) hIL-3 polypeptide) due to the precise nature of the signal peptidase. This is in contrast to the heterogeneity often observed at the N-terminus of proteins expressed in the cytoplasm in E. coli.

The hIL-3 mutant polypeptides of the present invention may have hIL-3 or hIL-3-like activity. For example, they may possess one or more of the biological activities of native hIL-3 and may be useful in stimulating the production of hematopoietic cells by human or primate progenitor cells. The hIL-3 muteins of the present invention and pharmaceutical compositions containing them may be useful in the treatment of conditions in which hematopoietic cell populations have been reduced or destroyed due to disease or to treatments such as radiation or chemotherapy.

hIL-3 muteins of the present invention may also be useful as antagonists which block the hIL-3 receptor by binding specifically to it and preventing binding of the agonist.

One potential advantage of the (15–125) hIL-3 muteins of the present invention, particularly those which retain activity similar to or better than that of native hIL-3, is that it may be possible to use a smaller amount of the biologically active mutein to produce the desired therapeutic effect. This may make it possible to reduce the number of treatments necessary to produce the desired therapeutic effect. The use of smaller amounts may also reduce the possibility of any potential antigenic effects or other possible undesirable side effects. For example, if a desired therapeutic effect can be achieved with a smaller amount of polypeptide it may be possible to reduce or eliminate side effects associated with the administration of native IL-3 such as the stimulation of leukotriene and/or histamine release. The hIL-3 muteins of the present invention may also be useful in the activation of stem cells or progenitors which have low receptor numbers. Pharmaceutical compositions containing hIL-3 muteins of the present invention can be administered parenterally, intravenously, or subcutaneously.

In variants which contain an additional cysteine the presence of the cysteine permits the labeling of the protein with ricin which permits targeting ricin and other toxins or tracers using a sulfhydryl linkage to the hIL-3 receptor.

As another aspect of the present invention, there is provided a novel method for producing the novel family of human IL-3 muteins. The method of the present invention involves culturing a suitable cell or cell line, which has been transformed with a vector containing a DNA sequence coding for expression of a novel hIL-3 mutant polypeptide. Suitable cells or cell lines may be bacterial cells. For example, the various strains of *E. coli* are well-known as host cells in the field of biotechnology. Examples of such strains include *E. coli* strains JM101 [Yanish-Perron, et al. (1985)] and MON105 [Obukowicz, et al. (1992)]. Various strains of *B. subtilis* may also be employed in this method. Many strains of yeast cells known to those skilled in the art are also available as host cells for expression of the polypeptides of the present invention.

Also suitable for use in the present invention are mammalian cells, such as Chinese hamster ovary cells (CHO). General methods for expression of foreign genes in mammalian cells are reviewed in: Kaufman, R. J. (1987) High level production of proteins in mammalian cells, in *Genetic Engineering, Principles and Methods*, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally fused to the coding region for the hIL-3 variant. For example, plasmids such as pcDNA I/Neo, pRc/RSV, and pRc/CMV (obtained from Invitrogen Corp., San Diego, Calif.) can be used. The eukaryotic secretion signal peptide coding region can be from the hIL-3 gene itself or it can be from another secreted mammalian protein (Bayne, M. L. et al. (1987) *Proc. Natl. Acad. Sci. USA* 84, 2638–2642). After construction of the vector containing the hIL-3 variant gene, the vector DNA is transfected into mammalian cells. Such cells can be, for example, the COS7, HeLa, BHK, CHO, or mouse L lines. The cells can be cultured, for example, in DMEM media (JRH Scientific). The hIL-3 variant secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al., U.S. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, *Genetic Engineering*, 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally fused to the coding region for the hIL-3 variant polypeptide. For example, the plasmid pVL1392 (obtained from Invitrogen Corp., San Diego, Calif.) can be used. After construction of the vector carrying the hIL-3 variant gene, two micrograms of this DNA is cotransfected with one microgram of Baculovirus DNA (see Summers & Smith, 1987) into insect cells, strain SF9. Pure recombinant Baculovirus carrying the hIL-3 variant is used to infect cells cultured, for example, in Excell 401 serum-free medium (JRH Biosciences, Lenexa, Kans.). The hIL-3 variant secreted into the medium can be recovered by standard biochemical approaches.

Another aspect of the present invention provides plasmid DNA vectors for use in the method of expression of these novel hIL-3 muteins. These vectors contain the novel DNA sequences described above which code for the novel polypeptides of the invention. Appropriate vectors which can transform microorganisms capable of expressing the hIL-3 muteins include expression vectors comprising nucleotide sequences coding for the hIL-3 muteins joined to transcriptional and translational regulatory sequences which are selected according to the host cells used.

Vectors incorporating modified sequences as described above are included in the present invention and are useful in the production of the hIL-3 mutant polypeptides. The vector employed in the method also contains selected regulatory sequences in operative association with the DNA coding sequences of the invention and capable of directing the replication and expression thereof in selected host cells.

The present invention also includes the construction and expression of (15–125)human interleukin-3 muteins having one or more amino acid substitutions in secretion vectors that optimize accumulation of correctly folded, active polypeptide. While many heterologous proteins have been secreted in *E. coli* there is still a great deal of unpredictability and limited success (Stader and Silhavy 1990). Full-length hIL-3 is such a protein, where attempts to secrete the protein in *E. coli* resulted in low levels of secretion. Secretion of the variant (15–125) hIL-3 mutant polypeptides of the present invention as a fusion with a signal peptide such as lamB results in correctly folded protein that can be removed from the periplasm of *E. coli* by osmotic shock fractionation. This property of the variant (15–125) hIL-3 muteins allows for the direct and rapid screening for bioactivity of the secreted material in the crude osmotic shock fraction, which is a significant advantage. Furthermore, it provides a means of using the (15–125)hIL-3 muteins to conduct structure activity relationship (SAR) studies of the hIL-3 molecule. A further advantage of secretion of (15–125) hIL-3 muteins fused to the lamB signal peptide is that the secreted polypeptide has the correct N-terminal amino acid (Asn) due to the precise nature of the cleavage of the signal peptide by signal peptidase, as part of the secretion process.

The (15–125)hIL-3 muteins of the present invention may include hIL-3 polypeptides having Met-, Ala- or Met-Ala- attached to the N-terminus. When the muteins are expressed in *E. coli*, polypeptides with and without Met attached to the N-terminus are obtained. The methionine can in some cases be removed by methionine aminopeptidase.

Amino terminal sequences of some of the hIL-3 muteins made in *E. coli* were determined using the method described by Hunkapillar et al., (1983). It was found that hIL-3 proteins made in *E. coli* from genes encoding Met-(15–125) hIL-3 were isolated as Met-(15–125) hIL-3. Proteins produced from genes encoding Met-Ala-(15–125) hIL-3 were produced as Ala-(15–125) hIL-3. The N-termini of proteins made in the cytoplasm of *E. coli* are affected by posttranslational processing by methionine aminopeptidase (Ben-Bassat et al., 1987) and possibly by other peptidases.

One method of creating the preferred hIL-3 (15–125) mutant genes is cassette mutagenesis [Wells, et al. (1985)] in which a portion of the coding sequence of hIL-3 in a plasmid is replaced with synthetic oligonucleotides that encode the desired amino acid substitutions in a portion of the gene between two restriction sites. In a similar manner amino acid substitutions could be made in the full-length hIL-3 gene, or genes encoding variants of hIL-3 in which from 1 to 14 amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed mutagenesis [Zoller and Smith (1982, 1983, 1984), Smith (1985), Kunkel (1985), Taylor, et al. (1985), Deng and Nickoloff (1992)] or polymerase chain reaction (PCR) techniques [Saiki, (1985)].

Pairs of complementary synthetic oligonucleotides encoding portions of the amino terminus of the hIL-3 gene can be made and annealed to each other. Such pairs would have protruding ends compatible with ligation to NcoI at one end. The NcoI site would include the codon for the initiator methionine. At the other end of oligonucleotide pairs, the protruding (or blunt) ends would be compatible with a restriction site that occurs within the coding sequence of the hIL-3 gene. The DNA sequence of the oligonucleotide would encode sequence for amino acids of hIL-3 with the exception of those substituted and/or deleted from the sequence.

The NcoI enzyme and the other restriction enzymes chosen should have recognition sites that occur only once in the DNA of the plasmid chosen. Plasmid DNA can be treated with the chosen restriction endonucleases then ligated to the annealed oligonucleotides. The ligated mixtures can be used to transform competent JM101 cells to resistance to an appropriate antibiotic. Single colonies can be picked and the plasmid DNA examined by restriction analysis and/or DNA sequencing to identify plasmids with mutant hIL-3 genes.

One example of a restriction enzyme which cleaves within the coding sequence of the hIL-3 gene is ClaI whose recognition site is at codons 20 and 21. The use of ClaI to cleave the sequence of hIL-3 requires that the plasmid DNA be isolated from an *E. coli* strain that fails to methylate adenines in the DNA at GATC recognition sites. This is because the recognition site for ClaI, ATCGAT, occurs within the sequence GATCGAT which occurs at codons 19, 20 and 21 in the hIL-3 gene. The A in the GATC sequence is methylated in most *E. coli* host cells. This methylation prevents ClaI from cleaving at that particular sequence. An example of a strain that does not methylate adenines is GM48.

Interpretation of activity of single amino acid mutants in IL-3 (15–125)

As illustrated in Tables 6 and 9, there are certain positions in the IL-3 (15–125) molecule which are intolerant of substitutions, in that most or all substitutions at these positions resulted in a considerable decrease in bioactivity. There are two likely classes of such "down-mutations": mutations that affect overall protein structure, and mutations that interfere directly with the interaction between the IL-3 molecule and its receptor. Mutations affecting the three-dimensional structure of the protein will generally lie in the interior of the protein, while mutations affecting receptor binding will generally lie on the surface of the protein. Although the three-dimensional structure of IL-3 is unknown, there are simple algorithms which can aid in the prediction of the structure. One such algorithm is the use of "helical wheels" (Kaiser, E. T. & Kezdy, F. J., Science, 223:249–255 (1984)). In this method, the presence of alpha helical protein structures can be predicted by virtue of their amphipathic nature. Helices in globular proteins commonly have an exposed hydrophilic side and a buried hydrophobic side. As a broad generalization, in globular proteins, hydrophobic residues are present in the interior of the protein, and hydrophilic residues are present on the surface. By displaying the amino acid sequence of a protein on such a "helical wheel" it is possible to derive a model for which amino acids in alpha helices are exposed and which are buried in the core of the protein. Such an analysis of the IL-3 (15–125) molecule predicts that the following helical residues are buried in the core:

M19, I20, I23, I24, L27, L58, F61, A64, L68, A71,
I74, I77, L78, L81, W104, F107, L111, Y114, L115, L118.

In addition, cysteine residues at positions 16 and 84 are linked by a disulfide bond, which is important for the overall structure or "folding" of the protein. Finally, mutations which result in a major disruption of the protein structure may be expressed at low level in the secretion system used in our study, for a variety of reasons: either because the mis-folded protein is poorly recognized by the secretion machinery of the cell; because mis-folding of the protein results in aggregation, and hence the protein cannot be readily extracted from the cells; or because the mis-folded protein is more susceptible to degradation by cellular proteases. Hence, a block in secretion may indicate which positions in the IL-3 molecule which are important for maintenance of correct protein structure.

In order to retain the activity of a variant of IL-3, it is necessary to retain both the structural integrity of the protein, and retain the specific residues important for receptor contact. Hence it is possible to define specific amino acid residues in IL-3 (15–125) which must be retained in order to preserve biological activity.

Residues predicted to be important for interaction with the receptor: D21, E22, E43, D44, L48, R54, R94, D103, K110, F113.

Residues predicted to be structurally important: C16, L58, F61, A64, I74, L78, L81, C84, P86, P92, P96, F107, L111, L115, L118.

The hIL-3 muteins of the present invention may be useful in the treatment of diseases characterized by a decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs and of infection or hemorrhage. Therapeutic treatment of leukopenia with these hIL-3 mutant polypeptides of the present invention may avoid undesirable side effects caused by treatment with presently available drugs.

The hIL-3 muteins of the present invention may be useful in the treatment of neutropenia and, for example, in the treatment of such conditions as aplastic anemia, cyclic neutropenia, idiopathic neutropenia, Chdiak-Higashi syndrome, systemic lupus erythematosus (SLE), leukemia, myelodysplastic syndrome and myelofibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin and sulfa drugs, phenothiazones, tranquilizers such as meprobamate, and diuretics. The hIL-3 muteins of the present invention may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. The hIL-3 muteins of the present invention may be useful in treating such hematopoietic deficiency.

The treatment of hematopoietic deficiency may include administration of the hIL-3 mutein of a pharmaceutical composition containing the hIL-3 mutein to a patient. The hIL-3 muteins of the present invention may also be useful for the activation and amplification of hematopoietic precursor cells by treating these cells in vitro with the muteins of the present invention prior to injecting the cells into a patient.

Various immunodeficiencies e.g., in T and/or B lymphocytes, or immune disorders, e.g., rheumatoid arthritis, may also be beneficially affected by treatment with the hIL-3 mutant polypeptides of the present invention. Immunodeficiencies may be the result of viral infections e.g. HTLVI, HTLVII, HTLVIII, severe exposure to radiation, cancer therapy or the result of other medical treatment. The hIL-3 mutant polypeptides of the present invention may also be employed, alone or in combination with other hematopoietins, in the treatment of other blood cell deficiencies, including thrombocytopenia (platelet deficiency), or anemia. Other uses for these novel polypeptides are in the treatment of patients recovering from bone marrow transplants in vivo and ex vivo, and in the development of monoclonal and polyclonal antibodies generated by standard methods for diagnostic or therapeutic use.

Other aspects of the present invention are methods and therapeutic compositions for treating the conditions referred to above. Such compositions comprise a therapeutically effective amount of one or more of the hIL-3 muteins of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.2–150 μg/kg of non-glycosylated IL-3 protein per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given mutein vs. the activity of native (reference) IL-3 and it would not be unreasonable to note that dosage regimens may include doses as low as 0.1 microgram and as high as 1 milligram per kilogram of body weight per day. In addition, there may exist specific circumstances where dosages of IL-3 mutein would be adjusted higher or lower than the range of 10–200 micrograms per kilogram of body weight. These include co-administration with other CSF or growth factors; co-administration with chemotherapeutic drugs and/or radiation; the use of glycosylated IL-3 mutein; and various patient-related issues mentioned earlier in this section. As indicated above, the therapeutic method and compositions may also include co-administration with other human factors. A non-exclusive list of other appropriate hematopoietins, CSFs and interleukins for simultaneous or serial co-administration with the polypeptides of the present invention includes GM-CSF, CSF-1, G-CSF, Meg-CSF, M-CSF, erythropoietin (EPO), IL-1, IL-4, IL-2, IL-5, IL-6, IL-7, IL-8, IL-9, IL-10, IL-11, LIF, B-cell growth factor, B-cell differentiation factor and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count and the like.

Materials and methods for hIL-3 Mutein Expression in *E. coli*

Unless noted otherwise, all specialty chemicals were obtained from Sigma Co., (St. Louis, Mo.). Restriction endonucleases, T4 poly-nucleotides kinase, *E. coli* DNA polymerase I large fragment (Klenow) and T4 DNA ligase were obtained from New England Biolabs (Beverly, Mass.) or Boehringer Mannheim (Indianapolis, Ind.). All chemicals and enzymes were used according to manufacturer's directions.

*Escherichia coli* strains

Strain JM101: delta (pro lac), supE, thi, F'(traD36, proAB, lacI-Q, lacZdeltaM15) (Messing, 1979). This strain can be obtained from the American Type Culture Collection (ATCC), 12301 Parklawn Drive, Rockville, Md. 20852, accession number 33876. MON 105 (W3110 rpoH358) (Obukowicz, et al., 1992) is a derivative of W3110 (Bachmann, 1972) and has been assigned ATCC accession number 55204. Strain GM48: dam-3, dcm-6, gal, ara, lac, thr, leu, tonA, tsx (Marinus, 1973) was used to make plasmid DNA that is not methylated at the sequence GATC.

Genes and plasmids

The gene used for hIL-3 production in *E. coli* was obtained from British Biotechnology Incorporated, Cambridge, England, catalogue number BBG14. This gene is carried on a pUC based plasmid designated pP0518. The human IL-3 gene sequence is from Yang, et al. (1986).

The plasmids used for production of hIL-3 in *E. coli* contain genetic elements whose use has been described (Olins et al., 1988; Olins and Rangwala, 1990). The replicon used is that of pBR327 [(Bolivar et al. (1977); Soberon et al., 1980] which is maintained at a copy number of about 50 in the cell (Covarrubias, et al., (1981)). A gene encoding the beta-lactamase protein is present on the plasmids. This protein confers ampicillin resistance on the cell. This resistance serves as a selectable phenotype for the presence of the plasmid in the cell.

Intracellular expression plasmids:

For cytoplasmic (intracellular) expression vectors the transcription promoter was derived from the recA gene of *E. coli* (Sancar et al., 1980). This promoter, designated precA, is contained on 72 base pairs (bp) BglII, BamHI fragment which includes the RNA polymerase binding site and the lexA repressor binding site (the operator). This segment of DNA provides high level transcription that is regulated even when the recA promoter is on a plasmid with the pBR327 origin of replication (Olins et al., 1988) incorporated herein by reference.

Secretion expression plasmids:

In secretion expression plasmids the transcription promoter was derived from the ara B, A, and D genes of *E. coli* (Greenfield et al., 1978). This promoter is designated pAra-BAD and is contained on a 323 base pair SacII, BglII restriction fragment. The lamb secretion leader (Wong et al., 1988, Clement et al., 1981) was fused to the N-terminus of the hIL-3 gene at the recognition sequence for the enzyme NcoI (5'CCATGG3'). The hIL-3 genes used were engineered to have a HindIII recognition site (5'AAGCTT3') following the coding sequence of the gene. Downstream of the gene is a 550 bp fragment containing the origin of replication of the single stranded phage f1 [Olins and Rangwala (1989)].

These hIL-3 variants were expressed as a fusion with the lamB signal peptide operatively joined to the araBAD promoter (Greenfield, 1978) and the g10-L ribosome binding site (Olins et al. 1988). The signal peptide is removed as part of the secretion process. The processed form was selectively released from the periplasm by osmotic shock as a correctly folded and fully active molecule. Secretion of (15–125) hIL-3 was further optimized by using low inducer (arabinose) concentration and by growth at 30° C. These conditions resulted in lower accumulation levels of unprocessed lamB signal peptide (15–125) hIL-3 fusion, maximal accumulation levels of processed (15–125) hIL-3 and selective release of (15–125) hIL-3 by osmotic shock fractionation. The use of a tightly regulated promoter such as araBAD from which the transcription level and hence the expression level can be modulated allowed for the optimization of secretion of (15–125) hIL-3.

The ribosome binding site (RBS) used is that from gene 10 of phage T7 (Olins et al., 1988). This is encoded in a 100 base pair (bp) fragment placed adjacent to precA. In the plasmids used herein, the recognition sequence for the enzyme NcoI (5'CCATGG3') follows the g10-L RBS. It is at this NcoI site that the hIL-3 genes are joined to the plasmid. It is expected that the nucleotide sequence at this junction will be recognized in mRNA as a functional start site for translation (Olins et al., 1988). The hIL-3 genes used were engineered to have a HindIII recognition site (5'AAGCTT3') following the coding sequence of the gene. Downstream of the gene is a 550 base pair fragment containing the origin of replication of the single stranded phage f1 (Dente et al., 1983; Olins, et al., 1990) both incorporated herein by reference. A plasmid containing these elements is pMON2341. Another plasmid containing these elements is pMON5847 which has been deposited at the American Type Culture Collection, 12301 Parklawn Drive, Rockville, Md. 20852 under the accession number ATCC 68912.

Synthesis of Oligonucleotides

Oligonucleotides were synthesized by the cyanoethyl method (Adams et al. 1983, McBride, et al. 1983, Sinba et al., 1984) on Nucleotide Synthesizer model 380A or 380B from Applied Biosystems, Inc. (Foster City, Calif.). Some oligonucleotides were purchased from Genosys Biotechnologies Inc. (The Woodlands, Tex.) or Midland Certified Reagent Co. (Midland, Tex.). The degenerate oligonucleotides were synthesized by machine mixing an equal molar ratio of the desired nucleosides in the condensation reaction at degenerate positions. Oligonucleotides were purified by polyacrylamide gel electrophoresis at concentrations from 12–20% (19:1 crosslinked) in 0.5× Tris borate (TBE) buffer (0.045 M Tris, 0.045 M boric acid, 1.25 mM EDTA) as described by Atkinson (1984). The oligonucleotides were desalted by passage through a Nensorb 20 column obtained from DuPont/New England Nuclear (Boston, Mass.) using a PREP Automated Sample Processor obtained from DuPont, Co. (Wilmington, Del.).

Quantitation of synthetic oligonucleotides

Synthetic oligonucleotides were resuspended in water (100 μl) and quantitated by reading the absorbance at 260 nm on a Beckman DU40 Spectrophotometer (Irvine, Calif.) using a one centimeter by one millimeter quartz cuvette (Maniatis, 1982). The concentration was determined using an extinction coefficient of $1 \times 10^4$ (Voet et al., 1963; Mahler and Cordes, 1966). The oligonucleotide was then diluted to the desired concentration.

Quantitation of synthetic DNA fragments can also be achieved by adding 10 to 100 picomoles of DNA to a solution containing kinase buffer (25 mM Tris pH 8.0, 10 mM $MgCl_2$, 10 mM DTT and 2 mM spermidine). To the reaction mix is added ATP to 20 micromolar, ATP radiolabeled at the gamma phosphate (5000–10,0000 dpm/pmol) and 5 units of T4 polynucleotide kinase. Radiolabelled material is obtained from New England Nuclear (Boston, Mass.). The 10 microliter mixture is incubated at 37° C. for one hour. A 1 microliter aliquot of the mixture is chromatographed on DEAE paper (DE81 from Whatman) in 0.35 M ammonium bicarbonate. The counts that remain at the origin are used to determine the concentration of the synthetic DNA.

Recombinant DNA methods

Isolation of plasmid DNA from *E. coli* cultures was performed as described (Birnboim and Doly, 1979). Some DNAs were purified by Magic™ miniprep columns, available from Promega (Madison, Wis.).

Purified plasmid DNA was treated with restriction endonucleases according to manufacturer's instructions. Analysis of the DNA fragments produced by treatment with restriction enzymes was done by agarose or polyacrylamide gel electrophoresis. Agarose (DNA grade from Fisher, Pittsburgh Pa.) was used at a concentration of 1.0% in a Tris-acetate running buffer (0.04 M Tris-acetate, 0.001M EDTA). Polyacrylamide (BioRad, Richmond Calif.) was used at a concentration of 6% (19:1 crosslinked) in 0.5× Tris-borate buffer (0.045 M Tris, 0.045 M boric acid, 1.25 mM EDTA), hereafter referred to as PAGE.

DNA polymerase I, large fragment, Klenow enzyme was used according to manufacturer's instructions to catalyze the addition of mononucleotides from 5' to 3' of DNA fragments which had been treated with restriction enzymes that leave protruding ends. The reactions were incubated at 65° C. for 10 minutes to heat inactivate the Klenow enzyme.

The synthetic oligonucleotides were made without 5' or 3' terminal phosphates. In cases where such oligonucleotides were ligated end to end, the oligonucleotides were treated at a concentration of 10 picomoles per microliter with T4 polynucleotide kinase in the following buffer: 25 mM Tris, pH 8.0, 10 mM $MgCl_2$, 10 mM dithiothreitol, 2 mM spermidine, 1 mM rATP. After incubation for 30 minutes at 37° C., the samples were incubated at 65° C. for five minutes to heat inactivate the kinase.

Synthetic gene assembly

The (15–125) hIL-3 gene was divided into four regions separated by five convenient restriction sites. In each of the four regions synthetic oligonucleotides were designed so that they would anneal in complementary pairs, with protruding single stranded ends "or blunt ends" and when the pairs were properly assembled would result in a DNA sequence that encoded a portion of the hIL-3 gene. Amino acid substitutions in the hIL-3 gene were made by designing the oligonucleotides to encode the desired substitutions. The complementary oligonucleotides were annealed at concentration of 1 picomole per microliter in ligation buffer plus 50 mM NaCl. The samples were heated in a 100 ml beaker of boiling water and permitted to cool slowly to room temperature. One picomole of each of the annealed pairs of oligonucleotides were ligated with approximately 0.2 picomoles of plasmid DNA, digested with the appropriate restriction enzymes, in ligation buffer (25 mM Tris pH 8.0, 10 mM $MgCl_2$, 10 mM dithiothreitol, 1 mM ATP, 2mM spermidine) with T4 DNA ligase obtained from New England Biolabs (Beverly, Mass.) in a total volume of 20 μl at room temperature overnight.

DNA fragments were isolated from agarose gels by intercepting the restriction fragments on DEAE membranes from Schleicher and Schuell (Keene, N.H.) and eluting the DNA in 10 mM Tris, 1 mM EDTA, 1 M NaCl at 55° C. for 1 hour, according to manufacturer's directions. The solutions containing the DNA fragment were concentrated and desalted by using Centricon 30 concentrators from Amicon (W. R. Grace, Beverly Mass.) according to the manufacturer's directions. Ligations were performed at 15° C. overnight, except as noted, in ligation buffer (66 mM Tris pH 7.5, 6.6 mM $MgCl_2$, 1 mM dithiothreitol, 0.4 mM ATP) with $T_4$ ligase obtained from New England Biolabs (Beverly, Mass.).

Polymerase Chain Reaction

Polymerase Chain Reaction (hereafter referred to as PCR) techniques (Saiki, 1985) used the reagent kit and thermal cycler from Perkin-Elmer Cetus (Norwalk, Conn.). PCR is based on a thermostable DNA polymerase from *Thermus aquaticus*. The PCR technique is a DNA amplification method that mimics the natural DNA replication process in that the number of DNA molecules doubles after each cycle, in a way similar to in vivo replication. The DNA polymerase mediated extension is in a 5'→43' direction. The term "primer" as used herein refers to an oligonucleotide sequence that provides an end to which the DNA polymerase can add nucleotides that are complementary to a nucleotide sequence. The latter nucleotide sequence is referred to as the "template", to which the primers are annealed. The amplified PCR product is defined as the region comprised between the 5' ends of the extension primers. Since the primers have defined sequences, the product will have discrete ends, corresponding to the primer sequences. The primer extension reaction was carried out using 20 picomoles (pmoles) of each of the oligonucleotides and 1 picogram of template plasmid DNA for 35 cycles (1 cycle is defined as 94° C. for one minute, 50° C. for two minutes and 72° C. for three minutes). The reaction mixture was extracted with an equal volume of phenol/chloroform (50% phenol and 50% chloroform, volume to volume) to remove proteins. The aqueous phase, containing the amplified DNA, and solvent phase were separated by centrifugation for 5 minutes in a microcentrifuge (Model 5414 Eppendorf Inc, Fremont Calif.). To precipitate the amplified DNA the aqueous phase was removed and transferred to a fresh tube to which was added ⅟₁₀ volume of 3M NaOAc (pH 5.2) and 2.5 volumes of ethanol (100% stored at minus 20° C.). The solution was mixed and placed on dry ice for 20 minutes. The DNA was pelleted by centrifugation for 10 minutes in a microcentrifuge and the solution was removed from the pellet. The DNA pellet was washed with 70% ethanol, ethanol removed and dried in a speedvac concentrator (Savant, Farmingdale, N.Y.). The pellet was resuspended in 25 microliters of TE (20 mM Tris-HCl pH 7.9, 1 mM EDTA). Alternatively the DNA was precipitated by adding equal volume of 4M $NH_4OAc$ and one volume of isopropanol [Treco, (1989)]. The solution was mixed and incubated at room temperature for 10 minutes and centrifuged. These conditions selectively precipitate DNA fragments larger than ~20 bases and were used to remove oligonucleotide primers. One quarter of the reaction was digested with restriction enzymes [Higuchi, (1989)] and on completion heated to 70° C. to inactivate the enzymes.

Two step site-directed PCR mutagenesis

Single amino acid substitution variants were created at positions 17–123 of hIL-3 in two site-directed mutagenesis steps by PCR (Bauer et al. manuscript in preparation).

The single amino acid substitution variants at positions 94–105 of hIL-3 were created as described below. In the first mutagenesis step plasmid DNA, containing the hIL-3 gene (amino acids 15–125), was the template in the PCR reaction. The DNA sequence of one of the oligonucleotide primers was designed to replace 12 base in the hIL-3 gene (15-125) with 12 bases encoding two translation stop codons (5'TAATAA3'), followed by the recognition sequence (5'GTCGAC3') restriction enzyme SalI. This 12 base sequence was substituted in the hIL-3 gene following the codon for amino acids 93, 97 and 101. Plasmids containing these mutagenized genes served as the templates for the second mutagenesis step.

In the second mutagenesis step, the 12 base substitution introduced in the first mutagenesis step, was replaced using a 32 fold degenerate oligonucleotide. The degenerate oligonucleotides were synthesized by machine mixing an equal molar ratio of the desired nucleosides in the condensation reaction at degenerate positions. The degenerate oligonucleotides have G, A, T or C in the first and second positions and G or C in the third position of a single codon. The other bases in the oligonucleotides corresponded to the hIL-3 sequence. The degenerate oligonucleotides theoretically contain 32 different codons, encoding all 20 amino acids and one translation stop codon, at a single position. At the other 9 bases the DNA sequence was restored to encode the native hIL-3 protein sequence. This pool of single amino acid substitutions at a single position is referred to as a "library". This two step PCR site-directed mutagenesis approach was used to facilitate the identification of single amino acid substitution variants by differential DNA hybridization.

The single amino acid substitution variants at positions 17–93 and 106–123 of hIL-3 (15-125) were created as described below. In the first mutagenesis step plasmid DNA, containing the hIL-3 gene (15-125), was the template in the PCR reaction. The DNA sequence of one of the oligonucleotide primers was designed to delete 18 bases in the hIL-3 gene that encode the following amino acids; 17–22, 23–28, 29–34, 35–40, 41–46, 47–52, 53–58, 59–64, 65–70, 71–76, 77–82, 83–88, 88–93, 106–111, 112–117 and 118–123. Plasmids containing these deletion genes served as the templates for the second mutagenesis step.

In the second mutagenesis step the 18 base deletion, created in the first mutagenesis step, was restored using a 32 fold degenerate oligonucleotide. The degenerate oligonucleotides have G, A, T or C in the first and second positions and G or C in the third position of a single codon. The other bases in the oligonucleotides corresponded to the hIL-3 sequence. The degenerate oligonucleotides theoretically contain 32 different codons, encoding all 20 amino acids and one translation stop codon, at a single position. At the other 9 bases the DNA sequence was restored to encode the native hIL-3 protein sequence. This pool of single amino acid substitutions at a single position is referred to as a "library". This two step PCR site-directed mutagenesis approach was used to facilitate the identification of single amino acid substitution variants by differential DNA hybridization.

Recovery of recombinant plasmids from ligation mixes and transformation of *E. coli* cells with recombinant plasmid DNA E. coli JM101 cells were made competent to take up DNA. Typically, 20 to 100 ml of cells were grown in LB medium to a density of approximately 150 Klett units and then collected by centrifugation. The cells were resuspended in one half culture volume of 50 mM $CaCl_2$ and held at 4° C. for one hour. The cells were again collected by centrifugation and resuspended in one tenth culture volume of 50 mM $CaCl_2$. DNA was added to a 150 microliter volume of these cells, and the samples were held at 4° C. for 30 minutes. The samples were shifted to 42° C. for one minute, one milliliter of LB was added, and the samples were shaken at 37° C. for one hour. Cells from these samples were spread on plates containing ampicillin to select for transformants. The plates were incubated overnight at 37° C. Single colonies were picked and grown in LB supplemented with ampicillin overnight at 37° C. with shaking. From these cultures DNA was isolated for restriction analysis.

Typically plasmids were constructed, using methods described herein or by references cited herein, as follows except as noted in examples included herein. DNA fragments were purified from agarose or polyacrylamide gels. Purified DNA fragments were ligated and the ligation reaction mixture was used to transform E. coli K-12 strain JM101. Transformant bacteria were selected on ampicillin containing plates. Plasmid DNA was isolated from a single colony grown in LB Broth and screened by restriction analysis for the desired construct and sequenced to determine that the DNA sequence was correct.

Culture media

LB medium (Maniatis et al., 1982) was used for growth of cells for DNA isolation. M9 minimal medium supplemented with 1.0% casamino acids, acid hydrolyzed casein, Difco (Detroit, Mich.) was used for cultures in which recombinant hIL-3 was produced. The ingredients in the M9 medium were as follows: 3 g/liter $KH_2PO_4$, 6 g/l $Na_2HPO_4$, 0.5 g/l NaCl, 1 g/l $NH_4Cl$, 1.2 mM $MgSO_4$, 0.025 mM $CaCl_2$, 0.2% glucose (0.2% glycerol with the AraBAD promoter), 1% casamino acids, 0.1 ml/l trace minerals (per liter 108 g $FeCl_3.6H_2O$, 4.0 g $ZnSO_4.7H_2O$, 7.0 $CoCl_2.2H_2O$, 7.0 g $Na_2MoO_4.2H_2O$, 8.0 g $CuSO_4.5H_2O$, 2.0 g $H_3BO_3$, 5.0 g $MnSO_4.H_2O$, 100 ml concentrated HCl). Bacto agar from Difco was used for solid media and ampicillin (Polycillin-N from Bristol-Meyers, Evansville, Ind.) was added to both liquid and solid LB media at 200 micrograms per milliliter.

DNA sequence analysis

The nucleotide sequencing of plasmid DNA was performed using a Genesis 2000 sequencer obtained from DuPont (Wilmington, Del.) according to the methods of Prober et al. (1987) and Sanger et al. (1977). Some DNA sequences were determined using Sequenase™ polymerase according to the protocol of its supplier, U.S. Biochemicals (Cleveland, Ohio).

Production of recombinant hIL-3 muteins in E. coli with vectors employing the recA promoter E. coli strains harboring the plasmids of interest were grown at 37° C. in M9 plus casamino acids medium with shaking in a Gyrotory water bath Model G76 from New Brunswick Scientific (Edison, N.J.). Growth was monitored with a Klett Summerson meter (green 54 filter), Klett Mfg. Co. (New York, N.Y.). At a Klett value of approximately 150, an aliquot of the culture (usually one milliliter) was removed for protein analysis. To the remaining culture, nalidixic acid (10 mg/ml) in 0.1 N NaOH was added to a final concentration of 50 µg/ml. The cultures were shaken at 37° C. for three to four hours after addition of nalidixic acid. A high degree of aeration was maintained throughout the bacterial growth in order to achieve maximal production of the desired gene product. The cells were examined under a light microscope for the presence of retractile bodies (RBs). One milliliter aliquots of the culture were removed for analysis of protein content.

Production of recombinant hIL-3 proteins from the AraBAD promoter in E. coli

E. coli strains harboring the plasmids of interest were grown at 30° C. with shaking in M9 medium plus casamino acids and glycerol. Growth was monitored with a Klett Summerson calorimeter, using a green 54 filter. At a Klett value of about 150, an aliquot of the culture (usually one milliliter) was removed for protein analysis. To the remaining culture, 20% arabinose was added to a final concentration of 0.05%. The cultures were shaken at 30° C. for three to four hours after addition of arabinose. A high degree of aeration was maintained throughout the bacterial growth in order to achieve maximal production of the desired gene product. One milliliter aliquots of the culture were removed for analysis of protein content.

Secretion and osmotic shock

Three hour post induction samples were fractionated by osmotic shock [Neu and Heppel (1965)]. The Klett value of the cultures was determined and 1 ml of cells were centrifuged in a Sigma microcentrifuge (West Germany) model 202MK in 1.5 mls snap top microcentrifuge tubes for 5 minutes at 10,000 rpm. The cell pellet was resuspended very gently by pipeting in a room temperature sucrose solution (20% sucrose w/v, 30 mM Tris-Hcl pH7.5, 1 mM EDTA), using 1 µl/1 Klett unit. Following a 10 minute incubation at room temperature, the cells were centrifuged for 5 minutes at 10,000 rpm. The sucrose fraction was carefully removed from the cell pellet. The cell pellet was then resuspended very gently by pipeting in ice cold distilled water, using 1 µl/1 Klett unit. Following a 10 minute incubation on ice, the cells were centrifuged for 5 minutes at 12,000 rpm. The water fraction was carefully removed. Equal volumes of the sucrose and water fractions were pooled and aliquoted to provide samples for ELISA and biological activity screening.

Analysis of protein content of E. coli cultures producing hIL-3 mutant polypeptides Bacterial cells from cultures treated as described above were collected from the medium by centrifugation. Aliquots of these cells were resuspended in SDS loading buffer (4×: 6 g SDS, 10 ml beta-mercaptoethanol, 25 ml upper Tris gel stock (0.5 M Tris HCl pH 6.8, 0.4% SDS) brought to 50 ml with glycerol, 0.2% bromophenol blue was added) at a concentration of one microliter per Klett unit. These samples were incubated at 85° C. for five minutes and vortexed. Five or ten microliter aliquots of these samples were loaded on 15% polyacrylamide gels prepared according to the method of Laemmli (1970). Protein bands were visualized by staining the gels with a solution of acetic acid, methanol and water at 5:1:5 (volume to volume) ratio to which Coomassie blue had been added to a final concentration of 1%. After staining, the gels were washed in the same solution without the Coomassie blue and then washed with a solution of 7% acetic acid, 5% methanol. Gels were dried on a gel drier Model SE1160 obtained from Hoeffer (San Francisco, Calif.). The amount of stained protein was measured using a densitometer obtained from Joyce-Loebl (Gateshead, England). The values obtained were a measure of the amount of the stained hIL-3 protein compared to the total of the stained protein of the bacterial cells.

Western blot analysis of hIL-3 muteins made in E. coli

In some E. coli cultures producing hIL-3, the level of accumulation of the hIL-3 protein is lower than 5% of total bacterial protein. To detect hIL-3 produced at this level, Western blot analysis was used. Proteins from cultures induced with nalidixic acid or arabinose were run on polyacrylamide gels as described above except that volumes of sample loaded were adjusted to produce appropriate signals. After electrophoresis, the proteins were electroblotted to APT paper, Transa-bind, Schleicher and Schuell (Keene, N.H.) according to the method of Renart et al. (1979). Antisera used to probe these blots had been raised in rabbits, using peptides of the sequence of amino acids 20 to 41 and 94 to 118 of hIL-3 as the immunogens. The presence of bound antibody was detected with Staphylococcal protein A radiolabeled with $^{125}$I, obtained from New England Nuclear (Boston, Mass.).

Fractionation of E. coli cells producing hIL-3 proteins in the cytoplasm

Cells from E. coli cultures harboring plasmids that produce hIL-3 muteins were induced with nalidixic acid. After three hours, the hIL-3 muteins accumulated in refractile bodies. The first step in purification of the hIL-3 muteins was to sonicate cells. Aliquots of the culture were resuspended from cell pellets in sonication buffer: 10 mM Tris, pH 8.0, 1 mM EDTA, 50 mM NaCl and 0.1 mM PMSF. These resuspended cells were subjected to several repeated sonication bursts using the microtip from a Sonicator cell disrupter, Model W-375 obtained from Heat Systems-Ultrasonics Inc. (Farmingdale, N.Y.). The extent of sonication was monitored by examining the homogenates under a light microscope. When nearly all of the cells had been broken, the homogenates were fractionated by centrifugation. The pellets, which contain most of the refractile bodies, are highly enriched for hIL-3 muteins.

Methods: Extraction, Refolding and Purification of Interleukin-3 (IL-3) Muteins Expressed as Refractile Bodies in E. coli For each gram of RB's (and typically one gram is obtained from a 300 ml E. coli culture), 5 ml of a solution containing 6M guanidine hydrochloride (GnHCl), 50 mM 2-N-cyclohexylaminoethanesulfonic acid (CHES) pH 9.5 and 20 mM dithiothreitol (DTT) was added. The RB's were extracted with a Bio-Homogenizer for 15–30 seconds and gently rocked for 2 hours at 5 degrees centigrade (5° C.) to allow the protein to completely reduce and denature.

Refolding of the IL-3 muteins

The protein solution was transferred to dialysis tubing (1000 molecular weight cut-off) and dialyzed against at least 100 volumes of 4M GnHCl—50 mM CHES pH 8.0. The dialysis was continued overnight at 5° C. while gently stirring. Subsequently dialysis was continued against at least 100 volumes of 2M GnHCl—50 mM CHES pH 8.0 and dialyzed overnight at 5° C. while gently stirring.

Purification of the IL-3 muteins

The protein solution was removed from the dialysis tubing and acidified by the addition of 40% acetonitrile ($CH_3CN$)—0.2% trifluoroacetic acid (TFA) to a final concentration of 20% $CH_3CN$—0.1% TFA. This was centrifuged (16,000×g for 5 minutes) to clarify and the supernatant was loaded onto a Vydac C-18 reversed phase column (10×250 mm) available from Vydac (Hesperia, Calif.) previously equilibrated in 20% $CH_3CN$—0.1% TFA. The column was eluted with a linear gradient (0.2% $CH_3CN$/minute) between 40–50% $CH_3CN$—0.1% TFA at a flow rate of 3 ml/minute while collecting 1.5 ml fractions. The fractions were analyzed by polyacrylamide gel electrophoresis (SDS-PAGE) and the appropriate fractions pooled. The pooled material was dried by lyophilization or in a Speed Vac concentrator. The dry powder was reconstituted with 10 mM ammonium bicarbonate pH 7.5, centrifuged (16,000×g for 5 minutes) to clarify and assayed for protein concentration by the method of Bradford (1976) with bovine serum albumin as the standard. Such protein can be further analyzed by additional techniques such as, SDS-PAGE, electrospray mass spectrometry, reverse phase HPLC, capillary zone electrophoresis, amino acid composition analysis, and ELISA (enzyme-linked immunosorbent assay).

hIL-3 SANDWICH ELISA

IL-3 protein concentrations were determined using a sandwich ELISA based on an affinity purified polyclonal goat anti-rhIL-3. Microtiter plates (Dynatech Immulon II) were coated with 150 μl goat-anti-rhIL-3 at a concentration of approximately 1 μg/ml in 100 mM NaHCO3, pH 8.2. Plates were incubated overnight at room temperature in a chamber maintaining 100% humidity. Wells were emptied and the remaining reactive sites on the plate were blocked with 200 μl of solution containing 10 mM PBS, 3% BSA and 0.05% Tween 20, pH 7.4 for 1 hour at 37° C. and 100% humidity. Wells were emptied and washed 4× with 150 mM NaCl containing 0.05% Tween 20 (wash buffer). Each well then received 150 μl of dilution buffer (10 mM PBS containing 0.1% BSA, 0.01% Tween 20, pH 7.4), containing rhIL-3 standard, control, sample or dilution buffer alone. A standard curve was prepared with concentrations ranging from 0.125 ng/ml to 5 ng/ml using a stock solution of rhIL-3 (concentration determined by amino acid composition analysis). Plates were incubated 2.5 hours at 37° C. and 100% humidity. Wells were emptied and each plate was washed 4× with wash buffer. Each well then received 150 μl of an optimal dilution (as determined in a checkerboard assay format) of goat anti-rhIL-3 conjugated to horseradish peroxidase. Plates were incubated 1.5 hours at 37° C. and 100% humidity. Wells were emptied and each plate was washed 4× with wash buffer. Each well then received 150 ul of ABTS substrate solution (Kirkegaard and Perry). Plates were incubated at room temperature until the color of the standard wells containing 5 ng/ml rhIL-3 had developed enough to yield an absorbance between 0.5–1.0 when read at a test wavelength of 410 nm and a reference wavelength of 570 nm on a Dynatech microtiter plate reader. Concentrations of immunoreactive rhIL-3 in unknown samples were calculated from the standard curve using software supplied with the plate reader.

AML Proliferation Assay for Bioactive Human Interleukin-3

The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM/CSF supplemented medium (Lange, B., et al., (1987); Valtieri, M., et al., (1987). The ability of AML 193 cells to proliferate in the presence of human IL-3 has also been documented. (Santoli, D., et al., (1987)). A cell line variant was used, AML 193 1.3, which was adapted for long term growth in IL-3 by washing out the growth factors and starving the cytokine dependent AML 193 cells for growth factors for 24 hours. The cells were then replated at $1 \times 10^5$ cells/well in a 24 well plate in media containing 100 U/ml IL-3. It took approximately 2 months for the cells to grow rapidly in IL-3. These cells were maintained as AML 193 1.3 thereafter by supplementing tissue culture medium (see below) with human IL-3.

AML 193 1.3 cells were washed 6 times in cold Hanks balanced salt solution (HBSS, Gibco, Grand Island, N.Y.) by centrifuging cell suspensions at 250×g for 10 minutes followed by decantation of supernatant. Pelleted cells were resuspended in HBSS and the procedure was repeated until six wash cycles were completed. Cells washed six times by this procedure were resuspended in tissue culture medium at a density ranging from $2\times10^5$ to $5\times10^5$ viable cells/ml. This medium was prepared by supplementing Iscove's modified Dulbecco's Medium (IMDM, Hazleton, Lenexa, Kans.) with albumin, transferrin, lipids and 2-mercaptoethanol. Bovine albumin (Boehringer-Mannheim, Indianapolis, Ind.) was added at 500 μg/ml; human transferrin (Boehringer-Mannheim, Indianapolis, Ind.) was added at 100 μg/ml; soybean lipid (Boehringer-Mannheim, Indianapolis, Ind.) was added at 50 μg/ml; and 2-mercaptoethanol (Sigma, St. Louis, Mo.) was added at $5\times10^{-5}$M.

Serial dilutions of human interleukin-3 or human interleukin-3 variant protein (hIL-3 mutein) were made in triplicate series in tissue culture medium supplemented as stated above in 96 well Costar 3596 tissue culture plates. Each well contained 50 μl of medium containing interleukin-3 or interleukin-3 variant protein once serial dilutions were completed. Control wells contained tissue culture medium alone (negative control). AML 193 1.3 cell suspensions prepared as above were added to each well by pipetting 50 μl ($2.5\times10^4$ cells) into each well. Tissue culture plates were incubated at 37° C. with 5% $CO_2$ in humidified air for 3 days. On day 3, 0.5 μCi $^3$H-thymidine (2 Ci/mM, New England Nuclear, Boston, Mass.) was added in 50 μl of tissue culture medium. Cultures were incubated at 37° C. with 5% $CO_2$ in humidified air for 18–24 hours. Cellular DNA was harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats were allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) was added. Beta emissions of samples from individual tissue culture wells were counted in a LKB Betaplate model 1205 scintillation counter (Pharmacia LKB, Gaithersburg, Md.) and data was expressed as counts per minute of $^3$H-thymidine incorporated into cells from each tissue culture well. Activity of each human interleukin-3 preparation or human interleukin-3 variant preparation was quantitated by measuring cell proliferation ($^3$H-thymidine incorporation) induced by graded concentrations of interleukin-3 or interleukin-3 variant. Typically, concentration ranges from 0.05 pM–$10^5$ pM are quantitated in these assays. Activity is determined by measuring the dose of interleukin-3 or interleukin-3 variant which provides 50% of maximal proliferation [$EC_{50}$=0.5×(maximum average counts per minute of $^3$H-thymidine incorporated per well among triplicate cultures of all concentrations of interleukin-3 tested—background proliferation measured by $^3$H-thymidine incorporation observed in triplicate cultures lacking interleukin-3]. This $EC_{50}$ value is also equivalent to 1 unit of bioactivity. Every assay was performed with native interleukin-3 as a reference standard so that relative activity levels could be assigned.

Relative biological activities of some IL-3 muteins of the present invention are shown in Table 1. The Relative Biological Activity of IL-3 mutants is calculated by dividing the $EC_{50}$ of (1-133) hIL-3 by the EC50 of the mutant. The Relative Biological Activity may represent the average of replicate assays.

TABLE 1

BIOLOGICAL ACTIVITY OF IL-3 MUTEINS

| Plasmid Code | Polypeptide Structure | Relative Biological Activity |
|---|---|---|
| Reference | (1–133) hIL-3 | 1.0 |
| pMON13286 | [SEQ ID NO. 69] | 8.0 |
| pMON13304 | [SEQ ID NO. 66] | 3.2 |

*The Relative Biological Activity of IL-3 mutants is calculated by dividing the $EC_{50}$ of (1–133) hIL-3 by the $EC_{50}$ of the mutant.

The following assay is used to measure IL-3 mediated sulfidoleukotriene release from human mononuclear cells.

IL-3 mediated sulfidoleukotriene release from human mononuclear cells

Heparin-containing human blood was collected and layered onto an equal volume of Ficoll-Paque (Pharmacia #17-0840-02) ready to use medium (density 1.077 g/ml.). The Ficoll was warmed to room temperature prior to use and clear 50 ml polystyrene tubes were utilized. The Ficoll gradient was spun at 300×g for 30 minutes at room temperature using a H1000B rotor in a Sorvall RT6000B refrigerated centrifuge. The band containing the mononuclear cells was carefully removed, the volume adjusted to 50 mls with Dulbecco's phosphate-buffered saline (Gibco Laboratories cat. #310-4040PK), spun at 400×g for 10 minutes at 4° C. and the supernatant was carefully removed. The cell pellet was washed twice with HA Buffer [20 mM Hepes (Sigma #H-3375), 125 mM NaCl (Fisher #S271-500), 5 mM KCl (Sigma #P-9541), 0.5 mM glucose (Sigma #G-5000),0.025% Human Serum Albumin (Calbiochem #126654) and spun at 300×g, 10 min., 4° C. The cells were resuspended in HACM Buffer (HA buffer supplemented with 1 mM $CaCl_2$ (Fisher #C79-500) and 1 mM $MgCl_2$ (Fisher #M-33) at a concentration of 1×106 cells/ml and 180 μl were transferred into each well of 96 well tissue culture plates. The cells were allowed to acclimate at 37° C. for 15 minutes. The cells were primed by adding 10 μls of a 20× stock of various concentrations of cytokine to each well (typically 100000, 20000, 4000, 800, 160, 32, 6.4, 1.28, 0 fM IL3). The cells were incubated for 15 minutes at 37° C. Sulfidoleukotriene release was activated by the addition of 10 μls of 20× (1000 nM) fmet-leu-phe (Calbiochem #344252) final concentration 50nM FMLP and incubated for 10 minutes at 37° C. The plates were spun at 350×g at 4° C. for 20 minutes. The supernatants were removed and assayed for sulfidoleukotrienes using Cayman's Leukotriene C4 EIA kit (Cat. #420211) according to manufacturers' directions. Native (15-125)hIL-3 was run as a standard control in each assay.

Native hIL-3 possesses considerable inflammatory activity and has been shown to stimulate synthesis of the arachidonic acid metabolites $LTC_4$, $LTD_4$, and $LTE_4$; histamine synthesis and histamine release. Human clinical trials with native hIL-3 have documented inflammatory responses (Biesma, et al., BLOOD, 80:1141–1148 (1992) and Postmus, et al., J. CLIN. ONCOL., 10:1131–1140 (1992)). A recent study indicates that leukotrienes are involved in IL-3 actions in vivo and may contribute significantly to the biological effects of IL-3 treatment (Denzlinger, C., et al., BLOOD, 81:2466–2470 (1993)), Some muteins of the present invention may have an improved therapeutic profile as compared to native hIL-3 or (15-125)hIL-3. For example, some muteins of the present invention may have a similar or more potent growth factor activity relative to native hIL-3 or (15-125)hIL-3 without having a similar or corresponding increase in the stimulation of leukotriene or histamine. These muteins would be expected to have a more favorable therapeutic profile since the amount of polypeptide which needs to be given to achieve the desired growth factor activity (e. g. cell proliferation) would have a lesser leukotriene or histamine stimulating effect. In studies with native hIL-3, the stimulation of inflammatory factors has been an undesirable side effect of the treatment. Reduction or elimination of the stimulation of mediators of inflammation would provide an advantage over the use of native hIL-3.

Some muteins of the present invention may have antigenic profiles which differ from that of native hIL-3. For example, in a competition ELISA with an affinity purified polyclonal goat anti-hIL-3 antibody, native hIL-3 significantly blocked the binding of labeled hIL-3 to polyclonal anti-hIL-3 antibody. Some polypeptides of the present invention, particularly those with several amino acids differing from those of native hIL-3, fail to block the binding of hIL-3 to anti-hIL-3 antibody.

Table 2 lists the sequences of some oligonucleotides used in making the muteins of the present invention.

Table 3 lists the amino acid sequence of native (15-125) hIL-3 (Peptide #1) and the amino acid sequences of some mutant polypeptides of the present invention. The sequences are shown with the amino acid numbering corresponding to that of native hIL-3 [FIG. 1].

TABLE 2

OLIGONUCLEOTIDES

Oligo #1

AATTCCGTCG TAAACTGACC TTCTATCTGA AAACCTTGGA GAACGCGCAG GCTCAACAGT  [SEQ ID NO:8]
AATA

Oligo #2

AGCTTATTAC TGTTGAGCCT GCGCGTTCTC CAAGGTTTTC AGATAGAAGG TCAGTTTACG  [SEQ ID NO:9]
ACGG

Oligo #3

CTAGCCACGG CCGCACCCAC GCGACATCCA ATCCATATCA AGGACGGTGA CTGGAATG    [SEQ ID NO:24]

Oligo #4

TTAACATTCC AGTCACCGTC CTTGATATGG ATTGGATGTC GCGTGGGTGC GGCCGTGG    [SEQ ID NO:25]

Oligo #5

CATGGCTAAC TGCTCTAACA TGAT                                         [SEQ ID NO:151]

Oligo #6

CGATCAT GTTAGAGCAGTTAGC                                            [SEQ ID NO:152]

Oligo #7 IL3MUTNCO

TGTCTGCTCA GGCCATGGCT                                              [SEQ ID NO:26]

Oligo #8 IL3T93

GCGCGAATTC ATTCCAGTCA CCGTCCTTGA TATGGTCGAC TTATTACGTG GGTGCGGCCG  [SEQ ID NO:27]
TGGCTAG

Oligo #9 IL3T97

GCGCGAATTC ATTCCAGTCA CCGTCGACTT ATTAGATTGG ATGTCGCGTG GGTGC       [SEQ ID NO:28]

Oligo #10 IL3T101

GCGCGAATTC GTCGACTTAT TAGTCCTTGA TATGGATTGG ATG                    [SEQ ID NO:31]

Oligo #11 IL3R94

GCGCGAATTC ATTCCAGTCA CCGTCCTTGA TATGGATTGG ATGSNNCGTG GGTGCGGCCG  [SEQ ID NO:32]
TGGCTAG

Oligo #12 IL3R95

GCGCGAATTC ATTCCAGTCA CCGTCCTTGA TATGGATTGG SNNTCGCGTG GGTGCGGCCG  [SEQ ID NO:33]
TGGC

TABLE 2-continued

OLIGONUCLEOTIDES

```
Oligo #13 IL3R96
GCGCGAATTC ATTCCAGTCA CCGTCCTTGA TATGGATSNN ATGTCGCGTG GGTGCGGCCG    [SEQ ID NO:34]
T Oligo #14 IL3R97
GCGCGAATTC ATTCCAGTCA CCGTCCTTGA TATGSNNTGG ATGTCGCGTG GGTGCGGC      [SEQ ID NO:35]

Oligo #15 IL3P9497
GATATGGATT GGATGTCGCG TGGG                                           [SEQ ID NO:36]

Oligo #16 IL3R98
GCGCGAATTC ATTCCAGTCA CCGTCCTTGA TSNNGATTGG ATGTCGCGTG GGTGC         [SEQ ID NO:37]

Oligo #17 IL3R99
GCGCGAATTC ATTCCAGTCA CCGTCCTTSN NATGGATTGG ATGTCGCGTG GG            [SEQ ID NO:38]

Oligo #18 IL3R100
GCGCGAATTC ATTCCAGTCA CCGTCSNNGA TATGGATTGG ATGTCGCGT                [SEQ ID NO:39]

Oligo #19 IL3R101
GCGCGAATTC ATTCCAGTCA CCSNNCTTGA TATGGATTGG ATGTCG                   [SEQ ID NO:40]

Oligo #20 IL3P98100
GTCACCGTCC TTGATATGGA TTGG                                           [SEQ ID NO:41]

Oligo #21 IL3R102
GCGCGAATTC ATTCCAGTCS NNGTCCTTGA TATGGATTGG ATG                      [SEQ ID NO:42]

Oligo #22 IL3R103
GCGCGAATTC ATTCCASNNA CCGTCCTTGA TATGGATTGG                          [SEQ ID NO:43]

Oligo #23 IL3R104
GCGCGAATTC ATTSNNGTCA CCGTCCTTGA TATGGAT                             [SEQ ID NO:44]

Oligo #24 IL3R105
GCGCGAATTC SNNCCAGTCA CCGTCCTTGA TATG                                [SEQ ID NO:45]

Oligo #25 IL3P102105
GAATTCATTC CAGTCACCGT TCCTT                                          [SEQ ID NO:46]

Oligo #26 IL3MUTR1
CGCGCGGAAT TCATTCCAGT CACCGT                                         [SEQ ID NO:47]

Oligo #27 DEL1722
CGCGCGCCAT GGCTAACTGC ATTATAACAC ACACTTAAAG CA                       [SEQ ID NO:48]

Oligo #28 DEL2328
CGCGCGCCAT GGCTAACTGC TCTAACATGA TCGATGAACA GCCACCTTTG CCTTTGCT      [SEQ ID NO:49]

Oligo #29 DEL2934
CGCGCGCCAT GGCTAACTGC TCTAACATGA TCGATGAAAT TATAACACAC TTAAAGCTGG    [SEQ ID NO:50]
ACTTCAACAA CCTCAA Oligo #30 DEL3540
GCGCGCGATA TCTTGGTCTT CTTCACCATT CAGCGGCAGC GGTGGCTGCT               [SEQ ID NO:51]

Oligo #31 DEL4146
```

TABLE 2-continued

OLIGONUCLEOTIDES

GCGCGCCTCG AGGTTTGGAC GACGAAGGTT ATTTTCCATC AGGATGAGGT TGTTGAAGTC [SEQ ID NO:52]
CAGCA

Oligo #32 DEL4752

GCGCGCCTCG AGGTTTGGAC GACGAAGATC TTGGTCTTCA CCATTGA [SEQ ID NO:53]

Oligo #33 DEL5358

GCGCGCTGAT GCATTCTGCA GAGACTTGAC AGCACGGTTG AATGCCTCGT TATTTTCCAT [SEQ ID NO:54]
CAGGATAT

Oligo #34 DEL5964

GCGCGCTGAT GCATTCTGCA GAGACTTGAC GAGGTTTGGA CGACGAAGGT [SEQ ID NO:55]

Oligo #35 DEL6570

GCGCGCCTCG AGGCATTCAA CCGTGCTGCA TCAGCAATTG AGAGCAT [SEQ ID NO:56]

Oligo #36 DEL7176

GCGCGCCTGC AGAATATTCT TAAAAATCTC CTGCC [SEQ ID NO:57]

Oligo #37 DEL7782

GCGCGCCTGC AGAATGCATC AGCAATTGAG AGCCCATGTC TGCCGCTAGC CAC [SEQ ID NO:58]

Oligo #38 DEL8388

GCGCGCCTGC AGAATGCATC AGCAATTGAG AGCATTCTTA AAAATCTCCT GACGGCCGCA [SEQ ID NO:59]
CCCACGCGAC A

Oligo #39 DEL8893

CGCGCGGAAT TCATTCCAGT CACCGTCCTT GATATGGATT GGATGTCGCA GGGCAGACAT [SEQ ID NO:60]
GGCAGGA

Oligo #40 DEL106111

CGCGCGAAGC TTATTACTGT TGAGCCTGCG CGTTCTCCAA GGTTTTCAGA TAGAAGGTAT [SEQ ID NO:61]
TCCAGTCACC GTCCTTGA

Oligo #41 DEL112117

CGCGCGAAGC TTATTACTGT TGAGCCTGCG CGTTCTCCAA CAGTTTACGA CGGAATTCAT [SEQ ID NO:62]

Oligo #42 DEL118123

CGCGCGAAGC TTATTACTGT TGGGTTTTCA GATAGAAGGT CA [SEQ ID NO:63]

Oligo #43 R17IL3 Length: 000058

CGCGCGCCAT GGCTAACTGC NNSAACATGA TCGATGAAAT TATAACACAC TTAAAGCA [SEQ ID NO:64]

Oligo #44 R18IL3 Length: 000058

CGCGCGCCAT GGCTAACTGC TCTNNSATGA TCGATGAAAT TATAACACAC TTAAAGCA [SEQ ID NO:222]

Oligo #45 R19IL3 Length: 000058

CGCGCGCCAT GGCTAACTGC TCTAACNNSA TCGATGAAAT TATAACACAC TTAAAGCA [SEQ ID NO:223]

Oligo #46 R20IL3 Length: 000058

CGCGCGCCAT GGCTAACTGC TCTAACATGN NSGATGAAAT TATAACACAC TTAAAGCA [SEQ ID NO:224]

Oligo #47 R21IL3 Length: 000058

CGCGCGCCAT GGCTAACTGC TCTAACATGA TCNNSGAAAT TATAACACAC TTAAAGCA [SEQ ID NO:225]

TABLE 2-continued

OLIGONUCLEOTIDES

Oligo #48 R22IL3 Length: 000058

CGCGCGCCAT GGCTAACTGC TCTAACATGA TCGATNNSAT TATAACACAC TTAAAGCA   [SEQ ID NO:226]

Oligo #49 R23IL3 Length: 000076

CGCGCGCCAT GGCTAACTGC TCTAACATGA TCGATGAANN SATAACACAC TTAAAGCAGC [SEQ ID NO:227]

CACCTTTGCC TTTGCT

Oligo #50 R24IL3 Length: 000076

CGCGCGCCAT GGCTAACTGC TCTAACATGA TCGATGAAAT TNNSACACAC TTAAAGCAGC [SEQ ID NO:228]

CACCTTTGCC TTTGCT

Oligo #51 R25IL3 Length: 000076

CGCGCGCCAT GGCTAACTGC TCTAACATGA TCGATGAAAT TATANNSCAC TTAAAGCAGC [SEQ ID NO:229]

CACCTTTGCC TTTGCT

Oligo #52 R26IL3 Length: 000076

CGCGCGCCAT GGCTAACTGC TCTAACATGA TCGATGAAAT TATAACANNS TTAAAGCAGC [SEQ ID NO:74]

CACCTTTGCC TTTGCT

Oligo #53 R27IL3 Length: 000076

CGCGCGCCAT GGCTAACTGC TCTAACATGA TCGATGAAAT TATAACACAC NNSAAGCAGC [SEQ ID NO:75]

CACCTTTGCC TTTGCT

Oligo #54 R28IL3 Length: 000076

CGCGCGCCAT GGCTAACTGC TCTAACATGA TCGATGAAAT TATAACACAC TTANNSCAGC [SEQ ID NO:76]

CACCTTTGCC TTTGCT

Oligo #55 R29IL3 Length: 000094

CGCGCGCCAT GGCTAACTGC TCTAACATGA TCGATGAAAT TATAACACAC TTAAAGNNSC [SEQ ID NO:77]

CACCTTTGCC TTTGCTGGAC TTCAACAACC TCAA

Oligo #56 R30IL3 Length: 000094

CGCGCGCCAT GGCTAACTGC TCTAACATGA TCGATGAAAT TATAACACAC TTAAAGCAGN [SEQ ID NO:78]

NSCCTTTGCC TTTGCTGGAC TTCAACAACC TCAA

Oligo #57 R31IL3 Length: 000094

CGCGCGCCAT GGCTAACTGC TCTAACATGA TCGATGAAAT TATAACACAC TTAAAGCAGC [SEQ ID NO:79]

CANNSTTGCC TTTGCTGGAC TTCAACAACC TCAA

Oligo #58 R32IL3 Length: 000094

CGCGCGCCAT GGCTAACTGC TCTAACATGA TCGATGAAAT TATAACACAC TTAAAGCAGC [SEQ ID NO:80]

CACCTNNSCC TTTGCTGGAC TTCAACAACC TCAA

Oligo #59 R33IL3 Length: 000094

CGCGCGCCAT GGCTAACTGC TCTAACATGA TCGATGAAAT TATAACACAC TTAAAGCAGC [SEQ ID NO:81]

CACCTTTGNN STTGCTGGAC TTCAACAACC TCAA

Oligo #60 R34IL3 Length: 000094

CGCGCGCCAT GGCTAACTGC TCTAACATGA TCGATGAAAT TATAACACAC TTAAAGCAGC [SEQ ID NO:82]

CACCTTTGCC TNNSCTGGAC TTCAACAACC TCAA

Oligo #61 R35IL3 Length: 000065

TABLE 2-continued

OLIGONUCLEOTIDES

GCGCGCGATA TCTTGGTCTT CACCATTGAG GTTGTTGAAG TCSNNCAGCG GCAGCGGTGG    [SEQ ID NO:83]

CTGCT

Oligo #62 R36IL3 Length: 000065

GCGCGCGATA TCTTGGTCTT CACCATTGAG GTTGTTGAAS NNCAGCAGCG GCAGCG    [SEQ ID NO:84]

GTGGCTGCT

Oligo #63 R37IL3 Length: 000065

GCGCGCGATA TCTTGGTCTT CACCATTGAG GTTGTTSNNG TCCAGCAGCG GCAGCGGTGG    [SEQ ID NO:85]

CTGCT

Oligo #64 R38IL3 Length: 000065

GCGCGCGATA TCTTGGTCTT CACCATTGAG GTTSNNGAAG TCCAGCAGCG GCAGCGGTGG    [SEQ ID NO:86]

CTGCT

Oligo #65 R39IL3 Length: 000065

GCGCGCGATA TCTTGGTCTT CACCATTGAG SNNGTTGAAG TCCAGCAGCG GCAGCGGTGG    [SEQ ID NO:87]

CTGCT

Oligo #66 R40IL3 Length: 000065

GCGCGCGATA TCTTGGTCTT CACCATTSNN GTTGTTGAAG TCCAGCAGCG GCAGCGGTGG    [SEQ ID NO:88]

CTGCT

Oligo #67 R41IL3 Length: 000083

GCGCGCCTCG AGGTTTGGAC GACGAAGGTT ATTTTCCATC AGGATATCTT GGTCTTCACC    [SEQ ID NO:89]

SNNGAGGTTG TTGAAGTCCA GCA

Oligo #68 R42IL3 Length: 000083

GCGCGCCTCG AGGTTTGGAC GACGAAGGTT ATTTTCCATC AGGATATCTT GGTCTTCSNN    [SEQ ID NO:90]

ATTGAGGTTG TTGAAGTCCA GCA

Oligo #69 R43IL3 Length: 000083

GCGCGCCTCG AGGTTTGGAC GACGAAGGTT ATTTTCCATC AGGATATCTT GGTCSNNACC    [SEQ ID NO:91]

ATTGAGGTTG TTGAAGTCCA GCA

Oligo #70 R44IL3 Length: 000083

GCGCGCCTCG AGGTTTGGAC GACGAAGGTT ATTTTCCATC AGGATATCTT GSNNTTCACC    [SEQ ID NO:92]

ATTGAGGTTG TTGAAGTCCA GCA

Oligo #71 R45IL3 Length: 000083

GCGCGCCTCG AGGTTTGGAC GACGAAGGTT ATTTTCCATC AGGATATCSN NGTCTTCACC    [SEQ ID NO:93]

ATTGAGGTTG TTGAAGTCCA GCA

Oligo #72 R46IL3 Length: 000083

GCGCGCCTCG AGGTTTGGAC GACGAAGGTT ATTTTCCATC AGGATSNNTT GGTCTTCACC    [SEQ ID NO:94]

ATTGAGGTTG TTGAAGTCCA GCA

Oligo #73 R47IL3 Length: 000065

GCGCGCCTCG AGGTTTGGAC GACGAAGGTT ATTTTCCATC AGSNNATCTT GGTCTTCACC    [SEQ ID NO:95]

ATTGA

TABLE 2-continued

OLIGONUCLEOTIDES

Oligo #74 R48IL3 Length: 000065

GCGCGCCTCG AGGTTTGGAC GACGAAGGTT ATTTTCCATS NNGATATCTT GGTCTTCACC [SEQ ID NO:96]

ATTGA

Oligo #75 R49IL3 Length: 000065

GCGCGCCTCG AGGTTTGGAC GACGAAGGTT ATTTTCSNNC AGGATATCTT GGTCTTCACC [SEQ ID NO:97]

ATTGA

Oligo #76 R50IL3 Length: 000065

GCGCGCCTCG AGGTTTGGAC GACGAAGGTT ATTSNNCATC AGGATATCTT GGTCTTCACC [SEQ ID NO:98]

ATTGA

Oligo #77 R51IL3 Length: 000065

GCGCGCCTCG AGGTTTGGAC GACGAAGGTT SNNTTCCATC AGGATATCTT GGTCTTCACC [SEQ ID NO:99]

ATTGA

Oligo #78 R52IL3 Length: 000065

GCGCGCCTCG AGGTTTGGAC GACGAAGSNN ATTTTCCATC AGGATATCTT GGTCTTCACC [SEQ ID NO:100]

ATTGA

Oligo #79 R53IL3 Length: 000086

GCGCGCTGAT GCATTCTGCA GAGACTTGAC AGCACGGTTG AATGCCTCGA GGTTTGGACG [SEQ ID NO:101]

ACGSNNGTTA TTTTCCATCA GGATAT

Oligo #80 R54IL3 Length: 000086

GCGCGCTGAT GCATTCTGCA GAGACTTGAC AGCACGGTTG AATGCCTCGA GGTTTGGACG [SEQ ID NO:102]

SNNAAGGTTA TTTTCCATCA GGATAT

Oligo #81 R55IL3 Length: 000086

GCGCGCTGAT GCATTCTGCA GAGACTTGAC AGCACGGTTG AATGCCTCGA GGTTTGGSNN [SEQ ID NO:103]

ACGAAGGTTA TTTTCCATCA GGATAT

Oligo #82 R56IL3 Length: 000086

GCGCGCTGAT GCATTCTGCA GAGACTTGAC AGCACGGTTG AATGCCTCGA GGTTSNNACG [SEQ ID NO:104]

ACGAAGGTTA TTTTCCATCA GGATAT

Oligo #83 R57IL3 Length: 000086

GCGCGCTGAT GCATTCTGCA GAGACTTGAC AGCACGGTTG AATGCCTCGA GSNNTGGACG [SEQ ID NO:105]

ACGAAGGTTA TTTTCCATCA GGATAT

Oligo #84 R58IL3 Length: 000086

GCGCGCTGAT GCATTCTGCA GAGACTTGAC AGCACGGTTG AATGCCTCSN NGTTTGGACG [SEQ ID NO:106]

ACGAAGGTTA TTTTCCATCA GGATAT

Oligo #85 R59IL3 Length: 000068

GCGCGCTGAT GCATTCTGCA GAGACTTGAC AGCACGGTTG AATGCSNNGA GGTTTGGACG [SEQ ID NO:107]

ACGAAGGT

Oligo #86 R60IL3 Length: 000068

GCGCGCTGAT GCATTCTGCA GAGACTTGAC AGCACGGTTG AASNNCTCGA GGTTTGGACG [SEQ ID NO:108]

ACGAAGGT

TABLE 2-continued

OLIGONUCLEOTIDES

Oligo #87 R61IL3 Length: 000068

GCGCGCTGAT GCATTCTGCA GAGACTTGAC AGCACGGTTS NNTGCCTCGA GGTTTGGACG    [SEQ ID NO:109]
ACGAAGGT

Oligo #88 R62IL3 Length: 000068

GCGCGCTGAT GCATTCTGCA GAGACTTGAC AGCACGSNNG AATGCCTCGA GGTTTGGACG    [SEQ ID NO:110]
ACGAAGGT

Oligo #89 R63IL3 Length: 000068

GCGCGCTGAT GCATTCTGCA GAGACTTGAC AGCSNNGTTG AATGCCTCGA GGTTTGGACG    [SEQ ID NO:111]
ACGAAGGT

Oligo #90 R64IL3 Length: 000068

GCGCGCTGAT GCATTCTGCA GAGACTTGAC SNNACGGTTG AATGCCTCGA GGTTTGGACG    [SEQ ID NO:112]
ACGAAGGT

Oligo #91 R65IL3 Length: 000065

GCGCGCCTCG AGGCATTCAA CCGTGCTNNS AAGTCTCTGC AGAATGCATC AGCAATTGAG    [SEQ ID NO:113]
AGCAT

Oligo #92 R66IL3 Length: 000065

GCGCGCCTCG AGGCATTCAA CCGTGCTGTC NNSTCTCTGC AGAATGCATC AGCAATTGAG    [SEQ ID NO:114]
AGCAT

Oligo #93 R67IL3 Length: 000065

GCGCGCCTCG AGGCATTCAA CCGTGCTGTC AAGNNSCTGC AGAATGCATC AGCAATTGAG    [SEQ ID NO:115]
AGCAT

Oligo #94 R68IL3 Length: 000065

GCGCGCCTCG AGGCATTCAA CCGTGCTGTC AAGTCTNNSC AGAATGCATC AGCAATTGAG    [SEQ ID NO:116]
AGCAT

Oligo #95 R69IL3 Length: 000065

GCGCGCCTCG AGGCATTCAA CCGTGCTGTC AAGTCTCTGN NSAATGCATC AGCAATTGAG    [SEQ ID NO:117]
AGCAT

Oligo #96 R70IL3 Length: 000065

GCGCGCCTCG AGGCATTCAA CCGTGCTGTC AAGTCTCTGC AGNNSGCATC AGCAATTGAG    [SEQ ID NO:118]
AGCAT

Oligo #97 R71IL3 Length: 000053

GCGCGCCTGC AGAATNNSTC AGCAATTGAG AGCATTCTTA AAAATCTCCT GCC           [SEQ ID NO:119]

Oligo #98 R72IL3 Length: 000053

GCGCGCCTGC AGAATGCANN SGCAATTGAG AGCATTCTTA AAAATCTCCT GCC           [SEQ ID NO:120]

Oligo #99 R73IL3 Length: 000053

GCGCGCCTGC AGAATGCATC ANNSATTGAG AGCATTCTTA AAAATCTCCT GCC           [SEQ ID NO:121]

Oligo #100 R74IL3 Length: 000053

GCGCGCCTGC AGAATGCATC AGCANNSGAG AGCATTCTTA AAAATCTCCT GCC           [SEQ ID NO:122]

TABLE 2-continued

OLIGONUCLEOTIDES

Oligo #101 R75IL3 Length: 000053

GCGCGCCTGC AGAATGCATC AGCAATTNNS AGCATTCTTA AAAATCTCCT GCC          [SEQ ID NO:123]

Oligo #102 R76IL3 Length: 000053

GCGCGCCTGC AGAATGCATC AGCAATTGAG NNSATTCTTA AAAATCTCCT GCC          [SEQ ID NO:124]

Oligo #103 R77IL3 Length: 000071

GCGCGCCTGC AGAATGCATC AGCAATTGAG AGCNNSCTTA AAAATCTCCT GCCATGTCTG   [SEQ ID NO:125]

CCGCTAGCCA C

Oligo #104 R78IL3 Length: 000071

GCGCGCCTGC AGAATGCATC AGCAATTGAG AGCATTNNSA AAAATCTCCT GCCATGTCTG   [SEQ ID NO:126]

CCGCTAGCCA C

Oligo #105 R79IL3 Length: 000071

GCGCGCCTGC AGAATGCATC AGCAATTGAG AGCATTCTTN NSAATCTCCT GCCATGTCTG   [SEQ ID NO:127]

CCGCTAGCCA C

Oligo #106 R80IL3 Length: 000071

GCGCGCCTGC AGAATGCATC AGCAATTGAG AGCATTCTTA AANNSCTCCT GCCATGTCTG   [SEQ ID NO:138]

CCGCTAGCCA C

Oligo #107 R81IL3 Length: 000071

GCGCGCCTGC AGAATGCATC AGCAATTGAG AGCATTCTTA AAAATNNSCT GCCATGTCTG   [SEQ ID NO:139]

CCGCTAGCCA C

Oligo #108 R82IL3 Length: 000071

GCGCGCCTGC AGAATGCATC AGCAATTGAG AGCATTCTTA AAAATCTCNN SCCATGTCTG   [SEQ ID NO:140]

CCGCTAGCCA C

Oligo #109 R83IL3 Length: 000089

GCGCGCCTGC AGAATGCATC AGCAATTGAG AGCATTCTTA AAAATCTCCT GNNSTGTCTG   [SEQ ID NO:141]

CCGCTAGCCA CGGCCGCACC CACGCGACA

Oligo #110 R84IL3 Length: 000089

GCGCGCCTGC AGAATGCATC AGCAATTGAG AGCATTCTTA AAAATCTCCT GCCANNSCTG   [SEQ ID NO:142]

CCGCTAGCCA CGGCCGCACC CACGCGACA

Oligo #111 R85IL3 Length: 000089

GCGCGCCTGC AGAATGCATC AGCAATTGAG AGCATTCTTA AAAATCTCCT GCCATGTNNS   ]SEQ ID NO:143]

CCGCTAGCCA CGGCCGCACC CACGCGACA

Oligo #112 R86IL3 Length: 000089

GCGCGCCTGC AGAATGCATC AGCAATTGAG AGCATTCTTA AAAATCTCCT GCCATGTCTG   [SEQ ID NO:157]

NNSCTAGCCA CGGCCGCACC CACGCGACA

Oligo #113 R87IL3 Length: 000089

GCGCGCCTGC AGAATGCATC AGCAATTGAG AGCATTCTTA AAAATCTCCT GCCATGTCTG   [SEQ ID NO:158]

CCGNNSGCCA CGGCCGCACC CACGCGACA

Oligo #114 R88IL3 Length: 000089

GCGCGCCTGC AGAATGCATC AGCAATTGAG AGCATTCTTA AAAATCTCCT GCCATGTCTG   [SEQ ID NO:159]

TABLE 2-continued

OLIGONUCLEOTIDES

CCGCTANNSA CGGCCGCACC CACGCGACA

Oligo #115 R89IL3 Length: 000086

CGCGCGGAAT TCATTCCAGT CACCGTCCTT GATATGGATT GGATGTCGCG TGGGTGCGGC    [SEQ ID NO:160]

SNNGGCCAGG GGCAGACATG GCAGGA

Oligo #116 R90IL3 Length: 000086

CGCGCGGAAT TCATTCCAGT CACCGTCCTT GATATGGATT GGATGTCGCG TGGGTGCSNN    [SEQ ID NO:161]

CGTGGCCAGG GGCAGACATG GCAGGA

Oligo #117 R91IL3 Length: 000086

CGCGCGGAAT TCATTCCAGT CACCGTCCTT GATATGGATT GGATGTCGCG TGGGSNNGGC    [SEQ ID NO:162]

CGTGGCCAGG GGCAGACATG GCAGGA

Oligo #118 R92IL3 Length: 000086

CGCGCGGAAT TCATTCCAGT CACCGTCCTT GATATGGATT GGATGTCGCG TSNNTGCGGC    [SEQ ID NO:163]

CGTGGCCAGG GGCAGACATG GCAGGA

Oligo #119 R93IL3 Length: 000086

CGCGCGGAAT TCATTCCAGT CACCGTCCTT GATATGGATT GGATGTCGSN NGGGTGCGGC    [SEQ ID NO:164]

CGTGGCCAGG GGCAGACATG GCAGGA

Oligo #120 3PR106 Length: 000048

TTTCAGATAG AAGGTCAGTT TACGACGGAA SNNATTCCAG TCACCGTC    [SEQ ID NO:165]

Oligo #121 3PR107 Length: 000048

TTTCAGATAG AAGGTCAGTT TACGACGSNN TTCATTCCAG TCACCGTC    [SEQ ID NO:166]

Oligo #122 3PR108 Length: 000048

TTTCAGATAG AAGGTCAGTT TACGSNNGAA TTCATTCCAG TCACCGTC    [SEQ ID NO:167]

Oligo #123 3PR109 Length: 000048

TTTCAGATAG AAGGTCAGTT TSNNACGGAA TTCATTCCAG TCACCGTC    [SEQ ID NO:168]

Oligo #124 3PR110 Length: 000048

TTTCAGATAG AAGGTCAGSN NACGACGGAA TTCATTCCAG TCACCGTC    [SEQ ID NO:169]

Oligo #125 3PR111 Length: 000048

TTTCAGATAG AAGGTSNNTT TACGACGGAA TTCATTCCAG TCACCGTC    [SEQ ID NO:170]

Oligo #126 IL3MUTD3 Length: 000023

CGCGCGAAGC TTATTACTGT TGA    [SEQ ID NO:171]

Oligo #127 R112IL3 Length: 000078

CGCGCGAAGC TTATTACTGT TGAGCCTGCG CGTTCTCCAA GGTTTTCAGA TAGAASNNCA    [SEQ ID NO:172]

GTTTACGACG GAATTCAT

Oligo #128 R113IL3 Length: 000078

CGCGCGAAGC TTATTACTGT TGAGCCTGCG CGTTCTCCAA GGTTTTCAGA TASNNGGTCA    [SEQ ID NO:173]

GTTTACGACG GAATTCAT

Oligo #129 R114IL3 Length: 000078

CGCGCGAAGC TTATTACTGT TGAGCCTGCG CGTTCTCCAA GGTTTTCAGS NNGAAGGTCA    [SEQ ID NO:174]

TABLE 2-continued

OLIGONUCLEOTIDES

GTTTACGACG GAATTCAT

Oligo #130 R115IL3 Length: 000078

CGCGCGAAGC TTATTACTGT TGAGCCTGCG CGTTCTCCAA GGTTTTCAGS NNGAAGGTCA [SEQ ID NO:175]

GTTTACGACG GAATTCAT

Oligo #131 R116IL3 Length: 000078

CGCGCGAAGC TTATTACTGT TGAGCCTGCG CGTTCTCCAA GGTSNNCAGA TAGAAGGTCA [SEQ ID NO:176]

GTTTACGACG GAATTCAT

Oligo #132 R117IL3 Length: 000078

CGCGCGAAGC TTATTACTGT TGAGCCTGCG CGTTCTCCAA SNNTTTCAGA TAGAAGGTCA [SEQ ID NO:177]

GTTTACGACG GAATTCAT

Oligo #133 R118IL3 Length: 000060

CGCGCGAAGC TTATTACTGT TGAGCCTGCG CGTTCTCSNN GGTTTTCAGA TAGAAGGTCA [SEQ ID NO:178]

Oligo #134 R119IL3 Length: 000060

CGCGCGAAGC TTATTACTGT TGAGCCTGCG CGTTSNNCAA GGTTTTCAGA TAGAAGGTCA [SEQ ID NO:179]

Oligo #135 R120IL3 Length: 000060

CGCGCGAAGC TTATTACTGT TGAGCCTGCG CSNNCTCCAA GGTTTTCAGA TAGAAGGTCA [SEQ ID NO:180]

Oligo #136 R121IL3 Length: 000060

CGCGCGAAGC TTATTACTGT TGAGCCTGSN NGTTCTCCAA GGTTTTCAGA TAGAAGGTCA [SEQ ID NO:181]

Oligo #137 R122IL3 Length: 000060

CGCGCGAAGC TTATTACTGT TGAGCSNNCG CGTTCTCCAA GGTTTTCAGA TAGAAGGTCA [SEQ ID NO:182]

Oligo #138 R123IL3 Length: 000060

CGCGCGAAGC TTATTACTGT TGSNNCTGCG CGTTCTCCAA GGTTTTCAGA TAGAAGGTCA [SEQ ID NO:183]

Oligo #139 P1722IL3 Length: 000024

TGCTCTAACA TGATCGATGA AATT [SEQ ID NO:184]

Oligo #140 P2328IL3 Length: 000024

GAAATTATAA CACACTTAAA GCAG [SEQ ID NO:185]

Oligo #141 P2934IL3 Length: 000024

AAGCAGCCAC CTTTGCCTTT GCTG [SEQ ID NO:186]

Oligo #142 P3540IL3 Length: 000024

AAGCAGCCAC CGCTGCCGCT GCTG [SEQ ID NO:187]

Oligo #143 PRB41-46 Length: 000024

CTCAATGGTG AAGACCAAGA TATC [SEQ ID NO:188]

Oligo #144 PRB47-52 Length: 000024

GATATCCTGA TGGAAAATAA CCTT [SEQ ID NO:189]

Oligo #145 PRB53-58 Length: 000024

AACCTTCGTC GTCCAAACCT CGAG [SEQ ID NO:190]

Oligo #146 PRB59-64 Length: 000024

CTCGAGGCAT TCAACCGTGC TGTC [SEQ ID NO:191]

Oligo #147 PRB65-70 Length: 000024

TABLE 2-continued

OLIGONUCLEOTIDES

GCTGTCAAGT CTCTGCAGAA TGCA  [SEQ ID NO:192]

Oligo #148 P7176IL3 Length: 000024

AATGCATCAG CAATTGAGAG CATT  [SEQ ID NO:193]

Oligo #149 P7782IL3 Length: 000024

AGCATTCTTA AAAATCTCCT GCCA  [SEQ ID NO:194]

Oligo #150 P8388IL3 Length: 000024

CTGCCATGTC TGCCCCTGGC CACG  [SEQ ID NO:195]

Oligo #151 P8893IL3 Length: 000024

CTGGCCACGG CCGCACCCAC GCGA  [SEQ ID NO:196]

Oligo #152 P106111 Length: 000024

AATGAATTCC GTCGTAAACT GACC  [SEQ ID NO:197]

Oligo #153 P112117 Length: 000024

CTGACCTTCT ATCTGAAAAC CTTG  [SEQ ID NO:198]

Oligo #154 P118123 Length: 000024

ACCTTGGAGA ACGCGCAGGC TCAA  [SEQ ID NO:199]

Oligo #155 PSTERCI1.REQ Length: 000022

GAATGCATCA GCAATTGAGA GC  [SEQ ID NO:200]

Oligo #156 PSTECRI5.REQ Length: 000020

AATTGCTGAT GCATTCTGCA  [SEQ ID NO:201]

Oligo #157 PSTECRI2.REQ Length: 000024

ATTCTTAAAA ATCTCCTGCC ATGT  [SEQ ID NO:202]

Oligo #158 PSTECRI6.REQ Length: 000024

CAGGAGATTT TTAAGAATGC TCTC  [SEQ ID NO:203]

Oligo #159 PSTECRI3.REQ Length: 000030

CTGCCCCTGG CCACGGCCGC ACCCACGCGA  [SEQ ID NO:204]

Oligo #160 PSTECRI7.REQ Length: 000030

GGGTGCGGCC GTGGCCAGGG GCAGACATGG  [SEQ ID NO:205]

Oligo #161 98I100R4.REQ Length: 000034

CATCCAATCA TCATCCGTGA CGGTGACTGG AATG  [SEQ ID NO:206]

Oligo #162 98I100R8.REQ Length: 000044

AATTCATTCC AGTCACCGTC ACGGATGATG ATTGGATGTC GCGT  [SEQ ID NO:207]

Oligo #163 95R8I0R4.REQ Length: 000034

CGCCCAATCA TCATCCGTGA CGGTGACTGG AATG  [SEQ ID NO:208]

Oligo #164 95R8I0R8.REQ Length: 000044

AATTCATTCC AGTCACCGTC ACGGATGATG ATTGGGCGTC GCGT  [SEQ ID NO:209]

Oligo #165 NCOECRV1.REQ Length: 000040

CATGGCTAAC TGCTCTAACA TGATCGATGA AATTATAACA  [SEQ ID NO:210]

Oligo #166 NCOECRV4.REQ Length: 000045

TABLE 2-continued

| OLIGONUCLEOTIDES | |
|---|---|
| CTTTAAGTGT GTTATAATTT CATCGATCAT GTTAGAGCAG TTAGC | [SEQ ID NO:211] |
| Oligo #167 NCOECRV2.REQ Length: 000036 | |
| CACTTAAAGC AGCCACCTTT GCCTTTGCTG GACTTC | [SEQ ID NO:212] |
| Oligo #168 NCOECRV5.REQ Length: 000036 | |
| GAGGTTGTTG AAGTCCAGCA AAGGCAAAGG TGGCTG | [SEQ ID NO:213] |
| Oligo #169 2D5M6SUP.REQ Length: 000027 | |
| AACAACCTCA ATGACGAAGA CATGTCT | [SEQ ID NO:214] |
| Oligo #170 2D5M6SLO.REQ Length: 000018 | |
| AGACATGTCT TCGTCATT | [SEQ ID NO:215] |
| Oligo #15(A) Length: 000016 | |
| TGAACCATAT GTCAGG | [SEQ ID NO:29] |
| Oligo #16(A) Length: 000024 | |
| AATTCCTGAC ATATGGTTCA TGCA | [SEQ ID NO:30] |
| Oligo #51(A) Length: 000034 | |
| GCCGATACCGCGGCATACTCCCACCATTCAGAGA | [SEQ ID NO:155] |
| Oligo #52(A) Length: 000033 | |
| GCCGATAAGATCTAAAACGGGTATGGAGAAACA | [SEQ ID NO:156] |
| Oligo #171 Length: 000040 | |
| CATGGCTAAC TGCTCTAACA TGATCAACGA AATTATAACA | [SEQ ID NO:69] |
| Oligo #172 Length: 000045 | |
| CTTTAAGTGT GTTATAATTT CGTTGATCAT GTTAGAGCAG TTAGC | [SEQ ID NO:70] |
| Oligo #173 Length: 000040 | |
| CATGGCTAAC TGCTCTAACA TGATCCAAGA AATTATAACA | [SEQ ID NO:71] |
| Oligo #174 Length: 000045 | |
| CTTTAAGTGT GTTATAATTT CTTGGATCAT GTTAGAGCAG TTAGC | [SEQ ID NO:72] |
| Oligo #175 Length: 000040 | |
| CATGGCTAAC TGCTCTAACA TGATCGAAGA AATTATAACA | [SEQ ID NO:73] |
| Oligo #176 Length: 000045 | |
| CTTTAAGTGT GTTATAATTT CTTCGATCAT GTTAGAGCAG TTAGC | [SEQ ID NO:219] |
| Oligo #177 Length: 000040 | |
| CATGGCTAAC TGCTCTAACA TGATCAGCGA AATTATAACA | [SEQ ID NO:230] |
| Oligo #178 Length: 000045 | |
| CTTTAAGTGT GTTATAATTT CGCTGATCAT GTTAGAGCAG TTAGC | [SEQ ID NO:231] |
| Oligo #179 Length: 000040 | |
| CATGGCTAAC TGCTCTAACA TGATCACCGA AATTATAACA | [SEQ ID NO:232] |
| Oligo #180 Length: 000045 | |
| CTTTAAGTGT GTTATAATTT CCGTGATCAT GTTAGAGCAG TTAGC | [SEQ ID NO:233] |
| Oligo #181 Length: 000040 | |
| CATGGCTAAC TGCTCTAACA TGATCGATAA CATTATAACA | [SEQ ID NO:234] |

TABLE 2-continued

OLIGONUCLEOTIDES

Oligo #182 Length: 000045

CTTTAAGTGT GTTATAATGT TATCGATCAT GTTAGAGCAG TTAGC  [SEQ ID NO:235]

Oligo #183 Length: 000040

CATGGCTAAC TGCTCTAACA TGATCGATGA CATTATAACA  [SEQ ID NO:236]

Oligo #184 Length: 000045

CTTTAAGTGT GTTATAATGT CATCGATCAT GTTAGAGCAG TTAGC  [SEQ ID NO:237]

Oligo #185 Length: 000040

CATGGCTAAC TGCTCTAACA TGATCGATCA GATTATAACA  [SEQ ID NO:238]

Oligo #186 Length: 000045

CTTTAAGTGT GTTATAATCT GATCGATCAT GTTAGAGCAG TTAGC  [SEQ ID NO:239]

Oligo #187 Length: 000040

CATGGCTAAC TGCTCTAACA TGATCGATCT GATTATAACA  [SEQ ID NO:240]

Oligo #188 Length: 000045

CTTTAAGTGT GTTATAATCA GATCGATCAT GTTAGAGCAG TTAGC  [SEQ ID NO:241]

Oligo #189 Length: 000040

CATGGCTAAC TGCTCTAACA TGATCGATGT TATTATAACA  [SEQ ID NO:242]

Oligo #190 Length: 000045

CTTTAAGTGT GTTATAATAA CATCGATCAT GTTAGAGCAG TTAGC  [SEQ ID NO:243]

Oligo #191 Length: 000036

CACTTAAAGC AGCCACCTTT GCCTGCTCTG GACTTC  [SEQ ID NO:244]

Oligo #192 Length: 000036

GAGGTTGTTG AAGTCCAGAG CAGGCAAAGG TGGCTG  [SEQ ID NO:245]

Oligo #193 Length: 000036

CACTTAAAGC AGCCACCTTT GCCTCGTCTG GACTTC  [SEQ ID NO:246]

Oligo #194 Length: 000036

GAGGTTGTTG AAGTCCAGAC GAGGCAAAGG TGGCTG  [SEQ ID NO:247]

Oligo #195 Length: 000036

CACTTAAAGC AGCCACCTTT GCCTCAGCTG GACTTC  [SEQ ID NO:248]

Oligo #196 Length: 000036

GAGGTTGTTG AAGTCCAGCT GAGGCAAAGG TGGCTG  [SEQ ID NO:249]

Oligo #197 Length: 000036

CACTTAAAGC AGCCACCTTT GCCTGAACTG GACTTC  [SEQ ID NO:250]

Oligo #198 Length: 000036

GAGGTTGTTG AAGTCCAGCT CAGGCAAAGG TGGCTG  [SEQ ID NO:251]

Oligo #199 Length: 000036

CACTTAAAGC AGCCACCTTT GCCTATCCTG GACTTC  [SEQ ID NO:252]

Oligo #200 Length: 000036

GAGGTTGTTG AAGTCCAGGA TAGGCAAAGG TGGCTG  [SEQ ID NO:253]

TABLE 2-continued

OLIGONUCLEOTIDES

Oligo #201 Length: 000036

CACTTAAAGC AGCCACCTTT CCCTTTCCTG GACTTC  [SEQ ID NO:254]

Oligo #202 Length: 000036

GAGGTTGTTG AAGTCCAGGA AAGGCAAAGG TGGCTG  [SEQ ID NO:255]

Oligo #203 Length: 000036

CACTTAAAGC AGCCACCTTT GCCTACCCTG GACTTC  [SEQ ID NO:256]

Oligo #204 Length: 000036

GAGGTTGTTG AAGTCCAGGG TAGGCAAAGG TGGCTG  [SEQ ID NO:257]

Oligo #205 Length: 000027

AACAACCTCA ATCGTGAAGA CCAAGAT  [SEQ ID NO:258]

Oligo #206 Length: 000018

ATCTTGGTCT TCACGATT  [SEQ ID NO:259]

Oligo #207 Length: 000027

AACAACCTCA ATAACGAAGA CCAAGAT  [SEQ ID NO:260]

Oligo #208 Length: 000018

ATCTTGGTCT TCGTTATT  [SEQ ID NO:261]

Oligo #209 Length: 000027

AACAACCTCA ATGAAGAAGA CCAAGAT  [SEQ ID NO:262]

Oligo #210 Length: 000018

ATCTTGGTCT TCTTCATT  [SEQ ID NO:263]

Oligo #211 Length: 000027

AACAACCTCA ATATCGAAGA CCAAGAT  [SEQ ID NO:264]

Oligo #212 Length: 000018

ATCTTGGTCT TCGATATT  [SEQ ID NO:265]

Oligo #213 Length: 000027

AACAACCTCA ATCTGGAAGA CCAAGAT  [SEQ ID NO:266]

Oligo #214 Length: 000018

ATCTTGGTCT TCCAGATT  [SEQ ID NO:267]

Oligo #215 Length: 000027

AACAACCTCA ATAAAGAAGA CCAAGAT  [SEQ ID NO:268]

Oligo #216 Length: 000018

ATCTTGGTCT TCTTTATT  [SEQ ID NO:269]

Oligo #217 Length: 000027

AACAACCTCA ATATGGAAGA CCAAGAT  [SEQ ID NO:270]

Oligo #218 Length: 000018

ATCTTGGTCT TCCATATT  [SEQ ID NO:271]

Oligo #219 Length: 000027

AACAACCTCA ATTTCGAAGA CCAAGAT  [SEQ ID NO:272]

Oligo #220 Length: 000018

TABLE 2-continued

OLIGONUCLEOTIDES

ATCTTGGTCT TCGAAATT [SEQ ID NO:273]

Oligo #221 Length: 000027

AACAACCTCA ATACCGAAGA CCAAGAT [SEQ ID NO:274]

Oligo #222 Length: 000018

ATCTTGGTCT TCGGTATT [SEQ ID NO:275]

Oligo #223 Length: 000027

AACAACCTCA ATTACGAAGA CCAAGAT [SEQ ID NO:276]

Oligo #224 Length: 000018

ATCTTGGTCT TCGTAATT [SEQ ID NO:277]

Oligo #225 Length: 000027

AACAACCTCA ATGTTGAAGA CCAAGAT [SEQ ID NO:278]

Oligo #226 Length: 000018

ATCTTGGTCT TCAACATT [SEQ ID NO:279]

Oligo #227 Length: 000027

AACAACCTCA ATGGCGTGA CCAAGAT [SEQ ID NO:280]

Oligo #228 Length: 000018

ATCTTGGTCT CGCCCATT [SEQ ID NO:281]

Oligo #229 Length: 000027

AACAACCTCA ATGGGCAGGA CCAAGAT [SEQ ID NO:282]

Oligo #230 Length: 000018

ATCTTGGTCC TGCCCATT [SEQ ID NO:283]

Oligo #231 Length: 000027

AACAACCTCA ATGGGGTGA CCAAGAT [SEQ ID NO:284]

Oligo #232 Length: 000018

ATCTTGGTCA CCCCCATT [SEQ ID NO:285]

Oligo #233 Length: 000027

AACAACCTCA ATGGGACCGA CCAAGAT [SEQ ID NO:286]

Oligo #234 Length: 000018

ATCTTGGTCG GTCCCATT [SEQ ID NO:287]

Oligo #235 Length: 000027

AACAACCTCA ATGGGAAGC TCAAGAT [SEQ ID NO:288]

Oligo #236 Length: 000018

ATCTTGAGCT TCCCCATT [SEQ ID NO:289]

Oligo #237 Length: 000027

AACAACCTCA ATGGGAAAA CCAAGAT [SEQ ID NO:290]

Oligo #238 Length: 000018

ATCTTGGTTT TCCCCATT [SEQ ID NO:291]

Oligo #239 Length: 000027

TABLE 2-continued

| OLIGONUCLEOTIDES | |
|---|---|
| AACAACCTCA ATGGGGAACA GCAAGAT | [SEQ ID NO:292] |

Oligo #240 Length: 000018

| ATCTTGCTGT TCCCCATT | [SEQ ID NO:293] |
|---|---|

Oligo #241 Length: 000027

| AACAACCTCA ATGGGGAAGA ACAAGAT | [SEQ ID NO:294] |
|---|---|

Oligo #242 Length: 000018

| ATCTTGTTCT TCCCCATT | [SEQ ID NO:295] |
|---|---|

Oligo #243 Length: 000027

| AACAACCTCA ATGGGGAAGA CGCTGAT | [SEQ ID NO:296] |
|---|---|

Oligo #244 Length: 000018

| ATCAGCGTCT TCCCCATT | [SEQ ID NO:297] |
|---|---|

Oligo #245 Length: 000027

| AACAACCTCA ATGGGGAAGA CCGTGAT | [SEQ ID NO:298] |
|---|---|

Oligo #246 Length: 000018

| ATCACGGTCT TCCCCATT | [SEQ ID NO:299] |
|---|---|

Oligo #247 Length: 000027

| AACAACCTCA ATGGGGAAGA CAACGAT | [SEQ ID NO:300] |
|---|---|

Oligo #248 Length: 000018

| ATCGTTGTCT TCCCCATT | [SEQ ID NO:301] |
|---|---|

Oligo #249 Length: 000027

| AACAACCTCA ATGGGGAAGA CGACGAT | [SEQ ID NO:302] |
|---|---|

Oligo #250 Length: 000018

| ATCGTCGTCT TCCCCATT | [SEQ ID NO:303] |
|---|---|

Oligo #251 Length: 000027

| AACAACCTCA ATGGTGAAGA CGAAGAT | [SEQ ID NO:304] |
|---|---|

Oligo #252 Length: 000018

| ATCTTCGTCT TCCCCATT | [SEQ ID NO:305] |
|---|---|

Oligo #253 Length: 000027

| AACAACCTCA ATGGTGAAGA CCACGAT | [SEQ ID NO:306] |
|---|---|

Oligo #254 Length: 000018

| ATCGTGGTCT TCCCCATT | [SEQ ID NO:307] |
|---|---|

Oligo #255 Length: 000027

| AACAACCTCA ATGGGGAAGA CATCGAT | [SEQ ID NO:308] |
|---|---|

Oligo #256 Length: 000018

| ATCGATGTCT TCCCCATT | [SEQ ID NO:309] |
|---|---|

Oligo #257 Length: 000027

| AACAACCTCA ATGGGGAAGA CTCCGAT | [SEQ ID NO:310] |
|---|---|

Oligo #258 Length: 000018

| ATCGGAGTCT TCCCCATT | [SEQ ID NO:311] |
|---|---|

TABLE 2-continued

OLIGONUCLEOTIDES

Oligo #259 Length: 000027

AACAACCTCA ATGGGAAGA CCAAGCT [SEQ ID NO:312]

Oligo #260 Length: 000018

AGCTTGGTCT TCCCCATT [SEQ ID NO:313]

Oligo #261 Length: 000027

AACAACCTCA ATGGGAAGA CCAAAAC [SEQ ID NO:314]

Oligo #262 Length: 000018

GTTTTGGTCT TCCCCATT [SEQ ID NO:315]

Oligo #263 Length: 000027

AACAACCTCA ATGGGAAGA CCAACAG [SEQ ID NO:316]

Oligo #264 Length: 000018

CTGTTGGTCT TCCCCATT [SEQ ID NO:317]

Oligo #265 Length: 000027

AACAACCTCA ATGGGAAGA CCAAGAA [SEQ ID NO:318]

Oligo #266 Length: 000018

TTCTTGGTCT TCCCCATT [SEQ ID NO:319]

Oligo #267 Length: 000027

AACAACCTCA ATGGGAAGA CCAACAC [SEQ ID NO:320]

Oligo #268 Length: 000018

GTGTTGGTCT TCCCCATT [SEQ ID NO:321]

Oligo #269 Length: 000027

AACAACCTCA ATGGGAAGA CCAAATC [SEQ ID NO:322]

Oligo #270 Length: 000018

GATTTGGTCT TCCCCATT [SEQ ID NO:323]

Oligo #271 Length: 000027

AACAACCTCA ATGGGAAGA CCAACTG [SEQ ID NO:324]

Oligo #272 Length: 000018

CAGTTGGTCT TCCCCATT [SEQ ID NO:325]

Oligo #273 Length: 000027

AACAACCTCA ATGGGAAGA CCAAAAA [SEQ ID NO:326]

Oligo #274 Length: 000018

TTTTTGGTCT TCCCCATT [SEQ ID NO:327]

Oligo #275 Length: 000027

AACAACCTCA ATGGGAAGA CCAATAC [SEQ ID NO:328]

Oligo #276 Length: 000018

GTATTGGTCT TCCCCATT [SEQ ID NO:329]

Oligo #277 Length: 000027

AACAACCTCA ATGGGAAGA CCAAGTT [SEQ ID NO:330]

TABLE 2-continued

OLIGONUCLEOTIDES

Oligo #278 Length: 000018

AACTTGGTCT TCCCCATT                                    [SEQ ID NO:331]

Oligo #279 Length: 000036

ATCGCTATGG AAAATAACCT TCGAAGGCCA AACCTG                [SEQ ID NO:332]

Oligo #280 Length: 000027

CCTTCGAAGG TTATTTTCCA TAGCGAT                          [SEQ ID NO:333]

Oligo #281 Length: 000036

ATCGAAATGG AAAATAACCT TCGAAGGCCA AACCTG                [SEQ ID NO:334]

Oligo #282 Length: 000027

CCTTCGAAGG TTATTTTCCA TTTCGAT                          [SEQ ID NO:335]

Oligo #283 Length: 000036

ATCAAAATGG AAAATAACT TCGAAGGCCA AACCTG                 [SEQ ID NO:336]

Oligo #284 Length: 000027

CCTTCGAAGG TTATTTTCCA TTTTGAT                          [SEQ ID NO:337]

Oligo #285 Length: 000036

ATCATGATGG AAAATAACCT TCGAAGGCCA AACCTG                [SEQ ID NO:338]

Oligo #286 Length: 000027

CCTTCGAAGG TTATTTTCA TCATGAT                           [SEQ ID NO:339]

Oligo #287 Length: 000036

ATCACCATGG AAAATAACCT TCGAAGGCCA AACCTG                [SEQ ID NO:340]

Oligo #288 Length: 000027

CCTTCGAAGG TTATTTTCCA TGGTGAT                          [SEQ ID NO:341]

Oligo #289 Length: 000036

ATCGTTATGG AAAATAACCT TCGAAGGCCA AACCTG                [SEQ ID NO:342]

Oligo #290 Length: 000027

CCTTCGAAGG TTATTTTCCA TAACGAT                          [SEQ ID NO:343]

Oligo #291 Length: 000036

ATCCTGATGC ACAATAACCT TCGAAGGCCA AACCTG                [SEQ ID NO:344]

Oligo #292 Length: 000027

CCTTCGAAGG TTATTGTGCA TCAGGAT                          [SEQ ID NO:345]

Oligo #293 Length: 000036

ATCCTGATGA TGAATAACCT TCGAAGGCCA AACCTG                [SEQ ID NO:346]

Oligo #294 Length: 000027

CCTTCGAAGG TTATTCATCA TCAGGAT                          [SEQ ID NO:347]

Oligo #295 Length: 000036

ATCCTGATGT TCAATAACCT TCGAAGGCA AACCTG                 [SEQ ID NO:348]

Oligo #296 Length: 000027

CCTTCGAAGG TTATTGAACA TCAGGAT                          [SEQ ID NO:349]

Oligo #297 Length: 000036

TABLE 2-continued

OLIGONUCLEOTIDES

ATCCTGATGG CTAATAACCT TCGAAGGCCA AACCTG [SEQ ID NO:350]

Oligo #298 Length: 000027

CCTTCGAAGG TTATTAGCCA TCAGGAT [SEQ ID NO:351]

Oligo #299 Length: 000036

ATCCTGATGA ACAATAACCT TCGAAGGCCA AACCTG [SEQ ID NO:352]

Oligo #300 Length: 000027

CCTTCGAAGG TTATTGTTCA TCAGGAT [SEQ ID NO:353]

Oligo #301 Length: 000036

ATCCTGATGA TCAATAACCT TCGAAGGCCA AACCTG [SEQ ID NO:354]

Oligo #302 Length: 000027

CCTTCGAAGG TTATTGATCA TCAGGAT [SEQ ID NO:355]

Oligo #303 Length: 000036

ATCCTGATGA AAAATAACCT TCGAAGGCCA AACCTG [SEQ ID NO:356]

Oligo #304 Length: 000027

CCTTCGAAGG TTATTTTTCA TCAGGAT [SEQ ID NO:357]

Oligo #305 Length: 000036

ATCCTGATGT CCAATAACCT TCGAAGGCCA AACCTG [SEQ ID NO:358]

Oligo #306 Length: 000027

CCTTCGAAGG TTATTGGACA TCAGGAT [SEQ ID NO:359]

Oligo #307 Length: 000036

ATCCTGATGG TTAATAACCT TCGAAGGCCA AACCTG [SEQ ID NO:360]

Oligo #308 Length: 000027

CCTTCGAAGG TTATTAACCA TCAGGAT [SEQ ID NO:361]

Oligo #309 Length: 000036

ATCCTGATGG AAAATAACCT TGCTAGGCCA AACCTG [SEQ ID NO:362]

Oligo #310 Length: 000027

CCTAGCAAGG TTATTTTCCA TCAGGAT [SEQ ID NO:363]

Oligo #311 Length: 000036

ATCCTGATGG AAAATAACCT TAACAGGCCA AACCTG [SEQ ID NO:364]

Oligo #312 Length: 000027

CCTGTTAAGG TTATTTTCCA TCAGGAT [SEQ ID NO:365]

Oligo #313 Length: 000036

ATCCTGATGG AAAATAACCT TCACAGGCCA AACCTG [SEQ ID NO:366]

Oligo #314 Length: 000027

CCTGTGAAGG TTATTTTCCA TCAGGAT [SEQ ID NO:367]

Oligo #315 Length: 000036

ATCCTGATGG AAAATAACCT TAAAAGGCCA AACCTG [SEQ ID NO:368]

Oligo #316 Length: 000027

TABLE 2-continued

OLIGONUCLEOTIDES

| | |
|---|---|
| CCTTTTAAGG TTATTTTCCA TCAGGAT | [SEQ ID NO:369] |
| Oligo #317 Length: 000036 | |
| ATCCTGATGG AAAATAACCT TCGAAGGGCT AACCTG | [SEQ ID NO:370] |
| Oligo #318 Length: 000024 | |
| CCTGTTGAAT GCCTCCAGGT TAGC | [SEQ ID NO:371] |
| Oligo #319 Length: 000036 | |
| ATCCTGATGG AAAATAACCT TCGAAGGCGT AACCTG | [SEQ ID NO:372] |
| Oligo #320 Length: 000024 | |
| CCTGTTGAAT GCCTCCAGGT TACG | [SEQ ID NO:373] |
| Oligo #321 Length: 000036 | |
| ATCCTGATGG AAAATAACCT TCGAAGGAAC AACCTG | [SEQ ID NO:374] |
| Oligo #322 Length: 000024 | |
| CCTGTTGAAT GCCTCCAGGT TGTT | [SEQ ID NO:375] |
| Oligo #323 Length: 000036 | |
| ATCCTGATGG AAAATAACCT TCGAAGGGAA AACCTG | [SEQ ID NO:376] |
| Oligo #324 Length: 000024 | |
| CCTGTTGAAT GCCTCCAGGT TTTC | [SEQ ID NO:377] |
| Oligo #325 Length: 000036 | |
| ATCCTGATGG AAAATAACCT TCGAAGGCAC AACCTG | [SEQ ID NO:378] |
| Oligo #326 Length: 000024 | |
| CCTGTTGAAT GCCTCCAGGT TGTG | [SEQ ID NO:379] |
| Oligo #327 Length: 000036 | |
| ATCCTGATGG AAAATAACCT TCGAAGGCTG AACCTG | [SEQ ID NO:380] |
| Oligo #328 Length: 000024 | |
| CCTGTTGAAT GCCTCCAGGT TCAG | [SEQ ID NO:381] |
| Oligo #329 Length: 000036 | |
| ATCCTGATGG AAAATAACCT TCGAAGGTTC AACCTG | [SEQ ID NO:382] |
| Oligo #330 Length: 000024 | |
| CCTGTTGAAT GCCTCCAGGT TGAA | [SEQ ID NO:383] |
| Oligo #331 Length: 000036 | |
| ATCCTGATGG AAAATAACCT TCGAAGGACC AACCTG | [SEQ ID NO:384] |
| Oligo #332 Length: 000024 | |
| CCTGTTGAAT GCCTCCAGGT TGGT | [SEQ ID NO:385] |
| Oligo #333 Length: 000036 | |
| ATCCTGATGG AAAATAACCT TCGAAGGTAC AACCTG | [SEQ ID NO:386] |
| Oligo #334 Length: 000024 | |
| CCTGTTGAAT GCCTCCAGGT TGTA | [SEQ ID NO:387] |
| Oligo #335 Length: 000036 | |
| ATCCTGATGG AAAATAACT TCGAAGGGTT AACCTG | [SEQ ID NO:388] |

TABLE 2-continued

OLIGONUCLEOTIDES

Oligo #336 Length: 000024

CCTGTTGAAT GCCTCCAGGT TAAC  [SEQ ID NO:389]

Oligo #337 Length: 000018

AAAAATCTCG CTCCATGT  [SEQ ID NO:390]

Oligo #338 Length: 000018

AGCGAGATTT TTAAGAAT  [SEQ ID NO:391]

Oligo #339 Length: 000018

AAAAATCTCA ACCCATGT  [SEQ ID NO:392]

Oligo #340 Length: 000018

GTTGAGATTT TTAAGAAT  [SEQ ID NO:393]

Oligo #341 Length: 000018

AAAAATCTCG AACCATGT  [SEQ ID NO:394]

Oligo #342 Length: 000018

TTCGAGATTT TTAAGAAT  [SEQ ID NO:395]

Oligo #343 Length: 000018

AAAAATCTCC ACCCATGT  [SEQ ID NO:396]

Oligo #344 Length: 000018

GTGGAGATTT TTAAGAAT  [SEQ ID NO:397]

Oligo #345 Length: 000018

AAAAATCTCA TCCCATGT  [SEQ ID NO:398]

Oligo #346 Length: 000018

GATGAGATTT TTAAGAAT  [SEQ ID NO:399]

Oligo #347 Length: 000018

AAAAATCTCA TGCCATGT  [SEQ ID NO:400]

Oligo #348 Length: 000018

CATGAGATTT TTAAGAAT  [SEQ ID NO:401]

Oligo #349 Length: 000018

AAAAATCTCT TCCCATGT  [SEQ ID NO:402]

Oligo #350 Length: 000018

GAAGAGATTT TTAAGAAT  [SEQ ID NO:403]

Oligo #351 Length: 000018

AAAAATCTCT CCCCATGT  [SEQ ID NO:404]

Oligo #352 Length: 000018

GGAGAGATTT TTAAGAAT  [SEQ ID NO:405]

Oligo #353 Length: 000018

AAAAATCTCA CCCCATGT  [SEQ ID NO:406]

Oligo #354 Length: 000018

GGTGAGATTT TTAAGAAT  [SEQ ID NO:407]

TABLE 2-continued

OLIGONUCLEOTIDES

Oligo #355 Length: 000018

AAAAATCTCT ACCCATGT [SEQ ID NO:408]

Oligo #356 Length: 000018

GTAGAGATTT TTAAGAAT [SEQ ID NO:409]

Oligo #357 Length: 000027

CTGCCCCTGG CCACGGCCGC AGCTACG [SEQ ID NO:410]

Oligo #358 Length: 000024

ATGGATTGGA TGTCGCGTAG CTGC [SEQ ID NO:411]

Oligo #359 Length: 000027

CTGCCCCTGG CCACGGCCGC AGGTACG [SEQ ID NO:412]

Oligo #360 Length: 000024

ATGGATTGGA TGTCGCGTAC CTGC [SEQ ID NO:413]

Oligo #361 Length: 000027

CTGCCCCTGG CCACGGCCGC AATCACG [SEQ ID NO:414]

Oligo #362 Length: 000024

ATGGATTGGA TGTCGCGTGA TTGC [SEQ ID NO:415]

Oligo #363 Length: 000021

GCTCATCCAA TCCATATCAA G [SEQ ID NO:416]

Oligo #364 Length: 000024

ATGGATTGGA TGAGCCGTGG GTGC [SEQ ID NO:417]

Oligo #365 Length: 000021

CAGCATCCAA TCCATATCAA G [SEQ ID NO:418]

Oligo #366 Length: 000024

ATGGATTGGA TGCTGCGTGG GTGC [SEQ ID NO:419]

Oligo #367 Length: 000021

CACCATCCAA TCCATATCAA G [SEQ ID NO:420]

Oligo #368 Length: 000024

ATGGATTGGA TGGTGCGTGG GTGC [SEQ ID NO:421]

Oligo #369 Length: 000021

AAACATCCAA TCCATATCAA G [SEQ ID NO:422]

Oligo #370 Length: 000024

ATGGATTGGA TGTTTCGTGG GTGC [SEQ ID NO:423]

Oligo #371 Length: 000021

CGAGCTCCAA TCCATATCAA G [SEQ ID NO:424]

Oligo #372 Length: 000024

ATGGATTGGA GCTCGCGTGG GTGC [SEQ ID NO:425]

Oligo #373 Length: 000021

CGAAACCCAA TCCATATCAA G [SEQ ID NO:426]

Oligo #374 Length: 000024

TABLE 2-continued

OLIGONUCLEOTIDES

ATGGATTGGG TTTCGCGTGG GTGC [SEQ ID NO:427]

Oligo #375 Length: 000021

CGAGACCCAA TCCATATCAA G [SEQ ID NO:428]

Oligo #376 Length: 000024

ATGGATTGGG TCTCGCGTGG GTGC [SEQ ID NO:429]

Oligo #377 Length: 000021

CGAATCCCAA TCCATATCAA G [SEQ ID NO:430]

Oligo #378 Length: 000024

ATGGATTGGG ATTCGCGTGG GTGC [SEQ ID NO:431]

Oligo #379 Length: 000021

CGAAAACCAA TCCATATCAA G [SEQ ID NO:432]

Oligo #380 Length: 000024

ATGGATTGGT TTTCGCGTGG GTGC [SEQ ID NO:433]

Oligo #381 Length: 000021

CGAATGCCAA TCCATATCAA G [SEQ ID NO:434]

Oligo #382 Length: 000024

ATGGATTGGC ATTCGCGTGG GTGC [SEQ ID NO:435]

Oligo #383 Length: 000021

CGATTCCCAA TCCATATCAA G [SEQ ID NO:436]

Oligo #384 Length: 000024

ATGGATTGGG AATCGCGTGG GTGC [SEQ ID NO:437]

Oligo #385 Length: 000021

CGATCCCCAA TCCATATCAA G [SEQ ID NO:438]

Oligo #386 Length: 000024

ATGGATTGGG GATCGCGTGG GTGC [SEQ ID NO:439]

Oligo #387 Length: 000021

CGATGGCCAA TCCATATCAA G [SEQ ID NO:440]

Oligo #388 Length: 000024

ATGGATTGGC CATCGCGTGG GTGC [SEQ ID NO:441]

Oligo #389 Length: 000021

CGATACCCAA TCCATATCAA G [SEQ ID NO:442]

Oligo #390 Length: 000024

ATGGATTGGG TATCGCGTGG GTGC [SEQ ID NO:443]

Oligo #391 Length: 000034

CATCCAATCC AAATCAAGGA CGGTGACTGG AATG [SEQ ID NO:444]

Oligo #392 Length: 000044

AATTCATTCC AGTCACCGTC CTTGATTTGG ATTGGATGTC GCGT [SEQ ID NO:445]

Oligo #393 Length: 000034

TABLE 2-continued

| OLIGONUCLEOTIDES | |
|---|---|
| CATCCAATCG AAATCAAGGA CGGTGACTGG AATG | [SEQ ID NO:446] |
| Oligo #394 Length: 000044 | |
| AATTCATTCC AGTCACCGTC CTTGATTTCG ATTGGATGTC GCGT | [SEQ ID NO:447] |
| Oligo #395 Length: 000034 | |
| CATCCAATCA TGATCAAGGA CGGTGACTGG AATG | [SEQ ID NO:448] |
| Oligo #396 Length: 000044 | |
| AATTCATTCC AGTCACCGTC CTTGATCATG ATTGGATGTC GCGT | [SEQ ID NO:449] |
| Oligo #397 Length: 000034 | |
| CATCCAATCT TCATCAAGGA CGGTGACTGG AATG | [SEQ ID NO:450] |
| Oligo #398 Length: 000044 | |
| AATTCATTCC AGTCACCGTC CTTGATGAAG ATTGGATGTC GCGT | [SEQ ID NO:451] |
| Oligo #399 Length: 000034 | |
| CATCCAATCT CCATCAAGGA CGGTGACTGG AATG | [SEQ ID NO:452] |
| Oligo #400 Length: 000044 | |
| AATTCATTCC AGTCACCGTC CTTGATGGAG ATTGGATGTC GCGT | [SEQ ID NO:453] |
| Oligo #401 Length: 000034 | |
| CATCCAATCg taATCAAGGA CGGTGACTGG AATG | [SEQ ID NO:454] |
| Oligo #402 Length: 000044 | |
| AATTCATTCC AGTCACCGTC CTTGATTACG ATTGGATGTC GCGT | [SEQ ID NO:455] |
| Oligo #403 Length: 000021 | |
| CGACATCCAA TCCGTATCAA G | [SEQ ID NO:456] |
| Oligo #404 Length: 000024 | |
| ACGGATTGGA TGTCGCGTGG GTGC | [SEQ ID NO:457] |
| Oligo #405 Length: 000021 | |
| CGACATCCAA TCAAAATCAA G | [SEQ ID NO:458] |
| Oligo #406 Length: 000024 | |
| TTTGATTGGA TGTCGCGTGG GTGC | [SEQ ID NO:459] |
| Oligo #407 Length: 000021 | |
| CGACATCCAA TCTACATCAA G | [SEQ ID NO:460] |
| Oligo #408 Length: 000024 | |
| GTAGATTGGA TGTCGCGTGG GTGC | [SEQ ID NO:461] |
| Oligo #409 Length: 000016 | |
| GCTGGTGACT GGAATG | [SEQ ID NO:462] |
| Oligo #410 Length: 000026 | |
| AATTCATTCC AGTCACCAGC CTTGAT | [SEQ ID NO:463] |
| Oligo #411 Length: 000016 | |
| AACGGTGACT GGAATG | [SEQ ID NO:464] |
| Oligo #412 Length: 000026 | |
| AATTCATTCC AGTCACCGTT CTTGAT | [SEQ ID NO:465] |

TABLE 2-continued

OLIGONUCLEOTIDES

Oligo #413 Length: 000016

GAAGGTGACT GGAATG                                              [SEQ ID NO:466]

Oligo #414 Length: 000026

AATTCATTCC AGTCACCTTC CTTGAT                                   [SEQ ID NO:467]

Oligo #415 Length: 000016

GGTGGTGACT GGAATG                                              [SEQ ID NO:468]

Oligo #416 Length: 000026

AATTCATTCC AGTCACCACC CTTGAT                                   [SEQ ID NO:469]

Oligo #417 Length: 000016

ATCGGTGACT GGAATG                                              [SEQ ID NO:470]

Oligo #418 Length: 000026

AATTCATTCC AGTCACCGAT CTTGAT                                   [SEQ ID NO:471]

Oligo #419 Length: 000016

CTGGGTGACT GGAATG                                              [SEQ ID NO:472]

Oligo #420 Length: 000026

AATTCATTCC AGTCACCCAG CTTGAT                                   [SEQ ID NO:473]

Oligo #421 Length: 000016

TTCGGTGACT GGAATG                                              [SEQ ID NO:474]

Oligo #422 Length: 000026

AATTCATTCC AGTCACCGAA CTTGAT                                   [SEQ ID NO:475]

Oligo #423 Length: 000016

TCCGGTGACT GGAATG                                              [SEQ ID NO:476]

Oligo #424 Length: 000026

AATTCATTCC AGTCACCGGA CTTGAT                                   [SEQ ID NO:477]

Oligo #425 Length: 000032

AATTCGCTAG GAAACTGACG TTCTATCTGA AA                            [SEQ ID NO:478]

Oligo #426 Length: 000037

CTCAAGGGTT TTCAGATAGA ACGTCAGTTT CCTAGCG                       [SEQ ID NO:479]

Oligo #427 Length: 000032

AATTCCAGAG GAAACTGACG TTCTATCTGA AA                            [SEQ ID NO:480]

Oligo #428 Length: 000037

CTCAAGGGTT TTCAGATAGA ACGTCAGTTT CCTCTGG                       [SEQ ID NO:481]

Oligo #429 Length: 000032

AATTCCACAG GAAACTGACG TTCTATCTGA AA                            [SEQ ID NO:482]

Oligo #430 Length: 000037

CTCAAGGGTT TTCAGATAGA ACGTCAGTTT CCTGTGG                       [SEQ ID NO:483]

Oligo #431 Length: 000032

AATTCTCCAG GAAACTGACG TTCTATCTGA AA                            [SEQ ID NO:484]

TABLE 2-continued

OLIGONUCLEOTIDES

Oligo #432 Length: 000037

CTCAAGGGTT TTCAGATAGA ACGTCAGTTT CCTGGAG  [SEQ ID NO:485]

Oligo #433 Length: 000032

AATTCCGGAG GCGTCTGACG TTCTATCTGA AA  [SEQ ID NO:486]

Oligo #434 Length: 000037

CTCAAGGGTT TTCAGATAGA ACGTCAGACG CCTCCGG  [SEQ ID NO:487]

Oligo #435 Length: 000032

AATTCCGGAG GGAACTGACG TTCTATCTGA AA  [SEQ ID NO:488]

Oligo #436 Length: 000037

CTCAAGGGTT TTCAGATAGA ACGTCAGTTC CCTCCGG  [SEQ ID NO:489]

Oligo #437 Length: 000032

AATTCCGGAG GCACCTGACG TTCTATCTGA AA  [SEQ ID NO:490]

Oligo #438 Length: 000037

CTCAAGGGTT TTCAGATAGA ACGTCAGGTG CCTCCGG  [SEQ ID NO:491]

Oligo #439 Length: 000032

AATTCCGGAG GATCCTGACG TTCTATCTGA AA  [SEQ ID NO:492]

Oligo #440 Length: 000037

CTCAAGGGTT TTCAGATAGA ACGTCAGGAT CCTCCGG  [SEQ ID NO:493]

Oligo #441 Length: 000032

AATTCCGGAG GTCCCTGACG TTCTATCTGA AA  [SEQ ID NO:494]

Oligo #442 Length: 000037

CTCAAGGGTT TTCAGATAGA ACGTCAGGGA CCTCCGG  [SEQ ID NO:495]

Oligo #443 Length: 000032

AATTCCGGAG GAAACTGACG GACTATCTGA AA  [SEQ ID NO:496]

Oligo #444 Length: 000037

CTCAAGGGTT TTCAGATAGT CCGTCAGTTT CCTCCGG  [SEQ ID NO:497]

Oligo #445 Length: 000032

AATTCCGGAG GAAACTGACG ATCTATCTGA AA  [SEQ ID NO:498]

Oligo #446 Length: 000037

CTCAAGGGTT TTCAGATAGA TCGTCAGTTT CCTCCGG  [SEQ ID NO:499]

Oligo #447 Length: 000032

AATTCCGGAG GAAACTGACG CTGTATCTGA AA  [SEQ ID NO:500]

Oligo #448 Length: 000037

CTCAAGGGTT TTCAGATACA GCGTCAGTTT CCTCCGG  [SEQ ID NO:501]

Oligo #449 Length: 000032

AATTCCGGAG GAAACTGACG AAATATCTGA AA  [SEQ ID NO:502]

Oligo #450 Length: 000037

CTCAAGGGTT TTCAGATATT TCGTCAGTTT CCTCCGG  [SEQ ID NO:503]

Oligo #451 Length: 000032

TABLE 2-continued

OLIGONUCLEOTIDES

AATTCCGGAG GAAACTGACG GTTTATCTGA AA [SEQ ID NO:504]

Oligo #452 Length: 000037

CTCAAGGGTT TTCAGATAAA CCGTCAGTTT CCTCCGG [SEQ ID NO:505]

Oligo #453 Length: 000032

AATTCCGGAG GAAACTGACG TTCTATCTGG CT [SEQ ID NO:506]

Oligo #454 Length: 000037

CTCAAGGGTA GCCAGATAGA ACGTCAGTTT CCTCCGG [SEQ ID NO:507]

Oligo #455 Length: 000032

AATTCCGGAG GAAACTGACG TTCTATCTGC GT [SEQ ID NO:508]

Oligo #456 Length: 000037

CTCAAGGGTA CGCAGATAGA ACGTCAGTTT CCTCCGG [SEQ ID NO:509]

Oligo #457 Length: 000032

AATTCCGGAG GAAACTGACG TTCTATCTGA AC [SEQ ID NO:510]

Oligo #458 Length: 000037

CTCAAGGGTG TTCAGATAGA ACGTCAGTTT CCTCCGG [SEQ ID NO:511]

Oligo #459 Length: 000032

AATTCCGGAG GAAACTGACG TTCTATCTGC AG [SEQ ID NO:512]

Oligo #460 Length: 000037

CTCAAGGGTC TGCAGATAGA ACGTCAGTTT CCTCCGG [SEQ ID NO:513]

Oligo #461 Length: 000032

AATTCCGGAG GAAACTGACG TTCTATCTGC AC [SEQ ID NO:514]

Oligo #462 Length: 000037

CTCAAGGGTG TGCAGATAGA ACGTCAGTTT CCTCCGG [SEQ ID NO:515]

Oligo #463 Length: 000032

AATTCCGGAG GAAACTGACG TTCTATCTGA TG [SEQ ID NO:516]

Oligo #464 Length: 000037

CTCAAGGGTC ATCAGATAGA ACGTCAGTTT CCTCCGG [SEQ ID NO:517]

Oligo #465 Length: 000032

AATTCCGGAG GAAACTGACG TTCTATCTGT TC [SEQ ID NO:518]

Oligo #466 Length: 000037

CTCAAGGGTG AACAGATAGA ACGTCAGTTT CCTCCGG [SEQ ID NO:519]

Oligo #467 Length: 000032

AATTCCGGAG GAAACTGACG TTCTATCTGT AC [SEQ ID NO:520]

Oligo #468 Length: 000037

CTCAAGGGTG TACAGATAGA ACGTCAGTTT CCTCCGG [SEQ ID NO:521]

Oligo #469 Length: 000040

CATGGCTAAC TGCTCTAACA TGATCGATGA AATTATAACA [SEQ ID NO:522]

Oligo #470 Length: 000036

TABLE 2-continued

| OLIGONUCLEOTIDES | |
|---|---|
| CACTTAAAGC AGCCACCTTT GCCTTTGCTG GACTTC | [SEQ ID NO:523] |
| Oligo #471 Length: 000027 | |
| AACAACCTCA ATGGGAAGA CCAAGAT | [SEQ ID NO:524] |
| Oligo #472 Length: 000045 | |
| CTTTAAGTGT GTTATAATTT CATCGATCAT GTTAGAGCAG TTAGC | [SEQ ID NO:525] |
| Oligo #473 Length: 000036 | |
| GAGGTTGTTG AAGTCCAGCA AAGGCAAAGG TGGCTG | [SEQ ID NO:526] |
| Oligo #474 Length: 000018 | |
| ATCTTGGTCT TCCCCATT | [SEQ ID NO:527] |
| Oligo #475 Length: 000036 | |
| ATCCTGATGG AAATAACCT TCGAAGGCCA AACCTG | [SEQ ID NO:528] |
| Oligo #476 Length: 000024 | |
| GAGGCATTCA ACAGGGCTGT CAAG | [SEQ ID NO:529] |
| Oligo #477 Length: 000015 | |
| AGTTTACAGA ATGCA | [SEQ ID NO:530] |
| Oligo #478 Length: 000027 | |
| CCTTCGAAGG TTATTTTCCA TCAGGAT | [SEQ ID NO:531] |
| Oligo #479 Length: 000024 | |
| CCTGTTGAAT GCCTCCAGGT TTGG | [SEQ ID NO:532] |
| Oligo #480 Length: 000020 | |
| TTCTGTAAAC TCTTGACAGC | [SEQ ID NO:533] |
| Oligo #481 Length: 000021 | |
| TCAGCAATTG AGAGCATTCT T | [SEQ ID NO:534] |
| Oligo #482 Length: 000018 | |
| AAAAATCTCC TGCCATGT | [SEQ ID NO:535] |
| Oligo #483 Length: 000048 | |
| CTGCCCCTGG CCACGGCCGC ACCCACGCGA CATCCAATCC ATATCAAG | [SEQ ID NO:536] |
| Oligo #484 Length: 000027 | |
| CTGCCCCTGG CCACGGCCGC ACCCACG | [SEQ ID NO:537] |
| Oligo #485 Length: 000021 | |
| CGACATCCAA TCCATATCAA G | [SEQ ID NO:538] |
| Oligo #486 Length: 000016 | |
| GACGGTGACT GGAATG | [SEQ ID NO:539] |
| Oligo #487 Length: 000019 | |
| GCTCTCAATT GCTGATGCA | [SEQ ID NO:540] |
| Oligo #488 Length: 000018 | |
| CAGGAGATTT TTAAGAAT | [SEQ ID NO:541] |
| Oligo #489 Length: 000048 | |
| ATGGATTGGA TGTCGCGTGG GTGCGGCCGT GTGCGGCCGT AGACATGG | [SEQ ID NO:542] |

TABLE 2-continued

OLIGONUCLEOTIDES

Oligo #490 Length: 000024

GGCCGTGGCC AGGGGCAGAC ATGG                                [SEQ ID NO:543]

Oligo #491 Length: 000024

ATGGATTGGA TGTCGCGTGG GTGC                                [SEQ ID NO:544]

Oligo #492 Length: 000026

AATTCATTCC AGTCACCGTC CTTGAT                              [SEQ ID NO:545]

Oligo #493 Length: 000032

AATTCCGGAG GAAACTGACG TTCTATCTGA AA                       [SEQ ID NO:546]

Oligo #494 Length: 000032

ACCCTTGAGA ATGCGCAGGC TCAACAGTAA TA                       [SEQ ID NO:547]

Oligo #495 Length: 000037

CTCAAGGGTT TTCAGATAGA ACGTCAGTTT CCTCCGG                  [SEQ ID NO:548]

Oligo #496 Length: 000027

AGCTTATTAC TGTTGAGCCT GCGCATT                             [SEQ ID NO:549]

TABLE 3

POLYPEPTIDES

PEPTIDE #1; pMON5988 (Example 9); (15-125)hIL-3

```
    Asn Cys Ser Asn Met Ile Asp Glu Ile Ile Thr His Leu        [SEQ ID NO:65]
    15              20                  25

Lys Gln Pro Pro Leu Pro Leu Leu Asp Phe Asn Asn Leu Asn Gly
        30              35                  40

Glu Asp Gln Asp Ile Leu Met Glu Asn Asn Leu Arg Arg Pro Asn
        45              50                  55

Leu Glu Ala Phe Asn Arg Ala Val Lys Ser Leu Gln Asn Ala Ser
        60              65                  70

Ala Ile Glu Ser Ile Leu Lys Asn Leu Leu Pro Cys Leu Pro Leu
        75              80                  85

Ala Thr Ala Ala Pro Thr Arg His Pro Ile His Ile Lys Asp Gly
        90              95                  100

Asp Trp Asn Glu Phe Arg Arg Lys Leu Thr Phe Tyr Leu Lys Thr
        105             110                 115

Leu Glu Asn Ala Gln Ala Gln Gln
        120             125
```

PEPTIDE #A1; pMON13304 (Example 55); Met-Ala-(15-125)hIL-3 (98I, 100R);

```
Met Ala Asn Cys Ser Asn Met Ile Asp Glu Ile Ile Thr His Leu    [SEQ ID NO:66]
        15              20                  25

Lys Gln Pro Pro Leu Pro Leu Leu Asp Phe Asn Asn Leu Asn Gly
        30              35                  40

Glu Asp Gln Asp Ile Leu Met Glu Asn Asn Leu Arg Arg Pro Asn
        45              50                  55

Leu Glu Ala Phe Asn Arg Ala Val Lys Ser Leu Gln Asn Ala Ser
        60              65                  70
```

TABLE 3-continued

POLYPEPTIDES

```
Ala Ile Glu Ser Ile Leu Lys Asn Leu Leu Pro Cys Leu Pro Leu
        75                  80                  85

Ala Thr Ala Ala Pro Thr Arg His Pro Ile Ile Ile Arg Asp Gly
        90                  95                 100

Asp Trp Asn Glu Phe Arg Arg Lys Leu Thr Phe Tyr Leu Lys Thr
       105                 110                 115

Leu Glu Asn Ala Gln Ala Gln Gln
       120                 125
```

PEPTIDE #A2; pMON13305 Met-Ala-(15-125)hIL-3; (95R, 98I, 100R);

```
Met Ala Asn Cys Ser Asn Met Ile Asp Glu Ile Ile Thr His Leu     [SEQ ID NO:67]
        15                  20                  25

Lys Gln Pro Pro Leu Pro Leu Leu Asp Phe Asn Asn Leu Asn Gly
        30                  35                  40

Glu Asp Gln Asp Ile Leu Met Glu Asn Asn Leu Arg Arg Pro Asn
        45                  50                  55

Leu Glu Ala Phe Asn Arg Ala Val Lys Ser Leu Gln Asn Ala Ser
        60                  65                  70

Ala Ile Glu Ser Ile Leu Lys Asn Leu Leu Pro Cys Leu Pro Leu
        75                  80                  85

Ala Thr Ala Ala Pro Thr Arg Arg Pro Ile Ile Ile Arg Asp Gly
        90                  95                 100

Asp Trp Asn Glu Phe Arg Arg Lys Leu Thr Phe Tyr Leu Lys Thr
       105                 110                 115

Leu Glu Asn Ala Gln Ala Gln Gln
       120                 125
```

PEPTIDE #A3; pMON13286 Met-Ala-(15-125)hIL-3; (42D, 45M, 46S);

```
Met Ala Asn Cys Ser Asn Met Ile Asp Glu Ile Ile Thr His Leu     [SEQ ID NO:69]
        15                  20                  25

Lys Gln Pro Pro Leu Pro Leu Leu Asp Phe Asn Asn Leu Asn Asp
        30                  35                  40

Glu Asp Met Ser Ile Leu Met Glu Asn Asn Leu Arg Arg Pro Asn
        45                  50                  55

Leu Glu Ala Phe Asn Arg Ala Val Lys Ser Leu Gln Asn Ala Ser
        60                  65                  70

Ala Ile Glu Ser Ile Leu Lys Asn Leu Leu Pro Cys Leu Pro Leu
        75                  80                  85

Ala Thr Ala Ala Pro Thr Arg His Pro Ile His Ile Lys Asp Gly
        90                  95                 100

Asp Trp Asn Glu Phe Arg Arg Lys Leu Thr Phe Tyr Leu Lys Thr
       105                 110                 115

Leu Glu Asn Ala Gln Ala Gln Gln
       120                 125
```

Polypeptides corresponding to SEQ ID NOS. 15, 16, 17, 18 and 129 comprising (1–133)hIL-3 containing one or more amino acid substitutions can be made using the procedures described above and in the following examples by starting with the appropriate oligonuctiotides and then constructing the DNA encoding the polypeptide and expressing it in an appropriate host cell. In a similar manner polypeptides which correspond to SEQ ID NOS. 19, 20, 21, 22 and 130 and contain one or more amino acid substitutions and wherein from 1 to 14 amino acids have been sequentially deleted from the N-terminus, or from 1 to 15 amino acids have been deleted from the C-terminus or deletions of amino acids have been made from both the N-terminus and the C-terminus can also be made by following the procedures described above and in the following examples, beginning with the appropriate starting materials.

Additional details may be found in U.S. patent application Ser. No. 07/981,044 filed Nov. 24, 1992, which is hereby incorporated by reference in its entirety.

Additional details may be found in co filed United States Patent Application Attorney docket number 2713/2, which is hereby incorporated by reference in its entirety.

All references, patents or applications cited herein are incorporated by reference in their entirety.

Further details known to those skilled in the art may be found in T. Maniatis, et al., *Molecular Cloning, A Laboratory Manual,* Cold Spring Harbor Laboratory (1982) and references cited therein, incorporated herein by reference in its entirety; and in J. Sambrook, et al., *Molecular Cloning, A Laboratory manual,* 2nd edition, Cold Spring Harbor Laboratory (1989) and references cited therein, incorporated herein by reference in its entirety.

The following examples will illustrate the invention in greater detail although it will be understood that the invention is not limited to these specific examples.

Amino acids are shown herein by standard one letter or three letter abbreviations as follows:

| Abbreviated Designation | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such other examples be included within the scope of the appended claims.

REFERENCES

Adams, S. P., Kavka, K. S., Wykes, E. J., Holder, S. B. and Galluppi, G. R. Hindered Dialkyamino Nucleoside Phosphate reagents in the synthesis of two DNA 51-mers. *J. Am. Chem. Soc.,* 105, 661–663 (1983).

Atkinson, T. and Smith, M., in Gait, M. J., Oligonucleotide Sythesis (1984) (IRL Press, Oxford England).

Bachmann, B., Pedigrees of some mutant strains of *Escherichia coli* K-12, *Bacteriological Reviews,* 36:525–557 (1972).

Bayne, M. L., Expression of a synthetic gene encoding human insulin-like growth factor I in cultured mouse fibroblasts. *Proc. Natl. Acad. Sci. USA* 84, 2638–2642 (1987).

Ben-Bassat, A., K. Bauer, S-Y. Chang, K. Myambo, A. Boosman and S. Ching. Processing of the initiating methionine from proteins: properties of the *Escherichia coli* methionine aminopeptidase and its gene structure. *J. Bacteriol.,* 169: 751–757 (1987).

Biesma, B. et al., Effects of interleukin-3 after chemotherapy for advanced ovarian cancer. *Blood,* 80:1141–1148 (1992).

Birnboim, H. C. and J. Doly. A rapid alkaline extraction method for screening recombinant plasmid DNA. *Nucleic Acids Research,* 7(6): 1513–1523 (1979).

Bradford, M. M., A rapid and sensitive method for the quantitation of microgram quantities of protein utilizing the principle of protein-dye binding, *Analytical Biochemistry,* 72: 248–254 (1976).

Clark-Lewis, I., L. E. Hood and S. B. H. Kent. Role of disulfide bridges in determining the biological activity of interleukin 3, *Proc. Natl. Acad. Sci., USA,* 85: 7897–7901 (1988).

Clement, J. M. and Hofnung, M. Gene sequence of the receptor, an outer membrane protein of *E. coli* K12. *Cell,* 27: 507–514 (1981).

Covarrubias, L., L. Cervantes, A. Covarrubias, X. Soberon, I. Vichido, A. Blanco, Y. M. Kupersztoch-Portnoy and F. Bolivar. Construction and characterization of new cloning vehicles. V. Mobilization and coding properties of pBR322 and several deletion derivates including pBR327 and pBR328. *Gene* 13: 25–35 (1981).

Deng, W. P. & Nickoloff, J. A. Site-directed mutagenesis of virtually any plasmid by eliminating a unique site. *Anal. Biochem.* 200:81 (1992).

Dente, L., G. Cesareni and R. Cortese, pEMBL: A new family of single stranded plasmids, *Nucleic Acids Research,* 11: 1645–1655 (1983).

Dunn, J. J. and Studier, F. W., Complete nucleotide sequence of bacteriophage T7 DNA and the locations of T7 genetic elements. *J. Mol. Biol.* 166:477–535 (1983).

Falk, S., G. Seipelt, A. Ganser, O. G. Ottmann, D. Hoelzer, H. J. Stutte and K. Hubner. *Hematopathology* 95: 355 (1991).

Fling, M. E., et al. Nucleotide sequence of the transposon Tn7 gene encoding an aminoglycoside-modifying enzyme, 3"(9)-O-nucleotidyltransferase. *Nucl. Acids Res.* 13:7095–7106 (1985).

Ganser, A., A. Lindemann, G. Seipelt, O. G. Ottmann, F. Herrmann, M. Eder, J. Frisch, G. Schulz, R. Mertelsmann and D. Hoelzer. Effects of Recombinant Human Interleukin-3 in Patients With Normal Hematopoiesis and in Patients with Bone Marrow Failure, *Blood* 76: 666 (1990).

Gething and Sambrook, Cell-surface expression of influenza haemagglutinin from a cloned DNA copy of the RNA gene, *Nature,* 293: 620–625 (1981).

Gillio, A. P., C. Gasparetto, J. Laver, M. Abboud, M. A. Bonilla, M. B. Garnick and R. J. O'Reilly. *J. Clin. Invest.* 85: 1560 (1990).

Gouy, M. and G. Gautier, Codon usage in bacteria: Correlation with gene expressivity, *Nucleic Acids Research,* 10: 7055–7074 (1982).

Greenfield, L., T. Boone, and G. Wilcox. DNA sequence of the araBAD promoter in *Escherichia coli* B/r. *Proc. Natl. Acad. Sci. USA,* 75: 4724–4728 (1978).

Higuchi, R, (1989) in *PCR Technology,* H. A. Erlich ed., Stockton Press, N.Y. chapter 2–6.

Hunkapiller, M. W., R. W. Hewick, R. J. Dreyer and L. E. Hood. High sensitivity sequencing with a gas-phase sequenator. *Methods in Enzymology* 153: 399–413 (1983).

Kaufman, et al., Coamplification and Coexpression of Human Tissue-Type Plasminogen Activator and Murine Dihydrofolate Reductase Sequences in Chinese Hamster Ovary Cells, *Mol. Cell. Biol.,* 5(7): 1750–1759 (1985).

Kaufman, R. J. High level production of proteins in mammalian cells, in *Genetic Engineering, Principles and Methods,* Vol. 9, J. K. Setlow, editor, Plenum Press, New York (1987).

Kunkel, T. A. Rapid and efficient site-specific mutagenesis without phenotypic selection. *Proc. Natl. Acad. Sci. USA,* 82: 488–492 (1985).

Laemmli, U. K., Cleavage of structural proteins during assembly of the head of bacteriophage T4, *Nature,* 227:680–685 (1970).

Lange, B., M. Valtieri, D. Santoli, D. Caracciolo, F. Mavilio, I. Gemperlein, C. Griffin, B. Emanuel, J. Finan, P. Nowell, and G. Rovera. Growth factor requirements of childhood acute leukemia: establishment of GM-CSF-defendent cell lines. *Blood* 70:192 (1987).

Mahler, H. R. and E. H. Cordes, in *Biological Chemistry,* p. 128, New York, Harper and Row (1966).

Maniatis, T., E. F. Fritsch and J. Sambrook, *Molecular Cloning, A Laboratory Manual.* Cold Spring Harbor Laboratory (1982).

Marinus, M. G. Location of DNA methylation genes on the *Escherichia coli* K-12 genetic map. *Molec. Gen. Genet.* 127: 47–55 (1973).

McBride, L. J. and Caruthers, M. H. An investigation of several deoxynucleoside phosphoramidites. Tetrahedron Lett., 24, 245–248 (1983).

Messing, J., A multipurpose cloning system based on the single-stranded DNA bacteriophage M13. *Recombinant DNA Technical Bulletin,* NIH Publication No. 79–99, Vol. 2, No. 2, pp. 43–48 (1979).

Neu, H. C. and L. A. Heppel. The release of enzymes from *Escherichia coli* by osmotic shock and during the formation of spheroplasts. *J. Biol. Chem.,* 240: 3685–3692 (1965).

Obukowicz, M. G., Staten, N. R. and Krivi, G. G., Enhanced Heterologous Gene Expression in Novel rpoH Mutants of *Escherichia coli. Applied and Environmental Microbiology* 58, No. 5, p. 1511–1523 (1992).

Olins, P. O., C. S. Devine, S. H. Rangwala and K. S. Kavka, The T7 phage gene 10 leader RNA, a ribosome-binding site that dramatically enhances the expression of foreign genes in *Escherichia coli, Gene,* 73:227–235 (1988).

Olins, P. O. and S. H. Rangwala, Vector for enhanced translation of foreign genes in *Escherichia coli, Methods in Enzymology,* 185: 115–119 (1990).

Postmus, et al., Effects of recombinant human interleukin-3 in patients with relapsed small-cell lung cancer treated with chemotherapy: a dose-finding study. *J. Clin. Oncol.,* 10:1131–1140 (1992).

Prober, J. M., G. L. Trainor, R. J. Dam, F. W. Hobbs, C. W. Robertson, R. J. Zagursky, A. J. Cocuzza, M. A. Jensen and K. Baumeister. A system for rapid DNA sequencing with fluorescent chain-terminating dideoxynucleotides. *Science* 238: 336–341 (1987).

Renart J., J. Reiser and G. R. Stark, Transfer of proteins from gels to diazobenzyloxymethyl-paper and detection with anti-sera: a method for studying antibody specificity and antigen structure, *Proc. Natl. Acad. Sci. USA,* 76:3116–3120 (1979).

Saiki, R. K., Schorf, S., Faloona, F., Mullis, K. B., Horn, G. T., Erlich, H. A. and Arnheim, N., Enzymatic Amplification of β-Globin Genomic Sequences and Restriction Site Analysis for Diagnosis of Sickle Cell Anemia, *Science,* 230: 1350–1354 (1985).

Sambrook, J., et al., *Molecular Cloning, A Laboratory Manual,* 2nd edition, Cold Spring Harbor Laboratory (1989).

Sancar, A., C. Stachelek, w. Konigsberg and W. D. Rupp, Sequences of the recA gene and protein, *Proc. Natl. Acad. Sci.,* 77: 2611–2615 (1980).

Sanger, F., S. Nicklen and A. R. Coulson. DNA sequencing with chain-terminating inhibitors. *Proc. Natl. Acad. Sci. U.S.A.* 74: 5463–5467 (1977).

Santoli, D., Y. Yang, S. C. Clark, B. L. Kreider, D. Caracciolo, and G. Rovera. Synergistic and antagonistic effects of recombinant human interleukin (IL-3), IL-1α, granulocyte and macrophage colony-stimulating factors (G-CSF and M-CSF) on the growth of GM-CSF-dependent leukemic cell lines. *J. Immunol.* 139:348 (1987).

Smith, M. In vitro mutagenesis. *Ann. Rev. Genet.,* 19:423–462 (1985).

Soberon, X., L. Covarrubias and F. Bolivar, Construction and characterization of new cloning vehicles. IV. Deletion derivatives of pBR322 and pBR325, *Gene,* 9: 211–223 (1980).

Stader, J. A. and T. J. Silhavy. Engineering *Escherichia coli* to secrete heterologous gene products, *Methods in Enzymology,* 185: 166–87 (1990).

Summers, M. D. and G. E. Smith. A manual of methods for Baculovirus vectors and insect cell culture procedures. *Texas Agricultural Experiment Station Bulletin No.* 1555 (1987).

Taylor, J. W., Ott, J. and Eckstein, F. The rapid generation of oligonucleotide-directed mutants at high frequency using phosphorothioate modified DNA. *Nucl. Acids Res.,* 13:8764–8785 (1985).

Treco, D. A., in *Current protocols in Molecular Biology,* Seidman et al., eds. J Wiley New York, unit 2.1. (1989)

Valtieri, M., D. Santoli, D. Caracciolo, B. L. Kreider, S. W. Altmann, D. J. Tweardy, I. Gemperlein, F. Mavilio, B. J. Lange and G. Rovera. Establishment and characterization of an undifferentiated human T leukemia cell line which requires granulocyte-macrophage colony stimulating factor for growth. *J. Immunol.* 138:4042 (1987).

Voet, D., W. B. Gatzer, R. A. Cox, P. Doty. Absorption spectra of the common bases. *Biopolymers* 1: 193 (1963).

Wells, J. A., Vasser, M., and Powers, D. B. Cassette mutagenesis: an effective method for generation of multiple mutants at defined sites. *Gene,* 34:315–323 (1985).

Wong, E. Y., R. Seetharam, C. Kotts, R. A. Heeren, B. K. Klein, S. B. Braford, K. J. Mathis, B. F. Bishop, N. R. Siegel, C. E. Smith and W. C. Tacon. Expression of secreted IGF-1 in *Escherichia coli. Gene,* 68: 193–203 (1988).

Yang, Y., A. B. Clarletta, P. A. Temple, M. P. Chung, S. Koviacic, J. S. Witek-Giannotti, A. C. Leary, R. Kriz, R. E. Donahue, G. G. Wong and S. C. Clark. Human IL-3 (Multi-CSF): Identification by expression cloning of a novel hematopoietic growth factor related to murine IL-3. Cell 47: 3–10 (1985).

Yanisch-Perron, C., J. Viera and J. Messing. Improved M13 phage cloning vectors and host strains: nucleotide sequences of the M13mp18 and pUC19 vectors. *Gene* 33: 103–119 (1985).

Zoller, M. J. and Smith, M. Oligonucleotide-directed mutagenesis using M13-derived vectors: an efficient and general procedure for the production of point mutations in any fragment of DNA. *Nucleic Acid Research,* 10: 6487–6500 (1982).

Zoller, M. J. and Smith, M. Oligonucleotide-directed mutagenesis of DNA fragments cloned into M13 vectors. *Methods in Enzymology,* 100:468–500 (1983).

Zoller, M. J. and Smith, M. Oligonucleotide-directed Mutagenesis: A simple method using two oligonucleotide primers and a single-stranded DNA template. *DNA,* 3: 479 (1984).

EXAMPLE 1

Construction of pMON 5846 (FIG. 4) which encodes [Met-(1-133)hIL-3 (Arg$^{129}$)]

A plasmid containing the gene for the cDNA of hIL-3 cloned into pUC18 on an EcoRI to HindIII fragment was obtained from British Biotechnology Limited (Cambridge, England). This plasmid was designated pPO518. The purified plasmid DNA was cleaved by the restriction endonucleases NheI and BamHI. Approximately 0.5 micrograms of cleaved plasmid DNA was ligated to 1.0 picomoles of a pair of annealed oligonucleotides with the following sequence:

5'-CTAGCGATCTTTTAATAAGCTTG-3' [SEQ ID NO: 1]

3'-GCTAGAAAATTATTCGAACCTAG-5' [SEQ ID NO: 2]

The ligation mixture was used to transform competent JM101 cells to ampicillin resistance. Colonies were picked, and plasmid DNA was purified and subjected to restriction enzyme analysis. An isolate was identified in which the above oligonucleotide sequence had replaced the portion of the gene that encodes the extreme C-terminus. Within the new sequence was a new stop codon, TAA, and a recognition site for the enzyme HindIII. The new plasmid was designated pMON5846.

EXAMPLE 2

(a) Construction of expression vector plasmid pMON2341

The plasmid pMON2341 was used to supply the particular replicon and expression elements used for construction of many of the plasmids used to produce hIL-3 and hIL-3 muteins in *E. coli*. These expression elements are described in the materials and methods section. pMON2341 is derived from pMON5515 (Olins et al., 1988) and from pMON2429. pMON2429 consists of the phage mp18 (Yanisch-Perron et al., 1985) with a BclI fragment carrying the chloramphenicol acetyl transferase (cat) gene from pBR328 (Covarrubias et al., 1981) inserted into the BamHI site. The cat gene in pMON2429 has been altered from that in pBR328 by site directed mutagenesis (Kunkel, 1985). The recognition sites for NcoI and EcoRI which occur in the native gene were altered so that these two restriction enzymes no longer recognize these sites. The changes did not alter the protein specified by the gene. Also, an NcoI site was introduced at the N-terminus of the coding sequence so that it overlaps the codon for initiator methionine.

The steps involved in construction of pMON2341 are listed below:

(1) The DNAs of pMON5515 and pMON2429 were treated with NcoI and HindIII. The fragments were ligated and used to transform competent *E. coli* to ampicillin resistance. From these colonies, some were identified that were chloramphenicol resistant. From one of these colonies, plasmid DNA was isolated in which the rat atriopeptigen gene of pMON5515 had been replaced by the NcoI to HindIII fragment containing the cat gene from pMON2429. This fragment contains the recognition sites for several restriction enzymes in the portion derived from the multi-linker region of mp18. The new plasmid was designated pMON2412.

(2) pMON2412 was treated with the enzyme ClaI which cleaves at one location in the pBR327 derived portion of the DNA. The protruding ends were rendered blunt by treatment with Klenow in the presence of nucleotide precursors. This DNA was mixed with an isolated 514 bp RsaI fragment derived from pEMBL8 (Dente et al., 1983). This RsaI fragment contains the origin of replication of phage f1. This ligation mixture was used to transform competent *E. coli* cells to ampicillin resistance. Among the plasmid DNAs isolated from these cells was pMON5578. This plasmid has the structure of pMON2412 with the f1 origin region inserted into the ClaI site. This is illustrated in the Figures and in Olins and Rangwala (1990).

(3) The DNA of pMON5578 was treated with restriction enzymes HindIII and MstII. The DNA was then treated with Klenow enzyme in the presence of nucleotide precursors to render the ends blunt. This treated DNA was ligated and used to transform competent *E. coli* to ampicillin resistance. From the ampicillin resistant colonies, one plasmid was recovered from which the portion between HindIII and MstII was absent. This deletion resulted in the removal of sequences from the plasmid which are recognized by a number of restriction endonuclease sites. The new plasmid was designated pMON5582.

(4) The DNA of pMON5582 was treated with SstII and BclI and ligated in the presence of annealed oligonucleotides with the sequences shown below.

5'-GGCAACAATTTCTACAAAACACTTGATACTGTATGAGCATACAGTATAATTGCTTCAACAGAACAGATC-3'  [SEQ ID NO:3]

3'-CGCCGTTGTTAAAGATGTTTTGTGAACTATGACATACTCGTATGTCATATTAACGAAGTTGTCTTGT-5'  [SEQ ID NO:4]

This sequence encodes the essential elements of the recA promoter of *E. coli* including the transcription start site and the lexA repressor binding site (the operator) (Sancar et al., 1980). The plasmid recovered from the ligation mixes contained this recA promoter in place of the one in pMON5582 (and in pMON5515). The functionality of the recA promoter was illustrated by Olins and Rangwala (1990). The new plasmid was designated pMON5594.

(5) To eliminate the single EcoRI site in pMON5594, the DNA was treated with EcoRI, then with Klenow in the presence of nucleotide precursors to render the ends blunt and then the DNA was ligated. From this ligation mix a plasmid was recovered whose DNA was not cleaved with EcoRI. This plasmid was designated pMON5630.

(6) To alter the single recognition site for PstI, plasmid pMON5630 was subjected to site directed mutagenesis (Kunkel, 1985). The oligonucleotide used in this procedure has the sequence shown below.

5'-CCATTGCTGCCGGCATCGTGGTC-3' [SEQ ID NO:5]

The result of the procedure was to construct pMON2341 which differs from pMON5630 in that the PstI site in the beta-lactamase gene was altered so that PstI no longer recognizes the site. The single nucleotide change does not alter the amino acid sequence of the beta-lactamase protein.
(b) Construction of pMON5847 (FIG. 5) which encodes [Met-(1-133)hIL-3(Arg$^{129}$)]

Plasmid pMON2341 was used to supply the replicon, promotor, ribosome binding site, transcription terminator and antibiotic resistance marker for the plasmids used to produce hIL-3 in *E. coli* from cDNA derived hIL-3 genes.

Plasmid pMON2341 was treated with restriction enzymes NcoI and HindIII. The restriction fragment containing the replication origin was purified. The DNA of plasmid pMON5846 was treated with NcoI and HindIII. The restriction fragment containing the hIL-3 gene was gel purified. These purified restriction fragments were mixed and ligated. The ligation mixture was used to transform competent JM101 cells to ampicillin resistance. Colonies were picked, and plasmid DNA was purified and analyzed using restriction enzymes. pMON5847 was identified as a plasmid with the replicon of pMON2341 and the hIL-3 gene in place of the chloramphenicol acetyl transferase gene. JM101 cells harboring this plasmid were cultured in M9 medium and treated with nalidixic acid as described above. Samples of the culture were examined for protein content. It was found that this hIL-3 mutein was produced at about 6% of total cell protein as measured on Coomassie stained polyacrylamide gels.

EXAMPLE 3

Construction of pMON5854 (FIG. 7) which encodes [Met-(1-133)hIL-3(Arg$^{129}$)]

To increase the accumulation of hIL-3 in *E. coli*, the coding sequence of the amino terminal portion of the protein was altered to more closely reflect the codon bias found in *E. coli* genes that produce high levels of proteins (Gouy and Gautier, 1982). To change the coding sequence for the amino terminal portion of the gene, a pair of synthetic oligonucleotides were inserted between the NcoI and HpaI sites within the coding sequence. About 0.5 micrograms of DNA of the plasmid pMON5847 (Example 2) was treated with NcoI and HpaI. This DNA was mixed with an annealed pair of oligonucleotides with the following sequence:

[SEQ ID NO:6]

5'-CATGGCTCCAATGACTCAGACTACTTCTCTTAAGACTTCTTGGGTT-3'

[SEQ ID NO:7]

3'-CGAGGTTACTGAGTCTGATGAAGAGAATTCTGAAGAACCCAA-5'

The fragments were ligated. The ligation mixture was used to transform competent JM101 to ampicillin resistance. Colonies were picked into broth. From the cultures plasmid DNA was made and examined for the presence of a DdeI site (CTNAG) which occurs in the synthetic sequence but not between the NcoI and HpaI sites in the sequence of pMON5847. The new recombinant plasmid was designated pMON5854. The nucleotide sequence of the DNA in the coding sequence of the amino terminal portion of the hIL-3 gene in pMON5854 was determined by DNA sequencing and found to be the same as that of the synthetic oligonucleotide used in ligation. Cultures of JM101 cells harboring this plasmid were grown and treated with nalidixic acid to induce production of the hIL-3 mutant protein. Analysis of the proteins on Coomassie gels showed that the accumulation of hIL-3 mutein was about 25% of total cell protein in cultures harboring pMON5854, significantly higher than it was in cultures harboring pMON5847.

EXAMPLE 4

Figure 12:
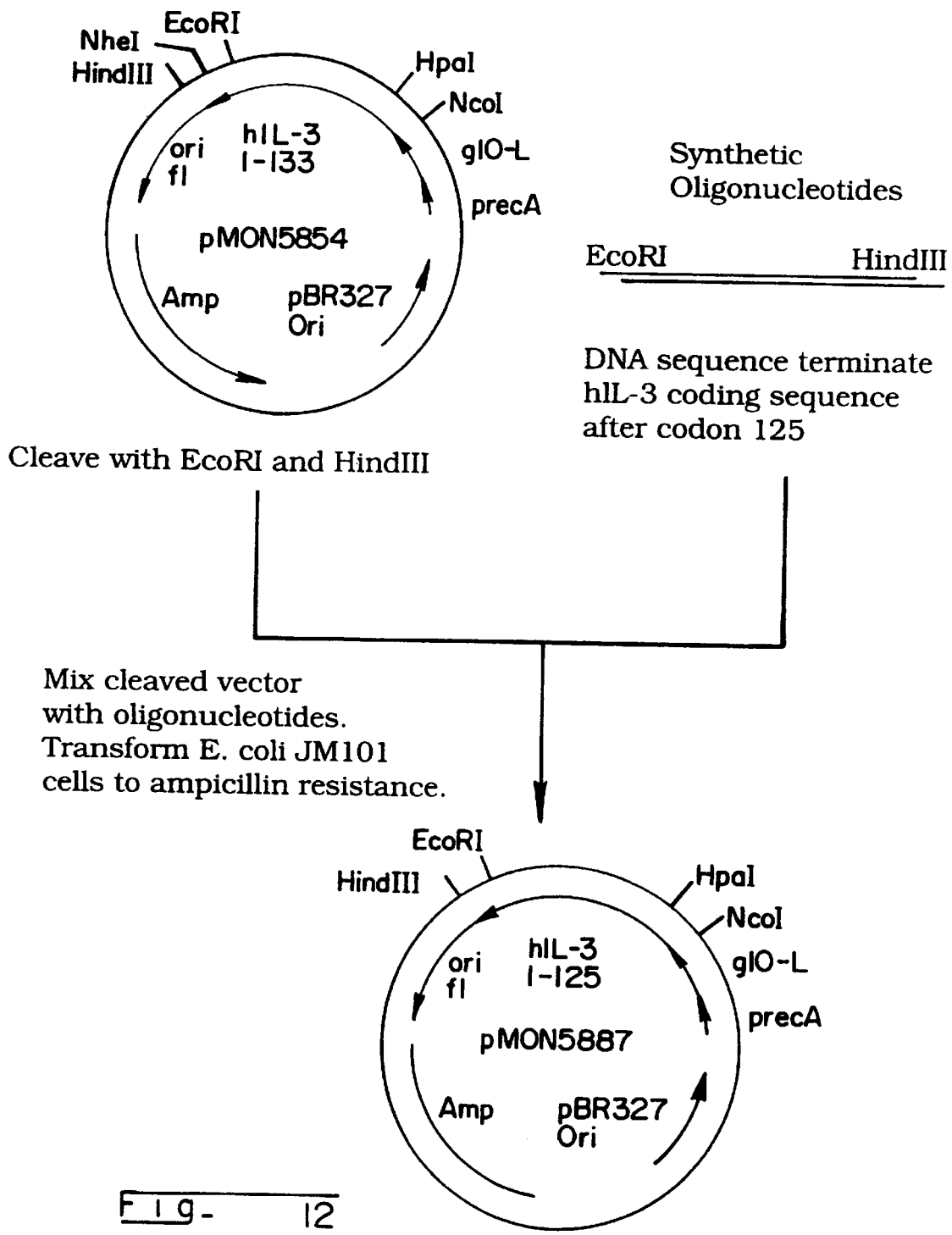
FIG. 12 shows the construction of the plasmid vector pMON5887 which encodes Met-(1–125)hIL-3.
Figure 13:
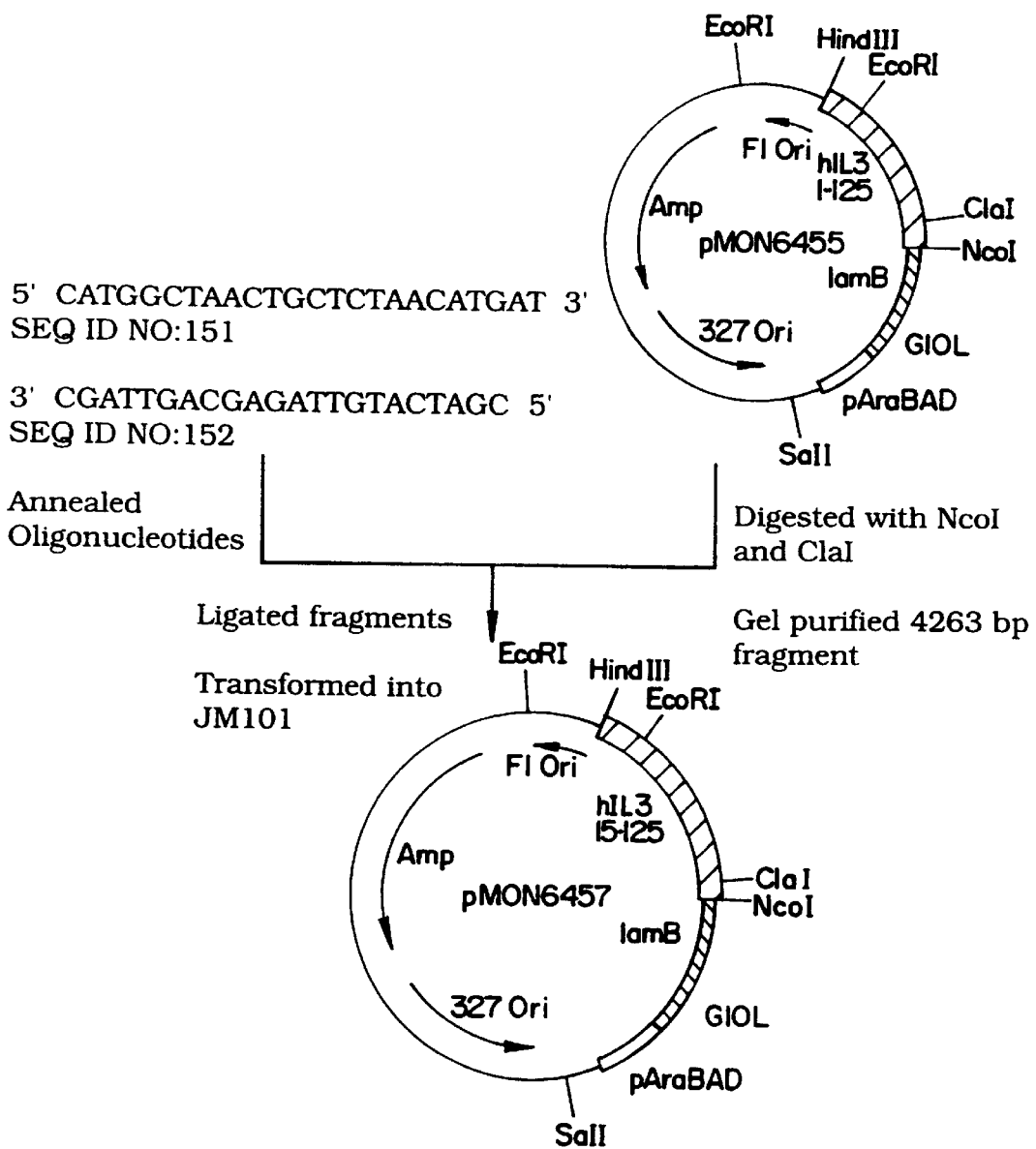
FIG. 13 shows the construction of pMON6457 which encodes (15–125)hIL-3; it contains the araBAD promoter and the lamB signal peptide fused to the variant hIL-3 amino acids 15–125.
Figure 14:
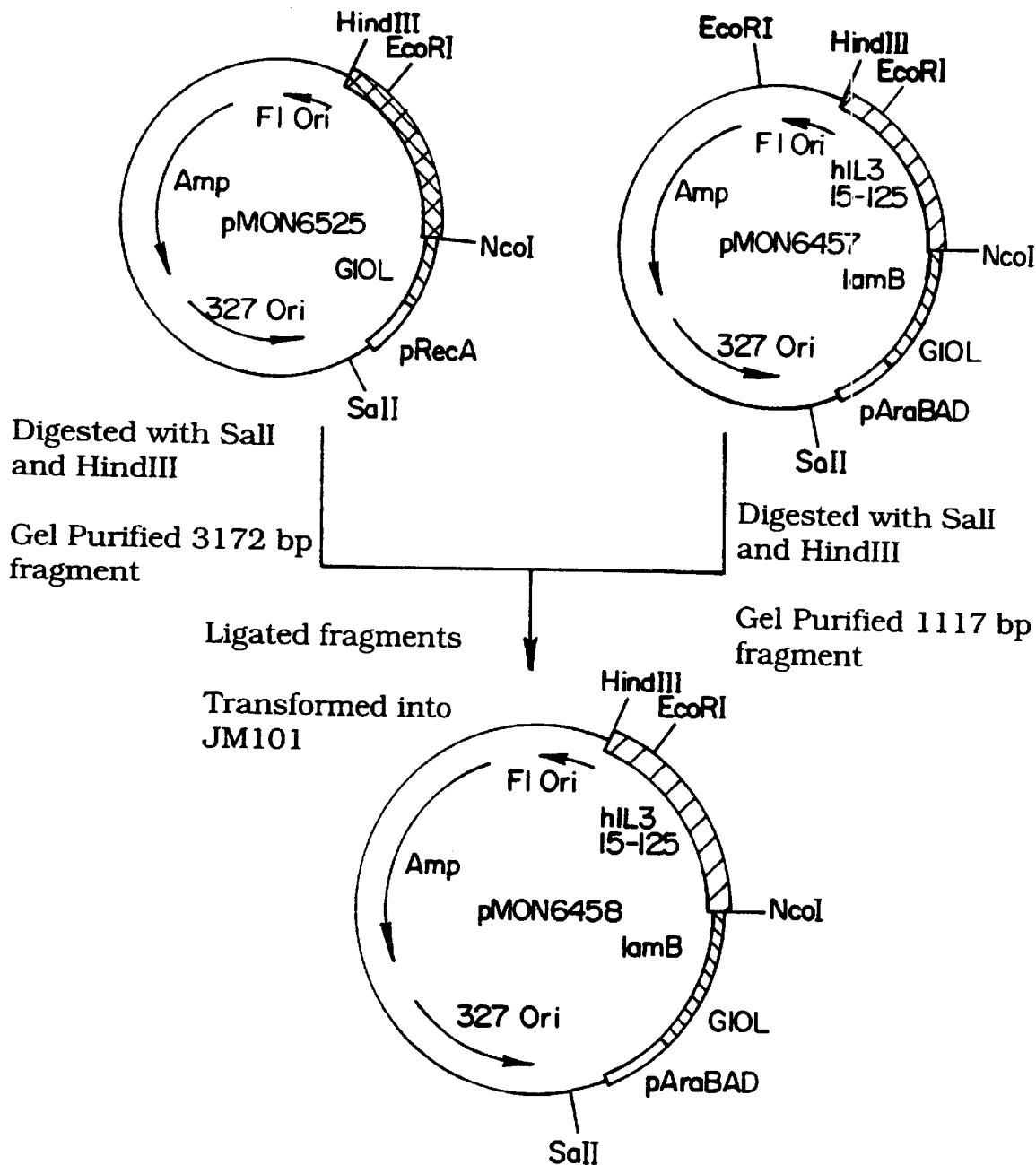
FIG. 14 shows the construction of pMON6458; it contains the araBAD promoter and the lamB signal peptide fused to the variant hIL-3 amino acids 15–125.
Figure 15:
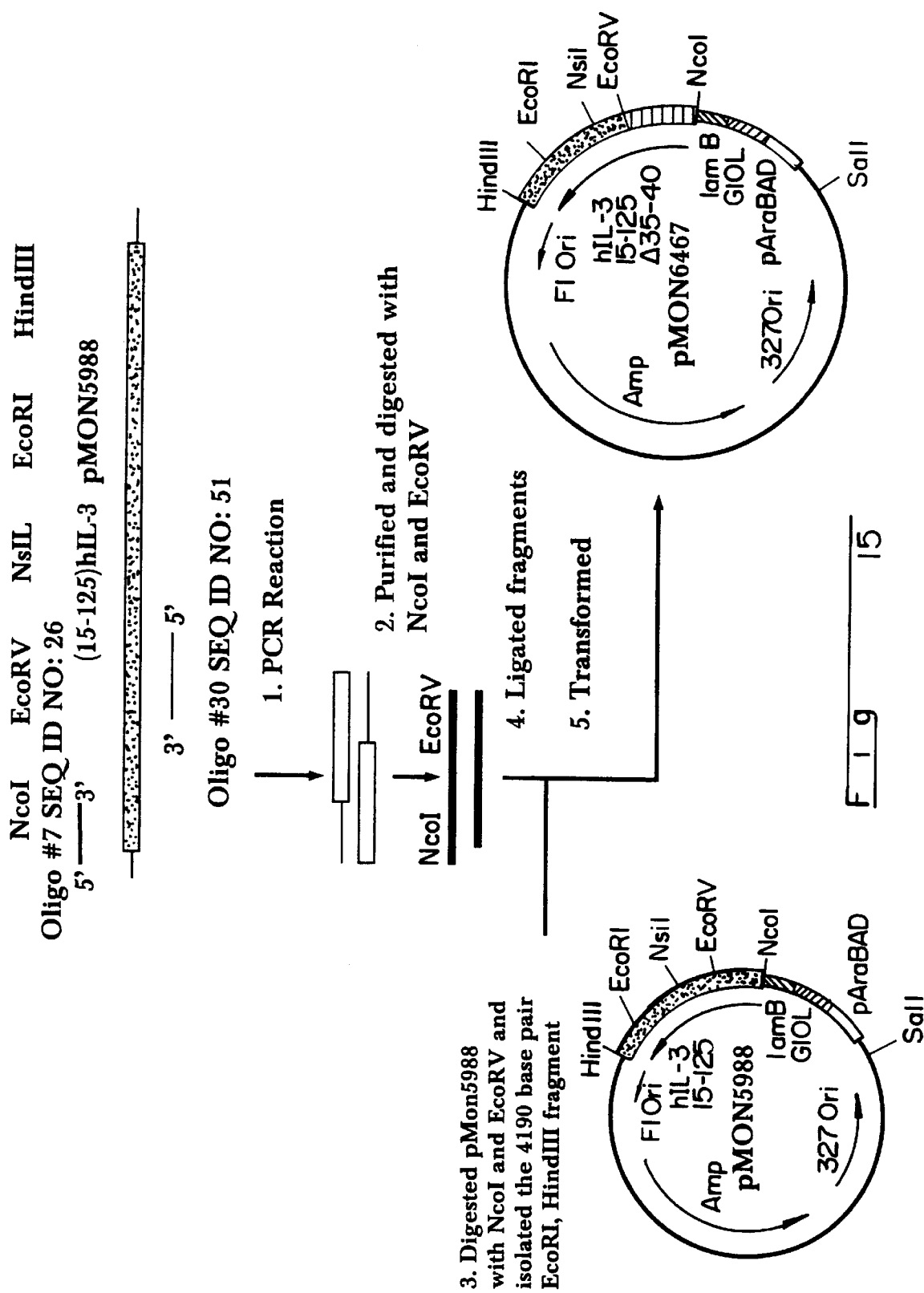
FIG. 15 shows the construction of pMON6467 in which the bases encoding amino acids 35–40 of hIL-3 were deleted using site-directed PCR mutagenesis methods. pMON6467 was used as the template for the generation of single amino acid variants at positions 35–40 of hIL-3.

Construction of pMON5887 (FIG. 12) which encodes [Met-(1-125)hIL-3]

The plasmid DNA of pMON5854 (Example 3) was treated with EcoRI and HindIII and the larger fragment was gel purified. About 0.5 microgram of this DNA was ligated to 1 picomole of an annealed pair of oligonucleotides which encode amino acids 107 through 125 of hIL-3. The sequences of these oligonucleotides are shown below.

```
EcoRI to HindIII
5'-AATTCCGTCGTAAACTGACCTTCTATCTGAAAACCTTGGAGAACGCGCAGGCTCAACAGTAATA-3'  [SEQ ID NO:8]

3'-GGCAGCATTTGACTGGAAGATAGACTTTTGGAACCTCTTGCGCGTCCGAGTTGTCATTATTCGA-5'  [SEQ ID NO:9]
```

After ligation, the DNA was used to transform competent JM101 cells to ampicillin resistance. Colonies were picked into broth and plasmid DNA was isolated from each culture. Restriction analysis of the plasmid DNA showed the presence of an EcoRI to HindIII fragment smaller than that of pMON5854. The nucleotide sequence of the portion of the coding sequence between the EcoRI and HindIII sites was determined to confirm the accuracy of the replaced sequence. The new plasmid was designated pMON5887 encoding Met-(1-125)hIL-3 which has the following amino acid sequence:

[SEQ ID NO:10]

Met Ala Pro Met Thr Gln Thr Thr Ser Leu Lys Thr Ser

Trp Val Asn Cys Ser Asn Met Ile Asp Glu Ile Ile Thr

His Leu Lys Gln Pro Pro Leu Pro Leu Leu Asp Phe Asn

Asn Leu Asn Gly Glu Asp Gln Asp Ile Leu Met Glu Asn

Asn Leu Arg Arg Pro Asn Leu Glu Ala Phe Asn Arg Ala

Val Lys Ser Leu Gln Asn Ala Ser Ala Ile Glu Ser Ile

Leu Lys Asn Leu Leu Pro Cys Leu Pro Leu Ala Thr Ala

-continued

Ala Pro Thr Arg His Pro Ile His Ile Lys Asp Gly Asp

Trp Asn Glu Phe Arg Arg Lys Leu Thr Phe Tyr Leu Lys

Thr Leu Glu Asn Ala Gln Ala Gln Gln

EXAMPLE 5

Construction of pMON5967 which encodes [Met-Ala-(15-125-)hIL-3]

Plasmid DNA of pMON5887 isolated from *E. coli* GM48 (dam-) was cleaved with NcoI and ClaI and ligated to 1 picomole of an annealed pair of oligonucleotides, Nco I and ClaI, encoding amino acids [Met Ala (15–20)hIL-3]. The sequence of these oligonucleotides is shown below.

```
5'-CATGGCTAACTGCTCTAACATGAT-3' [SEQ ID NO:11]
3'-CGATTGACGAGATTGTACTAGC-5'  [SEQ ID NO:12]
```

The resulting ligation mix was used to transform competent *E. coli* JM101 cells to ampicillin resistant colonies. Plasmid DNA was isolated from these cells and the size of the inserted fragment was determined to be smaller than that of pMON5887 by restriction analysis using NcoI and NsiI. The nucleotide sequence of the region between NcoI and ClaI was determined and found to be that of the synthetic oligonucleotides. The new plasmid was designated pMON5967 and cells containing it were induced for protein production. Sonicated cell pellets and supernatants were used for protein purification and bio-assay.

EXAMPLE 6

Construction of pMON5978 which encodes [Met-Ala-(15-125)hIL-3]

Plasmid DNA of pMON5967 isolated from *E. coli* GM48 (dam-) was cleaved with ClaI and NsiI and ligated to 1 picomole of an annealed assembly of six oligonucleotides encoding hIL-3 amino acids 20–70 (FIG. 2). This synthetic fragment encodes three unique restriction sites, EcoRV, XhoI and PstI. The sequence of these oligonucleotides is shown in FIG. 2.

The resulting ligation mix was used to transform competent *E. coli* JM101 cells to ampicillin resistant colonies. Plasmid DNA was isolated and screened with XbaI and EcoRV for the presence of the new restriction site EcoRV. The DNA sequence of the region between ClaI and NsiI was determined and found to be the same as that of the synthetic oligonucleotides. The new plasmid was designated pMON5978, and cells containing it were induced for protein production. Sonicated cell pellets and supernatants were used for protein purification and bio-assay.

Plasmid pMON5978 encodes [Met-Ala-(15-125)hIL-3] which has the following amino acid sequence:

[SEQ ID NO:13]

Met Ala Asn Cys Ser Asn Met Ile Asp Glu Ile Ile Thr

His Leu Lys Gln Pro Pro Leu Pro Leu Leu Asp Phe Asn

-continued

Asn Leu Asn Gly Glu Asp Gln Asp Ile Leu Met Glu Asn

Asn Leu Arg Arg Pro Asn Leu Glu Ala Phe Asn Arg Ala

Val Lys Ser Leu Gln Asn Ala Ser Ala Ile Glu Ser Ile

Leu Lys Asn Leu Leu Pro Cys Leu Pro Leu Ala Thr Ala

Ala Pro Thr Arg His Pro Ile His Ile Lys Asp Gly Asp

Trp Asn Glu Phe Arg Arg Lys Leu Thr Phe Tyr Leu Lys

Thr Leu Glu Asn Ala Gln Ala Gln Gln

EXAMPLE 7

Construction of pMON5898

Figure 8:
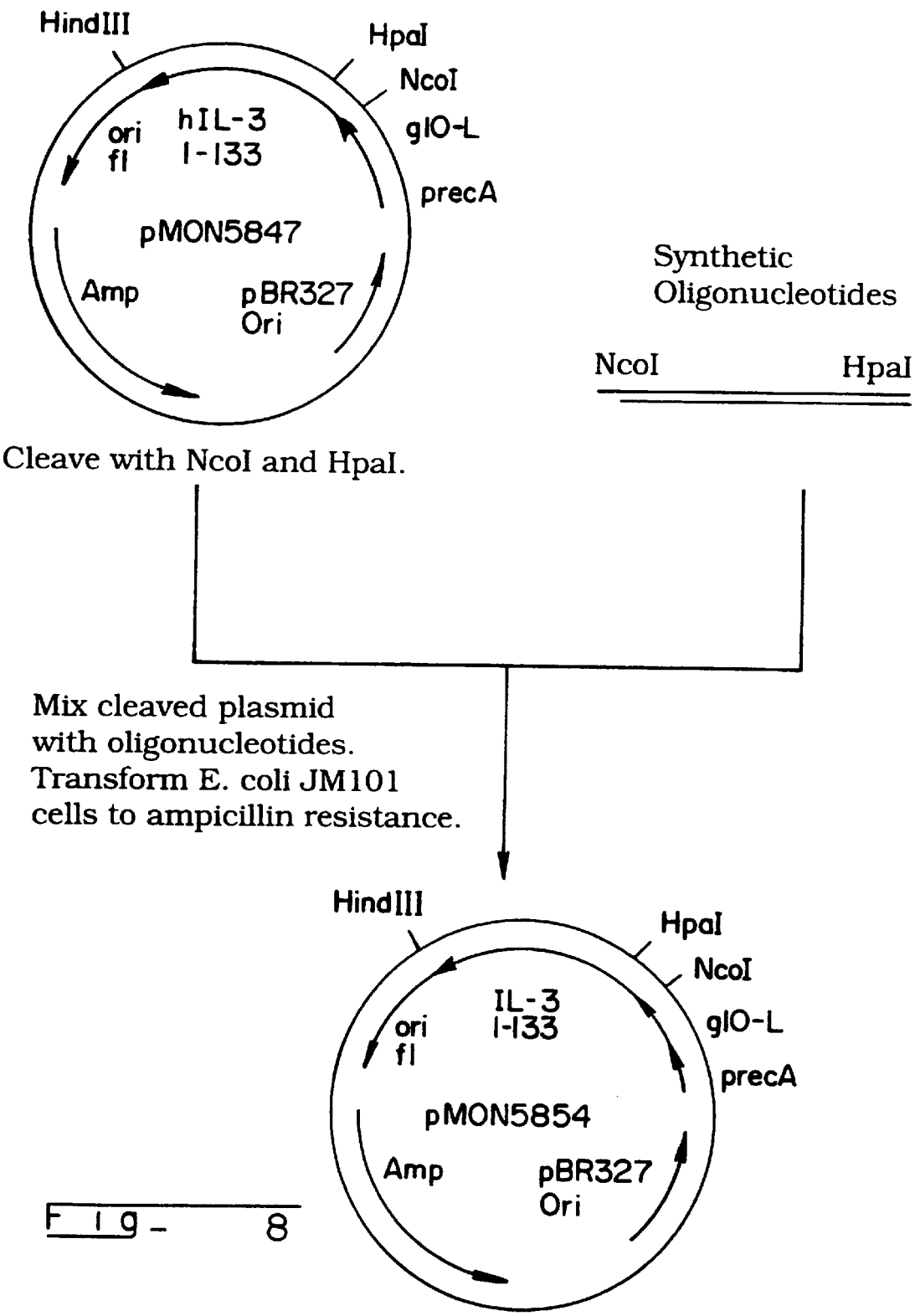
FIG. 8 shows the construction of the plasmid vector pMON5854 which encodes [Met-(1–133) hIL-3 (Arg$^{129}$)].
Figure 10:
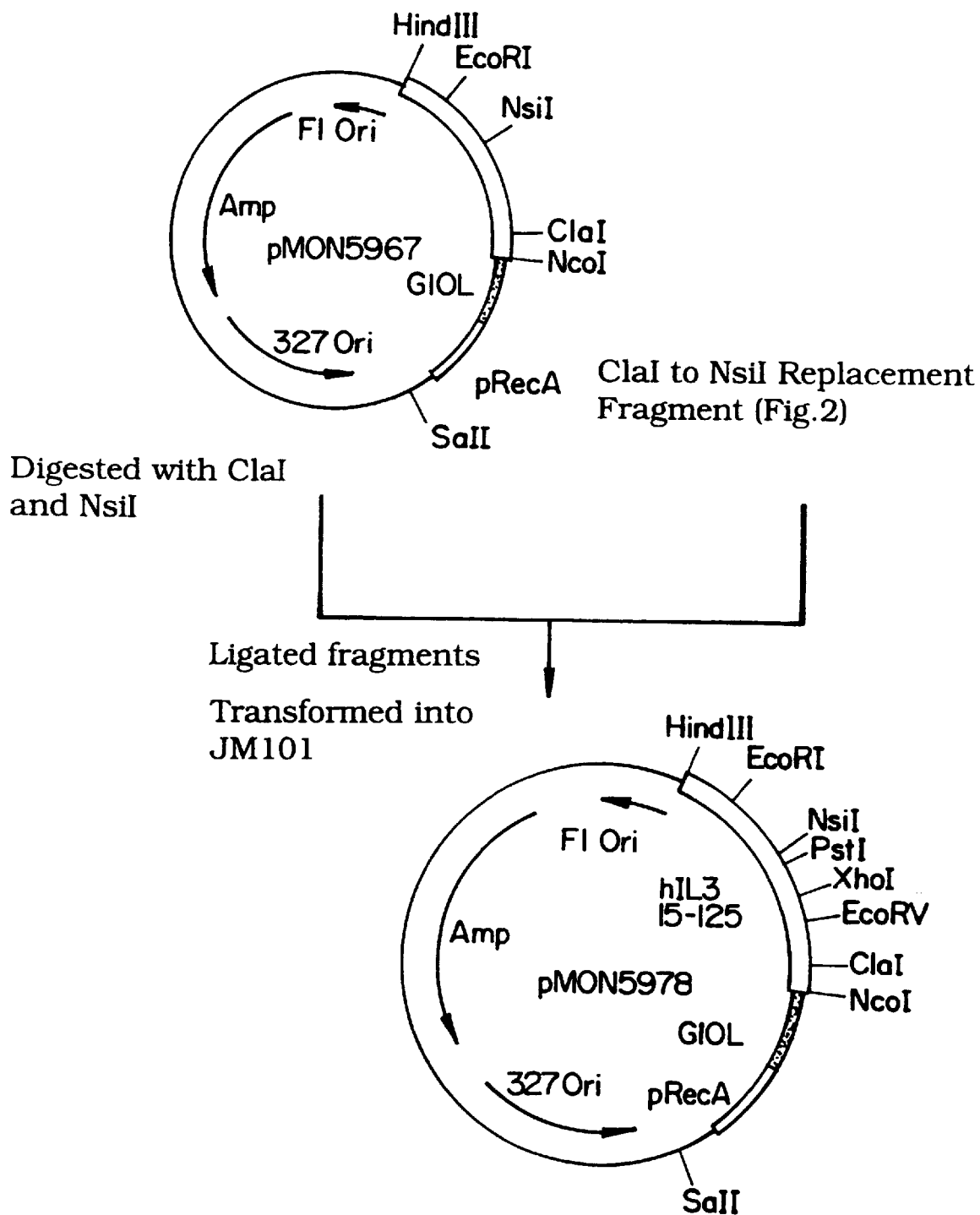
FIG. 10 shows the construction of the plasmid vector pMON5978 which encodes Met-Ala-(15–125)hIL-3.
Figure 11:
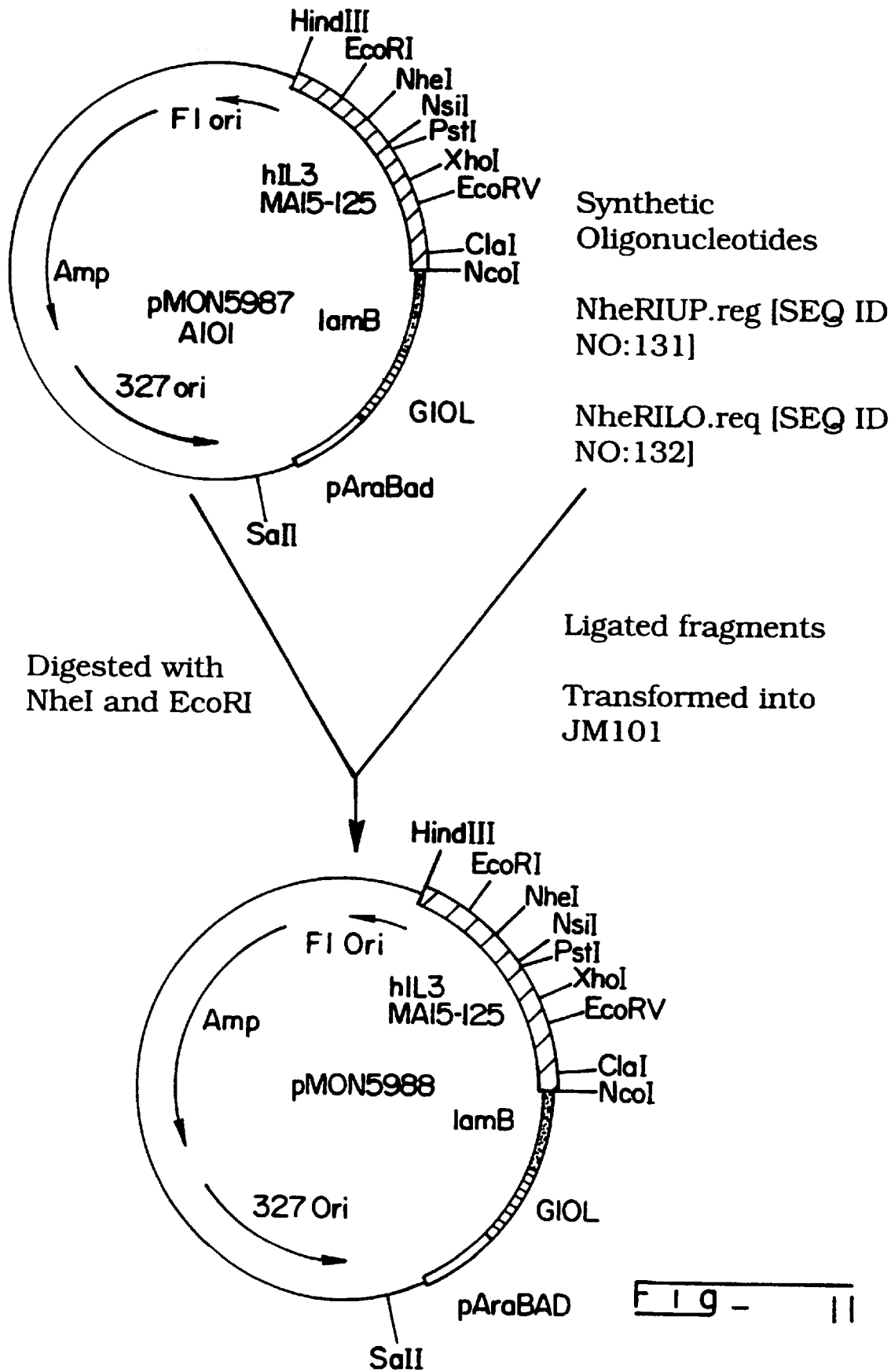
FIG. 11 shows the construction of the plasmid vector pMON5988 which encodes Met-Ala(15–125)hIL-3.

Plasmid pMON5851 DNA was digested with restriction enzymes HindIII and NcoI resulting in a 3695 base pair NcoI, HindIII fragment. The genetic elements derived from pMON5851 are the beta-lactamase gene (AMP), pBR327 origin of replication, phage f1 origin of replication as the transcription terminator, AraBAD promoter, g10L ribosome binding site and the lamb secretion leader. The AraBAD promoter is identical to that described in plasmid pMON6235 and the lamB signal peptide sequence used is that shown in FIG. 8 fused to hIL-3 at the NcoI recognition site. Plasmid pMON5873 DNA was digested with restriction enzymes HindIII and NcoI resulting in a 408 base pair NcoI,HindIII fragment. The genetic element derived from pMON5873 is the hIL-3 gene (1-133). Clones containing the hIL-3 (1-133) gene contained a 408 base pair NcoI, HindIII restriction fragment. This construct was designated pMON5898.

EXAMPLE 8

Construction of pMON5987

Plasmid pMON6458 DNA was digested with restriction enzymes NcoI and HindIII, resulting in a 3940 base pair NcoI,HindIII fragment. The genetic elements derived from pMON6458 are the beta-lactamase gene (AMP), pBR327 origin of replication, phage f1 origin of replication as the transcription terminator, AraBAD promoter, g10L ribosome binding site and lamB secretion leader. Plasmid pMON5978 DNA was digested with NcoI and NsiI. The resulting 170 base pair NcoI, NsiI fragment encodes amino acids 15–71 of (15-125)hIL-3. Plasmid pMON5976 DNA was digested with NsiI and HindIII. The resulting 175 base pair NsiI, HindIII fragment encodes amino acids 72–125 of (15-125) hIL-3. The restriction fragments were ligated, and the ligation reaction mixture was used to transform *E. coli* K-12 strain JM101. Transformant bacteria were selected on ampicillin-containing plates. Plasmid DNA was isolated and screened for the restriction sites EcoRV and NheI and DNA sequenced to confirm the correct insert.

EXAMPLE 9

Construction of pMON5988

The plasmid DNA of pMON5987 was digested with NheI and EcoRI, resulting in a 3903 base pair NheI, EcoRI fragment. The 3903 base pair NheI, EcoRI fragment was ligated to 1.0 picomoles of the following annealed oligo-nucleotides (Oligo #3 and Oligo #4):

5'-CTAGCCACGGCCGCACCCACGCGACATCCAATCCATATCAAGGACGGTGACTGGAATG-3' [SEQ ID NO:131]

3'-GGTGCCGGCGTGGGTGCGCTGTAGGTTAGGTATAGTTCCTGCCACTGACCTTACAATT-5' [SEQ ID NO:132]

The ligation reaction mixture was used to transform *E. coli* K-12 strain JM101 and transformant bacteria were selected on ampicillin-containing plates. Plasmid DNA was isolated and sequenced to confirm positive clones. This plasmid was constructed to change alanine 101 to aspartic acid in the hIL-3 gene (15-125). The Ala$^{101}$ to Asp$^{101}$ change was confirmed by DNA sequencing. This plasmid was designated pMON5988 and encodes Peptide #1 [SEQ ID NO:65].

EXAMPLE 10

Construction of pMON5873 which Encodes [Met-(1-133)hIL-3]

The gene obtained from British Biotechnology, Ltd. specified arginine at codon position 129. The amino acid specified in the native hIL-3 cDNA is serine. To produce a protein with the native sequence at this position, the portion of the coding sequence between the EcoRI site at codons 106 and 107 and the NheI site at codons 129 and 130 was replaced. Plasmid DNA of pMON5854 (Example 3) and pMON5853 (Example 64) were treated with EcoRI and NheI. The larger fragments of each were gel purified. These were ligated to a pair of an annealed oligonucleotides with the following sequences:

5'-AATTCCGTCGTAAACTGACCTTCTATCTGAAAACCTTGGAGAACGCGCAGGCTCAACAGACCACTCTGTCG-3' [SEQ ID NO: 136]

3'-GGCAGCATTTGACTGGAAGATAGACTTTTGGAACCTCTTGCGCGTCCGAGTTGTCTGGTGAGACAGCGATC-5' [SEQ ID NO: 137]

The ligation reaction mixtures were used to transform competent JM101 cells to ampicillin resistance. Colonies were picked into broth and grown. Plasmid DNA was isolated and screened for the presence of a new StyI recognition site present in the synthetic DNA and not in pMON5854 and pMON5853. The nucleotide sequence of the gene in the region between EcoRI and NheI was determined and found to be that of the synthetic oligonucleotides. The new plasmids were designated pMON5873 encoding [Met-(1-133)hIL-3] and pMON5872 encoding [Met-(15-133)hIL-3].

The plasmid, pMON5873, encodes Met-(1-133)hIL-3 which has the following amino acid sequence:

[SEQ ID NO:128]

Met Ala Pro Met Thr Gln Thr Thr Ser Leu Lys Thr Ser

Trp Val Asn Cys Ser Asn Met Ile Asp Glu Ile Ile Thr

His Leu Lys Gln Pro Pro Leu Pro Leu Leu Asp Phe Asn

Asn Leu Asn Gly Glu Asp Gln Asp Ile Leu Met Glu Asn

Asn Leu Arg Arg Pro Asn Leu Glu Ala Phe Asn Arg Ala

Val Lys Ser Leu Gln Asn Ala Ser Ala Ile Glu Ser Ile

Leu Lys Asn Leu Leu Pro Cys Leu Pro Leu Ala Thr Ala

Ala Pro Thr Arg His Pro Ile His Ile Lys Asp Gly Asp

Trp Asn Glu Phe Arg Arg Lys Leu Thr Phe Tyr Leu Lys

-continued

Thr Leu Glu Asn Ala Gln Ala Gln Gln Thr Thr Leu Ser

Leu Ala Ile Phe

EXAMPLE 11

Construction of pMON6458

Plasmid pMON6525 DNA was digested with restriction enzymes HindIII and SalI and the resulting 3172 base pair fragment was isolated from a 1% agarose gel by interception onto DEAE membrane. The genetic elements derived from pMON6525 are the beta-lactamase gene (AMP), pBR327 origin of replication, and phage f1 origin of replication as the transcription terminator. (The genetic elements derived from plasmid pMON6525 are identical to those in plasmid pMON2341 which could also be used to construct pMON6458.) Plasmid pMON6457 was digested with restriction enzymes HindIII and SalI and the resulting 1117 base pair fragment was isolated by PAGE and crush and soak elution. The genetic elements derived from pMON6457 are the pAraBAD promoter, g10L ribosome binding site, lamB secretion leader and the (15-125) hIL-3 gene. The restriction fragments were ligated and the ligation reaction mixture was used to transform *E. coli* K-12 strain JM101. Transformant bacteria were selected on ampicillin-containing plates. Plasmid DNA was isolated and the size of the inserted fragment was determined by restriction analysis employing restriction enzymes NcoI and HindIII in double digest. Clones containing the hIL-3 gene (encoding amino acids 15–125) contained a 345 base pair NcoI, HindIII restriction fragment. This construct was designated pMON6458. This plasmid was constructed to eliminate an EcoRI restriction site outside the hIL-3 gene coding region in plasmid pMON6457.

EXAMPLE 12

Construction of pMON6455

Plasmid pMON5905 DNA was digested with restriction enzymes HindIII and NcoI resulting in a 3936 base pair fragment. The genetic elements derived from pMON5905 are the beta-lactamase gene (AMP), pBR327 origin of replication, pAraBAD promoter, g10L ribosome binding site, lamB secretion leader and phage f1 origin of replication as the transcription terminator. The following genetic elements; beta-lactamase gene (AMP), pBR327 origin of replication, g10L ribosome binding site and phage f1 origin of replication as the transcription terminator, derived from plasmid pMON5905 are identical to those in plasmid pMON5594 which could also be used to construct pMON6455. The AraBAD promoter is identical to that described in pMON6235. The lamB signal peptide sequence used in pMON6455 is that shown in FIG. 8 fused to hIL-3 (15-125) at the NcoI site. Plasmid pMON5887 DNA was digested with restriction enzymes HindIII and NcoI, resulting in a 384 base pair NcoI, HindIII fragment. The restriction fragments were ligated, and the ligation reaction mixture was used to transform into E. coli K-12 strain JM101. Transformant bacteria were selected on ampicillin-containing plates. Plasmid DNA was isolated and the size of the inserted fragment was determined by restriction analysis employing restriction enzymes NcoI and HindIII in double digest. Positive clones containing the hIL-3 gene (encoding amino acids 1–125) contained a 384 base pair NcoI, HindIII restriction fragment. This construct was designated pMON6455.

EXAMPLE 13

Construction of pMON6456

Plasmid pMON5905 DNA was digested with restriction enzymes HindIII and NcoI resulting in a 3936 base pair fragment. The genetic elements derived from pMON5905 are the beta-lactamase gene (AMP), pBR327 origin of replication, phage f1 origin of replication as the transcription terminator, pAraBAD promoter, g10L ribosome binding site and the lamB secretion leader. Plasmid pMON5871 was digested with restriction enzymes HindIII and NcoI, resulting in a 330 base pair NcoI, HindIII fragment. The genetic element derived from pMON5871 encompassed the bases encoding the (1-107) hIL-3 gene. The restriction fragments were ligated, and the ligation reaction mixture was used to transform E. coli K-12 strain JM101. Transformant bacteria were selected on ampicillin-containing plates. Plasmid DNA was isolated and the size of the inserted fragment was determined by restriction analysis employing restriction enzymes NcoI and HindIII in double digest. Clones containing the hIL-3 gene (encoding amino acids 1–107) contained a 330 base pair NcoI, HindIII restriction fragment. This construct was designated pMON6456.

EXAMPLE 14

Construction of pMON6457

Plasmid pMON6455 DNA grown in E. coli strain GM48 (dam-) was digested with restriction enzymes NcoI and ClaI, resulting in a 4263 base pair NcoI, ClaI fragment. The restriction fragment was ligated to 1.0 picomoles of annealed oligonucleotides (Oligo #5 and Oligo #6) with the following sequence coding for Met Ala 14-20 hIL-3:

```
5'-CATGGCTAACTGCTCTAACATGAT-3'      [SEQ ID NO:151]

3'-CGATTGACGAGATTGTACTAGC-5'        [SEQ ID NO:152]
```

The resulting DNA was transformed into E. coli K-12 strain JM101 and transformant bacteria were selected on ampicillin-containing plates. Plasmid DNA was isolated and the size of the inserted fragment was determined by restriction analysis employing restriction enzymes XbaI and EcoRI in double digest. Positive clones containing the hIL-3 gene (encoding aa 15-125 of hIL-3) contained a 433 base pair XbaI, EcoRI restriction fragment and were DNA sequenced. This construct was designated pMON6457. This plasmid was constructed to delete the first 14 amino acids of hIL-3. The coding sequence of the resulting gene begins as follows:

```
5'    ATG GCT AAC TGC...    3'[SEQ ID NO:153]

Met Ala Asn Cys...      [SEQ ID NO:154]
       15
```

The first two amino acids (Methionine, Alanine) create an NcoI restriction site and a signal peptidase cleavage site between the lamB signal peptide and (15-125) hIL-3. Plasmid pMON6457 encodes (15-125) hIL-3 which has the amino acid sequence designated SEQ ID NO:65.

EXAMPLE 15

Construction of pMON6235

One of the DNA fragments used to create this plasmid was generated by site-directed mutagenesis employing PCR techniques described previously using the following oligonucleotides, Oligo #51(A) [SEQ ID NO:155] and Oligo #52(A) [SEQ ID NO:156], were used as primers in this procedure. The template for the PCR reaction was E. coli strain W3110 chromosomal DNA, prepared as described in Maniatis (1982). The oligonucleotide primers were designed to amplify the AraBAD promoter (Greenfield et al., 1978). The resulting DNA product was digested with the restriction enzymes SacII and BglII. The reaction mixture was purified as described previously. Plasmid, pMON5594, DNA was digested with SacII and BglII, resulting in a 4416 base pair SacII,BglII restriction fragment which contains the following genetic elements; beta-lactamase gene (AMP), pBR327 origin of replication, G10L ribosome binding site, phage f1 origin of replication as the transcription terminator and the chloramphenicol acetyl transferase (cat) gene. The 4416 base pair SacII,BglII restriction fragment from pMON5594 was ligated to the PCR-generated SacII, BglII DNA fragment. The ligation mixture was used to transform E. coli K-12 strain JM101. Positive clones contained a 323 base pair SacII,BglII fragment and were DNA sequenced to confirm that the SacII,BglII fragment was the AraBAD promoter. This construct was designated pMON6235.

EXAMPLE 16

Construction of pMON6460

One of the DNA fragments to construct this plasmid was generated by site-directed mutagenesis employing PCR techniques described previously using the oligonucleotides, Oligo #7 [SEQ ID NO: 26] and Oligo #8 [SEQ ID NO: 27] as primers. The template for the PCR reaction was plasmid pMON6458 DNA. The resulting DNA product was digested with the restriction enzymes NcoI and EcoRI. Upon completion, the digest was heated at 70° C. for 15 minutes to inactivate the enzymes. The restriction fragment was purified by phenol/chloroform extraction and precipitation with equal volume isopropanol in the presence of 2M NH$_4$OAc. The oligonucleotide, Oligo #8, introduces two stop codons (TAA) after amino acid 93 of hIL-3 and creates a SalI restriction endonuclease recognition sequence. The NcoI, EcoRI restriction fragment from pMON6458 was ligated to the PCR-generated NcoI, EcoRI restriction fragment. Positive clones containing the above mentioned changes released a 1023 base pair SalI fragment. This construct was designated pMON6460. This plasmid was constructed to serve as the template for the creation of single amino acid substitution variants at positions 94, 95, 96 and 97 of hIL-3.

EXAMPLE 17

Construction of pMON6461

One of the DNA fragments to create this plasmid was generated by site-directed mutagenesis employing PCR techniques described previously using the following oligonucleotide, Oligo #7 [SEQ. ID NO: 26] and Oligo #9

[SEQ. ID NO: 28], as primers. The template for the PCR reaction was plasmid pMON6458 DNA. The resulting DNA product was digested with the restriction enzymes NcoI and EcoRI. The oligonucleotide, Oligo #9, introduces two stop codons (TAA) after amino acid 97 of hIL-3 and creates a SalI restriction endonuclease recognition sequence. The NcoI, EcoRI restriction fragment from pMON5458 was ligated to the PCR-generated NcoI, EcoRI DNA fragment. Positive clones containing the above mentioned changes released a 1035 base pair SalI fragment. This construct was designated pMON6461. This plasmid was constructed to serve as the template for the creation of single amino acid substitution variants at positions 98, 99, 100 and 101 of hIL-3.

EXAMPLE 18

Construction of pMON6462

One of the DNA fragments to create this plasmid was generated by site-directed mutagenesis employing PCR techniques described previously using the following oligonucleotide, Oligo #7 [SEQ. ID NO: 26] and Oligo #10 [SEQ. ID NO: 31], as primers. The template for the PCR reaction was plasmid pMON6458 DNA. The resulting DNA product was digested with the restriction enzymes NcoI and EcoRI. The oligonucleotide, Oligo #10 [SEQ. ID NO: 31] introduces two stop codons (TAA) after amino acid 101 of hIL-3 and creates a SalI restriction endonuclease recognition sequence. The NcoI, EcoRI restriction fragment from pMON5458 was ligated to the PCR-generated NcoI, EcoRI DNA fragment. Positive clones containing the above mentioned changes released a 1047 base pair SalI fragment. This construct was designated pMON6462. This plasmid was constructed to serve as the template for the creation of single amino acid substitution variants at positions 102, 103, 104 and 105 of hIL-3.

EXAMPLE 19

Construction of Single Amino Acid Substitution Libraries at Positions 94, 95, 96 and 97

One of the DNA fragments used to construct the plasmids containing single amino acid substitution at positions 94, 95, 96 and 97 was generated by site-directed mutagenesis employing PCR techniques described previously. In the PCR reaction plasmid pMON6460 DNA was the template and the oligonucleotide, Oligo #7 [SEQ. ID NO: 26], was used as the primer at the N-terminus. The degenerate oligonucleotides, Oligo #11 [SEQ. ID NO: 32], Oligo #12 [SEQ. ID NO: 33], Oligo #13 [SEQ. ID NO: 34] and Oligo #14 [SEQ. ID NO: 35], were the primers at the C-terminus. These oligonucleotides are 32-fold degenerate, with G, A, T or C in the first and second positions and G or C in the third position of a single codon at amino acid positions 94, 95, 96 and 97 of hIL-3 respectively. These degenerate oligonucleotide primers theoretically contain 32 different codons encoding all 20 amino acid substitutions and one translational stop codon at a single position. The degenerate oligonucleotides (Oligo #11 [SEQ. ID NO: 32], Oligo #12 [SEQ. ID NO: 33], Oligo #13 [SEQ. ID NO: 34] and Oligo #14 [SEQ. ID NO: 35]) replace the twelve bases introduced into pMON6460, that encode the two stop codons (TAA) after amino acid 93 of hIL-3 and the SalI recognition sequence. At the other 9 bases the DNA sequence was restored to encode the native hIL-3 protein sequence. The resulting PCR-generated DNA products were digested with the restriction enzymes NcoI and EcoRI. The 4008 bp NcoI, EcoRI restriction fragment from pMON6460 was ligated to the PCR-generated NcoI, EcoRI DNA fragments. Plasmid DNA from individual colonies was isolated as described previously and screened by DNA dot blot differential hybridization using the oligonucleotide, Oligo #15 [SEQ. ID NO: 36], as the probe which had been labeled with $p^{32}$. Clones shown to be positive by hybridization were selected, plasmid DNA isolated and DNA sequenced to determine the amino acid substitution.

EXAMPLE 20

Construction of Single Amino Acid Substitution Libraries at Positions 98, 99, 100 and 101

Single amino acid substitutions variants were constructed at position 98, 99, 100 and 101 as described previously, with the following changes. In the PCR reaction the template was plasmid pMON6461 DNA and the oligonucleotide, Oligo #7 [SEQ. ID NO: 26], was used as the primer at the N-terminus. The degenerate oligonucleotides, Oligo #16 [SEQ. ID NO: 37], Oligo #17 [SEQ. ID NO: 38], Oligo #18 [SEQ. ID NO: 39] and Oligo #19 [SEQ. ID NO: 40], were used as primers at the C-terminus. The resulting PCR-generated DNA products were purified and digested with restriction enzymes NcoI and EcoRI. The 4008 bp NcoI, EcoRI restriction fragment from pMON6461 was ligated to the PCR-generated DNA NcoI, EcoRI restriction fragment. Single colonies were screened by DNA dot blot differential hybridization using the oligonucleotide, Oligo #20 [SEQ. ID NO: 41], as the probe. Clones shown to be positive by hybridization were selected, plasmid DNA isolated and DNA sequenced to determine the amino acid substitution.

EXAMPLE 21

Construction of Single Amino Acid Substitution Libraries at Positions 102, 103, 104 and 105

Single amino acid substitutions variants were constructed at position 102, 103, 104 and 105 as described previously, with the following changes. The template was pMON6462 and the oligonucleotide, Oligo #7 [SEQ. ID NO: 26], was used as the primer at the N-terminus. The degenerate oligonucleotides, Oligo #21 [SEQ. ID NO: 42], Oligo #22 [SEQ. ID NO: 43], Oligo #23 [SEQ. ID NO: 44] and Oligo #24 [SEQ. ID NO: 45] were used as primers at the C-terminus. The resulting PCR-generated DNA products were purified and digested with restriction enzymes, NcoI and EcoRI. The 4008 bp NcoI, EcoRI restriction fragment from pMON6462 was ligated to the PCR-generated NcoI, EcoRI restriction fragment. Single colonies were screened by DNA dot blot differential hybridization using the oligonucleotide, Oligo #25 [SEQ. ID NO: 46], as the probe. Clones shown to be positive by hybridization were selected, plasmid DNA isolated and DNA sequenced to determine the amino acid substitution.

EXAMPLE 22

Construction of Plasmid pMON6464

Amino acids 17–22 of hIL-3 were deleted using site-directed PCR mutagenesis methods described previously. Plasmid pMON6458 DNA was the template in the PCR reaction using the oligonucleotides, Oligo #26 and Oligo #27 as primers. The resulting PCR-generated DNA products were purified and digested with NcoI and EcoRI. The 4008 bp NcoI, EcoRI restriction fragment from pMON6458 was ligated to the PCR-generated NcoI, EcoRI restriction fragment. Positive clones contained a 263 base pair NcoI, EcoRI restriction fragment in which the bases encoding amino acids 17–22 of hIL-3 have been deleted. pMON6464 was made to serve as the template for the creation of single amino acid substitution variants at positions 17, 18, 19, 20, 21 and 22 of hIL-3.

EXAMPLE 23

Construction of Plasmid pMON6465

Amino acids 23–28 of hIL-3 were deleted using site-directed PCR mutagenesis methods described previously. Plasmid pMON6458 DNA was the template in the reaction using the oligonucleotides, Oligo #26 and Oligo #28, as primers. The resulting PCR-generated DNA product was purified and digested with NcoI and EcoRI. The 4008 bp NcoI, EcoRI restriction fragment from pMON6458 was ligated to the PCR-generated NcoI, EcoRI restriction fragment. Positive clones contained a 263 base pair NcoI, EcoRI restriction fragment in which the bases encoding amino acids 23–28 of hIL-3 have been deleted. pMON6465 was made to serve as the template for the creation of single amino acid substitution variants at positions 23, 24, 25, 26, 27 and 28 of hIL-3.

EXAMPLE 24

Construction of Plasmid pMON6466

Amino acids 29–34 of hIL-3 were deleted using site-directed PCR mutagenesis methods described previously. Plasmid pMON6458 DNA was the template in the reaction using the oligonucleotides, Oligo #26 and Oligo #29 as the primers. The resulting PCR-generated DNA product was purified and digested with NcoI and EcoRI. The 4008 bp NcoI, EcoRI restriction fragment from pMON6458 was ligated to the PCR-generated NcoI, EcoRI restriction fragment. Positive clones contained a 263 base pair NcoI, EcoRI restriction fragment in which the bases encoding amino acids 29–34 of hIL-3 have been deleted. pMON6466 was made to serve as the template for the creation of single amino acid substitution variants at positions 29, 30, 31, 32, 33 and 34 of hIL-3.

EXAMPLE 25

Construction of Plasmid pMON6467

Amino acids 35–40 of hIL-3 were deleted using site-directed PCR mutagenesis methods described previously. Plasmid pMON5988 DNA was the template in the reaction using the oligonucleotides, Oligo #7 and Oligo #30, as primers. The resulting PCR-generated DNA product was purified and digested with NcoI and EcoRV. The NcoI, EcoRV restriction fragment from pMON5988 was ligated to the PCR-generated NcoI, EcoRV restriction fragment. Positive clones contained a 81 base pair NcoI, EcoRV restriction fragment in which the bases encoding amino acids 35–40 of hIL-3 have been deleted. pMON6467 was made to serve as the template for the creation of single amino acid substitution variants at positions 35, 36, 37, 38, 39 and 40 of hIL-3.

EXAMPLE 26

Construction of Plasmid pMON6468

Amino acids 41–46 of hIL-3 were deleted using site-directed PCR mutagenesis methods described previously. Plasmid pMON5988 DNA was the template in the reaction using the oligonucleotides, Oligo #7 and Oligo #31, as the primers. The resulting PCR-generated DNA product was purified and digested with NcoI and XhoI. The NcoI, XhoI restriction fragment from pMON5988 was ligated to the PCR-generated NcoI, XhoI restriction fragment. Positive clones contained a 119 base pair NcoI, XhoI restriction fragment in which the bases encoding amino acids 41–46 of hIL-3 have been deleted. pMON6468 was made to serve as the template for the creation of single amino acid substitution variants at positions 41, 42, 43, 44, 45 and 46 of hIL-3.

EXAMPLE 27

Construction of Plasmid pMon6469

Amino acids 47–52 of hIL-3 were deleted using site-directed PCR mutagenesis methods described previously. Plasmid pMON5988 DNA was the template in the reaction using the oligonucleotides, Oligo #7 and Oligo #32, as the primers. The resulting PCR-generated DNA product was purified and digested with NcoI and XhoI. The NcoI, XhoI restriction fragment from pMON5988 was ligated to the PCR-generated NcoI, XhoI restriction fragment. Positive clones contained a 119 base pair NcoI, XhoI restriction fragment in which the bases encoding amino acids 47–52 of hIL-3 have been deleted. pMON6469 was made to serve as the template for the creation of single amino acid substitution variants at positions 47, 48, 49, 50, 51 and 52 of hIL-3.

EXAMPLE 28

Construction of Plasmid pMON6470

Amino acids 53–58 of hIL-3 were deleted using site-directed PCR mutagenesis methods described previously. Plasmid, pMON5988, DNA was the template in the reaction using the oligonucleotides, Oligo # 7 and Oligo #33, as primers. The resulting PCR-generated DNA product was purified and digested with NcoI and NsiI. The NcoI, NsiI restriction fragment from pMON5988 was ligated to the PCR-generated NcoI, NsiI restriction fragment. Positive clones contained a 152 base pair NcoI, NsiI restriction fragment in which the bases encoding amino acids 53–58 of hIL-3 have been deleted. pMON6470 was made to serve as the template for the creation of single amino acid substitution variants at positions 53, 54, 55, 56, 57 and 58 of hIL-3.

EXAMPLE 29

Construction of Plasmid pMON6471

Amino acids 59–64 of hIL-3 were deleted using site-directed PCR mutagenesis methods described previously. Plasmid pMON5988 DNA was the template in the reaction using the oligonucleotides, Oligo #7 and Oligo #34, as the primers. The resulting PCR-generated DNA product was purified and digested with NcoI and NsiI. The NcoI, NsiI restriction fragment from pMON5988 was ligated to the PCR-generated NcoI, NsiI restriction fragment. Positive clones contained a 152 base pair NcoI, NsiI restriction fragment in which the bases encoding amino acids 59–64 of hIL-3 have been deleted. pMON6471 was made to serve as the template for the creation of single amino acid substitution variants at positions 59, 60, 61, 62, 63 and 64 of hIL-3.

EXAMPLE 30

Construction of Plasmid pMon6472

Amino acids 65–70 of hIL-3 were deleted using site-directed PCR mutagenesis methods described previously.

Plasmid pMON5988 DNA was the template in the reaction using the oligonucleotides, Oligo #26 and Oligo # 35, as primers. The resulting PCR-generated DNA product was purified and digested with EcoRI and XhoI. The EcoRI, XhoI restriction fragment from pMON5988 was ligated to the PCR-generated EcoRI, XhoI restriction fragment. Positive clones contained a 126 base pair EcoRI, XhoI restriction fragment in which the bases encoding amino acids 65–70 of hIL-3 have been deleted. pMON6472 was made to serve as the template for the creation of single amino acid substitution variants at positions 65, 66, 67, 68, 69 and 70 of hIL-3.

EXAMPLE 31

Construction of Plasmid pMON6473

Amino acids 71–76 of hIL-3 were deleted using site-directed PCR mutagenesis methods described previously. Plasmid, pMON5988, DNA was the template in the reaction using the oligonucleotides, Oligo #26 and Oligo #36, as primers. The resulting PCR-generated DNA product was and digested with PstI and EcoRI. The PstI, EcoRI restriction fragment from pMON5988 was ligated to the PCR-generated PstI, EcoRI restriction fragment. Restriction analysis was with NcoI, NsiI and EcoRI in a triple digest. Positive clones contained a 263 base pair NcoI, EcoRI restriction fragment, in which the bases encoding amino acids 71–76 of hIL-3 have been deleted, and lost the NsiI restriction site. pMON6473 was made to serve as the template for the creation of single amino acid substitution variants at positions 71, 72, 73, 74, 75 and 76 of hIL-3.

EXAMPLE 32

Construction of Plasmid pMON6474

Amino acids 77–82 of hIL-3 were deleted using site-directed PCR mutagenesis methods described previously. Plasmid pMON5988 DNA was the template in the reaction using the oligonucleotides, Oligo #26 and Oligo #37, as primers. The resulting PCR-generated DNA product was purified and digested with PstI and EcoRI. The PstI, EcoRI restriction fragment from pMON5988 was ligated to the PCR-generated PstI, EcoRI restriction fragment. Restriction analysis was with NcoI, NsiI and EcoRI in a triple digest. Positive clones contained a 170 base pair NcoI, NsiI restriction fragment and a 93 base pair NsiI, EcoRI restriction fragment in which the bases encoding amino acids 77–82 of hIL-3 have been deleted. pMON6474 was made to serve as the template for the creation of single amino acid substitution variants at positions 77, 78, 79, 80, 81 and 82 of hIL-3.

EXAMPLE 33

Construction of Plasmid pMON6475

Amino acids 83–88 of hIL-3 were deleted using site-directed PCR mutagenesis methods described previously. Plasmid pMON5988 DNA was the template in the reaction using the oligonucleotides, Oligo #26 and Oligo #38, as primers. The resulting PCR-generated DNA product was digested with PstI and EcoRI. The PstI, EcoRI restriction fragment from pMON5988 was ligated to the PCR-generated PstI, EcoRI restriction fragment. Restriction analysis was with NcoI, NsiI and EcoRI in a triple digest. Positive clones contained a 170 base pair NcoI, NsiI restriction fragment and a 93 base pair NsiI, EcoRI restriction fragment in which the bases encoding amino acids 83–88 of hIL-3 have been deleted. pMON6475 was made to serve as the template for the creation of single amino acid substitution variants at positions 83, 84, 85, 86, 87 and 88 of hIL-3.

EXAMPLE 34

Construction of Plasmid pMON6476

Amino acids 88–93 of hIL-3 were deleted using site-directed PCR mutagenesis methods described previously. Plasmid pMON6458 DNA was the template in the reaction using the oligonucleotides, Oligo #7 and Oligo #39, as primers. The resulting PCR-generated DNA product was purified and digested with NcoI and EcoRI. The NcoI, EcoRI restriction fragment from pMON6458 was ligated to the PCR-generated NcoI, EcoRI restriction fragment. Positive clones contained a 263 base pair NcoI, EcoRI restriction fragment in which the bases encoding amino acids 88–93 of hIL-3 have been deleted. pMON6476 was made to serve as the template for the creation of single amino acid substitution variants at positions 88, 89, 90, 91, 92 and 93 of hIL-3.

EXAMPLE 35

Construction of Plasmid pMON6477

Amino acids 106–111 of hIL-3 were deleted using site-directed PCR mutagenesis methods described previously. Plasmid pMON6458 DNA was the template in the reaction using the oligonucleotides, Oligo #7 and Oligo #40, as primers. The resulting PCR-generated DNA fragment was purified and digested with NcoI and HindIII. The NcoI, HindIII restriction fragment from pMON6458 was ligated to the PCR-generated NcoI, HindIII restriction fragment. Positive clones contained a 327 base pair NcoI, HindIII restriction fragment in which the bases encoding amino acids 106–111 of hIL-3 have been deleted. pMON6477 was made to serve as the template for the creation of single amino acid substitution variants at positions 106, 107, 108, 109, 110 and 111 of hIL-3.

EXAMPLE 36

Construction of Plasmid pMON6478

Amino acids 112–117 of hIL-3 were deleted using site-directed PCR mutagenesis methods described previously. Plasmid pMON6458 DNA was the template in the reaction using the oligonucleotides, Oligo #7 and Oligo #41, as primers. The resulting PCR-generated DNA product was purified and digested with NcoI and HindIII. The 4008 bp NcoI, HindIII restriction fragment from pMON6458 was ligated to the PCR-generated NcoI, HindIII restriction fragment. Positive clones contained a 327 base pair NcoI, HindIII restriction fragment in which the bases encoding amino acids 112–117 of hIL-3 have been deleted. pMON6478 was made to serve as the template for the creation of single amino acid substitution variants at positions 112, 113, 114, 115, 116 and 117 of hIL-3.

EXAMPLE 37

Construction of Plasmid pMON6479

Amino acids 118–123 of hIL-3 were deleted using site-directed PCR mutagenesis methods described previously. Plasmid pMON6458 DNA was the template in the reaction using the oligonucleotides, Oligo #7 and Oligo #42, as primers. The resulting PCR-generated DNA product was purified and digested with NcoI and HindIII. The NcoI, HindIII restriction fragment from pMON6458 was ligated to the PCR-generated NcoI, HindIII restriction fragment. Positive clones contained a 327 base pair NcoI, HindIII restriction fragment in which the bases encoding amino acids 118–123 of hIL-3 have been deleted. pMON6479 was made to serve as the template for the creation of single amino acid substitution variants at positions 118, 119, 120, 121, 122 and 123 of hIL-3.

EXAMPLE 38

Construction of Single Amino Acid Substitution Libraries at Positions 17, 18, 19, 20, 21 and 22

One of the DNA fragments used to construct the plasmids containing single amino acid substitutions at positions 17, 18, 19, 20, 21 and 22 of hIL-3 was generated by site-directed mutagenesis employing PCR techniques described previously. In the PCR reaction the plasmid pMON6464 DNA was the template and the following 32 fold degenerate oligonucleotides, Oligo #43, Oligo #44, Oligo #45, Oligo #46, Oligo #47 and Oligo #48 were the primers at the C-terminus. The oligonucleotide, Oligo #26, was used as the primer at the N-terminus. The degenerate oligonucleotides replace the eighteen bases, encoding six amino acids, deleted in pMON6464. The degenerate oligonucleotides have G, A, T or C in the first and second positions and G or C in the third position of a single codon at amino acid positions 17, 18, 19, 20, 21 and 22 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA product was digested with NcoI and EcoRV. Plasmid pMON6464 DNA was digested with restriction enzymes NcoI and EcoRV resulting in a 4190 base pair fragment which was ligated to the PCR-generated NcoI, EcoRV restriction fragments. Plasmid DNA was isolated and screened by DNA dot blot differential hybridization using the oligonucleotide probe, Oligo #139, which had been labeled with $p^{32}$. Clones shown to be positive by colony hybridization were selected, plasmid DNA isolated and DNA sequenced to determine the amino acid substitution.

EXAMPLE 39

Construction of Single Amino Acid Substitution Libraries at Positions 23, 24, 25, 26, 27 and 28

One of the DNA fragments used to construct the plasmids containing single amino acid substitutions at positions 23, 24, 25, 26, 27 and 28 of hIL-3 was generated by site-directed mutagenesis employing PCR techniques described previously. In the PCR reaction the plasmid pMON6465 DNA was the template and the following 32 fold degenerate oligonucleotides, Oligo #49, Oligo #50, Oligo #51, Oligo #52, Oligo #53 and Oligo #54 were the primers at the C-terminus. The oligonucleotide, Oligo #26, was used as the primer at the N-terminus. The degenerate oligonucleotides replace the eighteen bases, encoding six amino acids, deleted in pMON6465. The degenerate oligonucleotides have G, A, T or C in the first and second positions and G or C in the third position of a single codon at amino acid positions 23, 24, 25, 26, 27 and 28 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with restriction enzymes NcoI and EcoRV. Plasmid pMON6465 DNA was digested with restriction enzymes NcoI and EcoRV and the resulting 4190 base pair fragment was ligated to the PCR-generated NcoI, EcoRV DNA fragments. Transformant bacteria were screened by DNA dot blot differential hybridization using the oligonucleotide probe, Oligo #140, which had been labeled with $p^{32}$ Clones shown to be positive by colony hybridization were selected, plasmid DNA isolated and DNA sequenced to determine the amino acid substitution.

EXAMPLE 40

Construction of Single Amino Acid Substitution Libraries at Positions 29, 30, 31, 32, 33 and 34

One of the DNA fragments used to construct the plasmids containing single amino acid substitutions at positions 29, 30, 31, 32, 33 and 34 of hIL-3 was generated by site-directed mutagenesis employing PCR techniques described previously. In the PCR reaction the plasmid pMON6466 DNA was the template and the following 32 fold degenerate oligonucleotides, Oligo #55, Oligo #56, Oligo #57, Oligo #58, Oligo #59 and Oligo #60 were the primers at the C-terminus. The oligonucleotide Oligo #26 was used as the primer at the N-terminus. The degenerate oligonucleotides replace the eighteen bases, encoding six amino acids, deleted in pMON6466. The degenerate oligonucleotides have G, A, T or C in the first and second positions and G or C in the third position of a single codon at amino acid positions 29, 30, 31, 32, 33 and 34 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes NcoI and EcoRV. Plasmid pMON6466 DNA was digested with restriction enzymes NcoI and EcoRV and the resulting 4190 base pair fragment was ligated to the PCR-generated NcoI, EcoRV DNA fragments. Transformant bacteria were screened by DNA dot blot differential hybridization using the oligonucleotide probe, Oligo #141, which had been labeled with $p^{32}$. Clones shown to be positive by colony hybridization were selected, plasmid DNA isolated and DNA sequenced to determine the amino acid substitution.

EXAMPLE 41

Construction of single amino acid substitution libraries at positions 35, 36, 37, 38, 39 and 40

One of the DNA fragments used to construct the plasmids containing single amino acid substitutions at positions 35, 36, 37, 38, 39 and 40 of hIL-3 were generated by site-directed mutagenesis employing PCR techniques described previously. In the PCR reaction the plasmid pMON6467 DNA was the template and the following 32 fold degenerate oligonucleotides, Oligo #61, Oligo #62, Oligo #63, Oligo #64, Oligo #65 and Oligo #66 were the primers at the C-terminus. The oligonucleotide, Oligo #7, was used as the primer at the N-terminus. The degenerate oligonucleotides replace the eighteen bases, encoding six amino acids, deleted in pMON6467. The degenerate oligonucleotides have G, A, T or C in the first and second positions and G or C in the third position of a single codon at amino acid positions 35, 36, 37, 38, 39 and 40 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored and at the other position, 32 different codons substitutions were created at positions independently. The resulting PCR-generated DNA products were purified and digested with the restriction enzymes NcoI and EcoRV. Plasmid pMON6467 DNA was digested with restriction enzymes NcoI and EcoRV and the resulting 4190 base pair fragment was ligated to the PCR-generated NcoI, EcoRV DNA fragments. Transformant bacteria were screened by DNA dot blot differential hybridization using the oligonucleotide probe, Oligo #142, which had been labeled with $P^{32}$. Clones shown to be positive by colony hybridization were selected, plasmid DNA isolated and DNA sequenced to determine the amino acid substitution.

EXAMPLES 42

Construction of single amino acid substitution libraries at positions 41, 42, 43, 44, 45 and 46

One of the DNA fragments used to construct the plasmids containing single amino acid substitutions at positions 41, 42, 43, 44, 45 and 46 of hIL-3 was generated by site-directed mutagenesis employing PCR techniques described previously. In the PCR reaction the plasmid pMON6468 DNA was the template and the following 32 fold degenerate oligonucleotides, Oligo #67, Oligo #68, Oligo #69, Oligo #70, Oligo #71 and Oligo #72 were the primers at the C-terminus. The oligonucleotide, Oligo #7, was used as the primer at the N-terminus. The degenerate oligonucleotides replace the eighteen bases, encoding six amino acids, deleted in pMON6468. The degenerate oligonucleotides have G, A, T or C in the first and second positions and G or C in the third position of a single codon at amino acid positions 41, 42, 43, 44, 45 and 46 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes NcoI and XhoI. Plasmid pMON6468 DNA was digested with restriction enzymes NcoI and XhoI and the resulting 4152 base pair fragment was ligated to the PCR-generated NcoI, XhoI DNA fragments. Transformant bacteria were screened by DNA dot blot differential hybridization using the oligonucleotide probe, Oligo #143, which had been labeled with $P^{32}$. Clones shown to be positive by colony hybridization were selected, plasmid DNA isolated and DNA sequenced to determine the amino acid substitution.

EXAMPLE 43

Construction of single amino acid substitution libraries at positions 47, 48, 49, 50, 51 and 52

One of the DNA fragments used to construct the plasmids containing single amino acid substitutions at positions 47, 48, 49, 50, 51 and 52 of hIL-3 was generated by site-directed mutagenesis employing PCR techniques described previously. In the PCR reaction the plasmid pMON6469 DNA was the template and the following 32 fold degenerate oligonucleotides, Oligo #73, Oligo #74, Oligo #75, Oligo #76, Oligo #77 and Oligo #78, were the primers at the C-terminus. The oligonucleotide, Oligo #7, was used as the primer at the N-terminus. The degenerate oligonucleotides replace the eighteen bases, encoding six amino acids, deleted in pMON6469. The degenerate oligonucleotides have G, A, T or C in the first and second positions and G or C in the third position of a single codon at amino acid positions 47, 48, 49, 50, 51 and 52 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes NcoI and XhoI. Plasmid pMON6469 DNA was digested with restriction enzymes NcoI and XhoI and the resulting 4152 base pair fragment was ligated to the PCR-generated NcoI, XhoI DNA fragments. Transformant bacteria were screened by DNA dot blot differential hybridization using the oligonucleotide probe, Oligo #144, which had been labeled with $P^{32}$. Clones shown to be positive by colony hybridization were selected, plasmid DNA isolated and DNA sequenced to determine the amino acid substitution.

EXAMPLE 44

Construction of single amino acid substitution libraries at positions 53, 54, 55, 56, 57 and 58

One of the DNA fragments used to construct the plasmids containing single amino acid substitutions at positions 53, 54, 55, 56, 57 and 58 of hIL-3 was generated by site-directed mutagenesis employing PCR techniques described previously. In the PCR reaction the plasmid pMON6470 DNA was the template and the following 32 fold degenerate oligonucleotides, Oligo #79, Oligo #80, Oligo #81, Oligo #82, Oligo #83 and Oligo #84, were the primers at the C-terminus. The oligonucleotide, Oligo #7, was used as the primer at the N-terminus. The degenerate oligonucleotides replace the eighteen bases, encoding six amino acids, deleted in pMON6470. The degenerate oligonucleotides have G, A, T or C in the first and second positions and G or C in the third position of a single codon at amino acid positions 53, 54, 55, 56, 57 and 58 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes NcoI and NsiI. Plasmid pMON6470 DNA was digested with restriction enzymes NcoI and NsiI and the resulting 4119 base pair fragment was ligated to the PCR-generated NcoI, NsiI DNA fragments. Transformant bacteria were screened by DNA dot blot differential hybridization using the oligonucleotide probe, Oligo #145, which had been labeled with $P^{32}$. Clones shown to be positive by colony hybridization were selected, plasmid DNA isolated and DNA sequenced to determine the amino acid substitution.

EXAMPLE 45

Construction of single amino acid substitution libraries at positions 59, 60, 61, 62, 63 and 64

One of the DNA fragments used to construct the plasmids containing single amino acid substitutions at positions 59, 60, 61, 62, 63 and 64 of hIL-3 was generated by site-directed mutagenesis employing PCR techniques described previously. In the PCR reaction the plasmid pMON6471 DNA was the template and the following 32 fold degenerate oligonucleotides, Oligo #85, Oligo #86, Oligo #87, Oligo #88, Oligo #89 and Oligo #90, were the primers at the C-terminus. The oligonucleotide, Oligo #7, was used as the primer at the N-terminus. The degenerate oligonucleotides replace the eighteen bases, encoding six amino acids, deleted in pMON6471. The degenerate oligonucleotides have G, A, T or C in the first and second positions and G or C in the third position of a single codon at amino acid positions 59, 60, 61, 62, 63 and 64 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes NcoI and NsiI. Plasmid pMON6471 DNA was digested with restriction enzymes NcoI and NsiI and the resulting 4119 base pair fragment was ligated to the PCR-generated NcoI, NaiI DNA fragments. Transformant bacteria were screened by DNA dot blot differential hybridization using the oligonucleotide probe, Oligo #146, which had been labeled with $P^{32}$. Clones shown to be positive by colony hybridization were selected, plasmid DNA isolated and DNA sequenced to determine the amino acid substitution.

EXAMPLE 46

Construction of single amino acid substitution libraries at positions 65, 66, 67, 68, 69 and 70

One of the DNA fragments used to construct the plasmids containing single amino acid substitutions at positions 65, 66, 67, 68, 69 and 70 of hIL-3 was generated by site-directed mutagenesis employing PCR techniques described previously. In the PCR reaction the plasmid pMON6472 DNA was the template and the following 32 fold degenerate oligonucleotides, Oligo #91, Oligo #92, Oligo #93, Oligo #94, Oligo #95 and Oligo #96, were the primers at the N-terminus. The oligonucleotide, Oligo #26, was used as the primer at the C-terminus. The degenerate oligonucleotides replace the eighteen bases, encoding six amino acids, deleted in pMON6472. The degenerate oligonucleotides have G, A, T or C in the first and second positions and G or C in the third position of a single codon at amino acid positions 65, 66, 67, 68, 69 and 70 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes EcoRI and XhoI. Plasmid pMON6472 DNA was digested with restriction enzymes EcoRI and XhoI and the resulting 4145 base pair fragment was ligated to the PCR-generated EcoRI, XhoI DNA fragments. Transformant bacteria were screened by DNA dot blot differential hybridization using the oligonucleotide probe, Oligo #147, which had been labeled with $P^{32}$. Clones shown to be positive by colony hybridization were selected, plasmid DNA isolated and DNA sequenced to determine the amino acid substitution.

EXAMPLE 47

Construction of single amino acid substitution libraries at positions 71, 72, 73, 74, 75 and 76

One of the DNA fragments used to construct the plasmids containing single amino acid substitutions at positions 71, 72, 73, 74, 75 and 76 of hIL-3 was generated by site-directed mutagenesis employing PCR techniques described previously. In the PCR reaction the plasmid pMON6473 DNA was the template and the following 32 fold degenerate oligonucleotides, Oligo #97, Oligo #98, Oligo #99, Oligo #100, Oligo #101 and Oligo #102, were the primers at the N-terminus. The oligonucleotide, Oligo #26, was used as the primer at the C-terminus. The degenerate oligonucleotides replace the eighteen bases, encoding six amino acids, deleted in pMON6473. The degenerate oligonucleotides have G, A, T or C in the first and second positions and G or C in the third position of a single codon at amino acid positions 71, 72, 73, 74, 75 and 76 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA fragments were purified and digested with the restriction enzymes EcoRI and PstI. Plasmid pMON6473 DNA was digested with restriction enzymes EcoRI and PstI and the resulting 4171 base pair fragment was ligated to the PCR-generated EcoRI, PstI DNA fragments. Transformant bacteria were screened by DNA dot blot differential hybridization using the oligonucleotide probe, Oligo #148, which had been labeled with $P^{32}$. Clones shown to be positive by colony hybridization were selected, plasmid DNA isolated and DNA sequenced to determine the amino acid substitution.

EXAMPLE 48

Construction of single amino acid substitution libraries at positions 77, 78, 79, 80, 81 and 82

One of the DNA fragments used to construct the plasmids containing single amino acid substitutions at positions 77, 78, 79, 80, 81 and 82 of hIL-3 was generated by site-directed mutagenesis employing PCR techniques described previously. In the reaction the plasmid pMON6474 DNA was the template and the following 32 fold degenerate oligonucleotides, Oligo #103, Oligo #104, Oligo #105, Oligo #106, Oligo #107 and Oligo #108, were the primers at the N-terminus. The oligonucleotide, Oligo #26, was used as the primer at the C-terminus. The degenerate oligonucleotides replace the eighteen bases, encoding six amino acids, deleted in pMON6474. The degenerate oligonucleotides have G, A, T or C in the first and second positions and G or C in the third position of a single codon at amino acid positions 77, 78, 79, 80, 81 and 82 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes EcoRI and PstI as described previosly. Plasmid pMON6474 DNA was digested with restriction enzymes EcoRI and PstI and the resulting 4171 base pair fragment was ligated to the PCR-generated EcoRI, PstI DNA fragments. Transformant bacteria were screened by DNA dot blot differential hybridization using the oligonucleotide probe, Oligo #149, which had been labeled with $P^{32}$. Clones shown to be positive by colony hybridization were selected, plasmid DNA isolated and DNA sequenced to determine the amino acid substitution.

EXAMPLE 49

Construction of single amino acid substitution libraries at positions 83, 84, 85, 86, 87 and 88

One of the DNA fragments used to construct the plasmids containing single amino acid substitutions at positions 83, 84, 85, 86, 87 and 88 of hIL-3 was generated by site-directed mutagenesis employing PCR techniques described previously. In the PCR reaction the plasmid pMON6475 DNA was the template and the following 32 fold degenerate oligonucleotides, Oligo #109, Oligo #110, Oligo #111, Oligo #112, Oligo #113 and Oligo #114, were the primers at the N-terminus. The oligonucleotide, Oligo #26, was used as the primer at the C-terminus. The degenerate oligonucleotides replace the eighteen bases, encoding six amino acids, deleted in pMON6475. The degenerate oligonucleotides have G, A, T or C in the first and second positions and G or C in the third position of a single codon at amino acid positions 83, 84, 85, 86, 87 and 88 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA producs were purified and digested with the restriction enzymes EcoRI and PstI. Plasmid pMON6475 DNA was digested with restriction enzymes EcoRI and PstI and the resulting 4171 base pair fragment was ligated to the PCR-generated EcoRI, PstI DNA fragments. Transformant bacteria were screened by DNA dot blot differential hybridization using the oligonucleotide probe, Oligo #150, which had been labeled with $P^{32}$. Clones shown to be positive by colony hybridization were selected, plasmid DNA isolated and DNA sequenced to determine the amino acid substitution.

EXAMPLE 50

Construction of single amino acid substitution libraries at positions 88, 89, 90, 91, 92 and 93

One of the DNA fragments used to construct the plasmids containing single amino acid substitutions at positions 88, 89, 90, 91, 92 and 93 of hIL-3 was generated by site-directed mutagenesis employing PCR techniques described previously. In the PCR reaction the plasmid pMON6476 DNA was the template and the following degenerate oligonucleotides, Oligo #114, Oligo #115, Oligo #116, Oligo #117, Oligo #118 and Oligo #119, were the primers at the C-terminus. The oligonucleotide, Oligo #7, was used as the primer at the N-terminus. The degenerate oligonucleotides replace the eighteen bases, encoding six amino acids, deleted in pMON6476. The degenerate oligonucleotides have G, A, T or C in the first and second positions and G or C in the third position of a single codon at amino acid positions 88, 89, 90, 91, 92 and 93 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes EcoRI and NcoI. Plasmid pMON6476 DNA was digested with restriction enzymes EcoRI and NcoI and the resulting 4008 base pair fragment was ligated to the PCR-generated EcoRI, NcoI DNA fragments. Transformant bacteria were screened by DNA dot blot differential hybridization using the oligonucleotide probe, Oligo #151, which had been labeled with $P^{32}$. Clones shown to be positive by colony hybridization were selected, plasmid DNA isolated and DNA sequenced to determine the amino acid substitution.

EXAMPLE 51

Construction of single amino acid substitution libraries at positions 106, 107, 108, 109, 110 and 111

One of the DNA fragments used to construct the plasmids containing the single amino acid substitutions at positions 106, 107, 108, 109, 110 and 111 of hIL-3 was generated by site-directed mutagenesis employing PCR techniques described previously in two sequential PCR reactions. In the first PCR reaction, plasmid pMON6477 DNA was the template and the following 32 fold degenerate oligonucleotides, Oligo #120, Oligo #121, Oligo #122, Oligo #123, Oligo #124 and Oligo #125 were the primers at the C-terminus. The oligonucleotide, Oligo #7 was the primer at the N-terminus. The degenerate oligonucleotides replace the eighteen bases, encoding six amino acids, deleted in pMON6477. The degenerate oligonucleotides have G, A, T or C in the first and second positions and G or C in the third position of a single codon at amino acid positions 106, 107, 108, 109, 110 and 111 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The DNA generated in this PCR reaction was purified by phenol/chloroform extraction and precipitation with equal volume isopropanol in the presence of 2M $NH_4OAc$ to remove any primer that was not extended. This DNA was then used as a primer in the second PCR reaction.

In the second PCR reaction plasmid pMON6477 DNA was the template, the DNA product generated in the first PCR reaction (described above) was the primer at the N-terminus and the oligonucleotide, Oligo #126 (DNA sequence shown in Table 1), was the primer at the C-terminus. The resulting PCR-generated DNA products were purified and digested with the restriction enzymes HindIII and NcoI. Plasmid pMON6477 was digested with restriction enzymes HindIII and NcoI and the resulting 3944 base pair fragment was ligated to the PCR-generated HindIII, NcoI DNA fragments. Transformant bacteria were screened by DNA dot blot differential hybridization using the oligonucleotide probe, Oligo #152, which had been labeled with $P^{32}$. Clones shown to be positive by colony hybridization were selected, plasmid DNA isolated and DNA sequenced to determine the amino acid substitution.

EXAMPLE 52

Construction of single amino acid substitution libraries at positions 112, 113, 114, 115, 116 and 117

One of the DNA fragments used to construct the plasmids containing single amino acid substitutions at positions 112, 113, 114, 115, 116 and 117 of hIL-3 was generated by site-directed mutagenesis employing PCR techniques described previously. In the PCR reaction the plasmid pMON6478 DNA was the template and the following 32 fold degenerate oligonucleotides, Oligo #127, Oligo #128, Oligo #129, Oligo #130, Oligo #131 and Oligo #132, were the primers at the C-terminus. The oligonucleotide, Oligo

7, was used as the primer at the N-terminus. The degenerate oligonucleotides replace the eighteen bases, encoding six amino acids, deleted in pMON6478. The degenerate oligonucleotides have G, A, T or C in the first and second positions and G or C in the third position of a single codon at amino acid positions 112, 113, 114, 115, 116 and 117 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes HindIII and NcoI. Plasmid pMON6478 was digested with restriction enzymes HindIII and NcoI and the resulting 3944 base pair fragment was ligated to the PCR-generated HindIII, NcoI DNA fragments. Transformant bacteria were screened by DNA dot blot differential hybridization using the oligonucleotide probe, Oligo #153, which had been labeled with $P^{32}$. Clones shown to be positive by colony hybridization were selected, plasmid DNA isolated and DNA sequenced to determine the amino acid substitution.

EXAMPLE 53

Construction of single amino acid substitution libraries at positions 118, 119, 120, 121, 122 and 123

One of the DNA fragments used to construct the plasmids containing single amino acid substitutions at positions 118, 119, 120, 121, 122 and 123 of hIL-3 was generated by site-directed mutagenesis employing PCR techniques described previously. In the PCR reaction the plasmid pMON6479 DNA was the template and the following 32 fold degenerate oligonucleotides, Oligo #133, Oligo #134, Oligo #135, Oligo #136, Oligo #137 and Oligo #138, were the primers at the C-terminus. The oligonucleotide, Oligo #7, was used as the primer at the N-terminus. The degenerate oligonucleotides replace the eighteen bases, encoding six amino acids, deleted in pMON6479. The degenerate oligonucleotides have G, A, T or C in the first and second positions and G or C in the third position of a single codon at amino acid positions 118, 119, 120, 121, 122 and 123 of hIL-3 respectively. These degenerate oligonucleotide primers result in libraries which theoretically contain 32 different codons encoding all 20 amino acid substitutions and one translational stop codon at one position. At the other five amino acid positions the native hIL-3 DNA sequence was restored. The resulting PCR-generated DNA products were purified and digested with the restriction enzymes HindIII and NcoI. Plasmid pMON6479 DNA was digested with restriction enzymes HindIII and NcoI and the resulting 3944 base pair fragment was ligated to the PCR-generated HindIII, NcoI DNA fragments. Transformant bacteria were screened by DNA dot blot differential hybridization using the oligonucleotide probe, Oligo #154, which had been labeled with $P^{32}$. Clones shown to be positive by colony hybridization were selected, plasmid DNA isolated and DNA sequenced to determine the amino acid substitution.

EXAMPLE 54

Construction of pMON13358

Plasmid pMON5978 DNA (Example 6) was digested with restriction enzymes NsiI and EcoRI and the resulting 3853 base pair NsiI, EcoRI fragment contains the following genetic elements; beta-lactamase gene (AMP), pBR327 origin of replication, phage f1 origin of replication as the transcription terminator, recA promoter, g10L ribosome binding site and the bases encoding amino acids 15–71 and 106–125 of (15–125) hIL-3. The 3853 base pair NsiI, EcoRI restriction fragment from pMON5978 was ligated to the following annealed complementary oligonucleotides.
Oligo #15(A) [SEQ ID NO: 29]
Oligo #16(A) [SEQ ID NO: 30]

In the resulting plasmid the 111 bases between the NsiI and EcoRI restriction sites in the (15–125) hIL-3 gene are replaced with 24 bases from the above mentioned oligonucleotides. This linker also creates a NdeI recognition sequence.

EXAMPLE 55

Construction of pMON13304

Plasmid pMON13358 DNA is digested with restriction enzymes PstI and EcoRI and the resulting 3846 base pair PstI, EcoRI fragment contains the following genetic elements; beta-lactamase gene (AMP), pBR327 origin of replication, phage f1 origin of replication as the transcription terminator, recA promoter, g10L ribosome binding site and the bases encoding amino acids 15–69 and 106–125 of (15–125) hIL-3. The 3846 base pair NsiI ,EcoRI restriction fragment from pMON13358 is ligated to the following annealed complementary oligonucleotides.
Oligo #155 [SEQ ID NO:200]
Oligo #156 [SEQ ID NO:201]

Oligo #157 [SEQ ID NO:202]
Oligo #158 [SEQ ID NO:203]

Oligo #159 [SEQ ID NO:204]
Oligo #160 [SEQ ID NO:205]

Oligo #161 [SEQ ID NO:206]
Oligo #162 [SEQ ID NO:207]

When assembled, the oligonucleotides create PstI and EcoRI restriction ends and the DNA sequence that encodes amino acids 70–105 of (15–125) hIL-3 with the following amino acid substitutions; 98I and 100R. The codons encoding amino acids 70–105 of (15–125) hIL-3 are those found in the hIL-3 cDNA sequence except at those positions where amino acid substitutions were made. The plasmid, pMON13304, encodes the (15–125) hIL-3 variant with the following amino acid sequence:
Peptide #A1 [SEQ ID NO:66]

EXAMPLE 56

Construction of pMON13305

Plasmid pMON13358 DNA is digested with restriction enzymes PstI and EcoRI and the resulting 3846 base pair PstI, EcoRI fragment contains the following genetic elements; beta-lactamase gene (AMP), pBR327 origin of replication, phage f1 origin of replication as the transcription terminator, recA promoter, g10L ribosome binding site and the bases encoding amino acids 15–69 and 106–125 of (15–125) hIL-3. The 3846 base pair NsiI , EcoRI restriction fragment from pMON13358 is ligated to the following annealed complementary oligonucleotides.
Oligo #155 [SEQ ID NO:200]
Oligo #156 [SEQ ID NO:201]

Oligo #157 [SEQ ID NO:202]
Oligo #158 [SEQ ID NO:203]

Oligo #159 [SEQ ID NO:204]
Oligo #160 [SEQ ID NO:205]

Oligo #163 [SEQ ID NO:208]
Oligo #164 [SEQ ID NO:209]

When assembled, the oligonucleotides create PstI and EcoRI restriction ends and the DNA sequence that encodes amino acids 70–105 of (15–125) hIL-3 with the following amino acid substitutions; 95R, 98I and 100R. The codons encoding amino acids 70–105 of (15–125) hIL-3 are those found in the hIL-3 cDNA sequence except at those positions where amino acid substitutions were made. The plasmid, pMON13305, encodes the (15–125) hIL-3 variant with the following amino acid sequence:

Peptide #A2 [SEQ ID NO:67]

EXAMPLE 57

Construction of pMON13286

Plasmid pMON5978 DNA was digested with restriction enzymes NcoI and EcoRV and the resulting 3865 base pair NcoI, EcoRV fragment contains the following genetic elements; beta-lactamase gene (AMP), pBR327 origin of replication, phage f1 origin of replication as the transcription terminator, precA promoter, g10L ribosome binding site and the bases encoding amino acids 47–125 of (15–125) hIL-3. The 3865 base pair NcoI, EcoRV restriction fragment from pMON5978 was ligated to the following annealed complementary oligonucleotides.

Oligo #165 [SEQ ID NO:210]
Oligo #166 [SEQ ID NO:211]

Oligo #167 [SEQ ID NO:212]
Oligo #168 [SEQ ID NO:213]

Oligo #169 [SEQ ID NO:214]
Oligo #170 [SEQ ID NO:215]

When assembled, the oligonucleotides create NcoI and EcoRV restriction ends and the DNA sequence that encodes amino acids 15–46 of (15–125) hIL-3 with the following amino acid substitutions; 42D, 45M and 46S. The codons encoding amino acids 15–46 of (15–125) hIL-3 are those found in the hIL-3 cDNA sequence except at those positions where amino acid substitutions were made. The plasmid, pMON13286, encodes the (15–125) hIL-3 variant with the following amino acid sequence:

EXAMPLE 58

Construction of pMON5853 (FIG. 6) which encodes [Met-(15–133) hIL-3 (Arg$^{129}$)]P Plasmid DNA of pMON5847 (Example 2) was treated with NcoI. The restriction enzyme was inactivated by heat treatment (65° C. for 10 minutes). The DNA was then treated with large fragment of DNA polymerase I (Klenow) in the presence of all four nucleotide precursors. This produces DNA termini with non-overlapping ends. After 5 minutes at 37° C., the polymerase was inactivated by heat treatment at 65° C. for 10 minutes. The DNA was then treated with HpaI, an enzyme which produces non-overlapping termini. The DNA was ethanol precipitated and ligated. The ligation reaction mixture was used to transform competent JM101 cells to ampicillin resistance. Colonies were picked and plasmid DNA was analyzed by restriction analysis. A plasmid designated pMON5853 was identified as one containing a deletion of the amino terminal 14 codons of the hIL-3 gene. The DNA sequence for the junction of the ribosome binding site to the (15–133) hIL-3 gene was determined to be the following:

```
5'-AAGGAGATATATCCATGAACTGCTCTAAC-3'[SEQ ID NO:133]
                M  N  C  S  N    [SEQ ID NO:134]
```

The lower line contains the one-letter code for the amino acids specified by the coding sequence of the amino terminus of the 15–133 hIL-3 gene. These are methionine, asparagine, cysteine, serine and asparagine.

When cultures of JM101 cells harboring this plasmid were induced with nalidixic acid, it was found that hIL-3 (15–133) accumulated at levels higher than hIL-3 (pMON5847).

The plasmid, pMON5853, encodes Met-(15–133) hIL-3 (Arg$^{129}$) which has the following amino acid sequence:

[SEQ ID NO:135]

```
    Met Asn Cys Ser Asn Met Ile Asp Glu Ile Ile Thr

His Leu Lys Gln Pro Pro Leu Pro Leu Leu Asp Phe Asn

Asn Leu Asn Gly Glu Asp Gln Asp Ile Leu Met Glu Asn

Asn Leu Arg Arg Pro Asn Leu Glu Ala Phe Asn Arg Ala

Val Lys Ser Leu Gln Asn Ala Ser Ala Ile Glu Ser Ile

Leu Lys Asn Leu Leu Pro Cys Leu Pro Leu Ala Thr Ala
```

Peptide #A3 [SEQ ID NO:69]

DNA sequence #A4 pMON13286 42D, 45M, 46S

```
ATGGCTAACT GCTCTAACAT GATCGATGAA ATCATCACCC ACCTGAAGCA [SEQ ID NO: 68]

GCCACCGCTG CCGCTGCTGG ACTTCAACAA CCTCAATGAC GAAGACATGT

CTATCCTGAT GGAAAATAAC CTTCGTCGTC CAAACCTCGA GGCATTCAAC

CGTGCTGTCA AGTCTCTGCA GAATGCATCA GCAATTGAGA GCATTCTTAA

AAATCTCCTG CCATGTCTGC CCCTGGCCAC GGCCGCACCC ACGCGACATC

CAATCCATAT CAAGGACGGT GACTGGAATG AATTCCGTCG TAAACTGACC

TTCTATCTGA AAACCTTGGA GAACGCGCAG GCTCAACAG
```

-continued

```
Ala Pro Thr Arg His Pro Ile His Ile Lys Asp Gly Asp

Trp Asn Glu Phe Arg Arg Lys Leu Thr Phe Tyr Leu Lys

Thr Leu Glu Asn Ala Gln Ala Gln Gln Thr Thr Leu Arg

Leu Ala Ile Phe
```

Formula XI shown below is a representation of a [(15–125) hIL-3 mutein] with numbers in bold type added above the amino acids to represent the position at which the amino acid below the bolded number appears in native (1–133) hIL-3 [e. g. the amino acid at position 1 of Formula XI corresponds to the Asn which appears at position 15 in native (1–133) hIL-3]. The number shown in bold indicates the amino acids that correspond to the native IL-3(1–133). The non-bold members below the amino acids sequences are for Seq Id reference numbers. When the muteins are expressed the initial amino acid may be preceded by Met- or Met-Ala-.

```
15                  20                  25
Asn Cys Ser Asn Met Ile Asp Glu Ile Ile Thr His Leu Lys Gln  [SEQ ID NO:23]
  1               5                  10                  15

30                  35                  40
Pro Pro Leu Pro Leu Leu Asp Phe Asn Asn Leu Asn Gly Glu Asp
             20                  25                  30

45                  50                  55
Gln Asp Ile Leu Met Glu Asn Asn Leu Arg Arg Pro Asn Leu Glu
             35                  40                  45

60                  65                  70
Ala Phe Asn Arg Ala Val Lys Ser Leu Gln Asn Ala Ser Ala Ile
             50                  55                  60

75                  80                  85
Glu Ser Ile Leu Lys Asn Leu Leu Pro Cys Leu Pro Leu Ala Thr
             65                  70                  75

90                  95                  100
Ala Ala Pro Thr Arg His Pro Ile His Ile Lys Asp Gly Asp Trp
             80                  85                  90

105                 110                 115
Asn Glu Phe Arg Arg Lys Leu Thr Phe Tyr Leu Lys Thr Leu Glu
             95                  100                 105

120                 125
Asn Ala Gln Ala Gln Gln
             110
```

Table 6 shows (15–125) hIL-3 muteins of the present invention which have one (and in some cases two) amino acid substitutions in the (15–125) hIL-3 polypeptide and which were constructed as described in the Examples. The mutants in Table 6 were secreted into the periplasmic space in E. coli. The periplasmic content was released by osmotic shock and the material in the crude osmotic shock fraction was screened for growth promoting activity. Biological activity is the growth promoting activity of AML cells relative to (15–125) hIL-3 (pMON6458 or pMMON5988). The numbers in parentheses indicate the number of repeat assays. When a variant was assayed more than once the standard deviation is indicated. An "-" indicates that the hIL3 variant protein level was less than 1.0 μg/ml and was not screened for growth promoting activity.

TABLE 6

(15–125) HUMAN INTERLEUKIN-3 MUTANTS

| hIL-3 POSITION[1] | PARENTAL aa | CO-DON | (15–125)hIL-3 MUTANT aa | SEQ ID NO: | CO-DON | BIOL ACTIVITY |
|---|---|---|---|---|---|---|
| 17/3[1] | SER | TCT | LYS | 19 | AAG | <0.018 (1) |
| 17/3 | SER | TCT | GLY | 19 | GGG | 1.2 ± 1.1 (3) |
| 17/3 | SER | TCT | ASP | 19 | GAC | 1.0 ± 0.7 (3) |
| 17/3 | SER | TCT | MET | 19 | ATG | 0.50 (1) |
| 17/3 | SER | TCT | GLN | 19 | CAG | 1.2 ± 0.7 (3) |
| 17/3 | SER | TCT | ARG | 19 | AGG | <0.070 (1) |
| 16/4 | ASN | AAC | HIS | 19 | CAC | 1.2 ± 0.3 (3) |
| 18/4 | ASN | AAC | LEU | 19 | CTC | 0.45 ± 0.42 (4) |
| 18/4 | ASN | AAC | ILE | 19 | ATC | 1.5 ± 0.2 (2) |
| 18/4 | ASN | AAC | PHE | 19 | TTC | 0.19 ± 0.26 (2) |
| 18/4 | ASN | AAC | ARG | 19 | CGC | 0.10 (1) |
| 18/4 | ASN | AAC | GLN | 19 | CAA | 0.37 (1) |

TABLE 6-continued (15–125) HUMAN INTERLEUKIN-3 MUTANTS

| hIL-3 POSITION[1] | PARENTAL aa | CO-DON | (15–125)hIL-3 MUTANT aa | SEQ ID NO: | CO-DON | BIOL ACTIVITY |
|---|---|---|---|---|---|---|
| 19/5 | MET | ATG | PHE | 19 | TTC | 0.25 (1) |
| 19/5 | MET | ATG | ILE | 19 | ATC | 0.77 ± 0.70 (9) |
| 19/5 | MET | ATG | ARG | 19 | AGG | 0.17 (1) |
| 19/5 | MET | ATC | GLY | 19 | GGA | 0.06 (1) |
| 19/5 | MET | ATC | ALA | 19 | GCG | 0.19 (1) |
| 19/5 | MET | ATG | CYS | 19 | TGC | — |
| 20/6 | ILE | ATC | CYS | 19 | TGC | — |
| 20/6 | ILE | ATC | GLN | 19 | CAG | — |
| 20/6 | ILE | ATC | GLU | 19 | GAG | <0.025 (1) |

TABLE 6-continued

(15–125) HUMAN INTERLEUKIN-3 MUTANTS

| hIL-3 POSITION[1] | PARENTAL aa | CODON | (15–125)hIL-3 MUTANT aa | SEQ ID NO: | CODON | BIOL ACTIVITY |
|---|---|---|---|---|---|---|
| 20/6 | ILE | ATC | ARG | 19 | CGC | <0.025 (1) |
| 20/6 | ILE | ATC | PRO | 19 | CCG | 0.29 ± 0.16 (3) |
| 20/6 | ILE | ATC | ALA | 19 | GCG | 0.18 (1) |
| 21/7 | ASP | GAT | PHE | 19 | TTC | <0.016 (1) |
| 21/7 | ASP | GAT | LYS | 19 | AAG | 0.027 ± 0.027 (2) |
| 21/7 | ASP | GAT | ARG | 19 | AGG | <0.008 (1) |
| 21/7 | ASP | GAT | ALA | 19 | GCG | 0.07 ± 0.06 (3) |
| 21/7 | ASP | GAT | GLY | 19 | GGG | 0.032 (1) |
| 21/7 | ASP | GAT | VAL | 19 | GTC | <0.008 (1) |
| 22/8 | GLU | GAA | TRP | 19 | TGG | — |
| 22/8 | GLU | GAA | PRO | 19 | CCG | <0.015 (1) |
| 22/8 | GLU | GAA | SER | 19 | TCG | <0.015 (1) |
| 22/8 | GLU | GAA | ALA | 19 | GCC | <0.015 (1) |
| 22/8 | GLU | GAA | HIS | 19 | CAC | <0.015 (1) |
| 22/8 | GLU | GAA | GLY | 19 | GGC | <0.008 (1) |
| 23/9 | ILE | ATT | VAL | 19 | GTG | 0.18 (1) |
| 23/9 | ILE | ATT | ALA[2] | 19 | GCG | 1.16 ± 0.16 (3) |
| 23/9 | ILE | ATT | LEU | 19 | TTG | 1.3 (1) |
| 23/9 | ILE | ATT | GLY[2] | 19 | GGG | 0.06 (1) |
| 23/9 | ILE | ATT | TRP | 19 | TCC | — |
| 23/9 | ILE | ATT | LYS[3] | 19 | AAC | — |
| 23/9 | ILE | ATT | PHE | 19 | TTC | — |
| 23/9 | ILE | ATT | LEU[2] | 19 | TTC | 3.0 ± 1.1 (3) |
| 23/9 | ILE | ATT | SER[2] | 19 | AGC | <0.005 (1) |
| 23/9 | ILE | ATT | ARG[2] | 19 | CGC | — |
| 24/10 | ILE | ATA | GLY | 19 | GGG | <0.004 (1) |
| 24/10 | ILE | ATA | VAL | 19 | GTC | 0.89 ± 0.23 (4) |
| 24/10 | ILE | ATA | ARG[3] | 19 | CGG | — |
| 24/10 | ILE | ATA | SER | 19 | AGC | <0.003 (1) |
| 24/10 | ILE | ATA | PHE | 19 | TTC | 0.29 ± 0.24 (2) |
| 24/10 | ILE | ATA | LEU | 19 | CTG | 0.52 ± 0.12 (3) |
| 25/11 | THR | ACA | HIS | 19 | CAC | 1.11 ± 0.2 (3) |
| 25/11 | THR | ACA | GLY | 19 | GGC | 0.48 ± 0.27 (4) |
| 25/11 | THR | ACA | GLN | 19 | CAG | 1.0 ± 0.8 (4) |
| 25/11 | THR | ACA | ARG | 19 | CGG | 0.26 ± 0.17 (2) |
| 25/11 | THR | ACA | PRO | 19 | CCG | 0.36 (1) |
| 31/17 | PRO | CCT | GLY | 19 | GGG | 0.79 ± 0.61 (2) |
| 31/17 | PRO | CCT | ALA | 19 | GCC | 0.49 (1) |
| 31/17 | PRO | CCT | ARG | 19 | CGC | 0.25 ± 0.20 (2) |
| 31/17 | PRO | CCT | LEU | 19 | CTG | 0.22 (1) |
| 31/17 | PRO | CCT | GLN | 19 | CAG | 0.62 ± 0.04 (2) |
| 31/17 | PRO | CCT | LEU[4] | 19 | CTG | 0.30 ± 0.20 (3) |
| 32/18 | LEU | TTG | VAL | 19 | GTG | 0.01 (1) |
| 32/18 | LEU | TTG | ARG | 19 | CGC | 1.5 ± 1.0 (4) |
| 32/18 | LEU | TTG | GLN | 19 | CAG | 0.93 ± 0.18 (3) |
| 32/18 | LEU | TTG | ASN | 19 | AAC | 1.2 ± 0.5 (5) |
| 32/18 | LEU | TTG | GLY[5] | 19 | GGC | 0.84 ± 1.0 (3) |
| 32/18 | LEU | TTG | ALA | 19 | GCG | 1.4 ± 0.7 (5) |
| 32/18 | LEU | TTG | GLU | 19 | GAG | 0.88 ± 0.37 (2) |
| 33/19 | PRO | CC(T/C) | LEU | 19 | CTG | 0.13 (1) |
| 33/19 | PRO | CC(T/C) | GLN | 19 | CAG | 0.22 ± 0.20 (2) |
| 33/19 | PRO | CC(T/C) | ALA | 19 | GCG | 0.30 ± 0.14 (2) |
| 33/19 | PRO | CC(T/C) | THR | 19 | ACC | <0.018 (1) |
| 33/19 | PRO | CC(T/C) | GLU | 19 | GAG | 0.54 ± 0.43 (2) |
| 34/20 | LEU | TTG | VAL | 19 | GTG | 1.2 ± 0.6 (3) |
| 34/20 | LEU | TTG | GLY | 19 | GGG | 0.64 ± 0.74 (2) |
| 34/20 | LEU | TTG | SER | 19 | TCG | 1.5 ± 0.7 (4) |
| 34/20 | LEU | TTG | LYS | 19 | AAG | 0.97 ± 0.28 (2) |
| 34/20 | LEU | TTG | MET | 19 | ATG | 1.7 ± 0.5 (3) |
| 35/21 | LEU | CTG | ALA | 19 | GCC | 1.6 ± 0.5 (3) |
| 35/21 | LEU | CTG | GLY | 19 | GGC | <0.006 ± 0.002 (3) |
| 35/21 | LEU | CTG | ASN | 19 | AAC | 1.1 ± 1.7 (5) |
| 35/21 | LEU | CTG | PRO | 19 | CCC | 1.8 ± 2.0 (5) |
| 35/21 | LEU | CTG | GLN | 19 | CAA | 0.98 ± 1.1 (5) |
| 35/21 | LEU | CTG | VAL | 19 | GTG | 0.76 ± 0.86 (5) |
| 36/22 | ASP | GAC | LEU | 19 | CTC | 0.20 (1) |
| 25/11 | THR | ACA | ALA | 19 | GCC | 0.86 ± 0.27 (3) |
| 26/12 | HIS | CAC | THR | 19 | ACG | 0.010 (1) |
| 26/12 | HIS | CAC | PHE | 19 | TTC | 0.26 (1) |
| 26/12 | HIS | CAC | GLY | 19 | GGG | 0.19 (1) |
| 26/12 | HIS | CAC | ARG | 19 | CGG | 0.21 (1) |
| 26/12 | HIS | CAC | ALA | 19 | GCC | 0.56 ± 0.03 (2) |
| 26/12 | HIS | CAC | TRP | 19 | TGG | — |
| 27/13 | LEU | TTA | GLY | 19 | GGG | — |
| 27/13 | LEU | TTA | ARG | 19 | AGG | — |
| 27/13 | LEU | TTA | THR | 19 | ATC | 0.084 (1) |
| 27/13 | LEU | TTA | SER | 19 | TCC | — |
| 27/13 | LEU | TTA | ALA | 19 | GCG | 0.01 (1) |
| 28/14 | LYS | AAG | ARG | 19 | CGG | 0.42 ± 0.07 (2) |
| 28/14 | LYS | AAG | LEU | 19 | TTG | — |
| 28/14 | LYS | AAG | TRP | 19 | TGG | — |
| 28/14 | LYS | AAG | GLN | 19 | CAG | 0.27 (1) |
| 28/14 | LYS | AAG | GLY | 19 | GGC | 0.36 ± 0.07 (2) |
| 28/14 | LYS | AAG | PRO | 19 | CCC | 0.10 ± 0.04 (2) |
| 28/14 | LYS | AAG | VAL | 19 | GTG | 0.19 ± 0.12 (2) |
| 29/15 | GLN | CAG | ASN | 19 | AAC | 1.62 ± 1.7 (3) |
| 29/15 | GLN | CAG | LEU | 19 | CTG | 0.284 |
| 29/15 | GLN | CAG | PRO | 19 | CCG | — |
| 29/15 | ARG | CAG | ARG | 19 | AGG | 0.44 ± 0.16 (4) |
| 29/15 | GLN | CAG | VAL | 19 | GTG | 0.62 ± 0.40 (4) |
| 30/16 | PRO | CCA | HIS | 19 | CAC | 0.26 (1) |
| 30/16 | PRO | CCA | THR | 19 | ACG | 0.36 (1) |
| 30/16 | PRO | CCA | GLY | 19 | GGG | 1.2 ± 0.8 (3) |
| 30/16 | PRO | CCA | ASP | 19 | GAC | — |
| 30/16 | PRO | CCA | GLN | 19 | CAG | 0.61 ± 0.37 (3) |
| 30/16 | PRO | CCA | SER | 19 | TCG | — |
| 30/16 | PRO | CCA | LEU | 19 | TTC | — |
| 30/16 | PRO | CCA | LYS | 19 | AAG | — |
| 31/17 | PRO | CCT | ASP | 19 | GAC | 0.66 ± 0.71 (3) |
| 36/22 | ASP | CAC | VAL | 19 | GTG | — |
| 37/23 | PHE | TTC | SER | 19 | AGC | 0.62 ± 0.40 (4) |
| 37/23 | PHE | TTC | PRO | 19 | CCG | 0.65 ± 0.39 (4) |
| 37/23 | PHE | TTC | TRP | 19 | TGG | — |
| 37/23 | PHE | TTC | ILE | 19 | ATC | 0.1 (1) |
| 38/24 | ASN | AAC | ALA | 19 | GCN | 1.9 (1) |
| 40/26 | LEU | CTC | TRP | 19 | TCC | — |
| 40/26 | LEU | CTC | ARC | 19 | CCC | — |
| 41/27 | ASN | AAT | CYS | 19 | TCC | 0.18 (1) |
| 41/27 | ASN | AAT | ARC | 19 | CCC | 0.13 ± 0.13 (2) |
| 41/27 | ASN | AAT | LEU | 19 | CTC | 0.09 ± 0.07 (2) |
| 41/27 | ASN | AAT | HIS | 19 | CAC | 0.49 ± 0.26 (4) |
| 41/27 | ASN | AAT | MET | 19 | ATC | 0.30 ± 0.38 (4) |
| 41/27 | ASN | AAT | PRO | 19 | CCC | 0.12 (1) |
| 42/28 | GLY | GGC | ASP | 19 | GAC | 5.7 ± 5.7 (6) |
| 42/28 | GLY | GGG | SER | 19 | ACC | 4.3 ± 4.8 (7) |
| 42/28 | GLY | CGC | CYS | 19 | TGC | 0.53 (1) |
| 42/28 | GLY | GGC | ALA | 19 | GCC | 5.9 ± 4.1 (7) |
| 43/29 | GLU | CAA | ASN | 19 | AAC | 0.050 (1) |
| 43/29 | GLU | CAA | TYR | 19 | TAC | 0.010 (1) |
| 43/29 | GLU | GAA | LEU | 19 | CTC | <0.009 (1) |
| 43/29 | GLU | CAA | PHE | 19 | TTC | <0.009 (1) |
| 43/29 | GLU | CAA | ASP | 19 | GAC | 0.044 (1) |
| 43/29 | GLU | GAA | ALA | 19 | GCC | <0.009 (1) |
| 43/29 | GLU | GAA | CYS | 19 | TG | <0.009 (1) |
| 43/29 | GLU | CAA | SER | 19 | AGC | <0.009 (1) |
| 44/30 | ASP | GAC | SER | 19 | TCA | 0.007 (1) |
| 44/30 | ASP | GAC | LEU | 19 | CTG <0.007 (1) | | |
| 44/30 | ASP | GAC | ARG | 19 | AGG | <0.007 (1) |
| 44/30 | ASP | GAC | LYS | 19 | AAG | <0.007 (1) |
| 44/30 | ASP | GAC | THR | 19 | ACG | — |
| 44/30 | ASP | GAC | MET | 19 | ATG | <0.007 (1) |
| 44/30 | ASP | GAC | TRP | 19 | TGG | <0.007 (1) |
| 44/30 | ASP | GAC | PRO | 19 | CCC | <0.007 (1) |
| 45/31 | GLN | CAA | PRO | 19 | CCC | — |
| 45/31 | GLN | CAA | PHE | 19 | TTC | 0.007 (1) |
| 45/31 | GLN | CAA | VAL | 19 | GTC | 6.7 ± 6.1 (5) |
| 45/31 | GLN | CAA | MET | 19 | ATG | 3.4 ± 1.8 (5) |
| 45/31 | GLN | CAA | LEU | 19 | TTG | 1.1 ± 1.3 (2) |

TABLE 6-continued

(15–125) HUMAN INTERLEUKIN-3 MUTANTS

| hIL-3 aa POSITION[1] | PARENTAL aa | CODON | (15–125)hIL-3 MUTANT aa | SEQ ID NO: | CODON | BIOL ACTIVITY |
|---|---|---|---|---|---|---|
| 45/31 | GLN | CAA | THR | 19 | ACG | 0.96 ± 1.5 (3) |
| 45/31 | GLN | CAA | LYS | 19 | AAG | 1.6 ± 2.2 (5) |
| 45/31 | GLN | CAA | TRP | 19 | TGG | 0.10 (1) |
| 46/32 | ASP | GAC | PHE | 19 | TTC | 1.2 ± 0.5 (3) |
| 46/32 | ASP | GAC | SER | 19 | TCC | 7.9 ± 6.4 (4) |
| 46/32 | ASP | GAC | THR | 19 | ACC | 1.8 ± 0.2 (2) |
| 46/32 | ASP | GAC | CYS | 19 | TGC | 0.80 (1) |
| 46/32 | ASP | GAC | GLY | 19 | GGC | 0.25 (1) |
| 47/33 | ILE | ATT | GLY | 19 | GGC | <0.015 (1) |
| 47/33 | ILE | ATT | VAL | 19 | GTG | 0.38 (1) |
| 47/33 | ILE | ATT | HIS | 19 | CAC | 0.10 (1) |
| 47/33 | ILE | ATT | SER | 19 | TCC | 0.03 (1) |
| 47/33 | ILE | ATT | ARC | 19 | AGG | 0.09 (1) |
| 47/33 | ILE | ATT | PRO | 19 | CCG | <0.015 (1) |
| 48/34 | LEU | CTG | SER | 19 | AGC | <0.009 (1) |
| 48/34 | LEU | CTG | CYS | 19 | TCG | — |
| 48/34 | LEU | CTG | ARG | 19 | CGC | <0.009 (1) |
| 48/34 | LEU | CTG | ILE | 19 | ATC | 0.036 (1) |
| 48/34 | LEU | CTG | HIS | 19 | CAC | <0.009 (1) |
| 48/34 | LEU | CTC | HIS | 19 | CAC | <0.009 (1) |
| 48/34 | LEU | CTG | PHE | 19 | TTC | <0.009 (1) |
| 48/34 | LEU | CTG | ASN | 19 | AAC | <0.009 (1) |
| 49/35 | MET | ATG | ARG | 19 | CGC | 0.007 (1) |
| 49/35 | MET | ATG | ALA | 19 | GCC | 0.091 (1) |
| 49/35 | MET | ATG | GLY | 19 | GGC | 0.036 (1) |
| 49/35 | MET | ATG | PRO | 19 | CCC | <0.009 (1) |
| 49/35 | MET | ATG | ASN | 19 | AAC | 0.23 (1) |
| 49/35 | MET | ATG | HIS | 19 | CAC | <0.009 (1) |
| 49/35 | MET | ATG | ASP | 19 | GAC | 0.28 ± 0.48 (3) |
| 50/36 | GLU | GAA | LEU | 19 | CTC | 0.01 (1) |
| 50/36 | GLU | GAA | THR | 19 | ACC | 0.20 (1) |
| 50/36 | GLU | GAA | ASP | 19 | GAC | — |
| 50/36 | GLU | GAA | TYR | 19 | TAC | 0.09 (1) |
| 50/36 | GLU | GAA | GLN | 19 | CTG | 0.02 (1) |
| 51/37 | ASN | AAT | ARG | 19 | CGC | 2.0 ± 0.8 (3) |
| 51/37 | ASN | AAT | MET | 19 | ATG | 0.75 ± 0.50 (2) |
| 51/37 | ASN | AAT | PRO | 19 | CCG | 2.77 ± 1.6 (3) |
| 51/37 | ASN | AAT | SER | 19 | TCC | 0.87 ± 0.44 (3) |
| 51/37 | ASN | AAT | THR | 19 | ACG | 2.3 ± 1.6 (3) |
| 51/37 | ASN | AAT | HIS | 19 | CAC | 1.3 ± 0.9 (5) |
| 52/38 | ASN | AAC | HIS | 19 | CAC | 0.004 (1) |
| 52/38 | ASN | AAC | ARG | 19 | CGC | 0.004 (1) |
| 52/38 | ASN | AAC | LEU | 19 | TGG | 0.003 (1) |
| 52/38 | ASN | AAC | GLY | 19 | GGC | 0.22 (1) |
| 52/38 | ASN | AAC | SER | 19 | AGC | 0.07 (1) |
| 52/38 | ASN | AAC | THR | 19 | ACG | 0.44 ± 0.30 (3) |
| 53/39 | LEU | CTT | THR | 19 | ACC | <0.005 (1) |
| 53/39 | LEU | CTT | ALA | 19 | GCG | — |
| 53/39 | LEU | CTT | GLY | 19 | GGC | <0.005 (1) |
| 53/39 | LEU | CTT | GLU | 19 | GAG | <0.005 (1) |
| 53/39 | LEU | CTT | PRO | 19 | CCG | <0.005 (1) |
| 53/39 | LEU | CTT | LYS | 19 | AAG | <0.005 (1) |
| 53/39 | LEU | CTT | SER | 19 | AGC | 0.008 (1) |
| 53/39 | LEU | CTT | MET | 19 | ATG | 0.31 (1) |
| 54/40 | ARG | CGA | ASP | 19 | GAC | <0.005 (1) |
| 54/40 | ARG | CGA | ILE | 19 | ATC | 0.05 (1) |
| 54/40 | ARG | CGA | SER | 19 | TCC | 0.10 (1) |
| 54/40 | ARG | CGA | VAL | 19 | GTG | <0.005 (1) |
| 54/40 | ARG | CGA | THR | 19 | ACC | 0.015 (1) |
| 54/40 | ARG | CGA | GLN | 19 | CAG | 0.04 (1) |
| 54/40 | ARG | CGA | LEU | 19 | TTG | 0.03 (1) |
| 55/41 | ARG | AGG | THR | 19 | ACC | 0.65 ± 1.1 (4) |
| 55/41 | ARG | AGG | VAL | 19 | GTC | 0.96 ± 0.36 (3) |
| 55/41 | ARG | AGG | SER | 19 | TCG | 0.065 (1) |
| 55/41 | ARG | AGG | LEU | 19 | CTG | 1.1 ± 1.2 (4) |
| 55/41 | ARG | AGG | GLY | 19 | GGC | 1.0 ± 0.6 (4) |
| 56/42 | PRO | CCA | GLY | 19 | GGC | 1.1 ± 0.8 (3) |
| 56/42 | PRO | CCA | CYS | 19 | TGC | 0.21 (1) |
| 56/42 | PRO | CCA | SER | 19 | AGC | 1.4 ± 0.4 (2) |
| 56/42 | PRO | CCA | GLN | 19 | CAG | 1.8 (1) |
| 56/42 | PRO | CCA | LYS | 19 | AAG | 0.60 (1) |
| 57/43 | ASN | AAC | GLY[4] | 19 | GGC | — |
| 58/44 | LEU | CTG | SER | 19 | AGC | <0.041 (1) |
| 58/44 | LEU | CTG | ASP | 19 | GAC | <0.041 (1) |
| 58/44 | LEU | CTG | ARG | 19 | CGG | <0.041 (1) |
| 59/44 | LEU | CTG | GLN | 19 | CAG | <0.041 (1) |
| 58/44 | LEU | CTG | VAL | 19 | GTC | <0.041 (1) |
| 58/44 | LEU | CTG | CYS | 19 | TGC | — |
| 59/45 | GLU | GAG | TYR | 19 | TAC | 0.41 ± 0.37 (5) |
| 59/45 | GLU | GAG | HIS | 19 | CAC | 0.38 ± 0.31 (2) |
| 59/45 | GLU | GAG | LEU | 19 | CTC | 0.46 ± 0.36 (6) |
| 59/45 | GLU | GAG | PRO | 19 | CCC | — |
| 59/45 | GLU | GAG | ARG | 19 | CGC | 0.15 (1) |
| 60/46 | ALA | GCA | SER | 19 | AGC | 0.91 ± 0.55 (4) |
| 60/46 | ALA | GCA | PRO | 19 | CCC | — |
| 60/46 | ALA | GCA | TYR | 19 | TAC | <0.008 (1) |
| 60/46 | ALA | GCA | ASN | 19 | AAC | 0.38 (1) |
| 60/46 | ALA | GCA | THR | 19 | ACG | 0.21 (1) |
| 61/47 | PHE | TTC | ASN | 19 | AAC | — |
| 61/47 | PHE | TTC | GLU | 19 | CAG | <0.010 (1) |
| 61/47 | PHE | TTC | PRO | 19 | CCC | — |
| 61/47 | PHE | TTC | LYS | 19 | AAG | <0.010 (1) |
| 61/47 | PHE | TTC | ARG | 19 | CGC | 0.006 (1) |
| 61/47 | PHE | TTC | SER | 19 | TCG | 0.17 (1) |
| 62/48 | ASN | AAC | HIS | 19 | CAC | — |
| 62/48 | ASN | AAC | VAL | 19 | GTG | 0.37 ± 0.25 (4) |
| 62/48 | ASN | AAC | ARG | 19 | ACG | — |
| 62/48 | ASN | AAC | PRO[7] | 19 | CCG | 1.6 ± 0.4 (3) |
| 62/48 | ASN | AAC | PRO | 19 | CCG | 2.0 ± 0.3 (3) |
| 62/48 | ASN | AAC | THR[8] | 19 | ACG | 2.3 ± 1.1 (3) |
| 62/48 | ASN | AAC | ASP | 19 | GAC | — |
| 62/48 | ASN | AAC | ILE | 19 | ATC | 0.56 ± 0.24 (4) |
| 63/49 | ARG | A(G/A)G | TYR | 19 | TAC | 0.47 (1) |
| 63/49 | ARG | A(G/A)G | TRP | 19 | TGG | 0.09 (1) |
| 63/49 | ARG | A(G/A)G | LYS | 19 | AGG | 0.52 (1) |
| 63/49 | ARG | A(G/A)G | SER[9] | 19 | TCC | 0.13 (1) |
| 63/49 | ARG | A(G/A)G | HIS | 19 | CAC | 0.42 ± 0.25 (7) |
| 63/49 | ARG | A(G/A)G | PRO | 19 | CCG | <0.014 ± 0.013 (2) |
| 63/49 | ARG | A(G/A)G | VAL | 19 | GTG | 0.39 ± 0.34 (3) |
| 64/50 | ALA | GCT | ASN | 19 | AAC | 1.5 ± 2.9 (4) |
| 64/50 | ALA | GCT | PRO | 19 | CCG | <0.023 (1) |
| 64/50 | ALA | GCT | SER | 19 | AGC | <0.023 (1) |
| 64/50 | ALA | GCT | LYS | 19 | AAG | <0.047 (1) |
| 65/51 | VAL | GTC | THR | 19 | ACC | 0.71 ± 0.64 (3) |
| 65/51 | VAL | GTC | PRO | 19 | CCG | <0.014 (1) |
| 65/51 | VAL | GTC | HIS | 19 | CAC | <0.014 (1) |
| 65/51 | VAL | GTC | LEU | 19 | CTC | 0.42 (1) |
| 65/51 | VAL | GTC | PHE | 19 | TTC | 0.061 (1) |
| 65/51 | VAL | GTC | SER | 19 | TCC | 0.34 (1) |
| 66/52 | LYS | AAG | ILE[10] | 19 | ATC | 0.42 (1) |
| 66/52 | LYS | AAG | ARG | 19 | AGG | 0.79 ± 0.18 (2) |
| 66/52 | LYS | AAG | VAL | 19 | GTC | 0.38 ± 0.17 (2) |
| 66/52 | LYS | AAG | ASN | 19 | AAC | 0.32 (1) |
| 66/52 | LYS | AAG | GLU | 19 | GAG | 0.14 (1) |
| 66/52 | LYS | AAG | SER | 19 | TCG | 0.31 (1) |
| 66/52 | LYS | AAG | VAL[11] | 19 | GTG | 0.055 (1) |
| 67/53 | SER | AGT | ALA | 19 | GCG | <0.014 (1) |
| 67/53 | SER | AGT | PHE | 19 | TTC | 1.2 ± 0.2 (2) |
| 67/53 | SER | AGT | VAL | 19 | GTG | 0.24 (1) |
| 67/53 | SER | AGT | GLY | 19 | GGG | 0.50 ± 0.29 (4) |
| 67/53 | SER | AGT | ASN | 19 | AAC | 0.52 ± 0.28 (7) |
| 67/53 | SER | AGT | ILE | 19 | ATC | 0.29 (1) |
| 67/53 | SER | AGT | PRO | 19 | CCG | 0.055 (1) |
| 67/53 | SER | AGT | HIS | 19 | CAC | 0.99 ± 0.62 (6) |
| 68/54 | LEU | TTA | VAL | 19 | GTC | 0.14 (1) |
| 68/54 | LEU | TTA | TRP | 19 | TGG | 0.07 (1) |
| 68/54 | LEU | TTA | SER | 19 | AGC | <0.003 (1) |
| 68/54 | LEU | TTA | ILE | 19 | ATC | 0.84 ± 0.47 (3) |
| 68/54 | LEU | TTA | PHE | 19 | TTC | 1.7 ± 0.3 (3) |
| 68/54 | LEU | TTA | THR | 19 | ACG | 0.011 (1) |
| 68/54 | LEU | TTA | HIS | 19 | CAC | 0.82 ± 0.45 (2) |

TABLE 6-continued

(15–125) HUMAN INTERLEUKIN-3 MUTANTS

| hIL-3 POSITION[1] | PARENTAL aa | CO-DON | (15–125)hIL-3 MUTANT aa | SEQ ID NO: | CO-DON | BIOL ACTIVITY |
|---|---|---|---|---|---|---|
| 69/55 | GLN | CAG | ALA | 19 | GCG | 1.2 ± 0.8 (3) |
| 69/55 | GLN | CAG | PRO | 19 | CCA | 0.74 0.45 (4) |
| 69/55 | GLN | CAG | THR | 19 | ACG | 0.97 ± 0.46 (4) |
| 69/55 | GLN | CAG | TRP | 19 | TGG | — |
| 69/55 | GLN | CAG | GLU | 19 | GAG | 1.4 ± 0.7 (3) |
| 69/55 | GLN | CAG | ARG | 19 | CGG | 1.4 ± 1.1 (3) |
| 69/55 | GLN | CAG | GLY | 19 | GGG | 0.68 ± 0.02 (2) |
| 69/55 | GLN | CAG | LEU | 19 | CTC | — |
| 70/56 | ASN | AA(C/T) | LEU | 19 | TTG | 0.032 (1) |
| 70/56 | ASN | AA(C/T) | VAL | 19 | GTG | — |
| 70/56 | ASN | AA(C/T) | TRP | 19 | TGG | — |
| 70/56 | ASN | AA(C/T) | PRO[12] | 19 | CCG | 0.43 ± 0.29 (2) |
| 70/56 | ASN | AA(C/T) | ALA[12] | 19 | GCC | 0.03 (1) |
| 71/57 | ALA | GCA | MET | 19 | ATG | 0.23 (1) |
| 71/57 | ALA | GCA | LEU | 19 | CTG | <0.005 (1) |
| 71/57 | ALA | GCA | PRO | 19 | CCC | 0.58 (1) |
| 71/57 | ALA | GCA | ARG | 19 | AGG | 0.66 (1) |
| 71/57 | ALA | GCA | GLU | 19 | GAG | 0.46 ± 0.27 |
| 71/57 | ALA | GCA | THR | 19 | ACC | 0.34 ± 0.41 (3) |
| 71/57 | ALA | GCA | GLN | 19 | GGC | 0.42 ± 0.32 (3) |
| 71/57 | ALA | GCA | TRP | 19 | TGG | — |
| 71/57 | ALA | GCA | ASN | 19 | AAC | 0.09 (1) |
| 72/58 | SER | TCA | GLU | 19 | GAG | 0.62 ± 0.27 (3) |
| 72/58 | SER | TCA | MET | 19 | ATG | 0.45 ± 0.55 (3) |
| 72/58 | SER | TCA | ALA | 19 | GCC | 0.48 ± 0.33 (3) |
| 72/58 | SER | TCA | HIS | 19 | GAC | 0.10 (1) |
| 72/58 | SER | TCA | ASN | 19 | AAC | 0.38 ± 0.44 (3) |
| 72/58 | SER | TCA | ARG | 19 | CGG | 0.81 ± 0.43 (4) |
| 72/58 | SER | TCA | ASP | 19 | GAC | 0.58 ± 0.39 (3) |
| 73/59 | ALA | GCA | GLU | 19 | GAG | 0.49 ± 0.32 (3) |
| 73/59 | ALA | GCA | ASP | 19 | GAC | 0.27 (1) |
| 73/59 | ALA | GCA | LEU | 19 | CTG | 0.55 ± 0.45 (4) |
| 73/59 | ALA | GCA | SER | 19 | AGC | 0.37 ± 0.36 (2) |
| 73/59 | ALA | GCA | GLY | 19 | GGG | 0.38 ± 0.32 (3) |
| 73/59 | ALA | GCA | THR | 19 | ACC | 0.31 (1) |
| 73/59 | ALA | GCA | ARG | 19 | AGG | 0.40 ± 0.18 (3) |
| 74/60 | ILE | AT(T/C) | MET | 19 | ATG | <0.16 (1) |
| 74/60 | ILE | AT(T/C) | THR | 19 | ACG | — |
| 74/60 | ILE | AT(T/C) | PRO | 19 | CCG | — |
| 74/60 | ILE | AT(T/C) | ARG | 19 | AGG | — |
| 74/60 | ILE | AT(T/C) | GLY | 19 | GGG | 0.006 (1) |
| 74/60 | ILE | AT(T/C) | ALA | 19 | GCG | — |
| 75/61 | GLU | CAG | LYS | 19 | AAG | 0.07 ± 0.07 (2) |
| 75/61 | GLU | CAG | GLY | 19 | GGG | 0.27 ± 0.20 (2) |
| 75/61 | GLU | GAG | ASP | 19 | GAC | 0.18 (1) |
| 75/61 | GLU | GAG | PRO | 19 | CCG | — |
| 75/61 | GLU | GAG | TRP | 19 | TGG | — |
| 75/61 | GLU | GAC | ARG | 19 | CGG | — |
| 75/61 | GLU | GAG | SER | 19 | TCG | 0.27 ± 0.22 (3) |
| 75/61 | GLU | GAG | GLN | 19 | CAG | 0.40 ± 0.38 (3) |
| 75/61 | GLU | GAG | LEU | 19 | TTG | — |
| 76/62 | SER | ACC | VAL | 19 | GTG | 1.0 ± 0.2 (2) |
| 76/62 | SER | ACC | ALA | 19 | GCG | 0.94 ± 0.46 (2) |
| 76/62 | SER | ACC | ASN | 19 | AAC | 1.2 (1) |
| 76/62 | SER | AGC | TRP | 19 | TCG | — |
| 76/62 | SER | AGC | GLU | 19 | GAG | 0.90 ± 0.19 (2) |
| 76/62 | SER | AGC | PRO | 19 | CCG | 2.1 ± 0.8 (4) |
| 76/62 | SER | AGC | GLY | 19 | GGC | 1.3 ± 1.0 (4) |
| 76/62 | SER | AGC | ASP | 19 | GAC | 0.29 (1) |
| 77/63 | ILE | ATT | SER | 19 | AGC | 0.48 ± 0.38 (4) |
| 77/63 | ILE | ATT | ARG | 19 | CGC | 0.09 ± 0.04 (2) |
| 77/63 | ILE | ATT | THR | 19 | ACG | <0.008 (1) |
| 77/63 | ILE | ATT | LEU | 19 | TTG | 2.0 ± 0.1 (3) |
| 78/64 | LEU | CTT | ALA | 19 | GCG | — |
| 75/64 | LEU | CTT | SER | 19 | TCC | — |
| 78/64 | LEU | CTT | GLU | 19 | GAG | <0.006 (1) |
| 78/64 | LEU | CTT | PRE | 19 | TTC | — |
| 78/64 | LEU | CTT | GLY | 19 | GGG | — |
| 78/64 | LEU | CTT | ARG | 19 | AGG | — |
| 79/65 | LYS | AA(A/G) | THR | 19 | ACA | 0.77 ± 0.91 (6) |
| 79/65 | LYS | AA(A/G) | GLY | 19 | CGC | 1.1 ± 0.9 (6) |
| 79/65 | LYS | AA(A/G) | ASN | 19 | AAC | 1.0 ± 0.6 (6) |
| 79/65 | LYS | AA(A/G) | MET | 19 | ATG | 1.6 ± 0.7 (6) |
| 79/65 | LYS | AA(A/G) | ARG | 19 | CGC | 1.04 ± 0.7 (7) |
| 79/65 | LYS | AA(A/G) | ILE | 19 | ATC | 1.0 ± 0.6 (6) |
| 79/65 | LYS | AA(A/G) | GLY | 19 | GGG | 1.2 ± 0.4 (6) |
| 79/65 | LYS | AA(A/G) | ASP | 19 | GAC | 0.72 ± 0.38 (7) |
| 80/66 | ASN | AAT | TRP | 19 | TGG | — |
| 80/66 | ASN | AAT | VAL | 19 | GTC | 0.32 (1) |
| 80/66 | ASN | AAT | GLY | 19 | GGC | 1.5 ± 1.4 (4) |
| 80/66 | ASN | AAT | THR | 19 | ACG | 0.13 (1) |
| 80/66 | ASN | AAT | LEU | 19 | CTG | 0.33 ± 0.14 (2) |
| 80/66 | ASN | AAT | GLU | 19 | GAG | 1.1 ± 0.8 (4) |
| 80/66 | ASN | AAT | ARG | 19 | AGG | 1.0 ± 0.8 (4) |
| 81/67 | LEU | CTC | GLN | 19 | CAA | — |
| 81/67 | LEU | CTC | GLY | 19 | GGC | <0.023 (1) |
| 81/67 | LEU | CTC | ALA | 19 | GCG | <0.047 (1) |
| 81/67 | LEU | CTC | TRP | 19 | TGG | <0.005 (1) |
| 81/67 | LEU | CTC | ARG | 19 | CGG | — |
| 81/67 | LEU | CTC | VAL | 19 | GTG | 0.16 ± 0.18 (2) |
| 81/67 | LEU | CTC | LYS | 19 | AAG | — |
| 82/68 | LEU | C(TG/CC) | GLN | 19 | CAG | 1.8 ± 0.3 (3) |
| 82/68 | LEU | C(TG/CC) | LYS | 19 | AAG | 0.05 (1) |
| 82/68 | LEU | C(TG/CC) | TRP | 19 | TGG | 2.7 ± 1.3 (4) |
| 82/68 | LEU | C(TG/CC) | ARG | 19 | AGC | 1.1 ± 0.2 (3) |
| 82/68 | LEU | C(TG/CC) | ASP | 19 | GAC | 2.7 ± 1.3 (4) |
| 82/68 | LEU | C(TG/CC) | VAL | 19 | GTG | 1.5 ± 1.1 (5) |
| 83/69 | PRO | CCA | ALA | 19 | GCA | 0.41 (1) |
| 83/69 | PRO | CCA | THR | 19 | ACC | 0.66 ± 0.12 (3) |
| 83/69 | PRO | CCA | ARG | 19 | CGG | — |
| 83/69 | PRO | CCA | TRP | 19 | TGG | 0.29 (1) |
| 83/69 | PRO | CCA | MET | 19 | ATG | 0.43 ± 0.28 (3) |
| 84/70 | CYS | TG(T/C) | GLU | 19 | GAG | <0.014 (1) |
| 84/70 | CYS | TG(T/C) | GLY | 19 | GGG | <0.006 (1) |
| 84/70 | CYS | TG(T/C) | ARG | 19 | AGG | — |
| 84/70 | CYS | TG(T/C) | MET | 19 | ATG | — |
| 84/70 | CYS | TG(T/C) | VAL | 19 | GTG | — |
| 85/71 | LEU | CTG | ASN | 19 | AAC | — |
| 85/71 | LEU | CTG | VAL | 19 | GTG | 0.52 ± 0.21 (5) |
| 85/71 | LEU | CTG | CLN | 19 | CAG | — |
| 86/72 | PRO | CCC | CYS | 19 | TGC | — |
| 86/72 | PRO | CCC | ARG | 19 | AGG | — |
| 86/72 | PRO | CCC | ALA | 19 | GCG | — |
| 86/72 | PRO | CCC | LYS | 19 | AAG | — |
| 87/73 | LEU | (C/A)TG | SER | 19 | AGC | 1.5 ± 0.4 (3) |
| 87/73 | LEU | (C/A)TG | TRP | 19 | TGG | — |
| 87/73 | LEU | (C/A)TG | GLY | 19 | GGG | — |
| 88/74 | ALA | GCC | LYS | 19 | AAG | — |
| 88/74 | ALA | GCC | ARG | 19 | AGG | 0.11 ± 0.10 (2) |
| 88/74 | ALA | GCC | VAL | 19 | GTG | 0.09 ± 0.02 (2) |
| 88/74 | ALA | GCC | TRP | 19 | TGG | 1.8 ± 0.2 (2) |
| 89/75 | THR | AC(G/A) | ASP | 19 | GAC | 0.24 ± 0.10 (2) |
| 89/75 | ThR | AC(G/A) | CYS | 19 | TGC | — |
| 89/75 | THR | AC(G/A) | LEU | 19 | CTC | 0.01 (1) |
| 89/75 | THR | AC(G/A) | VAL | 19 | GTG | 0.08 (1) |
| 89/75 | THR | AC(G/A) | GLU | 19 | GAG | 0.11 (1) |
| 89/75 | THR | AC(G/A) | HIS | 19 | CAC | 0.16 ± 0.06 (2) |
| 89/75 | THR | AC(C/A) | ASN | 19 | AAC | 0.21 ± 0.04 (2) |
| 89/75 | THR | AC(G/A) | SER | 19 | TCG | 0.25 ± 0.07 (2) |
| 90/76 | ALA | GCC | PRO | 19 | CCC | 0.03 (1) |
| 90/76 | ALA | GCC | SER | 19 | TCG | — |
| 90/76 | ALA | GCC | THR | 19 | ACC | 0.48 (1) |
| 90/76 | ALA | GCC | GLY | 19 | GGC | <0.006 (1) |
| 90/76 | ALA | GCC | ASP | 19 | GAC | 0.44 ± 0.29 (4) |
| 90/76 | ALA | GCC | TLE | 19 | ATC | — |
| 90/76 | ALA | GCC | MET | 19 | ATG | 0.25 ± 0.13 (2) |
| 91/77 | ALA | CCA | PRO | 19 | CCC | 1.9 ± 1.2 (3) |
| 91/77 | ALA | GCA | SER | 19 | TCC | 0.12 ± 0.07 (2) |
| 91/77 | ALA | GCA | THR | 19 | ACC | 0.48 ± 0.16 (2) |
| 91/77 | ALA | GCA | PHE | 19 | TTC | 0.44 ± 0.50 (3) |

TABLE 6-continued

(15–125) HUMAN INTERLEUKIN-3 MUTANTS

| hIL-3 aa POSITION[1] | PARENTAL aa | CO-DON | (15–125)hIL-3 MUTANT aa | SEQ ID NO: | CO-DON | BIOL ACTIVITY |
|---|---|---|---|---|---|---|
| 91/77 | ALA | GCA | LEU | 19 | CTC | 0.43 ± 0.27 (5) |
| 91/77 | ALA | GCA | ASP | 19 | GAC | 0.55 ± 0.09 (2) |
| 91/77 | ALA | GCA | HIS | 19 | GAC | — |
| 92/78 | PRO | CCC | PHE | 19 | TTC | — |
| 92/78 | PRO | CCC | ARG | 19 | CGG | — |
| 92/78 | PRO | CCC | SER | 19 | AGC | 0.26 (1) |
| 92/78 | PRO | CCC | LYS | 19 | AAG | — |
| 92/78 | PRO | CCC | HIS | 19 | CAC | — |
| 92/78 | PRO | CCC | LEU | 19 | CTG | — |
| 93/79 | THR | ACG | ASP | 19 | GAC | 1.3 ± 0.7 (4) |
| 93/79 | THR | ACG | SER | 19 | TCG | 0.70 ± 0.56 (4) |
| 93/79 | THR | ACG | ASN | 19 | AAC | — |
| 93/79 | THR | ACG | PRO | 19 | CCC | 0.53 ± 0.36 (4) |
| 93/79 | THR | ACG | ALA | 19 | GCG | 1.13 ± 0.2 (3) |
| 93/79 | THR | ACG | LEU | 19 | CTG | 0.69 ± 0.42 |
| 93/79 | THR | ACG | ARG | 19 | CGC | 0.93 ± 0.96 (4) |
| 94/80 | ARG | CGA | ILE | 19 | ATC | <0.020 (1) |
| 94/80 | ARG | CGA | SER | 19 | TCC | <0.100 (1) |
| 94/80 | ARG | CGA | GLU | 19 | GAG | <0.020 (1) |
| 94/80 | ARG | CGA | LEU | 19 | CTG | <0.020 (1) |
| 94/80 | ARC | CGA | VAL | 19 | GTG | <0.024 (1) |
| 94/80 | ARC | CGA | PRO | 19 | CCC | <0.024 (1) |
| 95/81 | HIS | CAT | GLN | 19 | CAG | <0.010 (1) |
| 95/81 | HIS | CAT | PRO | 19 | CCG | 1.6 ± 0.8 (3) |
| 95/81 | HIS | CAT | ARG | 19 | CGC | 4.7 ± 5.9 (2) |
| 95/81 | HIS | CAT | VAL | 19 | GTC | 1.2 ± 1.7 (2) |
| 95/81 | HIS | CAT | LEU | 19 | CTC | 0.7 (1) |
| 95/81 | HIS | CAT | GLY | 19 | GGC | 1.7 ± 2.4 (5) |
| 95/81 | HIS | CAT | THR | 19 | ACC | 2.9 ± 4.5 (4) |
| 95/81 | HIS | CAT | TYR | 19 | TAC | 0.07 (1) |
| 96/82 | PRO | CCA | LYS | 19 | AAG | <0.010 ± 0.001 (2) |
| 96/82 | PRO | CCA | TYR | 19 | TAC | 0.69 (1) |
| 96/82 | PRO | CCA | GLY | 19 | GGG | <0.040 (1) |
| 96/82 | PRO | CCA | ILE | 19 | ATC | <0.040 (1) |
| 96/82 | PRO | CCA | THR | 19 | ACC | <0.040 (1) |
| 97/83 | ILE | ATC | VAL | 19 | GTC | 0.91 ± 1.2 (8) |
| 97/83 | ILE | ATC | LYS | 19 | AAG | <0.024 |
| 97/83 | ILE | ATC | ALA | 19 | GCG | 0.15 (1) |
| 97/63 | ILE | ATC | ASN | 19 | AAT | <0.02 (1) |
| 98/84 | HIS | CAT | ILE | 19 | ATC | 5.0 ± 4.9 (12) |
| 98/84 | HIS | CAT | ASN | 19 | AAC | 1.4 ± 0.4 (2) |
| 98/84 | HIS | CAT | LEU | 19 | CTC | 2.4 ± 1.0 (2) |
| 98/84 | HIS | CAT | ASP | 19 | GAC | 0.38 ± 0.49 (5) |
| 98/84 | HIS | CAT | ALA | 19 | GCC | 2.0 ± 1.0 (3) |
| 98/84 | HIS | CAT | THR | 19 | ACG | 1.6 ± 0.3 (2) |
| 98/84 | HIS | CAT | LEU | 19 | TTG | 1.5 (1) |
| 98/84 | HIS | CAT | PRO | 19 | CCG | 0.55 (1) |
| 99/85 | ILE | ATC | LEU | 19 | CTG | 1.4 ± 1.4 (7) |
| 99/85 | ILE | ATC | ARG | 19 | CGC | <0.025 (1) |
| 99/85 | ILE | ATC | ASP | 19 | GAC | <0.025 (1) |
| 99/85 | ILE | ATC | VAL | 19 | GTC | 0.51 ± 0.59 (3) |
| 99/85 | ILE | ATC | PRO | 19 | CCG | <0.025 (1) |
| 99/85 | ILE | ATC | GLN | 19 | CAG | <0.018 ± 0.010 (2) |
| 99/85 | ILE | ATC | GLY | 19 | GGG | <0.018 ± 0.10 (2) |
| 99/85 | ILE | ATC | SER | 19 | TCG | <0.025 (1) |
| 99/85 | ILE | ATC | PHE | 19 | TTC | 0.45 (1) |
| 99/85 | ILE | ATC | HIS | 19 | cAC | <0.025 (1) |
| 100/86 | LYS | AAG | TYR | 19 | TAC | 0.03 (1) |
| 100/86 | LYS | AAG | LEU | 19 | TTG | 0.33 ± 0.31 (3) |
| 100/86 | LYS | AAG | HIS | 19 | CAC | 0.36 ± 0.22 (9) |
| 100/86 | LYS | AAG | ARG | 19 | AGC | 4.7 ± 5.9 (4) |
| 100/86 | LYS | AAG | ILE | 19 | ATC | 0.95 (1) |
| 100/86 | LYS | AAG | SER | 19 | AGC | 0.95 (1) |
| 100/86 | LYS | AAG | GLN | 19 | CAG | 0.78 ± 0.80 (7) |
| 100/86 | LYS | AAG | PRO | 19 | CCG | 0.70 (1) |
| 101/87 | ASP | GAC | PRO | 19 | CCC | 2.3 ± 3.1 (4) |
| 101/87 | ASP | GAC | MET | 19 | ATG | 1.8 ± 2.5 (6) |
| 101/87 | ASP | GAC | LYS | 19 | AAG | 1.2 ± 1.7 (3) |
| 101/87 | ASP | GAC | HIS | 19 | CAC | 2.5 (1) |
| 101/87 | ASP | GAC | ThR | 19 | ACG | 0.90 ± 0.77 (3) |
| 101/87 | ASP | GAC | TYR | 19 | TAC | 0.59 (1) |
| 101/87 | ASP | GAC | VAL | 19 | GTC | 0.42 (1) |
| 101/87 | ASP | GAC | TYR | 19 | TAC | 1.0 ± 0.02 (2) |
| 101/67 | ASP | GAC | GLN | 19 | CAG | 0.07 (1) |
| 102/88 | GLY | GGT | LEU | 19 | CTC | <0.015 ± 0.007 (2) |
| 102/88 | GLY | GGT | GLU | 19 | GAG | 0.40 ± 0.07 (3) |
| 102/88 | GLY | GGT | LYS | 19 | AGG | 0.16 ± 0.14 (2) |
| 102/88 | GLY | GGT | SER | 19 | TCC | 0.29 (1) |
| 102/88 | GLY | GGT | TYR | 19 | TAC | 0.04 (1) |
| 102/88 | GLY | GGT | PRO | 19 | CCC | <0.011 (1) |
| 103/89 | ASP | GAC | SER | 19 | TCC | 0.02 (1) |
| 104/90 | TRP | TGG | VAL | 19 | GTG | 0.11 ± 0.06 (5) |
| 104/90 | TRP | TGG | CYS | 19 | AGC | 0.07 ± 0.03 (5) |
| 104/90 | TRP | TGG | TYR | 19 | TAC | 0.34 ± 0.42 (5) |
| 104/90 | TRP | TGG | THR | 19 | ACC | 0.04 ± 0.02 (2) |
| 104/90 | TRP | TGG | MET | 19 | ATG | 0.14 (1) |
| 104/90 | TRP | TGG | PRO | 19 | CCC | 0.02 ± 0.02 (2) |
| 104/90 | TRP | TGG | LEU | 19 | TTG | 0.65 ± 1.0 (3) |
| 104/90 | TRP | TGG | GLN | 19 | CAG | 0.008 (1) |
| 104/90 | TRP | TGG | LYS | 19 | AAG | — |
| 104/90 | TRP | TGG | GLY | 19 | GAG | — |
| 104/90 | TRP | TGG | ALA | 19 | GCC | — |
| 104/90 | TRP | TGG | PHE | 19 | TTC | — |
| 104/90 | TRP | TGG | GLY | 19 | GGC | — |
| 105/91 | ASN | AAT | PRO | 19 | CCG | 4.8 ± 8.5 (5) |
| 105/91 | ASN | AAT | ALA | 19 | GCC | 0.65 ± 0.30 (3) |
| 105/91 | ASN | AAT | PHE | 19 | TTC | 0.13 (1) |
| 105/91 | ASN | AAT | SER | 19 | TCC | 1.9 ± 2.7 (5) |
| 105/91 | ASN | AAT | TRP | 19 | TGG | 0.95 (1) |
| 105/91 | ASN | AAT | GLN | 19 | CAA | 0.57 ± 0.52 (3) |
| 105/91 | ASN | AAT | TYR | 19 | TAC | 0.66 ± 0.53 (4) |
| 105/91 | ASN | AAT | LEU | 19 | CTC | 0.87 ± 0.79 (2) |
| 105/91 | ASN | AAT | LYS | 19 | AAG | 0.70 (1) |
| 105/91 | ASN | AAT | ILE | 19 | ATC | 1.0 (1) |
| 105/91 | ASN | AAT | ASP | 19 | GAC | 1.0 ± 0.9 (4) |
| 105/91 | ASN | AAT | HIS | 19 | CAC | 0.71 ± 0.48 (2) |
| 106/92 | GLU | GAA | SER | 19 | TCC | 0.17 ± 0.21 (2) |
| 106/92 | GLU | GAA | ALA | 19 | GCG | 0.235 ± 0.26 (2) |
| 106/92 | GLU | GAA | LYS | 19 | AAG | — |
| 106/92 | GLU | GAA | THR | 19 | ACC | — |
| 106/92 | GLU | GAA | ILE | 19 | ATC | — |
| 106/92 | GLU | GAA | GLY | 19 | GGC | 0.70 ± 0.76 (4) |
| 106/92 | GLU | GAA | PRO | 19 | CCC | — |
| 108/94 | ARG | CGG | LYS | 19 | AAG | 0.11 ± 0.03 (2) |
| 108/94 | ARG | CGG | ASP | 19 | GAC | — |
| 105/94 | ARG | CGG | LEU | 19 | TTG | 0.01 (1) |
| 108/94 | ARG | CGG | THR | 19 | ACG | 0.08 (1) |
| 106/94 | ARG | CGG | ILE | 19 | ATC | <0.01 (1) |
| 106/94 | ARG | CGG | PRO | 19 | CCC | — |
| 109/95 | ARG | AGG | THR | 19 | ACC | 1.1 ± 0.2 (3) |
| 109/95 | ARG | AGG | PRO | 19 | CCC | — |
| 109/95 | ARG | ACG | GLU | 19 | GAG | 1.1 ± 0.1 (3) |
| 109/95 | ARG | ACG | TYR | 19 | TAC | <0.006 (1) |
| 109/95 | ARG | AGG | LEU | 19 | CTC | 1.2 ± 0.9 (4) |
| 109/95 | ARG | AGG | SER | 19 | TCG | 1.7 ± 0.8 (4) |
| 109/95 | ARG | AGG | GLY | 19 | GGG | 0.17 (1) |
| 110/96 | LYS | AAA | ALA | 19 | GCC | <0.08 (1) |
| 110/96 | LYS | AAA | ASN | 19 | AAC | — |
| 110/96 | LYS | AAA | THR | 19 | ACG | — |
| 110/96 | LYS | AAA | LEU | 19 | CTC | — |
| 110/96 | LYS | AAA | ARG | 19 | CGG | — |
| 110/96 | LYS | AAA | GLN | 19 | CAG | — |
| 110/96 | LYS | AAA | TRP | 19 | TGG | — |
| 111/97 | LEU | CTG | ILE | 19 | ATC | — |
| 111/97 | LEU | CTG | ARG | 19 | CGG | — |
| 111/97 | LEU | CTG | ASP | 19 | GAC | — |
| 111/97 | LEU | CTG | MET | 19 | ATG | — |
| 112/98 | THR | ACG | VAL | 19 | GTG | 0.55 ± 0.44 (3) |
| 112/98 | THR | ACG | GLN | 19 | CAG | 1.7 ± 1.0 (3) |
| 112/98 | THR | ACG | TYR | 19 | TAC | <0.018 (1) |

TABLE 6-continued

(15–125) HUMAN INTERLEUKIN-3 MUTANTS

| hIL-3 POSI-TION[1] | PARENTAL aa | CO-DON | (15–125)hIL-3 MUTANT aa | SEQ ID NO: | CO-DON | BIOL ACTIVITY |
|---|---|---|---|---|---|---|
| 112/98 | THR | ACG | GLU | 19 | GAG | 0.12 (1) |
| 112/98 | THR | ACG | HIS | 19 | CAC | 0.25 ± 0.40 (3) |
| 112/98 | THR | ACG | SER | 19 | TCC | 0.17 ± 0.15 (2) |
| 112/98 | THR | ACG | PHE | 19 | TTC | — |
| 113/99 | PHE | TTC | SER | 19 | AGC | — |
| 113/99 | PHE | TTC | CYS | 19 | TGC | — |
| 113/99 | PHE | TTC | HIS | 19 | CAC | <0.009 (1) |
| 113/99 | PHE | TTC | GLY | 19 | GGC | — |
| 113/99 | PHE | TTC | TRP | 19 | TGG | — |
| 113/99 | PHE | TTC | TYR | 19 | TAC | 0.07 (1) |
| 113/99 | PHE | TTC | ASN | 19 | AAC | — |
| 114/100 | TYR | TAT | CYS | 19 | TGC | — |
| 114/100 | TYR | TAT | HIS | 19 | CAC | — |
| 114/100 | TYR | TAT | SER | 19 | AGC | — |
| 114/100 | TYR | TAT | TRP | 19 | TGG | 0.88 (1) |
| 114/100 | TYR | TAT | ARG | 19 | AGG | — |
| 114/100 | TYR | TAT | LEU | 19 | CTC | <0.018 (1) |
| 115/101 | LEU | CTG | ASN | 19 | AAC | <0.004 (1) |
| 115/101 | LEU | CTG | VAL | 19 | GTG | — |
| 115/101 | LEU | CTG | PRO | 19 | CCC | <0.004 |
| 115/101 | LEU | CTG | ARG | 19 | AGG | <0.004 (1) |
| 115/101 | LEU | CTG | ALA | 19 | GCG | 0.50 (1) |
| 115/101 | LEU | CTG | HIS | 19 | CAC | — |
| 115/101 | LEU | CTG | THR | 19 | ACC | — |
| 115/101 | LEU | CTG | TRP | 19 | TGG | — |
| 115/101 | LEU | CTG | MET | 19 | ATG | <0.008 (1) |
| 116/102 | LYS | AAA | LEU[14] | 19 | TTG | — |
| 116/102 | LYS | AAA | PRO[14] | 19 | CCG | <0.004 (1) |
| 116/102 | LYS | AAA | THR[14] | 19 | ACC | 0.50 (1) |
| 116/102 | LYS | AAA | MET[14] | 19 | ATG | 0.13 (1) |
| 116/102 | LYS | AAA | ASP[14] | 19 | GAC | <0.018 (1) |
| 116/102 | LYS | AAA | VAL | 19 | GTG | 2.3 ± 1.2 (5) |
| 116/102 | LYS | AAA | GLU | 19 | GAG | 0.06 (1) |
| 116/102 | LYS | AAA | ARG | 19 | CGC | 0.06 (1) |
| 116/102 | LYS | AAA | TRP | 19 | TGG | 2.3 ± 1.0 (4) |
| 116/102 | LYS | AAA | SER | 19 | TCG | 0.69 ± 0.51 (5) |
| 116/102 | LYS | AAA | LEU | 19 | CTC | 0.14 ± 0.02 (2) |
| 116/102 | LYS | AAA | ILE | 19 | ATC | 1.3 ± 0.3 (3) |
| 116/102 | LYS | AAA | THR | 19 | ACG | 0.84 ± 0.30 (4) |
| 117/103 | THR | ACC | SER | 19 | AGC | 1.1 ± 0.2 (3) |
| 117/103 | THR | ACC | ASN | 19 | AAC | 0.31 ± 0.39 (3) |
| 117/103 | THR | ACC | ILE | 19 | ATC | — |
| 117/103 | THR | ACC | TRP | 19 | TGG | 0.02 (1) |
| 117/103 | THR | ACC | LYS | 19 | AAG | <0.005 (1) |
| 117/103 | THR | ACC | PRO | 19 | CCG | — |
| 118/104 | LEU | CTT | SER | 19 | TCA | — |
| 118/104 | LEU | CTT | PRO | 19 | CCC | — |
| 118/104 | LEU | CTT | ALA | 19 | GCC | — |
| 118/104 | LEU | CTT | GLU | 19 | GAG | — |
| 118/104 | LEU | CTT | CYS | 19 | TGC | — |
| 118/104 | LEU | CTT | ASP | 19 | GAC | — |
| 118/104 | LEU | CTT | TYR | 19 | TAC | — |
| 119/105 | GLU | GAG | SER | 19 | TCC | 0.26 ± 0.19 (2) |
| 119/105 | GLU | GAG | LYS | 19 | AAG | 0.04 (1) |
| 119/105 | GLU | GAG | PRO | 19 | CCG | 0.31 ± 0.27 (3) |
| 119/105 | GLU | GAG | LEU | 19 | CTG | 0.35 ± 0.35 (3) |
| 119/105 | GLU | GAG | THR | 19 | ACC | 0.25 ± 0.27 (3) |
| 119/105 | GLU | GAG | TYR | 19 | TAC | 0.30 ± 0.32 (3) |
| 119/105 | GLU | GAG | ARG | 19 | CGC | 0.06 (1) |
| 120/106 | ASN | AAT | ALA | 19 | GCC | <0.009 (1) |
| 120/106 | ASN | AAT | PRO | 19 | CCC | 1.7 ± 0.7 (3) |
| 120/106 | ASN | AAT | LEU | 19 | TTG | 1.2 ± 0.3 (3) |
| 120/106 | ASN | AAT | HIS | 19 | CAC | 1.0 ± 0.3 (2) |
| 120/106 | ASN | AAT | VAL | 19 | GTG | 1.7 ± 0.3 (3) |
| 120/106 | ASN | AAT | GLN | 19 | CAG | 0.85 ± 0.16 (2) |
| 120/107 | ALA | GCG | SER | 19 | AGC | 1.2 ± 0.2 (3) |
| 120/107 | ALA | GCG | ILE | 19 | ATC | 2.8 ± 2.5 (2) |
| 121/107 | ALA | GCG | ASN | 19 | AAC | 0.91 ± 0.77 (5) |
| 121/107 | ALA | GCG | PRO | 19 | CCG | 1.3 (1) |
| 121/107 | ALA | GCG | LYS | 19 | AAG | 0.26 ± 0.24 (2) |
| 121/107 | ALA | GCG | ASP | 19 | GAC | 1.8* ± 0.9 (3) |
| 121/107 | ALA | GCG | GLY | 19 | GGC | 0.69 (1) |
| 122/108 | GLN | GCG | SER | 19 | AGC | 0.96 ± 0.41 (3) |
| 122/108 | GLN | CA(G/A) | MET | 19 | ATG | 1.7 ± 0.5 (3) |
| 122/108 | GLN | CA(G/A) | TRP | 19 | TGG | 1.4 (1) |
| 122/108 | GLN | CA(G/A) | ARG | 19 | AGG | 0.78 (1) |
| 122/108 | GLN | CA(G/A) | PHE | 19 | TTC | 2.3 ± 1.1 (3) |
| 122/108 | GLN | CA(G/A) | PRO | 19 | CCG | 1.0 (1) |
| 122/108 | GLN | CA(G/A) | HIS | 19 | CAC | 1.4 (1) |
| 122/108 | GLN | CA(G/A) | ILE | 19 | ATC | 2.7 ± 0.8 (3) |
| 122/108 | GLN | CA(G/A) | TYR | 19 | TAC | 1.7 ± 0.3 (2) |
| 122/108 | GLN | CA(G/A) | CYS | 19 | TGC | 0.58 (1) |
| 123/109 | ALA | GCT | MET | 19 | ATG | 2.0 ± 0.2 (3) |
| 123/109 | ALA | GCT | GLU | 19 | GAG | 2.1 ± 1.0 (3) |
| 123/109 | ALA | GCT | HIS | 19 | CAC | 0.98 ± 0.72 (3) |
| 123/109 | ALA | GCT | SER | 19 | AGC | 1.4 ± 0.8 (3) |
| 123/109 | ALA | GCT | PRO | 19 | CCC | 0.64 ± 0.16 (2) |
| 123/109 | ALA | GCT | TYR | 19 | TAC | 0.51 ± 0.25 (2) |
| 123/109 | ALA | GCT | LEU | 19 | CTG | 1.2 ± 0.1 (2) |

[1]The first position number representes the amino acid position in (1–133) hIL-3 and the second number represents the position in (15–125)hIL-3 in which the Asn at position 15 of native hIL-3 is position 1 in (15–125)hIL-3 (See the numbering for Formula XI)
[2]Double mutant; has PRO at position 35.
[3]Double mutant; has THR at position 49.
[4]Double mutant; has Gly at position 32.
[5]Double mutant; has Leu at position 31.
[6]Double mutant; has Gly at position 46.
[7]Double mutant; Arg at position 42.
[8]Double mutant; Phe at position 53.
[9]Double mutant; has Val at position 49.
[10]Double mutant; has Pro at position 73.
[11]Double mutant; has Thr at position 64.
[12]Double mutant: has Pro at position 73.
[13]Double mutant: has Met at position 74.
[14]Double mutant: has Ser at position 105.

The mutants in Table 6 were made as described in the Examples, particularly Examples 19, 20, 21 and 38 to 53.

It will be apparent to those skilled in the art that other codons besides those shown in Table 6 can also code for the substituted amino acids in the hIL-3 muteins. The present invention includes the DNAs encoding the mutant hIL-3 polypeptides of the invention including the various codons which can code for the parental and substituted amino acids of the hIL-3 muteins of the invention due to the degeneracy of the genetic code.

hIL-3 (15–125) variant genes encoding the variants listed in Table 6 can also be expressed from intracellular expression vectors to produce large quantities of the variant protein which can be purified and assayed for biological activity. The hIL-3 variant genes, from Table 6, can be excised from the secretion expression vector, as a 345 base pair NcoI/HindIII fragment and ligated into an appropriate intracellular expression vector, such as pMON2341 digested with NcoI and HindIII. Examples of variants transferred to pMON2341 in this manner are shown in Table 7. Two examples of such a transfer are described in the construction of pMON13215 (EXAMPLE 64) and pMON13252 (EXAMPLE 65).

EXAMPLE 64

Construction of pMON13215

Plasmid, pMON2341, DNA was digested with restriction enzymes NcoI and HindIII resulting in a 3619 base pair NcoI/HindIII fragment. The genetic elements derived from pMON2341 are the beta-lactamase gene (AMP), pBR327 origin of replication, F1 phage origin of replication as the transcription terminator, precA, g10L ribosome binding site. The plasmid encoding the hIL-3 (15–125) Trp$^{(116)}$ variant, from Table 6 was digested with NcoI and HindIII resulting in a 345 base pair NcoI/HindIII fragment. The 345 Base pair NcoI/HindIII fragment was ligated with the 3619 base pair fragment from pMON2341 and the ligation reaction mixture was used to transform *E. coli* K-12 strain JM101. Plasmid DNA was isolated and screened by restriction anaylsis using NcoI and HindIII. Positive clones contained a 345 base pair NcoI/HindIII. This construct was designated PMON13215. The plasmid, pMON13215, encodes the (15–125) hIL-3 variant with the following amino acid sequence:

EXAMPLE 65

Construction of pMON13252

Plasmid, pMON2341, DNA was digested with restriction enzymes NcoI and HindIII resulting in a 3619 base pair NcoI/HindIII fragment. The genetic elements derived from pMON2341 are the beta-lactamase gene (AMP), pBR327 origin of replication F1 phage origin of replication as the transcription terminator, precA, g10L ribosome binding site. The plasmid encoding the hIL-3 (15–125) Asp$^{(50)}$ variant, from Table 6, was digested with NcoI and HindIII resulting in a 345 base pair NcoI/HindIII fragment. This 345 Base pair NcoI/HindIII fragment was ligated with the 3619 base pair fragment from pMON2341 and the ligation reaction mixture was used to transform *E. coli* K-12 strain JM101. Plasmid DNA was isolated and screened by restriction analysis using NcoI and HindIII. Positive clones contained a 345 base pair NcoI/HindIII. This construct was designated pMON13252. The plasmid, pMON13252, encodes the (15–125) hIL-3 variant with the following amino acid sequence:

```
PEPTIDE A9;   (15-125)HIL-3 TRP(116) PMON13215

Asn Cys Ser Asn Met Ile Asp Glu Ile Ile Thr His Leu      [SEQ ID NO:217]
        15              20                  25

Lys Gln Pro Pro Leu Pro Leu Leu Asp Phe Asn Asn Leu Asn Gly
        30                  35                  40

Glu Asp Gln Asp Ile Leu Met Glu Asn Asn Leu Arg Arg Pro Asn
        45                  50                  55

Leu Glu Ala Phe Asn Arg Ala Val Lys Ser Leu Gln Asn Ala Ser
        60                  65                  70

Ala Ile Glu Ser Ile Leu Lys Asn Leu Leu Pro Cys Leu Pro Leu
        75                  80                  85

Ala Thr Ala Ala Pro Thr Arg His Pro Ile His Ile Lys Asp Gly
        90                  95                  100

Asp Trp Asn Glu Phe Arg Arg Lys Leu Thr Phe Tyr Leu Trp Thr
        105                 110                 115

Leu Glu Asn Ala Gln Ala Gln Gln
        120                 125

DNA sequence #A9 pMON13215    116w

ATGGCTAACT GCTCTAACAT GATCGATGAA ATCATCACCC ACCTGAAGCA      [SEQ ID NO:220]

GCCACCGCTG CCGCTGCTGG ACTTCAACAA CCTCAATGGT GAAGACCAAG

ATATCCTGAT GGAAAATAAC CTTCGTCGTC CAAACCTCGA GGCATTCAAC

CGTGCTGTCA ACTCTCTGCA GAATGCATCA GCAATTGAGA GCATTCTTAA

AAATCTCCTG CCATGTCTGC CCCTGGCCAC GGCCGCACCC ACGCGACATC

CAATCCATAT CAAGGACGGT GACTGGAATG AATTCCGTCG TAAACTGACC

TTCTATCTGT GGACCTTGGA GAACGCGCAG GCTCAACAG
```

PEPTIDE A10;   (15-125)HIL-3 ASP<sup>(50)</sup> pMON13252

```
      Asn Cys Ser Asn Met Ile Asp Glu Ile Ile Thr His Leu       [SEQ ID NO:218]
       15              20              25

Lys Gln Pro Pro Leu Pro Leu Leu Asp Phe Asn Asn Leu Asn Gly
           30              35              40

Glu Asp Gln Asp Ile Leu Met Asp Asn Asn Leu Arg Arg Pro Asn
           45              50              55

Leu Glu Ala Phe Asn Arg Ala Val Lys Ser Leu Gln Asn Ala Ser
           60              65              70

Ala Ile Glu Ser Ile Leu Lys Asn Leu Leu Pro Cys Leu Pro Leu
           75              80              85

Ala Thr Ala Ala Pro Thr Arg His Pro Ile His Ile Lys Asp Gly
           90              95              100

Asp Trp Asn Glu Phe Arg Arg Lys Leu Thr Phe Tyr Leu Lys Thr
           105             110             115

Leu Glu Asn Ala Gln Ala Gln Gln
           120             125
```

DNA sequence #A10 pMON13252   50D

```
ATGGCTAACT GCTCTAACAT GATCGATGAA ATCATCACCC ACCTGAAGCA      [SEQ ID NO:216]

GCCACCGCTG CCGCTGCTGG ACTTCAACAA CCTCAATGGT GAAGACCAAG

ATATCCTGAT GGAAATAAC CTTCGTCGTC CAAACCTCGA GGCATTCAAC

CGTGCTGTCA ACTCTCTGCA GAATGCATCA GCAATTGAGA GCATTCTTAA

AAATCTCCTG CCATGTCTGC CCCTGGCCAC GGCCGCACCC ACGCGACATC

CAATCCATAT CAAGGACGGT GACTGGAATG AATTCCGTCG TAAACTGACC

TTCTATCTGA AAACCTTGGA GAACGCGCAG GCTCAACAG
```

TABLE 7

| pMON number | position/ mutant (15–125) hIL-3 | NATIVE amino acid | SUBSTITUTION amino acid | SEQ ID NO: | RELATIVE POTENCY |
|---|---|---|---|---|---|
| pMON13201 | 45/31M | Gln | Met | 19 | 6.3 |
| pMON13202 | 51/37R | Asn | Arg | 19 | 1.58 |
| pMON13203 | 51/37P | Asn | Pro | 19 | 2.5 |
| pMON13204 | 51/37T | Asn | Thr | 19 | 3.16 |
| pMON13205 | 56/42S | Pro | ser | 19 | 6.3 |
| pMON13206 | 98/84I | His | Ile | 19 | 6.3 |
| pMON13207 | 45/31V | Gln | Val | 19 | 4 |
| pMON13208 | 42/28D | Gly | Asp | 19 | 6.3 |
| pMON13209 | 42/28S | Gly | Ser | 19 | 12.6 |
| pMONl3210 | 42/28A | Gly | Ala | 19 | 2.5 |
| pMON13211 | 46/32S | Asp | Ser | 19 | 16 |
| pMON13212 | 82/68W | Leu | Trp | 19 | 5 |
| pMON13213 | 82/68O | Leu | Asp | 19 | 4 |
| pMON13214 | 100/86R | Lys | Arg | 19 | 4 |
| pMON13215 | 116/102W | Lys | Trp | 19 | 31 |
| pMON13216 | 23/9L | Ile | Leu | 19 | 4 |
| pMON13217 | 32/18R | Leu | Arg | 19 | 7.9 |
| pMON13218 | 32/18N | Leu | Asn | 19 | 2 |
| pMON13219 | 32/18A | Leu | Ala | 19 | 1.58 |
| pMON13220 | 34/20S | Leu | Ser | 19 | 6.3 |
| pMON13221 | 34/20M | Leu | Met | 19 | 6.3 |
| pMON13222 | 50/36D | Glu | Asp | 19 | 7.9 |
| pMON13223 | 162/48I | Asn | Ile | 19 | * |
| pMON13224 | 66/52R | Lys | Arg | 19 | 4 |
| pMON13225 | 76/62P | Ser | Pro | 19 | 1.25 |
| pMON13226 | 77/63L | Ile | Leu | 19 | 1.58 |
| pMON13227 | 22/8G | Glu | Gly | 19 | 0.008 |
| pMON13228 | 115/101M | Leu | Met | 19 | 0.04 |
| pMON13229 | 122/108I | Gln | Ile | 19 | 1 |
| pMON13231 | 51/37H | Asn | His | 19 | 1.25 |
| pMON13232 | 59/45L | Glu | Leu | 19 | 1.99 |

TABLE 7-continued

| pMON number | position/ mutant (15–125) hIL-3 | NATIVE amino acid | SUBSTITUTION amino acid | SEQ ID NO: | RELATIVE POTENCY |
|---|---|---|---|---|---|
| pMON13233 | 63/49H | Arg | His | 19 | * |
| pMON13234 | 64/50N | Ala | Asn | 19 | 0.03 |
| pMON13235 | 65/51T | Val | Thr | 19 | 1.58 |
| pMON13236 | 76/62V | Ser | Val | 19 | 2.5 |
| pMON13237 | 76/62A | Ser | Ala | 19 | 5 |
| pMON13238 | 91/77P | Ala | Pro | 19 | * |
| pMON13240 | 100/860 | Lys | Gln | 19 | 2.5 |
| pMON13241 | 101/87M | Asp | Met | 19 | 6.3 |
| pMON13242 | 105/91N | Asn | Asn | 19 | * |
| pMON13243 | 116/102V | Lys | Val | 19 | 7.9 |
| pMON13244 | 122/108F | Gln | Phe | 19 | 6.3 |
| pMON13245 | 123/109E | Ala | Glu | 19 | 1.58 |
| pMON13246 | 42D | Gly | Asp | 15 | 20 |
| pMON13247 | 42S | Gly | Ser | 15 | * |
| pMON13248 | 42A | Gly | Ala | 15 | 16 |
| pMON13249 | 45V | Gln | Val | 15 | 5 |
| pMON13250 | 45M | Gln | Met | 15 | * |
| pMON13251 | 46S | Asp | Ser | 15 | 5 |
| pMON13252 | 50D | Glu | Asp | 15 | 5 |
| pMON13253 | 98I | His | Ile | 15 | * |
| pMON13264 | 97V | Ile | Val | 15 | 4 |
| pMON13266 | 75K | Glu | Lys | 15 | 0.25 |
| pMON13267 | 89N | Thr | Asn | 15 | 2.5 |

Table 7 shows the biological activity of (15–125) hIL-3 mutant polypeptides of the present invention expressed from intracellular expression vectors. Upon expression these muteins may have Met- or Met-Ala-preceding the initial (15–125) hIL-3 amino acid. The relative biological activity of IL-3 mutants is calculated by dividing the $EC_{50}$ (1–133) hIL-3 by the $EC_{50}$ of the mutant.

EXAMPLE 66

The variants in Table 8 were constructed by cassette mutagenesis using methods described in the Materials and Methods and the Examples contained herein, particularly Examples 54–57. Parental plasmid DNA (Table 8), digested with the appropriate restriction enzymes (Table 8), was ligated with the indicated annealed pairs of complementary oligonucleotides (Table 8). The assembled oligonucleotides create appropriate restriction ends and a portion of the (15–125) hIL-3 gene sequence Individual isolates were screened by restriction analysis and DNA sequenced to confirm that the desired changes in the (15–125) hIL-3 variant gene were made. The oligonucleotides create change (s) in the (15–125) hIL-3 gene which enclode the corresponding amino acid substitution in the variant polypeptide (Table 8). The amino acids substitutions in polypeptide #1 (SEQ ID NO:65) are indicated in Table 8.

TABLE 8

| position/native a.a. | substitution | codon | oligo pair | oligo pair | oligo pair | oligo pair | oligo pair |
|---|---|---|---|---|---|---|---|
| 21 asp | glu | GAA | 21glu1<br>SEQ ID NO:73<br>21glu4<br>SEQ ID NO:219 | NcoRv2<br>SEQ ID NO:523<br>NcoRV5<br>SEQ ID NO:526 | NcoRV3<br>SEQ ID NO:524<br>NcoRV6<br>SEQ ID NO:527 | | |
| 21 asp | gln | CAA | 21gln1<br>SEQ ID NO:71<br>21gln4<br>SEQ ID NO:72 | NcoRv2<br>SEQ ID NO:523<br>NcoRV5<br>SEQ ID NO:526 | NcoRV3<br>SEQ ID NO:524<br>NcoRV6<br>SEQ ID NO:527 | | |
| 21 asp | asn | AAC | 21asn1<br>SEQ ID NO:66<br>21asn4<br>SEQ ID NO:70 | NcoRv2<br>SEQ ID NO:523<br>NcoRV5<br>SEQ ID NO:526 | NcoRV3<br>SEQ ID NO:524<br>NcoRV6<br>SEQ ID NO:527 | | |
| 21 asp | thr | ACC | 21thr1<br>SEQ ID NO:232<br>21thr4<br>SEQ ID NO:233 | NcoRv2<br>SEQ ID NO:523<br>NcoRV5<br>SEQ ID NO:526 | NcoRV3<br>SEQ ID NO:524<br>NcoRV6<br>SEQ ID NO:527 | | |
| 21 asp | ser | AGC | 21ser1<br>SEQ ID NO:230<br>21ser4<br>SEQ ID NO:231 | NcoRv2<br>SEQ ID NO:523<br>NcoRV5<br>SEQ ID NO:526 | NcoRV3<br>SEQ ID NO:524<br>NcoRV6<br>SEQ ID NO:527 | | |
| 22 glu | asp | GAC | 22asp1<br>SEQ ID NO:236<br>22asp4<br>SEQ ID NO:237 | NcoRv2<br>SEQ ID NO:523<br>NcoRV5<br>SEQ ID NO:526 | NcoRV3<br>SEQ ID NO:524<br>NcoRV6<br>SEQ ID NO:527 | | |
| 22 glu | asn | AAC | 22asn1<br>SEQ ID NO:234 | NcoRv2<br>SEQ ID NO:523 | NcoRV3<br>SEQ ID NO:524 | | |

TABLE 8-continued

| | | | | | |
|---|---|---|---|---|---|
| | | | 22asn4 | NcoRV5 | NcoRV6 |
| | | | SEQ ID NO:236 | SEQ ID NO:526 | SEQ ID NO:527 |
| 22 glu | gln | CAG | 22gln1 | NcoRv2 | NcoRV3 |
| | | | SEQ ID NO:236 | SEQ ID NO:523 | SEQ ID NO:524 |
| | | | 22gln4 | NcoRV5 | NcoRV6 |
| | | | SEQ ID NO:239 | SEQ ID NO:526 | SEQ ID NO:527 |
| 22 glu | leu | CTG | 22leu1 | NcoRv2 | NcoRV3 |
| | | | SEQ ID NO:240 | SEQ ID NO:523 | SEQ ID NO:524 |
| | | | 22leu4 | NcoRV5 | NcoRV6 |
| | | | SEQ ID NO:241 | SEQ ID NO:526 | SEQ ID NO:527 |
| 22 glu | val | GTT | 22val1 | NcoRv2 | NcoRV3 |
| | | | SEQ ID NO:242 | SEQ ID NO:523 | SEQ ID NO:524 |
| | | | 22val4 | NcoRV5 | NcoRV6 |
| | | | SEQ ID NO:243 | SEQ ID NO:526 | SEQ ID NO:527 |
| 34 leu | glu | GAA | NcoRV1 | 34Glu2 | NcoRV3 |
| | | | SEQ ID NO:522 | SEQ ID NO:251 | SEQ ID NO:524 |
| | | | NcoRV4 | 34Glu5 | NcoRV6 |
| | | | SEQ ID NO:525 | SEQ ID NO:252 | SEQ ID NO:527 |
| 34 leu | gln | CAG | NcoRV1 | 34gln2 | NcoRV3 |
| | | | SEQ ID NO:522 | SEQ ID NO:248 | SEQ ID NO:524 |
| | | | NcoRV4 | 34gln5 | NcoRV5 |
| | | | SEQ ID NO:525 | SEQ ID NO:249 | SEQ ID NO:527 |
| 34 leu | thr | ACC | NcoRV1 | 34thr2 | NcoRV3 |
| | | | SEQ ID NO:522 | SEQ ID NO:256 | SEQ ID NO:524 |
| | | | NcoRV4 | 34thr5 | NcoRV6 |
| | | | SEQ ID NO:525 | SEQ ID NO:257 | SEQ ID NO:527 |
| 34 leu | arg | CGT | NcoRV1 | 34arg2 | NcoRV3 |
| | | | SEQ ID NO:522 | SEQ ID NO:246 | SEQ ID NO:524 |
| | | | NcoRV4 | 34arg5 | NcoRV6 |
| | | | SEQ ID NO:525 | SEQ ID NO:247 | SEQ ID NO:527 |
| 34 leu | ala | GCT | NcoRV1 | 34ala2 | NcoRV3 |
| | | | SEQ ID NO:522 | SEQ ID NO:244 | SEQ ID NO:524 |
| | | | NcoRV4 | 34ala5 | NcoRV6 |
| | | | SEQ ID NO:525 | SEQ ID NO:245 | SEQ ID NO:521 |
| 34 leu | phe | TTC | NcoRV1 | 34phe2 | NcoRV3 |
| | | | SEQ ID NO:522 | SEQ ID NO:254 | SEQ ID NO:524 |
| | | | NcoRV4 | 34phe5 | NcoRV6 |
| | | | SEQ ID NO:525 | SEQ ID NO:255 | SEQ ID NO:527 |
| 34 leu | ile | ATC | NcoRV1 | 34ile2 | NcoRV3 |
| | | | SEQ ID NO:522 | SEQ ID NO:252 | SEQ ID NO:524 |
| | | | NcoRV4 | 34ile5 | NcoRV6 |
| | | | SEQ ID NO:525 | SEQ ID NO:253 | SEQ ID NO:527 |
| 42 gly | lys | AAA | NcoRV1 | NcoRv2 | 42lys3 |
| | | | SEQ ID NO:522 | SEQ ID NO:523 | SEQ ID NO:268 |
| | | | NcoRV4 | NcoRV5 | 42lys6 |
| | | | SEQ ID NO:525 | SEQ ID NO:526 | SEQ ID NO:259 |
| 42 gly | asn | AAC | NcoRV1 | NcoRv2 | 42asn3 |
| | | | SEQ ID NO:522 | SEQ ID NO:523 | SEQ ID NO:260 |
| | | | NcoRV4 | NaoRV5 | 42asn6 |
| | | | SEQ ID NO:525 | SEQ ID NO:526 | SEQ ID NO:261 |
| 42 aly | thr | ACC | NcoRV1 | NcoRv2 | 42thr3 |
| | | | SEQ ID NO:522 | SEQ ID NO:523 | SEQ ID NO:274 |
| | | | NcoRV4 | NcoRV5 | 42thr6 |
| | | | SEQ ID NO:525 | SEQ ID NO:526 | SEQ ID NO:275 |
| 42 gly | leu | CTG | NcoRV1 | NcoRv2 | 42leu3 |
| | | | SEQ ID NO:522 | SEQ ID NO:523 | SEQ ID NO:266 |
| | | | NcoRV4 | NcoRV5 | 42leu6 |
| | | | SEQ ID NO:525 | SEQ ID NO:526 | SEQ ID NO:267 |
| 42 gly | val | GTT | NcoRV1 | NcoRv2 | 42val3 |
| | | | SEQ ID NO:522 | SEQ ID NO:523 | SEQ ID NO:278 |
| | | | NcoRV4 | NcoRV5 | 42val6 |
| | | | SEQ ID NO:525 | SEQ ID NO:526 | SEQ ID NO:279 |
| 42 gly | glu | GAA | NcoRV1 | NcoRv2 | 42glu3 |
| | | | SEQ ID NO:522 | SEQ ID NO:523 | SEQ ID NO:262 |
| | | | NcoRV4 | NcoRV5 | 42glu6 |
| | | | SEQ ID NO:525 | SEQ ID NO:526 | SEQ ID NO:263 |
| 42 aly | phe | TTC | NcoRV1 | NcoRv2 | 42phe3 |
| | | | SEQ ID NO:522 | SEQ ID NO:523 | SEQ ID NO:272 |
| | | | NcoRV4 | NcoRV5 | 42phe6 |
| | | | SEQ ID NO:525 | SEQ ID NO:526 | SEQ ID NO:273 |
| 42 aly | tyr | TAC | NcoRV1 | NcoRv2 | 42tyr3 |
| | | | SEQ ID NO:522 | SEQ ID NO:523 | SEQ ID NO:276 |
| | | | NcoRV4 | NcoRV5 | 42tyr6 |
| | | | SEQ ID NO:525 | SEQ ID NO:526 | SEQ ID NO:277 |
| 42 gly | ile | ATC | NcoRV1 | NcoRv2 | 42ile3 |
| | | | SEQ ID NO:522 | SEQ ID NO:523 | SEQ ID NO:264 |
| | | | NcoRV4 | NcoRV5 | 42ile6 |
| | | | SEQ ID NO:525 | SEQ ID NO:526 | SEQ ID NO:265 |
| 42 gly | met | ATG | NcoRV1 | NcoRv2 | 42met3 |

TABLE 8-continued

| | | | | | |
|---|---|---|---|---|---|
| | | | SEQ ID NO:522 | SEQ ID NO:523 | SEQ ID NO:270 |
| | | | NcoRV4 | NcoRV5 | 42met6 |
| | | | SEQ ID NO:525 | SEQ ID NO:526 | SEQ ID NO:271 |
| 43 alu | gln | CAG | NcoRV1 | NcoRv2 | 43gln3 |
| | | | SEQ ID NO:522 | SEQ ID NO:523 | SEQ ID NO:282 |
| | | | NcoRV4 | NcoRV5 | 43gln6 |
| | | | SEQ ID NO:525 | SEQ ID NO:526 | SEQ ID NO:283 |
| 43 glu | arg | CGT | NcoRV1 | NcoRv2 | 43arg3 |
| | | | SEQ ID NO:522 | SEQ ID NO:523 | SEQ ID NO:28O |
| | | | NcoRV4 | NcoRV5 | 43arg6 |
| | | | SEQ ID NO:525 | SEQ ID NO:526 | SEQ ID NO:281 |
| 43 glu | thr | ACC | NcoRV1 | NcoRv2 | 43thr3 |
| | | | SEQ ID NO:522 | SEQ ID NO:523 | SEQ ID NO:286 |
| | | | NcoRV4 | NcoRV5 | 43thr6 |
| | | | SEQ ED NO:525 | SEQ ID NO:526 | SEQ ID NO:287 |
| 43 glu | gly | GGT | NcoRV1 | NcoRv2 | 43gly3 |
| | | | SEQ ID NO:522 | SEQ ID NO:523 | SEQ ID NO:284 |
| | | | NcoRV4 | NcoRV5 | 43gly6 |
| | | | SEQ ID NO:525 | SEQ ID NO:526 | SEQ ID NO:285 |
| 44 asp | glu | GAA | NcoRV1 | NcoRv2 | 44glu3 |
| | | | SEQ ID NO:522 | SEQ ID NO:523 | SEQ ID NO:294 |
| | | | NcoRV4 | NcoRV5 | 44glu6 |
| | | | SEQ ID NO:525 | SEQ ID NO:526 | SEQ ID NO:265 |
| 44 asp | asn | AAC | NcoRV1 | NcoRv2 | 44asn3 |
| | | | SEQ ID NO:522 | SEQ ID NO:523 | SEQ ID NO:290 |
| | | | NcoRV4 | NcoRV5 | 44asn6 |
| | | | SEQ ID NO:525 | SEQ ID NO:526 | SEQ ID NO:291 |
| 44 asp | gln | CAG | NcoRV1 | NcoRv2 | 44gln3 |
| | | | SEQ ID NO:522 | SEQ ID NO:523 | SEQ ID NO:292 |
| | | | NcoRV4 | NcoRV5 | 44gln6 |
| | | | SEQ ID NO:525 | SEQ ID NO:526 | SEQ ID NO:293 |
| 44 asp | ala | GCT | NcoRV1 | NcoRv2 | 44ala3 |
| | | | SEQ ID NO:522 | SEQ ID NO:523 | SEQ ID NO:288 |
| | | | NcoRV4 | NcoRV5 | 44ala6 |
| | | | SEQ ID NO:525 | SEQ ID NO:526 | SEQ ID NO:289 |
| 45 gln | asp | GAC | NcoRV1 | NcoRv2 | 45asp3 |
| | | | SEQ ID NO:522 | SEQ ID NO:523 | SEQ ID NO:332 |
| | | | NcoRV4 | NcoRV5 | 45asp6 |
| | | | SEQ ID NO:525 | SEQ ID NO:526 | SEQ ID NO:303 |
| 45 gln | asn | AAC | NcoRV1 | NcoRv2 | 45asn3 |
| | | | SEQ ID NO:522 | SEQ ID NO:523 | SEQ ID NO:300 |
| | | | NcoRV4 | NcoRV5 | 45asn6 |
| | | | SEQ ID NO:525 | SEQ ID NO:526 | SEQ ID NO:301 |
| 45 gln | arg | CGT | NcoRV1 | NcoRv2 | 45arg3 |
| | | | SEQ ID NO:522 | SEQ ID NO:523 | SEQ ID NO:298 |
| | | | NcoRV4 | NcoRV5 | 45arg6 |
| | | | SEQ ID NO:525 | SEQ ID NO:526 | SEQ ID NO:299 |
| 45 gln | ser | TCC | NcoRV1 | NcoRv2 | 45ser3 |
| | | | SEQ ID NO:522 | SEQ ID NO:523 | SEQ ID NO:310 |
| | | | NcoRV4 | NcoRV5 | 45ser6 |
| | | | SEQ ID NO:525 | SEQ ID NO:526 | SEQ ID NO:311 |
| 45 gln | ala | GCT | NcoRV1 | NcoRv2 | 45ala3 |
| | | | SEQ ID NO:522 | SEQ ID NO:523 | SEQ ID NO:296 |
| | | | NcoRV4 | NcoRV5 | 45ala6 |
| | | | SEQ ID NO:525 | SEQ ID NO:526 | SEQ ID NO:297 |
| 45 gln | ile | ATC | NcoRV1 | NcoRv2 | 45ile3 |
| | | | SEQ ID NO:522 | SEQ ID NO:523 | SEQ ID NO:308 |
| | | | NcoRV4 | NcoRV5 | 45ile6 |
| | | | SEQ ID NO:525 | SEQ ID NO:526 | SEQ ID NO:309 |
| 45 gln | glu | GAA | NcoRV1 | NcoRv2 | 45glu3 |
| | | | SEQ ID NO:522 | SEQ ID NO:523 | SEQ ID NO:304 |
| | | | NcoRV4 | NcoRV5 | 45glu6 |
| | | | SEQ ID NO:525 | SEQ ID NO:526 | SEQ ID NO:305 |
| 45 gln | his | CAC | NcoRV1 | NcoRv2 | 45his3 |
| | | | SEQ ID NO:522 | SEQ ID NO:523 | SEQ ID NO:306 |
| | | | NcoRV4 | NcoRV5 | 45his6 |
| | | | SEQ ID NO:525 | SEQ ID NO:526 | SEQ ID NO:307 |
| 46 asp | glu | GAA | NcoRV1 | NcoRv2 | 46glu3 |
| | | | SEQ ID NO:522 | SEQ ID NO:523 | SEQ ID NO:318 |
| | | | NcoRV4 | NcoRV5 | 46glu6 |
| | | | SEQ ID NO:525 | SEQ ID NO:526 | SEQ ID NO:319 |
| 46 asp | asn | AAC | NcoRV1 | NcoRv2 | 46asn3 |
| | | | SEQ ID NO:522 | SEQ ID NO:523 | SEQ ID NO:314 |
| | | | NcoRV4 | NcoRV5 | 46asn6 |
| | | | SEQ ID NO:525 | SEQ ID NO:526 | SEQ ID NO:315 |
| 46 asp | gln | CAG | NcoRV1 | NcoRv2 | 46gln3 |
| | | | SEQ ID NO:522 | SEQ ID NO:523 | SEQ ID NO:316 |
| | | | NcoRV4 | NcoRV5 | 46gln6 |
| | | | SEQ ID NO:525 | SEQ ID NO:526 | SEQ ID NO:317 |

TABLE 8-continued

| | | | | | |
|---|---|---|---|---|---|
| 46 asp | lys | AAA | NcoRV1 | NcoRv2 | 46lys3 |
| | | | SEQ ID NO:522 | SEQ ID NO:523 | SEQ ID NO:326 |
| | | | NcoRV4 | NcoRV5 | 46lys6 |
| | | | SEQ ID NO:525 | SEQ ID NO:526 | SEQ ID NO:327 |
| 46 asp | his | CAC | NcoRV1 | NcoRv2 | 46his3 |
| | | | SEQ ID NO:522 | SEQ ID NO:523 | SEQ ID NO:320 |
| | | | NcoRV4 | NcoRV5 | 46his6 |
| | | | SEQ ID NO:525 | SEQ ID NO:526 | SEQ ID NO:321 |
| 46 asp | ala | GCT | NcoRV1 | NcoRv2 | 46ala3 |
| | | | SEQ ID NO:522 | SEQ ID NO:553 | SEQ ID NO:312 |
| | | | NcoRV4 | NcoRV5 | 46ala6 |
| | | | SEQ ID NO:525 | SEQ ID NO:526 | SEQ ID NO:313 |
| 46 asp | tyr | TAC | NcoRV1 | NcoRv2 | 46tyr3 |
| | | | SEQ ID NO:522 | SEQ ID NO:523 | SEQ ID NO:329 |
| | | | NcoRV4 | NcoRV5 | 46tyr6 |
| | | | SEQ ID NO:525 | SEQ ID NO:526 | SEQ ID NO:320 |
| 46 asp | ile | ATC | NcoRV1 | NcoRv2 | 46ile3 |
| | | | SEQ ID ND:522 | SEQ ID NO:553 | SEQ ID NO:322 |
| | | | NcoRV4 | NcoRV5 | 46ile6 |
| | | | SEQ ID NO:525 | SEQ ID NO:526 | SEQ ID NO:323 |
| 46 asp | val | GTT | NcoRV1 | NcoRv2 | 46val3 |
| | | | SEQ ID NO:522 | SEQ ID NO:523 | SEQ ID NO:320 |
| | | | NcoRV4 | NcoRV5 | 46val6 |
| | | | SEQ ID NO:525 | SEQ ID NO:526 | SEQ ID NO:331 |
| 48 leu | glu | GAA | 48glu1 | RVNsi2 | RVNsi3 |
| | | | SEQ ID NO:334 | SEQ ID NO:526 | SEQ ID NO:530 |
| | | | 48glu4 | RVNsi5 | RVNsi6 |
| | | | SEQ ID NO:535 | SEQ ID NO:532 | SEQ ID NO:533 |
| 48 leu | lys | AAA | 49lys1 | RVNsi2 | RVNsi3 |
| | | | SEQ ID NO:336 | SEQ ID NO:526 | SEQ ID NO:530 |
| | | | 48lys4 | RVNsi5 | RVNsi6 |
| | | | SEQ ID NO:337 | SEQ ID NO:532 | SEQ ID NO:533 |
| 48 leu | thr | ACC | 45thr1 | RVNsi2 | RVNsi3 |
| | | | SEQ ID NO:340 | SEQ ID NO:529 | SEQ ID NO:530 |
| | | | 48thr4 | RVNsi5 | RVNsi6 |
| | | | SEQ ID NO:341 | SEQ ID NO:532 | SEQ ID NO:533 |
| 48 leu | ala | GCT | 48ala1 | RVNsi2 | RVNsi3 |
| | | | SEQ ID NO:332 | SEQ ID NO:529 | SEQ ID NO:530 |
| | | | 48ala4 | RVNsi5 | RVNsi5 |
| | | | SEQ ID NO:333 | SEQ ID NO:532 | SEQ ID NO:533 |
| 48 leu | met | ATG | 48met1 | RVNsi2 | RVNsi3 |
| | | | SEQ ID NO:338 | SEQ ID NO:529 | SEQ ID NO:530 |
| | | | 48met4 | RVNsi5 | RVNsi5 |
| | | | SEQ ID NO:339 | SEQ ID NO:532 | SEQ ID NO:533 |
| 48 leu | val | CAC | 48val1 | RVNsi2 | RVNsi3 |
| | | | SEQ ID NO:342 | SEQ ID NO:529 | SEQ ID NO:530 |
| | | | 48val4 | RVNsi5 | RVNsi5 |
| | | | SEQ ID NO:343 | SEQ ID NO:532 | SEQ ID NO:533 |
| 50 glu | lys | AAA | 50lys1 | RVNsi2 | RVNsi3 |
| | | | SEQ ID ND:356 | SEQ ID NO:529 | SEQ ID NO:530 |
| | | | 50lys4 | RVNsi5 | RVNsi6 |
| | | | SEQ ID NO:357 | SEQ ID NO:532 | SEQ ID NO:533 |
| 50 glu | asn | AAC | 50asn1 | RVNsi2 | RVNsi3 |
| | | | SEQ ID NO:352 | SEQ ID NO:529 | SEQ ID NO:530 |
| | | | 50asn4 | RVNsi5 | RVNsi6 |
| | | | SEQ ID NO:353 | SEQ ID NO:532 | SEQ ID NO:533 |
| 50 glu | ser | TCC | 50ser1 | RVNsi2 | RVNsi3 |
| | | | SEQ ID NO:358 | SEQ ID NO:529 | SEQ ID NO:530 |
| | | | 50ser4 | RVNsi5 | RVNsi5 |
| | | | SEQ ID NO:359 | SEQ ID NO:532 | SEQ ID NO:533 |
| 50 glu | ala | GCT | 50ala1 | RVNsi2 | RVNsi3 |
| | | | SEQ ID NO:350 | SEQ ID NO:529 | SEQ ID NO:530 |
| | | | 50ala4 | RVNsi5 | RVNsi5 |
| | | | SEQ ID NO:351 | SEQ ID NO:532 | SEQ ID NO:533 |
| 50 glu | iIe | ATG | 50ile1 | RVNsi2 | RVNsi3 |
| | | | SEQ ID NO:354 | SEQ ID NO:529 | SEQ ID NO:530 |
| | | | 50ile4 | RVNsi5 | RVNsi5 |
| | | | SEQ ID NO:355 | SEQ ID NO:532 | SEQ ID NO:533 |
| 50 glu | val | GTT | 50val1 | RVNsi2 | RVNsi3 |
| | | | SEQ ID NO:360 | SEQ ID NO:529 | SEQ ID NO:530 |
| | | | 50val4 | RVNsi6 | RVNsi6 |
| | | | SEQ ID NO:361 | SEQ ID NO:532 | SEQ ID NO:533 |
| 50 glu | his | CAC | 50his1 | RVNsi2 | RVNsi3 |
| | | | SEQ ID NO:344 | SEQ ID NO:529 | SEQ ID NO:530 |
| | | | 50his4 | RVNsi5 | RVNsi6 |
| | | | SEQ ID NO:345 | SEQ ID NO:532 | SEQ ID NO:533 |
| 50 glu | phe | TTC | 50phe1 | RVNsi2 | RVNsi3 |
| | | | SEQ ID NO:349 | SEQ ID NO:529 | SEQ ID NO:530 |
| | | | 50phe4 | RVNsi5 | RVNsi6 |

TABLE 8-continued

| | | | | | | |
|---|---|---|---|---|---|---|
| 50 glu | met | ATG | SEQ ID NO:349<br>50met1<br>SEQ ID NO:346<br>50met4 | SEQ ID NO:532<br>RVNsi2<br>SEQ ID NO:529<br>RVNsi5 | SEQ ID NO:533<br>RVNsi3<br>SEQ ID NO:530<br>RVNsi6 | |
| 54 arg | asn | AAC | SEQ ID NO:347<br>54asn1<br>SEQ ID NO:364<br>54asn4 | SEQ ID NO:532<br>RVNsi2<br>SEQ ID NO:529<br>RVNsi5 | SEQ ID NO:533<br>RVNsi3<br>SEQ ID NO:530<br>RVNsi6 | |
| 54 arg | lys | AAA | SEQ ID NO:365<br>54lys1<br>SEQ ID NO:368<br>54lys4 | SEQ ID NO:532<br>RVNsi2<br>SEQ ID NO:529<br>RVNsi5 | SEQ ID NO:533<br>RVNsi3<br>SEQ ID NO:530<br>RVNsi6 | |
| 54 arg | his | GAC | SEQ ID NO:369<br>54his1<br>SEQ ID NO:366<br>54his4 | SEQ ID NO:532<br>RVNsi2<br>SEQ ID NO:529<br>RVNsi5 | SEQ ID NO:533<br>RVNsi3<br>SEQ ID NO:530<br>RVNsi6 | |
| 54 arg | ala | GCT | SEQ ID NO:367<br>54ala1<br>SEQ ID NO:362<br>54ala4 | SEQ ID NO:532<br>RVNsi2<br>SEQ ID NO:529<br>RVNsi5 | SEQ ID NO:533<br>RVNsi3<br>SEQ ID NO:530<br>RVNsi6 | |
| 56 pro | glu | GAA | SEQ ID NO:363<br>56glu1<br>SEQ ID NO:376<br>RVNsi4<br>SEQ ID NO:531 | SEQ ID NO:532<br>RVNsi2<br>SEQ ID NO:529<br>56glu5<br>SEQ ID NO:377 | SEQ ID NO:533<br>RVNsi3<br>SEQ ID NO:530<br>RVNsi6<br>SEQ ID NO:533 | |
| 56 pro | gln | | 56gln1<br>SEQ ID NO:374<br>RVNsi4<br>SEQ ID NO:531 | RVNsi2<br>SEQ ID NO:529<br>56gln5<br>SEQ ID NO:315 | RVNsi3<br>SEQ ID NO:530<br>RVNsi6<br>SEQ ID NO:533 | |
| 56 pro | arg | CGT | 56arg1<br>SEQ ID NO:372<br>RVNsi4<br>SEQ ID NO:531 | RVNsi2<br>SEQ ID NO:529<br>56arg5<br>SEQ ID NO:373 | RVNsi3<br>SEQ ID NO:530<br>RVNsi6<br>SEQ ID NO:533 | |
| 56 pro | his | CAC | 56his1<br>SEQ ID NO:378<br>RVNsi4<br>SEQ ID NO:531 | RVNsi2<br>SEQ ID NO:529<br>56his5<br>SEQ ID NO:379 | RVNsi3<br>SEQ ID NO:530<br>RVNsi6<br>SEQ ID NO:533 | |
| 56 pro | thr | ACC | 56thr1<br>SEQ ID NO:384<br>RVNsi4<br>SEQ ID NO:531 | RVNsi2<br>SEQ ID NO:529<br>56thr5<br>SEQ ID NO:365 | RVNsi3<br>SEQ ID NO:530<br>RVNsi6<br>SEQ ID NO:533 | |
| 56 pro | ala | GCT | 56ala1<br>SEQ ID NO:370<br>RVNsi4<br>SEQ ID NO:531 | RVNsi2<br>SEQ ID NO:529<br>56ala5<br>SEQ ID NO:371 | RVNsi3<br>SEQ ID NO:530<br>RVNsi6<br>SEQ ID NO:533 | |
| 56 pro | tyr | TAC | 56tyr1<br>SEQ ID NO:386<br>RVNsi4<br>SEQ ID NO:531 | RVNsi2<br>SEQ ID NO:529<br>56tyr5<br>SEQ ID NO:387 | RVNsi3<br>SEQ ID NO:530<br>RVNsi6<br>SEQ ID NO:533 | |
| 56 pro | phe | TTC | 56phe1<br>SEQ ID NO:382<br>RVNsi4<br>SEQ ID NO:531 | RVNsi2<br>SEQ ID NO:529<br>56phe5<br>SEQ ID NO:383 | RVNsi3<br>SEQ ID NO:530<br>RVNsi6<br>SEQ ID NO:533 | |
| 56 pro | leu | CTG | 56leu1<br>SEQ ID NO:380<br>RVNsi4<br>SEQ ID NO:531 | RVNsi2<br>SEQ ID NO:529<br>56leu5<br>SEQ ID NO:381 | RVNsi3<br>SEQ ID NO:530<br>RVNsi6<br>SEQ ID NO:533 | |
| 56 pro | val | GTT | 56val1<br>SEQ ID NO:388<br>RVNsi4<br>SEQ ID NO:531 | RVNsi2<br>SEQ ID NO:529<br>56val5<br>SEQ ID NO:389 | RVNsi3<br>SEQ ID NO:530<br>RVNsi6<br>SEQ ID NO:533 | |
| 82 leu | glu | GAA | NsiEco1<br>SEQ ID NO:534<br>NsiEco5<br>SEQ ID NO:540 | 82glu2<br>SEQ ID NO:394<br>82glu6<br>SEQ ID NO:395 | NsiEco3<br>SEQ ID NO:536<br>NsiEco7<br>SEQ ID NO:542 | NsiEco4<br>SEQ ID NO:539<br>NsiEco8<br>SEQ ID NO:545 |
| 82 leu | asn | AAC | NsiEco1<br>SEQ ID NO:534<br>NsiEco5<br>SEQ ID NO:540 | 82asn2<br>SEQ ID NO:392<br>82asn6<br>SEQ ID NO:393 | NsiEco3<br>SEQ ID NO:536<br>NsiEco7<br>SEQ ID NO:542 | NsiEco4<br>SEQ ID NO:539<br>NsiEco8<br>SEQ ID NO:545 |
| 82 leu | his | GAC | NsiEco1<br>SEQ ID NO:534<br>NsiEco5<br>SEQ ID NO:540 | 82his2<br>SEQ ID NO:396<br>82his6<br>SEQ ID NO:387 | NsiEco8<br>SEQ ID NO:536<br>NsiEco7<br>SEQ ID NO:542 | NsiEco4<br>SEQ ID NO:539<br>NsiEco8<br>SEQ ID NO:545 |
| 82 leu | thr | ACC | NsiEco1<br>SEQ ID NO:534<br>NsiEco5<br>SEQ ID NO:540 | 82thr2<br>SEQ ID NO:406<br>82thr6<br>SEQ ID NO:407 | NsiEco3<br>SEQ ID NO:536<br>NsiEco7<br>SEQ ID NO:542 | NsiEco4<br>SEQ ID NO:539<br>NsiEco8<br>SEQ ID NO:545 |
| 82 leu | ser | TCC | NsiEco1<br>SEQ ID NO:534 | 82ser2<br>SEQ ID NO:404 | NsiEco8<br>SEQ ID NO:536 | NsiEco4<br>SEQ ID NO:539 |

TABLE 8-continued

| | | | | | | | |
|---|---|---|---|---|---|---|---|
| | | | | NsiEco5 | 82ser6 | NsiEco7 | NsiEco8 |
| | | | | SEQ ID NO:540 | SEQ ID NO:405 | SEQ ID NO:542 | SEQ ID NO:545 |
| 82 leu | ala | GCT | | NsiEco1 | 82ala2 | NsiEco3 | NsiEco4 |
| | | | | SEQ ID NO:534 | SEQ ID NO:390 | SEQ ID NO:536 | SEQ ID NO:539 |
| | | | | NsiEco5 | 92ala6 | NsiEco7 | NsiEco8 |
| | | | | SEQ ID NO:540 | SEQ ID NO:391 | SEQ ID NO:542 | SEQ ID NO:545 |
| 92 leu | tyr | TAC | | NsiEco1 | 92tyr2 | NsiEco3 | NsiEco4 |
| | | | | SEQ ID NO:534 | SEQ ID NO:408 | SEQ ID NO:536 | SEQ ID NO:539 |
| | | | | NsiEco5 | 82tyr6 | NsiEco7 | NsiEco8 |
| | | | | SEQ ID NO:540 | SEQ ID NO:409 | SEQ ID NO:542 | SEQ ID NO:545 |
| 82 leu | phe | TTC | | NsiEco1 | 82phe2 | NsiEco3 | NsiEco4 |
| | | | | SEQ ID NO:534 | SEQ ID NO:402 | SEQ ID NO:536 | SEQ ID NO:539 |
| | | | | NsiEco5 | 82phe6 | NsiEco7 | NsiEco8 |
| | | | | SEQ ID NO:540 | SEQ ID NO:403 | SEQ ID NO:542 | SEQ ID NO:545 |
| 82 leu | ile | ATC | | NsiEco1 | 92ile2 | NsiEco3 | NsiEco4 |
| | | | | SEQ ID NO:534 | SEQ ID NO:338 | SEQ ID NO:539 | SEQ ID NO:539 |
| | | | | NsiEco5 | 92ile6 | NsiEco7 | NsiEco8 |
| | | | | SEQ ID NO:540 | SEQ ID NO:399 | SEQ ID NO:542 | SEQ ID NO:545 |
| 82 leu | met | ATG | | NsiEco1 | 92met2 | NsiEco3 | NsiEco4 |
| | | | | SEQ ID NO:534 | SEQ ID NO:400 | SEQ ID NO:536 | SEQ ID NO:539 |
| | | | | NsiEco5 | 82met6 | NsiEco7 | NsiEco8 |
| | | | | SEQ ID NO:540 | SEQ ID NO:401 | SEQ ID NO:542 | SEQ ID NO:545 |
| 92 pro | ala | GCT | | NsiEco1 | NsiEco2 | 92ala3A | NsiEco3B | NsiEco4 |
| | | | | SEQ ID NO:534 | SEQ ID NO:535 | SEQ ID NO:410 | SEQ ID NO:536 | SEQ ID NO:539 |
| | | | | NsiEco5 | NsiEco6 | NsiEco7A | 92ala7B | NsiEco8 |
| | | | | SEQ ID NO:540 | SEQ ID NO:541 | SEQ ID NO:543 | SEQ ID NO:411 | SEQ ID NO:545 |
| 92 pro | gly | GGT | | NsiEco1 | NsiEco2 | 92gly3A | NsiEco3B | NsiEco4 |
| | | | | SEQ ID NO:534 | SEQ ID NO:535 | SEQ ID NO:412 | SEQ ID NO:538 | SEQ ID NO:539 |
| | | | | NsiEco5 | NsiEco6 | NsiEco7A | 92ala7B | NsiEco8 |
| | | | | SEQ ID NO:540 | SEQ ID NO:541 | SEQ ID NO:543 | SEQ ID NO:415 | SEQ ID NO:545 |
| 92 pro | ile | ATC | | NsiEco1 | NsiEco2 | 92ile3A | NsiEco3B | NsiEco4 |
| | | | | SEQ ID NO:534 | SEQ ID NO:535 | SEQ ID NO:414 | SEQ ID NO:538 | SEQ ID NO:539 |
| | | | | NsiEco5 | NsiEco6 | NsiEco7A | 92ala7B | NsiEco8 |
| | | | | SEQ ID NO:540 | SEQ ID NO:541 | SEQ ID NO:543 | SEQ ID NO:415 | SEQ ID NO:545 |
| 94 arg | gln | CAG | | NsiEco1 | NsiEco2 | NsiEco3A | 94gln3B | NsiEco4 |
| | | | | SEQ ID NO:534 | SEQ ID NO:535 | SEQ ID NO:537 | SEQ ID NO:418 | SEQ ID NO:539 |
| | | | | NsiEco5 | NsiEco6 | NsiEco7A | 94gln7B | NsiEco8 |
| | | | | SEQ ID NO:540 | SEQ ID NO:541 | SEQ ID NO:543 | SEQ ID NO:419 | SEQ ID NO:545 |
| 94 arg | lys | AAA | | NsiEco1 | NsiEco2 | NsiEco3A | 94lys3B | NsiEco4 |
| | | | | SEQ ID NO:534 | SEQ ID NO:535 | SEQ ID NO:537 | SEQ ID NO:422 | SEQ ID NO:539 |
| | | | | NsiEco5 | NsiEco6 | NsiEco7A | 94lys7B | NsiEco8 |
| | | | | SEQ ID NO:540 | SEQ ID NO:541 | SEQ ID NO:543 | SEQ ID NO:423 | SEQ ID NO:545 |
| 94 arg | his | CAC | | NsiEco1 | NsiEco2 | NsiEco3A | 94his3B | NsiEco4 |
| | | | | SEQ ID NO:534 | SEQ ID NO:535 | SEQ ID NO:537 | SEQ ID NO:420 | SEQ ID NO:539 |
| | | | | NsiEco5 | NsiEco6 | NsiEco7A | 94his7B | NsiEco8 |
| | | | | SEQ ID NO:540 | SEQ ID NO:536 | SEQ ID NO:443 | SEQ ID NO:421 | SEQ ID NO:545 |
| 94 arg | ala | GCT | | NsiEco1 | NsiEco2 | NsiEo3A | 94ala3B | NsiEco4 |
| | | | | SEQ ID NO:534 | SEQ ID NO:535 | SEQ ID NO:537 | SEQ ID NO:416 | SEQ ID NO:539 |
| | | | | NsiEco5 | NsiEco6 | NsiEco7A | 94ala7B | NsiEco8 |
| | | | | SEQ ID NO:540 | SEQ ID NO:541 | SEQ ID NO:543 | SEQ ID NO:417 | SEQ ID NO:545 |
| 95 his | asn | AAC | | NsiEco1 | NsiEco2 | NsiEco3A | 95asn3B | NsiEco4 |
| | | | | SEQ ID NO:534 | SEQ ID NO:535 | SEQ ID NO:537 | SEQ ID NO:426 | SEQ ID NO:539 |
| | | | | NsiEco5 | NsIEco6 | NsiEco7A | 95asn7B | NsiEco8 |
| | | | | SEQ ID NO:540 | SEQ ID NO:541 | SEQ ID NO:543 | SEQ ID NO:427 | SEQ ID NO:545 |
| 95 his | lys | AAA | | NsiEco1 | NsiEco2 | NsiEco3A | 95lys3B | NsiEco4 |
| | | | | SEQ ID NO:534 | SEQ ID NO:535 | SEQ ID NO:537 | SEQ ID NO:432 | SEQ ID NO:539 |
| | | | | NsiEco5 | NsiEco6 | NsiEco7A | 95lys7B | NsiEco8 |
| | | | | SEQ ID NO:540 | SEQ ID NO:541 | SEQ ID NO:543 | SEQ ID NO:433 | SEQ ID NO:545 |
| 95 his | ser | TCC | | NsiEco1 | NsiEco2 | NsiEco3A | 95ser3B | NsiEco4 |
| | | | | SEQ ID NO:534 | SEQ ID NO:535 | SEQ ID NO:537 | SEQ ID NO:438 | SEQ ID NO:539 |
| | | | | NsiEco5 | NsiEc06 | NsiEco7A | 95ser7B | NsiEco8 |
| | | | | SEQ ID NO:540 | SEQ ID NO:541 | SEQ ID NO:543 | SEQ ID NO:439 | SEQ ID NO:545 |
| 95 his | ala | GCT | | NsiEco1 | NsiEco2 | NsiEco3A | 95ala3B | NsiEco4 |
| | | | | SEQ ID NO:534 | SEQ ID NO:535 | SEQ ID NO:537 | SEQ ID NO:424 | SEQ ID NO:539 |
| | | | | NsiEco5 | NsiEco6 | NsiEco7A | 95ala7B | NsiEco8 |
| | | | | SEQ ID NO:540 | SEQ ID NO:541 | SEQ ID NO:543 | SEQ ID NO:425 | SEQ ID NO:545 |
| 95 his | trp | TGG | | NsiEco1 | NsiEco2 | NsiEco3A | 95trp3B | NsiEco4 |
| | | | | SEQ ID NO:534 | SEQ ID NO:535 | SEQ ID NO:537 | SEQ ID NO:440 | SEQ ID NO:539 |
| | | | | NsiEco5 | NsiEco6 | NsiEco7A | 95trp7B | NsiEco8 |
| | | | | SEQ ID NO:540 | SEQ ID NO:541 | SEQ ID NO:543 | SEQ ID NO:441 | SEQ ID NO:545 |
| 95 his | phe | TTC | | NsiEco1 | NsiEco2 | NsiEco3A | 95phe3B | NsiEco4 |
| | | | | SEQ ID NO:534 | SEQ ID NO:555 | SEQ ID NO:537 | SEQ ID NO:11 | SEQ ID NO:539 |
| | | | | NsiEco5 | NsiEco6 | NsiEco7A | 95phe7B | NsiEco8 |
| | | | | SEQ ID NO:540 | SEQ ID NO:541 | SEQ ID NO:543 | SEQ ID NO:437 | SEQ ID NO:545 |
| 95 his | ile | ATC | | NsiEco1 | NsiEco2 | NsiEco3A | 96ile3B | NsiEco4 |
| | | | | SEQ ID NO:534 | SEQ ID NO:535 | SEQ ID NO:537 | SEQ ID NO:430 | SEQ ID NO:539 |
| | | | | NsiEco5 | NsiEco6 | NsiEco7A | 98ile7B | NsiEco8 |
| | | | | SEQ ID NO:540 | SEQ ID NO:541 | SEQ ID NO:543 | SEQ ID NO:431 | SEQ ID NO:545 |
| 98 his | glu | GAA | | NsiEco1 | NsiEco2 | NsiEco3A | 98glu3B | NsiEco4 |

TABLE 8-continued

| | | | | | | | |
|---|---|---|---|---|---|---|---|
| | | | | SEQ ID NO:534 | SEQ ID NO:535 | SEQ ID NO:537 | SEQ ID NO:446 | SEQ ID NO:539 |
| | | | | NsiEco5 | NsiEco6 | NsiEco7A | 98glu7B | NsiEco8 |
| | | | | SEQ ID NO:540 | SEQ ID NO:541 | SEQ ID NO:543 | SEQ ID NO:447 | SEQ ID NO:545 |
| 98 his | gln | CAA | NsiEco1 | NsEco2 | NsiECo3A | 98gln3B | NsiEco4 |
| | | | SEQ ID NO:534 | SEQ ID NO:535 | SEQ ID NO:537 | SEQ ID NO:444 | SEQ ID NO:539 |
| | | | NsiEco5 | NsiEco6 | NsiEco7A | 98gln7B | NsiEco8 |
| | | | SEQ ID NO:540 | SEQ ID NO:541 | SEQ ID NO:543 | SEQ ID NO:445 | SEQ ID NO:545 |
| 98 his | ser | TCC | NsiEco1 | NsiEco2 | NsiEco3A | 98ser3B | NsiEcor |
| | | | SEQ ID NO:534 | SEQ ID NO:535 | SEQ ID NO:537 | SEQ ID NO:452 | SEQ ID NO:539 |
| | | | NsiEco5 | NsiEco6 | NsiEco7A | 98ser7B | NsiEco8 |
| | | | SEQ ID NO:540 | SEQ ID NO:541 | SEQ ID NO:543 | SEQ ID NO:453 | SEQ ID NO:545 |
| 98 his | phe | TTC | NsiEco1 | NsiEco2 | NsiEco3A | 98phe3B | NsiEco4 |
| | | | SEQ ID NO:534 | SEQ ID NO:535 | SEQ ID NO:537 | SEQ ID NO:450 | SEQ ID NO:539 |
| | | | NsiEco5 | NsiEco6 | NsiEco7A | 98phe7B | NsiEco8 |
| | | | SEQ ID NO:540 | SEQ ID NO:541 | SEQ ID NO:543 | SEQ ID NO:451 | SEQ ID NO:545 |
| 98 his | met | ATG | NsiEco1 | NsiEco2 | NsiEco3A | 98met3B | NsiEco4 |
| | | | SEQ ID NO:534 | SEQ ID NO:535 | SEQ ID NO:537 | SEQ ID NO:448 | SEQ ID NO:539 |
| | | | NsiEco5 | NsiEco6 | NsiEco7A | 98met7B | NsiEco8 |
| | | | SEQ ID NO:540 | SEQ ID NO:541 | SEQ ID NO:543 | SEQ ID NO:449 | SEQ ID NO:545 |
| 98 his | val | GTA | NsiEco1 | NsiEco2 | NsiEco3A | 98val3B | NsiEco4 |
| | | | SEQ ID NO:534 | SEQ ID NO:535 | SEQ ID NO:537 | SEQ ID NO:454 | SEQ ID NO:539 |
| | | | NsiEco5 | NsiEco6 | NsiEco7A | 98val7B | NsiEco8 |
| | | | SEQ ID NO:540 | SEQ ID NO:541 | SEQ ID NO:543 | SEQ ID NO:455 | SEQ ID NO:545 |
| 98 Ns | lys | AAA | NsiEco1 | NsiEco2 | NsiEco3A | 98lys3B | NsiEco4 |
| | | | SEQ ID NO:534 | SEQ ID NO:535 | SEQ ID NO:537 | SEQ ID NO:458 | SEQ ID NO:539 |
| | | | NsiEco5 | NsiEco6 | NsiEco7A | 98lys7B | NsiEc08 |
| | | | SEQ ID NO:540 | SEQ ID NO:541 | SEQ ID NO:543 | SEQ ID NO:459 | SEQ ID NO:545 |
| 98 his | arg | CGT | NsiEco1 | NsiEco2 | NsiEco3A | 98arg3B | NsiEco4 |
| | | | SEQ ID NO:534 | SEQ ID NO:535 | SEQ ID NO:537 | SEQ ID NO:456 | SEQ ID NO:539 |
| | | | NsiEco5 | NsiEco6 | NsiEco7A | 98arg76 | NsiEco8 |
| | | | SEQ ID NO:540 | SEQ ID NO:541 | SEQ ID NO:543 | SEQ ID NO:457 | SEQ ID NO:545 |
| 98 his | tyr | TAC | NsiEco1 | NsiEco2 | NsiEco3A | 98tyr3B | NsiEco4 |
| | | | SEQ ID NO:534 | SEQ ID NO:535 | SEQ ID NO:537 | SEQ ID NO:60 | SEQ ID NO:539 |
| | | | NsiEco5 | NsiEco6 | NsiEco7A | 98tyr7B | NsiEco8 |
| | | | SEQ ID NO:540 | SEQ ID NO:541 | SEQ ID NO:543 | SEQ ID NO:461 | SEQ ID NO:545 |
| 101 asp | glu | GAA | NsiEco1 | NsiEco2 | NsiEco3 | 101glu4 | |
| | | | SEQ ID NO:534 | SEQ ID NO:535 | SEQ ID NO:535 | SEQ ID NO:466 | |
| | | | NsiEco5 | NsiEco6 | NsiEco7 | 101glu8 | |
| | | | SEQ ID NO:540 | SEQ ID NO:541 | SEQ ID NO:542 | SEQ ID NO:467 | |
| 101 asp | asn | AAC | NsiEco1 | NsiEco2 | NsiEco3 | 101asn4 | |
| | | | SEQ ID NO:534 | SEQ ID NO:535 | SEQ ID NO:538 | SEQ ID NO:464 | |
| | | | NsiEco5 | NsiEco6 | NsiEco7 | 101asn8 | |
| | | | SEQ ID NO:540 | SEQ ID NO:541 | SEQ ID NO:542 | SEQ ID NO:465 | |
| 101 asp | ser | TCC | NsiEco1 | NsiEco2 | NsiEco3 | 101ser4 | |
| | | | SEQ ID NO:534 | SEQ ID NO:535 | SEQ ID NO:536 | SEQ ID NO:476 | |
| | | | NsiEco5 | NsiEc06 | NsiEco7 | 101ser8 | |
| | | | SEQ ID NO:540 | SEQ ID NO:541 | SEQ ID NO:542 | SEQ ID NO:477 | |
| 101 asp | ala | GCT | NsiEco1 | NsiEco2 | NsiEco3 | 101ala4 | |
| | | | SEQ ID NO:534 | SEQ ID NO:535 | SEQ ID NO:538 | SEQ ID NO:462 | |
| | | | NsiEco5 | NsiEco6 | NsiEco7 | 101ala8 | |
| | | | SEQ ID NO:540 | SEQ ID NO:541 | SEQ ID NO:542 | SEQ ID NO:463 | |
| 101 asp | gly | GGT | NsiEco1 | NsiEco2 | NsiEco3 | 101gly4 | |
| | | | SEQ ID NO:534 | SEQ ID NO:535 | SEQ ID NO:536 | SEQ ID NO:468 | |
| | | | NsiEco5 | NsiEco6 | NsiEco7 | 101gly8 | |
| | | | SEQ ID NO:540 | SEQ ID NO:541 | SEQ ID NO:542 | SEQ ID NO:469 | |
| 101 asp | ile | ATC | NsiEco1 | NsiEco2 | NsiEco3 | 101ile4 | |
| | | | SEQ ID NO:534 | SEQ ID NO:535 | SEQ ID NO:536 | SEQ ID NO:470 | |
| | | | NsiEco5 | NsIEco6 | NsiEco7 | 101ile8 | |
| | | | SEQ ID NO:540 | SEQ ID NO:541 | SEQ ID NO:542 | SEQ ID NO:471 | |
| 101 asp | leu | CTG | NsiEco1 | NsiEco2 | NsiEco3 | 101leu4 | |
| | | | SEQ ID NO:534 | SEQ ID NO:535 | SEQ ID NO:536 | SEQ ID NO:472 | |
| | | | NsiEco5 | NsiEco6 | NsiEco7 | 101leu8 | |
| | | | SEQ ID NO:540 | SEQ ID NO:541 | SEQ ID NO:542 | SEQ ID NO:473 | |
| 108 arg | gln | CAG | 108gln1 | EcoHin2 | | | |
| | | | SEQ ID NO:480 | SEQ ID NO:547 | | | |
| | | | 108gln3 | EcoHin4 | | | |
| | | | SEQ ID NO:481 | SEQ ID NO:549 | | | |
| 108 arg | his | CAC | 108his1 | EcoHin2 | | | |
| | | | SEQ ID NO:482 | SEQ ID NO:547 | | | |
| | | | 108his3 | EcoHin4 | | | |
| | | | SEQ ID NO:483 | SEQ ID NO:549 | | | |
| 108 arg | ser | TCC | 108ser1 | EcoHin2 | | | |
| | | | SEQ ID NO:484 | SEQ ID NO:547 | | | |
| | | | 108ser3 | EcoHin4 | | | |
| | | | SEQ ID NO:485 | SEQ ID NO:549 | | | |
| 108 arg | ala | GCT | 108ala1 | EcoHin2 | | | |
| | | | SEQ ID NO:478 | SEQ ID NO:547 | | | |
| | | | 108ala3 | EcoHin4 | | | |
| | | | SEQ ID NO:479 | SEQ ID NO:549 | | | |

TABLE 8-continued

| | | | | |
|---|---|---|---|---|
| 110 lys | arg | CGT | 110arg1<br>SEQ ID NO:486<br>110arg3<br>SEQ ID NO:487 | EcoHin2<br>SEQ ID NO:547<br>EcoHin4<br>SEQ ID NO:549 |
| 110 lys | his | CAC | 110his1<br>SEQ ID NO:490<br>110his3<br>SEQ ID NO:491 | EcoHin2<br>SEQ ID NO:547<br>EcoHin4<br>SEQ ID NO:549 |
| 110 lys | glu | GAA | 110glu1<br>SEQ ID NO:488<br>110glu3<br>SEQ ID NO:489 | EcoHin2<br>SEQ lD NO:547<br>EcoHin4<br>SEQ ID NO:549 |
| 110 lys | ser | TCC | 110ser1<br>SEQ ID NO:494<br>110ser3<br>SEQ ID NO:495 | EcoHin2<br>SEQ ID NO:547<br>EcoHin4<br>SEQ ID NO:549 |
| 110 lys | ala | GCT | 110ala1<br>SEQ ID NO:492<br>110ala3<br>SEQ ID NO:493 | EcoHin2<br>SEQ ID NO:547<br>EcoHin4<br>SEQ ID NO:549 |
| 113 phe | asp | GAC | 113asp1<br>SEQ ID NO:495<br>113asp3<br>SEQ ID NO:497 | EcoHin2<br>SEQ ID NO:547<br>EcoHin4<br>SEQ ID NO:549 |
| 113 phe | lys | AAA | 113lys1<br>SEQ ID NO:502<br>113lys3<br>SEQ ID NO:503 | EcoHin2<br>SEQ lD NO:547<br>EcoHin4<br>SEQ ID NO:549 |
| 113 phe | leu | CTG | 113leu1<br>SEQ ID NO:500<br>113leu3<br>SEQ ID NO:501 | EcoHin2<br>SEQ ID NO:547<br>EcoHin4<br>SEQ ID NO:549 |
| 113 phe | ile | ATC | 113ile1<br>SEQ ID NO:499<br>113ile3<br>SEQ ID NO:499 | EcoHin2<br>SEQ ID NO:547<br>EcoHin4<br>SEQ ID NO:549 |
| 113 phe | val | GTT | 113val1<br>SEQ ID NO:504<br>113val3<br>SEQ ID NO:505 | EcoHin2<br>SEQ ID NO:547<br>EcoHin4<br>SEQ ID NO:549 |
| 116 lys | asn | AAC | 116asn1<br>SEQ ID NO:510<br>116asn3<br>SEQ ID NO:511 | EcoHin2<br>SEQ lD NO:547<br>EcoHin4<br>SEQ ID NO:549 |
| 116 lys | arg | CGT | 116ara1<br>SEQ ID NO:509<br>116arg3<br>SEQ ID NO:509 | EcoHin2<br>SEQ ID NO:547<br>EcoHin4<br>SEQ ID NO:549 |
| 116 lys | his | CAC | 116his1<br>SEQ ID NO:514<br>116his3<br>SEQ ID NO:515 | EcoHin2<br>SEQ ID NO:547<br>EcoHin4<br>SEQ ID NO:549 |
| 116 lys | ala | GCT | 116ala1<br>SEQ ID NO:506<br>116ala3<br>SEQ ID NO:507 | EcoHin2<br>SEQ ID NO:547<br>EcoHin4<br>SEQ ID NO:549 |
| 116 lys | tyr | TAC | 116tyr1<br>SEQ ID NO:520<br>116tyr3<br>SEQ ID NO:521 | EcoHin2<br>SEQ ID NO:547<br>EcoHin4<br>SEQ ID NO:549 |
| 116 lys | phe | TTC | 116phe1<br>SEQ ID NO:518<br>116phe3<br>SEQ ID NO:519 | EcoHin2<br>SEQ ID NO:547<br>EcoHin4<br>SEQ ID NO:549 |
| 116 lys | gln | CAG | 116gln1<br>SEQ ID NO:512<br>116gln3<br>SEQ ID NO:513 | EcoHin2<br>SEQ ID NO:547<br>EcoHin4<br>SEQ ID NO:549 |
| 116 lys | met | ATG | 116met1<br>SEQ ID NO:516<br>116met3<br>SEQ ID NO:517 | EcoHin2<br>SEQ ID NO:547<br>EcoHin4<br>SEQ ID NO:549 |

| position/native a.a. | substitution | codon | parental plasmid | restriction digest |
|---|---|---|---|---|
| 21 asp | glu | GAA | pMON13356 | NcoI, EcoRV |
| 21 asp | gln | CAA | pMON13356 | NcoI, EcoRV |
| 21 asp | asn | AAC | pMON13356 | NcoI, EcoRV |
| 21 asp | thr | ACC | pMON13356 | NcoI, EcoRV |

TABLE 8-continued

| | | | | |
|---|---|---|---|---|
| 21 asp | ser | AGC | pMON13356 | NcoI, EcoRV |
| 22 glu | asp | GAC | pMON13356 | NcoI, EcoRV |
| 22 glu | asn | AAC | pMON13356 | NcoI, EcoRV |
| 22 glu | gln | CAG | pMON13356 | NcoI, EcoRV |
| 22 glu | leu | CTG | pMON13356 | NcoI, EcoRV |
| 22 glu | val | GTT | pMON13356 | NcoI, EcoRV |
| 34 leu | glu | GAA | pMON13356 | NcoI, EcoRV |
| 34 leu | gln | CAG | pMON13356 | NcoI, EcoRV |
| 34 leu | thr | ACC | pMON13356 | NcoI, EcoRV |
| 34 leu | arg | CGT | pMON13356 | NcoI, EcoRV |
| 34 leu | ala | GCT | pMON13356 | NcoI, EcoRV |
| 34 leu | phe | TTC | pMON13356 | NcoI, EcoRV |
| 34 leu | ile | ATC | pMON13356 | NcoI, EcoRV |
| 42 gly | asn | AAC | pMON13356 | NcoI, EcoRV |
| 42 gly | thr | ACC | pMON13356 | NcoI, EcoRV |
| 42 gly | leu | CTG | pMON13356 | NcoI, EcoRV |
| 42 gly | val | GTT | pMON13356 | NcoI, EcoRV |
| 42 gly | glu | GAA | pMON13356 | NcoI, EcoRV |
| 42 gly | phe | TTC | pMON13356 | NcoI, EcoRV |
| 42 gly | tyr | TAC | pMON13356 | NcoI, EcoRV |
| 42 gly | ile | ATC | pMON13356 | NcoI, EcoRV |
| 42 gly | met | ATG | pMON13356 | NcoI, EcoRV |
| 43 glu | gln | CAG | pMON13356 | NcoI, EcoRV |
| 43 glu | arg | CGT | pMON13356 | NcoI, EcoRV |
| 43 glu | thr | ACC | pMON13356 | NcoI, EcoRV |
| 43 glu | gly | GGT | pMON13356 | NcoI, EcoRV |
| 44 asp | glu | GAA | pMON13356 | NcoI, EcoRV |
| 44 asp | asn | AAC | pMON13356 | NcoI, EcoRV |
| 44 asp | gln | CAG | pMON13356 | NcoI, EcoRV |
| 44 asp | ala | GCT | pMON13356 | NcoI, EcoRV |
| 45 gln | asp | GAC | pMON13356 | NcoI, EcoRV |
| 45 gln | asn | AAC | pMON13356 | NcoI, EcoRV |
| 45 gln | arg | CGT | pMON13356 | NcoI, EcoRV |
| 45 gln | ser | TCC | pMON13356 | NcoI, EcoRV |
| 45 gln | ala | GCT | pMON13356 | NcoI, EcoRV |
| 45 gln | ile | ATC | pMON13356 | NcoI, EcoRV |
| 45 gln | glu | GAA | pMON13356 | NcoI, EcoRV |
| 45 gln | his | CAC | pMON13356 | NcoI, EcoRV |
| 46 asp | glu | GAA | pMON13356 | NcoI, EcoRV |
| 46 asp | asn | AAC | pMON13356 | NcoI, EcoRV |
| 46 asp | gln | CAG | pMON13356 | NcoI, EcoRV |
| 46 asp | lys | AAA | pMON13356 | NcoI, EcoRV |
| 46 asp | his | CAC | pMON13356 | NcoI, EcoRV |
| 46 asp | ala | GCT | pMON13356 | NcoI, EcoRV |
| 46 asp | tyr | TAC | pMON13356 | NcoI, EcoRV |
| 46 asp | ile | ATC | pMON13356 | NcoI, EcoRV |
| 46 asp | val | GTT | pMON13356 | NcoI, EcoRV |
| 48 leu | glu | GAA | pMON13357 | EcoRV, NcoI |
| 48 leu | lys | AAA | pMON13357 | EcoRV, NcoI |
| 48 leu | thr | ACC | pMON13357 | EcoRV, NcoI |
| 48 leu | ala | GCT | pMON13357 | EcoRV, NcoI |
| 48 leu | met | ATG | pMON13357 | EcoRV, NcoI |
| 48 leu | val | CAC | pMON13357 | EcoRV, NcoI |
| 50 glu | lys | AAA | pMON13357 | EcoRV, NcoI |
| 50 glu | asn | AAC | pMON13357 | EcoRV, NcoI |
| 50 glu | ser | TCC | pMON13357 | EcoRV, NcoI |
| 50 glu | ala | GCT | pMON13357 | EcoRV, NcoI |
| 50 glu | ile | ATC | pMON13357 | EcoRV, NcoI |
| 50 glu | val | GTT | pMON13357 | EcoRV, NcoI |
| 50 glu | his | CAC | pMON13357 | EcoRV, NcoI |
| 50 glu | phe | TTC | pMON13357 | EcoRV, NcoI |
| 50 glu | met | ATG | pMON13357 | EcoRV, NcoI |
| 54 arg | asn | AAC | pMON13357 | EcoRV, NcoI |
| 54 arg | lys | AAA | pMON13357 | EcoRV, NcoI |
| 54 arg | his | CAC | pMON13357 | EcoRV, NcoI |
| 54 arg | ala | GCT | pMON13357 | EcoRV, NcoI |
| 56 pro | glu | GAA | pMON13357 | EcoRV, NcoI |
| 56 pro | gln | | pMON13357 | EcoRV, NcoI |
| 56 pro | arg | CGT | pMON13357 | EcoRV, NcoI |
| 56 pro | his | CAC | pMON13357 | EcoRV, NcoI |
| 56 pro | thr | ACC | pMON13357 | EcoRV, NcoI |
| 56 pro | ala | GCT | pMON13357 | EcoRV, NcoI |
| 56 pro | tyr | TAC | pMON13357 | EcoRV, NcoI |
| 56 pro | phe | TTC | pMON13357 | EcoRV, NcoI |
| 56 pro | leu | CTG | pMON13357 | EcoRV, NcoI |
| 56 pro | val | GTT | pMON13357 | EcoRV, NcoI |
| 82 leu | glu | GAA | pMON13358 | NsiI, EcoRI |
| 82 leu | asn | AAC | pMON13358 | NsiI, EcoRI |
| 82 leu | his | CAC | pMON13358 | NsiI, EcoRI |

TABLE 8-continued

| | | | | |
|---|---|---|---|---|
| 82 leu | thr | ACC | pMON13358 | NsiI, EcoRI |
| 82 leu | ser | TCC | pMON13358 | NsiI, EcoRI |
| 82 leu | ala | GCT | pMON13358 | NsiI, EcoRI |
| 82 leu | tyr | TAC | pMON13358 | NsiI, EcoRI |
| 82 leu | phe | TTC | pMON13358 | NsiI, EcoRI |
| 82 leu | ile | ATC | pMON13358 | NsiI, EcoRI |
| 82 leu | met | ATG | pMON13358 | NsiI, EcoRI |
| 92 pro | ala | GCT | pMON13358 | NsiI, EcoRI |
| 92 pro | gly | GGT | pMON13358 | NsiI, EcoRI |
| 92 pro | ile | ATC | pMON13358 | NsiI, EcoRI |
| 94 arg | gln | CAG | pMON13358 | NsiI, EcoRI |
| 94 arg | lys | AAA | pMON13358 | NsiI, EcoRI |
| 94 arg | his | CAC | pMON13358 | NsiI, EcoRI |
| 94 arg | ala | GCT | pMON13358 | NsiI, EcoRI |
| 95 his | asn | AAC | pMON13358 | NsiI, EcoRI |
| 95 his | lys | AAA | pMON13358 | NsiI, EcoRI |
| 95 his | ser | TCC | pMON13358 | NsiI, EcoRI |
| 95 his | ala | GCT | pMON13358 | NsiI, EcoRI |
| 95 his | trp | TGG | pMON13358 | NsiI, EcoRI |
| 95 his | phe | TTC | pMON13358 | NsiI, EcoRI |
| 95 his | ile | ATC | pMON13358 | NsiI, EcoRI |
| 98 his | glu | GAA | pMON13358 | NsiI, EcoRI |
| 98 his | gln | CAA | pMON13358 | NsiI, EcoRI |
| 98 his | ser | TCC | pMON13358 | NsiI, EcoRI |
| 98 his | phe | TTC | pMON13358 | NsiI, EcoRI |
| 98 his | met | ATG | pMON13358 | NsiI, EcoRI |
| 98 his | val | GTA | pMON13358 | NsiI, EcoRI |
| 98 his | lys | AAA | pMON13358 | NsiI, EcoRI |
| 98 his | arg | CGT | pMON13358 | NsiI, EcoRI |
| 98 his | tyr | TAC | pMON13358 | NsiI, EcoRI |
| 101 asp | glu | GAA | pMON13358 | NsiI, EcoRI |
| 101 asp | asn | AAC | pMON13358 | NsiI, EcoRI |
| 101 asp | ser | TCC | pMON13358 | NsiI, EcoRI |
| 101 asp | ala | GCT | pMON13358 | NsiI, EcoRI |
| 101 asp | gly | GGT | pMON13358 | NsiI, EcoRI |
| 101 asp | ile | ATC | pMON13358 | NsiI, EcoRI |
| 101 asp | leu | CTG | pMON13358 | NsiI, EcoRI |
| 108 arg | gln | CAG | pMON13359 | EcoRI, HinDIII |
| 108 arg | his | CAC | pMON13359 | EcoRI, HinDIII |
| 108 arg | ser | TCC | pMON13359 | EcoRI, HinDIII |
| 108 arg | ala | GCT | pMON13359 | EcoRI, HinDIII |
| 110 lys | arg | CGT | pMON13359 | EcoRI, HinDIII |
| 110 lys | his | CAC | pMON13359 | EcoRI, HinDIII |
| 110 lys | glu | GAA | pMON13359 | EcoRI, HinDIII |
| 110 lys | ser | TCC | pMON13359 | EcoRI, HinDIII |
| 110 lys | ala | GCT | pMON13359 | EcoRI, HinDIII |
| 113 phe | asp | GAC | pMON13359 | EcoRI, HinDIII |
| 113 phe | lys | AAA | pMON13359 | EcoRI, HinDIII |
| 113 phe | leu | CTG | pMON13359 | EcoRI, HinDIII |
| 113 phe | leu | CTG | pMON13359 | EcoRI, HinDIII |
| 113 phe | ile | ATC | pMON13359 | EcoRI, HinDIII |
| 113 phe | Val | GTT | pMON13359 | EcoRI, HinDIII |
| 116 lys | asn | AAC | pMON13359 | EcoRI, HinDIII |
| 116 lys | arg | CGT | pMON13359 | EcoRI, HinDIII |
| 116 lys | his | CAC | pMON13359 | EcoRI, HinDIII |
| 116 lys | ala | GCT | pMON13359 | EcoRI, HinDIII |
| 116 lys | tyr | TAC | pMON13359 | EcoRI, HinDIII |
| 116 lys | phe | TTC | pMON13359 | EcoRI, HinDIII |
| 116 lys | gln | CAG | pMON13359 | EcoRI, HinDIII |
| 116 lys | met | ATG | pMON13359 | EcoRI, HinDIII |

It will be apparent to those skilled in the art that other codons besides those shown in Table 8 can also code for the substituted amino acids in the hIL-3 muteins. The present invention includes the DNAs encoding the mutant hIL-3 polypeptides in the invention including the various codons which can code for the parental and substituted amino acids of the hIL-3 muteins of the invention due to the degeneracy of the genetic code.

hIL-3 (15–125) variant genes encoding the variants listed in Table 8 can also be expressed from intracellular expression vectors to produce large quantities of the variant protein which can be purified and assayed for biological activity. The hIL-3 variant genes, from Table 8, can be excised from the secretion expression vector, as a 345 base pair NcoI/HindIII fragment and ligated into an appropriate intrecellular expression vector, such as pMON2341 digested with NcoI and HindIII.

Table 9 shows the biological activity of (15–125) hIL-3 muteins of the present invention which have one amino acid substitutions in the (15–125) hIL-3 polypeptide and which were constructed as described in Example 66. The mutants in Table 9 were secreted into the periplasmic space in E. coli. The periplasmic content was released by osmotic shock and the material in the crude osmotic shock fraction was screened for growth promoting activity. Biological activity is the growth promoting activity of AML cells relative to (15–125) hIL-3 (pMON6458 or pMMON5988). The relative biological activity of IL-3 mutants is calculated by dividing the $EC_{50}$ (1–133) hIL-3 by the $EC_{50}$ of the mutant. The numbers in parentheses indicate the number of repeat assays. When a variant was assayed more than once the standard deviation is indicated. An "*" indicates that the hIL3 variant protein level was less than 1.0 μg/ml and was not screened for growth promoting activity.

TABLE 9

| | PARENTAL | | (15–125) hIL-3 MUTANT | | | BIOL |
|---|---|---|---|---|---|---|
| aa position | AA | codon | AA | SEQ ID NO: | codon | ACTIVITY |
| 21/7 | ASP | GAT | ASN | 19 | AAC | 0.01 |
| 21/7 | ASP | GAT | GLN | 19 | CAA | 0.07 |
| 21/7 | ASP | GAT | GLU | 19 | GAA | 0.5 |
| 21/7 | ASP | GAT | SER | 19 | AGC | 0.1 |
| 21/7 | ASP | GAT | THR | 19 | ACC | 0.1 |
| 22/8 | GLU | GAA | ASN | 19 | AAC | * |
| 22/8 | GLU | GAA | ASP | 19 | GAC | * |
| 22/8 | GLU | GAA | GLN | 19 | CAG | <0.01 |
| 22/8 | GLU | GAA | LEU | 19 | CTG | * |
| 22/8 | GLU | GAA | VAL | 19 | GTT | * |
| 34/20 | LEU | TTG | ALA | 19 | GLT | 2.2 |
| 34/20 | LEU | TTG | ARG | 19 | CGT | 2.2 |
| 34/20 | LEU | TTG | GLN | 19 | CAG | 1.1 |
| 34/20 | LEU | TTG | GLU | 19 | GAA | 1.5 |
| 34/20 | LEU | TTG | ILE | 19 | ATC | 1.3 |
| 34/20 | LEU | TTG | PHE | 19 | TTC | 1.8 |
| 34/20 | LEU | TTG | ILE | 19 | ACC | 1.1 |
| 42/28 | GLY | GGG | ASN | 19 | AAC | 1.3 (3) 0.28 |
| 42/28 | GLY | GGG | ILE | 19 | ATC | 10 |
| 42/28 | GLY | GGG | LEU | 19 | CTG | 10.1 (3) 7.57 |
| 42/28 | GLY | GGG | MET | 19 | ATG | 2.2 (3) 1.14 |
| 42/28 | GLY | GGG | THR | 19 | TAC | 11 (2) 8.9 |
| 42/28 | GLY | GGG | VAL | 19 | GTT | 0.33 |
| 43/29 | GLU | GAA | AAG | 19 | CGT | * |
| 43/29 | GLU | GAA | GLN | 19 | CAG | <0.004 |
| 43/29 | GLU | GAA | GLY | 19 | GGT | * |
| 43/29 | GLU | GAA | ILE | 19 | ACC | 0.005 |
| 44/30 | ASP | GAC | ALA | 19 | GCT | * |
| 44/30 | ASP | GAC | ASN | 19 | AAC | * |
| 44/30 | ASP | GAC | GLN | 19 | CAG | * |
| 44/30 | ASP | GAC | GLU | 19 | GAA | 0.66 |
| 45/31 | GLN | CAA | ALA | 19 | GCT | 1 |
| 45/31 | GLN | CAA | ASN | 19 | AAC | 15.8 |
| 45/31 | GLN | CAA | GLU | 19 | GAA | 2.3 |
| 45/31 | GLN | CAA | ILE | 19 | ATC | 4.9 |
| 45/31 | GLN | CAA | SER | 19 | TCC | 0.7 |
| 46/32 | ASP | GAC | ALA | 19 | GCT | 6.3 |
| 46/32 | ASP | GAC | ASN | 19 | AAC | 0.66, 1.1 |
| 46/32 | ASP | GAC | GLN | 19 | CAG | 6.3 |
| 46/32 | ASP | GAC | GLU | 19 | GAA | 1.97 (3) 2.14 |
| 46/32 | ASP | GAC | HIS | 19 | CAC | 3.2, 1.4 |
| 46/32 | ASP | GAC | ILE | 19 | ATC | 0.5 |
| 46/32 | ASP | GAC | LYS | 19 | AAA | 0.5 |
| 46/32 | ASP | GAC | TYR | 19 | TAC | 0.66 |
| 46/32 | ASP | GAC | VAL | 19 | GTT | 6.3 |
| 48/34 | LEU | CTG | GLU | 19 | GAA | * |
| 48/34 | LEU | CTG | HIS | 19 | | * |
| 48/34 | LEU | CTG | LYS | 19 | AAA | * |
| 48/34 | LEU | CTG | THR | 19 | ACC | * |
| 48/34 | LEU | CTG | VAL | 19 | CAC | * |
| 50/36 | GLU | GAA | ALA | 19 | GCT | 0.5 |
| 50/36 | GLU | GAA | ASN | 19 | AAC | 1.7 |
| 50/36 | GLU | GAA | HIS | 19 | CAC | * |
| 50/36 | GLU | GAA | LYS | 19 | AAA | * |
| 50/36 | GLU | GAA | TYR | 19 | TAC | 1.3 |
| 50/36 | GLU | GAA | VAL | 19 | GTT | * |
| 54/40 | ARG | CGA | ALA | 19 | GCT | 0.9 |
| 54/40 | ARG | CGA | ASN | 19 | AAC | * |
| 54/40 | ARG | CGA | HIS | 19 | CAC | 0.01 |
| 54/40 | ARG | CGA | LYS | 19 | AAA | 0.2 |
| 56/42 | PRO | CAA | ALA | 19 | GCT | 1.8 |
| 56/42 | PRO | CAA | ASN | 19 | | 0.6 |
| 56/42 | PRO | CAA | ARG | 19 | CGT | 1.2 |
| 56/42 | PRO | CAA | GLU | 19 | GAA | 0.9 |
| 56/42 | PRO | CAA | HIS | 19 | CAC | 0.4 |
| 56/42 | PRO | CAA | LEU | 19 | CTG | 1.2 |
| 56/42 | PRO | CAA | PHE | 19 | TTC | |
| 56/42 | PRO | CAA | THR | 19 | ACC | 0.6 |
| 56/42 | PRO | CAA | VAL | 19 | GTT | 1.1 |
| 82/68 | LEU | CTG | ALA | 19 | GCT | 0.5 |
| 82/68 | LEU | GTG | ASN | 19 | AAC | 2.9 |
| 82/68 | LEU | CTG | GLU | 19 | GAA | 4.57 (3) 5.0 |
| 82/68 | LEU | CTG | HIS | 19 | CAC | 2.2 |
| 82/68 | LEU | CTG | ILE | 19 | ATC | 0.8 |
| 82/68 | LEU | CTG | MET | 19 | ATG | 1.1 |
| 82/68 | LEU | CTG | PHE | 19 | TTC | 3.2 |
| 82/68 | LEU | CTG | SER | 19 | TCC | 2.2 |
| 82/68 | LEU | CTG | THR | 19 | ACC | 1.6 |
| 82/68 | LEU | CTG | TYR | 19 | TAC | 2.7 |
| 94/80 | ARG | CGA | GLN | 19 | CAG | 0.03 |
| 94/80 | ARG | CGA | HIS | 19 | CAC | 0.01 |
| 94/80 | ARG | CGA | LYS | 19 | AAA | * |
| 95/81 | HIS | CAT | ASN | 19 | AAC | 2.7 (2) 2.3 |
| 95/81 | HIS | CAT | ILE | 19 | ATC | 0.33 |
| 95/81 | HIS | CAT | LYS | 19 | AAA | 0.9 |
| 95/81 | HIS | CAT | MET | 19 | ATG | 1 |
| 95/81 | HIS | CAT | ILE | 19 | TTC | 0.66 |
| 95/81 | HIS | CAT | SER | 19 | TCC | 4 |
| 95/81 | HIS | CAT | TRP | 19 | TGG | * |
| 98/84 | HIS | CAT | ARG | 19 | CGT | 3.2 |
| 98/84 | HIS | CAT | GLN | 19 | CAA | 2.2 |
| 98/84 | HIS | CAT | GLU | 19 | GAA | 1.55 (2) 0.15 |
| 98/84 | HIS | CAT | LYS | 19 | AAA | 4 |
| 98/84 | HIS | CAT | MET | 19 | ATG | 2.2 |
| 98/84 | HIS | CAT | PHE | 19 | TTC | 1 |
| 98/84 | HIS | CAT | SER | 19 | TCC | 4 |
| 98/84 | HIS | CAT | THR | 19 | | 2.2 |
| 98/84 | HIS | CAT | VAL | 19 | GTA | 2.4 (2) 0.8 |
| 101/87 | ASP | GAC | ASN | 19 | AAC | 7 |
| 101/87 | ASP | GAC | GLU | 19 | GAA | * |
| 101/87 | ASP | GAC | ILE | 19 | ATC | 3.2 |
| 101/87 | ASP | GAC | LEU | 19 | CTG | 3.2 |
| 108/94 | ARG | CGG | ALA | 19 | GCT | 4 |
| 108/94 | ARG | CGG | GLN | 19 | CAG | 0.4 |
| 108/94 | ARG | CGG | HIS | 19 | CAC | * |
| 108/94 | ARG | CGG | SER | 19 | TCC | 3.7 |
| 110/96 | LYS | AAA | GLU | 19 | GAA | * |
| 110/96 | LYS | AAA | HIS | 19 | CAC | * |
| 110/96 | LYS | AAA | ILE | 19 | ATC | * |
| 113/99 | PHE | TTC | ASP | 19 | GAC | * |
| 113/99 | PHE | TTC | ILE | 19 | ATC | * |
| 113/99 | PHE | TTC | LEU | 19 | CTG | * |
| 113/99 | PHE | TTC | LYS | 19 | AAA | * |
| 116/102 | LYS | AAA | ALA | 19 | GCT | 5 |
| 116/102 | LYS | AAA | ARG | 19 | CGT | 0.03 |
| 116/102 | LYS | AAA | ASN | 19 | AAC | 0.22 |
| 116/102 | LYS | AAA | GLN | 19 | CAG | 0.33 |
| 116/102 | LYS | AAA | HIS | 19 | CAC | 3.2 |
| 116/102 | LYS | AAA | MET | 19 | ATG | 0.9 |
| 116/102 | LYS | AAA | PHE | 19 | TTC | 2.5 |
| 116/102 | LYS | AAA | TYR | 19 | TAC | 5.4 (2) 0.3 |

SEQUENCE LISTING (1) GENERAL INFORMATION:

(iii) NUMBER OF SEQUENCES: 549

(2) INFORMATION FOR SEQ ID NO:1:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:1:

CTAGCGATCT TTTAATAAGC TTG                                                23

(2) INFORMATION FOR SEQ ID NO:2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:2:

GATCCAAGCT TATTAAAAGA TCG                                                23

(2) INFORMATION FOR SEQ ID NO:3:

(i) SEQUENCE CHARACTERISTICS:
         (A) LENGTH: 69 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:3:

GGCAACAATT TCTACAAAAC ACTTGATACT GTATGAGCAT ACAGTATAAT TGCTTCAACA        60

GAACAGATC                                                                69

(2) INFORMATION FOR SEQ ID NO:4:

(i) SEQUENCE CHARACTERISTICS:
         (A) LENGTH: 67 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:4:

TGTTCTGTTG AAGCAATTAT ACTGTATGCT CATACAGTAT CAAGTGTTTT GTAGAAATTG        60

TTGCCGC                                                                  67

(2) INFORMATION FOR SEQ ID NO:5:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:5:

CCATTGCTGC CGGCATCGTG GTC                                                    23

(2) INFORMATION FOR SEQ ID NO:6:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:6:

CATGGCTCCA ATGACTCAGA CTACTTCTCT TAAGACTTCT TGGGTT                            46

(2) INFORMATION FOR SEQ ID NO:7:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:7:

AACCCAAGAA GTCTTAAGAG AAGTAGTCTG AGTCATTGGA GC                                42

(2) INFORMATION FOR SEQ ID NO:8:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:8:

AATTCCGTCG TAAACTGACC TTCTATCTGA AAACCTTGGA GAACGCGCAG GCTCAACAGT             60

AATA                                                                         64

(2) INFORMATION FOR SEQ ID NO:9:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:9:

AGCTTATTAC TGTTGAGCCT GCGCGTTCTC CAAGGTTTTC AGATAGAAGG TCAGTTTACG             60

ACGG                                                                         64

(2) INFORMATION FOR SEQ ID NO:10:

(i) SEQUENCE CHARACTERISTICS:
            (A) LENGTH: 126 amino acids
            (B) TYPE: amino acid
            (D) TOPOLOGY: linear (ii) MOLECULE TYPE: peptide (xi) SEQUENCE DESCRIPTION: SEQ ID NO:10:

Met Ala Pro Met Thr Gln Thr Thr Ser Leu Lys Thr Ser Trp Val Asn
1               5                   10                  15

Cys Ser Asn Met Ile Asp Glu Ile Ile Thr His Leu Lys Gln Pro Pro
            20                  25                  30

Leu Pro Leu Leu Asp Phe Asn Asn Leu Asn Gly Glu Asp Gln Asp Ile
        35                  40                  45

Leu Met Glu Asn Asn Leu Arg Arg Pro Asn Leu Glu Ala Phe Asn Arg
50                  55                  60

Ala Val Lys Ser Leu Gln Asn Ala Ser Ala Ile Glu Ser Ile Leu Lys
65                  70                  75                  80

Asn Leu Leu Pro Cys Leu Pro Leu Ala Thr Ala Ala Pro Thr Arg His
                85                  90                  95

Pro Ile His Ile Lys Asp Gly Asp Trp Asn Glu Phe Arg Arg Lys Leu
                100                 105                 110

Thr Phe Tyr Leu Lys Thr Leu Glu Asn Ala Gln Ala Gln Gln
            115                 120                 125

(2) INFORMATION FOR SEQ ID NO:11:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: DNA (synthetic)

(xi) SEQUENCE DESCRIPTION: SEQ ID NO:11:

CATGGCTAAC TGCTCTAACA TGAT  24

(2) INFORMATION FOR SEQ ID NO:12:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (synthetic)

(xi) SEQUENCE DESCRIPTION: SEQ ID NO:12:

CGATCATGTT AGAGCAGTTA GC  22

(2) INFORMATION FOR SEQ ID NO:13:

(i) SEQUENCE CHARACTERISTICS:
  (A) LENGTH: 113 amino acids
  (B) TYPE: amino acid
  (D) TOPOLOGY: linear (ii) MOLECULE TYPE: peptide (xi) SEQUENCE DESCRIPTION: SEQ ID NO:13:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
            20                  25                  30

Gln Asp Ile Leu Met Glu Asn Asn Leu Arg Arg Pro Asn Leu Glu Ala
        35                  40                  45

Phe Asn Arg Ala Val Lys Ser Leu Gln Asn Ala Ser Ala Ile Glu Ser
50                  55                  60

```
Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
                 85                  90                  95

Arg Lys Leu Thr Phe Tyr Leu Lys Thr Leu Glu Asn Ala Gln Ala Gln
                100                 105                 110

Gln
```

(2) INFORMATION FOR SEQ ID NO:14:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:14:

```
Met Met Ile Thr Leu Arg Lys Leu Pro Leu Ala Val Ala Val Ala Ala
 1               5                  10                  15

Gly Val Met Ser Ala Gln Ala Met Ala Asn Cys
                 20                  25
```

(2) INFORMATION FOR SEQ ID NO:15:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede the
            amino acid in position 1"

(ix) FEATURE:
        (A) NAME/KEY: Modified-site
        (B) LOCATION: 17
        (D) OTHER INFORMATION: /note= "Xaa at position 17 is Ser,
            Lys, Gly, Asp, Met, Gln, or Arg"

(ix) FEATURE:
        (A) NAME/KEY: Modified-site
        (B) LOCATION: 18
        (D) OTHER INFORMATION: /note= "Xaa at position 18 is Asn,
            His, Leu, Ile, Phe, Arg, or Gln"

(ix) FEATURE:
        (A) NAME/KEY: Modified-site
        (B) LOCATION: 19
        (D) OTHER INFORMATION: /note= "Xaa at positiion 19 is Met,
            Phe, Ile, Arg, Gly, Ala, or Cys"

(ix) FEATURE:
        (A) NAME/KEY: Modified-site
        (B) LOCATION: 20
        (D) OTHER INFORMATION: /note= "Xaa at position 20 is Ile,
            Cys, Gln, Glu, Arg, Pro, or Ala"

(ix) FEATURE:
        (A) NAME/KEY: Modified-site
        (B) LOCATION: 21
        (D) OTHER INFORMATION: /note= "Xaa at position 21 is Asp,
            Phe, Lys, Arg, Ala, Gly, Glu, Gln, Asn, Thr, Ser,
            or Val"

(ix) FEATURE:
        (A) NAME/KEY: Modified-site
        (B) LOCATION: 22
        (D) OTHER INFORMATION: /note= "Xaa at position 22 is Glu, -continued Trp, Pro, Ser, Ala, His, Asp, Asn, Gln, Leu, Val,
        or Gly"

(ix) FEATURE:
     (A) NAME/KEY: Modified-site
     (B) LOCATION: 23
     (D) OTHER INFORMATION: /note= "Xaa at position 23 is Ile,
         Val, Ala, Leu, Gly, Trp, Lys, Phe, Leu, Ser, or
         Arg"

(ix) FEATURE:
     (A) NAME/KEY: Modified-site
     (B) LOCATION: 24
     (D) OTHER INFORMATION: /note= "Xaa at position 24 is Ile,
         Gly, Val, Arg, Ser, Phe, or Leu"

(ix) FEATURE:
     (A) NAME/KEY: Modified-site
     (B) LOCATION: 25
     (D) OTHER INFORMATION: /note= "Xaa at position 25 is Thr,
         His, Gly, Gln, Arg, Pro, or Ala"

(ix) FEATURE:
     (A) NAME/KEY: Modified-site
     (B) LOCATION: 26
     (D) OTHER INFORMATION: /note= "Xaa at position 26 is His,
         Thr, Phe, Gly, Arg, Ala, or Trp"

(ix) FEATURE:
     (A) NAME/KEY: Modified-site
     (B) LOCATION: 27
     (D) OTHER INFORMATION: /note= "Xaa at position 27 is Leu,
         Gly, Arg, Thr, Ser, or Ala"

(ix) FEATURE:
     (A) NAME/KEY: Modified-site
     (B) LOCATION: 28
     (D) OTHER INFORMATION: /note= "Xaa at position 28 is Lys,
         Arg, Leu, Gln, Gly, Pro, Val, or Trp"

(ix) FEATURE:
     (A) NAME/KEY: Modified-site
     (B) LOCATION: 29
     (D) OTHER INFORMATION: /note= "Xaa at position 29 is Gln,
         Asn, Leu, Pro, Arg, or Val"

(ix) FEATURE:
     (A) NAME/KEY: Modified-site
     (B) LOCATION: 30
     (D) OTHER INFORMATION: /note= "Xaa at position 30 is Pro,
         His, Thr, Gly, Asp, Gln, Ser, Leu, or Lys"

(ix) FEATURE:
     (A) NAME/KEY: Modified-site
     (B) LOCATION: 31
     (D) OTHER INFORMATION: /note= "Xaa at position 31 is Pro,
         Asp, Gly, Ala, Arg, Leu, or Gln"

(ix) FEATURE:
     (A) NAME/KEY: Modified-site
     (B) LOCATION: 32
     (D) OTHER INFORMATION: /note= "Xaa at position 32 is Leu,
         Val, Arg, Gln, Asn, Gly, Ala, or Glu"

(ix) FEATURE:
     (A) NAME/KEY: Modified-site
     (B) LOCATION: 33
     (D) OTHER INFORMATION: /note= "Xaa at position 33 is Pro,
         Leu, Gln, Ala, Thr, or Glu"

(ix) FEATURE:
     (A) NAME/KEY: Modified-site
     (B) LOCATION: 34
     (D) OTHER INFORMATION: /note= "Xaa at position 34 is Leu,
         Val, Gly, Ser, Lys, Glu, Gln, Thr, Arg, Ala, Phe,
         Ile, or Met"

(ix) FEATURE:
     (A) NAME/KEY: Modified-site
     (B) LOCATION: 35

```
        (D) OTHER INFORMATION: /note= "Xaa at position 35 is Leu,
            Ala, Gly, Asn, Pro, Gln, or Val"

(ix) FEATURE:
        (A) NAME/KEY: Modified-site
        (B) LOCATION: 36
        (D) OTHER INFORMATION: /note= "Xaa at position 36 is Asp,
            Leu, or Val"

(ix) FEATURE:
        (A) NAME/KEY: Modified-site
        (B) LOCATION: 37
        (D) OTHER INFORMATION: /note= "Xaa at position 37 is Phe,
            Ser, Pro, Trp, or Ile"

(ix) FEATURE:
        (A) NAME/KEY: Modified-site
        (B) LOCATION: 38
        (D) OTHER INFORMATION: /note= "Xaa at position 38 is Asn,
            or Ala"

(ix) FEATURE:
        (A) NAME/KEY: Modified-site
        (B) LOCATION: 40
        (D) OTHER INFORMATION: /note= "Xaa at position 40 is Leu,
            Trp, or Arg"

(ix) FEATURE:
        (A) NAME/KEY: Modified-site
        (B) LOCATION: 41
        (D) OTHER INFORMATION: /note= "Xaa at position 41 is Asn,
            Cys, Arg, Leu, His, Met, or Pro"

(ix) FEATURE:
        (A) NAME/KEY: Modified-site
        (B) LOCATION: 42
        (D) OTHER INFORMATION: /note= "Xaa at position 42 is Gly,
            Asp, Ser, Cys, Asn, Lys, Thr, Leu, Val, Glu, Phe, Tyr,
            Ile, Met, or Ala"

(ix) FEATURE:
        (A) NAME/KEY: Modified-site
        (B) LOCATION: 43
        (D) OTHER INFORMATION: /note= "Xaa at position 43 is Glu,
            Asn, Tyr, Leu, Phe, Asp, Ala, Cys, Gln, Arg, Thr, Gly,
            or Ser"

(ix) FEATURE:
        (A) NAME/KEY: Modified-site
        (B) LOCATION: 44
        (D) OTHER INFORMATION: /note= "Xaa at position 44 is Asp,
            Ser, Leu, Arg, Lys, Thr, Met, Trp, Glu, Asn, Gln, Ala,
            or Pro"

(ix) FEATURE:
        (A) NAME/KEY: Modified-site
        (B) LOCATION: 45
        (D) OTHER INFORMATION: /note= "Xaa at position 45 is Gln,
            Pro, Phe, Val, Met, Leu, Thr, Lys, Trp, Asp, Asn, Arg,
            Ser, Ala, Ile, Glu, or His"

(ix) FEATURE:
        (A) NAME/KEY: Modified-site
        (B) LOCATION: 46
        (D) OTHER INFORMATION: /note= "Xaa at position 46 is Asp,
            Phe, Ser, Thr, Cys, Glu, Asn, Gln, Lys, His, Ala, Tyr,
            Ile, Val, or Gly"

(ix) FEATURE:
        (A) NAME/KEY: Modified-site
        (B) LOCATION: 47
        (D) OTHER INFORMATION: /note= "Xaa at position 47 is Ile,
            Gly, Val, Ser, Arg, Pro, or His"

(ix) FEATURE:
        (A) NAME/KEY: Modified-site
        (B) LOCATION: 48
        (D) OTHER INFORMATION: /note= "Xaa at position 48 is Leu,
            Ser, Cys, Arg, Ile, His, Phe, Glu, Lys, Thr, Ala, Met,
            Val, or Asn"
```

```
(ix) FEATURE:
    (A) NAME/KEY: Modified-site
    (B) LOCATION: 49
    (D) OTHER INFORMATION: /note= "Xaa at position 49 is Met,
        Arg, Ala, Gly, Pro, Asn, His, or Asp"

(ix) FEATURE:
    (A) NAME/KEY: Modified-site
    (B) LOCATION: 50
    (D) OTHER INFORMATION: /note= "Xaa at position 50 is Glu,
        Leu, Thr, Asp, Tyr, Lys, Asn, Ser, Ala, Ile, Val, His,
        Phe, Met, or Gln"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 52
    (D) OTHER INFORMATION: /note= "Xaa at position 52 is Asn,
        His, Arg, Leu, Gly, Ser, or Thr"

(ix) FEATURE:
    (A) NAME/KEY: Modified-site
    (B) LOCATION: 53
    (D) OTHER INFORMATION: /note= "Xaa at position 53 is
        Leu, Thr, Ala, Gly, Glu, Pro, Lys, Ser, or Met"

(ix) FEATURE:
    (A) NAME/KEY: Modified-site
    (B) LOCATION: 54
    (D) OTHER INFORMATION: /note= "Xaa at position 54 is Arg,
        Asp, Ile, Ser, Val, Thr, Gln, Asn, Lys, His, Ala,
        or Leu"

(ix) FEATURE:
    (A) NAME/KEY: Modified-site
    (B) LOCATION: 55
    (D) OTHER INFORMATION: /note= "Xaa at position 55 is Arg,
        Thr, Val, Ser, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Cys, Ser, Gln, Glu, Arg, His, Thr, Ala, Tyr,
        Phe, Leu, Val, or Lys"

(ix) FEATURE:
    (A) NAME/KEY: Modified-site
    (B) LOCATION: 57
    (D) OTHER INFORMATION: /note= "Xaa at position 57 is Asn
        or Gly"

(ix) FEATURE:
    (A) NAME/KEY: Modified-site
    (B) LOCATION: 58
    (D) OTHER INFORMATION: /note= "Xaa at position 58 is Leu,
        Ser, Asp, Arg, Gln, Val, or Cys"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, Pro, or Arg"

(ix) FEATURE:
    (A) NAME/KEY: Modified-site
    (B) LOCATION: 60
    (D) OTHER INFORMATION: /note= "Xaa at position 60 is Ala,
        Ser, Pro, Tyr, Asn, or Thr"

(ix) FEATURE:
    (A) NAME/KEY: Modified-site
    (B) LOCATION: 61
    (D) OTHER INFORMATION: /note= "Xaa at position 61 is Phe,
```

Asn, Glu, Pro, Lys, Arg, or Ser"

(ix) FEATURE:
      (A) NAME/KEY: Modified-site
      (B) LOCATION: 62
      (D) OTHER INFORMATION: /note= "Xaa at position 62 is Asn,
          His, Val, Arg, Pro, Thr, Asp, or Ile"

(ix) FEATURE:
      (A) NAME/KEY: Modified-site
      (B) LOCATION: 63
      (D) OTHER INFORMATION: /note= "Xaa at position 63 is Arg,
          Tyr, Trp, Lys, Ser, His, Pro, or Val"

(ix) FEATURE:
      (A) NAME/KEY: Modified-site
      (B) LOCATION: 64
      (D) OTHER INFORMATION: /note= "Xaa at position 64 is Ala,
          Asn, Pro, Ser, or Lys"

(ix) FEATURE:
      (A) NAME/KEY: Modified-site
      (B) LOCATION: 65
      (D) OTHER INFORMATION: /note= "Xaa at position 65 is Val,
          Thr, Pro, His, Leu, Phe, or Ser"

(ix) FEATURE:
      (A) NAME/KEY: Modified-site
      (B) LOCATION: 66
      (D) OTHER INFORMATION: /note= "Xaa at position 66 is Lys,
          Ile, Arg, Val, Asn, Glu, or Ser"

(ix) FEATURE:
      (A) NAME/KEY: Modified-site
      (B) LOCATION: 67
      (D) OTHER INFORMATION: /note= "Xaa at position 67 is Ser,
          Ala, Phe, Val, Gly, Asn, Ile, Pro, or His"

(ix) FEATURE:
      (A) NAME/KEY: Modified-site
      (B) LOCATION: 68
      (D) OTHER INFORMATION: /note= "Xaa at position 68 is Leu,
          Val, Trp, Ser, Ile, Phe, Thr, or His"

(ix) FEATURE:
      (A) NAME/KEY: Modified-site
      (B) LOCATION: 69
      (D) OTHER INFORMATION: /note= "Xaa at position 69 is Gln,
          Ala, Pro, Thr, Glu, Arg, Trp, Gly, or Leu"

(ix) FEATURE:
      (A) NAME/KEY: Modified-site
      (B) LOCATION: 70
      (D) OTHER INFORMATION: /note= "Xaa at position 70 is Asn,
          Leu, Val, Trp, Pro, or Ala"

(ix) FEATURE:
      (A) NAME/KEY: Modified-site
      (B) LOCATION: 71
      (D) OTHER INFORMATION: /note= "Xaa at position 71 is
          Ala,Met,Leu,Pro,Arg,Glu,Thr,Gln,Trp,or Asn"

(ix) FEATURE:
      (A) NAME/KEY: Modified-site
      (B) LOCATION: 72
      (D) OTHER INFORMATION: /note= "Xaa at position 72 is Ser,
          Glu, Met, Ala, His, Asn, Arg, or Asp"

(ix) FEATURE:
      (A) NAME/KEY: Modified-site
      (B) LOCATION: 73
      (D) OTHER INFORMATION: /note= "Xaa at position 73 is Ala,
          Glu, Asp, Leu, Ser, Gly, Thr, or Arg"

(ix) FEATURE:
      (A) NAME/KEY: Modified-site
      (B) LOCATION: 74
      (D) OTHER INFORMATION: /note= "Xaa at position 74 is Ile,
          Met, Thr, Pro, Arg, Gly, or Ala"

```
(ix) FEATURE:
      (A) NAME/KEY: Modified-site
      (B) LOCATION: 75
      (D) OTHER INFORMATION: /note= "Xaa at position 75 is
          Glu, Lys, Gly, Asp, Pro, Trp, Arg, Ser, Gln,
          or Leu"

(ix) FEATURE:
      (A) NAME/KEY: Modified-site
      (B) LOCATION: 76
      (D) OTHER INFORMATION: /note= "Xaa at position 76 is Ser,
          Val, Ala, Asn, Trp, Glu, Pro, Gly, or Asp"

(ix) FEATURE:
      (A) NAME/KEY: Modified-site
      (B) LOCATION: 77
      (D) OTHER INFORMATION: /note= "Xaa at position 77 is Ile,
          Ser, Arg, Thr, or Leu"

(ix) FEATURE:
      (A) NAME/KEY: Modified-site
      (B) LOCATION: 78
      (D) OTHER INFORMATION: /note= "Xaa at position 78 is Leu,
          Ala, Ser, Glu, Phe, Gly, or Arg"

(ix) FEATURE:
      (A) NAME/KEY: Modified-site
      (B) LOCATION: 79
      (D) OTHER INFORMATION: /note= "Xaa at position 79 is Lys, Thr,
          Asn, Met, Arg, Ile, Gly, or Asp"

(ix) FEATURE:
      (A) NAME/KEY: Modified-site
      (B) LOCATION: 80
      (D) OTHER INFORMATION: /note= "Xaa at position 80 is Asn,
          Trp, Val, Gly, Thr, Leu, Glu, or Arg"

(ix) FEATURE:
      (A) NAME/KEY: Modified-site
      (B) LOCATION: 81
      (D) OTHER INFORMATION: /note= "Xaa at position 81 is Leu,
          Gln, Gly, Ala, Trp, Arg, Val, or Lys"

(ix) FEATURE:
      (A) NAME/KEY: Modified-site
      (B) LOCATION: 82
      (D) OTHER INFORMATION: /note= "Xaa at position 82 is Leu,
          Gln, Lys, Trp, Arg, Asp, Glu, Asn, His, Thr, Ser, Ala,
          Tyr, Phe, Ile, Met, or Val"

(ix) FEATURE:
      (A) NAME/KEY: Modified-site
      (B) LOCATION: 83
      (D) OTHER INFORMATION: /note= "Xaa at position 83 is Pro,
          Ala, Thr, Trp, Arg, or Met"

(ix) FEATURE:
      (A) NAME/KEY: Modified-site
      (B) LOCATION: 84
      (D) OTHER INFORMATION: /note= "Xaa at position 84 is Cys,
          Glu, Gly, Arg, Met, or Val"

(ix) FEATURE:
      (A) NAME/KEY: Modified-site
      (B) LOCATION: 85
      (D) OTHER INFORMATION: /note= "Xaa at position 85 is Leu,
          Asn, Val, or Gln"

(ix) FEATURE:
      (A) NAME/KEY: Modified-site
      (B) LOCATION: 86
      (D) OTHER INFORMATION: /note= "Xaa at position 86 is Pro,
          Cys, Arg, Ala, or Lys"

(ix) FEATURE:
      (A) NAME/KEY: Modified-site
      (B) LOCATION: 87
      (D) OTHER INFORMATION: /note= "Xaa at position 87 is Leu,
          Ser, Trp, or Gly"
```

(ix) FEATURE:
      (A) NAME/KEY: Modified-site
      (B) LOCATION: 88
      (D) OTHER INFORMATION: /note= "Xaa at position 88 is Ala,
          Lys, Arg, Val, or Trp"

(ix) FEATURE:
      (A) NAME/KEY: Modified-site
      (B) LOCATION: 89
      (D) OTHER INFORMATION: /note= "Xaa at position 89 is Thr,
          Asp, Cys, Leu, Val, Glu, His, Asn, or Ser"

(ix) FEATURE:
      (A) NAME/KEY: Modified-site
      (B) LOCATION: 90
      (D) OTHER INFORMATION: /note= "Xaa at position 90 is Ala,
          Pro, Ser, Thr, Gly, Asp, Ile, or Met"

(ix) FEATURE:
      (A) NAME/KEY: Modified-site
      (B) LOCATION: 91
      (D) OTHER INFORMATION: /note= "Xaa at position 91 is Ala,
          Pro, Ser, Thr, Phe, Leu, Asp, or His"

(ix) FEATURE:
      (A) NAME/KEY: Modified-site
      (B) LOCATION: 92
      (D) OTHER INFORMATION: /note= "Xaa at position 92 is Pro,
          Phe, Arg, Ser, Lys, His, Ala, Gly, Ile, or Leu"

(ix) FEATURE:
      (A) NAME/KEY: Modified-site
      (B) LOCATION: 93
      (D) OTHER INFORMATION: /note= "Xaa at position 93 is Thr,
          Asp, Ser, Asn, Pro, Ala, Leu, or Arg"

(ix) FEATURE:
      (A) NAME/KEY: Modified-site
      (B) LOCATION: 94
      (D) OTHER INFORMATION: /note= "Xaa at position 94 is Arg,
          Ile, Ser, Glu, Leu, Val, Gln, Lys, His, Ala, or Pro"

(ix) FEATURE:
      (A) NAME/KEY: Modified-site
      (B) LOCATION: 95
      (D) OTHER INFORMATION: /note= "Xaa at position 95 is His,
          Gln, Pro, Arg, Val, Leu, Gly, Thr, Asn, Lys, Ser, Ala,
          Trp, Phe, Ile, or Tyr"

(ix) FEATURE:
      (A) NAME/KEY: Modified-site
      (B) LOCATION: 96
      (D) OTHER INFORMATION: /note= "Xaa at position 96 is Pro,
          Lys, Tyr, Gly, Ile, or Thr"

(ix) FEATURE:
      (A) NAME/KEY: Modified-site
      (B) LOCATION: 97
      (D) OTHER INFORMATION: /note= "Xaa at position 97 is Ile,
          Val, Lys, Ala, or Asn"

(ix) FEATURE:
      (A) NAME/KEY: Modified-site
      (B) LOCATION: 98
      (D) OTHER INFORMATION: /note= "Xaa at position 98 is His,
          Ile, Asn, Leu, Asp, Ala, Thr, Glu, Gln, Ser, Phe, Met,
          Val, Lys, Arg, Tyr, or Pro"

(ix) FEATURE:
      (A) NAME/KEY: Modified-site
      (B) LOCATION: 99
      (D) OTHER INFORMATION: /note= "Xaa at position 99 is Ile,
          Leu, Arg, Asp, Val, Pro, Gln, Gly, Ser, Phe,
          or His"

(ix) FEATURE:
      (A) NAME/KEY: Modified-site
      (B) LOCATION: 100
      (D) OTHER INFORMATION: /note= "Xaa at position 100 is
          Lys, Tyr, Leu, His, Arg, Ile, Ser, Gln, or Pro"

```
(ix) FEATURE:
    (A) NAME/KEY: Modified-site
    (B) LOCATION: 101
    (D) OTHER INFORMATION: /note= "Xaa at position 101 is
        Asp, Pro, Met, Lys, His, Thr, Val, Tyr, Glu, Asn, Ser,
        Ala, Gly, Ile, Leu, or Gln"

(ix) FEATURE:
    (A) NAME/KEY: Modified-site
    (B) LOCATION: 102
    (D) OTHER INFORMATION: /note= "Xaa at position 102 is Gly,
        Leu, Glu, Lys, Ser, Tyr, or Pro"

(ix) FEATURE:
    (A) NAME/KEY: Modified-site
    (B) LOCATION: 103
    (D) OTHER INFORMATION: /note= "Xaa at position 103 is Asp,
        or Ser"

(ix) FEATURE:
    (A) NAME/KEY: Modified-site
    (B) LOCATION: 104
    (D) OTHER INFORMATION: /note= "Xaa at position 104 is
        Trp, Val, Cys, Tyr, Thr, Met, Pro, Leu, Gln, Lys, Ala,
        Phe, or Gly"

(ix) FEATURE:
    (A) NAME/KEY: Modified-site
    (B) LOCATION: 105
    (D) OTHER INFORMATION: /note= "Xaa at position 105 is
        Asn, Pro, Ala, Phe, Ser, Trp, Gln, Tyr, Leu, Lys, Ile,
        Asp, or His"

(ix) FEATURE:
    (A) NAME/KEY: Modified-site
    (B) LOCATION: 106
    (D) OTHER INFORMATION: /note= "Xaa at position 106 is Glu,
        Ser, Ala, Lys, Thr, Ile, Gly, or Pro"

(ix) FEATURE:
    (A) NAME/KEY: Modified-site
    (B) LOCATION: 108
    (D) OTHER INFORMATION: /note= "Xaa at position 108 is Arg,
        Lys, Asp, Leu, Thr, Ile, Gln, His, Ser, Ala, or Pro"

(ix) FEATURE:
    (A) NAME/KEY: Modified-site
    (B) LOCATION: 109
    (D) OTHER INFORMATION: /note= "Xaa at position 109 is Arg,
        Thr, Pro, Glu, Tyr, Leu, Ser, or Gly"

(ix) FEATURE:
    (A) NAME/KEY: Modified-site
    (B) LOCATION: 110
    (D) OTHER INFORMATION: /note= "Xaa at position 110 is Lys,
        Ala, Asn, Thr, Leu, Arg, Gln, His, Glu, Ser, Ala,
        or Trp"

(ix) FEATURE:
    (A) NAME/KEY: Modified-site
    (B) LOCATION: 111
    (D) OTHER INFORMATION: /note= "Xaa at position 111 is Leu,
        Ile, Arg, Asp, or Met"

(ix) FEATURE:
    (A) NAME/KEY: Modified-site
    (B) LOCATION: 112
    (D) OTHER INFORMATION: /note= "Xaa at position 112 is Thr,
        Val, Gln, Tyr, Glu, His, Ser, or Phe"

(ix) FEATURE:
    (A) NAME/KEY: Modified-site
    (B) LOCATION: 113
    (D) OTHER INFORMATION: /note= "Xaa at position 113 is Phe,
        Ser, Cys, His, Gly, Trp, Tyr, Asp, Lys, Leu, Ile, Val,
        or Asn"

(ix) FEATURE:
    (A) NAME/KEY: Modified-site
```

(B) LOCATION: 114
          (D) OTHER INFORMATION: /note= "Xaa at position 114 is Tyr,
              Cys, His, Ser, Trp, Arg, or Leu"

(ix) FEATURE:
          (A) NAME/KEY: Modified-site
          (B) LOCATION: 115
          (D) OTHER INFORMATION: /note= "Xaa at position 115 is
              Leu, Asn, Val, Pro, Arg, Ala, His, Thr, Trp, or
              Met"

(ix) FEATURE:
          (A) NAME/KEY: Modified-site
          (B) LOCATION: 116
          (D) OTHER INFORMATION: /note= "Xaa at position 116 is Lys,
              Leu, Pro, Thr, Met, Asp, Val, Glu, Arg, Trp, Ser,
              Asn, His, Ala, Tyr, Phe, Gln, or Ile"

(ix) FEATURE:
          (A) NAME/KEY: Modified-site
          (B) LOCATION: 117
          (D) OTHER INFORMATION: /note= "Xaa at position 117 is Thr,
              Ser, Asn, Ile, Trp, Lys, or Pro"

(ix) FEATURE:
          (A) NAME/KEY: Modified-site
          (B) LOCATION: 118
          (D) OTHER INFORMATION: /note= "Xaa at position 118 is Leu,
              Ser, Pro, Ala, Glu, Cys, Asp, or Tyr"

(ix) FEATURE:
          (A) NAME/KEY: Modified-site
          (B) LOCATION: 119
          (D) OTHER INFORMATION: /note= "Xaa at position 119 is Glu,
              Ser, Lys, Pro, Leu, Thr, Tyr, or Arg"

(ix) FEATURE:
          (A) NAME/KEY: Modified-site
          (B) LOCATION: 120
          (D) OTHER INFORMATION: /note= "Xaa at position 120 is Asn,
              Ala, Pro, Leu, His, Val, or Gln"

(ix) FEATURE:
          (A) NAME/KEY: Modified-site
          (B) LOCATION: 121
          (D) OTHER INFORMATION: /note= "Xaa at position 121 is Ala,
              Ser, Ile, Asn, Pro, Lys, Asp, or Gly"

(ix) FEATURE:
          (A) NAME/KEY: Modified-site
          (B) LOCATION: 122
          (D) OTHER INFORMATION: /note= "Xaa at position 122 is
              Gln, Ser, Met, Trp, Arg, Phe, Pro, His, Ile, Tyr,
              or Cys"

(ix) FEATURE:
          (A) NAME/KEY: Modified-site
          (B) LOCATION: 123
          (D) OTHER INFORMATION: /note= "Xaa at position 123 is Ala,
              Met, Glu, His, Ser, Pro, Tyr, or Leu"

(xi) SEQUENCE DESCRIPTION: SEQ ID NO:15:

Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Asn Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

```
        Xaa Xaa Xaa Xaa Xaa Xaa Xaa Xaa Xaa Xaa Phe Xaa Xaa Xaa Xaa Xaa
                    100                 105                 110

Xaa Xaa Xaa Xaa Xaa Xaa Xaa Xaa Xaa Xaa Xaa Gln Gln Thr Thr Leu
                115                 120                 125

Ser Leu Ala Ile Phe
            130
```

(2) INFORMATION FOR SEQ ID NO:16:

(i) SEQUENCE CHARACTERISTICS:
      (A) LENGTH: 133 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 1
      (D) OTHER INFORMATION: /note= "Met- may or may not precede
          the amino acid in position 1"

(ix) FEATURE:
      (A) NAME/KEY: Modified-site
      (B) LOCATION: 17
      (D) OTHER INFORMATION: /note= "Xaa at position 17 is Ser,
          Gly, Asp, Met, or Gln"

(ix) FEATURE:
      (A) NAME/KEY: Modified-site
      (B) LOCATION: 18
      (D) OTHER INFORMATION: /note= "Xaa at position 18 is Asn,
          His, Leu, Ile, Phe, Arg, or Gln"

(ix) FEATURE:
      (A) NAME/KEY: Modified-site
      (B) LOCATION: 19
      (D) OTHER INFORMATION: /note= "Xaa at position 19 is Met,
          Phe, Ile, Arg, or Ala"

(ix) FEATURE:
      (A) NAME/KEY: Modified-site
      (B) LOCATION: 20
      (D) OTHER INFORMATION: /note= "Xaa at position 20 is Ile
          or Pro"

(ix) FEATURE:
      (A) NAME/KEY: Modified-site
      (B) LOCATION: 21
      (D) OTHER INFORMATION: /note; "Xaa at position 21 is Asp
          or Glu"

(ix) FEATURE:
      (A) NAME/KEY: Modified-site
      (B) LOCATION: 23
      (D) OTHER INFORMATION: /note= "Xaa at position 23 is Ile,
          Val, Ala, Leu, or Gly"

(ix) FEATURE:
      (A) NAME/KEY: Modified-site
      (B) LOCATION: 24
      (D) OTHER INFORMATION: /note= "Xaa at position 24 is Ile,
          Val, Phe, or Leu"

(ix) FEATURE:
      (A) NAME/KEY: Modified-site
      (B) LOCATION: 25
      (D) OTHER INFORMATION: /note= "Xaa at position 25 is Thr,
          His, Gly, Gln, Arg, Pro, or Ala"

(ix) FEATURE:
      (A) NAME/KEY: Modified-site
      (B) LOCATION: 26
      (D) OTHER INFORMATION: /note= "Xaa at position 26 is His,
          Phe, Gly, Arg, or Ala"

(ix) FEATURE:
          (A) NAME/KEY: Modified-site
          (B) LOCATION: 28
          (D) OTHER INFORMATION: /note= "Xaa at position 28 is Lys,
              Leu, Gln, Gly, Pro, or Val"

(ix) FEATURE:
          (A) NAME/KEY: Modified-site
          (B) LOCATION: 29
          (D) OTHER INFORMATION: /note= "Xaa at position 29 is Gln,
              Asn, Leu, Arg, or Val"

(ix) FEATURE:
          (A) NAME/KEY: Modified-site
          (B) LOCATION: 30
          (D) OTHER INFORMATION: /note= "Xaa at position 30 is Pro,
              His, Thr, Gly, or Gln"

(ix) FEATURE:
          (A) NAME/KEY: Modified-site
          (B) LOCATION: 31
          (D) OTHER INFORMATION: /note= "Xaa at position 31 is Pro,
              Asp, Gly, Ala, Arg, Leu, or Gln"

(ix) FEATURE:
          (A) NAME/KEY: Modified-site
          (B) LOCATION: 32
          (D) OTHER INFORMATION: /note= "Xaa at position 32 Leu,
              Arg, Gln, Asn, Gly, Ala, or Glu"

(ix) FEATURE:
          (A) NAME/KEY: Modified-site
          (B) LOCATION: 33
          (D) OTHER INFORMATION: /note= "Xaa at position 33 is Pro,
              Leu, Gln, Ala, or Glu"

(ix) FEATURE:
          (A) NAME/KEY: Modified-site
          (B) LOCATION: 34
          (D) OTHER INFORMATION: /note= "Xaa at position 34 is Leu,
              Val, Gly, Ser, Lys, Ala, Arg, Gln, Glu, Ile, Phe,
              Thr, or Met"

(ix) FEATURE:
          (A) NAME/KEY: Modified-site
          (B) LOCATION: 35
          (D) OTHER INFORMATION: /note= "Xaa at position 35 is Leu,
              Ala, Asn, Pro, Gln, or Val"

(ix) FEATURE:
          (A) NAME/KEY: Modified-site
          (B) LOCATION: 36
          (D) OTHER INFORMATION: /note= "Xaa at position 36 is Asp
              or Leu"

(ix) FEATURE:
          (A) NAME/KEY: Modified-site
          (B) LOCATION: 37
          (D) OTHER INFORMATION: /note= "Xaa at position 37 is Phe,
              Ser, Pro, Trp, or Ile"

(ix) FEATURE:
          (A) NAME/KEY: Modified-site
          (B) LOCATION: 38
          (D) OTHER INFORMATION: /note= "Xaa at position 38 is Asn
              or Ala"

(ix) FEATURE:
          (A) NAME/KEY: Modified-site
          (B) LOCATION: 41
          (D) OTHER INFORMATION: /note= "Xaa at position 41 is Asn,
              Cys, Arg, His, Met, or Pro"

(ix) FEATURE:
          (A) NAME/KEY: Modified-site
          (B) LOCATION: 42
          (D) OTHER INFORMATION: /note= "Xaa at position 42 is Gly,
              Asp, Ser, Cys, Ala, Asn, Ile, Leu, Met, Tyr, Val,
              or Arg"

```
(ix) FEATURE:
    (A) NAME/KEY: Modified-site
    (B) LOCATION: 44
    (D) OTHER INFORMATION: /note="Xaa at position 44 is Asp or Glu"

(ix) FEATURE:
    (A) NAME/KEY: Modified-site
    (B) LOCATION: 45
    (D) OTHER INFORMATION: /note= "Xaa at position 45 is Gln,
        Val, Met, Leu, Thr, Lys, Ala, Asn, Glu, Ser, or Trp"

(ix) FEATURE:
    (A) NAME/KEY: Modified-site
    (B) LOCATION: 46
    (D) OTHER INFORMATION: /note= "Xaa at position 46 is Asp,
        Phe, Ser, Thr, Cys, Ala, Asn, Gln, Glu, His, Ile, Lys,
        Tyr, Val, or Gly"

(ix) FEATURE:
    (A) NAME/KEY: Modified-site
    (B) LOCATION: 47
    (D) OTHER INFORMATION: /note= "Xaa at position 47 is Ile, Val,
        or His"

(ix) FEATURE:
    (A) NAME/KEY: Modified-site
    (B) LOCATION: 49
    (D) OTHER INFORMATION: /note= "Xaa at position 49 is Met,
        Asn, or Asp"

(ix) FEATURE:
    (A) NAME/KEY: Modified-site
    (B) LOCATION: 50
    (D) OTHER INFORMATION: /note= "Xaa at position 50 is Glu,
        Thr, Ala, Asn, Ser, or Asp"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 52
    (D) OTHER INFORMATION: /note= "Xaa at position 52 is Asn
        or Gly"

(ix) FEATURE:
    (A) NAME/KEY: Modified-site
    (B) LOCATION: 53
    (D) OTHER INFORMATION: /note= "Xaa at position 53 is Leu,
        Met, or Phe"

(ix) FEATURE:
    (A) NAME/KEY: Modified-site
    (B) LOCATION: 54
    (D) OTHER INFORMATION: /note= "Xaa at position 54 is Arg
        Ala, or Ser"

(ix) FEATURE:
    (A) NAME/KEY: Modified-site
    (B) LOCATION: 55
    (D) OTHER INFORMATION: /note= "Xaa at position 55 is Arg,
        Thr, Val, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Cys, Ser, Gln, Ala, Arg, Asn, Glu, His, Leu, Thr,
        Val, or Lys"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, or Arg"

(ix) FEATURE:
```

```
          (A) NAME/KEY: Modified-site
          (B) LOCATION: 60
          (D) OTHER INFORMATION: /note= "Xaa at position 60 is Ala,
              Ser, Asn, or Thr"

(ix) FEATURE:
          (A) NAME/KEY: Modified-site
          (B) LOCATION: 61
          (D) OTHER INFORMATION: /note= "Xaa at position 61 is Phe
              or Ser"

(ix) FEATURE:
          (A) NAME/KEY: Modified-site
          (B) LOCATION: 62
          (D) OTHER INFORMATION: /note= "Xaa at position 62 is Asn,
              Val, Pro, Thr, or Ile"

(ix) FEATURE:
          (A) NAME/KEY: Modified-site
          (B) LOCATION: 63
          (D) OTHER INFORMATION: /note= "Xaa at position 63 is Arg,
              Tyr, Lys, Ser, His, or Val"

(ix) FEATURE:
          (A) NAME/KEY: Modified-site
          (B) LOCATION: 64
          (D) OTHER INFORMATION: /note= "Xaa at position 64 is Ala
              or Asn"

(ix) FEATURE:
          (A) NAME/KEY: Modified-site
          (B) LOCATION: 65
          (D) OTHER INFORMATION: /note= "Xaa at position 65 is Val,
              Thr, Leu, or Ser"

(ix) FEATURE:
          (A) NAME/KEY: Modified-site
          (B) LOCATION: 66
          (D) OTHER INFORMATION: /note= "Xaa at position 66 is Lys,
              Ile, Arg, Val, Asn, Glu, or Ser"

(ix) FEATURE:
          (A) NAME/KEY: Modified-site
          (B) LOCATION: 67
          (D) OTHER INFORMATION: /note= "Xaa at position 67 is Ser,
              Phe, Val, Gly, Asn, Ile, or His"

(ix) FEATURE:
          (A) NAME/KEY: Modified-site
          (B) LOCATION: 68
          (D) OTHER INFORMATION: /note= "Xaa at position 68 is Leu,
              Val, Ile, Phe, or His"

(ix) FEATURE:
          (A) NAME/KEY: Modified-site
          (B) LOCATION: 69
          (D) OTHER INFORMATION: /note= "Xaa at position 69 is Gln,
              Ala, Pro, Thr, Glu, Arg, or Gly"

(ix) FEATURE:
          (A) NAME/KEY: Modified-site
          (B) LOCATION: 70
          (D) OTHER INFORMATION: /note= "Xaa at position 70 is Asn
              or Pro"

(ix) FEATURE:
          (A) NAME/KEY: Modified-site
          (B) LOCATION: 71
          (D) OTHER INFORMATION: /note= "Xaa at position 71 is Ala,
              Met, Pro, Arg, Glu, Thr, or Gln"

(ix) FEATURE:
          (A) NAME/KEY: Modified-site
          (B) LOCATION: 72
          (D) OTHER INFORMATION: /note= "Xaa at position 72 is Ser,
              Glu, Met, Ala, His, Asn, Arg, or Asp"

(ix) FEATURE:
          (A) NAME/KEY: Modified-site
          (B) LOCATION: 73
```

-continued

```
          (D) OTHER INFORMATION: /note= "Xaa at position 73 is Ala,
              Glu, Asp, Leu, Ser, Gly, Thr, Arg, or Pro"

(ix) FEATURE:
          (A) NAME/KEY: Modified-site
          (B) LOCATION: 74
          (D) OTHER INFORMATION: /note= "Xaa at position 74 is Ile
              or Met"

(ix) FEATURE:
          (A) NAME/KEY: Modified-site
          (B) LOCATION: 75
          (D) OTHER INFORMATION: /note= "Xaa at position 75 is Glu,
              Gly, Asp, Ser, or Gln"

(ix) FEATURE:
          (A) NAME/KEY: Modified-site
          (B) LOCATION: 76
          (D) OTHER INFORMATION: /note= "Xaa at position 76 is Ser,
              Val, Ala, Asn, Glu, Pro, Gly, or Asp"

(ix) FEATURE:
          (A) NAME/KEY: Modified-site
          (B) LOCATION: 77
          (D) OTHER INFORMATION: /note= "Xaa at position 77 is Ile,
              Ser, or Leu"

(ix) FEATURE:
          (A) NAME/KEY: Modified-site
          (B) LOCATION: 79
          (D) OTHER INFORMATION: /note= "Xaa at position 79 is Lys,
              Thr, Gly, Asn, Met, Arg, Ile, Gly, or Asp"

(ix) FEATURE:
          (A) NAME/KEY: Modified-site
          (B) LOCATION: 80
          (D) OTHER INFORMATION: /note= "Xaa at position 80 is Asn,
              Val, Gly, Thr, Leu, Glu, or Arg"

(ix) FEATURE:
          (A) NAME/KEY: Modified-site
          (B) LOCATION: 81
          (D) OTHER INFORMATION: /note= "Xaa at position 81 is Leu
              or Val"

(ix) FEATURE:
          (A) NAME/KEY: Modified-site
          (B) LOCATION: 82
          (D) OTHER INFORMATION: /note= "Xaa at position 82 is Leu,
              Gln, Trp, Arg, Asp, Ala, Asn, Glu, His, Met, Phe,
              Ser, Thr, Tyr, or Val"

(ix) FEATURE:
          (A) NAME/KEY: Modified-site
          (B) LOCATION: 83
          (D) OTHER INFORMATION: /note= "Xaa at position 83 is Pro,
              Ala, Thr, Trp, or Met"

(ix) FEATURE:
          (A) NAME/KEY: Modified-site
          (B) LOCATION: 85
          (D) OTHER INFORMATION: /note= "Xaa at position 85 is Leu
              or Val"

(ix) FEATURE:
          (A) NAME/KEY: Modified-site
          (B) LOCATION: 87
          (D) OTHER INFORMATION: /note= "Xaa at position 87 is Leu
              or Ser"

(ix) FEATURE:
          (A) NAME/KEY: Modified-site
          (B) LOCATION: 88
          (D) OTHER INFORMATION: /note= "Xaa at position 88 is Ala,
              Arg, or Trp"

(ix) FEATURE:
          (A) NAME/KEY: Modified-site
          (B) LOCATION: 89
          (D) OTHER INFORMATION: /note= "Xaa at position 89 is Thr,
```

```
            Asp, Glu, His, Asn, or Ser"

(ix) FEATURE:
     (A) NAME/KEY: Modified-site
     (B) LOCATION: 90
     (D) OTHER INFORMATION: /note= "Xaa at position 90 is Ala,
         Asp, or Met"

(ix) FEATURE:
     (A) NAME/KEY: Modified-site
     (B) LOCATION: 91
     (D) OTHER INFORMATION: /note= "Xaa at position 91 is Ala,
         Pro, Ser, Thr, Phe, Leu, or Asp"

(ix) FEATURE:
     (A) NAME/KEY: Modified-site
     (B) LOCATION: 92
     (D) OTHER INFORMATION: /note= "Xaa at position 92 is Pro
         or Ser"

(ix) FEATURE:
     (A) NAME/KEY: Modified-site
     (B) LOCATION: 93
     (D) OTHER INFORMATION: /note= "Xaa at position 93 is Thr,
         Asp, Ser, Pro, Ala, Leu, or Arg"

(ix) FEATURE:
     (A) NAME/KEY: Modified-site
     (B) LOCATION: 95
     (D) OTHER INFORMATION: /note= "Xaa at position 95 is His,
         Pro, Arg, Val, Leu, Gly, Asn, Ile, Phe, Ser,
         or Thr"

(ix) FEATURE:
     (A) NAME/KEY: Modified-site
     (B) LOCATION: 96
     (D) OTHER INFORMATION: /note= "Xaa at position 96 is Pro
         or Tyr"

(ix) FEATURE:
     (A) NAME/KEY: Modified-site
     (B) LOCATION: 97
     (D) OTHER INFORMATION: /note= "Xaa at position 97 is Ile,
         Val, or Ala"

(ix) FEATURE:
     (A) NAME/KEY: Modified-site
     (B) LOCATION: 98
     (D) OTHER INFORMATION: /note= "Xaa at position 98 is His,
         Ile, Asn, Leu, Asp, Ala, Thr, Leu, Arg, Gln, Glu,
         Lys, Met, Ser, Tyr, Val, or Pro"

(ix) FEATURE:
     (A) NAME/KEY: Modified-site
     (B) LOCATION: 99
     (D) OTHER INFORMATION: /note= "Xaa at position 99 is Ile,
         Leu, Val, or Phe"

(ix) FEATURE:
     (A) NAME/KEY: Modified-site
     (B) LOCATION: 100
     (D) OTHER INFORMATION: /note= "Xaa at position 100 is Lys,
         Leu, His, Arg, Ile, Gln, Pro, or Ser"

(ix) FEATURE:
     (A) NAME/KEY: Modified-site
     (B) LOCATION: 101
     (D) OTHER INFORMATION: /note= "Xaa at position 101 is Asp,
         Pro, Met, Lys, His, Thr, Val, Asn, Ile, Leu, or Tyr"

(ix) FEATURE:
     (A) NAME/KEY: Modified-site
     (B) LOCATION: 102
     (D) OTHER INFORMATION: /note= "Xaa at position 102 is Gly,
         Glu, Lys, or Ser"

(ix) FEATURE:
     (A) NAME/KEY: Modified-site
     (B) LOCATION: 104
     (D) OTHER INFORMATION: /note= "Xaa at position 104 is Trp,
```

```
              Val, Tyr, Met, or Leu"

(ix) FEATURE:
     (A) NAME/KEY: Modified-site
     (B) LOCATION: 105
     (D) OTHER INFORMATION: /note= "Xaa at position 105 is
         Asn, Pro, Ala, Phe, Ser, Trp, Gln, Tyr, Leu, Lys,
         Ile, Asp or His"

(ix) FEATURE:
     (A) NAME/KEY: Modified-site
     (B) LOCATION: 106
     (D) OTHER INFORMATION: /note= "Xaa at position 106 is Glu,
         Ser, Ala, or Gly"

(ix) FEATURE:
     (A) NAME/KEY: Modified-site
     (B) LOCATION: 108
     (D) OTHER INFORMATION: /note= "Xaa at position 108 is Arg,
         Ala, Gln, Ser, or Lys"

(ix) FEATURE:
     (A) NAME/KEY: Modified-site
     (B) LOCATION: 109
     (D) OTHER INFORMATION: /note= "Xaa at position 109 is Arg,
         Thr, Glu, Leu, Ser, or Gly"

(ix) FEATURE:
     (A) NAME/KEY: Modified-site
     (B) LOCATION: 112
     (D) OTHER INFORMATION: /note= "Xaa at position 112 is Thr,
         Val, Gln, Glu, His, or Ser"

(ix) FEATURE:
     (A) NAME/KEY: Modified-site
     (B) LOCATION: 114
     (D) OTHER INFORMATION: /note= "Xaa at position 114 is Tyr
         or Trp"

(ix) FEATURE:
     (A) NAME/KEY: Modified-site
     (B) LOCATION: 115
     (D) OTHER INFORMATION: /note= "Xaa at position 115 is Leu
         or Ala"

(ix) FEATURE:
     (A) NAME/KEY: Modified-site
     (B) LOCATION: 116
     (D) OTHER INFORMATION: /note= "Xaa at position 116 is Lys,
         Thr, Met, Val, Trp, Ser, Leu, Ala, Asn, Gln, His, Met,
         Phe, Tyr, or Ile"

(ix) FEATURE:
     (A) NAME/KEY: Modified-site
     (B) LOCATION: 117
     (D) OTHER INFORMATION: /note= "Xaa at position 117 is Thr,
         Ser, or Asn"

(ix) FEATURE:
     (A) NAME/KEY: Modified-site
     (B) LOCATION: 119
     (D) OTHER INFORMATION: /note= "Xaa at position 119 is
         Glu, Ser, Pro, Leu, Thr, or Tyr"

(ix) FEATURE:
     (A) NAME/KEY: Modified-site
     (B) LOCATION: 120
     (D) OTHER INFORMATION: /note= "Xaa at position 120 is Asn,
         Pro, Leu, His, Val, or Gln"

(ix) FEATURE:
     (A) NAME/KEY: Modified-site
     (B) LOCATION: 121
     (D) OTHER INFORMATION: /note= "Xaa at position 121 is Ala,
         Ser, Ile, Asn, Pro, Lys, Asp, or Gly"

(ix) FEATURE:
     (A) NAME/KEY: Modified-site
     (B) LOCATION: 122
     (D) OTHER INFORMATION: /note= "Xaa at position 122 is
```

Gln, Ser, Met, Trp, Arg, Phe, Pro, His, Ile, Tyr,
or Cys"

(ix) FEATURE:
    (A) NAME/KEY: Modified-site
    (B) LOCATION: 123
    (D) OTHER INFORMATION: /note= "Xaa at position 123 is Ala,
        Met, Glu, His, Ser, Pro, Tyr, or Leu"

(xi) SEQUENCE DESCRIPTION: SEQ ID NO:16:

Ala Pro Met Thr Gln Thr Thr Ser Leu Lys Thr Ser Trp Val Asn Cys
 1               5                  10                  15

Xaa Xaa Xaa Xaa Xaa Glu Xaa Xaa Xaa Xaa Leu Xaa Xaa Xaa Xaa Xaa
                20                  25                  30

Xaa Xaa Xaa Xaa Xaa Xaa Asn Leu Xaa Xaa Glu Xaa Xaa Xaa Xaa Leu
            35                  40                  45

Xaa Xaa Xaa Xaa Xaa Xaa Xaa Asn Leu Xaa Xaa Xaa Xaa Xaa
        50                  55                  60

Xaa Xaa Xaa Xaa Xaa Xaa Xaa Xaa Xaa Xaa Xaa Xaa Leu Xaa Xaa
65                  70                  75                  80

Xaa Xaa Xaa Cys Xaa Pro Xaa Xaa Xaa Xaa Xaa Xaa Arg Xaa Xaa
            85                  90                  95

Xaa Xaa Xaa Xaa Xaa Xaa Asp Xaa Xaa Xaa Phe Xaa Xaa Lys Leu Xaa
                100                 105                 110

Phe Xaa Xaa Xaa Xaa Leu Xaa Xaa Xaa Xaa Xaa Gln Gln Thr Thr Leu
        115                 120                 125

Ser Leu Ala Ile Phe
        130

(2) INFORMATION FOR SEQ ID NO:17:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, Met, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 19
        (D) OTHER INFORMATION: /note= "Xaa at position 19 is Met
            or Ile"

(ix) FEATURE:
        (A) NAME/KEY: Modified-site
        (B) LOCATION: 21
        (D) OTHER INFORMATION: /note= "Xaa at position 21 is Asp
            or Glu"

(ix) FEATURE:
        (A) NAME/KEY: Modified-site

```
          (B) LOCATION: 23
          (D) OTHER INFORMATION: /note= "Xaa at position 23 is Ile,
              Ala, Leu, or Gly"

(ix) FEATURE:
          (A) NAME/KEY: Modified-site
          (B) LOCATION: 24
          (D) OTHER INFORMATION: /note= "Xaa at position 24 is Ile,
              Val, or Leu"

(ix) FEATURE:
          (A) NAME/KEY: Modified-site
          (B) LOCATION: 25
          (D) OTHER INFORMATION: /note= "Xaa at position 25 is Thr,
              His, Gln, or Ala"

(ix) FEATURE:
          (A) NAME/KEY: Modified-site
          (B) LOCATION: 26
          (D) OTHER INFORMATION: /note= "Xaa at position 26 is His
              or Ala"

(ix) FEATURE:
          (A) NAME/KEY: Modified-site
          (B) LOCATION: 29
          (D) OTHER INFORMATION: /note= "Xaa at position 29 is Gln,
              Asn, or Val"

(ix) FEATURE:
          (A) NAME/KEY: Modified-site
          (B) LOCATION: 30
          (D) OTHER INFORMATION: /note= "Xaa at position 30 is Pro,
              Gly, or Gln"

(ix) FEATURE:
          (A) NAME/KEY: Modified-site
          (B) LOCATION: 31
          (D) OTHER INFORMATION: /note= "Xaa at position 31 is Pro,
              Asp, Gly, or Gln"

(ix) FEATURE:
          (A) NAME/KEY: Modified-site
          (B) LOCATION: 32
          (D) OTHER INFORMATION: /note= "Xaa at position 32 is Leu,
              Arg, Gln, Asn, Gly, Ala, or Glu"

(ix) FEATURE:
          (A) NAME/KEY: Modified-site
          (B) LOCATION: 33
          (D) OTHER INFORMATION: /note= "Xaa at position 33 is Pro
              or Glu"

(ix) FEATURE:
          (A) NAME/KEY: Modified-site
          (B) LOCATION: 34
          (D) OTHER INFORMATION: /note= "Xaa at position 34 is Leu,
              Val, Gly, Ser, Lys, Ala, Arg, Gln, Glu, Ile, Phe
              Thr, or Met"

(ix) FEATURE:
          (A) NAME/KEY: Modified-site
          (B) LOCATION: 35
          (D) OTHER INFORMATION: /note= "Xaa at position 35 is Leu,
              Ala, Asn, Pro, Gln, or Val"

(ix) FEATURE:
          (A) NAME/KEY: Modified-site
          (B) LOCATION: 37
          (D) OTHER INFORMATION: /note= "Xaa at position 37 is Phe,
              Ser, Pro, or Trp"

(ix) FEATURE:
          (A) NAME/KEY: Modified-site
          (B) LOCATION: 38
          (D) OTHER INFORMATION: /note= "Xaa at position 38 is Asn
              or Ala"

(ix) FEATURE:
          (A) NAME/KEY: Modified-site
          (B) LOCATION: 42
```

(D) OTHER INFORMATION: /note= "Xaa at position 42 is Gly,
                Asp, Ser, Cys, Ala, Asn, Ile, Leu, Met, Tyr, or Arg"

(ix) FEATURE:
            (A) NAME/KEY: Modified-site
            (B) LOCATION: 45
            (D) OTHER INFORMATION: /note= "Xaa at position 45 is Gln,
                Val, Met, Leu, Thr, Ala, Asn, Glu, Ser, or Lys"

(ix) FEATURE:
            (A) NAME/KEY: Modified-site
            (B) LOCATION: 46
            (D) OTHER INFORMATION: /note= "Xaa at position 46 is Asp,
                Phe, Ser, Thr, Ala, Asn, Gln, Glu, His, Ile, Lys,
                Tyr, Val, or Cys"

(ix) FEATURE:
            (A) NAME/KEY: Modified-site
            (B) LOCATION: 50
            (D) OTHER INFORMATION: /note= "Xaa at position 50 is Glu,
                Ala, Asn, Ser, or Asp"

(ix) FEATURE:
            (A) NAME/KEY: Modified-site
            (B) LOCATION: 51
            (D) OTHER INFORMATION: /note= "Xaa at position 51 is Asn,
                Arg, Met, Pro, Ser, Thr, or His"

(ix) FEATURE:
            (A) NAME/KEY: Modified-site
            (B) LOCATION: 54
            (D) OTHER INFORMATION: /note= "Xaa at position 54 is Arg
                or Ala"

(ix) FEATURE:
            (A) NAME/KEY: Modified-site
            (B) LOCATION: 55
            (D) OTHER INFORMATION: /note= "Xaa at position 55 is Arg,
                Thr, Val, Leu, or Gly"

(ix) FEATURE:
            (A) NAME/KEY: Modified-site
            (B) LOCATION: 56
            (D) OTHER INFORMATION: /note= "Xaa at position 56 is Pro,
                Gly, Ser, Gln, Ala, Arg, Asn, Glu, Leu, Thr, Val,
                or Lys"

(ix) FEATURE:
            (A) NAME/KEY: Modified-site
            (B) LOCATION: 60
            (D) OTHER INFORMATION: /note= "Xaa at position 60 is Ala
                or Ser"

(ix) FEATURE:
            (A) NAME/KEY: Modified-site
            (B) LOCATION: 62
            (D) OTHER INFORMATION: /note= "Xaa at position 62 is Asn,
                Pro, Thr, or Ile"

(ix) FEATURE:
            (A) NAME/KEY: Modified-site
            (B) LOCATION: 63
            (D) OTHER INFORMATION: /note= "Xaa at position 63 is Arg
                or Lys"

(ix) FEATURE:
            (A) NAME/KEY: Modified-site
            (B) LOCATION: 64
            (D) OTHER INFORMATION: /note= "Xaa at position 64 is Ala
                or Asn"

(ix) FEATURE:
            (A) NAME/KEY: Modified-site
            (B) LOCATION: 65
            (D) OTHER INFORMATION: /note= "Xaa at position 65 is Val
                or Thr"

(ix) FEATURE:
            (A) NAME/KEY: Modified-site
            (B) LOCATION: 66

(D) OTHER INFORMATION: /note= "Xaa at position 66 is Lys
                or Arg"

(ix) FEATURE:
            (A) NAME/KEY: Modified-site
            (B) LOCATION: 67
            (D) OTHER INFORMATION: /note= "Xaa at position 67 is Ser
                Phe or His"

(ix) FEATURE:
            (A) NAME/KEY: Modified-site
            (B) LOCATION: 68
            (D) OTHER INFORMATION: /note= "Xaa at position 68 is Leu,
                Ile, Phe, or His"

(ix) FEATURE:
            (A) NAME/KEY: Modified-site
            (B) LOCATION: 69
            (D) OTHER INFORMATION: /note= "Xaa at position 69 is Gln,
                Ala, Pro, Thr, Glu, Arg, or Gly"

(ix) FEATURE:
            (A) NAME/KEY: Modified-site
            (B) LOCATION: 71
            (D) OTHER INFORMATION: /note= "Xaa at position 71 is Ala,
                Pro, or Arg"

(ix) FEATURE:
            (A) NAME/KEY: Modified-site
            (B) LOCATION: 72
            (D) OTHER INFORMATION: /note= "Xaa at position 72 is Ser,
                Glu, Arg, or Asp"

(ix) FEATURE:
            (A) NAME/KEY: Modified-site
            (B) LOCATION: 73
            (D) OTHER INFORMATION: /note= "Xaa at position 73 is Ala
                or Leu"

(ix) FEATURE:
            (A) NAME/KEY: Modified-site
            (B) LOCATION: 76
            (D) OTHER INFORMATION: /note= "Xaa at position 76 is Ser,
                Val, Ala, Asn, Glu, Pro, or Gly"

(ix) FEATURE:
            (A) NAME/KEY: Modified-site
            (B) LOCATION: 77
            (D) OTHER INFORMATION: /note= "Xaa at position 77 is Ile
                or Leu"

(ix) FEATURE:
            (A) NAME/KEY: Modified-site
            (B) LOCATION: 79
            (D) OTHER INFORMATION: /note= "Xaa at position 79 is
                Lys, Thr, Gly, Asn, Met, Arg, Ile, Gly, or Asp"

(ix) FEATURE:
            (A) NAME/KEY: Modified-site
            (B) LOCATION: 80
            (D) OTHER INFORMATION: /note= "Xaa at position 80 is Asn,
                Gly, Glu, or Arg"

(ix) FEATURE:
            (A) NAME/KEY: Modified-site
            (B) LOCATION: 82
            (D) OTHER INFORMATION: /note= "Xaa at position 82 is Leu,
                Gln, Trp, Arg, Asp, Ala, Asn, Glu, His, Ile, Met,
                Phe, Ser, Thr, Tyr, or Val"

(ix) FEATURE:
            (A) NAME/KEY: Modified-site
            (B) LOCATION: 83
            (D) OTHER INFORMATION: /note= "Xaa at position 83 is Pro
                or Thr"

(ix) FEATURE:
            (A) NAME/KEY: Modified-site
            (B) LOCATION: 85
            (D) OTHER INFORMATION: /note= "Xaa at position 85 is Leu or Val"

(ix) FEATURE:
      (A) NAME/KEY: Modified-site
      (B) LOCATION: 87
      (D) OTHER INFORMATION: /note= "Xaa at position 87 is Leu
          or Ser"

(ix) FEATURE:
      (A) NAME/KEY: Modified-site
      (B) LOCATION: 88
      (D) OTHER INFORMATION: /note= "Xaa at position 88 is Ala
          or Trp"

(ix) FEATURE:
      (A) NAME/KEY: Modified-site
      (B) LOCATION: 91
      (D) OTHER INFORMATION: /note= "Xaa at position 91 is Ala
          or Pro"

(ix) FEATURE:
      (A) NAME/KEY: Modified-site
      (B) LOCATION: 93
      (D) OTHER INFORMATION: /note= "Xaa at position 93 is Thr,
          Asp, Ser, Pro, Ala, Leu, or Arg"

(ix) FEATURE:
      (A) NAME/KEY: Modified-site
      (B) LOCATION: 95
      (D) OTHER INFORMATION: /note= "Xaa at position 95 is His,
          Pro, Arg, Val, Leu, Gly, Asn, Phe, Ser, or Thr"

(ix) FEATURE:
      (A) NAME/KEY: Modified-site
      (B) LOCATION: 96
      (D) OTHER INFORMATION: /note= "Xaa at position 96 is Pro
          or Tyr"

(ix) FEATURE:
      (A) NAME/KEY: Modified-site
      (B) LOCATION: 97
      (D) OTHER INFORMATION: /note= "Xaa at position 97 is Ile
          or Val"

(ix) FEATURE:
      (A) NAME/KEY: Modified-site
      (B) LOCATION: 98
      (D) OTHER INFORMATION: /note= "Xaa at position 98 is His,
          Ile, Asn, Leu, Ala, Thr, Leu, Arg, Gln, Leu, Lys,
          Met, Ser, Tyr, Val, or Pro"

(ix) FEATURE:
      (A) NAME/KEY: Modified-site
      (B) LOCATION: 99
      (D) OTHER INFORMATION: /note= "Xaa at position 99 is Ile,
          Leu, or Val"

(ix) FEATURE:
      (A) NAME/KEY: Modified-site
      (B) LOCATION: 100
      (D) OTHER INFORMATION: /note= "Xaa at position 100 is Lys,
          Arg, Ile, Gln, Pro, or Ser"

(ix) FEATURE:
      (A) NAME/KEY: Modified-site
      (B) LOCATION: 101
      (D) OTHER INFORMATION: /note= "Xaa at position 101 is Asp,
          Pro, Met, Lys, His, Thr, Pro, Asn, Ile, Leu, or Tyr"

(ix) FEATURE:
      (A) NAME/KEY: Modified-site
      (B) LOCATION: 104
      (D) OTHER INFORMATION: /note= "Xaa at position 104 is Trp
          or Leu"

(ix) FEATURE:
      (A) NAME/KEY: Modified-site
      (B) LOCATION: 105
      (D) OTHER INFORMATION: /note= "Xaa at position 105 is
          Asn, Pro, Ala, Ser, Trp, Gln, Tyr, Leu, Lys, Ile, Asp, or His"

(ix) FEATURE:
      (A) NAME/KEY: Modified-site
      (B) LOCATION: 106
      (D) OTHER INFORMATION: /note= "Xaa at position 106 is Glu
          or Gly"

(ix) FEATURE:
      (A) NAME/KEY: Modified-site
      (B) LOCATION: 109
      (D) OTHER INFORMATION: /note= "Xaa at position 109 is Arg,
          Thr, Glu, Leu, or Ser"

(ix) FEATURE:
      (A) NAME/KEY: Modified-site
      (B) LOCATION: 112
      (D) OTHER INFORMATION: /note= "Xaa at position 112 is Thr,
          Val, or Gln"

(ix) FEATURE:
      (A) NAME/KEY: Modified-site
      (B) LOCATION: 114
      (D) OTHER INFORMATION: /note= "Xaa at position 114 is Tyr
          or Trp"

(ix) FEATURE:
      (A) NAME/KEY: Modified-site
      (B) LOCATION: 115
      (D) OTHER INFORMATION: /note= "Xaa at position 115 is Leu
          or Ala"

(ix) FEATURE:
      (A) NAME/KEY: Modified-site
      (B) LOCATION: 116
      (D) OTHER INFORMATION: /note= "Xaa at position 116 is Lys,
          Thr, Val, Trp, Ser, Ala, His, Met, Phe, Tyr, or Ile"

(ix) FEATURE:
      (A) NAME/KEY: Modified-site
      (B) LOCATION: 117
      (D) OTHER INFORMATION: /note= "Xaa at position 117 is Thr
          or Ser"

(ix) FEATURE:
      (A) NAME/KEY: Modified-site
      (B) LOCATION: 120
      (D) OTHER INFORMATION: /note= "Xaa at position 120 is Asn,
          Pro, Leu, His, Val, or Gln"

(ix) FEATURE:
      (A) NAME/KEY: Modified-site
      (B) LOCATION: 121
      (D) OTHER INFORMATION: /note= "Xaa at position 121 is Ala,
          Ser, Ile, Asn, Pro, Asp, or Gly"

(ix) FEATURE:
      (A) NAME/KEY: Modified-site
      (B) LOCATION: 122
      (D) OTHER INFORMATION: /note= "Xaa at position 122 is
          Gln, Ser, Met, Trp, Arg, Phe, Pro, His, Ile, Tyr,
          or Cys"

(ix) FEATURE:
      (A) NAME/KEY: Modified-site
      (B) LOCATION: 123
      (D) OTHER INFORMATION: /note= "Xaa at position 123 is Ala,
          Met, Glu, His, Ser, Pro, Tyr, or Leu"

(xi) SEQUENCE DESCRIPTION: SEQ ID NO:17:

Ala Pro Met Thr Gln Thr Thr Ser Leu Lys Thr Ser Trp Val Asn Cys
1               5                   10                  15

Xaa Xaa Xaa Ile Xaa Glu Xaa Xaa Xaa Xaa Leu Lys Xaa Xaa Xaa Xaa
            20                  25                  30

Xaa Xaa Xaa Asp Xaa Xaa Asn Leu Asn Xaa Glu Xaa Xaa Xaa Ile Leu
            35                  40                  45

```
Met Xaa Xaa Asn Leu Xaa Xaa Xaa Asn Leu Glu Xaa Phe Xaa Xaa Xaa
    50                  55                  60

Xaa Xaa Xaa Xaa Xaa Asn Xaa Xaa Xaa Ile Glu Xaa Xaa Leu Xaa Xaa
65                  70                  75                  80

Leu Xaa Xaa Cys Xaa Pro Xaa Xaa Thr Ala Xaa Pro Xaa Arg Xaa Xaa
                85                  90                  95

Xaa Xaa Xaa Xaa Xaa Gly Asp Xaa Xaa Xaa Phe Xaa Xaa Lys Leu Xaa
            100                 105                 110

Phe Xaa Xaa Xaa Xaa Leu Glu Xaa Xaa Xaa Xaa Gln Gln Thr Thr Leu
        115                 120                 125

Ser Leu Ala Ile Phe
    130
```

(2) INFORMATION FOR SEQ ID NO:18:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 25
        (D) OTHER INFORMATION: /note= "Xaa at position 25 is Thr,
            His, or Gln"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note="Xaa at position 29 is Gln
            or Asn"

(ix) FEATURE:
        (A) NAME/KEY: Modified-site
        (B) LOCATION: 30
        (D) OTHER INFORMATION: /note= "Xaa at position 30 is Pro
            or Gly"

(ix) FEATURE:
        (A) NAME/KEY: Modified-site
        (B) LOCATION: 32
        (D) OTHER INFORMATION: /note= "Xaa at position 32 is Leu, -continued Arg, Asn, or Ala"

(ix) FEATURE:
    (A) NAME/KEY: Modified-site
    (B) LOCATION: 34
    (D) OTHER INFORMATION: /note= "Xaa at position 34 is Leu,
        Val, Ser, Ala, Arg, Gln, Glu, Ile, Phe, Thr, or Met"

(ix) FEATURE:
    (A) NAME/KEY: Modified-site
    (B) LOCATION: 35
    (D) OTHER INFORMATION: /note= "Xaa at position 35 is Leu,
        Ala, Asn, or Pro"

(ix) FEATURE:
    (A) NAME/KEY: Modified-site
    (B) LOCATION: 38
    (D) OTHER INFORMATION: /note= "Xaa at position 38 is Asn
        or Ala"

(ix) FEATURE:
    (A) NAME/KEY: Modified-site
    (B) LOCATION: 42
    (D) OTHER INFORMATION: /note= "Xaa at position 42 is Gly,
        Asp, Ser, Ala, Asn, Ile, Leu, Met, Tyr, or Arg"

(ix) FEATURE:
    (A) NAME/KEY: Modified-site
    (B) LOCATION: 45
    (D) OTHER INFORMATION: /note= "Xaa at position 45 is Gln,
        Val, Met, Leu, Ala, Asn, Glu, or Lys"

(ix) FEATURE:
    (A) NAME/KEY: Modified-site
    (B) LOCATION: 46
    (D) OTHER INFORMATION: /note= "Xaa at position 46 is Asp,
        Phe, Ser, Ala, Gln, Glu, His, Val, or Thr"

(ix) FEATURE:
    (A) NAME/KEY: Modified-site
    (B) LOCATION: 50
    (D) OTHER INFORMATION: /note= "Xaa at position 50 is Glu,
        Asn, Ser, or Asp"

(ix) FEATURE:
    (A) NAME/KEY: Modified-site
    (B) LOCATION: 51
    (D) OTHER INFORMATION: /note= "Xaa at position 51 is Asn,
        Arg, Pro, Thr, or His"

(ix) FEATURE:
    (A) NAME/KEY: Modified-site
    (B) LOCATION: 55
    (D) OTHER INFORMATION: /note= "Xaa at position 55 is Arg,
        Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Ser, Ala, Asn, Val, Leu, or Gln"

(ix) FEATURE:
    (A) NAME/KEY: Modified-site
    (B) LOCATION: 62
    (D) OTHER INFORMATION: /note= "Xaa at position 62 is Asn,
        Pro, or Thr"

(ix) FEATURE:
    (A) NAME/KEY: Modified-site
    (B) LOCATION: 64
    (D) OTHER INFORMATION: /note= "Xaa at position 64 is Ala
        or Asn"

(ix) FEATURE:
    (A) NAME/KEY: Modified-site
    (B) LOCATION: 65
    (D) OTHER INFORMATION: /note= "Xaa at position 65 is Val
        or Thr"

```
(ix) FEATURE:
     (A) NAME/KEY: Modified-site
     (B) LOCATION: 67
     (D) OTHER INFORMATION: /note= "Xaa at position 67 is Ser
         or Phe"

(ix) FEATURE:
     (A) NAME/KEY: Modified-site
     (B) LOCATION: 68
     (D) OTHER INFORMATION: /note= "Xaa at position 68 is Leu
         or Phe"

(ix) FEATURE:
     (A) NAME/KEY: Modified-site
     (B) LOCATION: 69
     (D) OTHER INFORMATION: /note= "Xaa at position 69 is Gln,
         Ala, Glu, or Arg"

(ix) FEATURE:
     (A) NAME/KEY: Modified-site
     (B) LOCATION: 76
     (D) OTHER INFORMATION: /note= "Xaa at position 76 is Ser,
         Val, Asn, Pro, or Gly"

(ix) FEATURE:
     (A) NAME/KEY: Modified-site
     (B) LOCATION: 77
     (D) OTHER INFORMATION: /note= "Xaa at position 77 is Ile
         or Leu"

(ix) FEATURE:
     (A) NAME/KEY: Modified-site
     (B) LOCATION: 79
     (D) OTHER INFORMATION: /note= "Xaa at position 79 is Lys,
         Gly, Asn, Met, Arg, Ile, or Gly"

(ix) FEATURE:
     (A) NAME/KEY: Modified-site
     (B) LOCATION: 80
     (D) OTHER INFORMATION: /note= "Xaa at position 80 is Asn,
         Gly, Glu, or Arg"

(ix) FEATURE:
     (A) NAME/KEY: Modified-site
     (B) LOCATION: 82
     (D) OTHER INFORMATION: /note= "Xaa at position 82 is Leu,
         Gln, Trp, Arg, Asp, Asn, Glu, His, Met, Phe, Ser,
         Thr, Tyr, or Val"

(ix) FEATURE:
     (A) NAME/KEY: Modified-site
     (B) LOCATION: 87
     (D) OTHER INFORMATION: /note= "Xaa at position 87 is Leu
         or Ser"

(ix) FEATURE:
     (A) NAME/KEY: Modified-site
     (B) LOCATION: 88
     (D) OTHER INFORMATION: /note= "Xaa at position 88 is Ala
         or Trp"

(ix) FEATURE:
     (A) NAME/KEY: Modified-site
     (B) LOCATION: 91
     (D) OTHER INFORMATION: /note= "Xaa at position 91 is Ala
         or Pro"

(ix) FEATURE:
     (A) NAME/KEY: Modified-site
     (B) LOCATION: 93
     (D) OTHER INFORMATION: /note= "Xaa at position 93 is Thr,
         Asp, or Ala"

(ix) FEATURE:
     (A) NAME/KEY: Modified-site
     (B) LOCATION: 95
     (D) OTHER INFORMATION: /note= "Xaa at position 95 is His,
         Pro, Arg, Val, Gly, Asn, Ser, or Thr"

(ix) FEATURE:
```

-continued

```
          (A) NAME/KEY: Modified-site
          (B) LOCATION: 98
          (D) OTHER INFORMATION: /note= "Xaa at position 98 is His,
              Ile, Asn, Ala, Thr, Arg, Gln, Glu, Lys, Met, Ser,
              Tyr, Val, or Leu"

(ix) FEATURE:
          (A) NAME/KEY: Modified-site
          (B) LOCATION: 99
          (D) OTHER INFORMATION: /note= "Xaa at position 99 is Ile
              or Leu"

(ix) FEATURE:
          (A) NAME/KEY: Modified-site
          (B) LOCATION: 100
          (D) OTHER INFORMATION: /note= "Xaa at position 100 is Lys
              or Arg"

(ix) FEATURE:
          (A) NAME/KEY: Modified-site
          (B) LOCATION:  101
          (D) OTHER INFORMATION: /note= "Xaa at position 101 is Asp,
              Pro, Met, Lys, Thr, His, Pro, Asn, Ile, Leu, or Tyr"

(ix) FEATURE:
          (A) NAME/KEY: Modified-site
          (B) LOCATION: 105
          (D) OTHER INFORMATION: /note= "Xaa at position 105 is Asn,
              Pro, Ser, Ile, or Asp"

(ix) FEATURE:
          (A) NAME/KEY:  Modified-site
          (B) LOCATION:  108
          (D) OTHER INFORMATION:  /note= "Xaa at position 108 is Arg, Ala,
              or Ser"

(ix) FEATURE:
          (A) NAME/KEY: Modified-site
          (B) LOCATION: 109
          (D) OTHER INFORMATION: /note= "Xaa at position 109 is Arg,
              Thr, Glu, Leu, or Ser"

(ix) FEATURE:
          (A) NAME/KEY: Modified-site
          (B) LOCATION: 112
          (D) OTHER INFORMATION: /note= "Xaa at position 112 is Thr
              or Gln"

(ix) FEATURE:
          (A) NAME/KEY: Modified-site
          (B) LOCATION: 116
          (D) OTHER INFORMATION: /note= "Xaa at position 116 is Lys,
              Val, Trp, Ala, His, Phe, Tyr, or Ile"

(ix) FEATURE:
          (A) NAME/KEY: Modified-site
          (B) LOCATION: 117
          (D) OTHER INFORMATION: /note= "Xaa at position 117 is Thr
              or Ser"

(ix) FEATURE:
          (A) NAME/KEY: Modified-site
          (B) LOCATION: 120
          (D) OTHER INFORMATION: /note= "Xaa at position 120 is Asn,
              Pro, Leu, His, Val, or Gln"

(ix) FEATURE:
          (A) NAME/KEY: Modified-site
          (B) LOCATION: 121
          (D) OTHER INFORMATION: /note= "Xaa at position 121 is Ala,
              Ser, Ile, Pro, or Asp"

(ix) FEATURE:
          (A) NAME/KEY: Modified-site
          (B) LOCATION: 122
          (D) OTHER INFORMATION: /note= "Xaa at position 122 is Gln,
              Met, Trp, Phe, Pro, His, Ile, or Tyr"

(ix) FEATURE:
          (A) NAME/KEY: Modified-site
```

(B) LOCATION: 123
        (D) OTHER INFORMATION: /note= "Xaa at position 123 is Ala,
            Met, Glu, Ser, or Leu"

(xi) SEQUENCE DESCRIPTION: SEQ ID NO:18:

Ala Pro Met Thr Gln Thr Thr Ser Leu Lys Thr Ser Trp Val Asn Cys
1               5                   10                  15

Xaa Xaa Met Ile Asp Glu Xaa Ile Xaa Xaa Leu Lys Xaa Xaa Pro Xaa
            20                  25                  30

Pro Xaa Xaa Asp Phe Xaa Asn Leu Asn Xaa Glu Asp Xaa Xaa Ile Leu
        35                  40                  45

Met Xaa Xaa Asn Leu Arg Xaa Xaa Asn Leu Glu Ala Phe Xaa Arg Xaa
    50                  55                  60

Xaa Lys Xaa Xaa Xaa Asn Ala Ser Ala Ile Glu Xaa Xaa Leu Xaa Xaa
65                  70                  75                  80

Leu Xaa Pro Cys Leu Pro Xaa Xaa Thr Ala Xaa Pro Xaa Arg Xaa Pro
                85                  90                  95

Ile Xaa Xaa Xaa Xaa Gly Asp Trp Xaa Glu Phe Xaa Xaa Lys Leu Xaa
            100                 105                 110

Phe Tyr Leu Xaa Xaa Leu Glu Xaa Xaa Xaa Gln Gln Thr Thr Leu
        115                 120                 125

Ser Leu Ala Ile Phe
        130

(2) INFORMATION FOR SEQ ID NO:19:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Lys, Gly, Asp, Met, Gln, or Arg"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, Gly, Ala, or Cys"

(ix) FEATURE:
        (A) NAME/KEY: Modified-site
        (B) LOCATION: 6
        (D) OTHER INFORMATION: /note= "Xaa at position 6 is Ile,
            Cys, Gln, Glu, Arg, Pro, or Ala"

(ix) FEATURE:
        (A) NAME/KEY: Modified-site
        (B) LOCATION: 7
        (D) OTHER INFORMATION: /note= "Xaa at position 7 is Asp,
            Phe, Lys, Arg, Ala, Gly, Glu, Gln, Asn, Thr, Ser,
            or Val"

```
    (ix) FEATURE:
          (A) NAME/KEY: Modified-site
          (B) LOCATION: 8
          (D) OTHER INFORMATION: /note= "Xaa at position 8 is Glu,
              Trp, Pro, Ser, Ala, His, Asp, Asn, Gln, Leu, Val,
              or Gly"

(ix) FEATURE:
          (A) NAME/KEY: Modified-site
          (B) LOCATION: 9
          (D) OTHER INFORMATION: /note= "Xaa at position 9 is
              Ile, Val, Ala, Leu, Gly, Trp, Lys, Phe, Leu, Ser
              or Arg"

(ix) FEATURE:
          (A) NAME/KEY: Modified-site
          (B) LOCATION: 10
          (D) OTHER INFORMATION: /note= "Xaa at position 10 is Ile,
              Gly, Val, Arg, Ser, Phe, or Leu"

(ix) FEATURE:
          (A) NAME/KEY: Modified-site
          (B) LOCATION: 11
          (D) OTHER INFORMATION: /note= "Xaa at position 11 is Thr,
              His, Gly, Gln, Arg, Pro, or Ala"

(ix) FEATURE:
          (A) NAME/KEY: Modified-site
          (B) LOCATION: 12
          (D) OTHER INFORMATION: /note= "Xaa at position 12 is His,
              Thr, Phe, Gly, Arg, Ala, or Trp"

(ix) FEATURE:
          (A) NAME/KEY: Modified-site
          (B) LOCATION: 13
          (D) OTHER INFORMATION: /note= "Xaa at position 13 is Leu,
              Gly, Arg, Thr, Ser, or Ala"

(ix) FEATURE:
          (A) NAME/KEY: Modified-site
          (B) LOCATION: 14
          (D) OTHER INFORMATION: /note= "Xaa at position 14 is Lys,
              Arg, Leu, Gln, Gly, Pro, Val, or Trp"

(ix) FEATURE:
          (A) NAME/KEY: Modified-site
          (B) LOCATION: 15
          (D) OTHER INFORMATION: /note= "Xaa at position 15 is Gln,
              Asn, Leu, Pro, Arg, or Val"

(ix) FEATURE:
          (A) NAME/KEY: Modified-site
          (B) LOCATION: 16
          (D) OTHER INFORMATION: /note= "Xaa at position 16 is Pro,
              His, Thr, Gly, Asp, Gln, Ser, Leu, or Lys"

(ix) FEATURE:
          (A) NAME/KEY: Modified-site
          (B) LOCATION: 17
          (D) OTHER INFORMATION: /note= "Xaa at position 17 is Pro,
              Asp, Gly, Ala, Arg, Leu, or Gln"

(ix) FEATURE:
          (A) NAME/KEY: Modified-site
          (B) LOCATION: 18
          (D) OTHER INFORMATION: /note= "Xaa at position 18 is Leu,
              Val, Arg, Gln, Asn, Gly, Ala, or Glu"

(ix) FEATURE:
          (A) NAME/KEY: Modified-site
          (B) LOCATION: 19
          (D) OTHER INFORMATION: /note= "Xaa at position 19 is Pro,
              Leu, Gln, Ala, Thr, or Glu"

(ix) FEATURE:
          (A) NAME/KEY: Modified-site
          (B) LOCATION: 20
          (D) OTHER INFORMATION: /note= "Xaa at position 20 is Leu,
              Val, Gly, Ser, Lys, Glu, Gln, Thr, Arg, Ala, Phe,
              Ile, or Met"
```

(ix) FEATURE:
    (A) NAME/KEY: Modified-site
    (B) LOCATION: 21
    (D) OTHER INFORMATION: /note= "Xaa at position 21 is Leu,
        Ala, Gly, Asn, Pro, Gln, or Val"

(ix) FEATURE:
    (A) NAME/KEY: Modified-site
    (B) LOCATION: 22
    (D) OTHER INFORMATION: /note= "Xaa at position 22 is Asp,
        Leu, or Val"

(ix) FEATURE:
    (A) NAME/KEY: Modified-site
    (B) LOCATION: 23
    (D) OTHER INFORMATION: /note= "Xaa at position 23 is Phe,
        Ser, Pro, Trp, or Ile"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 26
    (D) OTHER INFORMATION: /note= "Xaa at position 26 is Leu,
        Trp, or Arg"

(ix) FEATURE:
    (A) NAME/KEY: Modified-site
    (B) LOCATION: 27
    (D) OTHER INFORMATION: /note= "Xaa at position 27 is Asn,
        Cys, Arg, Leu, His, Met, or Pro"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Lys, Asn, Thr, Leu, Val, Glu,
        Phe, Tyr, Ile, or Met"

(ix) FEATURE:
    (A) NAME/KEY: Modified-site
    (B) LOCATION: 29
    (D) OTHER INFORMATION: /note= "Xaa at position 29 is Glu,
        Asn, Tyr, Leu, Phe, Asp, Ala, Cys, Gln, Arg, Thr,
        Gly, or Ser"

(ix) FEATURE:
    (A) NAME/KEY: Modified-site
    (B) LOCATION: 30
    (D) OTHER INFORMATION: /note= "Xaa at position 30 is Asp,
        Ser, Leu, Arg, Lys, Thr, Met, Trp, Glu, Asn, Gln,
        Ala, or Pro"

(ix) FEATURE:
    (A) NAME/KEY: Modified-site
    (B) LOCATION: 31
    (D) OTHER INFORMATION: /note= "Xaa at position 31 is Gln,
        Pro, Phe, Val, Met, Leu, Thr, Lys, Asp, Asn, Arg,
        Ser, Ala, Ile, Glu, His, or Trp"

(ix) FEATURE:
    (A) NAME/KEY: Modified-site
    (B) LOCATION: 32
    (D) OTHER INFORMATION: /note= "Xaa at position 32 is Asp,
        Phe, Ser, Thr, Cys, Glu, Asn, Gln, Lys, His, Ala,
        Tyr, Ile, Val, or Gly"

(ix) FEATURE:
    (A) NAME/KEY: Modified-site
    (B) LOCATION: 33
    (D) OTHER INFORMATION: /note= "Xaa at position 33 is Ile,
        Gly, Val, Ser, Arg, Pro, or His"

(ix) FEATURE:
    (A) NAME/KEY: Modified-site (B) LOCATION: 34
           (D) OTHER INFORMATION: /note= "Xaa at position 34 is Leu,
               Ser, Cys, Arg, Ile, His, Phe, Glu, Lys, Thr, Ala,
               Met, Val, or Asn"

(ix) FEATURE:
           (A) NAME/KEY: Modified-site
           (B) LOCATION: 35
           (D) OTHER INFORMATION: /note= "Xaa at position 35 is Met,
               Arg, Ala, Gly, Pro, Asn, His, or Asp"

(ix) FEATURE:
           (A) NAME/KEY: Modified-site
           (B) LOCATION: 36
           (D) OTHER INFORMATION: /note= "Xaa at position 36 is Glu,
               Leu, Thr, Asp, Tyr, Lys, Asn, Ser, Ala, Ile, Val,
               His, Phe, Met, or Gln"

(ix) FEATURE:
           (A) NAME/KEY: Modified-site
           (B) LOCATION: 37
           (D) OTHER INFORMATION: /note= "Xaa at position 37 is Asn,
               Arg, Met, Pro, Ser, Thr, or His"

(ix) FEATURE:
           (A) NAME/KEY: Modified-site
           (B) LOCATION: 38
           (D) OTHER INFORMATION: /note= "Xaa at position 38 is Asn,
               His, Arg, Leu, Gly, Ser, or Thr"

(ix) FEATURE:
           (A) NAME/KEY: Modified-site
           (B) LOCATION: 39
           (D) OTHER INFORMATION: /note= "Xaa at position 39 is
               Leu, Thr, Ala, Gly, Glu, Pro, Lys, Ser, or Met"

(ix) FEATURE:
           (A) NAME/KEY: Modified-site
           (B) LOCATION: 40
           (D) OTHER INFORMATION: /note= "Xaa at position 40 is Arg,
               Asp, Ile, Ser, Val, Thr, Gln, Asn, Lys, His,
               Ala, or Leu"

(ix) FEATURE:
           (A) NAME/KEY: Modified-site
           (B) LOCATION: 41
           (D) OTHER INFORMATION: /note= "Xaa at position 41 is Arg,
               Thr, Val, Ser, Leu, or Gly"

(ix) FEATURE:
           (A) NAME/KEY: Modified-site
           (B) LOCATION: 42
           (D) OTHER INFORMATION: /note= "Xaa at position 42 is Pro,
               Gly, Cys, Ser, Gln, Glu, Arg, His, Thr, Ala, Tyr,
               Phe, Leu, Val, or Lys"

(ix) FEATURE:
           (A) NAME/KEY: Modified-site
           (B) LOCATION: 43
           (D) OTHER INFORMATION: /note= "Xaa at position 43 is Asn
               or Gly"

(ix) FEATURE:
           (A) NAME/KEY: Modified-site
           (B) LOCATION: 44
           (D) OTHER INFORMATION: /note= "Xaa at position 44 is Leu,
               Ser, Asp, Arg, Gln, Val, or Cys"

(ix) FEATURE:
           (A) NAME/KEY: Modified-site
           (B) LOCATION: 45
           (D) OTHER INFORMATION: /note= "Xaa at position 45 is Glu,
               Tyr, His, Leu, Pro, or Arg"

(ix) FEATURE:
           (A) NAME/KEY: Modified-site
           (B) LOCATION: 46
           (D) OTHER INFORMATION: /note= "Xaa at position 46 is Ala,
               Ser, Pro, Tyr, Asn, or Thr"

```
(ix) FEATURE:
    (A) NAME/KEY: Modified-site
    (B) LOCATION: 47
    (D) OTHER INFORMATION: /note= "Xaa at position 47 is Phe,
        Asn, Glu, Pro, Lys, Arg, or Ser"

(ix) FEATURE:
    (A) NAME/KEY: Modified-site
    (B) LOCATION: 48
    (D) OTHER INFORMATION: /note= "Xaa at position 48 is Asn,
        His, Val, Arg, Pro, Thr, Asp, or Ile"

(ix) FEATURE:
    (A) NAME/KEY: Modified-site
    (B) LOCATION: 49
    (D) OTHER INFORMATION: /note= "Xaa at position 49 is Arg,
        Tyr, Trp, Lys, Ser, His, Pro, or Val"

(ix) FEATURE:
    (A) NAME/KEY: Modified-site
    (B) LOCATION: 50
    (D) OTHER INFORMATION: /note= "Xaa at position 50 is Ala,
        Asn, Pro, Ser, or Lys"

(ix) FEATURE:
    (A) NAME/KEY: Modified-site
    (B) LOCATION: 51
    (D) OTHER INFORMATION: /note= "Xaa at position 51 is Val,
        Thr, Pro, His, Leu, Phe, or Ser"

(ix) FEATURE:
    (A) NAME/KEY: Modified-site
    (B) LOCATION: 52
    (D) OTHER INFORMATION: /note= "Xaa at position 52 is Lys,
        Ile, Arg, Val, Asn, Glu, or Ser"

(ix) FEATURE:
    (A) NAME/KEY: Modified-site
    (B) LOCATION: 53
    (D) OTHER INFORMATION: /note= "Xaa at position 53 is Ser,
        Ala, Phe, Val, Gly, Asn, Ile, Pro, or His"

(ix) FEATURE:
    (A) NAME/KEY: Modified-site
    (B) LOCATION: 54
    (D) OTHER INFORMATION: /note= "Xaa at position 54 is Leu,
        Val, Trp, Ser, Ile, Phe, Thr, or His"

(ix) FEATURE:
    (A) NAME/KEY: Modified-site
    (B) LOCATION: 55
    (D) OTHER INFORMATION: /note= "Xaa at position 55 is Gln,
        Ala, Pro, Thr, Glu, Arg, Trp, Gly, or Leu"

(ix) FEATURE:
    (A) NAME/KEY: Modified-site
    (B) LOCATION: 56
    (D) OTHER INFORMATION: /note= "Xaa at position 56 is Asn,
        Leu, Val, Trp, Pro, or Ala"

(ix) FEATURE:
    (A) NAME/KEY: Modified-site
    (B) LOCATION: 57
    (D) OTHER INFORMATION: /note= "Xaa at position 57 is Ala,
        Met, Leu, Pro, Arg, Glu, Thr, Gln, Trp, or Asn"

(ix) FEATURE:
    (A) NAME/KEY: Modified-site
    (B) LOCATION: 58
    (D) OTHER INFORMATION: /note= "Xaa at position 58 is Ser,
        Glu, Met, Ala, His, Asn, Arg, or Asp"

(ix) FEATURE:
    (A) NAME/KEY: Modified-site
    (B) LOCATION: 59
    (D) OTHER INFORMATION: /note= "Xaa at position 59 is Ala,
        Glu, Asp, Leu, Ser, Gly, Thr, or Arg"

(ix) FEATURE:
    (A) NAME/KEY: Modified-site
```

(B) LOCATION: 60
            (D) OTHER INFORMATION: /note= "Xaa at position 60 is Ile,
                Met, Thr, Pro, Arg, Gly, Ala"

(ix) FEATURE:
            (A) NAME/KEY: Modified-site
            (B) LOCATION: 61
            (D) OTHER INFORMATION: /note= "Xaa at position 61 is
                Glu, Lys, Gly, Asp, Pro, Trp, Arg, Ser, Gln,
                or Leu"

(ix) FEATURE:
            (A) NAME/KEY: Modified-site
            (B) LOCATION: 62
            (D) OTHER INFORMATION: /note= "Xaa at position 62 is Ser,
                Val, Ala, Asn, Trp, Glu, Pro, Gly, or Asp"

(ix) FEATURE:
            (A) NAME/KEY: Modified-site
            (B) LOCATION: 63
            (D) OTHER INFORMATION: /note= "Xaa at position 63 is Ile,
                Ser, Arg, Thr, or Leu"

(ix) FEATURE:
            (A) NAME/KEY: Modified-site
            (B) LOCATION: 64
            (D) OTHER INFORMATION: /note= "Xaa at position 64 is Leu,
                Ala, Ser, Glu, Phe, Gly, or Arg"

(ix) FEATURE:
            (A) NAME/KEY: Modified-site
            (B) LOCATION: 65
            (D) OTHER INFORMATION: /note= "Xaa at position 65 is Lys,
                Thr, Gly, Asn, Met, Arg, Ile, or Asp"

(ix) FEATURE:
            (A) NAME/KEY: Modified-site
            (B) LOCATION: 66
            (D) OTHER INFORMATION: /note= "Xaa at position 66 is Asn,
                Trp, Val, Gly, Thr, Leu, Glu, or Arg"

(ix) FEATURE:
            (A) NAME/KEY: Modified-site
            (B) LOCATION: 67
            (D) OTHER INFORMATION: /note= "Xaa at position 67 is Leu,
                Gln, Gly, Ala, Trp, Arg, Val, or Lys"

(ix) FEATURE:
            (A) NAME/KEY: Modified-site
            (B) LOCATION: 68
            (D) OTHER INFORMATION: /note= "Xaa at position 68 is Leu,
                Gln, Lys, Trp, Arg, Asp, Glu, Asn, His, Thr, Ser, Ala,
                Tyr, Phe, Ile, Met, or Val"

(ix) FEATURE:
            (A) NAME/KEY: Modified-site
            (B) LOCATION: 69
            (D) OTHER INFORMATION: /note= "Xaa at position 69 is Pro,
                Ala, Thr, Trp, Arg, or Met"

(ix) FEATURE:
            (A) NAME/KEY: Modified-site
            (B) LOCATION: 70
            (D) OTHER INFORMATION: /note= "Xaa at position 70 is Cys,
                Glu, Gly, Arg, Met, or Val"

(ix) FEATURE:
            (A) NAME/KEY: Modified-site
            (B) LOCATION: 71
            (D) OTHER INFORMATION: /note= "Xaa at position 71 is Leu,
                Asn, Val, or Gln"

(ix) FEATURE:
            (A) NAME/KEY: Modified-site
            (B) LOCATION: 72
            (D) OTHER INFORMATION: /note= "Xaa at position 72 is Pro,
                Cys, Arg, Ala, or Lys"

(ix) FEATURE:
            (A) NAME/KEY: Modified-site

-continued

```
       (B) LOCATION: 73
       (D) OTHER INFORMATION: /note= "Xaa at position 73 is Leu,
           Ser, Trp, or Gly"

(ix) FEATURE:
       (A) NAME/KEY: Modified-site
       (B) LOCATION: 74
       (D) OTHER INFORMATION: /note= "Xaa at position 74 is Ala,
           Lys, Arg, Val, or Trp"

(ix) FEATURE:
       (A) NAME/KEY: Modified-site
       (B) LOCATION: 75
       (D) OTHER INFORMATION: /note= "Xaa at position 75 is Thr,
           Asp, Cys, Leu, Val, Glu, His, Asn, or Ser"

(ix) FEATURE:
       (A) NAME/KEY: Modified-site
       (B) LOCATION: 76
       (D) OTHER INFORMATION: /note= "Xaa at position 76 is Ala,
           Pro, Ser, Thr, Gly, Asp, Ile, or Met"

(ix) FEATURE:
       (A) NAME/KEY: Modified-site
       (B) LOCATION: 77
       (D) OTHER INFORMATION: /note= "Xaa at position 77 is Ala,
           Pro, Ser, Thr, Phe, Leu, Asp, or His"

(ix) FEATURE:
       (A) NAME/KEY: Modified-site
       (B) LOCATION: 78
       (D) OTHER INFORMATION: /note= "Xaa at position 78 is Pro,
           Phe, Arg, Ser, Lys, His, Ala, Gly, Ile, or Leu"

(ix) FEATURE:
       (A) NAME/KEY: Modified-site
       (B) LOCATION: 79
       (D) OTHER INFORMATION: /note= "Xaa at position 79 is Thr,
           Asp, Ser, Asn, Pro, Ala, Leu, or Arg"

(ix) FEATURE:
       (A) NAME/KEY: Modified-site
       (B) LOCATION: 80
       (D) OTHER INFORMATION: /note= "Xaa at position 80 is Arg,
           Ile, Ser, Glu, Leu, Val, Gln, Lys, His, Ala, or Pro"

(ix) FEATURE:
       (A) NAME/KEY: Modified-site
       (B) LOCATION: 81
       (D) OTHER INFORMATION: /note= "Xaa at position 81 is His,
           Gln, Pro, Arg, Val, Leu, Gly, Thr, Asn, Lys, Ser,
           Ala, Trp, Phe, Ile, or Tyr"

(ix) FEATURE:
       (A) NAME/KEY: Modified-site
       (B) LOCATION: 82
       (D) OTHER INFORMATION: /note= "Xaa at position 82 is Pro,
           Lys, Tyr, Gly, Ile, or Thr"

(ix) FEATURE:
       (A) NAME/KEY: Modified-site
       (B) LOCATION: 83
       (D) OTHER INFORMATION: /note= "Xaa at position 83 is Ile,
           Val, Lys, Ala, or Asn"

(ix) FEATURE:
       (A) NAME/KEY: Modified-site
       (B) LOCATION: 84
       (D) OTHER INFORMATION: /note= "Xaa at position 84 is His,
           Ile, Asn, Leu, Asp, Ala, Thr, Glu, Gln, Ser,
           Phe, Met, Val, Lys, Arg, Tyr, or Pro"

(ix) FEATURE:
       (A) NAME/KEY: Modified-site
       (B) LOCATION: 85
       (D) OTHER INFORMATION: /note= "Xaa at position 85 is
           Ile, Leu, Arg, Asp, Val, Pro, Gln, Gly, Ser,
           Phe, or His"

(ix) FEATURE:
```

(A) NAME/KEY: Modified-site
        (B) LOCATION: 86
        (D) OTHER INFORMATION: /note= "Xaa at position 86 is
            Lys, Tyr, Leu, His, Arg, Ile, Ser, Gln, or Pro"

(ix) FEATURE:
        (A) NAME/KEY: Modified-site
        (B) LOCATION: 87
        (D) OTHER INFORMATION: /note= "Xaa at position 87 is
            Asp, Pro, Met, Lys, His, Thr, Val, Tyr, Glu, Asn,
            Ser, Ala, Gly, Ile, Leu, or Gln"

(ix) FEATURE:
        (A) NAME/KEY: Modified-site
        (B) LOCATION: 88
        (D) OTHER INFORMATION: /note= "Xaa at position 88 Gly,
            Leu, Glu, Lys, Ser, Tyr, or Pro"

(ix) FEATURE:
        (A) NAME/KEY: Modified-site
        (B) LOCATION: 89
        (D) OTHER INFORMATION: /note= "Xaa at position 89 is Asp
            or Ser"

(ix) FEATURE:
        (A) NAME/KEY: Modified-site
        (B) LOCATION: 90
        (D) OTHER INFORMATION: /note= "Xaa at position 90 is
            Trp, Val, Cys, Tyr, Thr, Met, Pro, Leu, Gln, Lys,
            Ala, Phe, or Gly"

(ix) FEATURE:
        (A) NAME/KEY: Modified-site
        (B) LOCATION: 91
        (D) OTHER INFORMATION: /note= "Xaa at position 91 is
            Asn, Pro, Ala, Phe, Ser, Trp, Gln, Tyr, Leu, Lys,
            Ile, Asp, or His"

(ix) FEATURE:
        (A) NAME/KEY: Modified-site
        (B) LOCATION: 92
        (D) OTHER INFORMATION: /note= "Xaa at position 92 is Glu,
            Ser, Ala, Lys, Thr, Ile, Gly, or Pro"

(ix) FEATURE:
        (A) NAME/KEY: Modified-site
        (B) LOCATION: 94
        (D) OTHER INFORMATION: /note= "Xaa at position 94 is Arg,
            Lys, Asp, Leu, Thr, Ile, Gln, His, Ser, Ala, or Pro"

(ix) FEATURE:
        (A) NAME/KEY: Modified-site
        (B) LOCATION: 95
        (D) OTHER INFORMATION: /note= "Xaa at position 95 is Arg,
            Thr, Pro, Glu, Tyr, Leu, Ser, or Gly"

(ix) FEATURE:
        (A) NAME/KEY: Modified-site
        (B) LOCATION: 96
        (D) OTHER INFORMATION: /note= "Xaa at position 96 is Lys,
            Asn, Thr, Leu, Gln, Arg, His, Glu, Ser, Ala,
            or Trp"

(ix) FEATURE:
        (A) NAME/KEY: Modified-site
        (B) LOCATION: 97
        (D) OTHER INFORMATION: /note= "Xaa at position 97 is Leu,
            Ile, Arg, Asp, or Met"

(ix) FEATURE:
        (A) NAME/KEY: Modified-site
        (B) LOCATION: 98
        (D) OTHER INFORMATION: /note= "Xaa at position 98 is Thr,
            Val, Gln, Tyr, Glu, His, Ser, or Phe"

(ix) FEATURE:
        (A) NAME/KEY: Modified-site
        (B) LOCATION: 99
        (D) OTHER INFORMATION: /note= "Xaa at position 99 is Phe,
            Ser, Cys, His, Gly, Trp, Tyr, Asp, Lys, Leu, Ile, Val, or Asn"

(ix) FEATURE:
    (A) NAME/KEY: Modified-site
    (B) LOCATION: 100
    (D) OTHER INFORMATION: /note= "Xaa at position 100 is Tyr,
        Cys, His, Ser, Trp, Arg, or Leu"

(ix) FEATURE:
    (A) NAME/KEY: Modified-site
    (B) LOCATION: 101
    (D) OTHER INFORMATION: /note= "Xaa at position 101 is Leu,
        Asn, Val, Pro, Arg, Ala, His, Thr, Trp, or Met"

(ix) FEATURE:
    (A) NAME/KEY: Modified-site
    (B) LOCATION: 102
    (D) OTHER INFORMATION: /note= "Xaa at position 102 is
        Lys, Leu, Pro, Thr, Met, Asp, Val, Glu, Arg, Trp,
        Ser, Asn, His, Ala, Tyr, Phe, Gln, or Ile"

(ix) FEATURE:
    (A) NAME/KEY: Modified-site
    (B) LOCATION: 103
    (D) OTHER INFORMATION: /note= "Xaa at position 103 is Thr,
        Ser, Asn, Ile, Trp, Lys, or Pro"

(ix) FEATURE:
    (A) NAME/KEY: Modified-site
    (B) LOCATION: 104
    (D) OTHER INFORMATION: /note= "Xaa at position 104 is Leu,
        Ser, Pro, Ala, Glu, Cys, Asp, or Tyr"

(ix) FEATURE:
    (A) NAME/KEY: Modified-site
    (B) LOCATION: 105
    (D) OTHER INFORMATION: /note= "Xaa at position 105 is Glu,
        Ser, Lys, Pro, Leu, Thr, Tyr, or Arg"

(ix) FEATURE:
    (A) NAME/KEY: Modified-site
    (B) LOCATION: 106
    (D) OTHER INFORMATION: /note= "Xaa at position 106 is Asn,
        Ala, Pro, Leu, His, Val or Gln"

(ix) FEATURE:
    (A) NAME/KEY: Modified-site
    (B) LOCATION: 107
    (D) OTHER INFORMATION: /note= "Xaa at position 107 is Ala,
        Ser, Ile, Asn, Pro, Lys, Asp, or Gly"

(ix) FEATURE:
    (A) NAME/KEY: Modified-site
    (B) LOCATION: 108
    (D) OTHER INFORMATION: /note= "Xaa at position 108 is
        Gln, Ser, Met, Trp, Arg, Phe, Pro, His, Ile, Tyr,
        or Cys"

(ix) FEATURE:
    (A) NAME/KEY: Modified-site
    (B) LOCATION: 109
    (D) OTHER INFORMATION: /note= "Xaa at position 109 is Ala,
        Met, Glu, His, Ser, Pro, Tyr, or Leu"

(xi) SEQUENCE DESCRIPTION: SEQ ID NO:19:

Asn Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Asn Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

```
        Xaa Xaa Xaa Xaa Xaa Xaa Xaa Xaa Xaa Xaa Xaa Phe Xaa Xaa Xaa
                    85                  90                  95

Xaa Xaa Xaa Xaa Xaa Xaa Xaa Xaa Xaa Xaa Xaa Xaa Xaa Gln Gln
                100                 105                 110
```

(2) INFORMATION FOR SEQ ID NO:20:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, Met, or Gln"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, or Ala"

(ix) FEATURE:
        (A) NAME/KEY: Modified-site
        (B) LOCATION: 6
        (D) OTHER INFORMATION: /note= "Xaa at position 6 is Ile or
            Pro"

(ix) FEATURE:
        (A) NAME/KEY: Modified-site
        (B) LOCATION: 7
        (D) OTHER INFORMATION: /note= "Xaa at position 7 is Asp or
            Glu"

(ix) FEATURE:
        (A) NAME/KEY: Modified-site
        (B) LOCATION: 9
        (D) OTHER INFORMATION: /note= "Xaa at position 9 is Ile,
            Val, Ala, Leu, or Gly"

(ix) FEATURE:
        (A) NAME/KEY: Modified-site
        (B) LOCATION: 10
        (D) OTHER INFORMATION: /note= "Xaa at position 10 is Ile,
            Val, Phe, or Leu"

(ix) FEATURE:
        (A) NAME/KEY: Modified-site
        (B) LOCATION: 11
        (D) OTHER INFORMATION: /note= "Xaa at position 11 is Thr,
            His, Gly, Gln, Arg, Pro, or Ala"

(ix) FEATURE:
        (A) NAME/KEY: Modified-site
        (B) LOCATION: 12
        (D) OTHER INFORMATION: /note= "Xaa at position 12 is His,
            Phe, Gly, Arg, or Ala"

(ix) FEATURE:
        (A) NAME/KEY: Modified-site
        (B) LOCATION: 14

(D) OTHER INFORMATION: /note= "Xaa at position 14 is Lys,
                 Leu, Gln, Gly, Pro, or Val"

(ix) FEATURE:
             (A) NAME/KEY: Modified-site
             (B) LOCATION: 15
             (D) OTHER INFORMATION: /note= "Xaa at position 15 is Gln,
                 Asn, Leu, Arg, or Val"

(ix) FEATURE:
             (A) NAME/KEY: Modified-site
             (B) LOCATION: 16
             (D) OTHER INFORMATION: /note= "Xaa at position 16 is Pro,
                 His, Thr, Gly, or Gln"

(ix) FEATURE:
             (A) NAME/KEY: Modified-site
             (B) LOCATION: 17
             (D) OTHER INFORMATION: /note= "Xaa at position 17 is Pro,
                 Asp, Gly, Ala, Arg, Leu, or Gln"

(ix) FEATURE:
             (A) NAME/KEY: Modified-site
             (B) LOCATION: 18
             (D) OTHER INFORMATION: /note= "Xaa at position 18 is Leu,
                 Arg, Gln, Asn, Gly, Ala or Glu"

(ix) FEATURE:
             (A) NAME/KEY: Modified-site
             (B) LOCATION: 19
             (D) OTHER INFORMATION: /note= "Xaa at poisiton 19 is Pro,
                 Leu, Gln, Ala, or Glu"

(ix) FEATURE:
             (A) NAME/KEY: Modified-site
             (B) LOCATION: 20
             (D) OTHER INFORMATION: /note= "Xaa at positon 20 is Leu,
                 Val, Gly, Ser, Lys, Ala, Arg, Gln, Glu, Ile, Phe,
                 Thr, or Met"

(ix) FEATURE:
             (A) NAME/KEY: Modified-site
             (B) LOCATION: 21
             (D) OTHER INFORMATION: /note= "Xaa at position 21 is Leu,
                 Ala, Asn, Pro, Gln, or Val"

(ix) FEATURE:
             (A) NAME/KEY: Modified-site
             (B) LOCATION: 22
             (D) OTHER INFORMATION: /note= "Xaa at position 22 is Asp
                 or Leu"

(ix) FEATURE:
             (A) NAME/KEY: Modified-site
             (B) LOCATION: 23
             (D) OTHER INFORMATION: /note= "Xaa at position 23 is Phe,
                 Ser, Pro, Trp, or Ile"

(ix) FEATURE:
             (A) NAME/KEY: Modified-site
             (B) LOCATION: 24
             (D) OTHER INFORMATION: /note= "Xaa at position 24 is Asn
                 or Ala"

(ix) FEATURE:
             (A) NAME/KEY: Modified-site
             (B) LOCATION: 27
             (D) OTHER INFORMATION: /note= "Xaa at position 27 is Asn,
                 Cys, Arg, His, Met, or Pro"

(ix) FEATURE:
             (A) NAME/KEY: Modified-site
             (B) LOCATION: 28
             (D) OTHER INFORMATION: /note= "Xaa at position 28 is Gly,
                 Asp, Ser, Cys, Ala, Asn, Ile, Leu, Met, Tyr, or Arg"

(ix) FEATURE:
             (A) NAME/KEY: Modified-site
             (B) LOCATION: 30
             (C) OTHER INFORMATION:  /note= "Xaa at position 30 is Asp or Glu"

(ix) FEATURE:
      (A) NAME/KEY: Modified-site
      (B) LOCATION: 31
      (D) OTHER INFORMATION: /note= "Xaa at position 31 is Gln,
          Val, Met, Leu, Thr, Lys, Ala, Asn, Glu, Ser, or Trp"

(ix) FEATURE:
      (A) NAME/KEY: Modified-site
      (B) LOCATION: 32
      (D) OTHER INFORMATION: /note= "Xaa at position 32 is Asp,
          Phe, Ser, Thr, Cys, Ala, Asn, Gln, Glu, His, Ile,
          Lys, Tyr, Val, or Gly"

(ix) FEATURE:
      (A) NAME/KEY: Modified-site
      (B) LOCATION: 33
      (D) OTHER INFORMATION: /note= "Xaa at position 33 is Ile,
          Val, or His"

(ix) FEATURE:
      (A) NAME/KEY: Modified-site
      (B) LOCATION: 35
      (D) OTHER INFORMATION: /note= "Xaa at position 35 is Met,
          Asn, or Asp"

(ix) FEATURE:
      (A) NAME/KEY: Modified-site
      (B) LOCATION: 36
      (D) OTHER INFORMATION: /note= "Xaa at position 36 is Glu,
          Thr, Ala, Asn, Ser, or Asp"

(ix) FEATURE:
      (A) NAME/KEY: Modified-site
      (B) LOCATION: 37
      (D) OTHER INFORMATION: /note= "Xaa at position 37 is Asn,
          Arg, Met, Pro, Ser, Thr, or His"

(ix) FEATURE:
      (A) NAME/KEY: Modified-site
      (B) LOCATION: 38
      (D) OTHER INFORMATION: /note= "Xaa at position 38 is Asn
          or Gly"

(ix) FEATURE:
      (A) NAME/KEY: Modified-site
      (B) LOCATION: 39
      (D) OTHER INFORMATION: /note= "Xaa at position 39 is Leu,
          Met, or Phe"

(ix) FEATURE:
      (A) NAME/KEY: Modified-site
      (B) LOCATION: 40
      (D) OTHER INFORMATION: /note= "Xaa at position 40 is Arg,
          Ala, or Ser"

(ix) FEATURE:
      (A) NAME/KEY: Modified-site
      (B) LOCATION: 41
      (D) OTHER INFORMATION: /note= "Xaa at position 41 is Arg,
          Thr, Val, Leu, or Gly"

(ix) FEATURE:
      (A) NAME/KEY: Modified-site
      (B) LOCATION: 42
      (D) OTHER INFORMATION: /note= "Xaa at position 42 is Pro,
          Gly, Cys, Ser, Gln, Ala, Arg, Asn, Glu, His, Leu,
          Thr, Val, or Lys"

(ix) FEATURE:
      (A) NAME/KEY: Modified-site
      (B) LOCATION: 45
      (D) OTHER INFORMATION: /note= "Xaa at position 45 is Glu,
          Tyr, His, Leu, or Arg"

(ix) FEATURE:
      (A) NAME/KEY: Modified-site
      (B) LOCATION: 46
      (D) OTHER INFORMATION: /note= "Xaa at position 46 is Ala,

```
              Ser, Asn, or Thr"

(ix) FEATURE:
      (A) NAME/KEY: Modified-site
      (B) LOCATION: 47
      (D) OTHER INFORMATION: /note= "Xaa at position 47 is Phe
           or Ser"

(ix) FEATURE:
      (A) NAME/KEY: Modified-site
      (B) LOCATION: 48
      (D) OTHER INFORMATION: /note= "Xaa at position 48 is Asn,
           Val, Pro, Thr, or Ile"

(ix) FEATURE:
      (A) NAME/KEY: Modified-site
      (B) LOCATION: 49
      (D) OTHER INFORMATION: /note= "Xaa at position 49 is Arg,
           Tyr, Lys, Ser, His, or Val"

(ix) FEATURE:
      (A) NAME/KEY: Modified-site
      (B) LOCATION: 50
      (D) OTHER INFORMATION: /note= "Xaa at position 50 is Ala
           or Asn"

(ix) FEATURE:
      (A) NAME/KEY: Modified-site
      (B) LOCATION: 51
      (D) OTHER INFORMATION: /note= "Xaa at position 51 is Val,
           Thr, Leu, or Ser"

(ix) FEATURE:
      (A) NAME/KEY: Modified-site
      (B) LOCATION: 52
      (D) OTHER INFORMATION: /note= "Xaa at position 52 is Lys,
           Ile, Arg, Val, Asn, Glu, or Ser"

(ix) FEATURE:
      (A) NAME/KEY: Modified-site
      (B) LOCATION: 53
      (D) OTHER INFORMATION: /note= "Xaa at position 53 is Ser,
           Phe, Val, Gly, Asn, Ile, or His"

(ix) FEATURE:
      (A) NAME/KEY: Modified-site
      (B) LOCATION: 54
      (D) OTHER INFORMATION: /note= "Xaa at position 54 is Leu,
           Val, Ile, Phe, or His"

(ix) FEATURE:
      (A) NAME/KEY: Modified-site
      (B) LOCATION: 55
      (D) OTHER INFORMATION: /note= "Xaa at position 55 is Gln,
           Ala, Pro, Thr, Glu, Arg, or Gly"

(ix) FEATURE:
      (A) NAME/KEY: Modified-site
      (B) LOCATION: 56
      (D) OTHER INFORMATION: /note= "Xaa at position 56 is Asn
           or Pro"

(ix) FEATURE:
      (A) NAME/KEY: Modified-site
      (B) LOCATION: 57
      (D) OTHER INFORMATION: /note= "Xaa at position 57 is Ala,
           Met, Pro, Arg, Glu, Thr, or Gln"

(ix) FEATURE:
      (A) NAME/KEY: Modified-site
      (B) LOCATION: 58
      (D) OTHER INFORMATION: /note= "Xaa at position 58 is Ser,
           Glu, Met, Ala, His, Asn, Arg, or Asp"

(ix) FEATURE:
      (A) NAME/KEY: Modified-site
      (B) LOCATION: 59
      (D) OTHER INFORMATION: /note= "Xaa at position 59 is Ala,
           Glu, Asp, Leu, Ser, Gly, Thr, Arg, or Pro"
```

(ix) FEATURE:
    (A) NAME/KEY: Modified-site
    (B) LOCATION: 60
    (D) OTHER INFORMATION: /note= "Xaa at position 60 is Ile or Met"

(ix) FEATURE:
    (A) NAME/KEY: Modified-site
    (B) LOCATION: 61
    (D) OTHER INFORMATION: /note= "Xaa at position 61 is Glu, Gly, Asp, Ser, or Gln"

(ix) FEATURE:
    (A) NAME/KEY: Modified-site
    (B) LOCATION: 62
    (D) OTHER INFORMATION: /note= "Xaa at position 62 is Ser, Val, Ala, Asn, Glu, Pro, Gly, or Asp"

(ix) FEATURE:
    (A) NAME/KEY: Modified-site
    (B) LOCATION: 63
    (D) OTHER INFORMATION: /note= "Xaa at position 63 is Ile, Ser, or Leu"

(ix) FEATURE:
    (A) NAME/KEY: Modified-site
    (B) LOCATION: 65
    (D) OTHER INFORMATION: /note= "Xaa at position 65 is Lys, Thr, Gly, Asn, Met, Arg, Ile, or Asp"

(ix) FEATURE:
    (A) NAME/KEY: Modified-site
    (B) LOCATION: 66
    (D) OTHER INFORMATION: /note= "Xaa at position 66 is Asn, Val, Gly, Thr, Leu, Glu, or Arg"

(ix) FEATURE:
    (A) NAME/KEY: Modified-site
    (B) LOCATION: 67
    (D) OTHER INFORMATION: /note= "Xaa at position 67 is Leu or Val"

(ix) FEATURE:
    (A) NAME/KEY: Modified-site
    (B) LOCATION: 68
    (D) OTHER INFORMATION: /note= "Xaa at position 68 is Leu, Gln, Trp, Arg, Asp, Ala, Asn, Glu, His, Met, Phe, Ser, Thr, Tyr, or Val"

(ix) FEATURE:
    (A) NAME/KEY: Modified-site
    (B) LOCATION: 69
    (D) OTHER INFORMATION: /note= "Xaa at position 69 is Pro, Ala, Thr, Trp, or Met"

(ix) FEATURE:
    (A) NAME/KEY: Modified-site
    (B) LOCATION: 71
    (D) OTHER INFORMATION: /note= "Xaa at position 71 is Leu or Val"

(ix) FEATURE:
    (A) NAME/KEY: Modified-site
    (B) LOCATION: 73
    (D) OTHER INFORMATION: /note= "Xaa at position 73 is Leu or Ser"

(ix) FEATURE:
    (A) NAME/KEY: Modified-site
    (B) LOCATION: 74
    (D) OTHER INFORMATION: /note= "Xaa at position 74 is Ala, Arg, or Trp"

(ix) FEATURE:
    (A) NAME/KEY: Modified-site
    (B) LOCATION: 75
    (D) OTHER INFORMATION: /note= "Xaa at position 75 is Thr, Asp, Glu, His, Asn, or Ser"

(ix) FEATURE:

-continued

```
            (A) NAME/KEY: Modified-site
            (B) LOCATION: 76
            (D) OTHER INFORMATION: /note= "Xaa at position 76 is Ala,
                Asp, or Met"

(ix) FEATURE:
            (A) NAME/KEY: Modified-site
            (B) LOCATION: 77
            (D) OTHER INFORMATION: /note= "Xaa at position 77 is Ala,
                Pro, Ser, Thr, Phe, Leu, or Asp"

(ix) FEATURE:
            (A) NAME/KEY: Modified-site
            (B) LOCATION: 78
            (D) OTHER INFORMATION: /note= "Xaa at position 78 is Pro
                or Ser"

(ix) FEATURE:
            (A) NAME/KEY: Modified-site
            (B) LOCATION: 79
            (D) OTHER INFORMATION: /note= "Xaa at position 79 is Thr,
                Asp, Ser, Pro, Ala, Leu, or Arg"

(ix) FEATURE:
            (A) NAME/KEY: Modified-site
            (B) LOCATION: 81
            (D) OTHER INFORMATION: /note= "Xaa at position 81 is His,
                Pro, Arg, Val, Leu, Gly, Asn, Ile, Phe, Ser, or Thr"

(ix) FEATURE:
            (A) NAME/KEY: Modified-site
            (B) LOCATION: 82
            (D) OTHER INFORMATION: /note= "Xaa at position 82 is Pro
                or Tyr"

(ix) FEATURE:
            (A) NAME/KEY: Modified-site
            (B) LOCATION: 83
            (D) OTHER INFORMATION: /note= "Xaa at position 83 is Ile,
                Val, or Ala"

(ix) FEATURE:
            (A) NAME/KEY: Modified-site
            (B) LOCATION: 84
            (D) OTHER INFORMATION: /note= "Xaa at position 84 is His,
                Ile, Asn, Leu, Asp, Ala, Thr, Arg, Gln, Glu, Lys,
                Met, Ser, Tyr, Val, or Pro"

(ix) FEATURE:
            (A) NAME/KEY: Modified-site
            (B) LOCATION: 85
            (D) OTHER INFORMATION: /note= "Xaa at position 85 is Ile,
                Leu, Val, or Phe"

(ix) FEATURE:
            (A) NAME/KEY: Modified-site
            (B) LOCATION: 86
            (D) OTHER INFORMATION: /note= "Xaa at position 86 is Lys,
                Leu, His, Arg, Ile, Gln, Pro, or Ser"

(ix) FEATURE:
            (A) NAME/KEY: Modified-site
            (B) LOCATION: 87
            (D) OTHER INFORMATION: /note= "Xaa at position 87 is Asp,
                Pro, Met, Lys, His, Thr, Val, Asn, Ile, Leu, or Tyr"

(ix) FEATURE:
            (A) NAME/KEY: Modified-site
            (B) LOCATION: 88
            (D) OTHER INFORMATION: /note= "Xaa at position 88 is Gly,
                Glu, Lys, or Ser"

(ix) FEATURE:
            (A) NAME/KEY: Modified-site
            (B) LOCATION: 90
            (D) OTHER INFORMATION: /note= "Xaa at position 90 is Trp,
                Val, Tyr, Met, or Leu"

(ix) FEATURE:
            (A) NAME/KEY: Modified-site
```

```
        (B) LOCATION: 91
        (D) OTHER INFORMATION: /note=
            "Xaa at position 91 is Asn, Pro, Ala, Phe, Ser,
            Trp, Gln, Tyr, Leu, Lys, Ile, Asp, or His"

(ix) FEATURE:
        (A) NAME/KEY: Modified-site
        (B) LOCATION: 92
        (D) OTHER INFORMATION: /note= "Xaa at position 92 is Glu,
            Ser, Ala, or Gly"

(ix) FEATURE:
        (A) NAME/KEY: Modified-site
        (B) LOCATION: 94
        (D) OTHER INFORMATION: /note= "Xaa at position 94 is Arg,
            Ala, Gln, Ser, or Lys"

(ix) FEATURE:
        (A) NAME/KEY: Modified-site
        (B) LOCATION: 95
        (D) OTHER INFORMATION: /note= "Xaa at position 95 Arg,
            Thr, Glu, Leu, Ser, or Gly"

(ix) FEATURE:
        (A) NAME/KEY: Modified-site
        (B) LOCATION: 98
        (D) OTHER INFORMATION: /note= "Xaa at position 98 is Thr,
            Val, Gln, Glu, His, or Ser"

(ix) FEATURE:
        (A) NAME/KEY: Modified-site
        (B) LOCATION: 100
        (D) OTHER INFORMATION: /note= "Xaa at position 100 is Tyr
            or Trp"

(ix) FEATURE:
        (A) NAME/KEY: Modified-site
        (B) LOCATION: 101
        (D) OTHER INFORMATION: /note= "Xaa at position 101 is Leu
            or Ala"

(ix) FEATURE:
        (A) NAME/KEY: Modified-site
        (B) LOCATION: 102
        (D) OTHER INFORMATION: /note= "Xaa at position 102 is Lys,
            Thr, Met, Val, Trp, Ser, Leu, Ala, Asn, Gln, His,
            Met, Phe, Tyr, or Ile"

(ix) FEATURE:
        (A) NAME/KEY: Modified-site
        (B) LOCATION: 103
        (D) OTHER INFORMATION: /note= "Xaa at position 103 is Thr,
            Ser, or Asn"

(ix) FEATURE:
        (A) NAME/KEY: Modified-site
        (B) LOCATION: 105
        (D) OTHER INFORMATION: /note= "Xaa at position 105 is Glu,
            Ser, Pro, Leu, Thr, or Tyr"

(ix) FEATURE:
        (A) NAME/KEY: Modified-site
        (B) LOCATION: 106
        (D) OTHER INFORMATION: /note= "Xaa at position 106 is Asn,
            Pro, Leu, His, Val, or Gln"

(ix) FEATURE:
        (A) NAME/KEY: Modified-site
        (B) LOCATION: 107
        (D) OTHER INFORMATION: /note= "Xaa at position 107 is Ala,
            Ser, Ile, Asn, Pro, Lys, Asp, or Gly"

(ix) FEATURE:
        (A) NAME/KEY: Modified-site
        (B) LOCATION: 108
        (D) OTHER INFORMATION: /note=
            "Xaa at position 108 is Gln, Ser, Met, Trp, Arg, Phe,
            Pro, His, Ile, Tyr, or Cys"

(ix) FEATURE:
```

-continued (A) NAME/KEY: Modified-site
(B) LOCATION: 109
(D) OTHER INFORMATION: /note= "Xaa at position 109 is Ala, Met, Glu, His, Ser, Pro, Tyr, or Leu"

(xi) SEQUENCE DESCRIPTION: SEQ ID NO:20:

```
Asn Cys Xaa Xaa Xaa Xaa Xaa Glu Xaa Xaa Xaa Xaa Leu Xaa Xaa Xaa
1               5                   10                  15

Xaa Xaa Xaa Xaa Xaa Xaa Xaa Xaa Asn Leu Xaa Xaa Glu Xaa Xaa Xaa
            20                  25                  30

Xaa Leu Xaa Xaa Xaa Xaa Xaa Xaa Xaa Xaa Asn Leu Xaa Xaa Xaa Xaa
        35                  40                  45

Xaa Xaa Xaa Xaa Xaa Xaa Xaa Xaa Xaa Xaa Xaa Xaa Xaa Xaa Xaa Leu
    50                  55                  60

Xaa Xaa Xaa Xaa Xaa Cys Xaa Pro Xaa Xaa Xaa Xaa Xaa Xaa Xaa Arg
65                  70                  75                  80

Xaa Xaa Xaa Xaa Xaa Xaa Xaa Xaa Asp Xaa Xaa Xaa Phe Xaa Xaa Lys
            85                  90                  95

Leu Xaa Phe Xaa Xaa Xaa Xaa Leu Xaa Xaa Xaa Xaa Xaa Gln Gln
            100                 105                 110
```

(2) INFORMATION FOR SEQ ID NO:21:

(i) SEQUENCE CHARACTERISTICS:
(A) LENGTH: 111 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Met- or Met-Ala- may or may not precede the amino acid in position 1"

(ix) FEATURE:
(A) NAME/KEY: Modified-site
(B) LOCATION: 3
(D) OTHER INFORMATION: /note= "Xaa at position 3 is Ser, Gly, Asp, Met, or Gln"

(ix) FEATURE:
(A) NAME/KEY: Modified-site
(B) LOCATION: 4
(D) OTHER INFORMATION: /note= "Xaa at position 4 is Asn, His, or Ile"

(ix) FEATURE:
(A) NAME/KEY: Modified-site
(B) LOCATION: 5
(D) OTHER INFORMATION: /note= "Xaa at position 5 is Met or Ile"

(ix) FEATURE:
(A) NAME/KEY: Modified-site
(B) LOCATION: 7
(C) OTHER INFORMATION: /note= "Xaa at position 7 is Asp or Glu"

(ix) FEATURE:
(A) NAME/KEY: Modified-site
(B) LOCATION: 9
(D) OTHER INFORMATION: /note= "Xaa at position 9 is Ile, Ala, Leu, or Gly"

(ix) FEATURE:
(A) NAME/KEY: Modified-site
(B) LOCATION: 10
(D) OTHER INFORMATION: /note= "Xaa at position 10 is Ile, Val, or Leu"

(ix) FEATURE:

(A) NAME/KEY: Modified-site
     (B) LOCATION: 11
     (D) OTHER INFORMATION: /note= "Xaa at position 11 is Thr,
         His, Gln, or Ala"

(ix) FEATURE:
     (A) NAME/KEY: Modified-site
     (B) LOCATION: 12
     (D) OTHER INFORMATION: /note= "Xaa at position 12 is His
         or Ala"

(ix) FEATURE:
     (A) NAME/KEY: Modified-site
     (B) LOCATION: 15
     (D) OTHER INFORMATION: /note= "Xaa at position 15 is Gln,
         Asn, or Val"

(ix) FEATURE:
     (A) NAME/KEY: Modified-site
     (B) LOCATION: 16
     (D) OTHER INFORMATION: /note= "Xaa at position 16 is Pro,
         Gly, or Gln"

(ix) FEATURE:
     (A) NAME/KEY: Modified-site
     (B) LOCATION: 17
     (D) OTHER INFORMATION: /note= "Xaa at position 17 is Pro,
         Asp, Gly, or Gln"

(ix) FEATURE:
     (A) NAME/KEY: Modified-site
     (B) LOCATION: 18
     (D) OTHER INFORMATION: /note= "Xaa at position 18 is Leu,
         Arg, Gln, Asn, Gly, Ala, or Glu"

(ix) FEATURE:
     (A) NAME/KEY: Modified-site
     (B) LOCATION: 19
     (D) OTHER INFORMATION: /note= "Xaa at position 19 is Pro
         or Glu"

(ix) FEATURE:
     (A) NAME/KEY: Modified-site
     (B) LOCATION: 20
     (D) OTHER INFORMATION: /note= "Xaa at position 20 is Leu,
         Val, Gly, Ser, Lys, Ala, Arg, Gln, Glu, Ile, Phe,
         Thr, or Met"

(ix) FEATURE:
     (A) NAME/KEY: Modified-site
     (B) LOCATION: 21
     (D) OTHER INFORMATION: /note= "Xaa at position 21 is Leu,
         Ala, Asn, Pro, Gln, or Val"

(ix) FEATURE:
     (A) NAME/KEY: Modified-site
     (B) LOCATION: 23
     (D) OTHER INFORMATION: /note= "Xaa at position 23 is Phe,
         Ser, Pro, or Trp"

(ix) FEATURE:
     (A) NAME/KEY: Modified-site
     (B) LOCATION: 24
     (D) OTHER INFORMATION: /note= "Xaa at position 24 is Asn
         or Ala"

(ix) FEATURE:
     (A) NAME/KEY: Modified-site
     (B) LOCATION: 28
     (D) OTHER INFORMATION: /note= "Xaa at position 28 is Gly,
         Asp, Ser, Cys, Ala, Asn, Ile, Leu, Met, Tyr, or Arg"

(ix) FEATURE:
     (A) NAME/KEY: Modified-site
     (B) LOCATION: 30
     (D) OTHER INFORMATION: /note= "Xaa at position 30 is Asp
         or Glu"

(ix) FEATURE:
     (A) NAME/KEY: Modified-site (B) LOCATION: 31
        (D) OTHER INFORMATION: /note= "Xaa at position 31 is Gln,
            Val, Met, Leu, Thr, Ala, Asn, Glu, Ser, or Lys"

(ix) FEATURE:
        (A) NAME/KEY: Modified-site
        (B) LOCATION: 32
        (D) OTHER INFORMATION: /note= "Xaa at position 32 is Asp,
            Phe, Ser, Thr, Ala, Asn, Gln, Glu, His, Ile, Lys,
            Tyr, Val, or Cys"

(ix) FEATURE:
        (A) NAME/KEY: Modified-site
        (B) LOCATION: 36
        (D) OTHER INFORMATION: /note= "Xaa at position 36 is Glu,
            Ala, Asn, Ser, or Asp"

(ix) FEATURE:
        (A) NAME/KEY: Modified-site
        (B) LOCATION: 37
        (D) OTHER INFORMATION: /note= "Xaa at position 37 is Asn,
            Arg, Met, Pro, Ser, Thr, or His"

(ix) FEATURE:
        (A) NAME/KEY: Modified-site
        (B) LOCATION: 40
        (D) OTHER INFORMATION: /note= "Xaa at position 40 is Arg
            or Ala"

(ix) FEATURE:
        (A) NAME/KEY: Modified-site
        (B) LOCATION: 41
        (D) OTHER INFORMATION: /note= "Xaa at position 41 is Arg,
            Thr, Val, Leu, or Gly"

(ix) FEATURE:
        (A) NAME/KEY: Modified-site
        (B) LOCATION: 42
        (D) OTHER INFORMATION: /note= "Xaa at position 42 is Pro,
            Gly, Ser, Gln, Ala, Arg, Asn, Glu, Leu, Thr, Val,
            or Lys"

(ix) FEATURE:
        (A) NAME/KEY: Modified-site
        (B) LOCATION: 46
        (D) OTHER INFORMATION: /note= "Xaa at position 46 is Ala
            or Ser"

(ix) FEATURE:
        (A) NAME/KEY: Modified-site
        (B) LOCATION: 48
        (D) OTHER INFORMATION: /note= "Xaa at position 48 is Asn,
            Pro, Thr, or Ile"

(ix) FEATURE:
        (A) NAME/KEY: Modified-site
        (B) LOCATION: 49
        (D) OTHER INFORMATION: /note= "Xaa at position 49 is Arg
            or Lys"

(ix) FEATURE:
        (A) NAME/KEY: Modified-site
        (B) LOCATION: 50
        (D) OTHER INFORMATION: /note= "Xaa at position 50 is Ala
            or Asn"

(ix) FEATURE:
        (A) NAME/KEY: Modified-site
        (B) LOCATION: 51
        (D) OTHER INFORMATION: /note= "Xaa at position 51 is Val
            or Thr"

(ix) FEATURE:
        (A) NAME/KEY: Modified-site
        (B) LOCATION: 52
        (D) OTHER INFORMATION: /note= "Xaa at position 52 is Lys
            or Arg"

(ix) FEATURE:
        (A) NAME/KEY: Modified-site

-continued (B) LOCATION: 53
            (D) OTHER INFORMATION: /note= "Xaa at position 53 is Ser,
                Phe, or His"

(ix) FEATURE:
            (A) NAME/KEY: Modified-site
            (B) LOCATION: 54
            (D) OTHER INFORMATION: /note= "Xaa at position 54 is Leu,
                Ile, Phe, or His"

(ix) FEATURE:
            (A) NAME/KEY: Modified-site
            (B) LOCATION: 55
            (D) OTHER INFORMATION: /note= "Xaa at position 55 is Gln,
                Ala, Pro, Thr, Glu, Arg, or Gly"

(ix) FEATURE:
            (A) NAME/KEY: Modified-site
            (B) LOCATION: 57
            (D) OTHER INFORMATION: /note= "Xaa at position 57 is Ala,
                Pro, or Arg"

(ix) FEATURE:
            (A) NAME/KEY: Modified-site
            (B) LOCATION: 58
            (D) OTHER INFORMATION: /note= "Xaa at position 58 is Ser,
                Glu, Arg, or Asp"

(ix) FEATURE:
            (A) NAME/KEY: Modified-site
            (B) LOCATION: 59
            (D) OTHER INFORMATION: /note= "Xaa at position 59 is Ala
                or Leu"

(ix) FEATURE:
            (A) NAME/KEY: Modified-site
            (B) LOCATION: 62
            (D) OTHER INFORMATION: /note= "Xaa at position 62 is Ser,
                Val, Ala, Asn, Glu, Pro, or Gly"

(ix) FEATURE:
            (A) NAME/KEY: Modified-site
            (B) LOCATION: 63
            (D) OTHER INFORMATION: /note= "Xaa at position 63 is Ile
                or Leu"

(ix) FEATURE:
            (A) NAME/KEY: Modified-site
            (B) LOCATION: 65
            (D) OTHER INFORMATION: /note= "Xaa at position 65 is Lys,
                Thr, Gly, Asn, Met, Arg, Ile, Gly, or Asp"

(ix) FEATURE:
            (A) NAME/KEY: Modified-site
            (B) LOCATION: 66
            (D) OTHER INFORMATION: /note= "Xaa at position 66 is Asn,
                Gly, Glu, or Arg"

(ix) FEATURE:
            (A) NAME/KEY: Modified-site
            (B) LOCATION: 68
            (D) OTHER INFORMATION: /note= "Xaa at position 68 is Leu,
                Gln, Trp, Arg, Asp, Ala, Asn, Glu, His, Ile, Met,
                Phe, Ser, Thr, Tyr, or Val"

(ix) FEATURE:
            (A) NAME/KEY: Modified-site
            (B) LOCATION: 69
            (D) OTHER INFORMATION: /note= "Xaa at position 69 is Pro
                or Thr"

(ix) FEATURE:
            (A) NAME/KEY: Modified-site
            (B) LOCATION: 71
            (D) OTHER INFORMATION: /note= "Xaa at position 71 is Leu
                or Val"

(ix) FEATURE:
            (A) NAME/KEY: Modified-site
            (B) LOCATION: 73

-continued (D) OTHER INFORMATION: /note= "Xaa at position 73 is Leu
              or Ser"

(ix) FEATURE:
          (A) NAME/KEY: Modified-site
          (B) LOCATION: 74
          (D) OTHER INFORMATION: /note= "Xaa at position 74 is Ala
              or Trp"

(ix) FEATURE:
          (A) NAME/KEY: Modified-site
          (B) LOCATION: 77
          (D) OTHER INFORMATION: /note= "Xaa at position 77 is Ala
              or Pro"

(ix) FEATURE:
          (A) NAME/KEY: Modified-site
          (B) LOCATION: 79
          (D) OTHER INFORMATION: /note= "Xaa at position 79 is Thr,
              Asp, Ser, Pro, Ala, Leu, or Arg"

(ix) FEATURE:
          (A) NAME/KEY: Modified-site
          (B) LOCATION: 81
          (D) OTHER INFORMATION: /note= "Xaa at position 81 is His,
              Pro, Arg, Val, Leu, Gly, Asn, Phe, Ser, or Thr"

(ix) FEATURE:
          (A) NAME/KEY: Modified-site
          (B) LOCATION: 82
          (D) OTHER INFORMATION: /note= "Xaa at position 82 is Pro
              or Tyr"

(ix) FEATURE:
          (A) NAME/KEY: Modified-site
          (B) LOCATION: 83
          (D) OTHER INFORMATION: /note= "Xaa at position 83 is Ile
              or Val"

(ix) FEATURE:
          (A) NAME/KEY: Modified-site
          (B) LOCATION: 84
          (D) OTHER INFORMATION: /note= "Xaa at position 84 is His,
              Ile, Asn, Leu, Ala, Thr, Leu, Arg, Gln, Leu, Lys,
              Met, Ser, Tyr, Val, or Pro"

(ix) FEATURE:
          (A) NAME/KEY: Modified-site
          (B) LOCATION: 85
          (D) OTHER INFORMATION: /note= "Xaa at position 85 is Ile,
              Leu, or Val"

(ix) FEATURE:
          (A) NAME/KEY: Modified-site
          (B) LOCATION: 86
          (D) OTHER INFORMATION: /note= "Xaa at position 86 is Lys,
              Arg, Ile, Gln, Pro, or Ser"

(ix) FEATURE:
          (A) NAME/KEY: Modified-site
          (B) LOCATION: 87
          (D) OTHER INFORMATION: /note= "Xaa at position 87 is Asp,
              Pro, Met, Lys, His, Thr, Asn, Ile, Leu, or Tyr"

(ix) FEATURE:
          (A) NAME/KEY: Modified-site
          (B) LOCATION: 90
          (D) OTHER INFORMATION: /note= "Xaa at position 90 is Trp
              or Leu"

(ix) FEATURE:
          (A) NAME/KEY: Modified-site
          (B) LOCATION: 91
          (D) OTHER INFORMATION: /note="Xaa at position 91 is Asn,
              Pro, Ala, Ser, Trp, Gln, Tyr, Leu, Lys, Ile, Asp,
              or His"

(ix) FEATURE:
          (A) NAME/KEY: Modified-site
          (B) LOCATION: 92

(D) OTHER INFORMATION: /note= "Xaa at position 92 is Glu
             or Gly"

(ix) FEATURE:
        (A) NAME/KEY: Modified-site
        (B) LOCATION: 94
        (C) OTHER INFORMATION: /note= "Xaa at position 94 is Arg,
             Ala, or Ser"

(ix) FEATURE:
        (A) NAME/KEY: Modified-site
        (B) LOCATION: 95
        (D) OTHER INFORMATION: /note= "Xaa at position 95 is Arg,
             Thr, Glu, Leu, or Ser"

(ix) FEATURE:
        (A) NAME/KEY: Modified-site
        (B) LOCATION: 98
        (D) OTHER INFORMATION: /note= "Xaa at position 98 is Thr,
             Val, or Gln"

(ix) FEATURE:
        (A) NAME/KEY: Modified-site
        (B) LOCATION: 100
        (D) OTHER INFORMATION: /note= "Xaa at position 100 is Tyr
             or Trp"

(ix) FEATURE:
        (A) NAME/KEY: Modified-site
        (B) LOCATION: 101
        (D) OTHER INFORMATION: /note= "Xaa at position 101 is Leu
             or Ala"

(ix) FEATURE:
        (A) NAME/KEY: Modified-site
        (B) LOCATION: 102
        (D) OTHER INFORMATION: /note= "Xaa at position 102 is Lys,
             Thr, Val, Trp, Ser, Ala, His, Met, Phe, Tyr, or Ile"

(ix) FEATURE:
        (A) NAME/KEY: Modified-site
        (B) LOCATION: 103
        (D) OTHER INFORMATION: /note= "Xaa at position 103 is Thr
             or Ser"

(ix) FEATURE:
        (A) NAME/KEY: Modified-site
        (B) LOCATION: 106
        (D) OTHER INFORMATION: /note= "Xaa at position 106 is Asn,
             Pro, Leu, His, Val, or Gln"

(ix) FEATURE:
        (A) NAME/KEY: Modified-site
        (B) LOCATION: 107
        (D) OTHER INFORMATION: /note= "Xaa at position 107 is Ala,
             Ser, Ile, Asn, Pro, Asp, or Gly"

(ix) FEATURE:
        (A) NAME/KEY: Modified-site
        (B) LOCATION: 108
        (D) OTHER INFORMATION: /note= "Xaa at position 108 is Gln,
             Ser, Met, Trp, Arg, Phe, Pro, His, Ile, Tyr, or Cys"

(ix) FEATURE:
        (A) NAME/KEY: Modified-site
        (B) LOCATION: 109
        (D) OTHER INFORMATION: /note= "Xaa at position 109 is Ala,
             Met, Glu, His, Ser, Pro, Tyr, or Leu"

(xi) SEQUENCE DESCRIPTION: SEQ ID NO:21:

Asn Cys Xaa Xaa Xaa Ile Xaa Glu Xaa Xaa Xaa Xaa Leu Lys Xaa Xaa
 1               5                  10                  15

Xaa Xaa Xaa Xaa Xaa Asp Xaa Xaa Asn Leu Asn Xaa Glu Xaa Xaa Xaa
             20                  25                  30

Ile Leu Met Xaa Xaa Asn Leu Xaa Xaa Xaa Asn Leu Glu Xaa Phe Xaa
             35                  40                  45

```
Xaa Xaa Xaa Xaa Xaa Xaa Xaa Asn Xaa Xaa Xaa Ile Glu Xaa Xaa Leu
 50                      55                  60
Xaa Xaa Leu Xaa Xaa Cys Xaa Pro Xaa Xaa Thr Ala Xaa Pro Xaa Arg
 65              70              75                      80
Xaa Xaa Xaa Xaa Xaa Xaa Xaa Gly Asp Xaa Xaa Xaa Phe Xaa Xaa Lys
                 85              90                  95
Leu Xaa Phe Xaa Xaa Xaa Xaa Leu Glu Xaa Xaa Xaa Xaa Gln Gln
        100             105             110
```

(2) INFORMATION FOR SEQ ID NO:22:

(i) SEQUENCE CHARACTERISTICS:
    (A) LENGTH: 111 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Met- or Met-Ala- may or may
        not precede the amino acid in position 1"

(ix) FEATURE:
    (A) NAME/KEY: Modified-site
    (B) LOCATION: 3
    (D) OTHER INFORMATION: /note= "Xaa at position 3 is Ser,
        Gly, Asp, or Gln"

(ix) FEATURE:
    (A) NAME/KEY: Modified-site
    (B) LOCATION: 4
    (D) OTHER INFORMATION: /note= "Xaa at position 4 is Asn,
        His, or Ile"

(ix) FEATURE:
    (A) NAME/KEY: Modified-site
    (B) LOCATION: 9
    (D) OTHER INFORMATION: /note= "Xaa at position 9 is Ile,
        Ala, Leu, or Gly"

(ix) FEATURE:
    (A) NAME/KEY: Modified-site
    (B) LOCATION: 11
    (D) OTHER INFORMATION: /note= "Xaa at position 11 is Thr,
        His, or Gln"

(ix) FEATURE:
    (A) NAME/KEY: Modified-site
    (B) LOCATION: 12
    (D) OTHER INFORMATION: /note= "Xaa at position 12 is His
        or Ala"

(ix) FEATURE:
    (A) NAME/KEY: Modified-site
    (B) LOCATION: 15
    (D) OTHER INFORMATION: /note= "Xaa at position 15 is Gln
        or Asn"

(ix) FEATURE:
    (A) NAME/KEY: Modified-site
    (B) LOCATION: 16
    (D) OTHER INFORMATION: /note= "Xaa at position 16 is Pro
        or Gly"

(ix) FEATURE:
    (A) NAME/KEY: Modified-site
    (B) LOCATION: 18
    (D) OTHER INFORMATION: /note= "Xaa at position 18 is Leu,
        Arg, Asn, or Ala"

(ix) FEATURE:
    (A) NAME/KEY: Modified-site
    (B) LOCATION: 20
    (D) OTHER INFORMATION: /note= "Xaa at position 20 is Leu, Val, Ser, Ala, Arg, Gln, Glu, Ile, Phe, Thr, or Met"

(ix) FEATURE:
  (A) NAME/KEY: Modified-site
  (B) LOCATION: 21
  (D) OTHER INFORMATION: /note= "Xaa at position 21 is Leu,
      Ala, Asn, or Pro"

(ix) FEATURE:
  (A) NAME/KEY: Modified-site
  (B) LOCATION: 24
  (D) OTHER INFORMATION: /note= "Xaa at position 24 is Asn
      or Ala"

(ix) FEATURE:
  (A) NAME/KEY: Modified-site
  (B) LOCATION: 28
  (D) OTHER INFORMATION: /note= "Xaa at position 28 is Gly,
      Asp, Ser, Ala, Asn, Ile, Leu, Met, Tyr, or Arg"

(ix) FEATURE:
  (A) NAME/KEY: Modified-site
  (B) LOCATION: 31
  (D) OTHER INFORMATION: /note= "Xaa at position 31 is Gln,
      Val, Met, Leu, Ala, Asn, Glu, or Lys"

(ix) FEATURE:
  (A) NAME/KEY: Modified-site
  (B) LOCATION: 32
  (D) OTHER INFORMATION: /note= "Xaa at position 32 is Asp,
      Phe, Ser, Ala, Gln, Glu, His, Val, or Thr"

(ix) FEATURE:
  (A) NAME/KEY: Modified-site
  (B) LOCATION: 36
  (D) OTHER INFORMATION: /note= "Xaa at position 36 is Glu,
      Asn, Ser, or Asp"

(ix) FEATURE:
  (A) NAME/KEY: Modified-site
  (B) LOCATION: 37
  (D) OTHER INFORMATION: /note= "Xaa at position 37 is Asn,
      Arg, Pro, Thr, or His"

(ix) FEATURE:
  (A) NAME/KEY: Modified-site
  (B) LOCATION: 41
  (D) OTHER INFORMATION: /note= "Xaa at position 41 is Arg,
      Leu, or Gly"

(ix) FEATURE:
  (A) NAME/KEY: Modified-site
  (B) LOCATION: 42
  (D) OTHER INFORMATION: /note= "Xaa at position 42 is Pro,
      Gly, Ser, Ala, Asn, Val, Leu, or Gln"

(ix) FEATURE:
  (A) NAME/KEY: Modified-site
  (B) LOCATION: 48
  (D) OTHER INFORMATION: /note= "Xaa at position 48 is Asn,
      Pro, or Thr"

(ix) FEATURE:
  (A) NAME/KEY: Modified-site
  (B) LOCATION: 50
  (D) OTHER INFORMATION: /note= "Xaa at position 50 is Ala
      or Asn"

(ix) FEATURE:
  (A) NAME/KEY: Modified-site
  (B) LOCATION: 51
  (D) OTHER INFORMATION: /note= "Xaa at position 51 is Val
      or Thr"

(ix) FEATURE:
  (A) NAME/KEY: Modified-site
  (B) LOCATION: 53
  (D) OTHER INFORMATION: /note= "Xaa at position 53 is Ser
      or Phe"

(ix) FEATURE:
   (A) NAME/KEY: Modified-site
   (B) LOCATION: 54
   (D) OTHER INFORMATION: /note= "Xaa at position 54 is Leu or Phe"

(ix) FEATURE:
   (A) NAME/KEY: Modified-site
   (B) LOCATION: 55
   (D) OTHER INFORMATION: /note= "Xaa at position 55 is Gln, Ala, Glu, or Arg"

(ix) FEATURE:
   (A) NAME/KEY: Modified-site
   (B) LOCATION: 62
   (D) OTHER INFORMATION: /note= "Xaa at position 62 is Ser, Val, Asn, Pro, or Gly"

(ix) FEATURE:
   (A) NAME/KEY: Modified-site
   (B) LOCATION: 63
   (D) OTHER INFORMATION: /note= "Xaa at position 63 is Ile or Leu"

(ix) FEATURE:
   (A) NAME/KEY: Modified-site
   (B) LOCATION: 65
   (D) OTHER INFORMATION: /note= "Xaa at position 65 is Lys, Asn, Met, Arg, Ile, or Gly"

(ix) FEATURE:
   (A) NAME/KEY: Modified-site
   (B) LOCATION: 66
   (D) OTHER INFORMATION: /note= "Xaa at position 66 is Asn, Gly, Glu, or Arg"

(ix) FEATURE:
   (A) NAME/KEY: Modified-site
   (B) LOCATION: 68
   (D) OTHER INFORMATION: /note= "Xaa at position 68 is Leu, Gln, Trp, Arg, Asp, Asn, Glu, His, Met, Phe, Ser, Thr, Tyr, or Val"

(ix) FEATURE:
   (A) NAME/KEY: Modified-site
   (B) LOCATION: 73
   (D) OTHER INFORMATION: /note= "Xaa at position 73 is Leu or Ser"

(ix) FEATURE:
   (A) NAME/KEY: Modified-site
   (B) LOCATION: 74
   (D) OTHER INFORMATION: /note= "Xaa at position 74 is Ala or Trp"

(ix) FEATURE:
   (A) NAME/KEY: Modified-site
   (B) LOCATION: 77
   (D) OTHER INFORMATION: /note= "Xaa at position 77 is Ala or Pro"

(ix) FEATURE:
   (A) NAME/KEY: Modified-site
   (B) LOCATION: 79
   (D) OTHER INFORMATION: /note= "Xaa at position 79 is Thr, Asp, or Ala"

(ix) FEATURE:
   (A) NAME/KEY: Modified-site
   (B) LOCATION: 81
   (D) OTHER INFORMATION: /note= "Xaa at position 81 is His, Pro, Arg, Val, Gly, Asn, Ser, or Thr"

(ix) FEATURE:
   (A) NAME/KEY: Modified-site
   (B) LOCATION: 84
   (D) OTHER INFORMATION: /note= "Xaa at position 84 is His, Ile, Asn, Ala, Thr, Arg, Gln, Glu, Lys, Met, Ser, Tyr, Val, or Leu"

```
(ix) FEATURE:
    (A) NAME/KEY: Modified-site
    (B) LOCATION: 85
    (D) OTHER INFORMATION: /note= "Xaa at position 85 is Ile
        or Leu"

(ix) FEATURE:
    (A) NAME/KEY: Modified-site
    (B) LOCATION: 86
    (D) OTHER INFORMATION: /note= "Xaa at position 86 is Lys
        or Arg"

(ix) FEATURE:
    (A) NAME/KEY: Modified-site
    (B) LOCATION: 87
    (D) OTHER INFORMATION: /note= "Xaa at position 87 is Asp,
        Pro, Met, Lys, His, Pro, Asn, Ile, Leu, or Tyr"

(ix) FEATURE:
    (A) NAME/KEY: Modified-site
    (B) LOCATION: 91
    (D) OTHER INFORMATION: /note= "Xaa at position 91 is Asn,
        Pro, Ser, Ile, or Asp"

(ix) FEATURE:
    (A) NAME/KEY: Modified-site
    (B) LOCATION: 94
    (D) OTHER INFORMATION: /note= "Xaa at position 94 is Arg,
        Ala, or Ser"

(ix) FEATURE:
    (A) NAME/KEY: Modified-site
    (B) LOCATION: 95
    (D) OTHER INFORMATION: /note= "Xaa at position 95 is Arg,
        Thr, Glu, Leu, or Ser"

(ix) FEATURE:
    (A) NAME/KEY: Modified-site
    (B) LOCATION: 98
    (D) OTHER INFORMATION: /note= "Xaa at position 98 is Thr
        or Gln"

(ix) FEATURE:
    (A) NAME/KEY: Modified-site
    (B) LOCATION: 102
    (D) OTHER INFORMATION: /note= "Xaa at position 102 is Lys,
        Val, Trp, or Ile"

(ix) FEATURE:
    (A) NAME/KEY: Modified-site
    (B) LOCATION: 103
    (D) OTHER INFORMATION: /note= "Xaa at position 103 is Thr,
        Ala, His, Phe, Tyr, or Ser"

(ix) FEATURE:
    (A) NAME/KEY: Modified-site
    (B) LOCATION: 106
    (D) OTHER INFORMATION: /note= "Xaa at position 106 is Asn,
        Pro, Leu, His, Val, or Gln"

(ix) FEATURE:
    (A) NAME/KEY: Modified-site
    (B) LOCATION: 107
    (D) OTHER INFORMATION: /note= "Xaa at position 107 is Ala,
        Ser, Ile, Pro, or Asp"

(ix) FEATURE:
    (A) NAME/KEY: Modified-site
    (B) LOCATION: 108
    (D) OTHER INFORMATION: /note= "Xaa at position 108 is Gln,
        Met, Trp, Phe, Pro, His, Ile, or Tyr"

(ix) FEATURE:
    (A) NAME/KEY: Modified-site
    (B) LOCATION: 109
    (D) OTHER INFORMATION: /note= "Xaa at position 109 is Ala,
        Met, Glu, Ser, or Leu"

(xi) SEQUENCE DESCRIPTION: SEQ ID NO:22:
```

```
Asn Cys Xaa Xaa Met Ile Asp Glu Xaa Ile Xaa Xaa Leu Lys Xaa Xaa
1               5                   10                  15

Pro Xaa Pro Xaa Xaa Asp Phe Xaa Asn Leu Asn Xaa Glu Asp Xaa Xaa
        20                  25                  30

Ile Leu Met Xaa Xaa Asn Leu Arg Xaa Xaa Asn Leu Glu Ala Phe Xaa
            35                  40                  45

Arg Xaa Xaa Lys Xaa Xaa Xaa Asn Ala Ser Ala Ile Glu Xaa Xaa Leu
    50                  55                  60

Xaa Xaa Leu Xaa Pro Cys Leu Pro Xaa Xaa Thr Ala Xaa Pro Xaa Arg
65              70                  75                      80

Xaa Pro Ile Xaa Xaa Xaa Xaa Gly Asp Trp Xaa Glu Phe Xaa Xaa Lys
            85                  90                  95

Leu Xaa Phe Tyr Leu Xaa Xaa Leu Glu Xaa Xaa Xaa Xaa Gln Gln
        100                 105                 110
```

(2) INFORMATION FOR SEQ ID NO:23:

(i) SEQUENCE CHARACTERISTICS:
      (A) LENGTH: 111 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 1
      (D) OTHER INFORMATION: /note= "Met- or Met-Ala- may or may
          not precede the amino acid in position 1"

(xi) SEQUENCE DESCRIPTION: SEQ ID NO:23:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
        20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
    50                  55                  60

Lys Asn Leu Leu Pro Cys Leu Pro Leu Ala Thr Ala Ala Pro Thr Arg
65              70                  75                      80

His Pro Ile His Ile Lys Asp Gly Asp Trp Asn Glu Phe Arg Arg Lys
            85                  90                  95

Leu Thr Phe Tyr Leu Lys Thr Leu Glu Asn Ala Gln Ala Gln Gln
        100                 105                 110
```

(2) INFORMATION FOR SEQ ID NO:24:

(i) SEQUENCE CHARACTERISTICS:
      (A) LENGTH: 58 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:24:

CTAGCCACGG CCGCACCCAC GCGACATCCA ATCCATATCA AGGACGGTGA CTGGAATG        58

(2) INFORMATION FOR SEQ ID NO:25:

(i) SEQUENCE CHARACTERISTICS:
      (A) LENGTH: 58 base pairs (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:25:

TTAACATTCC AGTCACCGTC CTTGATATGG ATTGGATGTC GCGTGGGTGC GGCCGTGG         58

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:26:

TGTCTGCTCA GGCCATGGCT                                                  20

(2) INFORMATION FOR SEQ ID NO:27:

(i) SEQUENCE CHARACTERISTICS:
            (A) LENGTH: 67 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:27:

GCGCGAATTC ATTCCAGTCA CCGTCCTTGA TATGGTCGAC TTATTACGTG GGTGCGGCCG      60

TGGCTAG                                                                67

(2) INFORMATION FOR SEQ ID NO:28:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:28:

GCGCGAATTC ATTCCAGTCA CCGTCGACTT ATTAGATTGG ATGTCGCGTG GGTGC           55

(2) INFORMATION FOR SEQ ID NO:29:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:29:

TGAACCATAT GTCAGG                                                      16

(2) INFORMATION FOR SEQ ID NO:30:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:30:

AATTCCTGAC ATATGGTTCA TGCA                                                   24

(2) INFORMATION FOR SEQ ID NO:31:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:31:

GCGCGAATTC GTCGACTTAT TAGTCCTTGA TATGGATTGG ATG                              43

(2) INFORMATION FOR SEQ ID NO:32:

(i) SEQUENCE CHARACTERISTICS:
            (A) LENGTH: 67 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:32:

GCGCGAATTC ATTCCAGTCA CCGTCCTTGA TATGGATTGG ATGSNNCGTG GGTGCGGCCG            60

TGGCTAG                                                                     67

(2) INFORMATION FOR SEQ ID NO:33:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:33:

GCGCGAATTC ATTCCAGTCA CCGTCCTTGA TATGGATTGG SNNTCGCGTG GGTGCGGCCG            60

TGGC                                                                        64

(2) INFORMATION FOR SEQ ID NO:34:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:34:

GCGCGAATTC ATTCCAGTCA CCGTCCTTGA TATGGATSNN ATGTCGCGTG GGTGCGGCCG            60

T                                                                           61

(2) INFORMATION FOR SEQ ID NO:35:

(i) SEQUENCE CHARACTERISTICS:
            (A) LENGTH: 58 base pairs
            (B) TYPE: nucleic acid
            (C) STRANDEDNESS: single (D) TOPOLOGY: linear (ii) MOLECULE TYPE: DNA (synthetic)

(xi) SEQUENCE DESCRIPTION: SEQ ID NO:35:

GCGCGAATTC ATTCCAGTCA CCGTCCTTGA TATGSNNTGG ATGTCGCGTG GGTGCGGC         58

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:36:

GATATGGATT GGATGTCGCG TGGG                                              24

(2) INFORMATION FOR SEQ ID NO:37:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:37:

GCGCGAATTC ATTCCAGTCA CCGTCCTTGA TSNNGATTGG ATGTCGCGTG GGTGC            55

(2) INFORMATION FOR SEQ ID NO:38:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:38:

GCGCGAATTC ATTCCAGTCA CCGTCCTTSN NATGGATTGG ATGTCGCGTG GG               52

(2) INFORMATION FOR SEQ ID NO:39:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:39:

GCGCGAATTC ATTCCAGTCA CCGTCSNNGA TATGGATTGG ATGTCGCGT                   49

(2) INFORMATION FOR SEQ ID NO:40:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:40:

```
GCGCGAATTC ATTCCAGTCA CCSNNCTTGA TATGGATTGG ATGTCG                    46

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:41:

GTCACCGTCC TTGATATGGA TTGG                                            24

(2) INFORMATION FOR SEQ ID NO:42:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:42:

GCGCGAATTC ATTCCAGTCS NNGTCCTTGA TATGGATTGG ATG                       43

(2) INFORMATION FOR SEQ ID NO:43:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:43:

GCGCGAATTC ATTCCASNNA CCGTCCTTGA TATGGATTGG                           40

(2) INFORMATION FOR SEQ ID NO:44:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:44:

GCGCGAATTC ATTSNNGTCA CCGTCCTTGA TATGGAT                              37

(2) INFORMATION FOR SEQ ID NO:45:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:45:

GCGCGAATTC SNNCCAGTCA CCGTCCTTGA TATG                                 34

(2) INFORMATION FOR SEQ ID NO:46:
```

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:46:

GAATTCATTC CAGTCACCGT TCCTT                                              25

(2) INFORMATION FOR SEQ ID NO:47:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:47:

CGCGCGGAAT TCATTCCAGT CACCGT                                             26

(2) INFORMATION FOR SEQ ID NO:48:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:48:

CGCGCGCCAT GGCTAACTGC ATTATAACAC ACACTTAAAG CA                           42

(2) INFORMATION FOR SEQ ID NO:49:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:49:

CGCGCGCCAT GGCTAACTGC TCTAACATGA TCGATGAACA GCCACCTTTG CCTTTGCT          58

(2) INFORMATION FOR SEQ ID NO:50:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:50:

CGCGCGCCAT GGCTAACTGC TCTAACATGA TCGATGAAAT TATAACACAC TTAAAGCTGG        60

ACTTCAACAA CCTCAA                                                        76

(2) INFORMATION FOR SEQ ID NO:51:

(i) SEQUENCE CHARACTERISTICS:
        (A) LENGTH: 50 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:51:

GCGCGCGATA TCTTGGTCTT CTTCACCATT CAGCGGCAGC GGTGGCTGCT            50

(2) INFORMATION FOR SEQ ID NO:52:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:52:

GCGCGCCTCG AGGTTTGGAC GACGAAGGTT ATTTTCCATC AGGATGAGGT TGTTGAAGTC    60

CAGCA                                                                65

(2) INFORMATION FOR SEQ ID NO:53:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:53:

GCGCGCCTCG AGGTTTGGAC GACGAAGATC TTGGTCTTCA CCATTGA                47

(2) INFORMATION FOR SEQ ID NO:54:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:54:

GCGCGCTGAT GCATTCTGCA GAGACTTGAC AGCACGGTTG AATGCCTCGT TATTTTCCAT    60

CAGGATAT                                                             68

(2) INFORMATION FOR SEQ ID NO:55:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:55:

GCGCGCTGAT GCATTCTGCA GAGACTTGAC GAGGTTTGGA CGACGAAGGT             50

(2) INFORMATION FOR SEQ ID NO:56:

(i) SEQUENCE CHARACTERISTICS:
        (A) LENGTH: 47 base pairs
        (B) TYPE: nucleic acid

```
        (C) STRANDEDNESS: single
        (D) TOPOLOGY: linear (ii) MOLECULE TYPE: DNA (synthetic)

(xi) SEQUENCE DESCRIPTION: SEQ ID NO:56:

GCGCGCCTCG AGGCATTCAA CCGTGCTGCA TCAGCAATTG AGAGCAT              47

(2) INFORMATION FOR SEQ ID NO:57:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:57:

GCGCGCCTGC AGAATATTCT TAAAAATCTC CTGCC                           35

(2) INFORMATION FOR SEQ ID NO:58:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:58:

GCGCGCCTGC AGAATGCATC AGCAATTGAG AGCCCATGTC TGCCGCTAGC CAC       53

(2) INFORMATION FOR SEQ ID NO:59:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:59:

GCGCGCCTGC AGAATGCATC AGCAATTGAG AGCATTCTTA AAAATCTCCT GACGGCCGCA     60

CCCACGCGAC A                                                          71

(2) INFORMATION FOR SEQ ID NO:60:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:60:

CGCGCGGAAT TCATTCCAGT CACCGTCCTT GATATGGATT GGATGTCGCA GGGCAGACAT     60

GGCAGGA                                                               67

(2) INFORMATION FOR SEQ ID NO:61:

(i) SEQUENCE CHARACTERISTICS:
        (A) LENGTH: 78 base pairs
        (B) TYPE: nucleic acid
        (C) STRANDEDNESS: single
```

```
            (D) TOPOLOGY: linear (ii) MOLECULE TYPE: DNA (synthetic)

(xi) SEQUENCE DESCRIPTION: SEQ ID NO:61:

CGCGCGAAGC TTATTACTGT TGAGCCTGCG CGTTCTCCAA GGTTTTCAGA TAGAAGGTAT     60

TCCAGTCACC GTCCTTGA                                                   78

(2) INFORMATION FOR SEQ ID NO:62:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:62:

CGCGCGAAGC TTATTACTGT TGAGCCTGCG CGTTCTCCAA CAGTTTACGA CGGAATTCAT     60

(2) INFORMATION FOR SEQ ID NO:63:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:63:

CGCGCGAAGC TTATTACTGT TGGGTTTTCA GATAGAAGGT CA                        42

(2) INFORMATION FOR SEQ ID NO:64:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:64:

CGCGCGCCAT GGCTAACTGC NNSAACATGA TCGATGAAAT TATAACACAC TTAAAGCA       58

(2) INFORMATION FOR SEQ ID NO:65:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:65:

Asn Cys Ser Asn Met Ile Asp Glu Ile Ile Thr His Leu Lys Gln Pro
    1               5                  10                  15

Pro Leu Pro Leu Leu Asp Phe Asn Asn Leu Asn Gly Glu Asp Gln Asp
                    20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Ala Ile Glu Ser Ile Leu
            50                  55                  60

Lys Asn Leu Leu Pro Cys Leu Pro Leu Ala Thr Ala Ala Pro Thr Arg
```

```
                 65                  70                  75                  80
        His Pro Ile His Ile Lys Asp Gly Asp Trp Asn Glu Phe Arg Arg Lys
                        85                  90                  95

Leu Thr Phe Tyr Leu Lys Thr Leu Glu Asn Ala Gln Ala Gln Gln
                       100                 105                 110
```

(2) INFORMATION FOR SEQ ID NO:66:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:66:

```
Met Ala Asn Cys Ser Asn Met Ile Asp Glu Ile Ile Thr His Leu Lys
1               5                  10                  15

Gln Pro Pro Leu Pro Leu Leu Asp Phe Asn Asn Leu Asn Gly Glu Asp
               20                  25                  30

Gln Asp Ile Leu Met Glu Asn Asn Leu Arg Arg Pro Asn Leu Glu Ala
               35                  40                  45

Phe Asn Arg Ala Val Lys Ser Leu Gln Asn Ala Ser Ala Ile Glu Ser
           50                  55                  60

Ile Leu Lys Asn Leu Leu Pro Cys Leu Pro Leu Ala Thr Ala Ala Pro
65                  70                  75                  80

Thr Arg His Pro Ile Ile Ile Arg Asp Gly Asp Trp Asn Glu Phe Arg
                   85                  90                  95

Arg Lys Leu Thr Phe Tyr Leu Lys Thr Leu Glu Asn Ala Gln Ala Gln
                  100                 105                 110

Gln
```

(2) INFORMATION FOR SEQ ID NO:67:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:67:

```
Met Ala Asn Cys Ser Asn Met Ile Asp Glu Ile Ile Thr His Leu Lys
1               5                  10                  15

Gln Pro Pro Leu Pro Leu Leu Asp Phe Asn Asn Leu Asn Gly Glu Asp
               20                  25                  30

Gln Asp Ile Leu Met Glu Asn Asn Leu Arg Arg Pro Asn Leu Glu Ala
               35                  40                  45

Phe Asn Arg Ala Val Lys Ser Leu Gln Asn Ala Ser Ala Ile Glu Ser
           50                  55                  60

Ile Leu Lys Asn Leu Leu Pro Cys Leu Pro Leu Ala Thr Ala Ala Pro
65                  70                  75                  80

Thr Arg Arg Pro Ile Ile Ile Arg Asp Gly Asp Trp Asn Glu Phe Arg
                   85                  90                  95

Arg Lys Leu Thr Phe Tyr Leu Lys Thr Leu Glu Asn Ala Gln Ala Gln
                  100                 105                 110

Gln
```

(2) INFORMATION FOR SEQ ID NO:68:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:68:

ATGGCTAACT GCTCTAACAT GATCGATGAA ATCATCACCC ACCTGAAGCA GCCACCGCTG      60

CCGCTGCTGG ACTTCAACAA CCTCAATGAC GAAGACATGT CTATCCTGAT GGAAAATAAC     120

CTTCGTCGTC CAAACCTCGA GGCATTCAAC CGTGCTGTCA AGTCTCTGCA GAATGCATCA     180

GCAATTGAGA GCATTCTTAA AAATCTCCTG CCATGTCTGC CCCTGGCCAC GGCCGCACCC     240

ACGCGACATC CAATCCATAT CAAGGACGGT GACTGGAATG AATTCCGTCG TAAACTGACC     300

TTCTATCTGA AACCTTGGA GAACGCGCAG GCTCAACAG                              339

(2) INFORMATION FOR SEQ ID NO:69:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:69:

Met Ala Asn Cys Ser Asn Met Ile Asp Glu Ile Ile Thr His Leu Lys
    1               5                   10                  15

Gln Pro Pro Leu Pro Leu Leu Asp Phe Asn Asn Leu Asn Asp Glu Asp
                20                  25                  30

Met Ser Ile Leu Met Glu Asn Asn Leu Arg Arg Pro Asn Leu Glu Ala
                35                  40                  45

Phe Asn Arg Ala Val Lys Ser Leu Gln Asn Ala Ser Ala Ile Glu Ser
        50                  55                  60

Ile Leu Lys Asn Leu Leu Pro Cys Leu Pro Leu Ala Thr Ala Ala Pro
    65                  70                  75                  80

Thr Arg His Pro Ile His Ile Lys Asp Gly Asp Trp Asn Glu Phe Arg
                    85                  90                  95

Arg Lys Leu Thr Phe Tyr Leu Lys Thr Leu Glu Asn Ala Gln Ala Gln
                100                 105                 110

Gln (2) INFORMATION FOR SEQ ID NO:70:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:70:

CTTTAAGTGT GTTATAATTT CGTTGATCAT GTTAGAGCAG TTAGC                      45

(2) INFORMATION FOR SEQ ID NO:71:

(i) SEQUENCE CHARACTERISTICS:
        (A) LENGTH: 40 base pairs
        (B) TYPE: nucleic acid
        (C) STRANDEDNESS: single (D) TOPOLOGY: linear (ii) MOLECULE TYPE: DNA (synthetic)

(xi) SEQUENCE DESCRIPTION: SEQ ID NO:71:

CATGGCTAAC TGCTCTAACA TGATCCAAGA AATTATAACA                              40

(2) INFORMATION FOR SEQ ID NO:72:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:72:

CTTTAAGTGT GTTATAATTT CTTGGATCAT GTTAGAGCAG TTAGC                        45

(2) INFORMATION FOR SEQ ID NO:73:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:73:

CATGGCTAAC TGCTCTAACA TGATCGAAGA AATTATAACA                              40

(2) INFORMATION FOR SEQ ID NO:74:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:74:

CGCGCGCCAT GGCTAACTGC TCTAACATGA TCGATGAAAT TATAACANNS TTAAAGCAGC        60

CACCTTTGCC TTTGCT                                                        76

(2) INFORMATION FOR SEQ ID NO:75:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:75:

CGCGCGCCAT GGCTAACTGC TCTAACATGA TCGATGAAAT TATAACACAC NNSAAGCAGC        60

CACCTTTGCC TTTGCT                                                        76

(2) INFORMATION FOR SEQ ID NO:76:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:76:

CGCGCGCCAT GGCTAACTGC TCTAACATGA TCGATGAAAT TATAACACAC TTANNSCAGC    60

CACCTTTGCC TTTGCT    76

(2) INFORMATION FOR SEQ ID NO:77:

(i) SEQUENCE CHARACTERISTICS:
      (A) LENGTH: 94 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:77:

CGCGCGCCAT GGCTAACTGC TCTAACATGA TCGATGAAAT TATAACACAC TTAAAGNNSC    60

CACCTTTGCC TTTGCTGGAC TTCAACAACC TCAA    94

(2) INFORMATION FOR SEQ ID NO:78:

(i) SEQUENCE CHARACTERISTICS:
      (A) LENGTH: 94 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:78:

CGCGCGCCAT GGCTAACTGC TCTAACATGA TCGATGAAAT TATAACACAC TTAAAGCAGN    60

NSCCTTTGCC TTTGCTGGAC TTCAACAACC TCAA    94

(2) INFORMATION FOR SEQ ID NO:79:

(i) SEQUENCE CHARACTERISTICS:
      (A) LENGTH: 94 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:79:

CGCGCGCCAT GGCTAACTGC TCTAACATGA TCGATGAAAT TATAACACAC TTAAAGCAGC    60

CANNSTTGCC TTTGCTGGAC TTCAACAACC TCAA    94

(2) INFORMATION FOR SEQ ID NO:80:

(i) SEQUENCE CHARACTERISTICS:
      (A) LENGTH: 94 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:80:

CGCGCGCCAT GGCTAACTGC TCTAACATGA TCGATGAAAT TATAACACAC TTAAAGCAGC    60

CACCTNNSCC TTTGCTGGAC TTCAACAACC TCAA    94

(2) INFORMATION FOR SEQ ID NO:81:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:81:

CGCGCGCCAT GGCTAACTGC TCTAACATGA TCGATGAAAT TATAACACAC TTAAAGCAGC      60

CACCTTTGNN STTGCTGGAC TTCAACAACC TCAA      94

(2) INFORMATION FOR SEQ ID NO:82:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:82:

CGCGCGCCAT GGCTAACTGC TCTAACATGA TCGATGAAAT TATAACACAC TTAAAGCAGC      60

CACCTTTGCC TNNSCTGGAC TTCAACAACC TCAA      94

(2) INFORMATION FOR SEQ ID NO:83:

(i) SEQUENCE CHARACTERISTICS:
            (A) LENGTH: 65 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:83:

GCGCGCGATA TCTTGGTCTT CACCATTGAG GTTGTTGAAG TCSNNCAGCG GCAGCGGTGG      60

CTGCT      65

(2) INFORMATION FOR SEQ ID NO:84:

(i) SEQUENCE CHARACTERISTICS:
            (A) LENGTH: 65 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:84:

GCGCGCGATA TCTTGGTCTT CACCATTGAG GTTGTTGAAS NNCAGCAGCG GCAGCGGTGG      60

CTGCT      65

(2) INFORMATION FOR SEQ ID NO:85:

(i) SEQUENCE CHARACTERISTICS:
            (A) LENGTH: 65 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:85:

GCGCGCGATA TCTTGGTCTT CACCATTGAG GTTGTTSNNG TCCAGCAGCG GCAGCGGTGG      60

CTGCT 65

(2) INFORMATION FOR SEQ ID NO:86:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:86:

GCGCGCGATA TCTTGGTCTT CACCATTGAG GTTSNNGAAG TCCAGCAGCG GCAGCGGTGG 60

CTGCT 65

(2) INFORMATION FOR SEQ ID NO:87:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:87:

GCGCGCGATA TCTTGGTCTT CACCATTGAG SNNGTTGAAG TCCAGCAGCG GCAGCGGTGG 60

CTGCT 65

(2) INFORMATION FOR SEQ ID NO:88:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:88:

GCGCGCGATA TCTTGGTCTT CACCATTSNN GTTGTTGAAG TCCAGCAGCG GCAGCGGTGG 60

CTGCT 65

(2) INFORMATION FOR SEQ ID NO:89:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:89:

GCGCGCCTCG AGGTTTGGAC GACGAAGGTT ATTTTCCATC AGGATATCTT GGTCTTCACC 60

SNNGAGGTTG TTGAAGTCCA GCA 83

(2) INFORMATION FOR SEQ ID NO:90:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:90:

GCGCGCCTCG AGGTTTGGAC GACGAAGGTT ATTTTCCATC AGGATATCTT GGTCTTCSNN    60

ATTGAGGTTG TTGAAGTCCA GCA    83

(2) INFORMATION FOR SEQ ID NO:91:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:91:

GCGCGCCTCG AGGTTTGGAC GACGAAGGTT ATTTTCCATC AGGATATCTT GGTCSNNACC    60

ATTGAGGTTG TTGAAGTCCA GCA    83

(2) INFORMATION FOR SEQ ID NO:92:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:92:

GCGCGCCTCG AGGTTTGGAC GACGAAGGTT ATTTTCCATC AGGATATCTT GSNNTTCACC    60

ATTGAGGTTG TTGAAGTCCA GCA    83

(2) INFORMATION FOR SEQ ID NO:93:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:93:

GCGCGCCTCG AGGTTTGGAC GACGAAGGTT ATTTTCCATC AGGATATCSN NGTCTTCACC    60

ATTGAGGTTG TTGAAGTCCA GCA    83

(2) INFORMATION FOR SEQ ID NO:94:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:94:

GCGCGCCTCG AGGTTTGGAC GACGAAGGTT ATTTTCCATC AGGATSNNTT GGTCTTCACC    60

ATTGAGGTTG TTGAAGTCCA GCA    83

(2) INFORMATION FOR SEQ ID NO:95:

(i) SEQUENCE CHARACTERISTICS:
        (A) LENGTH: 65 base pairs (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:95:

GCGCGCCTCG AGGTTTGGAC GACGAAGGTT ATTTTCCATC AGSNNATCTT GGTCTTCACC      60

ATTGA      65

(2) INFORMATION FOR SEQ ID NO:96:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:96:

GCGCGCCTCG AGGTTTGGAC GACGAAGGTT ATTTTCCATS NNGATATCTT GGTCTTCACC      60

ATTGA      65

(2) INFORMATION FOR SEQ ID NO:97:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:97:

GCGCGCCTCG AGGTTTGGAC GACGAAGGTT ATTTTCSNNC AGGATATCTT GGTCTTCACC      60

ATTGA      65

(2) INFORMATION FOR SEQ ID NO:98:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:98:

GCGCGCCTCG AGGTTTGGAC GACGAAGGTT ATTSNNCATC AGGATATCTT GGTCTTCACC      60

ATTGA      65

(2) INFORMATION FOR SEQ ID NO:99:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:99:

GCGCGCCTCG AGGTTTGGAC GACGAAGGTT SNNTTCCATC AGGATATCTT GGTCTTCACC      60

ATTGA      65

-continued (2) INFORMATION FOR SEQ ID NO:100:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:100:

GCGCGCCTCG AGGTTTGGAC GACGAAGSNN ATTTTCCATC AGGATATCTT GGTCTTCACC    60

ATTGA    65

(2) INFORMATION FOR SEQ ID NO:101:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:101:

GCGCGCTGAT GCATTCTGCA GAGACTTGAC AGCACGGTTG AATGCCTCGA GGTTTGGACG    60

ACGSNNGTTA TTTTCCATCA GGATAT    86

(2) INFORMATION FOR SEQ ID NO:102:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:102:

GCGCGCTGAT GCATTCTGCA GAGACTTGAC AGCACGGTTG AATGCCTCGA GGTTTGGACG    60

SNNAAGGTTA TTTTCCATCA GGATAT    86

(2) INFORMATION FOR SEQ ID NO:103:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:103:

GCGCGCTGAT GCATTCTGCA GAGACTTGAC AGCACGGTTG AATGCCTCGA GGTTTGGSNN    60

ACGAAGGTTA TTTTCCATCA GGATAT    86

(2) INFORMATION FOR SEQ ID NO:104:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:104:

```
GCGCGCTGAT GCATTCTGCA GAGACTTGAC AGCACGGTTG AATGCCTCGA GGTTSNNACG    60

ACGAAGGTTA TTTTCCATCA GGATAT                                        86

(2) INFORMATION FOR SEQ ID NO:105:

(i) SEQUENCE CHARACTERISTICS:
           (A) LENGTH: 86 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:105:

GCGCGCTGAT GCATTCTGCA GAGACTTGAC AGCACGGTTG AATGCCTCGA GSNNTGGACG    60

ACGAAGGTTA TTTTCCATCA GGATAT                                        86

(2) INFORMATION FOR SEQ ID NO:106:

(i) SEQUENCE CHARACTERISTICS:
           (A) LENGTH: 86 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:106:

GCGCGCTGAT GCATTCTGCA GAGACTTGAC AGCACGGTTG AATGCCTCSN NGTTTGGACG    60

ACGAAGGTTA TTTTCCATCA GGATAT                                        86

(2) INFORMATION FOR SEQ ID NO:107:

(i) SEQUENCE CHARACTERISTICS:
           (A) LENGTH: 68 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:107:

GCGCGCTGAT GCATTCTGCA GAGACTTGAC AGCACGGTTG AATGCSNNGA GGTTTGGACG    60

ACGAAGGT                                                            68

(2) INFORMATION FOR SEQ ID NO:108:

(i) SEQUENCE CHARACTERISTICS:
           (A) LENGTH: 68 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:108:

GCGCGCTGAT GCATTCTGCA GAGACTTGAC AGCACGGTTG AASNNCTCGA GGTTTGGACG    60

ACGAAGGT                                                            68

(2) INFORMATION FOR SEQ ID NO:109:

(i) SEQUENCE CHARACTERISTICS:
           (A) LENGTH: 68 base pairs
           (B) TYPE: nucleic acid
           (C) STRANDEDNESS: single
```

(D) TOPOLOGY: linear (ii) MOLECULE TYPE: DNA (synthetic)

(xi) SEQUENCE DESCRIPTION: SEQ ID NO:109:

GCGCGCTGAT GCATTCTGCA GAGACTTGAC AGCACGGTTS NNTGCCTCGA GGTTTGGACG      60

ACGAAGGT                                                              68

(2) INFORMATION FOR SEQ ID NO:110:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:110:

GCGCGCTGAT GCATTCTGCA GAGACTTGAC AGCACGSNNG AATGCCTCGA GGTTTGGACG      60

ACGAAGGT                                                              68

(2) INFORMATION FOR SEQ ID NO:111:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:111:

GCGCGCTGAT GCATTCTGCA GAGACTTGAC AGCSNNGTTG AATGCCTCGA GGTTTGGACG      60

ACGAAGGT                                                              68

(2) INFORMATION FOR SEQ ID NO:112:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:112:

GCGCGCTGAT GCATTCTGCA GAGACTTGAC SNNACGGTTG AATGCCTCGA GGTTTGGACG      60

ACGAAGGT                                                              68

(2) INFORMATION FOR SEQ ID NO:113:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:113:

GCGCGCCTCG AGGCATTCAA CCGTGCTNNS AAGTCTCTGC AGAATGCATC AGCAATTGAG      60

AGCAT                                                                 65

(2) INFORMATION FOR SEQ ID NO:114:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:114:

GCGCGCCTCG AGGCATTCAA CCGTGCTGTC NNSTCTCTGC AGAATGCATC AGCAATTGAG        60

AGCAT        65

(2) INFORMATION FOR SEQ ID NO:115:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:115:

GCGCGCCTCG AGGCATTCAA CCGTGCTGTC AAGNNSCTGC AGAATGCATC AGCAATTGAG        60

AGCAT        65

(2) INFORMATION FOR SEQ ID NO:116:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:116:

GCGCGCCTCG AGGCATTCAA CCGTGCTGTC AAGTCTNNSC AGAATGCATC AGCAATTGAG        60

AGCAT        65

(2) INFORMATION FOR SEQ ID NO:117:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:117:

GCGCGCCTCG AGGCATTCAA CCGTGCTGTC AAGTCTCTGN NSAATGCATC AGCAATTGAG        60

AGCAT        65

(2) INFORMATION FOR SEQ ID NO:118:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:118:

GCGCGCCTCG AGGCATTCAA CCGTGCTGTC AAGTCTCTGC AGNNSGCATC AGCAATTGAG        60

```
AGCAT                                                                           65

(2) INFORMATION FOR SEQ ID NO:119:

(i) SEQUENCE CHARACTERISTICS:
         (A) LENGTH: 53 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:119:

GCGCGCCTGC AGAATNNSTC AGCAATTGAG AGCATTCTTA AAAATCTCCT GCC             53

(2) INFORMATION FOR SEQ ID NO:120:

(i) SEQUENCE CHARACTERISTICS:
         (A) LENGTH: 53 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:120:

GCGCGCCTGC AGAATGCANN SGCAATTGAG AGCATTCTTA AAAATCTCCT GCC             53

(2) INFORMATION FOR SEQ ID NO:121:

(i) SEQUENCE CHARACTERISTICS:
         (A) LENGTH: 53 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:121:

GCGCGCCTGC AGAATGCATC ANNSATTGAG AGCATTCTTA AAAATCTCCT GCC             53

(2) INFORMATION FOR SEQ ID NO:122:

(i) SEQUENCE CHARACTERISTICS:
         (A) LENGTH: 53 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:122:

GCGCGCCTGC AGAATGCATC AGCANNSGAG AGCATTCTTA AAAATCTCCT GCC             53

(2) INFORMATION FOR SEQ ID NO:123:

(i) SEQUENCE CHARACTERISTICS:
         (A) LENGTH: 53 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:123:

GCGCGCCTGC AGAATGCATC AGCAATTNNS AGCATTCTTA AAAATCTCCT GCC             53

(2) INFORMATION FOR SEQ ID NO:124:
```

(i) SEQUENCE CHARACTERISTICS:
    (A) LENGTH: 53 base pairs
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:124:

GCGCGCCTGC AGAATGCATC AGCAATTGAG NNSATTCTTA AAAATCTCCT GCC          53

(2) INFORMATION FOR SEQ ID NO:125:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:125:

GCGCGCCTGC AGAATGCATC AGCAATTGAG AGCNNSCTTA AAAATCTCCT GCCATGTCTG     60

CCGCTAGCCA C                                                          71

(2) INFORMATION FOR SEQ ID NO:126:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:126:

GCGCGCCTGC AGAATGCATC AGCAATTGAG AGCATTNNSA AAAATCTCCT GCCATGTCTG     60

CCGCTAGCCA C                                                          71

(2) INFORMATION FOR SEQ ID NO:127:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:127:

GCGCGCCTGC AGAATGCATC AGCAATTGAG AGCATTCTTN NSAATCTCCT GCCATGTCTG     60

CCGCTAGCCA C                                                          71

(2) INFORMATION FOR SEQ ID NO:128:

(i) SEQUENCE CHARACTERISTICS:
        (A) LENGTH: 134 amino acids
        (B) TYPE: amino acid
        (D) TOPOLOGY: linear (ii) MOLECULE TYPE: peptide (xi) SEQUENCE DESCRIPTION: SEQ ID NO:128:

Met Ala Pro Met Thr Gln Thr Thr Ser Leu Lys Thr Ser Trp Val Asn
    1               5                   10                  15

Cys Ser Asn Met Ile Asp Glu Ile Ile Thr His Leu Lys Gln Pro Pro

-continued

```
                    20                  25                  30
        Leu Pro Leu Leu Asp Phe Asn Asn Leu Asn Gly Glu Asp Gln Asp Ile
                35                  40                  45

Leu Met Glu Asn Asn Leu Arg Arg Pro Asn Leu Glu Ala Phe Asn Arg
         50                  55                  60

Ala Val Lys Ser Leu Gln Asn Ala Ser Ala Ile Glu Ser Ile Leu Lys
         65                  70                  75                  80

Asn Leu Leu Pro Cys Leu Pro Leu Ala Thr Ala Ala Pro Thr Arg His
                        85                  90                  95

Pro Ile His Ile Lys Asp Gly Asp Trp Asn Glu Phe Arg Arg Lys Leu
                    100                 105                 110

Thr Phe Tyr Leu Lys Thr Leu Glu Asn Ala Gln Ala Gln Gln Thr Thr
                    115                 120                 125

Leu Ser Leu Ala Ile Phe
                    130
```

(2) INFORMATION FOR SEQ ID NO:129:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 18
        (D) OTHER INFORMATION: /note= "Xaa at position 18 is Asn
            or Ile"

(ix) FEATURE:
        (A) NAME/KEY: Modified-site
        (B) LOCATION: 25
        (D) OTHER INFORMATION: /note= "Xaa at position 25 is Thr
            or His"

(ix) FEATURE:
        (A) NAME/KEY: Modified-site
        (B) LOCATION: 29
        (D) OTHER INFORMATION: /note= "Xaa at position 29 is Gln,
            Arg, or Val"

(ix) FEATURE:
        (A) NAME/KEY: Modified-site
        (B) LOCATION: 32
        (D) OTHER INFORMATION: /note= "Xaa at position 32 is Leu,
            Ala, or Asn"

(ix) FEATURE:
        (A) NAME/KEY: Modified-site
        (B) LOCATION: 37
        (D) OTHER INFORMATION: /note= "Xaa at position 37 is Phe,
            Pro, or Ser"

(ix) FEATURE:
        (A) NAME/KEY: Modified-site
        (B) LOCATION: 42
        (D) OTHER INFORMATION: /note= "Xaa at position 42 is Glu,
            Ala, or Ser"

(ix) FEATURE:
        (A) NAME/KEY: Modified-site
        (B) LOCATION: 45
        (D) OTHER INFORMATION: /note= "Xaa at position 45 is Gln,
            Val, or Met"

```
(ix) FEATURE:
    (A) NAME/KEY: Modified-site
    (B) LOCATION: 51
    (D) OTHER INFORMATION: /note= "Xaa at position 51 is Asn
        or Arg"

(ix) FEATURE:
    (A) NAME/KEY: Modified-site
    (B) LOCATION: 55
    (D) OTHER INFORMATION: /note= "Xaa at position 55 is Arg,
        Leu, or Thr"

(ix) FEATURE:
    (A) NAME/KEY: Modified-site
    (B) LOCATION: 59
    (D) OTHER INFORMATION: /note= "Xaa at position 59 is Glu
        or Leu"

(ix) FEATURE:
    (A) NAME/KEY: Modified-site
    (B) LOCATION: 60
    (D) OTHER INFORMATION: /note= "Xaa at position 60 is Ala
        or Ser"

(ix) FEATURE:
    (A) NAME/KEY: Modified-site
    (B) LOCATION: 62
    (D) OTHER INFORMATION: /note= "Xaa at position 62 is Asn
        or Val"

(ix) FEATURE:
    (A) NAME/KEY: Modified-site
    (B) LOCATION: 67
    (D) OTHER INFORMATION: /note= "Xaa at position 67 is Ser,
        Asn, or His"

(ix) FEATURE:
    (A) NAME/KEY: Modified-site
    (B) LOCATION: 69
    (D) OTHER INFORMATION: /note= "Xaa at position 69 is Gln
        or Glu"

(ix) FEATURE:
    (A) NAME/KEY: Modified-site
    (B) LOCATION: 73
    (D) OTHER INFORMATION: /note= "Xaa at position 73 is Ala
        or Gly"

(ix) FEATURE:
    (A) NAME/KEY: Modified-site
    (B) LOCATION: 76
    (D) OTHER INFORMATION: /note= "Xaa at position 76 is Ser
        or Ala"

(ix) FEATURE:
    (A) NAME/KEY: Modified-site
    (B) LOCATION: 79
    (D) OTHER INFORMATION: /note= "Xaa at position 79 is Lys
        or Arg"

(ix) FEATURE:
    (A) NAME/KEY: Modified-site
    (B) LOCATION: 82
    (D) OTHER INFORMATION: /note= "Xaa at position 82 is Leu,
        Glu, or Val"

(ix) FEATURE:
    (A) NAME/KEY: Modified-site
    (B) LOCATION: 87
    (D) OTHER INFORMATION: /note= "Xaa at position 87 is Leu
        or Ser"

(ix) FEATURE:
    (A) NAME/KEY: Modified-site
    (B) LOCATION: 93
    (D) OTHER INFORMATION: /note= "Xaa at position 93 is Pro
        or Ser"

(ix) FEATURE:
```

```
          (A) NAME/KEY: Modified-site
          (B) LOCATION: 98
          (D) OTHER INFORMATION: /note= "Xaa at position 98 is His,
              Ile, or Thr"

(ix) FEATURE:
          (A) NAME/KEY: Modified-site
          (B) LOCATION: 101
          (D) OTHER INFORMATION: /note= "Xaa at position 101 is Asp
              or Ala"

(ix) FEATURE:
          (A) NAME/KEY: Modified-site
          (B) LOCATION: 105
          (D) OTHER INFORMATION: /note= "Xaa at position 105 is Asn
              or Glu"

(ix) FEATURE:
          (A) NAME/KEY: Modified-site
          (B) LOCATION: 109
          (D) OTHER INFORMATION: /note= "Xaa at position 109 is Arg
              or Glu"

(ix) FEATURE:
          (A) NAME/KEY: Modified-site
          (B) LOCATION: 116
          (D) OTHER INFORMATION: /note= "Xaa at position 116 is Lys
              or Val"

(ix) FEATURE:
          (A) NAME/KEY: Modified-site
          (B) LOCATION: 120
          (D) OTHER INFORMATION: /note= "Xaa at position 120 is Asn,
              Gln, or His"

(ix) FEATURE:
          (A) NAME/KEY: Modified-site
          (B) LOCATION: 123
          (D) OTHER INFORMATION: /note= "Xaa at position 123 is Ala
              or Glu"

(xi) SEQUENCE DESCRIPTION: SEQ ID NO:129:

Ala Pro Met Thr Gln Thr Thr Ser Leu Lys Thr Ser Trp Val Asn Cys
   1               5                   10                  15

Ser Xaa Met Ile Asp Glu Ile Ile Xaa His Leu Lys Xaa Pro Pro Xaa
               20                  25                  30

Pro Leu Leu Asp Xaa Asn Asn Leu Asn Xaa Glu Asp Xaa Asp Ile Leu
               35                  40                  45

Met Glu Xaa Asn Leu Arg Xaa Pro Asn Leu Xaa Xaa Phe Xaa Arg Ala
   50                  55                  60

Val Lys Xaa Leu Xaa Asn Ala Ser Xaa Ile Glu Xaa Ile Leu Xaa Asn
   65                  70                  75                  80

Leu Xaa Pro Cys Leu Pro Xaa Ala Thr Ala Ala Pro Xaa Arg His Pro
               85                  90                  95

Ile Xaa Ile Lys Xaa Gly Asp Trp Xaa Glu Phe Arg Xaa Lys Leu Thr
               100                 105                 110

Phe Tyr Leu Xaa Thr Leu Glu Xaa Ala Gln Xaa Gln Gln Thr Thr Leu
               115                 120                 125

Ser Leu Ala Ile Phe
               130

(2) INFORMATION FOR SEQ ID NO:130:

(i) SEQUENCE CHARACTERISTICS:
          (A) LENGTH: 111 amino acids
          (B) TYPE: amino acid
          (D) TOPOLOGY: linear (ii) MOLECULE TYPE: peptide
```

```
(ix) FEATURE:
    (A) NAME/KEY: Modified-site
    (B) LOCATION: 1
    (D) OTHER INFORMATION: /note= "Met- or Met-Ala may or may
        not precede the amino acid in position 1"

(ix) FEATURE:
    (A) NAME/KEY: Modified-site
    (B) LOCATION: 4
    (D) OTHER INFORMATION: /note= "Xaa at position 4 is Asn or
        Ile"

(ix) FEATURE:
    (A) NAME/KEY: Modified-site
    (B) LOCATION: 11
    (D) OTHER INFORMATION: /note= "Xaa at position 11 is Thr
        or His"

(ix) FEATURE:
    (A) NAME/KEY: Modified-site
    (B) LOCATION: 15
    (D) OTHER INFORMATION: /note= "Xaa at position 15 is Gln,
        Arg, or Val"

(ix) FEATURE:
    (A) NAME/KEY: Modified-site
    (B) LOCATION: 18
    (D) OTHER INFORMATION: /note= "Xaa at position 18 is Leu,
        Ala, or Asn"

(ix) FEATURE:
    (A) NAME/KEY:  Modified-site
    (B) LOCATION: 23
    (C) OTHER INFORMATION: /note= "Xaa at position 23 is Phe,
        Pro, or Ser"

(ix) FEATURE:
    (A) NAME/KEY: Modified-site
    (B) LOCATION: 28
    (D) OTHER INFORMATION: /note= "Xaa at position 28 is Glu,
        Ala, or Ser"

(ix) FEATURE:
    (A) NAME/KEY: Modified-site
    (B) LOCATION: 31
    (D) OTHER INFORMATION: /note= "Xaa at position 31 is Gln,
        Val, or Met"

(ix) FEATURE:
    (A) NAME/KEY: Modified-site
    (B) LOCATION: 37
    (D) OTHER INFORMATION: /note= "Xaa at position 37 is Asn
        or Arg"

(ix) FEATURE:
    (A) NAME/KEY: Modified-site
    (B) LOCATION: 41
    (D) OTHER INFORMATION: /note= "Xaa at position 41 is Arg,
        Leu, or Thr"

(ix) FEATURE:
    (A) NAME/KEY: Modified-site
    (B) LOCATION: 45
    (D) OTHER INFORMATION: /note= "Xaa at position 45 is Glu
        or Leu"

(ix) FEATURE:
    (A) NAME/KEY: Modified-site
    (B) LOCATION: 46
    (D) OTHER INFORMATION: /note= "Xaa at position 46 is Ala
        or Ser"

(ix) FEATURE:
    (A) NAME/KEY: Modified-site
    (B) LOCATION: 48
    (D) OTHER INFORMATION: /note= "Xaa at position 48 is Asn
        or Val"

(ix) FEATURE:
    (A) NAME/KEY: Modified-site
```

-continued

```
      (B) LOCATION: 53
      (D) OTHER INFORMATION: /note= "Xaa at position 53 is Ser,
          Asn, or His"

(ix) FEATURE:
      (A) NAME/KEY: Modified-site
      (B) LOCATION: 55
      (D) OTHER INFORMATION: /note= "Xaa at position 55 is Gln
          or Glu"

(ix) FEATURE:
      (A) NAME/KEY: Modified-site
      (B) LOCATION: 59
      (D) OTHER INFORMATION: /note= "Xaa at position 59 is Ala
          or Gly"

(ix) FEATURE:
      (A) NAME/KEY: Modified-site
      (B) LOCATION: 62
      (D) OTHER INFORMATION: /note= "Xaa at position 62 is Ser
          or Ala"

(ix) FEATURE:
      (A) NAME/KEY: Modified-site
      (B) LOCATION: 65
      (D) OTHER INFORMATION: /note= "Xaa at position 65 is Lys
          or Arg"

(ix) FEATURE:
      (A) NAME/KEY: Modified-site
      (B) LOCATION: 68
      (D) OTHER INFORMATION: /note= "Xaa at position 68 is Leu,
          Glu, or Val"

(ix) FEATURE:
      (A) NAME/KEY: Modified-site
      (B) LOCATION: 73
      (D) OTHER INFORMATION: /note= "Xaa at position 73 is Leu
          or Ser"

(ix) FEATURE:
      (A) NAME/KEY: Modified-site
      (B) LOCATION: 79
      (D) OTHER INFORMATION: /note= "Xaa at position 79 is Pro
          or Ser"

(ix) FEATURE:
      (A) NAME/KEY: Modified-site
      (B) LOCATION: 84
      (D) OTHER INFORMATION: /note= "Xaa at position 84 is His,
          Ile, or Thr"

(ix) FEATURE:
      (A) NAME/KEY: Modified-site
      (B) LOCATION: 87
      (D) OTHER INFORMATION: /note= "Xaa at position 87 is Asp
          or Ala"

(ix) FEATURE:
      (A) NAME/KEY: Modified-site
      (B) LOCATION: 91
      (D) OTHER INFORMATION: /note= "Xaa at position 91 is Asn
          or Glu"

(ix) FEATURE:
      (A) NAME/KEY: Modified-site
      (B) LOCATION: 95
      (D) OTHER INFORMATION: /note= "Xaa at position 95 is Arg
          or Glu"

(ix) FEATURE:
      (A) NAME/KEY: Modified-site
      (B) LOCATION: 102
      (D) OTHER INFORMATION: /note= "Xaa at position 102 is Lys
          or Val"

(ix) FEATURE:
      (A) NAME/KEY: Modified-site
      (B) LOCATION: 106
      (D) OTHER INFORMATION: /note= "Xaa at position 106 is Asn,
```

Gln, or His"

(ix) FEATURE:
        (A) NAME/KEY: Modified-site
        (B) LOCATION: 109
        (D) OTHER INFORMATION: /note= "Xaa at position 109 is Ala
            or Glu"

(xi) SEQUENCE DESCRIPTION: SEQ ID NO:130:

Asn Cys Ser Xaa Met Ile Asp Glu Ile Ile Xaa His Leu Lys Xaa Pro
1               5                   10                  15

Pro Xaa Pro Leu Leu Asp Xaa Asn Asn Leu Asn Xaa Glu Asp Xaa Asp
        20                  25                  30

Ile Leu Met Glu Xaa Asn Leu Arg Xaa Pro Asn Leu Xaa Xaa Phe Xaa
            35                  40                  45

Arg Ala Val Lys Xaa Leu Xaa Asn Ala Ser Xaa Ile Glu Xaa Ile Leu
        50                  55                  60

Xaa Asn Leu Xaa Pro Cys Leu Pro Xaa Ala Thr Ala Ala Pro Xaa Arg
65                  70                  75                  80

His Pro Ile Xaa Ile Lys Xaa Gly Asp Trp Xaa Glu Phe Arg Xaa Lys
            85                  90                  95

Leu Thr Phe Tyr Leu Xaa Thr Leu Glu Xaa Ala Gln Xaa Gln Gln
                100                 105                 110

(2) INFORMATION FOR SEQ ID NO:131:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:131:

CTAGCCACGG CCGCACCCAC GCGACATCCA ATCCATATCA AGGACGGTGA CTGGAATG        58

(2) INFORMATION FOR SEQ ID NO:132:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:132:

TTAACATTCC AGTCACCGTC CTTGATATGG ATTGGATGTC GCGTGGGTGC GGCCGTGG        58

(2) INFORMATION FOR SEQ ID NO:133:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:133:

AAGGAGATAT ATCCATGAAC TGCTCTAAC                                        29

(2) INFORMATION FOR SEQ ID NO:134:

(i) SEQUENCE CHARACTERISTICS:

(A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:134:

Met Asn Cys Ser Asn
1               5

(2) INFORMATION FOR SEQ ID NO:135:

(i) SEQUENCE CHARACTERISTICS:
        (A) LENGTH: 120 amino acids
        (B) TYPE: amino acid
        (D) TOPOLOGY: linear (ii) MOLECULE TYPE: peptide (xi) SEQUENCE DESCRIPTION: SEQ ID NO:135:

Met Asn Cys Ser Asn Met Ile Asp Glu Ile Ile Thr His Leu Lys Gln
1               5                  10                  15

Pro Pro Leu Pro Leu Leu Asp Phe Asn Asn Leu Asn Gly Glu Asp Gln
            20                  25                  30

Asp Ile Leu Met Glu Asn Asn Leu Arg Arg Pro Asn Leu Glu Ala Phe
        35                  40                  45

Asn Arg Ala Val Lys Ser Leu Gln Asn Ala Ser Ala Ile Glu Ser Ile
    50                  55                  60

Leu Lys Asn Leu Leu Pro Cys Leu Pro Leu Ala Thr Ala Ala Pro Thr
65                  70                  75                  80

Arg His Pro Ile His Ile Lys Asp Gly Asp Trp Asn Glu Phe Arg Arg
                85                  90                  95

Lys Leu Thr Phe Tyr Leu Lys Thr Leu Glu Asn Ala Gln Ala Gln Gln
            100                 105                 110

Thr Thr Leu Arg Leu Ala Ile Phe
            115                 120

(2) INFORMATION FOR SEQ ID NO:136:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:136:

AATTCCGTCG TAAACTGACC TTCTATCTGA AAACCTTGGA GAACGCGCAG GCTCAACAGA     60

CCACTCTGTC G                                                          71

(2) INFORMATION FOR SEQ ID NO:137:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:137:

CTAGCGACAG AGTGGTCTGT TGAGCCTGCG CGTTCTCCAA GGTTTTCAGA TAGAAGGTCA     60

GTTTACGACG G                                                          71

(2) INFORMATION FOR SEQ ID NO:138:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:138:

```
GCGCGCCTGC AGAATGCATC AGCAATTGAG AGCATTCTTA AANNSCTCCT GCCATGTCTG      60

CCGCTAGCCA C                                                          71
```

(2) INFORMATION FOR SEQ ID NO:139:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:139:

```
GCGCGCCTGC AGAATGCATC AGCAATTGAG AGCATTCTTA AAAATNNSCT GCCATGTCTG      60

CCGCTAGCCA C                                                          71
```

(2) INFORMATION FOR SEQ ID NO:140:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:140:

```
GCGCGCCTGC AGAATGCATC AGCAATTGAG AGCATTCTTA AAAATCTCNN SCCATGTCTG      60

CCGCTAGCCA C                                                          71
```

(2) INFORMATION FOR SEQ ID NO:141:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:141:

```
GCGCGCCTGC AGAATGCATC AGCAATTGAG AGCATTCTTA AAAATCTCCT GNNSTGTCTG      60

CCGCTAGCCA CGGCCGCACC CACGCGACA                                       89
```

(2) INFORMATION FOR SEQ ID NO:142:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:142:

GCGCGCCTGC AGAATGCATC AGCAATTGAG AGCATTCTTA AAAATCTCCT GCCANNSCTG    60

CCGCTAGCCA CGGCCGCACC CACGCGACA    89

(2) INFORMATION FOR SEQ ID NO:143:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:143:

GCGCGCCTGC AGAATGCATC AGCAATTGAG AGCATTCTTA AAAATCTCCT GCCATGTNNS    60

CCGCTAGCCA CGGCCGCACC CACGCGACA    89

(2) INFORMATION FOR SEQ ID NO:144:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:144:

ATGGCTCCAA TGACTCAGAC TACTTCTCTT AAGACTTCTT GGGTTAACTG CTCTAACATG    60

ATCGATGAAA TTATAACACA CTTAAAGCAG CCACCTTTGC CTTTGCTGGA CTTCAACAAC    120

CTCAATGGGG AAGACCAAGA CATTCTGATG GAAAATAACC TTCGAAGGCC AAACCTGGAG    180

GCATTCAACA GGGCTGTCAA GAGTTTACAG AATGCATCAG CAATTGAGAG CATTCTTAAA    240

AATCTCCTGC CATGTCTGCC CCTGGCCACG GCCGCACCCA CGCGACATCC AATCCATATC    300

AAGGACGGTG ACTGGAATGA ATTCCGTCGT AAACTGACCT TCTATCTGAA AACCTTGGAG    360

AACGCGCAGG CTCAACAGAC CACTCTGTCG CTAGCGATCT TTTAATAA    408

(2) INFORMATION FOR SEQ ID NO:145:

(i) SEQUENCE CHARACTERISTICS:
        (A) LENGTH: 157 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..156

(xi) SEQUENCE DESCRIPTION: SEQ ID NO:145:

```
ATC GAT GAA ATC ATC ACC CAC CTG AAG CAG CCA CCG CTG CCG CTG CTG       48
Ile Asp Glu Ile Ile Thr His Leu Lys Gln Pro Pro Leu Pro Leu Leu
 1               5                  10                  15

GAC TTC AAC AAC CTC AAT GGT GAA GAC CAA GAT ATC CTG ATG GAA AAT       96
Asp Phe Asn Asn Leu Asn Gly Glu Asp Gln Asp Ile Leu Met Glu Asn
                20                  25                  30

AAC CTT CGT CGT CCA AAC CTC GAG GCA TTC AAC CGT GCT GTC AAG TCT      144
Asn Leu Arg Arg Pro Asn Leu Glu Ala Phe Asn Arg Ala Val Lys Ser
        35                  40                  45

CTG CAG AAT GCA T                                                    157
```

```
Leu Gln Asn Ala
    50

(2) INFORMATION FOR SEQ ID NO:146:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:146:

Ile Asp Glu Ile Ile Thr His Leu Lys Gln Pro Pro Leu Pro Leu Leu
 1               5                  10                  15

Asp Phe Asn Asn Leu Asn Gly Glu Asp Gln Asp Ile Leu Met Glu Asn
            20                  25                  30

Asn Leu Arg Arg Pro Asn Leu Glu Ala Phe Asn Arg Ala Val Lys Ser
        35                  40                  45

Leu Gln Asn Ala
    50

(2) INFORMATION FOR SEQ ID NO:147:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:147:

CCATGGCTCC AATGACTCAG ACTACTTCTC TTAAGACTTC TTGGGTTAAC TGCTCTAACA      60

TGATCGATGA AATTATAACA CACTTAAAGC AGCCACCTTT GCCTTTGCTG GACTTCAACA     120

ACCTCAATGG GGAAGACCAA GACATTCTGA TGGAAAATAA CCTTCGAAGG CCAAACCTGG     180

AGGCATTCAA CAGGGCTGTC AAGAGTTTAC AGAATGCATC AGCAATTGAG AGCATTCTTA     240

AAAATCTCCT GCCATGTCTG CCCCTGGCCA CGGCCGCACC CACGCGACAT CCAATCCATA     300

TCAAGGACGG TGACTGGAAT GAATTCCGTC GTAAACTGAC CTTCTATCTG AAAACCTTGG     360

AGAACGCGCA GGCTCAACAG ACCACTCTGT CGCTAGCGAT CTTTTAATAA GCTT           414

(2) INFORMATION FOR SEQ ID NO:148:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:148:

AAGCTTATTA AAAGATCGCT AGCGACAGAG TGGTCTGTTG AGCCTGCGCG TTCTCCAAGG      60

TTTTCAGATA GAAGGTCAGT TTACGACGGA ATTCATTCCA GTCACCGTCC TTGATATGGA     120

TTGGATGTCG CGTGGGTGCG GCCGTGGCCA GGGGCAGACA TGGCAGGAGA TTTTTAAGAA     180

TGCTCTCAAT TGCTGATGCA TTCTGTAAAC TCTTGACAGC CCTGTTGAAT GCCTCCAGGT     240

TTGGCCTTCG AAGGTTATTT TCCATCAGAA TGTCTTGGTC TTCCCCATTG AGGTTGTTGA     300

AGTCCAGCAA AGGCAAAGGT GGCTGCTTTA AGTGTGTTAT AATTTCATCG ATCATGTTAG     360

AGCAGTTAAC CCAAGAAGTC TTAAGAGAAG TAGTCTGAGT CATTGGAGCC ATGG           414
```

(2) INFORMATION FOR SEQ ID NO:149:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:149:

```
ATGATGATTA CTCTGCGCAA ACTTCCTCTG GCGGTTGCCG TCGCAGCGGG CGTAATGTCT      60

GCTCAGGCCA TGGCTAACTG C                                               81
```

(2) INFORMATION FOR SEQ ID NO:150:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:150:

```
GCAGTTAGCC ATGGCCTGAG CAGACATTAC GCCCGCTGCG ACGGCAACCG CCAGAGGAAG      60

TTTGCGCAGA GTAATCATCA T                                               81
```

(2) INFORMATION FOR SEQ ID NO:151:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:151:

```
CATGGCTAAC TGCTCTAACA TGAT                                            24
```

(2) INFORMATION FOR SEQ ID NO:152:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:152:

```
CGATCATGTT AGAGCAGTTA GC                                              22
```

(2) INFORMATION FOR SEQ ID NO:153:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:153:

```
ATGGCTAACT GC                                                         12
```

(2) INFORMATION FOR SEQ ID NO:154:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:154:

Met Ala Asn Cys
1

(2) INFORMATION FOR SEQ ID NO:155:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:155:

GCCGATACCG CGGCATACTC CCACCATTCA GAGA                                   34

(2) INFORMATION FOR SEQ ID NO:156:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:156:

GCCGATAAGA TCTAAAACGG GTATGGAGAA ACA                                    33

(2) INFORMATION FOR SEQ ID NO:157:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:157:

GCGCGCCTGC AGAATGCATC AGCAATTGAG AGCATTCTTA AAAATCTCCT GCCATGTCTG      60

NNSCTAGCCA CGGCCGCACC CACGCGACA                                              89

(2) INFORMATION FOR SEQ ID NO:158:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:158:

GCGCGCCTGC AGAATGCATC AGCAATTGAG AGCATTCTTA AAAATCTCCT GCCATGTCTG      60

CCGNNSGCCA CGGCCGCACC CACGCGACA                                              89

(2) INFORMATION FOR SEQ ID NO:159:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:159:

```
GCGCGCCTGC AGAATGCATC AGCAATTGAG AGCATTCTTA AAAATCTCCT GCCATGTCTG      60

CCGCTANNSA CGGCCGCACC CACGCGACA                                       89
```

(2) INFORMATION FOR SEQ ID NO:160:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:160:

```
CGCGCGGAAT TCATTCCAGT CACCGTCCTT GATATGGATT GGATGTCGCG TGGGTGCGGC      60

SNNGGCCAGG GGCAGACATG GCAGGA                                          86
```

(2) INFORMATION FOR SEQ ID NO:161:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:161:

```
CGCGCGGAAT TCATTCCAGT CACCGTCCTT GATATGGATT GGATGTCGCG TGGGTGCSNN      60

CGTGGCCAGG GGCAGACATG GCAGGA                                          86
```

(2) INFORMATION FOR SEQ ID NO:162:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:162:

```
CGCGCGGAAT TCATTCCAGT CACCGTCCTT GATATGGATT GGATGTCGCG TGGGSNNGGC      60

CGTGGCCAGG GGCAGACATG GCAGGA                                          86
```

(2) INFORMATION FOR SEQ ID NO:163:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:163:

```
CGCGCGGAAT TCATTCCAGT CACCGTCCTT GATATGGATT GGATGTCGCG TSNNTGCGGC         60

CGTGGCCAGG GGCAGACATG GCAGGA                                             86

(2) INFORMATION FOR SEQ ID NO:164:

(i) SEQUENCE CHARACTERISTICS:
         (A) LENGTH: 86 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:164:

CGCGCGGAAT TCATTCCAGT CACCGTCCTT GATATGGATT GGATGTCGSN NGGGTGCGGC         60

CGTGGCCAGG GGCAGACATG GCAGGA                                             86

(2) INFORMATION FOR SEQ ID NO:165:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:165:

TTTCAGATAG AAGGTCAGTT TACGACGGAA SNNATTCCAG TCACCGTC                      48

(2) INFORMATION FOR SEQ ID NO:166:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:166:

TTTCAGATAG AAGGTCAGTT TACGACGSNN TTCATTCCAG TCACCGTC                      48

(2) INFORMATION FOR SEQ ID NO:167:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:167:

TTTCAGATAG AAGGTCAGTT TACGSNNGAA TTCATTCCAG TCACCGTC                      48

(2) INFORMATION FOR SEQ ID NO:168:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:168:

TTTCAGATAG AAGGTCAGTT TSNNACGGAA TTCATTCCAG TCACCGTC                      48
```

(2) INFORMATION FOR SEQ ID NO:169:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:169:

TTTCAGATAG AAGGTCAGSN NACGACGGAA TTCATTCCAG TCACCGTC          48

(2) INFORMATION FOR SEQ ID NO:170:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:170:

TTTCAGATAG AAGGTSNNTT TACGACGGAA TTCATTCCAG TCACCGTC          48

(2) INFORMATION FOR SEQ ID NO:171:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:171:

CGCGCGAAGC TTATTACTGT TGA          23

(2) INFORMATION FOR SEQ ID NO:172:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:172:

CGCGCGAAGC TTATTACTGT TGAGCCTGCG CGTTCTCCAA GGTTTTCAGA TAGAASNNCA          60

GTTTACGACG GAATTCAT          78

(2) INFORMATION FOR SEQ ID NO:173:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:173:

CGCGCGAAGC TTATTACTGT TGAGCCTGCG CGTTCTCCAA GGTTTTCAGA TASNNGGTCA          60

GTTTACGACG GAATTCAT          78

(2) INFORMATION FOR SEQ ID NO:174:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:174:

```
CGCGCGAAGC TTATTACTGT TGAGCCTGCG CGTTCTCCAA GGTTTTCAGS NNGAAGGTCA      60

GTTTACGACG GAATTCAT                                                   78
```

(2) INFORMATION FOR SEQ ID NO:175:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:175:

```
CGCGCGAAGC TTATTACTGT TGAGCCTGCG CGTTCTCCAA GGTTTTSNNA TAGAAGGTCA      60

GTTTACGACG GAATTCAT                                                   78
```

(2) INFORMATION FOR SEQ ID NO:176:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:176:

```
CGCGCGAAGC TTATTACTGT TGAGCCTGCG CGTTCTCCAA GGTSNNCAGA TAGAAGGTCA      60

GTTTACGACG GAATTCAT                                                   78
```

(2) INFORMATION FOR SEQ ID NO:177:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:177:

```
CGCGCGAAGC TTATTACTGT TGAGCCTGCG CGTTCTCCAA SNNTTTCAGA TAGAAGGTCA      60

GTTTACGACG GAATTCAT                                                   78
```

(2) INFORMATION FOR SEQ ID NO:178:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:178:

CGCGCGAAGC TTATTACTGT TGAGCCTGCG CGTTCTCSNN GGTTTTCAGA TAGAAGGTCA    60

(2) INFORMATION FOR SEQ ID NO:179:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:179:

CGCGCGAAGC TTATTACTGT TGAGCCTGCG CGTTSNNCAA GGTTTTCAGA TAGAAGGTCA    60

(2) INFORMATION FOR SEQ ID NO:180:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:180:

CGCGCGAAGC TTATTACTGT TGAGCCTGCG CSNNCTCCAA GGTTTTCAGA TAGAAGGTCA    60

(2) INFORMATION FOR SEQ ID NO:181:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:181:

CGCGCGAAGC TTATTACTGT TGAGCCTGSN NGTTCTCCAA GGTTTTCAGA TAGAAGGTCA    60

(2) INFORMATION FOR SEQ ID NO:182:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:182:

CGCGCGAAGC TTATTACTGT TGAGCSNNCG CGTTCTCCAA GGTTTTCAGA TAGAAGGTCA    60

(2) INFORMATION FOR SEQ ID NO:183:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:183:

CGCGCGAAGC TTATTACTGT TGSNNCTGCG CGTTCTCCAA GGTTTTCAGA TAGAAGGTCA    60

(2) INFORMATION FOR SEQ ID NO:184:

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:184:

TGCTCTAACA TGATCGATGA AATT                                            24

(2) INFORMATION FOR SEQ ID NO:185:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:185:

GAAATTATAA CACACTTAAA GCAG                                            24

(2) INFORMATION FOR SEQ ID NO:186:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:186:

AAGCAGCCAC CTTTGCCTTT GCTG                                            24

(2) INFORMATION FOR SEQ ID NO:187:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:187:

AAGCAGCCAC CGCTGCCGCT GCTG                                            24

(2) INFORMATION FOR SEQ ID NO:188:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:188:

CTCAATGGTG AAGACCAAGA TATC                                            24

(2) INFORMATION FOR SEQ ID NO:189:

(i) SEQUENCE CHARACTERISTICS:
        (A) LENGTH: 24 base pairs
        (B) TYPE: nucleic acid
        (C) STRANDEDNESS: single
```

(D) TOPOLOGY: linear (ii) MOLECULE TYPE: DNA (synthetic)

(xi) SEQUENCE DESCRIPTION: SEQ ID NO:189:

GATATCCTGA TGGAAAATAA CCTT                                              24

(2) INFORMATION FOR SEQ ID NO:190:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:190:

AACCTTCGTC GTCCAAACCT CGAG                                              24

(2) INFORMATION FOR SEQ ID NO:191:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:191:

CTCGAGGCAT TCAACCGTGC TGTC                                              24

(2) INFORMATION FOR SEQ ID NO:192:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:192:

GCTGTCAAGT CTCTGCAGAA TGCA                                              24

(2) INFORMATION FOR SEQ ID NO:193:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:193:

AATGCATCAG CAATTGAGAG CATT                                              24

(2) INFORMATION FOR SEQ ID NO:194:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:194:

```
AGCATTCTTA AAAATCTCCT GCCA                                              24

(2) INFORMATION FOR SEQ ID NO:195:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:195:

CTGCCATGTC TGCCCCTGGC CACG                                              24

(2) INFORMATION FOR SEQ ID NO:196:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:196:

CTGGCCACGG CCGCACCCAC GCGA                                              24

(2) INFORMATION FOR SEQ ID NO:197:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:197:

AATGAATTCC GTCGTAAACT GACC                                              24

(2) INFORMATION FOR SEQ ID NO:198:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:198:

CTGACCTTCT ATCTGAAAAC CTTG                                              24

(2) INFORMATION FOR SEQ ID NO:199:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:199:

ACCTTGGAGA ACGCGCAGGC TCAA                                              24

(2) INFORMATION FOR SEQ ID NO:200:
```

```
         (i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:200:

GAATGCATCA GCAATTGAGA GC                                              22

(2) INFORMATION FOR SEQ ID NO:201:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:201:

AATTGCTGAT GCATTCTGCA                                                 20

(2) INFORMATION FOR SEQ ID NO:202:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:202:

ATTCTTAAAA ATCTCCTGCC ATGT                                            24

(2) INFORMATION FOR SEQ ID NO:203:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:203:

CAGGAGATTT TTAAGAATGC TCTC                                            24

(2) INFORMATION FOR SEQ ID NO:204:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:204:

CTGCCCCTGG CCACGGCCGC ACCCACGCGA                                      30

(2) INFORMATION FOR SEQ ID NO:205:

(i) SEQUENCE CHARACTERISTICS:
              (A) LENGTH: 30 base pairs
              (B) TYPE: nucleic acid
              (C) STRANDEDNESS: single
```

```
         (D) TOPOLOGY: linear (ii) MOLECULE TYPE: DNA (synthetic)

(xi) SEQUENCE DESCRIPTION: SEQ ID NO:205:

GGGTGCGGCC GTGGCCAGGG GCAGACATGG                                    30

(2) INFORMATION FOR SEQ ID NO:206:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:206:

CATCCAATCA TCATCCGTGA CGGTGACTGG AATG                               34

(2) INFORMATION FOR SEQ ID NO:207:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:207:

AATTCATTCC AGTCACCGTC ACGGATGATG ATTGGATGTC GCGT                    44

(2) INFORMATION FOR SEQ ID NO:208:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:208:

CGCCCAATCA TCATCCGTGA CGGTGACTGG AATG                               34

(2) INFORMATION FOR SEQ ID NO:209:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:209:

AATTCATTCC AGTCACCGTC ACGGATGATG ATTGGGCGTC GCGT                    44

(2) INFORMATION FOR SEQ ID NO:210:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:210:
```

CATGGCTAAC TGCTCTAACA TGATCGATGA AATTATAACA                    40

(2) INFORMATION FOR SEQ ID NO:211:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:211:

CTTTAAGTGT GTTATAATTT CATCGATCAT GTTAGAGCAG TTAGC              45

(2) INFORMATION FOR SEQ ID NO:212:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:212:

CACTTAAAGC AGCCACCTTT GCCTTTGCTG GACTTC                        36

(2) INFORMATION FOR SEQ ID NO:213:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:213:

GAGGTTGTTG AAGTCCAGCA AAGGCAAAGG TGGCTG                        36

(2) INFORMATION FOR SEQ ID NO:214:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:214:

AACAACCTCA ATGACGAAGA CATGTCT                                  27

(2) INFORMATION FOR SEQ ID NO:215:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:215:

AGACATGTCT TCGTCATT                                            18

(2) INFORMATION FOR SEQ ID NO:216:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:216:

```
ATGGCTAACT GCTCTAACAT GATCGATGAA ATCATCACCC ACCTGAAGCA GCCACCGCTG    60

CCGCTGCTGG ACTTCAACAA CCTCAATGGT GAAGACCAAG ATATCCTGAT GGAAAATAAC   120

CTTCGTCGTC CAAACCTCGA GGCATTCAAC CGTGCTGTCA ACTCTCTGCA GAATGCATCA   180

GCAATTGAGA GCATTCTTAA AAATCTCCTG CCATGTCTGC CCCTGGCCAC GGCCGCACCC   240

ACGCGACATC CAATCCATAT CAAGGACGGT GACTGGAATG AATTCCGTCG TAAACTGACC   300

TTCTATCTGA AAACCTTGGA GAACGCGCAG GCTCAACAG                         339
```

(2) INFORMATION FOR SEQ ID NO:217:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:217:

```
Asn Cys Ser Asn Met Ile Asp Glu Ile Ile Thr His Leu Lys Gln Pro
  1               5                  10                  15

Pro Leu Pro Leu Leu Asp Phe Asn Asn Leu Asn Gly Glu Asp Gln Asp
             20                  25                  30

Ile Leu Met Glu Asn Asn Leu Arg Arg Pro Asn Leu Glu Ala Phe Asn
         35                  40                  45

Arg Ala Val Lys Ser Leu Gln Asn Ala Ser Ala Ile Glu Ser Ile Leu
     50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Trp Thr Leu Glu Asn Ala Gln Ala Gln Gln
                100                 105                 110
```

(2) INFORMATION FOR SEQ ID NO:218:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:218:

```
Asn Cys Ser Asn Met Ile Asp Glu Ile Ile Thr His Leu Lys Gln Pro
  1               5                  10                  15

Pro Leu Pro Leu Leu Asp Phe Asn Asn Leu Asn Gly Glu Asp Gln Asp
             20                  25                  30

Ile Leu Met Asp Asn Asn Leu Arg Arg Pro Asn Leu Glu Ala Phe Asn
         35                  40                  45

Arg Ala Val Lys Ser Leu Gln Asn Ala Ser Ala Ile Glu Ser Ile Leu
     50                  55                  60
```

```
Lys Asn Leu Leu Pro Cys Leu Pro Leu Ala Thr Ala Ala Pro Thr Arg
 65              70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
            100                 105                 110
```

(2) INFORMATION FOR SEQ ID NO:219:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:219:

```
CTTTAAGTGT GTTATAATTT CTTCGATCAT GTTAGAGCAG TTAGC            45
```

(2) INFORMATION FOR SEQ ID NO:220:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:220:

```
ATGGCTAACT GCTCTAACAT GATCGATGAA ATCATCACCC ACCTGAAGCA GCCACCGCTG     60
CCGCTGCTGG ACTTCAACAA CCTCAATGGT GAAGACCAAG ATATCCTGAT GGAAAATAAC    120
CTTCGTCGTC CAAACCTCGA GGCATTCAAC CGTGCTGTCA ACTCTCTGCA GAATGCATCA    180
GCAATTGAGA GCATTCTTAA AAATCTCCTG CCATGTCTGC CCCTGGCCAC GGCCGCACCC    240
ACGCGACATC CAATCCATAT CAAGGACGGT GACTGGAATG AATTCCGTCG TAAACTGACC    300
TTCTATCTGT GGACCTTGGA GAACGCGCAG GCTCAACAG                          339
```

(2) INFORMATION FOR SEQ ID NO:221:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:221:

```
CATGGCTAAC TGCTCTAACA TGATCAACGA AATTATAACA              40
```

(2) INFORMATION FOR SEQ ID NO:222:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:222:

```
CGCGCGCCAT GGCTAACTGC TCTNNSATGA TCGATGAAAT TATAACACAC TTAAAGCA          58
```

```
(2) INFORMATION FOR SEQ ID NO:223:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:223:

CGCGCGCCAT GGCTAACTGC TCTAACNNSA TCGATGAAAT TATAACACAC TTAAAGCA          58

(2) INFORMATION FOR SEQ ID NO:224:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:224:

CGCGCGCCAT GGCTAACTGC TCTAACATGN NSGATGAAAT TATAACACAC TTAAAGCA          58

(2) INFORMATION FOR SEQ ID NO:225:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:225:

CGCGCGCCAT GGCTAACTGC TCTAACATGA TCNNSGAAAT TATAACACAC TTAAAGCA          58

(2) INFORMATION FOR SEQ ID NO:226:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:226:

CGCGCGCCAT GGCTAACTGC TCTAACATGA TCGATNNSAT TATAACACAC TTAAAGCA          58

(2) INFORMATION FOR SEQ ID NO:227:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:227:

CGCGCGCCAT GGCTAACTGC TCTAACATGA TCGATGAANN SATAACACAC TTAAAGCAGC        60

CACCTTTGCC TTTGCT                                                        76

(2) INFORMATION FOR SEQ ID NO:228:

(i) SEQUENCE CHARACTERISTICS:
```

(A) LENGTH: 76 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:228:

CGCGCGCCAT GGCTAACTGC TCTAACATGA TCGATGAAAT TNNSACACAC TTAAAGCAGC        60

CACCTTTGCC TTTGCT        76

(2) INFORMATION FOR SEQ ID NO:229:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:229:

CGCGCGCCAT GGCTAACTGC TCTAACATGA TCGATGAAAT TATANNSCAC TTAAAGCAGC        60

CACCTTTGCC TTTGCT        76

(2) INFORMATION FOR SEQ ID NO:230:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:230:

CATGGCTAAC TGCTCTAACA TGATCAGCGA AATTATAACA        40

(2) INFORMATION FOR SEQ ID NO:231:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:231:

CTTTAAGTGT GTTATAATTT CGCTGATCAT GTTAGAGCAG TTAGC        45

(2) INFORMATION FOR SEQ ID NO:232:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:232:

CATGGCTAAC TGCTCTAACA TGATCACCGA AATTATAACA        40

(2) INFORMATION FOR SEQ ID NO:233:

(i) SEQUENCE CHARACTERISTICS:
        (A) LENGTH: 45 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:233:

CTTTAAGTGT GTTATAATTT CCGTGATCAT GTTAGAGCAG TTAGC            45

(2) INFORMATION FOR SEQ ID NO:234:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:234:

CATGGCTAAC TGCTCTAACA TGATCGATAA CATTATAACA                 40

(2) INFORMATION FOR SEQ ID NO:235:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:235:

CTTTAAGTGT GTTATAATGT TATCGATCAT GTTAGAGCAG TTAGC            45

(2) INFORMATION FOR SEQ ID NO:236:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:236:

CATGGCTAAC TGCTCTAACA TGATCGATGA CATTATAACA                 40

(2) INFORMATION FOR SEQ ID NO:237:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:237:

CTTTAAGTGT GTTATAATGT CATCGATCAT GTTAGAGCAG TTAGC            45

(2) INFORMATION FOR SEQ ID NO:238:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:238:

CATGGCTAAC TGCTCTAACA TGATCGATCA GATTATAACA                    40

(2) INFORMATION FOR SEQ ID NO:239:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:239:

CTTTAAGTGT GTTATAATCT GATCGATCAT GTTAGAGCAG TTAGC              45

(2) INFORMATION FOR SEQ ID NO:240:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:240:

CATGGCTAAC TGCTCTAACA TGATCGATCT GATTATAACA                    40

(2) INFORMATION FOR SEQ ID NO:241:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:241:

CTTTAAGTGT GTTATAATCA GATCGATCAT GTTAGAGCAG TTAGC              45

(2) INFORMATION FOR SEQ ID NO:242:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:242:

CATGGCTAAC TGCTCTAACA TGATCGATGT TATTATAACA                    40

(2) INFORMATION FOR SEQ ID NO:243:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:243:

CTTTAAGTGT GTTATAATAA CATCGATCAT GTTAGAGCAG TTAGC              45

(2) INFORMATION FOR SEQ ID NO:244:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:244:

CACTTAAAGC AGCCACCTTT GCCTGCTCTG GACTTC        36

(2) INFORMATION FOR SEQ ID NO:245:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:245:

GAGGTTGTTG AAGTCCAGAG CAGGCAAAGG TGGCTG        36

(2) INFORMATION FOR SEQ ID NO:246:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:246:

CACTTAAAGC AGCCACCTTT GCCTCGTCTG GACTTC        36

(2) INFORMATION FOR SEQ ID NO:247:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:247:

GAGGTTGTTG AAGTCCAGAC GAGGCAAAGG TGGCTG        36

(2) INFORMATION FOR SEQ ID NO:248:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:248:

CACTTAAAGC AGCCACCTTT GCCTCAGCTG GACTTC        36

(2) INFORMATION FOR SEQ ID NO:249:

(i) SEQUENCE CHARACTERISTICS:
        (A) LENGTH: 36 base pairs (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:249:

GAGGTTGTTG AAGTCCAGCT GAGGCAAAGG TGGCTG                               36

(2) INFORMATION FOR SEQ ID NO:250:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:250:

CACTTAAAGC AGCCACCTTT GCCTGAACTG GACTTC                               36

(2) INFORMATION FOR SEQ ID NO:251:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:251:

GAGGTTGTTG AAGTCCAGCT CAGGCAAAGG TGGCTG                               36

(2) INFORMATION FOR SEQ ID NO:252:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:252:

CACTTAAAGC AGCCACCTTT GCCTATCCTG GACTTC                               36

(2) INFORMATION FOR SEQ ID NO:253:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:253:

GAGGTTGTTG AAGTCCAGGA TAGGCAAAGG TGGCTG                               36

(2) INFORMATION FOR SEQ ID NO:254:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:254:

CACTTAAAGC AGCCACCTTT CCCTTTCCTG GACTTC                              36

(2) INFORMATION FOR SEQ ID NO:255:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:255:

GAGGTTGTTG AAGTCCAGGA AAGGCAAAGG TGGCTG                              36

(2) INFORMATION FOR SEQ ID NO:256:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:256:

CACTTAAAGC AGCCACCTTT GCCTACCCTG GACTTC                              36

(2) INFORMATION FOR SEQ ID NO:257:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:257:

GAGGTTGTTG AAGTCCAGGG TAGGCAAAGG TGGCTG                              36

(2) INFORMATION FOR SEQ ID NO:258:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:258:

AACAACCTCA ATCGTGAAGA CCAAGAT                                        27

(2) INFORMATION FOR SEQ ID NO:259:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:259:

ATCTTGGTCT TCACGATT                                                  18

(2) INFORMATION FOR SEQ ID NO:260:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:260:

AACAACCTCA ATAACGAAGA CCAAGAT                                           27

(2) INFORMATION FOR SEQ ID NO:261:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:261:

ATCTTGGTCT TCGTTATT                                                           18

(2) INFORMATION FOR SEQ ID NO:262:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:262:

AACAACCTCA ATGAAGAAGA CCAAGAT                                         27

(2) INFORMATION FOR SEQ ID NO:263:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:263:

ATCTTGGTCT TCTTCATT                                                          18

(2) INFORMATION FOR SEQ ID NO:264:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:264:

AACAACCTCA ATATCGAAGA CCAAGAT                                         27

(2) INFORMATION FOR SEQ ID NO:265:

(i) SEQUENCE CHARACTERISTICS:
        (A) LENGTH: 18 base pairs

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:265:

ATCTTGGTCT TCGATATT                                                 18

(2) INFORMATION FOR SEQ ID NO:266:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:266:

AACAACCTCA ATCTGGAAGA CCAAGAT                                       27

(2) INFORMATION FOR SEQ ID NO:267:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:267:

ATCTTGGTCT TCCAGATT                                                 18

(2) INFORMATION FOR SEQ ID NO:268:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:268:

AACAACCTCA ATAAAGAAGA CCAAGAT                                       27

(2) INFORMATION FOR SEQ ID NO:269:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:269:

ATCTTGGTCT TCTTTATT                                                 18

(2) INFORMATION FOR SEQ ID NO:270:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO:270:

AACAACCTCA ATATGGAAGA CCAAGAT                                                    27

(2) INFORMATION FOR SEQ ID NO:271:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:271:

ATCTTGGTCT TCCATATT                                                              18

(2) INFORMATION FOR SEQ ID NO:272:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:272:

AACAACCTCA ATTTCGAAGA CCAAGAT                                                    27

(2) INFORMATION FOR SEQ ID NO:273:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:273:

ATCTTGGTCT TCGAAATT                                                              18

(2) INFORMATION FOR SEQ ID NO:274:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:274:

AACAACCTCA ATACCGAAGA CCAAGAT                                                    27

(2) INFORMATION FOR SEQ ID NO:275:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:275:

ATCTTGGTCT TCGGTATT                                                              18

(2) INFORMATION FOR SEQ ID NO:276:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:276:

AACAACCTCA ATTACGAAGA CCAAGAT                          27

(2) INFORMATION FOR SEQ ID NO:277:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:277:

ATCTTGGTCT TCGTAATT                                18

(2) INFORMATION FOR SEQ ID NO:278:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:278:

AACAACCTCA ATGTTGAAGA CCAAGAT                          27

(2) INFORMATION FOR SEQ ID NO:279:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:279:

ATCTTGGTCT TCAACATT                                18

(2) INFORMATION FOR SEQ ID NO:280:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:280:

AACAACCTCA ATGGGCGTGA CCAAGAT                          27

(2) INFORMATION FOR SEQ ID NO:281:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:281:

ATCTTGGTCT CGCCCATT                                                        18

(2) INFORMATION FOR SEQ ID NO:282:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:282:

AACAACCTCA ATGGGCAGGA CCAAGAT                                              27

(2) INFORMATION FOR SEQ ID NO:283:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:283:

ATCTTGGTCC TGCCCATT                                                        18

(2) INFORMATION FOR SEQ ID NO:284:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:284:

AACAACCTCA ATGGGGTGA CCAAGAT                                               27

(2) INFORMATION FOR SEQ ID NO:285:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:285:

ATCTTGGTCA CCCCCATT                                                        18

(2) INFORMATION FOR SEQ ID NO:286:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:286:

AACAACCTCA ATGGGACCGA CCAAGAT                                                                27

(2) INFORMATION FOR SEQ ID NO:287:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:287:

ATCTTGGTCG GTCCCATT                                                                          18

(2) INFORMATION FOR SEQ ID NO:288:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:288:

AACAACCTCA ATGGGAAGC TCAAGAT                                                                 27

(2) INFORMATION FOR SEQ ID NO:289:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:289:

ATCTTGAGCT TCCCCATT                                                                          18

(2) INFORMATION FOR SEQ ID NO:290:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:290:

AACAACCTCA ATGGGAAAA CCAAGAT                                                                 27

(2) INFORMATION FOR SEQ ID NO:291:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:291:

ATCTTGGTTT TCCCCATT                                                                          18

(2) INFORMATION FOR SEQ ID NO:292:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:292:

AACAACCTCA ATGGGGAACA GCAAGAT                                              27

(2) INFORMATION FOR SEQ ID NO:293:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:293:

ATCTTGCTGT TCCCCATT                                                        18

(2) INFORMATION FOR SEQ ID NO:294:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:294:

AACAACCTCA ATGGGGAAGA ACAAGAT                                              27

(2) INFORMATION FOR SEQ ID NO:295:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:295:

ATCTTGTTCT TCCCCATT                                                        18

(2) INFORMATION FOR SEQ ID NO:296:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:296:

AACAACCTCA ATGGGGAAGA CGCTGAT                                              27

(2) INFORMATION FOR SEQ ID NO:297:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:297:

ATCAGCGTCT TCCCCATT                                                         18

(2) INFORMATION FOR SEQ ID NO:298:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:298:

AACAACCTCA ATGGGGAAGA CCGTGAT                                                27

(2) INFORMATION FOR SEQ ID NO:299:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:299:

ATCACGGTCT TCCCCATT                                                         18

(2) INFORMATION FOR SEQ ID NO:300:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:300:

AACAACCTCA ATGGGGAAGA CAACGAT                                                27

(2) INFORMATION FOR SEQ ID NO:301:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:301:

ATCGTTGTCT TCCCCATT                                                         18

(2) INFORMATION FOR SEQ ID NO:302:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:302:

AACAACCTCA ATGGGGAAGA CGACGAT                27

(2) INFORMATION FOR SEQ ID NO:303:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:303:

ATCGTCGTCT TCCCCATT                18

(2) INFORMATION FOR SEQ ID NO:304:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:304:

AACAACCTCA ATGGTGAAGA CGAAGAT                27

(2) INFORMATION FOR SEQ ID NO:305:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:305:

ATCTTCGTCT TCCCCATT                18

(2) INFORMATION FOR SEQ ID NO:306:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:306:

AACAACCTCA ATGGTGAAGA CCACGAT                27

(2) INFORMATION FOR SEQ ID NO:307:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:307:

ATCGTGGTCT TCCCCATT                18

(2) INFORMATION FOR SEQ ID NO:308:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:308:

AACAACCTCA ATGGGGAAGA CATCGAT                             27

(2) INFORMATION FOR SEQ ID NO:309:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:309:

ATCGATGTCT TCCCCATT                                   18

(2) INFORMATION FOR SEQ ID NO:310:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:310:

AACAACCTCA ATGGGGAAGA CTCCGAT                             27

(2) INFORMATION FOR SEQ ID NO:311:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:311:

ATCGGAGTCT TCCCCATT                                   18

(2) INFORMATION FOR SEQ ID NO:312:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:312:

AACAACCTCA ATGGGGAAGA CCAAGCT                             27

(2) INFORMATION FOR SEQ ID NO:313:

(i) SEQUENCE CHARACTERISTICS:
        (A) LENGTH: 18 base pairs (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:313:

AGCTTGGTCT TCCCCATT                                                    18

(2) INFORMATION FOR SEQ ID NO:314:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:314:

AACAACCTCA ATGGGGAAGA CCAAAAC                                          27

(2) INFORMATION FOR SEQ ID NO:315:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:315:

GTTTTGGTCT TCCCCATT                                                    18

(2) INFORMATION FOR SEQ ID NO:316:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:316:

AACAACCTCA ATGGGGAAGA CCAACAG                                          27

(2) INFORMATION FOR SEQ ID NO:317:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:317:

CTGTTGGTCT TCCCCATT                                                    18

(2) INFORMATION FOR SEQ ID NO:318:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:318:

AACAACCTCA ATGGGGAAGA CCAAGAA                                27

(2) INFORMATION FOR SEQ ID NO:319:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:319:

TTCTTGGTCT TCCCCATT                                          18

(2) INFORMATION FOR SEQ ID NO:320:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:320:

AACAACCTCA ATGGGGAAGA CCAACAC                                27

(2) INFORMATION FOR SEQ ID NO:321:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:321:

GTGTTGGTCT TCCCCATT                                          18

(2) INFORMATION FOR SEQ ID NO:322:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:322:

AACAACCTCA ATGGGGAAGA CCAAATC                                27

(2) INFORMATION FOR SEQ ID NO:323:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:323:

GATTTGGTCT TCCCCATT                                          18

(2) INFORMATION FOR SEQ ID NO:324:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:324:

AACAACCTCA ATGGGGAAGA CCAACTG                                            27

(2) INFORMATION FOR SEQ ID NO:325:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:325:

CAGTTGGTCT TCCCCATT                                                      18

(2) INFORMATION FOR SEQ ID NO:326:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:326:

AACAACCTCA ATGGGGAAGA CCAAAAA                                            27

(2) INFORMATION FOR SEQ ID NO:327:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:327:

TTTTTGGTCT TCCCCATT                                                      18

(2) INFORMATION FOR SEQ ID NO:328:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:328:

AACAACCTCA ATGGGGAAGA CCAATAC                                            27

(2) INFORMATION FOR SEQ ID NO:329:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:329:

GTATTGGTCT TCCCCATT                                                   18

(2) INFORMATION FOR SEQ ID NO:330:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:330:

AACAACCTCA ATGGGGAAGA CCAAGTT                                         27

(2) INFORMATION FOR SEQ ID NO:331:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:331:

AACTTGGTCT TCCCCATT                                                   18

(2) INFORMATION FOR SEQ ID NO:332:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:332:

ATCGCTATGG AAAATAACCT TCGAAGGCCA AACCTG                               36

(2) INFORMATION FOR SEQ ID NO:333:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:333:

CCTTCGAAGG TTATTTTCCA TAGCGAT                                         27

(2) INFORMATION FOR SEQ ID NO:334:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:334:

ATCGAAATGG AAAATAACCT TCGAAGGCCA AACCTG                                36

(2) INFORMATION FOR SEQ ID NO:335:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:335:

CCTTCGAAGG TTATTTTCCA TTTCGAT                                          27

(2) INFORMATION FOR SEQ ID NO:336:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:336:

ATCAAAATGG AAAATAACCT TCGAAGGCCA AACCTG                                36

(2) INFORMATION FOR SEQ ID NO:337:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:337:

CCTTCGAAGG TTATTTTCCA TTTTGAT                                          27

(2) INFORMATION FOR SEQ ID NO:338:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:338:

ATCATGATGG AAAATAACCT TCGAAGGCCA AACCTG                                36

(2) INFORMATION FOR SEQ ID NO:339:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:339:

CCTTCGAAGG TTATTTTCCA TCATGAT                                          27

(2) INFORMATION FOR SEQ ID NO:340:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:340:

ATCACCATGG AAAATAACCT TCGAAGGCCA AACCTG                                     36

(2) INFORMATION FOR SEQ ID NO:341:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:341:

CCTTCGAAGG TTATTTTCCA TGGTGAT                                               27

(2) INFORMATION FOR SEQ ID NO:342:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:342:

ATCGTTATGG AAAATAACCT TCGAAGGCCA AACCTG                                     36

(2) INFORMATION FOR SEQ ID NO:343:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:343:

CCTTCGAAGG TTATTTTCCA TAACGAT                                               27

(2) INFORMATION FOR SEQ ID NO:344:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:344:

ATCCTGATGC ACAATAACCT TCGAAGGCCA AACCTG                                     36

(2) INFORMATION FOR SEQ ID NO:345:

(i) SEQUENCE CHARACTERISTICS:
        (A) LENGTH: 27 base pairs (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:345:

CCTTCGAAGG TTATTGTGCA TCAGGAT                                27

(2) INFORMATION FOR SEQ ID NO:346:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:346:

ATCCTGATGA TGAATAACCT TCGAAGGCCA AACCTG                      36

(2) INFORMATION FOR SEQ ID NO:347:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:347:

CCTTCGAAGG TTATTCATCA TCAGGAT                                27

(2) INFORMATION FOR SEQ ID NO:348:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:348:

ATCCTGATGT TCAATAACCT TCGAAGGCCA AACCTG                      36

(2) INFORMATION FOR SEQ ID NO:349:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:349:

CCTTCGAAGG TTATTGAACA TCAGGAT                                27

(2) INFORMATION FOR SEQ ID NO:350:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:350:

ATCCTGATGG CTAATAACCT TCGAAGGCCA AACCTG                36

(2) INFORMATION FOR SEQ ID NO:351:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:351:

CCTTCGAAGG TTATTAGCCA TCAGGAT                27

(2) INFORMATION FOR SEQ ID NO:352:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:352:

ATCCTGATGA ACAATAACCT TCGAAGGCCA AACCTG                36

(2) INFORMATION FOR SEQ ID NO:353:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:353:

CCTTCGAAGG TTATTGTTCA TCAGGAT                27

(2) INFORMATION FOR SEQ ID NO:354:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:354:

ATCCTGATGA TCAATAACCT TCGAAGGCCA AACCTG                36

(2) INFORMATION FOR SEQ ID NO:355:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:355:

CCTTCGAAGG TTATTGATCA TCAGGAT                27

(2) INFORMATION FOR SEQ ID NO:356:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:356:

ATCCTGATGA AAATAACCT TCGAAGGCCA AACCTG       36

(2) INFORMATION FOR SEQ ID NO:357:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:357:

CCTTCGAAGG TTATTTTTCA TCAGGAT       27

(2) INFORMATION FOR SEQ ID NO:358:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:358:

ATCCTGATGT CCAATAACCT TCGAAGGCCA AACCTG       36

(2) INFORMATION FOR SEQ ID NO:359:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:359:

CCTTCGAAGG TTATTGGACA TCAGGAT       27

(2) INFORMATION FOR SEQ ID NO:360:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:360:

ATCCTGATGG TTAATAACCT TCGAAGGCCA AACCTG       36

(2) INFORMATION FOR SEQ ID NO:361:

(i) SEQUENCE CHARACTERISTICS:
        (A) LENGTH: 27 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:361:

CCTTCGAAGG TTATTAACCA TCAGGAT                                           27

(2) INFORMATION FOR SEQ ID NO:362:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:362:

ATCCTGATGG AAAATAACCT TGCTAGGCCA AACCTG                                 36

(2) INFORMATION FOR SEQ ID NO:363:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:363:

CCTAGCAAGG TTATTTTCCA TCAGGAT                                           27

(2) INFORMATION FOR SEQ ID NO:364:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:364:

ATCCTGATGG AAAATAACCT TAACAGGCCA AACCTG                                 36

(2) INFORMATION FOR SEQ ID NO:365:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:365:

CCTGTTAAGG TTATTTTCCA TCAGGAT                                           27

(2) INFORMATION FOR SEQ ID NO:366:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:366:

ATCCTGATGG AAAATAACCT TCACAGGCCA AACCTG                                        36

(2) INFORMATION FOR SEQ ID NO:367:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:367:

CCTGTGAAGG TTATTTTCCA TCAGGAT                                                  27

(2) INFORMATION FOR SEQ ID NO:368:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:368:

ATCCTGATGG AAAATAACCT TAAAAGGCCA AACCTG                                        36

(2) INFORMATION FOR SEQ ID NO:369:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:369:

CCTTTTAAGG TTATTTTCCA TCAGGAT                                                  27

(2) INFORMATION FOR SEQ ID NO:370:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:370:

ATCCTGATGG AAAATAACCT TCGAAGGGCT AACCTG                                        36

(2) INFORMATION FOR SEQ ID NO:371:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:371:

CCTGTTGAAT GCCTCCAGGT TAGC                                                     24

(2) INFORMATION FOR SEQ ID NO:372:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:372:

ATCCTGATGG AAAATAACCT TCGAAGGCGT AACCTG                      36

(2) INFORMATION FOR SEQ ID NO:373:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:373:

CCTGTTGAAT GCCTCCAGGT TACG                                  24

(2) INFORMATION FOR SEQ ID NO:374:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:374:

ATCCTGATGG AAAATAACCT TCGAAGGAAC AACCTG                      36

(2) INFORMATION FOR SEQ ID NO:375:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:375:

CCTGTTGAAT GCCTCCAGGT TGTT                                  24

(2) INFORMATION FOR SEQ ID NO:376:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:376:

ATCCTGATGG AAAATAACCT TCGAAGGGAA AACCTG                      36

(2) INFORMATION FOR SEQ ID NO:377:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:377:

CCTGTTGAAT GCCTCCAGGT TTTC                                          24

(2) INFORMATION FOR SEQ ID NO:378:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:378:

ATCCTGATGG AAAATAACCT TCGAAGGCAC AACCTG                             36

(2) INFORMATION FOR SEQ ID NO:379:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:379:

CCTGTTGAAT GCCTCCAGGT TGTG                                          24

(2) INFORMATION FOR SEQ ID NO:380:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:380:

ATCCTGATGG AAAATAACCT TCGAAGGCTG AACCTG                             36

(2) INFORMATION FOR SEQ ID NO:381:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:381:

CCTGTTGAAT GCCTCCAGGT TCAG                                          24

(2) INFORMATION FOR SEQ ID NO:382:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:382:

ATCCTGATGG AAAATAACCT TCGAAGGTTC AACCTG          36

(2) INFORMATION FOR SEQ ID NO:383:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:383:

CCTGTTGAAT GCCTCCAGGT TGAA          24

(2) INFORMATION FOR SEQ ID NO:384:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:384:

ATCCTGATGG AAAATAACCT TCGAAGGACC AACCTG          36

(2) INFORMATION FOR SEQ ID NO:385:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:385:

CCTGTTGAAT GCCTCCAGGT TGGT          24

(2) INFORMATION FOR SEQ ID NO:386:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:386:

ATCCTGATGG AAAATAACCT TCGAAGGTAC AACCTG          36

(2) INFORMATION FOR SEQ ID NO:387:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:387:

CCTGTTGAAT GCCTCCAGGT TGTA          24

(2) INFORMATION FOR SEQ ID NO:388:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:388:

ATCCTGATGG AAAATAACCT TCGAAGGGTT AACCTG                              36

(2) INFORMATION FOR SEQ ID NO:389:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:389:

CCTGTTGAAT GCCTCCAGGT TAAC                                            24

(2) INFORMATION FOR SEQ ID NO:390:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:390:

AAAAATCTCG CTCCATGT                                                      18

(2) INFORMATION FOR SEQ ID NO:391:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:391:

AGCGAGATTT TTAAGAAT                                                      18

(2) INFORMATION FOR SEQ ID NO:392:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:392:

AAAAATCTCA ACCCATGT                                                      18

(2) INFORMATION FOR SEQ ID NO:393:

(i) SEQUENCE CHARACTERISTICS:
        (A) LENGTH: 18 base pairs

```
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:393:

GTTGAGATTT TTAAGAAT                                                       18

(2) INFORMATION FOR SEQ ID NO:394:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:394:

AAAAATCTCG AACCATGT                                                       18

(2) INFORMATION FOR SEQ ID NO:395:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:395:

TTCGAGATTT TTAAGAAT                                                       18

(2) INFORMATION FOR SEQ ID NO:396:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:396:

AAAAATCTCC ACCCATGT                                                       18

(2) INFORMATION FOR SEQ ID NO:397:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:397:

GTGGAGATTT TTAAGAAT                                                       18

(2) INFORMATION FOR SEQ ID NO:398:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (synthetic)
```

(xi) SEQUENCE DESCRIPTION: SEQ ID NO:398:

AAAAATCTCA TCCCATGT                                                    18

(2) INFORMATION FOR SEQ ID NO:399:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:399:

GATGAGATTT TTAAGAAT                                                    18

(2) INFORMATION FOR SEQ ID NO:400:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:400:

AAAAATCTCA TGCCATGT                                                    18

(2) INFORMATION FOR SEQ ID NO:401:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:401:

CATGAGATTT TTAAGAAT                                                    18

(2) INFORMATION FOR SEQ ID NO:402:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:402:

AAAAATCTCT TCCCATGT                                                    18

(2) INFORMATION FOR SEQ ID NO:403:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:403:

GAAGAGATTT TTAAGAAT                                                    18

(2) INFORMATION FOR SEQ ID NO:404:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:404:

AAAAATCTCT CCCCATGT        18

(2) INFORMATION FOR SEQ ID NO:405:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:405:

GGAGAGATTT TTAAGAAT        18

(2) INFORMATION FOR SEQ ID NO:406:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:406:

AAAAATCTCA CCCCATGT        18

(2) INFORMATION FOR SEQ ID NO:407:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:407:

GGTGAGATTT TTAAGAAT        18

(2) INFORMATION FOR SEQ ID NO:408:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:408:

AAAAATCTCT ACCCATGT        18

(2) INFORMATION FOR SEQ ID NO:409:

(i) SEQUENCE CHARACTERISTICS:
        (A) LENGTH: 18 base pairs (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:409:

GTAGAGATTT TTAAGAAT                                              18

(2) INFORMATION FOR SEQ ID NO:410:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:410:

CTGCCCCTGG CCACGGCCGC AGCTACG                                    27

(2) INFORMATION FOR SEQ ID NO:411:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:411:

ATGGATTGGA TGTCGCGTAG CTGC                                       24

(2) INFORMATION FOR SEQ ID NO:412:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:412:

CTGCCCCTGG CCACGGCCGC AGGTACG                                    27

(2) INFORMATION FOR SEQ ID NO:413:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:413:

ATGGATTGGA TGTCGCGTAC CTGC                                       24

(2) INFORMATION FOR SEQ ID NO:414:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (synthetic)

-continued (xi) SEQUENCE DESCRIPTION: SEQ ID NO:414:

CTGCCCCTGG CCACGGCCGC AATCACG                                           27

(2) INFORMATION FOR SEQ ID NO:415:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:415:

ATGGATTGGA TGTCGCGTGA TTGC                                              24

(2) INFORMATION FOR SEQ ID NO:416:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:416:

GCTCATCCAA TCCATATCAA G                                                 21

(2) INFORMATION FOR SEQ ID NO:417:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:417:

ATGGATTGGA TGAGCCGTGG GTGC                                              24

(2) INFORMATION FOR SEQ ID NO:418:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:418:

CAGCATCCAA TCCATATCAA G                                                 21

(2) INFORMATION FOR SEQ ID NO:419:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:419:

ATGGATTGGA TGCTGCGTGG GTGC                                              24

(2) INFORMATION FOR SEQ ID NO:420:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:420:

CACCATCCAA TCCATATCAA G                                                    21

(2) INFORMATION FOR SEQ ID NO:421:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:421:

ATGGATTGGA TGGTGCGTGG GTGC                                                 24

(2) INFORMATION FOR SEQ ID NO:422:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:422:

AAACATCCAA TCCATATCAA G                                                    21

(2) INFORMATION FOR SEQ ID NO:423:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:423:

ATGGATTGGA TGTTTCGTGG GTGC                                                 24

(2) INFORMATION FOR SEQ ID NO:424:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:424:

CGAGCTCCAA TCCATATCAA G                                                    21

(2) INFORMATION FOR SEQ ID NO:425:

(i) SEQUENCE CHARACTERISTICS:
        (A) LENGTH: 24 base pairs

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:425:

ATGGATTGGA GCTCGCGTGG GTGC                                              24

(2) INFORMATION FOR SEQ ID NO:426:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:426:

CGAAACCCAA TCCATATCAA G                                                 21

(2) INFORMATION FOR SEQ ID NO:427:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:427:

ATGGATTGGG TTTCGCGTGG GTGC                                              24

(2) INFORMATION FOR SEQ ID NO:428:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:428:

CGAGACCCAA TCCATATCAA G                                                 21

(2) INFORMATION FOR SEQ ID NO:429:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:429:

ATGGATTGGG TCTCGCGTGG GTGC                                              24

(2) INFORMATION FOR SEQ ID NO:430:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO:430:

CGAATCCCAA TCCATATCAA G                                             21

(2) INFORMATION FOR SEQ ID NO:431:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:431:

ATGGATTGGG ATTCGCGTGG GTGC                                          24

(2) INFORMATION FOR SEQ ID NO:432:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:432:

CGAAAACCAA TCCATATCAA G                                             21

(2) INFORMATION FOR SEQ ID NO:433:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:433:

ATGGATTGGT TTTCGCGTGG GTGC                                          24

(2) INFORMATION FOR SEQ ID NO:434:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:434:

CGAATGCCAA TCCATATCAA G                                             21

(2) INFORMATION FOR SEQ ID NO:435:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:435:

ATGGATTGGC ATTCGCGTGG GTGC                                          24

(2) INFORMATION FOR SEQ ID NO:436:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:436:

CGATTCCCAA TCCATATCAA G                                  21

(2) INFORMATION FOR SEQ ID NO:437:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:437:

ATGGATTGGG AATCGCGTGG GTGC                             24

(2) INFORMATION FOR SEQ ID NO:438:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:438:

CGATCCCCAA TCCATATCAA G                                  21

(2) INFORMATION FOR SEQ ID NO:439:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:439:

ATGGATTGGG GATCGCGTGG GTGC                             24

(2) INFORMATION FOR SEQ ID NO:440:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:440:

CGATGGCCAA TCCATATCAA G                                  21

(2) INFORMATION FOR SEQ ID NO:441:

(i) SEQUENCE CHARACTERISTICS:
        (A) LENGTH: 24 base pairs

```
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:441:

ATGGATTGGC CATCGCGTGG GTGC                                              24

(2) INFORMATION FOR SEQ ID NO:442:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:442:

CGATACCCAA TCCATATCAA G                                                 21

(2) INFORMATION FOR SEQ ID NO:443:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:443:

ATGGATTGGG TATCGCGTGG GTGC                                              24

(2) INFORMATION FOR SEQ ID NO:444:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:444:

CATCCAATCC AAATCAAGGA CGGTGACTGG AATG                                   34

(2) INFORMATION FOR SEQ ID NO:445:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:445:

AATTCATTCC AGTCACCGTC CTTGATTTGG ATTGGATGTC GCGT                        44

(2) INFORMATION FOR SEQ ID NO:446:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (synthetic)
```

(xi) SEQUENCE DESCRIPTION: SEQ ID NO:446:

CATCCAATCG AAATCAAGGA CGGTGACTGG AATG                               34

(2) INFORMATION FOR SEQ ID NO:447:

(i) SEQUENCE CHARACTERISTICS:
           (A) LENGTH: 44 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:447:

AATTCATTCC AGTCACCGTC CTTGATTTCG ATTGGATGTC GCGT                    44

(2) INFORMATION FOR SEQ ID NO:448:

(i) SEQUENCE CHARACTERISTICS:
           (A) LENGTH: 34 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:448:

CATCCAATCA TGATCAAGGA CGGTGACTGG AATG                               34

(2) INFORMATION FOR SEQ ID NO:449:

(i) SEQUENCE CHARACTERISTICS:
           (A) LENGTH: 44 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:449:

AATTCATTCC AGTCACCGTC CTTGATCATG ATTGGATGTC GCGT                    44

(2) INFORMATION FOR SEQ ID NO:450:

(i) SEQUENCE CHARACTERISTICS:
           (A) LENGTH: 34 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:450:

CATCCAATCT TCATCAAGGA CGGTGACTGG AATG                               34

(2) INFORMATION FOR SEQ ID NO:451:

(i) SEQUENCE CHARACTERISTICS:
           (A) LENGTH: 44 base pairs
           (B) TYPE: nucleic acid
           (C) STRANDEDNESS: single
           (D) TOPOLOGY: linear (ii) MOLECULE TYPE: DNA (synthetic)

(xi) SEQUENCE DESCRIPTION: SEQ ID NO:451:

AATTCATTCC AGTCACCGTC CTTGATGAAG ATTGGATGTC GCGT                    44

(2) INFORMATION FOR SEQ ID NO:452:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:452:

CATCCAATCT CCATCAAGGA CGGTGACTGG AATG                                    34

(2) INFORMATION FOR SEQ ID NO:453:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:453:

AATTCATTCC AGTCACCGTC CTTGATGGAG ATTGGATGTC GCGT                      44

(2) INFORMATION FOR SEQ ID NO:454:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:454:

CATCCAATCG TAATCAAGGA CGGTGACTGG AATG                                    34

(2) INFORMATION FOR SEQ ID NO:455:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:455:

AATTCATTCC AGTCACCGTC CTTGATTACG ATTGGATGTC GCGT                      44

(2) INFORMATION FOR SEQ ID NO:456:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:456:

CGACATCCAA TCCGTATCAA G                                                    21

(2) INFORMATION FOR SEQ ID NO:457:

(i) SEQUENCE CHARACTERISTICS:
        (A) LENGTH: 24 base pairs (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:457:

ACGGATTGGA TGTCGCGTGG GTGC                                              24

(2) INFORMATION FOR SEQ ID NO:458:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:458:

CGACATCCAA TCAAAATCAA G                                                 21

(2) INFORMATION FOR SEQ ID NO:459:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:459:

TTTGATTGGA TGTCGCGTGG GTGC                                              24

(2) INFORMATION FOR SEQ ID NO:460:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:460:

CGACATCCAA TCTACATCAA G                                                 21

(2) INFORMATION FOR SEQ ID NO:461:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:461:

GTAGATTGGA TGTCGCGTGG GTGC                                              24

(2) INFORMATION FOR SEQ ID NO:462:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:462:

GCTGGTGACT GGAATG                                                             16

(2) INFORMATION FOR SEQ ID NO:463:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:463:

AATTCATTCC AGTCACCAGC CTTGAT                                                  26

(2) INFORMATION FOR SEQ ID NO:464:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:464:

AACGGTGACT GGAATG                                                             16

(2) INFORMATION FOR SEQ ID NO:465:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:465:

AATTCATTCC AGTCACCGTT CTTGAT                                                  26

(2) INFORMATION FOR SEQ ID NO:466:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:466:

GAAGGTGACT GGAATG                                                             16

(2) INFORMATION FOR SEQ ID NO:467:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:467:

AATTCATTCC AGTCACCTTC CTTGAT                                                  26

(2) INFORMATION FOR SEQ ID NO:468:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:468:

GGTGGTGACT GGAATG              16

(2) INFORMATION FOR SEQ ID NO:469:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:469:

AATTCATTCC AGTCACCACC CTTGAT      26

(2) INFORMATION FOR SEQ ID NO:470:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:470:

ATCGGTGACT GGAATG              16

(2) INFORMATION FOR SEQ ID NO:471:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:471:

AATTCATTCC AGTCACCGAT CTTGAT      26

(2) INFORMATION FOR SEQ ID NO:472:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:472:

CTGGGTGACT GGAATG              16

(2) INFORMATION FOR SEQ ID NO:473:

(i) SEQUENCE CHARACTERISTICS:
        (A) LENGTH: 26 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:473:

AATTCATTCC AGTCACCCAG CTTGAT                                              26

(2) INFORMATION FOR SEQ ID NO:474:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:474:

TTCGGTGACT GGAATG                                                         16

(2) INFORMATION FOR SEQ ID NO:475:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:475:

AATTCATTCC AGTCACCGAA CTTGAT                                              26

(2) INFORMATION FOR SEQ ID NO:476:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:476:

TCCGGTGACT GGAATG                                                         16

(2) INFORMATION FOR SEQ ID NO:477:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:477:

AATTCATTCC AGTCACCGGA CTTGAT                                              26

(2) INFORMATION FOR SEQ ID NO:478:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:478:

AATTCGCTAG GAAACTGACG TTCTATCTGA AA                                               32

(2) INFORMATION FOR SEQ ID NO:479:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:479:

CTCAAGGGTT TTCAGATAGA ACGTCAGTTT CCTAGCG                                          37

(2) INFORMATION FOR SEQ ID NO:480:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:480:

AATTCCAGAG GAAACTGACG TTCTATCTGA AA                                               32

(2) INFORMATION FOR SEQ ID NO:481:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:481:

CTCAAGGGTT TTCAGATAGA ACGTCAGTTT CCTCTGG                                          37

(2) INFORMATION FOR SEQ ID NO:482:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:482:

AATTCCACAG GAAACTGACG TTCTATCTGA AA                                               32

(2) INFORMATION FOR SEQ ID NO:483:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:483:

CTCAAGGGTT TTCAGATAGA ACGTCAGTTT CCTGTGG                                          37

(2) INFORMATION FOR SEQ ID NO:484:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:484:

AATTCTCCAG GAAACTGACG TTCTATCTGA AA                    32

(2) INFORMATION FOR SEQ ID NO:485:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:485:

CTCAAGGGTT TTCAGATAGA ACGTCAGTTT CCTGGAG               37

(2) INFORMATION FOR SEQ ID NO:486:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:486:

AATTCCGGAG GCGTCTGACG TTCTATCTGA AA                    32

(2) INFORMATION FOR SEQ ID NO:487:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:487:

CTCAAGGGTT TTCAGATAGA ACGTCAGACG CCTCCGG               37

(2) INFORMATION FOR SEQ ID NO:488:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:488:

AATTCCGGAG GGAACTGACG TTCTATCTGA AA                    32

(2) INFORMATION FOR SEQ ID NO:489:

(i) SEQUENCE CHARACTERISTICS:
        (A) LENGTH: 37 base pairs

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:489:

CTCAAGGGTT TTCAGATAGA ACGTCAGTTC CCTCCGG                                    37

(2) INFORMATION FOR SEQ ID NO:490:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:490:

AATTCCGGAG GCACCTGACG TTCTATCTGA AA                                         32

(2) INFORMATION FOR SEQ ID NO:491:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:491:

CTCAAGGGTT TTCAGATAGA ACGTCAGGTG CCTCCGG                                    37

(2) INFORMATION FOR SEQ ID NO:492:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:492:

AATTCCGGAG GATCCTGACG TTCTATCTGA AA                                         32

(2) INFORMATION FOR SEQ ID NO:493:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:493:

CTCAAGGGTT TTCAGATAGA ACGTCAGGAT CCTCCGG                                    37

(2) INFORMATION FOR SEQ ID NO:494:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO:494:

AATTCCGGAG GTCCCTGACG TTCTATCTGA AA                           32

(2) INFORMATION FOR SEQ ID NO:495:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:495:

CTCAAGGGTT TTCAGATAGA ACGTCAGGGA CCTCCGG                      37

(2) INFORMATION FOR SEQ ID NO:496:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:496:

AATTCCGGAG GAAACTGACG GACTATCTGA AA                           32

(2) INFORMATION FOR SEQ ID NO:497:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:497:

CTCAAGGGTT TTCAGATAGT CCGTCAGTTT CCTCCGG                      37

(2) INFORMATION FOR SEQ ID NO:498:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:498:

AATTCCGGAG GAAACTGACG ATCTATCTGA AA                           32

(2) INFORMATION FOR SEQ ID NO:499:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:499:

CTCAAGGGTT TTCAGATAGA TCGTCAGTTT CCTCCGG                      37

(2) INFORMATION FOR SEQ ID NO:500:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:500:

AATTCCGGAG GAAACTGACG CTGTATCTGA AA                                     32

(2) INFORMATION FOR SEQ ID NO:501:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:501:

CTCAAGGGTT TTCAGATACA GCGTCAGTTT CCTCCGG                               37

(2) INFORMATION FOR SEQ ID NO:502:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:502:

AATTCCGGAG GAAACTGACG AAATATCTGA AA                                     32

(2) INFORMATION FOR SEQ ID NO:503:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:503:

CTCAAGGGTT TTCAGATATT TCGTCAGTTT CCTCCGG                               37

(2) INFORMATION FOR SEQ ID NO:504:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:504:

AATTCCGGAG GAAACTGACG GTTTATCTGA AA                                     32

(2) INFORMATION FOR SEQ ID NO:505:

(i) SEQUENCE CHARACTERISTICS:
        (A) LENGTH: 37 base pairs (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:505:

CTCAAGGGTT TTCAGATAAA CCGTCAGTTT CCTCCGG                                 37

(2) INFORMATION FOR SEQ ID NO:506:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:506:

AATTCCGGAG GAAACTGACG TTCTATCTGG CT                                      32

(2) INFORMATION FOR SEQ ID NO:507:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:507:

CTCAAGGGTA GCCAGATAGA ACGTCAGTTT CCTCCGG                                 37

(2) INFORMATION FOR SEQ ID NO:508:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:508:

AATTCCGGAG GAAACTGACG TTCTATCTGC GT                                      32

(2) INFORMATION FOR SEQ ID NO:509:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:509:

CTCAAGGGTA CGCAGATAGA ACGTCAGTTT CCTCCGG                                 37

(2) INFORMATION FOR SEQ ID NO:510:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:510:

AATTCCGGAG GAAACTGACG TTCTATCTGA AC                                             32

(2) INFORMATION FOR SEQ ID NO:511:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:511:

CTCAAGGGTG TTCAGATAGA ACGTCAGTTT CCTCCGG                                        37

(2) INFORMATION FOR SEQ ID NO:512:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:512:

AATTCCGGAG GAAACTGACG TTCTATCTGC AG                                             32

(2) INFORMATION FOR SEQ ID NO:513:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:513:

CTCAAGGGTC TGCAGATAGA ACGTCAGTTT CCTCCGG                                        37

(2) INFORMATION FOR SEQ ID NO:514:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:514:

AATTCCGGAG GAAACTGACG TTCTATCTGC AC                                             32

(2) INFORMATION FOR SEQ ID NO:515:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:515:

CTCAAGGGTG TGCAGATAGA ACGTCAGTTT CCTCCGG                                        37

(2) INFORMATION FOR SEQ ID NO:516:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:516:

AATTCCGGAG GAAACTGACG TTCTATCTGA TG                        32

(2) INFORMATION FOR SEQ ID NO:517:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:517:

CTCAAGGGTC ATCAGATAGA ACGTCAGTTT CCTCCGG                   37

(2) INFORMATION FOR SEQ ID NO:518:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:518:

AATTCCGGAG GAAACTGACG TTCTATCTGT TC                        32

(2) INFORMATION FOR SEQ ID NO:519:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:519:

CTCAAGGGTG AACAGATAGA ACGTCAGTTT CCTCCGG                   37

(2) INFORMATION FOR SEQ ID NO:520:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:520:

AATTCCGGAG GAAACTGACG TTCTATCTGT AC                        32

(2) INFORMATION FOR SEQ ID NO:521:

(i) SEQUENCE CHARACTERISTICS:
        (A) LENGTH: 37 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:521:

CTCAAGGGTG TACAGATAGA ACGTCAGTTT CCTCCGG                    37

(2) INFORMATION FOR SEQ ID NO:522:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:522:

CATGGCTAAC TGCTCTAACA TGATCGATGA AATTATAACA                 40

(2) INFORMATION FOR SEQ ID NO:523:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:523:

CACTTAAAGC AGCCACCTTT GCCTTTGCTG GACTTC                     36

(2) INFORMATION FOR SEQ ID NO:524:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:524:

AACAACCTCA ATGGGAAGA CCAAGAT                                27

(2) INFORMATION FOR SEQ ID NO:525:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:525:

CTTTAAGTGT GTTATAATTT CATCGATCAT GTTAGAGCAG TTAGC           45

(2) INFORMATION FOR SEQ ID NO:526:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:526:

GAGGTTGTTG AAGTCCAGCA AAGGCAAAGG TGGCTG                                          36

(2) INFORMATION FOR SEQ ID NO:527:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:527:

ATCTTGGTCT TCCCCATT                                                              18

(2) INFORMATION FOR SEQ ID NO:528:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:528:

ATCCTGATGG AAAATAACCT TCGAAGGCCA AACCTG                                          36

(2) INFORMATION FOR SEQ ID NO:529:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:529:

GAGGCATTCA ACAGGGCTGT CAAG                                                       24

(2) INFORMATION FOR SEQ ID NO:530:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:530:

AGTTTACAGA ATGCA                                                                 15

(2) INFORMATION FOR SEQ ID NO:531:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:531:

CCTTCGAAGG TTATTTTCCA TCAGGAT                                                    27

(2) INFORMATION FOR SEQ ID NO:532:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:532:

CCTGTTGAAT GCCTCCAGGT TTGG                                         24

(2) INFORMATION FOR SEQ ID NO:533:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:533:

TTCTGTAAAC TCTTGACAGC                                             20

(2) INFORMATION FOR SEQ ID NO:534:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:534:

TCAGCAATTG AGAGCATTCT T                                          21

(2) INFORMATION FOR SEQ ID NO:535:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:535:

AAAAATCTCC TGCCATGT                                               18

(2) INFORMATION FOR SEQ ID NO:536:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:536:

CTGCCCCTGG CCACGGCCGC ACCCACGCGA CATCCAATCC ATATCAAG           48

(2) INFORMATION FOR SEQ ID NO:537:

(i) SEQUENCE CHARACTERISTICS:
        (A) LENGTH: 27 base pairs (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:537:

CTGCCCCTGG CCACGGCCGC ACCCACG                27

(2) INFORMATION FOR SEQ ID NO:538:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:538:

CGACATCCAA TCCATATCAA G                      21

(2) INFORMATION FOR SEQ ID NO:539:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:539:

GACGGTGACT GGAATG                            16

(2) INFORMATION FOR SEQ ID NO:540:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:540:

GCTCTCAATT GCTGATGCA                         19

(2) INFORMATION FOR SEQ ID NO:541:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:541:

CAGGAGATTT TTAAGAAT                          18

(2) INFORMATION FOR SEQ ID NO:542:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:542:

ATGGATTGGA TGTCGCGTGG GTGCGGCCGT GGCCAGGGGC AGACATGG                48

(2) INFORMATION FOR SEQ ID NO:543:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:543:

GGCCGTGGCC AGGGGCAGAC ATGG                                         24

(2) INFORMATION FOR SEQ ID NO:544:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:544:

ATGGATTGGA TGTCGCGTGG GTGC                                         24

(2) INFORMATION FOR SEQ ID NO:545:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:545:

AATTCATTCC AGTCACCGTC CTTGAT                                       26

(2) INFORMATION FOR SEQ ID NO:546:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:546:

AATTCCGGAG GAAACTGACG TTCTATCTGA AA                                32

(2) INFORMATION FOR SEQ ID NO:547:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:547:

ACCCTTGAGA ATGCGCAGGC TCAACAGTAA TA                                32

(2) INFORMATION FOR SEQ ID NO:548:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:548:

CTCAAGGGTT TTCAGATAGA ACGTCAGTTT CCTCCGG        37

(2) INFORMATION FOR SEQ ID NO:549:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:549:

AGCTTATTAC TGTTGAGCCT GCGCATT        27

What is claimed is:

1. A method of treating a patient having an immunodeficiency or hematopoietic disorder comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:15)
wherein;
    Xaa at position 17 is Ser, Lys, Gly, Asp, Met, Gln, or Arg;
    Xaa at position 18 is Asn, His, Leu, Ile, Phe, Arg, or Gln;
    Xaa at position 19 is Met, Phe, Ile, Arg, Gly, Ala, or Cys;
    Xaa at position 20 is Ile, Cys, Gln, Glu, Arg, Pro, or Ala;
    Xaa at position 21 is Asp, Phe, Lys, Arg, Ala, Gly, Glu, Gln, Asn, Thr, Ser or Val;
    Xaa at position 22 is Glu, Trp, Pro, Ser, Ala, His, Asp, Asn, Gln, Leu, Val or Gly;
    Xaa at position 23 is Ile, Val, Ala, Leu, Gly, Trp, Lys, Phe, Ser, or Arg;
    Xaa at position 24 is Ile, Gly, Val, Arg, Ser, Phe, or Leu;
    Xaa at position 25 is Thr, His, Gly, Gln, Arg, Pro, or Ala;
    Xaa at position 26 is His, Thr, Phe, Gly, Arg, Ala, or Trp;
    Xaa at position 27 is Leu, Gly, Arg, Thr, Ser, or Ala;
    Xaa at position 28 is Lys, Arg, Leu, Gln, Gly, Pro, Val or Trp;
    Xaa at position 29 is Gln, Asn, Leu, Pro, Arg, or Val;
    Xaa at position 30 is Pro, His, Thr, Gly, Asp, Gln, Ser, Leu, or Lys;
    Xaa at position 31 is Pro, Asp, Gly, Ala, Arg, Leu, or Gln;
    Xaa at position 32 is Leu, Val, Arg, Gln, Asn, Gly, Ala, or Glu;
    Xaa at position 33 is Pro, Leu, Gln, Ala, Thr, or Glu;
    Xaa at position 34 is Leu, Val, Gly, Ser, Lys, Glu, Gln, Thr, Arg, Ala, Phe, Ile or Met;
    Xaa at position 35 is Leu, Ala, Gly, Asn, Pro, Gln, or Val;
    Xaa at position 36 is Asp, Leu, or Val;
    Xaa at position 37 is Phe, Ser, Pro, Trp, or Ile;
    Xaa at position 38 is Asn, or Ala;
    Xaa at position 40 is Leu, Trp, or Arg;
    Xaa at position 41 is Asn, Cys, Arg, Leu, His, Met, or Pro;
    Xaa at position 42 is Gly, Asp, Ser, Cys, Asn, Lys, Thr, Leu, Val, Glu, Phe, Tyr, Ile, Met or Ala;
    Xaa at position 43 is Glu, Asn, Tyr, Leu, Phe, Asp, Ala, Cys, Gln, Arg, Thr, Gly or Ser;
    Xaa at position 44 is Asp, Ser, Leu, Arg, Lys, Thr, Met, Trp, Glu, Asn, Gln, Ala or Pro;
    Xaa at position 45 is Gln, Pro, Phe, Val, Met, Leu, Thr, Lys, Trp, Asp, Asn, Arg, Ser, Ala, Ile, Glu or His;
    Xaa at position 46 is Asp, Phe, Ser, Thr, Cys, Glu, Asn, Gln, Lys, His, Ala, Tyr, Ile, Val or Gly;
    Xaa at position 47 is Ile, Gly, Val, Ser, Arg, Pro, or His;
    Xaa at position 48 is Leu, Ser, Cys, Arg, Ile, His, Phe, Glu, Lys, Thr, Ala, Met, Val or Asn;
    Xaa at position 49 is Met, Arg, Ala, Gly, Pro, Asn, His, or Asp;
    Xaa at position 50 is Glu, Leu, Thr, Asp, Tyr, Lys, Asn, Ser, Ala, Ile, Val, His, Phe, Met or Gln;
    Xaa at position 51 is Asn, Arg, Met, Pro, Ser, Thr, or His;
    Xaa at position 52 is Asn, His, Arg, Leu, Gly, Ser, or Thr;
    Xaa at position 53 is Leu, Thr, Ala, Gly, Glu, Pro, Lys, Ser, or Met;
    Xaa at position 54 is Arg, Asp, Ile, Ser, Val, Thr, Gln, Asn, Lys, His, Ala or Leu;
    Xaa at position 55 is Arg, Thr, Val, Ser, Leu, or Gly;
    Xaa at position 56 is Pro, Gly, Cys, Ser, Gln, Glu, Arg, His, Thr, Ala, Tyr, Phe, Leu, Val or Lys;
    Xaa at position 57 is Asn or Gly;
    Xaa at position 58 is Leu, Ser, Asp, Arg, Gln, Val, or Cys;
    Xaa at position 59 is Glu, Tyr, His, Leu, Pro, or Arg;

Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

2. The method according to claim 1, wherein said mutant human interleukin-3 polypeptide has at least ten times greater cell proliferative activity than native human interleukin-3.

3. The method according to claim 1 wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

4. The method according to claim 3, wherein said mutant human interleukin-3 polypeptide has at least ten times greater cell proliferative activity than native human interleukin-3.

5. A method of treating a patient having an immunodeficiency or hematopoietic disorder comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:17) wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Arg, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

6. The method according to claim 5, wherein said mutant human interleukin-3 polypeptide has at least ten times greater cell proliferative activity than native human interleukin-3.

7. A method of treating a patient having an immunodeficiency or hematopoietic disorder comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:19) wherein;

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Arg, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, or Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

wherein from one to three of the amino acids designated by Xaa are different from the corresponding native amino acids of (1–133) human interleukin-3; and said mutant human interleukin-3 polypeptide has at least three times greater cell proliferative activity than native human interleukin-3 wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

8. The method according to claim 7, wherein said mutant human interleukin-3 polypeptide has at least ten times greater cell proliferative activity than native human interleukin-3.

9. The method according to claim 7, wherein said mutant human interleukin-3 polypeptide is selected from the group consisting of:

(a) a polypeptide having an amino acid sequence of
  (i) (residues 3–113 of SEQ ID NO:66);
  (ii) (residues 3–113 of SEQ ID NO:67);
  (iii) (residues 3–113 of SEQ ID NO:69); or
  (iv) (SEQ ID NO:218); and (b) a polypeptide comprising an N-terminal methionine residue, alanine residue or methionine-alanine di-peptide immediately preceding said sequence according to (a).

10. The method according to claim 9, wherein said mutant human interleukin-3 polypeptide has at least ten times greater cell proliferative activity than native human interleukin-3.

11. The method according to claim 7, wherein in said mutant human interleukin-3 (hIL-3) sequence the amino acids which differ from the corresponding residue in native human interleukin-3 are selected from the group consisting of:

position 28 wherein Xaa is Gly, Asp, Ser, Ile, Leu, Met, Tyr, or Ala;
position 31 wherein Xaa is Gln, Val, Met or Asn;
position 32 wherein Xaa is Asp, Ser, Ala, Gln, His or Val;
position 36 wherein Xaa is Glu or Asp;
position 37 wherein Xaa is Asn, Pro or Thr;
position 48 wherein Xaa is Asn or Pro;
position 62 wherein Xaa is Ser, or Pro;
position 68 wherein Xaa is Leu, Trp, Asp, Asn, Glu, His, Phe, Ser or Tyr;
position 81 wherein Xaa is His, Arg, Thr, Asn or Ser;
position 84 wherein Xaa is His, Ile, Leu, Ala, Arg, Gln, Lys, Met, Ser, Tyr or Val;
position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;

position 107 wherein Xaa is Ala, or Ile;
position 108 wherein Xaa is Gln, or Ile;
position 109 wherein Xaa is Ala, Met or Glu.

12. The method according to claim 11, wherein said mutant human interleukin-3 polypeptide has at least ten times greater cell proliferative activity than native human interleukin-3.

13. A method of treating a patient having an immunodeficiency or hematopoietic disorder comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:21) wherein;

Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Arg, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;

Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

14. The method according to claim 13, wherein said mutant human interleukin-3 polypeptide has at least ten times greater cell proliferative activity than native human interleukin-3.

15. The method according to claim 1, 2, 5, 6, 3, 4, 7, 8, 9, 10, 13, 14, 11 or 12 wherein said immunodeficiency or hematopoietic disorder is the result of a viral infection, bacterial infection or fungal infection.

16. The method according to claim 1, 2, 5, 6, 3, 4, 7, 8, 9, 10, 13, 14, 11 or 12 wherein said immunodeficiency or hematopoietic disorder is the result of cancer radiation therapy or chemotherapy.

17. The method according to claim 1, 2, 5, 6, 3, 4, 7, 8, 9, 10, 13, 14, 11 or 12 wherein said immunodeficiency is the result of the treatment of a patient with a drug which causes bone marrow suppression.

18. A method of treating a patient comprising the steps of:
(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:
(a) a sequence of (SEQ ID NO:15)
wherein;
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

19. The method according to claim 18, wherein said mutant human interleukin-3 polypeptide has at least ten times greater cell proliferative activity than native human interleukin-3.

20. The method according to claim 18, wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

21. The method according to claim 20, wherein said mutant human interleukin-3 polypeptide has at least ten times greater cell proliferative activity than native human interleukin-3.

22. A method of treating a patient comprising the steps of:
(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:
(a) a sequence of(SEQ ID NO:17)
wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Arg, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);
(ii) removing hematopoietic cells from said patient;
(iii) administering to said patient cancer radiation therapy or chemotherapy; and
(iv) returning said hematopoietic cells to said patient.

23. The method according to claim 22, wherein said mutant human interleukin-3 polypeptide has at least ten times greater cell proliferative activity than native human interleukin-3.

24. A method of treating a patient comprising the steps of:
(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:

(a) a sequence of(SEQ ID NO:19)
wherein;

Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, or Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from one to three of the amino acids designated by Xaa are different from the corresponding native amino acids of (1–133) human interleukin-3; and said mutant human interleukin-3 polypeptide has at least three times greater cell proliferative activity than native human interleukin-3 wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

25. The method according to claim 24, wherein said mutant human interleukin-3 polypeptide has at least ten times greater cell proliferative activity than native human interleukin-3.

26. The method according to claim 24, wherein said mutant human interleukin-3 polypeptide is selected from the group consisting of:

(a) a polypeptide having an amino acid sequence of (i) (residues 3–113 of SEQ ID NO:66);

(ii) (residues 3–113 of SEQ ID NO:67);

(iii) (residues 3–113 of SEQ ID NO:69); or (iv) (SEQ ID NO:218); and (b) an N-terminal methionine residue, alanine residue or methionine-alanine di-peptide immediately preceding said sequence according to (a).

27. The method according to claim 26, wherein said mutant human interleukin-3 polypeptide has at least ten times greater cell proliferative activity than native human interleukin-3.

28. The method according to claim 24, wherein in said mutant human interleukin-3 (hIL-3) sequence the amino acids which differ from the corresponding residue in native human interleukin-3 are selected from the group consisting of:

position 28 wherein Xaa is Gly, Asp, Ser, Ile, Leu, Met, Tyr, or Ala;

position 31 wherein Xaa is Gln, Val, Met or Asn;

position 32 wherein Xaa is Asp, Ser, Ala, Gln, His or Val;

position 36 wherein Xaa is Glu or Asp;

position 37 wherein Xaa is Asn, Pro or Thr;

position 48 wherein Xaa is Asn or Pro;

position 62 wherein Xaa is Ser, or Pro;

position 68 wherein Xaa is Leu, Trp, Asp, Asn, Glu, His, Phe, Ser or Tyr;

position 81 wherein Xaa is His, Arg, Thr, Asn or Ser;

position 84 wherein Xaa is His, Ile, Leu, Ala, Arg, Gln, Lys, Met, Ser, Tyr or Val;

position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;
position 107 wherein Xaa is Ala, or Ile;
position 108 wherein Xaa is Gln, or Ile;
position 109 wherein Xaa is Ala, Met or Glu.

29. The method according to claim 28, wherein said mutant human interleukin-3 polypeptide has at least ten times greater cell proliferative activity than native human interleukin-3.

30. A method of treating a patient comprising the steps of:
(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:
(a) a sequence of (SEQ ID NO:21) wherein;

Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Arg, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);
(ii) removing hematopoietic cells from said patient;
(iii) administering to said patient cancer radiation therapy or chemotherapy; and (iv) returning said hematopoietic cells to said patient.

31. The method according to claim 30, wherein said mutant human interleukin-3 polypeptide has at least ten times greater cell proliferative activity than native human interleukin-3.

32. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:15) wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

33. The method according to claim 32, wherein said mutant human interleukin-3 polypeptide has at least ten times greater cell proliferative activity than native human interleukin-3.

34. The method according to claim 32 wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 101 wherein Xaa is Asp;

position 105 wherein Xaa is Asn, or Pro;

position 108 wherein Xaa is Arg, Ala, or Ser;

position 116 wherein Xaa is Lys;

position 121 wherein Xaa is Ala, or Ile;

position 122 wherein Xaa is Gln, or Ile;

position 123 wherein Xaa is Ala, Met or Glu.

35. The method according to claim 34, wherein said mutant human interleukin-3 polypeptide has at least ten times greater cell proliferative activity than native human interleukin-3.

36. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:17) wherein;

Xaa at position 17 is Ser, Gly, Asp, Met, or Gln;

Xaa at position 18 is Asn, His, or Ile;

Xaa at position 19 is Met or Ile;

Xaa at position 21 is Asp or Glu;

Xaa at position 23 is Ile, Ala, Leu, or Gly;

Xaa at position 24 is Ile, Val, or Leu;

Xaa at position 25 is Thr, His, Gln, or Ala;

Xaa at position 26 is His or Ala;

Xaa at position 29 is Gln, Asn, or Val;

Xaa at position 30 is Pro, Gly, or Gln;

Xaa at position 31 is Pro, Asp, Gly, or Gln;

Xaa at position 32 is Leu, Arg, Gln, Asn, Gly, Ala, or Glu;

Xaa at position 33 is Pro or Glu;

Xaa at position 34 is Leu, Val, Gly, Ser, Lys, Ala, Arg, Gln, Glu, Ile, Phe, Thr or Met;

Xaa at position 35 is Leu, Ala, Asn, Pro, Gln, or Val;

Xaa at position 37 is Phe, Ser, Pro, or Trp;

Xaa at position 38 is Asn or Ala;

Xaa at position 42 is Gly, Asp, Ser, Cys, Ala, Asn, Ile, Leu, Met, Tyr or Arg;

Xaa at position 44 is Asp or Glu;

Xaa at position 45 is Gln, Val, Met, Leu, Thr, Ala, Asn, Glu, Ser or Lys;

Xaa at position 46 is Asp, Phe, Ser, Thr, Ala, Asn, Gln, Glu, His, Ile, Lys, Tyr, Val or Cys;

Xaa at position 50 is Glu, Ala, Asn, Ser or Asp;

Xaa at position 51 is Asn, Arg, Met, Pro, Ser, Thr, or His;

Xaa at position 54 is Arg or Ala;

Xaa at position 55 is Arg, Thr, Val, Leu, or Gly;

Xaa at position 56 is Pro, Gly, Ser, Gln, Ala, Arg, Asn, Glu, Leu, Thr, Val or Lys;

Xaa at position 60 is Ala or Ser;

Xaa at position 62 is Asn, Pro, Thr, or Ile;

Xaa at position 63 is Arg or Lys;

Xaa at position 64 is Ala or Asn;

Xaa at position 65 is Val or Thr;

Xaa at position 66 is Lys or Arg;

Xaa at position 67 is Ser, Phe, or His;

Xaa at position 68 is Leu, Ile, Phe, or His;

Xaa at position 69 is Gln, Ala, Pro, Thr, Glu, Arg, or Gly;

Xaa at position 71 is Ala, Pro, or Arg;

Xaa at position 72 is Ser, Glu, Arg, or Asp;

Xaa at position 73 is Ala or Leu;

Xaa at position 76 is Ser, Val, Ala, Asn, Glu, Pro, or Gly;

Xaa at position 77 is Ile or Leu;

Xaa at position 79 is Lys, Thr, Gly, Asn, Met, Arg, Ile, or Asp;

Xaa at position 80 is Asn, Gly, Glu, or Arg;

Xaa at position 82 is Leu, Gln, Trp, Arg, Asp, Ala, Asn, Glu, His, Ile, Met, Phe, Ser, Thr, Tyr or Val;

Xaa at position 83 is Pro or Thr;

Xaa at position 85 is Leu or Val;

Xaa at position 87 is Leu or Ser;

Xaa at position 88 is Ala or Trp;

Xaa at position 91 is Ala or Pro;

Xaa at position 93 is Thr, Asp, Ser, Pro, Ala, Leu, or Arg;

Xaa at position 95 is His, Pro, Arg, Val, Leu, Gly, Asn, Phe, Ser or Thr;

Xaa at position 96 is Pro or Tyr;

Xaa at position 97 is Ile or Val;

Xaa at position 98 is His, Ile, Asn, Leu, Ala, Thr, Arg, Gln, Lys, Met, Ser, Tyr, Val or Pro;

Xaa at position 99 is Ile, Leu, or Val;

Xaa at position 100 is Lys, Arg, Ile, Gln, Pro, or Ser;

Xaa at position 101 is Asp;

Xaa at position 104 is Trp or Leu;

Xaa at position 105 is Asn, Pro, Ala, Ser, Trp, Gln, Tyr, Leu, Lys, Ile, Asp, or His;

Xaa at position 106 is Glu or Gly;

Xaa at position 108 is Arg, Ala, or Ser;

Xaa at position 109 is Arg, Thr, Glu, Leu, or Ser;

Xaa at position 112 is Thr, Val, or Gln;

Xaa at position 114 is Tyr or Trp;

Xaa at position 115 is Leu or Ala;

Xaa at position 116 is Lys;

Xaa at position 117 is Thr or Ser;

Xaa at position 120 is Asn, Pro, Leu, His, Val, or Gln;

Xaa at position 121 is Ala, Ser, Ile, Asn, Pro, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

37. The method according to claim 36, wherein said mutant human interleukin-3 polypeptide has at least ten times greater cell proliferative activity than native human interleukin-3.

38. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:19)
wherein;

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, or Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from one to three of the amino acids designated by Xaa are different from the corresponding native amino acids of (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and
(b) a polypeptide comprising an N-terminal methionine residue, alanine residue or methionine-alanine di-peptide immediately preceding said sequence according to (a).

39. The method according to claim 38, wherein said mutant human interleukin-3 polypeptide has at least ten times greater cell proliferative activity than native human interleukin-3.

40. The method according to claim 38, wherein said mutant human interleukin-3 polypeptide is selected from the group consisting of:
(a) a polypeptide having an amino acid sequence of
  (i) (residues 3–113 of SEQ ID NO:66);
  (ii) (residues 3–113 of SEQ ID NO:67);
  (iii) (residues 3–113 of SEQ ID NO:69); or
  (iv) (SEQ ID NO:218); and
(b) an N-terminal methionine residue, alanine residue or methionine-alanine di-peptide immediately preceding said sequence according to (a).

41. The method according to claim 40, wherein said mutant human interleukin-3 polypeptide has at least ten times greater cell proliferative activity than native human interleukin-3.

42. The method according to claim 38, wherein in said mutant human interleukin-3 (hIL-3) sequence the amino acids which differ from the corresponding residue in native human interleukin-3 are selected from the group consisting of:
position 28 wherein Xaa is Gly, Asp, Ser, Ile, Leu, Met, Tyr, or Ala;
position 31 wherein Xaa is Gln, Val, Met or Asn;
position 32 wherein Xaa is Asp, Ser, Ala, Gln, His or Val;
position 36 wherein Xaa is Glu or Asp;
position 37 wherein Xaa is Asn, Pro or Thr;
position 48 wherein Xaa is Asn or Pro;
position 62 wherein Xaa is Ser, or Pro;
position 68 wherein Xaa is Leu, Trp, Asp, Asn, Glu, His, Phe, Ser or Tyr;
position 81 wherein Xaa is His, Arg, Thr, Asn or Ser;
position 84 wherein Xaa is His, Ile, Leu, Ala, Arg, Gln, Lys, Met, Ser, Tyr or Val;
position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;
position 107 wherein Xaa is Ala, or Ile;
position 108 wherein Xaa is Gln, or Ile;
position 109 wherein Xaa is Ala, Met or Glu.

43. The method according to claim 42, wherein said mutant human interleukin-3 polypeptide has at least ten times greater cell proliferative activity than native human interleukin-3.

44. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:
(a) a sequence of (SEQ ID NO:21) wherein;
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;

Xaa at position 57 is Ala, Pro, or Arg;

Xaa at position 58 is Ser, Glu, Arg, or Asp;

Xaa at position 59 is Ala or Leu;

Xaa at position 62 is Ser, Val, Ala, Asn, Glu, Pro, or Gly;

Xaa at position 63 is Ile or Leu;

Xaa at position 65 is Lys, Thr, Gly, Asn, Met, Arg, Ile, or Asp;

Xaa at position 66 is Asn, Gly, Glu, or Arg;

Xaa at position 68 is Leu, Gln, Trp, Arg, Asp, Ala, Asn, Glu, His, Ile, Met, Phe, Ser, Thr, Tyr or Val;

Xaa at position 69 is Pro or Thr;

Xaa at position 71 is Leu or Val;

Xaa at position 73 is Leu or Ser;

Xaa at position 74 is Ala or Trp;

Xaa at position 77 is Ala or Pro;

Xaa at position 79 is Thr, Asp, Ser, Pro, Ala, Leu, or Arg;

Xaa at position 81 is His, Pro, Arg, Val, Leu, Gly, Asn, Phe, Ser or Thr;

Xaa at position 82 is Pro or Tyr;

Xaa at position 83 is Ile or Val;

Xaa at position 84 is His, Ile, Asn, Leu, Ala, Thr, Arg, Gln, Lys, Met, Ser, Tyr, Val or Pro;

Xaa at position 85 is Ile, Leu, or Val;

Xaa at position 86 is Lys, Arg, Ile, Gln, Pro, or Ser;

Xaa at position 87 is Asp;

Xaa at position 90 is Trp or Leu;

Xaa at position 91 is Asn, Pro, Ala, Ser, Trp, Gln, Tyr, Leu, Lys, Ile, Asp, or His;

Xaa at position 92 is Glu, or Gly;

Xaa at position 94 is Arg, Ala, or Ser;

Xaa at position 95 is Arg, Thr, Glu, Leu, or Ser;

Xaa at position 98 is Thr, Val, or Gln;

Xaa at position 100 is Tyr or Trp;

Xaa at position 101 is Leu or Ala;

Xaa at position 102 is Lys;

Xaa at position 103 is Thr or Ser;

Xaa at position 106 is Asn, Pro, Leu, His, Val, or Gln;

Xaa at position 107 is Ala, Ser, Ile, Asn, Pro, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

45. The method according to claim 44, wherein said mutant human interleukin-3 polypeptide has at least ten times greater cell proliferative activity than native human interleukin-3.

46. A method of treating a patient having an immunodeficiency or hematopoietic disorder consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:15)

wherein;

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

47. The method according to claim 46, wherein said mutant human interleukin-3 polypeptide has at least ten times greater cell proliferative activity than native human interleukin-3.

48. The method according to claim 46 wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

49. The method according to claim 48, wherein said mutant human interleukin-3 polypeptide has at least ten times greater cell proliferative activity than native human interleukin-3.

50. A method of treating a patient having an immunodeficiency or hematopoietic disorder consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:17)
wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Arg, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

51. The method according to claim 50, wherein said mutant human interleukin-3 polypeptide has at least ten times greater cell proliferative activity than native human interleukin-3.

52. A method of treating a patient having an immunodeficiency or hematopoietic disorder consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:19)
wherein;

Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, or Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from one to three of the amino acids designated by Xaa are different from the corresponding native amino acids of (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

53. The method according to claim 52, wherein said mutant human interleukin-3 polypeptide has at least ten times greater cell proliferative activity than native human interleukin-3.

54. The method according to claim 52, wherein said mutant human interleukin-3 polypeptide is selected from the group consisting of:

(a) a polypeptide having an amino acid sequence of
(i) (residues 3–113 of SEQ ID NO:66);
(ii) (residues 3–113 of SEQ ID NO:67);
(iii) (residues 3–113 of SEQ ID NO:69); or
(iv) (SEQ ID NO:218); and (b) an N-terminal methionine residue, alanine residue or methionine-alanine di-peptide immediately preceding said sequence according to (a).

55. The method according to claim 54, wherein said mutant human interleukin-3 polypeptide has at least ten times greater cell proliferative activity than native human interleukin-3.

56. The method according to claim 52, wherein in said mutant human interleukin-3 (hIL-3) sequence the amino acids which differ from the corresponding residue in native human interleukin-3 are selected from the group consisting of:

position 28 wherein Xaa is Gly, Asp, Ser, Ile, Leu, Met, Tyr, or Ala;

position 31 wherein Xaa is Gln, Val, Met or Asn;

position 32 wherein Xaa is Asp, Ser, Ala, Gln, His or Val;

position 36 wherein Xaa is Glu or Asp;

position 37 wherein Xaa is Asn, Pro or Thr;

position 48 wherein Xaa is Asn or Pro;

position 62 wherein Xaa is Ser, or Pro;

position 68 wherein Xaa is Leu, Trp, Asp, Asn, Glu, His, Phe, Ser or Tyr;

position 81 wherein Xaa is His, Arg, Thr, Asn or Ser;

position 84 wherein Xaa is His, Ile, Leu, Ala, Arg, Gln, Lys, Met, Ser, Tyr or Val;

position 86 wherein Xaa is Lys or Arg;

position 87 wherein Xaa is Asp;

position 91 wherein Xaa is Asn, or Pro;

position 94 wherein Xaa is Arg, Ala, or Ser;

position 102 wherein Xaa is Lys;

position 107 wherein Xaa is Ala, or Ile;

position 108 wherein Xaa is Gln, or Ile;

position 109 wherein Xaa is Ala, Met or Glu.

57. The method according to claim 56, wherein said mutant human interleukin-3 polypeptide has at least ten times greater cell proliferative activity than native human interleukin-3.

58. A method of treating a patient having an immunodeficiency or hematopoietic disorder consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:21) wherein;

Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Arg, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

59. The method according to claim 58, wherein said mutant human interleukin-3 polypeptide has at least ten times greater cell proliferative activity than native human interleukin-3.

60. The method according to claim 46, 47, 50, 57, 48, 49, 52, 53, 54, 55, 58, 59, 56 or 57 wherein said immunodeficiency or hematopoietic disorder is the result of a viral infection, bacterial infection or fungal infection.

61. The method according to claim 46, 47, 50, 57, 48, 49, 52, 53, 54, 55, 58, 59, 56 or 57 wherein said immunodeficiency or hematopoietic disorder is the result of cancer radiation therapy or chemotherapy.

62. The method according to claim 46, 47, 50, 57, 48, 49, 52, 53, 54, 55, 58, 59, 56 or 57 wherein said immunodeficiency is the result of the treatment of a patient with a drug which causes bone marrow suppression.

63. A method of treating a patient consisting of the steps of:
  (i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:
    (a) a sequence of (SEQ ID NO:15)
  wherein;
  Xaa at position 17 is Ser, Lys, Gly, Asp, Met, Gln, or Arg;
  Xaa at position 18 is Asn, His, Leu, Ile, Phe, Arg, or Gln;
  Xaa at position 19 is Met, Phe, Ile, Arg, Gly, Ala, or Cys;
  Xaa at position 20 is Ile, Cys, Gln, Glu, Arg, Pro, or Ala;
  Xaa at position 21 is Asp, Phe, Lys, Arg, Ala, Gly, Glu, Gln, Asn, Thr, Ser or Val;
  Xaa at position 22 is Glu, Trp, Pro, Ser, Ala, His, Asp, Asn, Gln, Leu, Val or Gly;
  Xaa at position 23 is Ile, Val, Ala, Leu, Gly, Trp, Lys, Phe, Ser, or Arg;
  Xaa at position 24 is Ile, Gly, Val, Arg, Ser, Phe, or Leu;
  Xaa at position 25 is Thr, His, Gly, Gln, Arg, Pro, or Ala;
  Xaa at position 26 is His, Thr, Phe, Gly, Arg, Ala, or Trp;
  Xaa at position 27 is Leu, Gly, Arg, Thr, Ser, or Ala;
  Xaa at position 28 is Lys, Arg, Leu, Gln, Gly, Pro, Val or Trp;
  Xaa at position 29 is Gln, Asn, Leu, Pro, Arg, or Val;
  Xaa at position 30 is Pro, His, Thr, Gly, Asp, Gln, Ser, Leu, or Lys;
  Xaa at position 31 is Pro, Asp, Gly, Ala, Arg, Leu, or Gln;
  Xaa at position 32 is Leu, Val, Arg, Gln, Asn, Gly, Ala, or Glu;
  Xaa at position 33 is Pro, Leu, Gln, Ala, Thr, or Glu;
  Xaa at position 34 is Leu, Val, Gly, Ser, Lys, Glu, Gln, Thr, Arg, Ala, Phe, Ile or Met;
  Xaa at position 35 is Leu, Ala, Gly, Asn, Pro, Gln, or Val;
  Xaa at position 36 is Asp, Leu, or Val;
  Xaa at position 37 is Phe, Ser, Pro, Trp, or Ile;
  Xaa at position 38 is Asn, or Ala;
  Xaa at position 40 is Leu, Trp, or Arg;
  Xaa at position 41 is Asn, Cys, Arg, Leu, His, Met, or Pro;
  Xaa at position 42 is Gly, Asp, Ser, Cys, Asn, Lys, Thr, Leu, Val, Glu, Phe, Tyr, Ile, Met or Ala;
  Xaa at position 43 is Glu, Asn, Tyr, Leu, Phe, Asp, Ala, Cys, Gln, Arg, Thr, Gly or Ser;
  Xaa at position 44 is Asp, Ser, Leu, Arg, Lys, Thr, Met, Trp, Glu, Asn, Gln, Ala or Pro;
  Xaa at position 45 is Gln, Pro, Phe, Val, Met, Leu, Thr, Lys, Trp, Asp, Asn, Arg, Ser, Ala, Ile, Glu or His;
  Xaa at position 46 is Asp, Phe, Ser, Thr, Cys, Glu, Asn, Gln, Lys, His, Ala, Tyr, Ile, Val or Gly;
  Xaa at position 47 is Ile, Gly, Val, Ser, Arg, Pro, or His;
  Xaa at position 48 is Leu, Ser, Cys, Arg, Ile, His, Phe, Glu, Lys, Thr, Ala, Met, Val or Asn;
  Xaa at position 49 is Met, Arg, Ala, Gly, Pro, Asn, His, or Asp;
  Xaa at position 50 is Glu, Leu, Thr, Asp, Tyr, Lys, Asn, Ser, Ala, Ile, Val, His, Phe, Met or Gln;
  Xaa at position 51 is Asn, Arg, Met, Pro, Ser, Thr, or His;
  Xaa at position 52 is Asn, His, Arg, Leu, Gly, Ser, or Thr;
  Xaa at position 53 is Leu, Thr, Ala, Gly, Glu, Pro, Lys, Ser, or Met;
  Xaa at position 54 is Arg, Asp, Ile, Ser, Val, Thr, Gln, Asn, Lys, His, Ala or Leu;
  Xaa at position 55 is Arg, Thr, Val, Ser, Leu, or Gly;
  Xaa at position 56 is Pro, Gly, Cys, Ser, Gln, Glu, Arg, His, Thr, Ala, Tyr, Phe, Leu, Val or Lys;
  Xaa at position 57 is Asn or Gly;
  Xaa at position 58 is Leu, Ser, Asp, Arg, Gln, Val, or Cys;
  Xaa at position 59 is Glu, Tyr, His, Leu, Pro, or Arg;
  Xaa at position 60 is Ala, Ser, Pro, Tyr, Asn, or Thr;
  Xaa at position 61 is Phe, Asn, Glu, Pro, Lys, Arg, or Ser;
  Xaa at position 62 is Asn, His, Val, Arg, Pro, Thr, Asp, or Ile;
  Xaa at position 63 is Arg, Tyr, Trp, Lys, Ser, His, Pro, or Val;
  Xaa at position 64 is Ala, Asn, Pro, Ser, or Lys;
  Xaa at position 65 is Val, Thr, Pro, His, Leu, Phe, or Ser;
  Xaa at position 66 is Lys, Ile, Arg, Val, Asn, Glu, or Ser;
  Xaa at position 67 is Ser, Ala, Phe, Val, Gly, Asn, Ile, Pro, or His;
  Xaa at position 68 is Leu, Val, Trp, Ser, Ile, Phe, Thr, or His;
  Xaa at position 69 is Gln, Ala, Pro, Thr, Glu, Arg, Trp, Gly, or Leu;
  Xaa at position 70 is Asn, Leu, Val, Trp, Pro, or Ala;
  Xaa at position 71 is Ala, Met, Leu, Pro, Arg, Glu, Thr, Gln, Trp, or Asn;
  Xaa at position 72 is Ser, Glu, Met, Ala, His, Asn, Arg, or Asp;
  Xaa at position 73 is Ala, Glu, Asp, Leu, Ser, Gly, Thr, or Arg;
  Xaa at position 74 is Ile, Met, Thr, Pro, Arg, Gly, Ala;
  Xaa at position 75 is Glu, Lys, Gly, Asp, Pro, Trp, Arg, Ser, Gln, or Leu;
  Xaa at position 76 is Ser, Val, Ala, Asn, Trp, Glu, Pro, Gly, or Asp;
  Xaa at position 77 is Ile, Ser, Arg, Thr, or Leu;
  Xaa at position 78 is Leu, Ala, Ser, Glu, Phe, Gly, or Arg;
  Xaa at position 79 is Lys, Thr, Asn, Met, Arg, Ile, Gly, or Asp;
  Xaa at position 80 is Asn, Trp, Val, Gly, Thr, Leu, Glu, or Arg;
  Xaa at position 81 is Leu, Gln, Gly, Ala, Trp, Arg, Val, or Lys;
  Xaa at position 82 is Leu, Gln, Lys, Trp, Arg, Asp, Glu, Asn, His, Thr, Ser, Ala, Tyr, Phe, Ile, Met or Val;
  Xaa at position 83 is Pro, Ala, Thr, Trp, Arg, or Met;
  Xaa at position 84 is Cys, Glu, Gly, Arg, Met, or Val;
  Xaa at position 85 is Leu, Asn, Val, or Gln;
  Xaa at position 86 is Pro, Cys, Arg, Ala, or Lys;
  Xaa at position 87 is Leu, Ser, Trp, or Gly;
  Xaa at position 88 is Ala, Lys, Arg, Val, or Trp;
  Xaa at position 89 is Thr, Asp, Cys, Leu, Val, Glu, His, Asn, or Ser;
  Xaa at position 90 is Ala, Pro, Ser, Thr, Gly, Asp, Ile, or Met;
  Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

64. The method according to claim 63, wherein said mutant human interleukin-3 polypeptide has at least ten times greater cell proliferative activity than native human interleukin-3.

65. The method according to claim 63, wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 101 wherein Xaa is Asp;

position 105 wherein Xaa is Asn, or Pro;

position 108 wherein Xaa is Arg, Ala, or Ser;

position 116 wherein Xaa is Lys;

position 121 wherein Xaa is Ala, or Ile;

position 122 wherein Xaa is Gln, or Ile;

position 123 wherein Xaa is Ala, Met or Glu.

66. The method according to claim 65, wherein said mutant human interleukin-3 polypeptide has at least ten times greater cell proliferative activity than native human interleukin-3.

67. A method of treating a patient consisting of the steps of:

(i) administering to said patient, an amount of a mutant human interleukin-3 (IL-3) polypeptide, effective to promote the proliferation and/or differentiation of hematopoietic calls in said patient, wherein said mutant human interleukin-3 (hIL-3) polypeptide consists of a modified hIL-3 amino acid sequence selected from the group consisting of:

(a) a sequence of(SEQ ID NO:17)

wherein;

Xaa at position 17 is Ser, Gly, Asp, Met, or Gln;

Xaa at position 18 is Asn, His, or Ile;

Xaa at position 19 is Met or Ile;

Xaa at position 21 is Asp or Glu;

Xaa at position 23 is Ile, Ala, Leu, or Gly;

Xaa at position 24 is Ile, Val, or Leu;

Xaa at position 25 is Thr, His, Gln, or Ala;

Xaa at position 26 is His or Ala;

Xaa at position 29 is Gln, Asn, or Val;

Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;

Xaa at position 96 is Pro or Tyr;

Xaa at position 97 is Ile or Val;

Xaa at position 98 is His, Ile, Asn, Leu, Ala, Thr, Arg, Gln, Lys, Met, Ser, Tyr, Val or Pro;

Xaa at position 99 is Ile, Leu, or Val;

Xaa at position 100 is Lys, Arg, Ile, Gln, Pro, or Ser;

Xaa at position 101 is Asp;

Xaa at position 104 is Trp or Leu;

Xaa at position 105 is Asn, Pro, Ala, Ser, Trp, Gln, Tyr, Leu, Lys, Ile, Asp, or His;

Xaa at position 106 is Glu or Gly;

Xaa at position 108 is Arg, Ala, or Ser;

Xaa at position 109 is Arg, Thr, Glu, Leu, or Ser;

Xaa at position 112 is Thr, Val, or Gln;

Xaa at position 114 is Tyr or Trp;

Xaa at position 115 is Leu or Ala;

Xaa at position 116 is Lys;

Xaa at position 117 is Thr or Ser;

Xaa at position 120 is Asn, Pro, Leu, His, Val, or Gln;

Xaa at position 121 is Ala, Ser, Ile, Asn, Pro, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

68. The method according to claim 67, wherein said mutant human interleukin-3 polypeptide has at least ten times greater cell proliferative activity than native human interleukin-3.

69. A method of treating a patient consisting of the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:

(a) a sequence of(SEQ ID NO:19)

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, or Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from one to three of the amino acids designated by Xaa are different from the corresponding native amino acids of (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a);
  (ii) removing hematopoietic cells from said patient;
  (iii) administering to said patient cancer radiation therapy or chemotherapy; and
  (iv) returning said hematopoietic cells to said patient.

70. The method according to claim 69, wherein said mutant human interleukin-3 polypeptide has at least ten times greater cell proliferative activity than native human interleukin-3.

71. The method according to claim 69, wherein said mutant human interleukin-3 polypeptide is selected from the group consisting of:
  (a) a polypeptide having an amino acid sequence of
    (i) (residues 3–113 of SEQ ID NO:66);
    (ii) (residues 3–113 of SEQ ID NO:67);
    (iii) (residues 3–113 of SEQ ID NO:69); or
    (iv) (SEQ ID NO:218); and
  (b) an N-terminal methionine residue, alanine residue or methionine-alanine di-peptide immediately preceding said sequence according to (a).

72. The method according to claim 71, wherein said mutant human interleukin-3 polypeptide has at least ten times greater cell proliferative activity than native human interleukin-3.

73. The method according to claim 69, wherein in said mutant human interleukin-3 (hIL-3) sequence the amino acids which differ from the corresponding residue in native human interleukin-3 are selected from the group consisting of:

position 28 wherein Xaa is Gly, Asp, Ser, Ile, Leu, Met, Tyr, or Ala;

position 31 wherein Xaa is Gln, Val, Met or Asn;

position 32 wherein Xaa is Asp, Ser, Ala, Gln, His or Val;

position 36 wherein Xaa is Glu or Asp;

position 37 wherein Xaa is Asn, Pro or Thr;

position 48 wherein Xaa is Asn or Pro;

position 62 wherein Xaa is Ser, or Pro;

position 68 wherein Xaa is Leu, Trp, Asp, Asn, Glu, His, Phe, Ser or Tyr;

position 81 wherein Xaa is His, Arg, Thr, Asn or Ser;

position 84 wherein Xaa is His, Ile, Leu, Ala, Arg, Gln, Lys, Met, Ser, Tyr or Val;

position 86 wherein Xaa is Lys or Arg;

position 87 wherein Xaa is Asp;

position 91 wherein Xaa is Asn, or Pro;

position 94 wherein Xaa is Arg, Ala, or Ser;

position 102 wherein Xaa is Lys;

position 107 wherein Xaa is Ala, or Ile;

position 108 wherein Xaa is Gln, or Ile;

position 109 wherein Xaa is Ala, Met or Glu.

74. The method according to claim 73, wherein said mutant human interleukin-3 polypeptide has at least ten times greater cell proliferative activity than native human interleukin-3.

75. A method of treating a patient consisting of the steps of:
  (i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:
  (a) a sequence of (SEQ ID NO:21)
wherein;

Xaa at position 3 is Ser, Gly, Asp, Met, or Gln;

Xaa at position 4 is Asn, His, or Ile;

Xaa at position 5 is Met or Ile;

Xaa at position 7 is Asp or Glu;

Xaa at position 9 is Ile, Ala, Leu, or Gly;

Xaa at position 10 is Ile, Val, or Leu;

Xaa at position 11 is Thr, His, Gln, or Ala;

Xaa at position 12 is His or Ala;

Xaa at position 15 is Gln, Asn, or Val;

Xaa at position 16 is Pro, Gly, or Gln;

Xaa at position 17 is Pro, Asp, Gly, or Gln;

Xaa at position 18 is Leu, Arg, Gln, Asn, Gly, Ala, or Glu;

Xaa at position 19 is Pro or Glu;

Xaa at position 20 is Leu, Val, Gly, Ser, Lys, Ala, Arg, Gln, Glu, Ile, Phe, Thr or Met;

Xaa at position 21 is Leu, Ala, Asn, Pro, Gln, or Val;

Xaa at position 23 is Phe, Ser, Pro, or Trp;

Xaa at position 24 is Asn or Ala;

Xaa at position 28 is Gly, Asp, Ser, Cys, Ala, Asn, Ile, Leu, Met Tyr or Arg;

Xaa at position 30 is Asp or Glu;

Xaa at position 31 is Gln, Val, Met, Leu, Thr, Ala, Asn, Glu, Ser or Lys;

Xaa at position 32 is Asp, Phe, Ser, Thr, Ala, Asn, Gln, Glu, His, Ile, Lys, Tyr, Val or Cys;

Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Arg, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a);
(ii) removing hematopoietic cells from said patient;
(iii) administering to said patient cancer radiation therapy or chemotherapy; and
(iv) returning said hematopoietic cells to said patient.

76. The method according to claim 75, wherein said mutant human interleukin-3 polypeptide has at least ten times greater cell proliferative activity than native human interleukin-3.

77. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:15)
wherein;
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

78. The method according to claim 77, wherein said mutant human interleukin-3 polypeptide has at least ten times greater cell proliferative activity than native human interleukin-3.

79. The method according to claim 77 wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 101 wherein Xaa is Asp;

position 105 wherein Xaa is Asn, or Pro;

position 108 wherein Xaa is Arg, Ala, or Ser;

position 116 wherein Xaa is Lys;

position 121 wherein Xaa is Ala, or Ile;

position 122 wherein Xaa is Gln, or Ile;

position 123 wherein Xaa is Ala, Met or Glu.

80. The method according to claim 79, wherein said mutant human interleukin-3 polypeptide has at least ten times greater cell proliferative activity than native human interleukin-3.

81. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:17) wherein;

Xaa at position 17 is Ser, Gly, Asp, Met, or Gln;

Xaa at position 18 is Asn, His, or Ile;

Xaa at position 19 is Met or Ile;

Xaa at position 21 is Asp or Glu;

Xaa at position 23 is Ile, Ala, Leu, or Gly;

Xaa at position 24 is Ile, Val, or Leu;

Xaa at position 25 is Thr, His, Gln, or Ala;

Xaa at position 26 is His or Ala;

Xaa at position 29 is Gln, Asn, or Val;

Xaa at position 30 is Pro, Gly, or Gln;

Xaa at position 31 is Pro, Asp, Gly, or Gln;

Xaa at position 32 is Leu, Arg, Gln, Asn, Gly, Ala, or Glu;

Xaa at position 33 is Pro or Glu;

Xaa at position 34 is Leu, Val, Gly, Ser, Lys, Ala, Arg, Gln, Glu, Ile, Phe, Thr or Met;

Xaa at position 35 is Leu, Ala, Asn, Pro, Gln, or Val;

Xaa at position 37 is Phe, Ser, Pro, or Trp;

Xaa at position 38 is Asn or Ala;

Xaa at position 42 is Gly, Asp, Ser, Cys, Ala, Asn, Ile, Leu, Met, Tyr or Arg;

Xaa at position 44 is Asp or Glu;

Xaa at position 45 is Gln, Val, Met, Leu, Thr, Ala, Asn, Glu, Ser or Lys;

Xaa at position 46 is Asp, Phe, Ser, Thr, Ala, Asn, Gln, Glu, His, Ile, Lys, Tyr, Val or Cys;

Xaa at position 50 is Glu, Ala, Asn, Ser or Asp;

Xaa at position 51 is Asn, Arg, Met, Pro, Ser, Thr, or His;

Xaa at position 54 is Arg or Ala;

Xaa at position 55 is Arg, Thr, Val, Leu, or Gly;

Xaa at position 56 is Pro, Gly, Ser, Gln, Ala, Arg, Asn, Glu, Leu, Thr, Val or Lys;

Xaa at position 60 is Ala or Ser;

Xaa at position 62 is Asn, Pro, Thr, or Ile;

Xaa at position 63 is Arg or Lys;

Xaa at position 64 is Ala or Asn;

Xaa at position 65 is Val or Thr;

Xaa at position 66 is Lys or Arg;

Xaa at position 67 is Ser, Phe, or His;

Xaa at position 68 is Leu, Ile, Phe, or His;

Xaa at position 69 is Gln, Ala, Pro, Thr, Glu, Arg, or Gly;

Xaa at position 71 is Ala, Pro, or Arg;

Xaa at position 72 is Ser, Glu, Arg, or Asp;

Xaa at position 73 is Ala or Leu;

Xaa at position 76 is Ser, Val, Ala, Asn, Glu, Pro, or Gly;

Xaa at position 77 is Ile or Leu;

Xaa at position 79 is Lys, Thr, Gly, Asn, Met, Arg, Ile, or Asp;

Xaa at position 80 is Asn, Gly, Glu, or Arg;

Xaa at position 82 is Leu, Gln, Trp, Arg, Asp, Ala, Asn, Glu, His, Ile, Met, Phe, Ser, Thr, Tyr or Val;

Xaa at position 83 is Pro or Thr;

Xaa at position 85 is Leu or Val;

Xaa at position 87 is Leu or Ser;

Xaa at position 88 is Ala or Trp;

Xaa at position 91 is Ala or Pro;

Xaa at position 93 is Thr, Asp, Ser, Pro, Ala, Leu, or Arg;

Xaa at position 95 is His, Pro, Arg, Val, Leu, Gly, Asn, Phe, Ser or Thr;

Xaa at position 96 is Pro or Tyr;

Xaa at position 97 is Ile or Val;

Xaa at position 98 is His, Ile, Asn, Leu, Ala, Thr, Arg, Gln, Lys, Met, Ser, Tyr, Val or Pro;

Xaa at position 99 is Ile, Leu, or Val;

Xaa at position 100 is Lys, Arg, Ile, Gln, Pro, or Ser;

Xaa at position 101 is Asp;

Xaa at position 104 is Trp or Leu;

Xaa at position 105 is Asn, Pro, Ala, Ser, Trp, Gln, Tyr, Leu, Lys, Ile, Asp, or His;

Xaa at position 106 is Glu or Gly;

Xaa at position 108 is Arg, Ala, or Ser;

Xaa at position 109 is Arg, Thr, Glu, Leu, or Ser;

Xaa at position 112 is Thr, Val, or Gln;

Xaa at position 114 is Tyr or Trp;

Xaa at position 115 is Leu or Ala;

Xaa at position 116 is Lys;

Xaa at position 117 is Thr or Ser;

Xaa at position 120 is Asn, Pro, Leu, His, Val, or Gln;

Xaa at position 121 is Ala, Ser, Ile, Asn, Pro, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from one to three of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

82. The method according to claim 81, wherein said mutant human interleukin-3 polypeptide has at least ten times greater cell proliferative activity than native human interleukin-3.

83. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:19) wherein;

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, or Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from one to three of the amino acids designated by Xaa are different from the corresponding native amino acids of (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

84. The method according to claim 83, wherein said mutant human interleukin-3 polypeptide has at least ten times greater cell proliferative activity than native human interleukin-3.

85. The method according to claim 83, wherein said mutant human interleukin-3 polypeptide is selected from the group consisting of:

(a) a polypeptide having an amino acid sequence of
(i) (residues 3–113 of SEQ ID NO:66);
(ii) (residues 3–113 of SEQ ID NO:67);
(iii) (residues 3–113 of SEQ ID NO:69); or
(iv) (SEQ ID NO:218); and (b) an N-terminal methionine residue, alanine residue or methionine-alanine di-peptide immediately preceding said sequence according to (a).

86. The method according to claim 85, wherein said mutant human interleukin-3 polypeptide has at least ten times greater cell proliferative activity than native human interleukin-3.

87. The method according to claim 83, wherein in said mutant human interleukin-3 (hIL-3) sequence the amino acids which differ from the corresponding residue in native human interleukin-3 are selected from the group consisting of:

position 28 wherein Xaa is Gly, Asp, Ser, Ile, Leu, Met, Tyr, or Ala;

position 31 wherein Xaa is Gln, Val, Met or Asn;
position 32 wherein Xaa is Asp, Ser, Ala, Gln, His or Val;
position 36 wherein Xaa is Glu or Asp;
position 37 wherein Xaa is Asn, Pro or Thr;
position 48 wherein Xaa is Asn or Pro;
position 62 wherein Xaa is Ser, or Pro;
position 68 wherein Xaa is Leu, Trp, Asp, Asn, Glu, His, Phe, Ser or Tyr;
position 81 wherein Xaa is His, Arg, Thr, Asn or Ser;
position 84 wherein Xaa is His, Ile, Leu, Ala, Arg, Gln, Lys, Met, Ser, Tyr or Val;
position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;
position 107 wherein Xaa is Ala, or Ile;
position 108 wherein Xaa is Gln, or Ile;
position 109 wherein Xaa is Ala, Met or Glu.

88. The method according to claim 87, wherein said mutant human interleukin-3 polypeptide has at least ten times greater cell proliferative activity than native human interleukin-3.

89. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:21)
wherein;
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Arg, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

wherein from one to three of the amino acids designated by Xaa are different from the corresponding amino acids of native (1–133) human interleukin-3; and said mutant human interleukin-3 polypeptide has at least three times greater cell proliferative activity than native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

90. The method according to claim 89, wherein said mutant human interleukin-3 polypeptide has at least ten times greater cell proliferative activity than native human interleukin-3.

* * * * *